(12) United States Patent
Shirai et al.

(10) Patent No.: US 8,592,454 B2
(45) Date of Patent: Nov. 26, 2013

(54) NITROGEN-CONTAINING HETEROCYCLIC COMPOUND AND USE OF SAME

(75) Inventors: Junya Shirai, Osaka (JP); Hideyuki Sugiyama, Osaka (JP); Taku Kamei, Osaka (JP); Hironobu Maezaki, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 13/119,743

(22) PCT Filed: Sep. 18, 2009

(86) PCT No.: PCT/JP2009/066458
§ 371 (c)(1),
(2), (4) Date: Mar. 18, 2011

(87) PCT Pub. No.: WO2010/032856
PCT Pub. Date: Mar. 25, 2010

(65) Prior Publication Data
US 2011/0178060 A1    Jul. 21, 2011

Related U.S. Application Data

(60) Provisional application No. 61/136,625, filed on Sep. 19, 2008.

(51) Int. Cl.
| | | |
|---|---|---|
| A61K 31/445 | (2006.01) | |
| A61K 31/40 | (2006.01) | |
| A61K 31/535 | (2006.01) | |
| A61K 31/00 | (2006.01) | |
| C07D 211/58 | (2006.01) | |
| C07D 295/03 | (2006.01) | |

(52) U.S. Cl.
USPC ...... 514/317; 514/423; 514/392; 514/210.08; 514/235.5; 546/224; 546/192; 546/276.4; 548/311.1; 548/531

(58) Field of Classification Search
None
See application file for complete search history.

(56) References Cited

U.S. PATENT DOCUMENTS

| | | | |
|---|---|---|---|
| 5,278,176 A | 1/1994 | Lin | |
| 7,381,741 B2 | 6/2008 | Humphrey et al. | |
| 2005/0009815 A1* | 1/2005 | DeVita et al. | 514/227.5 |
| 2005/0214204 A1 | 9/2005 | Burns et al. | |
| 2005/0256164 A1 | 11/2005 | O'Neill et al. | |
| 2005/0288358 A1 | 12/2005 | Humphrey et al. | |
| 2007/0167433 A1 | 7/2007 | Herold et al. | |
| 2007/0244158 A1 | 10/2007 | Miyake et al. | |
| 2007/0270429 A1 | 11/2007 | Shibayama et al. | |
| 2008/0076773 A1 | 3/2008 | Cox et al. | |
| 2008/0221151 A1 | 9/2008 | Humphrey et al. | |
| 2008/0275021 A1 | 11/2008 | Bissantz et al. | |
| 2009/0312327 A1 | 12/2009 | Bissantz et al. | |
| 2011/0190278 A1 | 8/2011 | Nakahira et al. | |

FOREIGN PATENT DOCUMENTS

| | | |
|---|---|---|
| DE | 2600557 | * 7/1977 |
| EP | 1 623 721 | 2/2006 |
| JP | 2007-8913 | 1/2007 |
| JP | 2007-277231 | 10/2007 |
| JP | 2007-537233 | 12/2007 |
| JP | 2008-500324 | 1/2008 |
| WO | 94/04152 | 3/1994 |

(Continued)

OTHER PUBLICATIONS

Wolff, Manfred E. "Burger's Medicinal Chemistry, 5ed, Part I", John Wiley & Sons, 1995, pp. 975-997.*

(Continued)

*Primary Examiner* — Noble Jarrell
*Assistant Examiner* — Valerie Rodriguez-Garcia
(74) *Attorney, Agent, or Firm* — Wenderoth, Lind & Ponack, L.L.P.

(57) ABSTRACT

The present invention relates to a compound represented by the formula

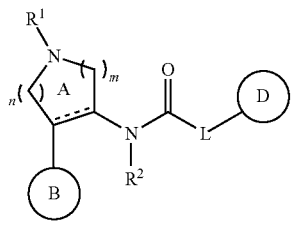

wherein ring A is a nitrogen-containing heterocycle;
ring B is an aromatic ring optionally having substituent(s);
ring D is an aromatic ring optionally having substituent(s);
L is a group represented by the formula

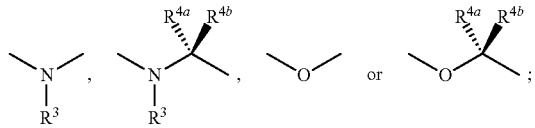

$R^2$, $R^3$, $R^{4a}$ and $R^{4b}$ are each independently a hydrogen atom, an optionally halogenated $C_{1-6}$ alkyl group or an optionally halogenated $C_{3-6}$ cycloalkyl group, or $R^2$ and $R^3$ are optionally bonded via an alkylene chain or an alkenylene chain, or $R^{4a}$ and $R^{4b}$ are optionally bonded via an alkylene chain or an alkenylene chain;
$R^1$ is a hydrogen atom or a substituent;
m and n are each independently an integer of 0 to 5;
m+n is an integer of 2 to 5; and
----- is a single bond or double bond, or a salt thereof; and the like. The compound has a superior tachykinin receptor antagonistic action, and is useful as an agent for the prophylaxis or treatment of various diseases such as lower urinary tract diseases, digestive tract diseases, central neurological disease and the like.

17 Claims, No Drawings

(56) References Cited

FOREIGN PATENT DOCUMENTS

| WO | 99/09984 | 3/1999 |
| WO | 00/18403 | 4/2000 |
| WO | 00/26211 | 5/2000 |
| WO | 02/088101 | 11/2002 |
| WO | 03/045920 | 6/2003 |
| WO | 2004/029024 | 4/2004 |
| WO | 2004/111000 | 12/2004 |
| WO | 2006/005741 | 1/2006 |
| WO | 2006/030984 | 3/2006 |
| WO | 2006/039325 | 4/2006 |
| WO | 2008/038841 | 4/2008 |
| WO | 2008/133344 | 11/2008 |
| WO | 2009/072643 | 6/2009 |
| WO | 2009/078481 | 6/2009 |

OTHER PUBLICATIONS

Banker et al, "Modern Pharmaceutics, 3ed.", Marcel Dekker, New York, 1996, pp. 451 and 596.*

Jordan, V. C. Nature Reviews: Drug Discovery, 2, 2003, pp. 205-213.*

Dörwald, F. Zaragoza. Side Reactions in Organic Synthesis: A Guide to Successful Synthesis Design, Weinheim: Wiley-VCH Verlag GmbH & Co. KGaA, 2005, Preface.*

Maxson et al. (Med. Clin. North. Am. Nov. 1994; 78(6):1259-1273-abstract).*

Extended European Search Report issued Feb. 23, 2012 in corresponding European Application No. 09814700.2.

K. Kim et al., "Quantitative Structure—Activity Relationships of Nicotine Analogues as Neuronal Nicotinic Acetylcholine Receptor Ligands", Bioorganic & Medicinal Chemistry, vol. 4, No. 12, pp. 2211-2217, 1996.

M. Ahari et al., "A Direct Stereoselective Approach to *trans*-2,3-Disubstituted Piperidines: Application in the Synthesis of 2-Epi-CP-99,994 and (+)-Epilupinine", Organic Letters, vol. 10, No. 12, pp. 2473-2476, 2008.

Otsuka et al., "Neurotransmitter Functions of Mammalian Tachykinins", *Physiological Reviews*, vol. 73, No. 2, Apr. 1993, pp. 229-308.

Maggi et al., "Tachykinin receptors and tachykinin receptor antagonists", *Journal of Autonomic Pharmacology*, vol. 13, Issue 1, Feb. 1993, pp. 23-93.

Lecci et al., "Peripheral Tachykinin Receptors as Potential Therapeutic Targets in Visceral Diseases", *Expert Opinion, Ther. Targets*, 7(3), 2003, pp. 343-362.

Saloméet al., "Selective Blockade of NK2 or NK3 Receptors Produces Anxiolytic- and Antidepressant-like Affects in Gerbils", *Pharmacology, Biochemistry and Behavior*, 83, 2006, pp. 533-539.

Spooren et al., "NK3 Receptor Antagonists: the Next Generation of Antipsychotics?", *Nature Reviews, Drug Discovery*, vol. 4, Dec. 2005, pp. 967-975.

De Giorgio et al., "Novel Therapeutic Targets for Enteric Nervous System Disorders", *TRENDS in Pharmacological Sciences*, vol. 28, No. 9, 2007, pp. 473- 481.

Andrews et al., "Abdominal Vagal Afferent Neurones: an Important Target for the Treatment of Gastrointestinal Dysfunction", *Current Opinion in Pharmacology*, 2(6), 2002, pp. 650-656.

Stanghellini et al., "New Developments in the Treatment of Functional Dyspepsia", *Drugs*, 63 (9), 2003, pp. 869-892.

Kris et al., "American Society of Clinical Oncology Guideline for Antiemetics in Oncology: Update 2006", *Journal of Clinical Oncolony*, vol. 24, No. 18, Jun. 20, 2006, pp. 2932-2947.

Talley, Nicholas J., "New and Emerging Treatments for Irritable Bowel Syndrome and Functional Dyspepsia", *Expert Opinion, Emerging Drugs*, 7(1), 2002, pp. 91-98.

Improta et al., "Central Effects of Selective NK1 and NK3 Tachykinin Receptor Agonists on Two Moderls of Experimentally-Induced Colitis in Rats", *Peptides*, 24, 2003, pp. 903-911.

O'Connor et al., "The Role of Substance P in Inflammatory Disease", *Journal of Cellular Physiology*, 201, 2004, pp. 167-180.

* cited by examiner

NITROGEN-CONTAINING HETEROCYCLIC COMPOUND AND USE OF SAME

This application is a U.S. national stage of International Application No. PCT/JP2009/066458 filed Sep. 18, 2009 which claims the benefit of U.S. provisional application Ser. No. 61/136,625 filed Sep. 19, 2008.

TECHNICAL FIELD

The present invention relates to a novel nitrogen-containing heterocyclic compound having excellent antagonistic action for a tachykinin receptor and use thereof.

BACKGROUND OF THE INVENTION

Tachykinin is a generic term for a group of neuropeptides. Substance P (SP), neurokinin A (NK-A) and neurokinin B (NK-B) are known in mammals, and these peptides are known to bind to the corresponding receptors (neurokinin-1 (NK-1), neurokinin-2 (NK-2) and neurokinin-3 (NK-3)) that exist in a living body and thereby to exhibit various biological activities.

Of such neuropeptides, SP has the longest history and has been studied in detail. In 1931, the existence of SP in the extract from equine intestines was confirmed, and in 1971, its structure was determined. SP is a peptide consisting of 11 amino acids.

SP is broadly distributed over the central and peripheral nervous systems, and has various physiological activities such as vasodilation, enhancement of vascular permeability, contraction of smooth muscles, excitation of neurons, salivation, enhancement of diuresis, immunological enhancement and the like, in addition to the function as a transmitter substance for primary sensory neurons. In particular, it is known that SP released from the terminal of the spinal (dorsal) horn due to a pain impulse transmits the information of pain to secondary neurons, and that SP released from the peripheral terminal induces an inflammatory response in the receptor thereof. Thus, it is considered that SP is involved in various disorders (e.g., pain, headache, particularly migraine, Alzheimer's disease, multiple sclerosis, cardiovascular modulation, chronic inflammatory diseases such as chronic rheumatic arthritis, respiratory diseases including asthma or allergic rhinitis, intestinal inflammatory diseases including ulcerative colitis and Crohn's disease, ocular damage and ocular inflammatory diseases, proliferative vitreoretinopathy, an irritable bowel syndrome, urinary frequency, psychosis, vomiting, etc.) [see, for example, Physiological Reviews, Vol. 73, pp. 229-308 (1993); Journal of Autonomic Pharmacology, Vol. 13, pp. 23-93 (1993)].

At present, as a compound having an SP receptor antagonistic action, WO03/057668 describes a compound represented by the formula

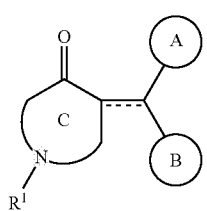

(I)

wherein each of rings A and B is an optionally substituted aromatic ring, or rings A and B may be bonded to each other to form a ring by linking bonds or substituents thereof; ring C is a nitrogenous saturated heterocyclic ring optionally having substituents besides oxo (excluding 2,3-dioxopyrrolidine ring); $R^1$ is a hydrogen atom, an optionally substituted hydrocarbon group or an optionally substituted heterocyclic group; and ----- is a single bond or a double bond, or a salt thereof.

In addition, WO03/101964 describes a compound represented by the formula

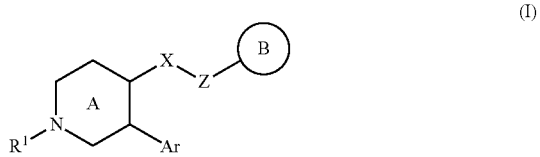

(I)

wherein Ar is an aryl group, an aralkyl group or an aromatic heterocyclic group, each of which may be substituted, $R^1$ is a hydrogen atom, an optionally substituted hydrocarbon group, an acyl group or an optionally substituted heterocyclic group, X is an oxygen atom or an optionally substituted imino group, Z is an optionally substituted methylene group, Ring A is a further optionally substituted piperidine ring, and Ring B is an optionally substituted aromatic ring, provided that when Z is a methylene group substituted with an oxo group, $R^1$ is not a methyl group, and when Z is a methylene group substituted with a methyl group, Ring B is a substituted aromatic ring, or a salt thereof.

Furthermore, WO2005/068427 describes a compound represented by the formula

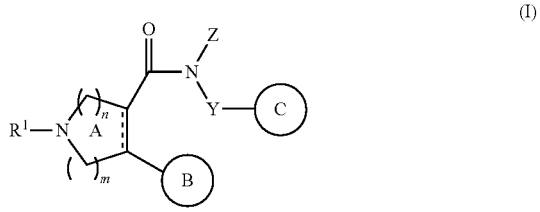

(I)

wherein ring A is a nitrogen-containing heterocycle optionally further having substituent(s), ring B and ring C are each an aromatic ring optionally having substituent(s), $R^1$ is a hydrogen atom, a hydrocarbon group optionally having substituent(s), an acyl group or a heterocyclic group optionally having substituent(s), Z is an optionally halogenated $C_{1-6}$ alkyl group, Y is a methylene group optionally having substituent(s), m and n are each an integer of 0 to 5, m+n is an integer of 2 to 5, and ----- is a single bond or a double bond, or a salt thereof.

Moreover, WO2006/030975 describes a compound represented by the formula

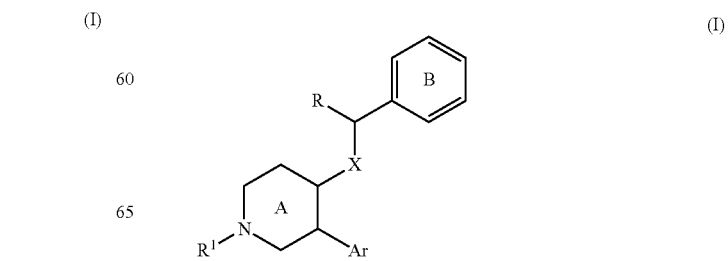

(I)

wherein Ar is an aryl group optionally having substituent(s), R is a $C_{1-6}$ alkyl group, $R^1$ is a hydrogen atom, a hydrocarbon group optionally having substituent(s), an acyl group or a heterocyclic group optionally having substituent(s), X is an oxygen atom or an imino group optionally having a substituent, ring A is a piperidine ring optionally further having substituent(s), and ring B is a benzene ring having substituent(s), or a salt thereof.

In addition, WO2006/115286 describes an optically active compound represented by the formula

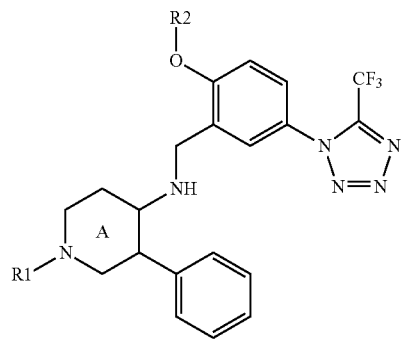

(I)

wherein ring A is an optionally further substituted piperidine ring, R1 is a hydrogen atom or a group represented by R1'—C(=O)— wherein R1' is
(i) an optionally substituted 5- or 6-membered nitrogen-containing heterocyclic group,
(ii) an optionally substituted $C_{1-6}$ alkyl group, or
(iii) an optionally substituted $C_{1-6}$ alkoxy group, and
R2 is a hydrogen atom, an optionally substituted $C_{1-3}$ alkyl group, or a $C_{3-6}$ cycloalkyl group, excluding cis-1-(methoxyacetyl)-N-[2-methoxy-5-[5-(trifluoromethyl)-1H-tetrazol-1-yl]benzyl]-3-phenyl-4-piperidinamine and cis-1-[(1-acetyl-4-piperidinyl)carbonyl]-N-[2-methoxy-5-[5-(trifluoromethyl)-H-tetrazol-1-yl]benzyl]-3-phenyl-4-piperidinamine, or a salt thereof.

Moreover, WO2007/015588 describes a compound represented by the formula

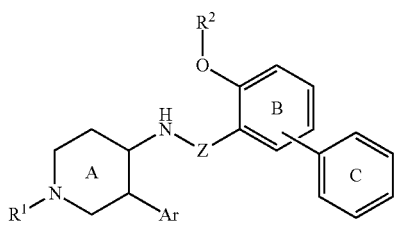

(I)

wherein Ar is a phenyl group optionally having substituent(s), $R^1$ is a hydrogen atom, a hydrocarbon group optionally having substituent(s), an acyl group or a heterocyclic group optionally having substituent(s), $R^2$ is a hydrogen atom, a $C_{1-6}$ alkyl group optionally having substituent(s) or a $C_{3-6}$ cycloalkyl group optionally having substituent(s), Z is a methylene group optionally having a $C_{1-6}$ alkyl group, ring A is a piperidine ring optionally further having substituent(s), ring B and ring C are benzene rings optionally further having substituent(s), and $R^2$ optionally forms a ring together with the adjacent substituent on the ring B, excluding the compounds represented by the formula:

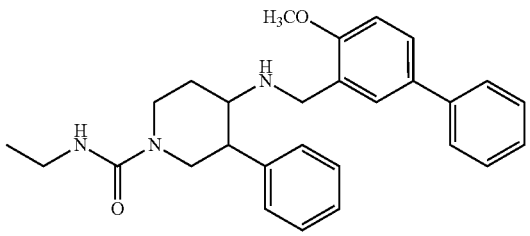 [SMILES: CCNC(=O)N1CCC(NCc2cc(-c3ccccc3)ccc2OC)C(c2ccccc2)C1]

and the formula:

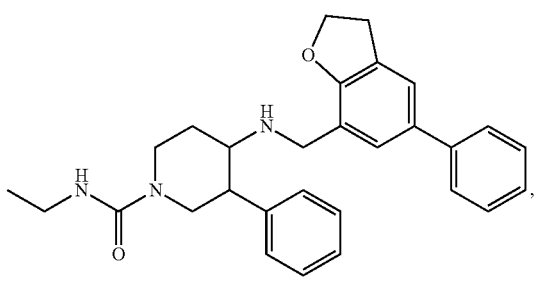 [SMILES: CCNC(=O)N1CCC(NCc2cc(-c3ccccc3)cc3c2OCC3)C(c2ccccc2)C1]

or a salt thereof.

Furthermore, WO2007/089031 describes a compound represented by the formula

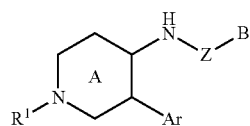

(1)

wherein
Ar is a phenyl group optionally having substituent(s),
$R^1$ is a hydrogen atom, a hydrocarbon group optionally having substituent(s), an acyl group or a heterocyclic group optionally having substituent(s),
Z is a methylene group optionally having $C_{1-6}$ alkyl group(s),
ring A is a piperidine ring optionally further having substituent(s), and
B is a monocyclic aromatic heterocyclic group optionally having substituent(s) (substituents of the monocyclic aromatic heterocycle may be bonded to each other to form a ring), or a salt thereof.

Also, WO2008/133344 describes a compound represented by the formula

wherein $R^1$ is carbamoylmethyl, methylsulfonylethylcarbonyl and the like; $R^2$ is methyl or cyclopropyl; $R^3$ is a hydrogen atom or methyl; R⁴ is a chlorine atom or trifluoromethyl; R⁵ is a chlorine atom or trifluoromethyl; and a group represented by the formula

is a group represented by the formula

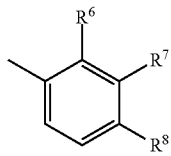

wherein R⁶ is a hydrogen atom, methyl, ethyl or isopropyl; R⁷ is a hydrogen atom, methyl or a chlorine atom; and R⁸ is a hydrogen atom, a fluorine atom, a chlorine atom or methyl, or 3-methylthiophen-2-yl, or a salt thereof.

WO2009/072643 describes a compound represented by the formula

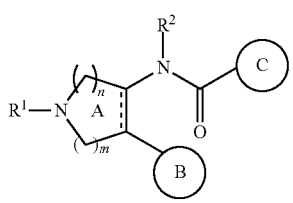

wherein ring A is a nitrogen-containing heterocycle optionally further having substituent(s), ring B is an aromatic ring optionally having substituent(s), ring C is a cyclic group optionally having substituent(s), R¹ is a hydrogen atom, a hydrocarbon group optionally having substituent(s), an acyl group, a heterocyclic group optionally having substituent(s) or an amino group optionally having substituent(s), R² is an optionally halogenated $C_{1-6}$ alkyl group, m and n are each an integer of 0 to 5, m+n is an integer of 2 to 5, and

- - - - - is a single bond or a double bond, excluding N-[(rac.)-(3R,4R)-1-benzyl-4-phenylpiperidin-3-yl]-N-isopropyl-4-methoxy-3-(3-methoxypropoxy)benzamide, N-isopropyl-4-methoxy-3-(3-methoxypropoxy)-N-[(rac.)-(3R,4R)-4-phenylpiperidin-3-yl]benzamide, N-isopropyl-4-methoxy-3-(3-methoxypropoxy)-N-[(rac.)-(3R,4R)-4-(3-(methylsulfonyl)amino-phenyl)-piperidin-3-yl]benzamide, N-isopropyl-[(rac.)-(3R,4R)-4-[1,1'-biphenyl]-3-yl-3-piperidinyl]-4-methoxy-3-(3-methoxypropoxy)benzamide, N-ethyl-[(rac.)-(3R,4R)-4-[1,1'-biphenyl]-3-yl-3-piperidinyl]-4-methoxy-3-(3-methoxypropoxy)benzamide, N-propyl-[(rac.)-(3R,4R)-4-[1,1'-biphenyl]-3-yl-3-piperidinyl]-4-methoxy-3-(3-methoxypropoxy)benzamide, N-ethyl-[(rac.)-(3R,4R)-4-[3-[(3,5-dimethoxyphenyl)methoxy]phenyl]-3-piperidinyl]-4-methoxy-3-(3-methoxypropoxy)benzamide and 4-methoxy-3-(3-methoxypropoxy)-N-isopropyl-N-[(rac.)-4-(4-phenyl-2-oxazolyl)-3-piperidinyl]benzamide, or a salt thereof.

In addition, US Patent Application Publication No. 2005/0256164 describes the following compound

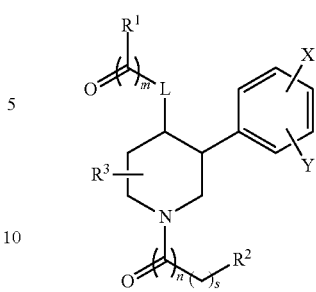

wherein m, n and s are each independently 0 or 1, L is —O— or —NR⁴—, R¹ and R² are each independently hydrogen, aryl, heteroaryl, $(C_1-C_6)$alkyl, $(C_1-C_6)$alkyl-heteroaryl and the like, R³ is hydrogen and the like, and X and Y are each independently hydrogen, $(C_1-C_6)$alkyl and the like, as a NK-1 and NK-3 receptor antagonist.

Xenobiotica (2006), 36(2/3), 235-258, describes the following compound

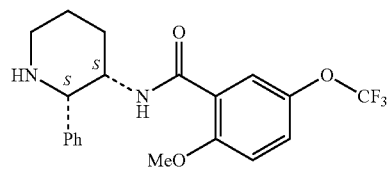

as a receptor antagonist for tachykinin, SP, NK-A or NK-B.

In addition, WO2004/111000 describes a compound represented by the following formula (I)

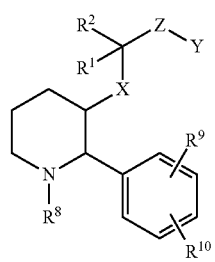

wherein
—X— is —NH— or —O—,
Y is

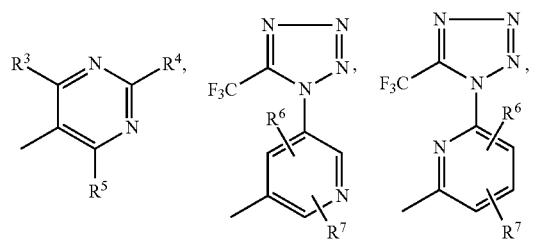

wherein
R³, R⁴ and R⁵ are independently hydrogen, lower alkyl, mono (or di or tri)halo(lower)alkyl and the like; and
R⁶ and R⁷ are each independently hydrogen or lower alkoxy, and the like, —Z— is a bond or —CH($R^{11}$)— wherein $R^{11}$ is hydrogen or lower alkyl, $R^1$ and $R^2$ are independently hydrogen or lower alkyl, or in combination form oxo, $R^8$ is hydrogen, (5-oxo-4,5-dihydro-1H-1,2,4-triazol-3-yl) methyl or an amino protecting group, $R^9$ and $R^{10}$ are hydrogen, halogen and the like, or a salt thereof, as a compound having a tachykinin receptor antagonistic action.

In addition, a selective peptidic antagonist of NK-2 receptor is known (Br. J. Pharmacol., 1990, vol. 100, pages 588-592 and WO97/31941). However, these known peptidic NK-2 antagonists have low activity and are metabolically unstable. Therefore, it is difficult to provide them as practical prophylactic drugs or therapeutic drugs.

As the selective non-peptidic NK-2 receptor antagonists, SR 48968 (Brit. J. Pharmacol. 1992, vol. 105, page 77), GR-159897 (Bioorg. Med. Chem. Lett. 1994, vol. 4, page 1951), CP 96345 (Science, 1991, vol. 251, page 435), RP 67580 (Proc. Nat. Acad. Sci. 1991, vol. 88, page 10208), ZD 7944 (Abstracts of Papers, Part 1, 214th NATIONAL Meeting of the American Chemical Society, Las Vegas, Nev., Sep. 7-11, 1997, MEDI 264), WO02/38547, WO02/38548, WO02/083663, WO02/083664 and the like are known.

In addition, as the quinoline derivatives to be condensed with a nitrogen-containing heterocycle, the compounds described in J. Org. Chem., 2000, 65, 655-666; J. Org. Chem., 2003, 68, 442-451; Org. Lett., 2001, 3, 2189-2191; Org. Lett., 2001, 3, 4217-4220; Tetrahedron 57, 2001, 5615-5624; Tetrahedron Letters 40, 1999, 1215-1218; Tetrahedron Letters 40, 1999, 3339-3342; Heterocycles, 2004, 63, 1685-1712 and U.S. Pat. No. 5,288,725 and the like are known. Furthermore, WO05/105802 is known.

JP-A-2007-277231 and WO 2006/030984 describe, as synthesis intermediates for tachykinin receptor antagonist, the following compounds.

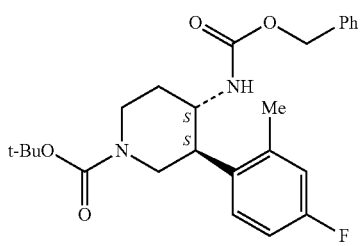

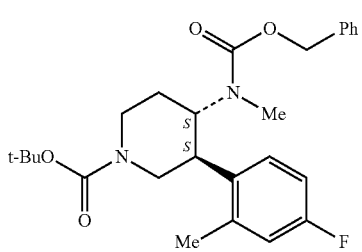

In addition, WO2004/111000 discloses, as synthesis intermediates for tachykinin receptor antagonist, the following compounds.

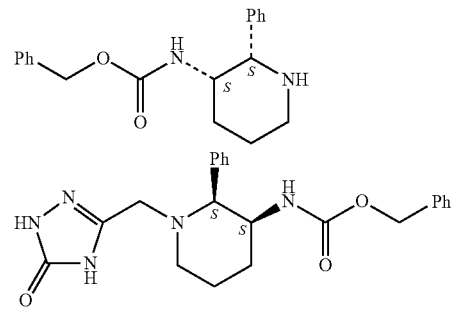

In addition, WO2000/018403 discloses, as synthesis intermediates for NK1 receptor antagonist, the following compounds.

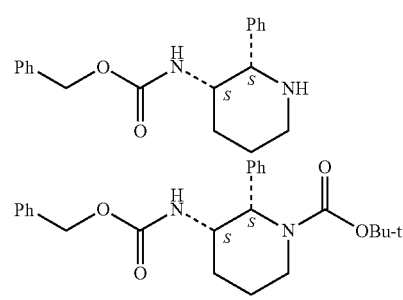

In addition, US 2007/0167433 describes, as synthesis intermediates for β-secretase, cathepsin D, plasmepsin II and/or HIV protease inhibitor, and WO2006/005741 describes, as synthesis intermediates for rennin inhibitory substance, the following compounds.

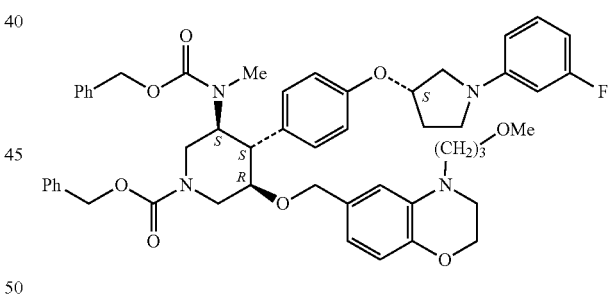

In addition, WO2003/045920 discloses, as melanin coagulation hormone receptor (MCH-1R) antagonists, the following compounds.

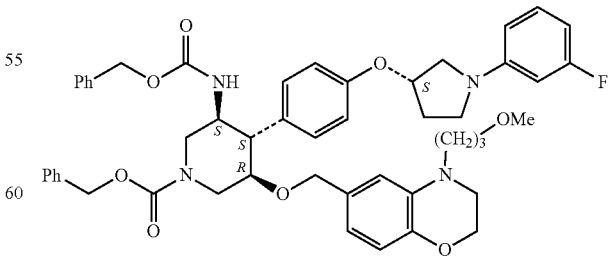

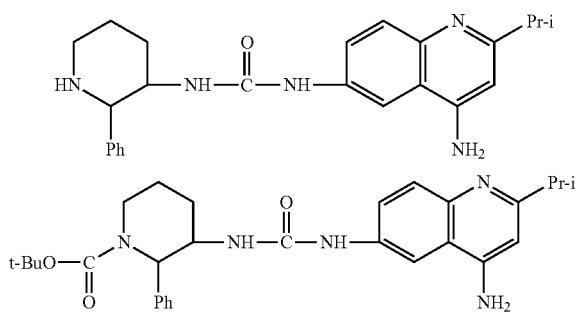

In addition, WO2002/088101 discloses, as a BACE (β amyloid precursor protease) inhibitor, the following compound.

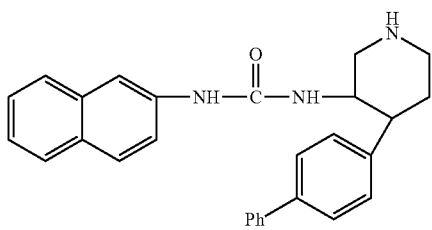 [SMILES: O=C(Nc1ccc2ccccc2c1)NC1CNCCC1c1ccc(-c2ccccc2)cc1]

Moreover, the relationship between NK-3 receptor and central nervous system diseases, particularly depression, has been pointed out (Pharmacol. Biochem. Behav., 83 (2006), 533-539; Nature Rev. Drug Discov., 4, 967-975, 2005). Therefore, a compound showing an NK-3 receptor binding action is considered to be promising as a therapeutic drug for the central nervous system diseases.

SUMMARY OF THE INVENTION

Problems to be Solved by the Invention

An object of the present invention is to provide a nitrogen-containing heterocyclic compound having an antagonistic action for a tachykinin receptor, etc. and having a chemical structure different from that of known compounds including the above-mentioned compounds, a medicament comprising the compound, and the like.

Means of Solving the Problems

The present inventors have made extensive studies in view of the above-mentioned situation and, as a result, have unexpectedly found that a nitrogen-containing heterocyclic compound represented by the following formula (I) (hereinafter sometimes to be simply referred to as compound (I)) or a salt thereof has, based on its specific chemical structure, a strong tachykinin receptor antagonistic action, particularly, an NK-1 receptor antagonistic action, an NK-2 receptor antagonistic action, an NK-3 receptor antagonistic action and the like, and is sufficiently satisfactory as a medicament. On the basis of these findings, the present inventors have completed the present invention.

Accordingly, the present invention relates to
[1] a compound represented by the formula

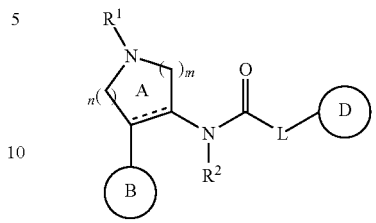

wherein ring A is a nitrogen-containing heterocycle;
ring B is an aromatic ring optionally having substituent(s);
ring D is an aromatic ring optionally having substituent(s);
L is a group represented by the formula

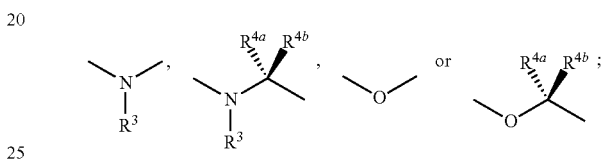

$R^2$, $R^3$, $R^{4a}$ and $R^{4b}$ are each independently a hydrogen atom, an optionally halogenated $C_{1-6}$ alkyl group or an optionally halogenated $C_{3-6}$ cycloalkyl group, or $R^2$ and $R^3$ are optionally bonded via an alkylene chain or an alkenylene chain, or $R^{4a}$ and $R^{4b}$ are optionally bonded via an alkylene chain or an alkenylene chain;
$R^1$ is a hydrogen atom or a substituent;
m and n are each independently an integer of 0 to 5;
m+n is an integer of 2 to 5; and
⁃⁃⁃⁃⁃ is a single bond or double bond,
provided when L is a group represented by the formula

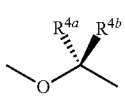

wherein each symbol is as defined above, then ring D is an aromatic ring having substituent(s) (excluding N-(4-amino-2-isopropylquinolin-6-yl)-N'-[2-phenylpiperidin-3-yl]urea, N-(4-amino-2-isopropylquinolin-6-yl)-N'-[1-(tert-butoxycarbonyl)-2-phenylpiperidin-3-yl]urea and N-[4-(biphenyl-4-yl)piperidin-3-yl]-N'-(naphthalen-2-yl)urea) or a salt thereof;
[2] the compound of the above-mentioned [1], wherein ring A is a piperidine ring or a pyrrolidine ring;
[3] the compound of the above-mentioned [1], wherein ring B is a phenyl group optionally having substituent(s) or a pyridyl group optionally having substituent(s);
[4] the compound of the above-mentioned [1], wherein ring B is a phenyl group optionally having substituent(s) or a thienyl group optionally having substituent(s);
[5] the compound of the above-mentioned [1], wherein ring D is a phenyl group optionally having substituent(s);
[6] the compound of the above-mentioned [1], wherein $R^1$ is a hydrogen atom, a hydrocarbon group optionally having substituent(s), an acyl group, a heterocyclic group optionally having substituent(s), or a group represented by —$NR^5R^6$ wherein $R^5$ and $R^6$ are each independently a hydrogen atom, a hydrocarbon group optionally having substituent(s) or an acyl group, or in combination shows an oxygen atom;

[7] the compound of the above-mentioned [1], wherein $R^2$ is a hydrogen atom or a $C_{1-6}$ alkyl group;

[8] the compound of the above-mentioned [1], wherein L is a group represented by the formula

wherein $R^{3'}$ is a hydrogen atom or a $C_{1-6}$ alkyl group;

[9] the compound of the above-mentioned [1], wherein ring D is a 3,5-bis(trifluoromethyl)phenyl group or a 3,5-dichlorophenyl group;

[10] methyl 4-{[(3S,4R)-3-[{[3,5-bis(trifluoromethyl)phenyl](methyl)carbamoyl}(methyl)amino]-4-(4-fluorophenyl)pyrrolidin-1-yl]carbonyl}piperidine-1-carboxylate of the above-mentioned [1], or a salt thereof;

[11] 1-[(3S,4R)-4-(4-chlorophenyl)-1-{[4-(methylsulfonyl)piperazin-1-yl]carbonyl}pyrrolidin-3-yl]-3-(3,5-dichlorophenyl)-1,3-dimethylurea of the above-mentioned [1], or a salt thereof;

[12] 1-[3,5-bis(trifluoromethyl)phenyl]-3-[(3S,4R)-4-(5-fluoropyridin-2-yl)-1-({trans-4-[5-(trifluoromethyl)-1H-tetrazol-1-yl]cyclohexyl}carbonyl)pyrrolidin-3-yl]-1,3-dimethylurea of the above-mentioned [1], or a salt thereof;

[13] a prodrug of the compound of the above-mentioned [1];

[14] a medicament comprising the compound of the above-mentioned [1] or a prodrug thereof;

[15] the medicament of the above-mentioned [14], which is an NK1 receptor antagonist;

[16] the medicament of the above-mentioned [15], which also has an NK2 receptor antagonistic action and/or an NK3 receptor antagonistic action;

[17] the medicament of the above-mentioned [14], which is an NK2 receptor antagonist;

[18] the medicament of the above-mentioned [17], which also has an NK1 receptor antagonistic action and/or an NK3 receptor antagonistic action;

[19] the medicament of the above-mentioned [14], which is an agent for the prophylaxis or treatment of a lower urinary tract disease, a digestive tract disease or a central neurological disease;

[20] the medicament of the above-mentioned [14], which is an agent for the prophylaxis or treatment of overactive bladder, irritable bowel syndrome, functional dyspepsia, inflammatory bowel disease, gastroesophageal reflux, vomiting, nausea, depression, anxiety neurosis, anxiety, pelvic organ pain or interstitial cystitis;

[21] a method for the prophylaxis or treatment of a lower urinary tract disease, a digestive tract disease or a central neurological disease, comprising administering an effective amount of the compound of the above-mentioned [1] or a prodrug thereof to a mammal;

[22] use of the compound of the above-mentioned [1] or a prodrug thereof for the production of an agent for the prophylaxis or treatment of a lower urinary tract disease, a digestive tract disease or a central neurological disease; and the like.

Effect of the Invention

Compound (I) or a salt thereof of the present invention is superior in the tachykinin receptor antagonistic action, particularly, an NK-1 receptor antagonistic action, an NK-2 receptor antagonistic action, an NK-3 receptor antagonistic action and the like, and safe as a medicament due to low toxicity thereof. Accordingly, compound (I) or a salt thereof of the present invention is useful as a medicament, for example, an agent for the prophylaxis or treatment of various diseases such as a lower urinary tract disease, a digestive tract disease or a central nervous system disease and the like.

DETAILED DESCRIPTION OF THE INVENTION

The present invention is explained in detail in the following.

(Explanation of Ring A)

In the aforementioned formulas, ring A is a nitrogen-containing heterocycle, m and n are each an integer of 0 to 5, m+n is an integer of 2 to 5, and

----- is a single bond or a double bond. Namely, ring A is a 5- to 8-membered saturated or unsaturated nitrogen-containing heterocycle containing, as a ring-constituting atom, one nitrogen atom and 4 to 7 carbon atoms, and having, as substituents, $R^1$, ring B and a partial structure:

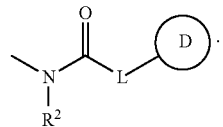

As ring A, for example, a ring having the following structure is preferable.

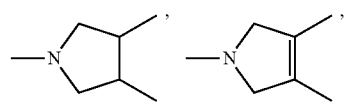

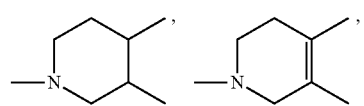

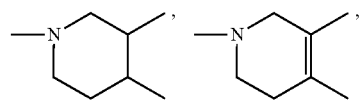

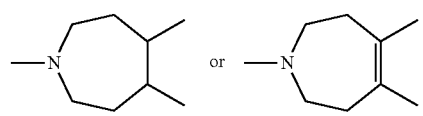

As ring A, a piperidine ring or a pyrrolidine ring is more preferable.

When m=1 and n=1, an optically active compound represented by the formula

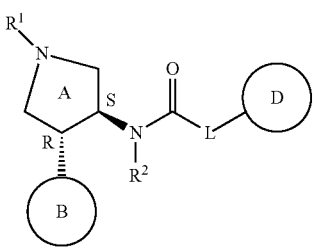

wherein each symbol is as defined above, is preferable; or when m=2 and n=1, an optically active compound represented by the formula

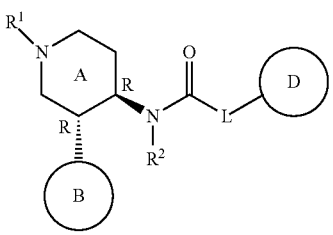

wherein each symbol is as defined above,
is preferable.
(Explanation of Ring B and Ring D)

In the aforementioned formulas, ring B and ring D are each an aromatic ring optionally having substituent(s).

Examples of the "aromatic ring" include an aryl group and an aromatic heterocyclic group.

As the "aryl group", a $C_{6-14}$ aryl group such as phenyl, naphthyl, anthryl, phenanthryl etc. and the like is used, with preference given to phenyl.

As the "aromatic heterocyclic group", a 5- or 6-membered aromatic heterocyclic group containing, besides carbon atoms, 1 to 4 hetero atoms of one or two kinds selected from a nitrogen atom, an oxygen atom and a sulfur atom (e.g., furyl, thienyl, pyridyl, pyrrolyl, imidazolyl, pyrazolyl, indolyl, thiazolyl, oxazolyl, thiadiazolyl, triazolyl, tetrazolyl etc.), a bicyclic or tricyclic fused ring group containing, besides carbon atoms, 1 to 4 hetero atoms of one or two kinds selected from a nitrogen atom, an oxygen atom and a sulfur atom (preferably, a group formed by condensation of the above-mentioned 5- to 6-membered aromatic heterocycle and one or two 5- or 6-membered heterocycles optionally containing, besides carbon atoms, 1 to 4 hetero atoms selected from an oxygen atom, a sulfur atom and a nitrogen atom (e.g., thienyl etc.), or a benzene ring; for example, benzimidazolyl etc.) and the like are used.

Examples of the substituent of ring B and ring D include 1 to 3 substituents selected from (1) a halogen atom (e.g., fluorine, chlorine, bromine, iodine, etc.),
(2) a nitro group,
(3) a cyano group,
(4) a $C_{1-6}$ alkyl group optionally having 1 to 5 (preferably 1 to 3) substituents selected from a carbamoyl group, a $C_{1-3}$ alkoxy group, a $C_{1-3}$ alkyl-carbonyl amino group, a $C_{1-6}$ alkoxy-carbonyl amino group, a $C_{6-14}$ aryl-carbonyl amino group and a halogen atom (e.g., methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl, etc.),
(5) a $C_{2-6}$ alkenyl group optionally having 1 to 3 halogen atoms (e.g., vinyl, allyl, isopropenyl, butenyl, isobutenyl, sec-butenyl, 3,3,3-trifluoro-1-propenyl, 4,4,4-trifluoro-1-butenyl, etc.),
(6) a $C_{2-6}$ alkynyl group optionally having 1 to 3 halogen atoms (e.g., ethynyl, propargyl, butynyl, 1-hexynyl, 3,3,3-trifluoro-1-propynyl, 4,4,4-trifluoro-1-butynyl, etc.),
(7) a $C_{3-8}$ cycloalkyl group optionally containing unsaturated moiety and having optionally having 1 to 5 (preferably 1 to 3) substituents selected from an oxo group and a halogen atom (e.g., cyclopropyl, cyclobutyl, cyclopentyl, cyclohexyl, 4,4-dichlorocyclohexyl, 2,2,3,3-tetrafluorocyclopentyl, 4-chlorocyclohexyl, etc.),
(8) a $C_{6-14}$ aryl group optionally having 1 to 3 substituents selected from a $C_{1-6}$ alkoxy group (e.g., methoxy, ethoxy) and a halogen atom (e.g., halogen atom) (e.g., phenyl, 1-naphthyl, 2-naphthyl, biphenylyl, 2-anthryl etc.),
(9) a $C_{7-16}$ aralkyl group (e.g., benzyl, phenethyl, diphenylmethyl, 1-naphthylmethyl, 2-naphthylmethyl, 2,2-diphenylethyl, 3-phenylpropyl, 4-phenylbutyl, 5-phenylpentyl, etc.),
(10) a hydroxy group,
(11) a $C_{1-6}$ alkoxy group optionally having 1 to 3 halogen atoms (e.g., methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy, etc.),
(12) a $C_{6-14}$ aryloxy group (e.g., phenyloxy, naphthyloxy, etc.),
(13) a mercapto group,
(14) a $C_{1-6}$ alkylthio group optionally having 1 to 3 halogen atoms (e.g., methylthio, difluoromethylthio, trifluoromethylthio, ethylthio, propylthio, isopropylthio, butylthio, 4,4,4-trifluorobutylthio, pentylthio, hexylthio, etc.),
(15) a $C_{6-14}$ arylthio group (e.g., phenylthio, naphthylthio, etc.),
(16) an amino group,
(17) a mono-$C_{1-6}$ alkylamino group (e.g., methylamino, ethylamino, etc.),
(18) a mono-$C_{6-14}$ arylamino group (e.g., phenylamino, 1-naphthylamino, 2-naphthylamino, etc.),
(19) a di-$C_{1-6}$ alkylamino group (e.g., dimethylamino, diethylamino etc.),
(20) a di-$C_{6-14}$ arylamino group (e.g., diphenylamino, etc.),
(21) a formyl group,
(22) a $C_{1-6}$ alkyl-carbonyl group optionally having 1 to 5 (preferably 1 to 3) substituents selected from a $C_{1-3}$ alkoxy group, heteroaryl group (e.g., tetrazolyl), a halogen atom (e.g., fluorine atom), a cyano group, a $C_{1-3}$ alkylsulfonyl group (e.g., methylsulfonyl), a $C_{3-8}$ cycloalkyl group, a $C_{1-3}$ alkyl-carbonyl amino group (e.g., acetylcarbonylamino) and a hydroxyl group (e.g., acetyl, propionyl, hydroxyacetyl etc.),
(23) $C_{3-6}$ cycloalkyl-carbonyl optionally having 1 to 5 (preferably 1 to 3) substituents selected from a halogen atom and a hydroxyl group,
(24) $C_{6-14}$ aryl-carbonyl group (e.g., benzoyl, 1-naphthoyl, 2-naphthoyl, etc.) optionally having a cyano group,
(25) a 3- to 14-membered (monocyclic, bicyclic or tricyclic) heterocyclyl-carbonyl group containing, besides carbon atoms, 1 to 5 hetero atoms of one to three kinds selected from a nitrogen atom, a sulfur atom and an oxygen atom (e.g., tetrahydropyranylcarbonyl),
(26) a carboxy group,
(27) a $C_{1-6}$ alkoxy-carbonyl group (e.g., methoxycarbonyl, ethoxycarbonyl, propoxycarbonyl, tert-butoxycarbonyl, etc.),

(28) a $C_{6-14}$ aryloxy-carbonyl group (e.g., phenoxycarbonyl, etc.),
(29) a carbamoyl group,
(30) a thiocarbamoyl group,
(31) a mono-$C_{1-6}$ alkyl-carbamoyl group (e.g., methylcarbamoyl, ethylcarbamoyl, etc.),
(32) a di-$C_{1-6}$ alkyl-carbamoyl group (e.g., dimethylcarbamoyl, diethylcarbamoyl, ethylmethylcarbamoyl, etc.),
(33) a $C_{6-14}$ aryl-carbamoyl group (e.g., phenylcarbamoyl, 1-naphthylcarbamoyl, 2-naphthylcarbamoyl, etc.),
(34) a $C_{1-6}$ alkylsulfonyl group (e.g., methylsulfonyl, ethylsulfonyl, isopropylsulfonyl, etc.) optionally having a halogen atom,
(35) a mono- or di-$C_{1-3}$ alkylaminosulfonyl group (e.g., dimethylaminosulfonyl),
(36) a $C_{3-8}$ cycloalkylsulfonyl group (e.g., cyclopropylsulfonyl),
(37) a $C_{6-14}$ arylsulfonyl group (e.g., phenylsulfonyl, 1-naphthylsulfonyl, 2-naphthylsulfonyl, etc.),
(38) a $C_{1-6}$ alkylsulfinyl group (e.g., methylsulfinyl, ethylsulfinyl, etc.),
(39) a $C_{6-14}$ arylsulfinyl group (e.g., phenylsulfinyl, 1-naphthylsulfinyl, 2-naphthylsulfinyl, etc.),
(40) a formylamino group,
(41) a $C_{1-6}$ alkyl-carbonylamino group (e.g., acetylamino, etc.),
(42) a $C_{6-14}$ aryl-carbonylamino group (e.g., benzoylamino, naphthoylamino, etc.),
(43) a $C_{1-6}$ alkoxy-carbonylamino group (e.g., methoxycarbonylamino, ethoxycarbonylamino, propoxycarbonylamino, butoxycarbonylamino, etc.),
(44) a $C_{1-6}$ alkylsulfonylamino group (e.g., methylsulfonylamino, ethylsulfonylamino, etc.),
(45) a $C_{6-14}$ arylsulfonylamino group (e.g., phenylsulfonylamino, 2-naphthylsulfonylamino, 1-naphthylsulfonylamino, etc.),
(46) a $C_{1-6}$ alkyl-carbonyloxy group (e.g., acetoxy, propionyloxy, etc.),
(47) a $C_{6-14}$ aryl-carbonyloxy group (e.g., benzoyloxy, naphthylcarbonyloxy, etc.),
(48) a $C_{1-6}$ alkoxy-carbonyloxy group (e.g., methoxycarbonyloxy, ethoxycarbonyloxy, propoxycarbonyloxy, butoxycarbonyloxy, etc.),
(49) a mono-$C_{1-6}$ alkyl-carbamoyloxy group (e.g., methylcarbamoyloxy, ethylcarbamoyloxy, etc.),
(50) a di-$C_{1-6}$ alkyl-carbamoyloxy group (e.g., dimethylcarbamoyloxy, diethylcarbamoyloxy, etc.),
(51) a $C_{6-14}$ aryl-carbamoyloxy group (e.g., phenylcarbamoyloxy, naphthylcarbamoyloxy, etc.),
(52) a 3- to 14-membered (monocyclic, bicyclic or tricyclic) heterocyclic group containing, besides carbon atoms, 1 to 5 hetero atoms of one to three kinds selected from a nitrogen atom, a sulfur atom and an oxygen atom, and optionally having 1 to 4 substituents selected from a $C_{1-6}$ alkyl group optionally having 1 to 3 halogen atoms (e.g., methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl etc.), an oxo group, a $C_{1-6}$ alkoxy-carbonyl group (e.g., methoxycarbonyl, ethoxycarbonyl, propoxycarbonyl, tert-butoxycarbonyl etc.) and $C_{1-6}$ alkyl-carbonyl (e.g., acetyl etc.) [e.g., aromatic heterocyclic groups such as pyrrolyl (e.g., 1-pyrrolyl, 2-pyrrolyl, 3-pyrrolyl), furyl (e.g., 2-furyl, 3-furyl), thienyl (e.g., 2-thienyl, 3-thienyl), pyrazolyl (e.g., 1-pyrazolyl, 3-pyrazolyl, 4-pyrazolyl), imidazolyl (e.g., 1-imidazolyl, 2-imidazolyl, 4-imidazolyl, 5-imidazolyl), isoxazolyl (e.g., 3-isoxazolyl, 4-isoxazolyl, 5-isoxazolyl), oxazolyl (e.g., 2-oxazolyl, 4-oxazolyl, 5-oxazolyl), isothiazolyl (e.g., 3-isothiazolyl, 4-isothiazolyl, 5-isothiazolyl), thiazolyl (e.g., 2-thiazolyl, 4-thiazolyl, 5-thiazolyl), triazolyl (1,2,3-triazol-4-yl, 1,2,4-triazol-3-yl), oxadiazolyl (1,2,4-oxadiazol-3-yl, 1,2,4-oxadiazol-5-yl, 1,3,4-oxadiazol-2-yl), thiadiazolyl (1,2,4-thiadiazol-3-yl, 1,2,4-thiadiazol-5-yl, 1,3,4-thiadiazol-2-yl), tetrazolyl, pyridyl (e.g., 2-pyridyl, 3-pyridyl, 4-pyridyl), pyridazinyl (e.g., 3-pyridazinyl, 4-pyridazinyl), pyrimidinyl (e.g., 2-pyrimidinyl, 4-pyrimidinyl), pyrazinyl, isoindolyl (e.g., 1-isoindolyl, 2-isoindolyl, 3-isoindolyl, 4-isoindolyl, 5-isoindolyl, 6-isoindolyl, 7-isoindolyl), indolyl (e.g., 1-indolyl, 2-indolyl, 3-indolyl, 4-indolyl, 5-indolyl, 6-indolyl, 7-indolyl), benzo[b]furanyl (e.g., 2-benzo[b]furanyl, 3-benzo[b]furanyl, 4-benzo[b]furanyl, 5-benzo[b]furanyl, 6-benzo[b]furanyl, 7-benzo[b]furanyl), benzo[c]furanyl (e.g., 1-benzo[c]furanyl, 4-benzo[c]furanyl, 5-benzo[c]furanyl), benzo[b]thienyl (e.g., 2-benzo[b]thienyl, 3-benzo[b]thienyl, 4-benzo[b]thienyl, 5-benzo[b]thienyl, 6-benzo[b]thienyl, 7-benzo[b]thienyl), benzo[c]thienyl (e.g., 1-benzo[c]thienyl, 4-benzo[c]thienyl, 5-benzo[c]thienyl), indazolyl (e.g., 1-indazolyl, 2-indazolyl, 3-indazolyl, 4-indazolyl, 5-indazolyl, 6-indazolyl, 7-indazolyl), benzimidazolyl (e.g., 1-benzimidazolyl, 2-benzimidazolyl, 4-benzimidazolyl, 5-benzimidazolyl), 1,2-benzisoxazolyl (e.g., 1,2-benzisoxazol-3-yl, 1,2-benzisoxazol-4-yl, 1,2-benzisoxazol-5-yl, 1,2-benzisoxazol-6-yl, 1,2-benzisoxazol-7-yl), benzoxazolyl (e.g., 2-benzoxazolyl, 4-benzoxazolyl, 5-benzoxazolyl, 6-benzoxazolyl, 7-benzoxazolyl), 1,2-benzisothiazolyl (e.g., 1,2-benzisothiazol-3-yl, 1,2-benzisothiazol-4-yl, 1,2-benzisothiazol-5-yl, 1,2-benzisothiazol-6-yl, 1,2-benzisothiazol-7-yl), benzothiazolyl (e.g., 2-benzothiazolyl, 4-benzothiazolyl, 5-benzothiazolyl, 6-benzothiazolyl, 7-benzothiazolyl), isoquinolyl (e.g., 1-isoquinolyl, 3-isoquinolyl, 4-isoquinolyl, 5-isoquinolyl), quinolyl (e.g., 2-quinolyl, 3-quinolyl, 4-quinolyl, 5-quinolyl, 8-quinolyl), cinnolinyl (e.g., 3-cinnolinyl, 4-cinnolinyl, 5-cinnolinyl, 6-cinnolinyl, 7-cinnolinyl, 8-cinnolinyl), phthalazinyl (e.g., 1-phthalazinyl, 4-phthalazinyl, 5-phthalazinyl, 6-phthalazinyl, 7-phthalazinyl, 8-phthalazinyl), quinazolinyl (e.g., 2-quinazolinyl, 4-quinazolinyl, 5-quinazolinyl, 6-quinazolinyl, 7-quinazolinyl, 8-quinazolinyl), quinoxalinyl (e.g., 2-quinoxalinyl, 3-quinoxalinyl, 5-quinoxalinyl, 6-quinoxalinyl, 7-quinoxalinyl, 8-quinoxalinyl), pyrazolo[1,5-a]pyridyl (pyrazolo[1,5-a]pyridin-2-yl, pyrazolo[1,5-a]pyridin-3-yl, pyrazolo[1,5-a]pyridin-4-yl, pyrazolo[1,5-a]pyridin-5-yl, pyrazolo[1,5-a]pyridin-6-yl, pyrazolo[1,5-a]pyridin-7-yl), imidazo[1,2-a]pyridyl(imidazo[1,2-a]pyridin-2-yl, imidazo[1,2-a]pyridin-3-yl, imidazo[1,2-a]pyridin-5-yl, imidazo[1,2-a]pyridin-6-yl, imidazo[1,2-a]pyridin-7-yl, imidazo[1,2-a]pyridin-8-yl) and the like; nonaromatic heterocyclic groups such as oxazolidinyl (e.g., 2-oxazolidinyl, 5-oxazolidinyl), imidazolinyl (e.g., 1-imidazolinyl, 2-imidazolinyl, 4-imidazolinyl), aziridinyl (e.g., 1-aziridinyl, 2-aziridinyl), azetidinyl (e.g., 1-azetidinyl, 2-azetidinyl), pyrrolidinyl (e.g., 1-pyrrolidinyl, 2-pyrrolidinyl, 3-pyrrolidinyl), piperidyl (e.g., 1-piperidyl, 2-piperidyl, 3-piperidyl, 4-piperidyl), azepanyl (e.g., 1-azepanyl, 2-azepanyl, 3-azepanyl, 4-azepanyl), azocanyl (e.g., 1-azocanyl, 2-azocanyl, 3-azocanyl, 4-azocanyl), piperazinyl (e.g., 1,4-piperazin-1-yl, 1,4-piperazin-2-yl), diazepanyl (e.g., 1,4-diazepan-1-yl, 1,4-diazepan-2-yl, 1,4-diazepan-5-yl, 1,4-diazepan-6-yl), diazocanyl (1,4-diazocan-1-yl, 1,4-diazocan-2-yl, 1,4-diazocan-5-yl, 1,4-diazocan-6-yl, 1,5-diazocan-1-yl, 1,5-diazocan-2-yl, 1,5-diazocan-3-yl), 4-morpholinyl, 4-thiomorpholinyl, 2-oxazolidinyl and the like; a heterocyclic group wherein the above-mentioned aromatic heterocyclic group is partially hydrogenated, such as indolinyl, dihydroquinolyl and the like; a heterocyclic group wherein the above-mentioned nonaromatic heterocyclic group is partially dehydrogenated, such as oxazolinyl (e.g., 2-oxazolinyl), dihydrofuryl (e.g., 2,5-dihydrofuran-3-yl) and the like],

(53) a $C_{1-3}$ alkylenedioxy group (e.g., methylenedioxy, ethylenedioxy etc.),

(54) an oxo group,

(55) a $C_{7-14}$ aralkyloxy-carbonyl group (e.g., benzyloxycarbonyl etc.), and the like.

Ring B is preferably a phenyl group optionally having substituent(s), a thienyl group or a pyridyl group each of which optionally has substituent(s), (1) a phenyl group optionally having 1 to 3 substituents selected from (i) a $C_{1-6}$ alkyl group optionally having 1 to 3 halogen atoms and (ii) a halogen atom, (2) a thienyl group optionally having 1 to 3 $C_{1-6}$ alkyl groups optionally having 1 to 3 halogen atoms or (3) a pyridyl group optionally having 1 to 3 substituents selected from (i) a $C_{1-6}$ alkyl group optionally having 1 to 3 halogen atoms and (ii) a halogen atom is more preferable, and (1) a phenyl group optionally having 1 or 2 substituents selected from (i) a $C_{1-6}$ alkyl group optionally having 1 to 3 halogen atoms (e.g., fluorine atom) (e.g., methyl, trifluoromethyl) and (ii) a halogen atom (e.g., fluorine atom, chlorine atom), (2) a thienyl group optionally having one $C_{1-6}$ alkyl group (e.g., methyl) or (3) a pyridyl group optionally having 1 or 2 substituents selected from (i) a $C_{1-6}$ alkyl group (e.g., methyl) and (ii) a halogen atom (e.g., fluorine atom, chlorine atom) is further preferable. Of these, (1) a phenyl group optionally having 1 or 2 substituents selected from (i) a $C_{1-6}$ alkyl group optionally having 1 to 3 halogen atoms (e.g., fluorine atom) (e.g., methyl, trifluoromethyl) and (ii) a halogen atom (e.g., fluorine atom, chlorine atom) or (2) a pyridyl group optionally having one halogen atom (e.g., fluorine atom, chlorine atom) is particularly preferable.

Ring D is preferably a phenyl group, a pyrrolyl group, a thienyl group, a furyl group, a pyrazolyl group, an indolyl group, a benzimidazolyl group or a pyridyl group, each of which optionally has substituent(s). Preferably, ring D is not 6-quinolyl and naphthyl. Ring D is preferably monocyclic.

As the substituent of ring D, 1 to 3 substituents selected from
(1) a $C_{1-6}$ alkyl group optionally having 1 to 3 halogen atoms,
(2) a halogen atom,
(3) a $C_{1-6}$ alkoxy group optionally having 1 to 3 halogen atoms,
(4) a cyano group,
(5) a di-$C_{1-6}$ alkylamino group,
(6) a $C_{3-8}$ cycloalkyl group,
(7) a $C_{6-14}$ aryl group optionally substituted by 1 to 3 substituents selected from a $C_{1-6}$ alkoxy group and a halogen atom,
(8) a 5- to 10-membered aromatic heterocyclic group containing, besides carbon atoms, 1 to 4 hetero atoms of one or two kinds selected from a nitrogen atom, a sulfur atom and an oxygen atom, and optionally substituted by 1 to 3 alkyl groups optionally having 1 to 3 halogen atoms
and the like are preferable.

More preferable examples of the ring D include
[1] a phenyl group optionally having 1 or 2 substituents selected from
(1) a $C_{1-6}$ alkyl group optionally having 1 to 3 halogen atoms (e.g., fluorine atom) (e.g., methyl, isopropyl, tert-butyl, trifluoromethyl),
(2) a halogen atom (e.g., fluorine atom, chlorine atom, bromine atom),
(3) a $C_{1-6}$ alkoxy group optionally having 1 to 3 halogen atoms (e.g., fluorine atom)(e.g., methoxy, trifluoromethoxy),
(4) a cyano group,
(5) a di-$C_{1-6}$ alkylamino group (e.g., dimethylamino),
(6) a $C_{3-8}$ cycloalkyl group (e.g., cyclopentyl, cyclohexyl),
(7) a $C_{6-14}$ aryl group optionally having 1 to 3 halogen atoms (e.g., chlorine atom)(e.g., phenyl, chlorophenyl), and
(8) a 5- to 10-membered aromatic heterocyclic group containing, besides carbon atoms, 1 to 4 hetero atoms of one or two kinds selected from a nitrogen atom, a sulfur atom and an oxygen atom, and optionally substituted by 1 to 3 $C_{1-6}$ alkyl groups optionally having 1 to 3 halogen atoms (e.g., methyl, trifluoromethyl) (e.g., pyrazolyl, tetrazolyl, trifluoromethyltetrazolyl), or
[2] a pyrrolyl group, a thienyl group, a furyl group, a pyrazolyl group, or a pyridyl group each of which optionally is substituted by 1 to 3, preferably 1, $C_{6-14}$ aryl (e.g., phenyl) optionally substituted by 1 to 3 $C_{1-6}$ alkoxy groups (e.g., methoxy).

Furthermore, ring D is preferably a phenyl group optionally having substituent(s),
more preferably, a phenyl group optionally having 1 or 2 substituents selected from (1) a $C_{1-6}$ alkyl group optionally having 1 to 3 halogen atoms (e.g., fluorine atom) (e.g., methyl, trifluoromethyl), (2) a halogen atom (e.g., chlorine atom, bromine atom), (3) a $C_{1-6}$ alkoxy group optionally having 1 to 3 halogen atoms (e.g., fluorine atom) (e.g., methoxy, trifluoromethoxy) and (4) a 5- to 10-membered aromatic heterocyclic group containing, besides carbon atoms, 1 to 4 hetero atoms of one or two kinds selected from a nitrogen atom, a sulfur atom and an oxygen atom, and optionally substituted by 1 to 3 $C_{1-6}$ alkyl groups optionally having 1 to 3 halogen atoms (e.g., methyl, trifluoromethyl) (e.g., tetrazolyl, 5-trifluoromethyltetrazolyl),
particularly preferably, a 3,5-bis(trifluoromethyl)phenyl group, a 4-chlorophenyl group, a 3,5-dichlorophenyl group, a 3,5-dibromophenyl group, a 3-chloro-5-(trifluoromethyl) phenyl group, a 3-methyl-5-(trifluoromethyl)phenyl group or a 3-bromo-5-(trifluoromethyl)phenyl group.

When ring D is a 3,5-bis(trifluoromethyl)phenyl group, it is preferable for expression of NK1 receptor antagaonistic activity, and when ring D is a 3,5-dichlorophenyl group, it is preferable for expression of NK3 receptor antagaonistic activity.

(Explanation of $R^1$)

In the aforementioned formula, $R^1$ is a hydrogen atom or a substituent.

Examples of the "substituent" for $R^1$ include a hydrocarbon group optionally having substituent(s), an acyl group, a heterocyclic group optionally having substituent(s), and a group represented by —$NR^5R^6$ wherein $R^5$ and $R^6$ are each independently a hydrogen atom, a hydrocarbon group optionally having substituent(s), or an acyl group, or in combination show an oxygen atom.

Examples of the "hydrocarbon group" of the "hydrocarbon group optionally having substituent(s)" for $R^1$ include an aliphatic hydrocarbon group, a monocyclic saturated hydrocarbon group, a monocyclic unsaturated hydrocarbon group and an aromatic hydrocarbon group, with preference given to one having 1 to 16 carbon atoms. Specifically, for example, an alkyl group, an alkenyl group, an alkynyl group, a cycloalkyl group, a cycloalkenyl group, an aryl group and an aralkyl group are used.

As the "alkyl group", for example, a $C_{1-6}$ alkyl group (e.g., methyl, ethyl, propyl, isopropyl, butyl, isobutyl, sec-butyl, tert-butyl, pentyl, hexyl, etc.) and the like are preferable, and $C_{1-4}$ alkyl is more preferable.

As the "alkenyl group", for example, a $C_{2-6}$ alkenyl group (e.g., vinyl, allyl, isopropenyl, 1-butenyl, 2-butenyl, 3-butenyl, 2-methyl-2-propenyl, 1-methyl-2-propenyl, 2-methyl-1-propenyl, etc.) and the like are preferable.

As the "alkynyl group", for example, a $C_{2-6}$ alkynyl group (e.g., ethynyl, propargyl, 1-butynyl, 2-butynyl, 3-butynyl, 1-hexynyl, etc.) and the like are preferable.

As the "cycloalkyl group", for example, a $C_{3-8}$ cycloalkyl group (e.g., cyclopropyl, cyclobutyl, cyclopentyl, cyclohexyl, etc.) and the like are preferable, and a $C_{3-6}$ cycloalkyl group is more preferable.

As the "cycloalkenyl group", for example, a $C_{3-8}$ cycloalkenyl group (e.g., cyclopropenyl, cyclobutenyl, cyclopentenyl, cyclohexenyl, etc.) and the like are preferable, and a $C_{3-6}$ cycloalkenyl group is more preferable.

As the "aryl group", for example, a $C_{6-14}$ aryl group (e.g., phenyl, 1-naphthyl, 2-naphthyl, 2-biphenylyl, 3-biphenylyl, 4-biphenylyl, 2-anthryl, etc.) and the like are preferable.

As the "aralkyl group", for example, a $C_{7-16}$ aralkyl group (e.g., benzyl, phenethyl, diphenylmethyl, 1-naphthylmethyl, 2-naphthylmethyl, 2,2-diphenylethyl, 3-phenylpropyl, 4-phenylbutyl, 5-phenylpentyl, etc.) and the like are preferable.

Examples of the substituent of the "hydrocarbon group" include 1 to 3 substituents selected from
(1) a halogen atom (e.g., fluorine, chlorine, bromine, iodine etc.),
(2) a nitro group,
(3) a cyano group,
(4) a $C_{3-8}$ cycloalkyl group optionally having 1 to 5 (preferably 1 to 3) halogen atoms (e.g., cyclopropyl, cyclobutyl, cyclopentyl, cyclohexyl, 4,4-dichlorocyclohexyl, 2,2,3,3-tetrafluorocyclopentyl, 4-chlorocyclohexyl etc.),
(5) a $C_{6-14}$ aryl group (e.g., phenyl, 1-naphthyl, 2-naphthyl, biphenylyl, 2-anthryl etc.),
(6) a hydroxy group,
(7) a $C_{1-6}$ alkyl group optionally having 1 to 5, preferably 1 to 3, substituents selected from a halogen atom, an amino group, a $C_{1-6}$ alkoxy-carbonylamino group and a $C_{1-3}$ alkyl-carbonylamino group,
(8) a $C_{1-6}$ alkoxy group optionally having 1 to 3 halogen atoms (e.g., methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy etc.),
(9) a $C_{6-14}$ aryloxy group (e.g., phenyloxy, naphthyloxy etc.),
(10) a mercapto group,
(11) a alkylthio group optionally having 1 to 3 halogen atoms (e.g., methylthio, difluoromethylthio, trifluoromethylthio, ethylthio, propylthio, isopropylthio, butylthio, 4,4,4-trifluorobutylthio, pentylthio, hexylthio etc.),
(12) a $C_{6-14}$ arylthio group (e.g., phenylthio, naphthylthio etc.),
(13) an amino group,
(14) a mono-$C_{1-6}$ alkylamino group (e.g., methylamino, ethylamino etc.),
(15) a $C_{3-8}$ cycloalkyl-carbonylamino group optionally having 1 to 3 halogen atoms,
(16) a mono-$C_{6-14}$ arylamino group (e.g., phenylamino, 1-naphthylamino, 2-naphthylamino etc.),
(17) a di-$C_{1-6}$ alkylamino group (e.g., dimethylamino, diethylamino etc.),
(18) a di-$C_{6-14}$ arylamino group (e.g., diphenylamino etc.),
(19) a formyl group,
(20) a $C_{1-6}$ alkyl-carbonyl group (e.g., acetyl, propionyl etc.) optionally having 1 to 3 substituents selected from a hydroxyl group,
(21) a $C_{6-14}$ aryl-carbonyl group (e.g., benzoyl, 1-naphthoyl, 2-naphthoyl etc.),
(22) a carboxy group,
(23) a $C_{1-6}$ alkoxy-carbonyl group (e.g., methoxycarbonyl, ethoxycarbonyl, propoxycarbonyl, tert-butoxycarbonyl etc.),
(24) a $C_{6-14}$ aryloxy-carbonyl group (e.g., phenoxycarbonyl etc.),
(25) a 3- to 14-membered (monocyclic, bicyclic or tricyclic) heterocyclyl-carbonyl group (e.g., piperidinocarbonyl, morpholinocarbonyl) containing, besides carbon atoms, 1 to 5 hetero atoms of one to three kinds selected from a nitrogen atom, a sulfur atom and an oxygen atom, and optionally having 1 to 3 halogen atoms (e.g., fluorine atom),
(26) a $C_{3-8}$ cycloalkylcarbamoyl group,
(27) a carbamoyl group,
(28) a thiocarbamoyl group,
(29) a mono-$C_{1-6}$ alkyl-carbamoyl group (e.g., methylcarbamoyl, ethylcarbamoyl etc.),
(30) a di-$C_{1-6}$ alkyl-carbamoyl group (e.g., dimethylcarbamoyl, diethylcarbamoyl, ethylmethylcarbamoyl etc.),
(31) a $C_{6-14}$ aryl-carbamoyl group (e.g., phenylcarbamoyl, 1-naphthylcarbamoyl, 2-naphthylcarbamoyl etc.),
(32) a $C_{1-6}$ alkylsulfonyl group (e.g., methylsulfonyl, ethylsulfonyl etc.),
(33) a $C_{6-14}$ arylsulfonyl group (e.g., phenylsulfonyl, 1-naphthylsulfonyl, 2-naphthylsulfonyl etc.),
(34) a $C_{1-6}$ alkylsulfinyl group (e.g., methylsulfinyl, ethylsulfinyl etc.),
(34) a $C_{6-14}$ arylsulfinyl group (e.g., phenylsulfinyl, 1-naphthylsulfinyl, 2-naphthylsulfinyl etc.),
(35) a $C_{6-14}$ arylsulfinyl group (e.g., phenylsulfinyl, 1-naphthylsulfinyl, 2-naphthylsulfinyl etc.),
(36) a formylamino group,
(37) a $C_{1-6}$ alkyl-carbonylamino group (e.g., acetylamino, propionylamino, isobutyrylamino, pivaloylamino etc.) optionally having 1 to 5, preferably 1 to 3, substituents selected from a hydroxyl group and a $C_{1-3}$ alkoxy group,
(38) a $C_{1-6}$ alkyl-carbonyl-$C_{1-6}$ alkyl-amino group (e.g., N-acetyl-N-methylamino),
(39) a $C_{6-14}$ aryl-carbonylamino group (e.g., benzoylamino, naphthoylamino etc.),
(40) a 3- to 14-membered (monocyclic, bicyclic or tricyclic) heterocyclyl-carbonylamino group (e.g., pyridylcarbonylamino) containing, besides carbon atoms, 1 to 5 hetero atoms of one to three kinds selected from a nitrogen atom, a sulfur atom and an oxygen atom, and optionally having a halogen atom, or a $C_{1-3}$ alkyl group,
(41) a 3- to 14-membered (monocyclic, bicyclic or tricyclic) heterocyclyl-oxycarbonylamino group (e.g., tetrahydropyranyloxycarbonylamino) containing, besides carbon atoms, 1 to 5 hetero atoms of one to three kinds selected from a nitrogen atom, a sulfur atom and an oxygen atom,
(42) a $C_{6-14}$ aryloxycarbonylamino group optionally having a nitro group,
(43) a $C_{1-6}$ alkoxy-carbonylamino group (e.g., methoxycarbonylamino, ethoxycarbonylamino, propoxycarbonylamino, isopropoxycarbonylamino, butoxycarbonylamino, tert-butoxycarbonylamino etc.),
(44) a $C_{1-6}$ alkoxy-carbonyl-$C_{1-6}$ alkyl-amino group (e.g., N-methoxycarbonyl-N-methylamino, N-ethoxycarbonyl-N-methylamino, N-propoxycarbonyl-N-methylamino, N-isobutoxycarbonyl-N-methylamino, N-tert-butoxycarbonyl-N-methylamino etc.),
(45) a $C_{1-6}$ alkylsulfonylamino group (e.g., methylsulfonylamino, ethylsulfonylamino etc.),

(46) a $C_{1-6}$ alkylsulfonyl-$C_{1-6}$ alkyl-amino group (e.g., N-methylsulfonyl-N-methylamino, N-ethylsulfonyl-N-methylamino etc.),
(47) a $C_{6-14}$ arylsulfonylamino group (e.g., phenylsulfonylamino, 2-naphthylsulfonylamino, 1-naphthylsulfonylamino etc.),
(48) a $C_{1-6}$ alkyl-carbonyloxy group (e.g., acetoxy, propionyloxy etc.),
(49) a $C_{6-14}$ aryl-carbonyloxy group (e.g., benzoyloxy, naphthylcarbonyloxy etc.),
(50) a $C_{1-6}$ alkoxy-carbonyloxy group (e.g., methoxycarbonyloxy, ethoxycarbonyloxy, propoxycarbonyloxy, butoxycarbonyloxy etc.),
(51) a mono-$C_{1-6}$ alkyl-carbamoyloxy group (e.g., methylcarbamoyloxy, ethylcarbamoyloxy etc.),
(52) a di-$C_{1-6}$ alkyl-carbamoyloxy group (e.g., dimethylcarbamoyloxy, diethylcarbamoyloxy etc.),
(53) a $C_{6-14}$ aryl-carbamoyloxy group (e.g., phenylcarbamoyloxy, naphthylcarbamoyloxy etc.),
(54) 3-mono-, or 3,3-di-$C_{1-3}$ alkylureido,
(55) 1,3,3-tri-$C_{1-3}$ alkylureido,
(56) 3-$C_{3-8}$ cycloalkylureido,
(57) a 3- to 14-membered (monocyclic, bicyclic or tricyclic) heterocyclic group containing, besides carbon atoms, 1 to 5 hetero atoms of one to three kinds selected from a nitrogen atom, a sulfur atom and an oxygen atom, and optionally having 1 to 4 substituents selected from a $C_{1-6}$ alkyl group optionally having 1 to 3 halogen atoms (e.g., methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl etc.), an oxo group, a $C_{1-6}$ alkoxy-carbonyl group (e.g., methoxycarbonyl, ethoxycarbonyl, propoxycarbonyl, tert-butoxycarbonyl etc.) and $C_{1-6}$ alkyl-carbonyl (e.g., acetyl etc.) [e.g., aromatic heterocyclic groups such as pyrrolyl (e.g., 1-pyrrolyl, 2-pyrrolyl, 3-pyrrolyl), furyl (e.g., 2-furyl, 3-furyl), thienyl (e.g., 2-thienyl, 3-thienyl), pyrazolyl (e.g., 1-pyrazolyl, 3-pyrazolyl, 4-pyrazolyl), imidazolyl (e.g., 1-imidazolyl, 2-imidazolyl, 4-imidazolyl), isoxazolyl (e.g., 3-isoxazolyl, 4-isoxazolyl, 5-isoxazolyl), oxazolyl (e.g., 2-oxazolyl, 4-oxazolyl, 5-oxazolyl), isothiazolyl (e.g., 3-isothiazolyl, 4-isothiazolyl, 5-isothiazolyl), thiazolyl (e.g., 2-thiazolyl, 4-thiazolyl, 5-thiazolyl), triazolyl (1,2,3-triazol-4-yl, 1,2,4-triazol-3-yl), oxadiazolyl (1,2,4-oxadiazol-3-yl, 1,2,4-oxadiazol-5-yl), thiadiazolyl (1,2,4-thiadiazol-3-yl, 1,2,4-thiadiazol-5-yl), tetrazolyl, pyridyl (e.g., 2-pyridyl, 3-pyridyl, 4-pyridyl), pyridazinyl (e.g., 3-pyridazinyl, 4-pyridazinyl), pyrimidinyl (e.g., 2-pyrimidinyl, 4-pyrimidinyl), pyrazinyl, isoindolyl (e.g., 1-isoindolyl, 2-isoindolyl, 3-isoindolyl, 4-isoindolyl, 5-isoindolyl, 6-isoindolyl, 7-isoindolyl), indolyl (e.g., 1-indolyl, 2-indolyl, 3-indolyl, 4-indolyl, 5-indolyl, 6-indolyl, 7-indolyl), benzo[b]furanyl (e.g., 2-benzo[b]furanyl, 3-benzo[b]furanyl, 4-benzo[b]furanyl, 5-benzo[b]furanyl, 6-benzo[b]furanyl, 7-benzo[b]furanyl), benzo[c]furanyl (e.g., 1-benzo[c]furanyl, 4-benzo[c]furanyl, 5-benzo[c]furanyl), benzo[b]thienyl (e.g., 2-benzo[b]thienyl, 3-benzo[b]thienyl, 4-benzo[b]thienyl, 5-benzo[b]thienyl, 6-benzo[b]thienyl, 7-benzo[b]thienyl), benzo[c]thienyl (e.g., 1-benzo[c]thienyl, benzo[c]thienyl, 5-benzo[c]thienyl), indazolyl (e.g., 1-indazolyl, 2-indazolyl, 4-indazolyl, 5-indazolyl, 6-indazolyl, 7-indazolyl), benzimidazolyl (e.g., 1-benzimidazolyl, 2-benzimidazolyl, 4-benzimidazolyl, 5-benzimidazolyl), 1,2-benzisoxazolyl (e.g., 1,2-benzisoxazol-3-yl, 1,2-benzisoxazol-4-yl, 1,2-benzisoxazol-5-yl, 1,2-benzisoxazol-6-yl, 1,2-benzisoxazol-7-yl), benzoxazolyl (e.g., 2-benzoxazolyl, 4-benzoxazolyl, 5-benzoxazolyl, 6-benzoxazolyl, 7-benzoxazolyl), 1,2-benzisothiazolyl (e.g., 1,2-benzisothiazol-3-yl, 1,2-benzisothiazol-4-yl, 1,2-benzisothiazol-5-yl, 1,2-benzisothiazol-6-yl, 1,2-benzisothiazol-7-yl), benzothiazolyl (e.g., 2-benzothiazolyl, 4-benzothiazolyl, 5-benzothiazolyl, 6-benzothiazolyl, 7-benzothiazolyl), isoquinolyl (e.g., 1-isoquinolyl, 3-isoquinolyl, 4-isoquinolyl, 5-isoquinolyl), quinolyl (e.g., 2-quinolyl, 3-quinolyl, 4-quinolyl, 5-quinolyl, 8-quinolyl), cinnolinyl (e.g., 3-cinnolinyl, 4-cinnolinyl, 5-cinnolinyl, 6-cinnolinyl, 7-cinnolinyl, 8-cinnolinyl), phthalazinyl (e.g., 1-phthalazinyl, 4-phthalazinyl, 5-phthalazinyl, 6-phthalazinyl, 7-phthalazinyl, 8-phthalazinyl), quinazolinyl (e.g., 2-quinazolinyl, 4-quinazolinyl, 5-quinazolinyl, 6-quinazolinyl, 7-quinazolinyl, 8-quinazolinyl), quinoxalinyl (e.g., 2-quinoxalinyl, 3-quinoxalinyl, 5-quinoxalinyl, 6-quinoxalinyl, 7-quinoxalinyl, 8-quinoxalinyl), pyrazolo[1,5-a]pyridyl(pyrazolo[1,5-a]pyridin-2-yl, pyrazolo[1,5-a]pyridin-3-yl, pyrazolo[1,5-a]pyridin-4-yl, pyrazolo[1,5-a]pyridin-5-yl, pyrazolo[1,5-a]pyridin-6-yl, pyrazolo[1,5-a]pyridin-7-yl), imidazo[1,2-a]pyridyl(imidazo[1,2-a]pyridin-2-yl, imidazo[1,2-a]pyridin-3-yl, imidazo[1,2-a]pyridin-5-yl, imidazo[1,2-a]pyridin-6-yl, imidazo[1,2-a]pyridin-7-yl, imidazo[1,2-a]pyridin-8-yl) and the like; nonaromatic heterocyclic groups such as oxazolidinyl (e.g., 2-oxazolidinyl, 5-oxazolidinyl), imidazolinyl (e.g., 1-imidazolinyl, aziridinyl (e.g., 1-aziridinyl, 2-aziridinyl), azetidinyl (e.g., 1-azetidinyl, 2-azetidinyl), pyrrolidinyl (e.g., 1-pyrrolidinyl, 2-pyrrolidinyl, 3-pyrrolidinyl), piperidyl (e.g., 1-piperidyl, 4-piperidyl), azepanyl (e.g., 1-azepanyl, 2-azepanyl, 3-azepanyl, 4-azepanyl), azocanyl (e.g., 1-azocanyl, 2-azocanyl, 3-azocanyl, 4-azocanyl), piperazinyl (e.g., 1,4-piperazin-1-yl, 1,4-piperazin-2-yl), diazepanyl (e.g., 1,4-diazepan-1-yl, 1,4-diazepan-2-yl, 1,4-diazepan-5-yl, 1,4-diazepan-6-yl), diazocanyl (1,4-diazocan-1-yl, 1,4-diazocan-2-yl, 1,4-diazocan-5-yl, 1,4-diazocan-6-yl, 1,5-diazocan-1-yl, 1,5-diazocan-2-yl, 1,5-diazocan-3-yl), 4-morpholinyl, 4-thiomorpholinyl, 2-oxazolidinyl, isothiazolidinyl (e.g., 2-isothiazolidinyl) and the like; a heterocyclic group wherein the above-mentioned aromatic heterocyclic group is partially hydrogenated, such as indolinyl, dihydroquinolyl and the like; a heterocyclic group wherein the above-mentioned nonaromatic heterocyclic group is partially dehydrogenated, such as dihydrofuryl and the like],
(58) a $C_{1-3}$ alkylenedioxy group (e.g., methylenedioxy, ethylenedioxy etc.),
(59) an oxo group,
(60) a $C_{7-14}$ aralkyloxy-carbonyl group (e.g., benzyloxycarbonyl etc.), and the like.

Examples of the "heterocyclic group" of the "heterocyclic group optionally having substituent(s)" for $R^1$ include a 4- to 14-membered (preferably 4- to 10-membered, more preferably 5- to 10-membered) monocyclic, bicyclic or tricyclic (preferably monocyclic or bicyclic) aromatic or nonaromatic heterocyclic group containing, besides carbon atoms, 1 to 4 (preferably 1 to 3) hetero atoms of one or two kinds selected from a nitrogen atom, an oxygen atom and a sulfur atom, and the like. For example, a 4-membered ring group containing, besides carbon atoms, 1 to 4 hetero atoms selected from an oxygen atom, a sulfur atom and a nitrogen atom such as 2- or 3-azetidinyl, 2- or 3-oxetanyl and the like; a 5-membered ring group containing, besides carbon atoms, 1 to 4 hetero atoms selected from an oxygen atom, a sulfur atom and a nitrogen atom such as 2- or 3-thienyl, 2- or 3-furyl, 1-, 2- or 3-pyrrolyl, 1-, 2- or 3-pyrrolidinyl, 2-, 4- or 5-oxazolyl, 3-, 4- or 5-isoxazolyl, 2-, 4- or 5-thiazolyl, 3-, 4- or 5-isothiazolyl, 3-, 4- or 5-pyrazolyl, 2-, 3- or 4-pyrazolidinyl, 2-, 4- or 5-imidazolyl, 1-, 2- or 4-imidazolidinyl, 1,2,3-triazolyl, 1,2,4-triazolyl, 1H- or 2H-tetrazolyl, 2- or 3-tetrahydrofuryl, dihydrofuran-2 or 3-yl, 2-, 4- or 5-oxazolinyl and the like; a 6-membered ring group containing, besides carbon atoms, 1 to 4 hetero atoms selected from an oxygen atom, a sulfur atom and a nitrogen atom such as 2-, 3- or 4-pyridyl, N-oxido-2-, 3- or 4-pyridyl, 2-, 4- or 5-pyrimidinyl, N-oxido-2-, 4- or 5-pyrimidinyl, thiomorpholinyl, morpholinyl, piperidino, 2-, 3- or 4-piperidyl, pyranyl, tetrahydropyranyl, thiopyranyl, tetrahydrothiopyranyl, 1,4-oxazinyl, 1,4-thiazinyl, 1,3-thiazinyl, piperazinyl, triazinyl, 3- or 4-pyridazinyl, pyrazinyl, N-oxido-3- or 4-pyridazinyl and the like; a bicyclic or tricyclic fused cyclic group containing, besides carbon atoms, 1 to 4 hetero atoms selected from an oxygen atom, a sulfur atom and a nitrogen atom such as indolyl, benzo[b]furyl, benzo[c]furyl, benzothiazolyl, benzoxazolyl, benzimidazolyl, quinolyl, isoquinolyl, phthalazinyl, quinazolinyl, quinoxalinyl, indolizinyl, quinolizinyl, 1,8-naphthyridinyl, dibenzofuryl, carbazolyl, acrydinyl, phenanthridinyl, chromanyl, phenothiazinyl, phenoxazinyl and the like (preferably, a group formed by condensation of the above-mentioned 5- or 6-membered ring with one or two 5- or 6-membered ring groups optionally containing, besides carbon atoms, 1 to 4 hetero atoms selected from an oxygen atom, a sulfur atom and a nitrogen atom) and the like are used. Of these, a 5- to 7-membered (preferably 5- or 6-membered) aromatic or non-aromatic heterocyclic group containing, besides carbon atoms, 1 to 4 hetero atoms selected from an oxygen atom, a sulfur atom and a nitrogen atom is preferable.

As the "substituent" of the "heterocyclic group", 1 to 3 substituents similar to the substituents (1) to (60) exemplified as the substituent of the "aromatic ring" of the above-mentioned ring B and ring D are used.

Examples of the "acyl group" for $R^1$ include an acyl group represented by the formula: $-(C=O)-R^7$, $-(C=O)-OR^7$, $-(C=O)-NR^7R^8$, $-(C=S)-R^7$, $-(C=S)-NHR^7$, $-(C=O)-NR^8-NR^{8'}-(C=O)-R^9$ or $-SO_2-R^9$ wherein $R^7$ is a hydrogen atom, a hydrocarbon group optionally having substituent(s), a heterocyclic group optionally having substituent(s) or a carbamoyl group, $R^8$ and $R^{8'}$ are each a hydrogen atom or a $C_{1-6}$ alkyl group, and $R^9$ is a hydrocarbon group optionally having substituent(s) or a heterocyclic group optionally having substituent(s).

As the "hydrocarbon group optionally having substituent(s)" and "heterocyclic group optionally having substituent(s)" for $R^7$ or $R^9$, those similar to the "hydrocarbon group optionally having substituent(s)" or "heterocyclic group optionally having substituent(s)" for $R^1$ are used.

Examples of the "$C_{1-6}$ alkyl group" for $R^8$ or $R^{8'}$ include methyl, ethyl, propyl, isopropyl, butyl, isobutyl, sec-butyl, tert-butyl, pentyl, hexyl and the like.

As the "hydrocarbon group optionally having substituent(s)" and "acyl group" for $R^5$ or $R^6$ of "—$NR^5R^6$" for $R^1$, those similar to the "hydrocarbon group optionally having substituent(s)" and the "acyl group" for $R^1$ are used.

When $R^5$ and $R^6$ of "—$NR^5R^6$" in combination show an oxygen atom, $R^1$ is a nitroso group (—NO).

$R^1$ is preferably
(1) a hydrogen atom,
(2) a $C_{1-6}$ alkyl group (e.g., methyl, ethyl) optionally having 1 to 3 substituents selected from (a) a carbamoyl group, (b) a hydroxy group, (c) a $C_{1-6}$ alkoxy-carbonyl group (e.g., methoxycarbonyl, ethoxycarbonyl, propoxycarbonyl, tert-butoxycarbonyl etc.) and (d) a 5- to 7-membered aromatic or non-aromatic heterocyclic group (e.g., piperidyl) containing, besides carbon atoms, 1 to 4 hetero atoms selected from an oxygen atom, a sulfur atom and a nitrogen atom, and optionally substituted by 1 to 3 substituents selected from a $C_{1-6}$ alkyl-carbonyl group (e.g., acetyl etc.) and a $C_{1-6}$ alkoxy-carbonyl group (e.g., tert-butoxycarbonyl etc.),
(3) a $C_{3-6}$ cycloalkenyl group (e.g., cyclopentenyl, cyclohexenyl etc.) optionally substituted by an oxo group,
(4) a 4- to 7-membered aromatic or nonaromatic heterocyclic group (e.g., piperidyl, tetrahydrothiopyranyl, oxadiazolyl, pyridyl, oxazolinyl, dihydrofuranyl) containing, besides carbon atoms, 1 to 4 hetero atoms selected from an oxygen atom, a sulfur atom and a nitrogen atom, and optionally having 1 to 3 substituents selected from (a) a $C_{1-6}$ alkyl-carbonyl group (e.g., acetyl), (b) a $C_{1-6}$ alkoxy-carbonyl group (e.g., tert-butoxycarbonyl), (c) an oxo group, (d) a 5- to 7-membered aromatic or nonaromatic heterocyclic group (e.g., piperidyl) containing, besides carbon atoms, 1 to 4 hetero atoms selected from an oxygen atom, a sulfur atom and a nitrogen atom, and optionally having 1 to 3 substituents selected from a $C_{1-6}$ alkyl-carbonyl group (e.g., acetyl), a $C_{1-6}$ alkoxy-carbonyl group (e.g., tert-butoxycarbonyl) and an oxo group, (e) a halogen atom and (f) a cyano group,
(5) a group represented by the formula: $-(C=O)-R^{7'}$
wherein $R^{7'}$ is
(a) a $C_{1-6}$ alkyl group (e.g., methyl) optionally having 1 to 3 substituents selected from
(i) a hydroxy group,
(ii) a $C_{1-6}$ alkyl-carbonylamino group (e.g., acetylamino),
(iii) a 5- to 7-membered aromatic or nonaromatic heterocyclic group (e.g., oxazolidinyl, tetrazolyl, piperidyl) containing, besides carbon atoms, 1 to 4 hetero atoms selected from an oxygen atom, a sulfur atom and a nitrogen atom, and optionally having 1 to 4 substituents selected from a $C_{1-6}$ alkyl group (e.g., methyl), a $C_{1-3}$ alkyl-carbonyl group (e.g., acetyl), a $C_{1-6}$ alkoxy-carbonyl group (e.g., tert-butoxycarbonyl) and an oxo group,
(iv) a $C_{1-6}$ alkylsulfonyl group (e.g., methylsulfonyl),
(v) a $C_{6-12}$ aryl-carbonylamino group (e.g., benzoylamino),
(vi) a 5- to 7-membered aromatic or nonaromatic heterocyclyl-carbonylamino group (e.g., pyridylcarbonylamino group) containing, besides carbon atoms, 1 to 4 hetero atoms selected from an oxygen atom, a sulfur atom and a nitrogen atom, and
(vii) a cyano group,
(b) a 4- to 7-membered aromatic or nonaromatic heterocyclic group containing, besides carbon atoms, 1 to 4 hetero atoms selected from an oxygen atom, a sulfur atom and a nitrogen atom (e.g., piperidyl, azetinyl, piperazinyl, tetrahydropyranyl, tetrahydrothiopyranyl, pyridyl, pyrimidinyl, thiazolyl, tetrahydrofuranyl, pyrrolidinyl, morpholinyl, thiomorpholinyl), and optionally having 1 to 3 substituents selected from
(i) an oxo group,
(ii) a $C_{1-6}$ alkyl-carbonyl group (e.g., acetyl, propionyl, isobutyryl) optionally having 1 to 4 substituents selected from (a) a halogen atom (e.g., fluorine atom), (b) a $C_{1-3}$ alkoxy group (e.g., methoxy, ethoxy), (c) a $C_{3-8}$ cycloalkyl group (e.g., cyclopropyl), (d) a cyano group, (e) a hydroxy group, (f) a $C_{1-6}$ alkylsulfonyl group (e.g., methylsulfonyl), (g) a 4- to 7-membered aromatic or nonaromatic heterocyclic group containing, besides carbon atoms, 1 to 4 hetero atoms selected from an oxygen atom, a sulfur atom and a nitrogen atom (e.g., tetrazolyl), and optionally having 1 to 3 substituents selected from a $C_{1-6}$ alkyl-carbonyl group and a $C_{1-6}$ alkoxy-carbonyl group, and (h) a $C_{1-3}$ alkyl-carbonylamino group (e.g., acetylamino),
(iii) a $C_{1-6}$ alkoxy-carbonyl group (e.g., methoxycarbonyl, ethoxycarbonyl, tert-butoxycarbonyl etc.), (iv) a $C_{6-14}$ aryl-carbonyl group (e.g., benzoyl) optionally having a cyano group,
(v) a $C_{1-6}$ alkylsulfonyl group or a $C_{3-6}$ cycloalkylsulfonyl group (e.g., methylsulfonyl, ethylsulfonyl, isopropylsulfonyl, cyclopropylsulfonyl) each of which is optionally substituted by 1 to 3 halogen atoms,
(vi) an aminosulfonyl group (e.g., dimethylaminosulfonyl) optionally mono- or di-substituted by a $C_{1-6}$ alkyl group,
(vii) a halogen atom (e.g., fluorine atom),
(viii) a $C_{3-6}$ cycloalkenyl group (e.g., cyclopentenyl) optionally substituted by an oxo group,
(ix) a $C_{3-8}$ cycloalkyl-carbonyl group (e.g., cyclopropylcarbonyl, cyclohexylcarbonyl) optionally substituted by 1 to 3 substituents selected from a halogen atom and a hydroxy group,
(x) a 4- to 7-membered aromatic or nonaromatic heterocyclic group containing, besides carbon atoms, 1 to 4 hetero atoms selected from an oxygen atom, a sulfur atom and a nitrogen atom (e.g., dihydrofuranyl, oxazolinyl), and optionally substituted by an oxo group,
(xi) a 5- to 7-membered aromatic or nonaromatic heterocyclylcarbonyl group containing, besides carbon atoms, 1 to 4 hetero atoms selected from an oxygen atom, a sulfur atom and a nitrogen atom (e.g., tetrahydropyranylcarbonyl),
(xii) a $C_{1-6}$ alkyl or $C_{6-14}$ aryl-carbamoyl group (e.g., ethylcarbamoyl, phenylcarbamoyl),
(xiii) a alkyl group (e.g., methyl) optionally having 1 to 3 substituents selected from a $C_{1-6}$ alkoxy-carbonylamino group (e.g., methoxycarbonylamino, tert-butoxycarbonyl), a alkyl-carbonylamino group (e.g., acetylamino), a $C_{6-14}$ aryl-carbonylamino group (e.g., benzoylcarbonylamino), a carbamoyl group and a $C_{1-3}$ alkoxy group,
(xiv) a formyl group, and
(xv) a cyano group,
(c) a $C_{3-8}$ cycloalkyl group (e.g., cyclohexyl, cyclobutyl) optionally having 1 to 3 substituents selected from
(i) a $C_{1-6}$ alkyl-carbonylamino group (e.g., acetylamino, propionylamino, isobutyrylamino, pivaloylamino) optionally having 1 to 3 substituents selected from a hydroxy group and a $C_{1-3}$ alkoxy group (e.g., methoxy), the nitrogen atom of which is optionally substituted by a $C_{1-3}$ alkyl group (e.g., methyl),
(ii) a $C_{1-6}$ alkoxy-carbonylamino group (e.g., methoxycarbonylamino, ethoxycarbonylamino, isopropoxycarbonylamino, isobutoxycarbonylamino, tert-butoxycarbonylamino), the nitrogen atom of which is optionally substituted by a $C_{1-3}$ alkyl group (e.g., methyl),
(iii) a $C_{6-14}$ aryl-carbonylamino group (e.g., benzoylamino),
(iv) a halogen atom (e.g., fluorine atom),
(v) a 5- to 10-membered aromatic or nonaromatic heterocyclic group containing, besides carbon atoms, 1 to 4 hetero atoms of one or two kinds selected from a nitrogen atom, a sulfur atom and an oxygen atom, and optionally having 1 to 3 substituents selected from a $C_{1-6}$ alkyl group optionally having 1 to 3 halogen atoms (e.g., methyl, trifluoromethyl) and an oxo group (e.g., tetrazolyl, 5-trifluoromethyltetrazolyl, oxazolidinyl, pyrrolidinyl, isothiazolidinyl, morpholinyl, imidazolidinyl),
(vi) a $C_{1-6}$ alkyl group optionally having 1 to 3 substituents selected from a halogen atom (e.g., fluorine atom), a $C_{1-6}$ alkoxy-carbonylamino group (e.g., methoxycarbonylamino, tert-butoxycarbonylamino), a $C_{1-6}$ alkyl-carbonylamino group (e.g., acetylamino) and an amino group,
(vii) a ureido group optionally substituted by 1 to 3 substituents selected from a $C_{1-3}$ alkyl group (e.g., methyl, ethyl) and a $C_{3-6}$ cycloalkyl group (e.g., cyclopropyl group),
(viii) a $C_{1-3}$ alkylsulfonylamino group (e.g., methylsulfonylamino), the nitrogen atom of which is optionally substituted by a $C_{1-3}$ alkyl group,
(ix) a $C_{1-6}$ alkoxy-carbonyl group,
(x) a carbamoyl group optionally substituted by a $C_{1-3}$ alkyl group (e.g., methyl) and a $C_{3-8}$ cycloalkyl group (e.g., cyclopropyl),
(xi) an amino group optionally mono- or di-substituted by a $C_{1-3}$ alkyl group,
(xii) a 5- to 10-membered aromatic or nonaromatic heterocyclecarbonylamino group containing, besides carbon atoms, 1 to 4 hetero atoms of one or two kinds selected from a nitrogen atom, a sulfur atom and an oxygen atom (e.g., pyridylcarbonylamino), and optionally substituted by 1 to 3 substituents selected from a $C_{1-3}$ alkyl group (e.g., methyl) and a halogen atom (e.g., fluorine atom),
(xiii) a $C_{3-8}$ cycloalkyl-carbonylamino group (e.g., cyclopropylcarbonylamino, cyclobutylcarbonylamino, cyclohexylcarbonylamino) optionally substituted by 1 to 3 halogen atoms,
(xiv) a 5- to 7-membered aromatic or nonaromatic heterocyclyl(e.g., tetrahydropyranyl)oxy-carbonylamino group containing, besides carbon atoms, 1 to 4 hetero atoms selected from an oxygen atom, a sulfur atom and a nitrogen atom,
(xv) a 5- to 7-membered aromatic or nonaromatic heterocyclylcarbonyl group containing, besides carbon atoms, 1 to 4 hetero atoms selected from an oxygen atom, a sulfur atom and a nitrogen atom (e.g., piperidinylcarbonyl, morpholinylcarbonyl), and optionally substituted by 1 to 3 halogen atoms (e.g., fluorine atom),
(xvi) a $C_{6-12}$ aryloxy-carbonylamino group optionally substituted by a nitro group, and
(xvii) a carboxy group,
(d) a $C_{6-12}$ aryl group (e.g., phenyl) optionally having 1 to 3 substituents selected from
(i) a $C_{1-6}$ alkyl-carbonylamino group (e.g., acetylamino) optionally having a hydroxy group,
(ii) a $C_{1-3}$ alkoxy group (e.g., methoxy, difluoromethoxy) optionally having 1 to 3 halogen atoms,
(iii) a 5- to 10-membered aromatic or nonaromatic heterocyclic group containing, besides carbon atoms, 1 to 4 hetero atoms of one or two kinds selected from a nitrogen atom, a sulfur atom and an oxygen atom (e.g., tetrazolyl, pyrazolyl, imidazolyl, morpholinyl), and optionally substituted by 1 to 3 substituents selected from a $C_{1-6}$ alkyl group optionally having 1 to 3 halogen atoms (e.g., methyl, trifluoromethyl) and an oxo group, and
(iv) a halogen atom (e.g., fluorine atom), or
(e) a carbamoyl group,
(6) a group represented by the formula: $-(C=O)-OR^{7''}$ wherein $R^{7''}$ is
(a) a $C_{1-6}$ alkyl group (e.g., methyl, tert-butyl),
(b) a 5- to 7-membered aromatic or nonaromatic heterocyclic group containing, besides carbon atoms, 1 to 4 hetero atoms selected from an oxygen atom, a sulfur atom and a nitrogen atom (e.g., tetrahydropyranyl), or
(c) a $C_{6-12}$ aryl group optionally substituted by a nitro group, (7) a group represented by the formula: —SO$_2$—R$^{9'}$
    wherein R$^{9'}$ is
    (a) a C$_{1-6}$ alkyl group (e.g., methyl) optionally having 1 to 3 halogen atoms (e.g., fluorine atom),
    (b) a C$_{3-8}$ cycloalkyl group (e.g., cyclopropyl), or
    (c) a 5- to 7-membered aromatic or nonaromatic heterocyclic group containing, besides carbon atoms, 1 to 4 hetero atoms selected from an oxygen atom, a sulfur atom and a nitrogen atom (e.g., piperidyl, pyridyl), and optionally having 1 to 3 substituents selected from a C$_{1-6}$ alkyl-carbonyl group (e.g., acetyl) and a C$_{7-14}$ aralkyloxy-carbonyl group (e.g., benzyloxycarbonyl),
(8) a group represented by the formula: —NR$^{5'}$R$^{6'}$
    wherein R$^{5'}$ and R$^{6'}$ are independently
    (a) a hydrogen atom,
    (b) a C$_{1-4}$ alkyl group (e.g., methyl),
    (c) a C$_{1-6}$ alkyl-carbonyl group (e.g., acetyl), or
    (d) a 5- to 7-membered aromatic or nonaromatic heterocyclylcarbonyl group containing, besides carbon atoms, 1 to 4 hetero atoms selected from an oxygen atom, a sulfur atom and a nitrogen atom (e.g., piperidylcarbonyl), and optionally having a C$_{1-6}$ alkyl-carbonyl group (e.g., acetyl), or
    (e) in combination shows an oxygen atom,
(9) a group represented by the formula: —(C=O)—NR$^{7'''}$R$^{8''}$
    wherein R$^{7'''}$ and R$^{8''}$ are independently
    (a) a hydrogen atom,
    (b) a C$_{1-6}$ alkyl group (e.g., methyl, ethyl, propyl, isopropyl, tert-butyl) optionally substituted by 1 to 3 substituents selected from a C$_{6-12}$ aryl group (e.g., phenyl group), a C$_{1-3}$ alkoxy group (e.g., methoxy) and a C$_{1-3}$ alkyl-carbonylamino group (e.g., acetylamino),
    (c) a 5- to 7-membered aromatic or nonaromatic heterocyclic group containing, besides carbon atoms, 1 to 4 hetero atoms selected from an oxygen atom, a sulfur atom and a nitrogen atom (e.g., piperidyl, tetrahydropyranyl, tetrahydrothiopyranyl), and optionally having 1 to 3 substituents selected from a C$_{1-6}$ alkyl carbonyl group (e.g., acetyl), a C$_{1-6}$ alkoxy-carbonyl group (e.g., methoxycarbonyl, tert-butoxycarbonyl), a C$_{1-6}$ alkyl group (e.g., methyl) and an oxo group,
    (d) a C$_{3-8}$ cycloalkyl group (e.g., cyclopropyl, cyclopentyl, cyclohexyl) optionally substituted by 1 to 3 substituents selected from (i) a halogen atom (e.g., fluorine atom), (ii) a C$_{1-6}$ alkoxy-carbonylamino group (e.g., methoxycarbonylamino, ethoxycarbonylamino, tert-butoxycarbonylamino), (iii) a C$_{1-3}$ alkyl group, (iv) an amino group and (v) a 5- to 10-membered aromatic or nonaromatic heterocyclic group containing, besides carbon atoms, 1 to 4 hetero atoms of one or two kinds selected from a nitrogen atom, a sulfur atom and an oxygen atom, and optionally substituted by 1 to 3 substituents selected from a C$_{1-6}$ alkyl group optionally having 1 to 3 halogen atoms (e.g., methyl, trifluoromethyl) and an oxo group (e.g., tetrazolyl, 5-trifluoromethyltetrazolyl, oxazolidinyl),
    (e) a phenyl group optionally substituted by a C$_{1-3}$ alkoxy group (e.g., methoxy), or
    (f) a 5- to 10-membered aromatic or nonaromatic heterocyclyl-carbonylamino group containing, besides carbon atoms, 1 to 4 hetero atoms of one or two kinds selected from a nitrogen atom, a sulfur atom and an oxygen atom (e.g., piperidylcarbonylamino), and optionally having a C$_{1-6}$ alkoxy-carbonyl group (e.g., tert-butoxycarbonyl), or
(10) a group represented by the formula: —(C=S)—R$^{7''''}$
    wherein R$^{7''''}$ is
    a 5- to 7-membered aromatic or nonaromatic heterocyclic group containing, besides carbon atoms, 1 to 4 hetero atoms selected from an oxygen atom, a sulfur atom and a nitrogen atom (e.g., imidazolyl).

More preferably, R$^1$ is
(1) a hydrogen atom,
(2) a C$_{1-6}$ alkyl group (e.g., methyl, ethyl) optionally having 1 to 3 substituents selected from (a) a carbamoyl group, (b) a hydroxy group, (c) a C$_{1-6}$ alkoxy-carbonyl group (e.g., methoxycarbonyl, ethoxycarbonyl, propoxycarbonyl, tert-butoxycarbonyl etc.) and (d) a 5- to 7-membered aromatic or nonaromatic heterocyclic group containing, besides carbon atoms, 1 to 4 hetero atoms selected from an oxygen atom, a sulfur atom and a nitrogen atom (e.g., piperidyl), and optionally substituted by a C$_{1-6}$ alkyl-carbonyl group (e.g., acetyl etc.),
(3) a C$_{3-6}$ cycloalkenyl group (e.g., cyclopentenyl, cyclohexenyl etc.) optionally substituted by an oxo group,
(4) a 4- to 7-membered aromatic or nonaromatic heterocyclic group containing, besides carbon atoms, 1 to 4 hetero atoms selected from an oxygen atom, a sulfur atom and a nitrogen atom (e.g., piperidyl, tetrahydrothiopyranyl, oxadiazolyl, pyridyl, oxazolinyl, dihydrofuranyl), and optionally having 1 to 3 substituents selected from (a) a C$_{1-6}$ alkyl-carbonyl group (e.g., acetyl), (b) a C$_{1-6}$ alkoxy-carbonyl group (e.g., tert-butoxycarbonyl), (c) an oxo group, (d) a 5- to 7-membered aromatic or nonaromatic heterocyclic group containing, besides carbon atoms, 1 to 4 hetero atoms selected from an oxygen atom, a sulfur atom and a nitrogen atom (e.g., piperidyl), and optionally having 1 to 3 substituents selected from a C$_{1-6}$ alkyl-carbonyl group (e.g., acetyl), a C$_{1-6}$ alkoxy-carbonyl group (e.g., tert-butoxycarbonyl) and an oxo group and (e) a halogen atom,
(5) a group represented by the formula: —(C=O)—R$^{7'}$
    wherein R$^{7'}$ is
    (a) a C$_{1-6}$ alkyl group (e.g., methyl) optionally having 1 to 3 substituents selected from
        (i) a hydroxy group,
        (ii) a C$_{1-6}$ alkyl-carbonylamino group (e.g., acetylamino),
        (iii) a 5- to 7-membered aromatic or nonaromatic heterocyclic group containing, besides carbon atoms, 1 to 4 hetero atoms selected from an oxygen atom, a sulfur atom and a nitrogen atom (e.g., oxazolidinyl, tetrazolyl, piperidyl), and optionally having 1 to 4 substituents selected from a C$_{1-6}$ alkyl group (e.g., methyl), a C$_{1-3}$ alkyl-carbonyl group (e.g., acetyl), a C$_{1-6}$ alkoxy-carbonyl group (e.g., tert-butoxycarbonyl) and an oxo group,
        (iv) a C$_{1-6}$ alkylsulfonyl group (e.g., methylsulfonyl),
        (v) a C$_{6-12}$ aryl-carbonylamino group (e.g., benzoylamino), and
        (vi) a 5- to 7-membered aromatic or nonaromatic heterocyclyl-carbonylamino group containing, besides carbon atoms, 1 to 4 hetero atoms selected from an oxygen atom, a sulfur atom and a nitrogen atom (e.g., pyridylcarbonylamino group),
    (b) a 4- to 7-membered aromatic or nonaromatic heterocyclic group containing, besides carbon atoms, 1 to 4 hetero atoms selected from an oxygen atom, a sulfur atom and a nitrogen atom (e.g., piperidyl, azetinyl, piperazinyl, tetrahydropyranyl, tetrahydrothiopyranyl, pyridyl, pyrimidinyl, thiazolyl, tetrahydrofuranyl, pyrrolidinyl, morpholinyl, thiomorpholinyl), and optionally having 1 to 3 substituents selected from (i) an oxo group,
(ii) a $C_{1-6}$ alkyl-carbonyl group (e.g., acetyl, propionyl, isobutyryl) optionally having 1 to 4 substituents selected from (a) a halogen atom (e.g., fluorine atom), (b) a $C_{1-3}$ alkoxy group (e.g., methoxy, ethoxy), (c) a $C_{3-8}$ cycloalkyl group (e.g., cyclopropyl), (d) a cyano group, (e) a hydroxy group, (f) a $C_{1-6}$ alkylsulfonyl group (e.g., methylsulfonyl), (g) a 4- to 7-membered aromatic or nonaromatic heterocyclic group containing, besides carbon atoms, 1 to 4 hetero atoms selected from an oxygen atom, a sulfur atom and a nitrogen atom (e.g., tetrazolyl), and optionally having 1 to 3 substituents selected from a $C_{1-6}$ alkyl-carbonyl group and a $C_{1-6}$ alkoxy-carbonyl group, (h) a $C_{1-3}$ alkyl-carbonylamino group (e.g., acetylamino),
(iii) a $C_{1-6}$ alkoxy-carbonyl group (e.g., methoxycarbonyl, ethoxycarbonyl, tert-butoxycarbonyl etc.),
(iv) a $C_{6-14}$ aryl-carbonyl group (e.g., benzoyl).
(v) a $C_{1-6}$ alkylsulfonyl group or $C_{3-6}$ cycloalkylsulfonyl group (e.g., methylsulfonyl, ethylsulfonyl, isopropylsulfonyl, cyclopropylsulfonyl) each of which is optionally substituted by 1 to 3 halogen atoms,
(vi) an aminosulfonyl group (e.g., dimethylaminosulfonyl) optionally mono- or di-substituted by a $C_{1-6}$ alkyl group,
(vii) a halogen atom (e.g., fluorine atom),
(viii) a $C_{3-6}$ cycloalkenyl group (e.g., cyclopentenyl) optionally substituted by an oxo group,
(ix) a $C_{3-8}$ cycloalkyl-carbonyl group optionally substituted by 1 to 3 substituents selected from a halogen atom and a hydroxy group,
(x) a 4- to 7-membered aromatic or nonaromatic heterocyclic group containing, besides carbon atoms, 1 to 4 hetero atoms selected from an oxygen atom, a sulfur atom and a nitrogen atom (e.g., dihydrofuranyl, oxazolinyl), and optionally substituted by an oxo group,
(xi) a 5- to 7-membered aromatic or nonaromatic heterocyclylcarbonyl group containing, besides carbon atoms, 1 to 4 hetero atoms selected from an oxygen atom, a sulfur atom and a nitrogen atom (e.g., tetrahydropyranylcarbonyl),
(xii) a $C_{1-6}$ alkyl or $C_{6-14}$ aryl-carbamoyl group (e.g., ethylcarbamoyl, phenylcarbamoyl),
(xiii) a $C_{1-3}$ alkyl group (e.g., methyl) optionally having 1 to 3 substituents selected from a $C_{1-6}$ alkoxy-carbonylamino group (e.g., methoxycarbonylamino, tert-butoxycarbonylamino), a $C_{1-3}$ alkyl-carbonylamino group (e.g., acetylamino), a $C_{6-14}$ aryl-carbonylamino group (e.g., benzoylcarbonylamino), a carbamoyl group and a $C_{1-3}$ alkoxy group,
(xiv) a formyl group, and
(xv) a cyano group,
(c) a $C_{3-8}$ cycloalkyl group (e.g., cyclohexyl, cyclobutyl) optionally having 1 to 3 substituents selected from
(i) a $C_{1-6}$ alkyl-carbonylamino group (e.g., acetylamino, propionylamino, isobutyrylamino, pivaloylamino) optionally having 1 to 3 substituents selected from a hydroxy group and a $C_{1-3}$ alkoxy group (e.g., methoxy), the nitrogen atom of which is optionally substituted by a $C_{1-3}$ alkyl group (e.g., methyl),
(ii) a $C_{1-6}$ alkoxy-carbonylamino group (e.g., methoxycarbonylamino, ethoxycarbonylamino, isopropoxycarbonylamino, isobutoxycarbonylamino, tert-butoxycarbonylamino), the nitrogen atom of which is optionally substituted by a $C_{1-3}$ alkyl group (e.g., methyl),
(iii) a $C_{6-14}$ aryl-carbonylamino group (e.g., benzoylamino),
(iv) a halogen atom (e.g., fluorine atom),
(v) a 5- to 10-membered aromatic or nonaromatic heterocyclic group containing, besides carbon atoms, 1 to 4 hetero atoms of one or two kinds selected from a nitrogen atom, a sulfur atom and an oxygen atom, and optionally having 1 to 3 substituents selected from a $C_{1-6}$ alkyl group optionally having 1 to 3 halogen atoms (e.g., methyl, trifluoromethyl) and an oxo group (e.g., tetrazolyl, 5-trifluoromethyltetrazolyl, oxazolidinyl, pyrrolidinyl, isothiazolidinyl, morpholinyl, imidazolidinyl),
(vi) a $C_{1-6}$ alkyl group optionally having 1 to 3 substituents selected from a $C_{1-6}$ alkoxy-carbonylamino group (e.g., methoxycarbonylamino, tert-butoxycarbonylamino), a $C_{1-6}$ alkyl-carbonylamino group (e.g., acetylamino) and an amino group,
(vii) a ureido group optionally substituted by 1 to 3 substituents selected from a $C_{1-3}$ alkyl group (e.g., methyl, ethyl) and a $C_{3-6}$ cycloalkyl group (e.g., cyclopropyl group),
(viii) a $C_{1-3}$ alkylsulfonylamino group (e.g., methylsulfonylamino), the nitrogen atom of which is optionally substituted by a $C_{1-3}$ alkyl group,
(ix) a $C_{1-6}$ alkoxy-carbonyl group,
(x) a carbamoyl group,
(xi) an amino group optionally mono- or di-substituted by a $C_{1-3}$ alkyl group,
(xii) a 5- to 10-membered aromatic or nonaromatic heterocyclecarbonylamino group containing, besides carbon atoms, 1 to 4 hetero atoms of one or two kinds selected from a nitrogen atom, a sulfur atom and an oxygen atom (e.g., pyridylcarbonylamino), and optionally substituted by 1 to 3 substituents selected from a $C_{1-3}$ alkyl group (e.g., methyl) and a halogen atom (e.g., fluorine atom),
(xiii) a $C_{3-8}$ cycloalkyl-carbonylamino group (e.g., cyclopropylcarbonylamino, cyclobutylcarbonylamino, cyclohexylcarbonylamino), and
(xiv) a 5- to 7-membered aromatic or nonaromatic heterocyclyl(e.g., tetrahydropyranyl)oxy-carbonylamino group containing, besides carbon atoms, 1 to 4 hetero atoms selected from an oxygen atom, a sulfur atom and a nitrogen atom,
(d) a $C_{6-12}$ aryl group (e.g., phenyl) optionally having 1 to 3 substituents selected from
(i) a $C_{1-6}$ alkyl-carbonylamino group (e.g., acetylamino) optionally having a hydroxy group, and
(ii) a 5- to 10-membered aromatic or nonaromatic heterocyclic group containing, besides carbon atoms, 1 to 4 hetero atoms of one or two kinds selected from a nitrogen atom, a sulfur atom and an oxygen atom (e.g., tetrazolyl, pyrazolyl, imidazolyl, morpholinyl), and optionally substituted by 1 to 3 substituents selected from a $C_{1-6}$ alkyl group optionally having 1 to 3 halogen atoms (e.g., methyl, trifluoromethyl) and an oxo group, or
(e) a carbamoyl group,
(6) a group represented by the formula: —(C=O)—OR$^{7'}$
wherein is a $C_{1-6}$ alkyl group (e.g., methyl, tert-butyl) or a 5- to 7-membered aromatic or nonaromatic heterocyclic group containing, besides carbon atoms, 1 to 4 hetero atoms selected from an oxygen atom, a sulfur atom and a nitrogen atom (e.g., tetrahydropyranyl), (7) a group represented by the formula: $-SO_2-R^{9'}$
  wherein $R^{9'}$ is
  (a) a $C_{1-6}$ alkyl group (e.g., methyl), or
  (b) a 5- to 7-membered aromatic or nonaromatic heterocyclic group containing, besides carbon atoms, 1 to 4 hetero atoms selected from an oxygen atom, a sulfur atom and a nitrogen atom (e.g., piperidyl, pyridyl), and optionally having 1 to 3 substituents selected from a $C_{1-6}$ alkyl-carbonyl group (e.g., acetyl) and a $C_{7-14}$ aralkyloxy-carbonyl group (e.g., benzyloxycarbonyl),
(8) a group represented by the formula: $-NR^{5'}R^{6'}$
  wherein $R^{5'}$ and $R^{6'}$ are independently
  (a) a hydrogen atom,
  (b) a $C_{1-6}$ alkyl group (e.g., methyl),
  (c) a $C_{1-6}$ alkyl-carbonyl group (e.g., acetyl), or
  (d) a 5- to 7-membered aromatic or nonaromatic heterocylcarbonyl group containing, besides carbon atoms, 1 to 4 hetero atoms selected from an oxygen atom, a sulfur atom and a nitrogen atom (e.g., piperidylcarbonyl), and optionally having a $C_{1-6}$ alkyl-carbonyl group (e.g., acetyl), or
(9) a group represented by the formula: $-(C=O)-NR^{7'''}R^{8''}$
  wherein $R^{7'''}$ and $R^{8''}$ are independently
  (a) a hydrogen atom,
  (b) a $C_{1-6}$ alkyl group (e.g., methyl, ethyl, propyl, isopropyl, tert-butyl) optionally substituted by 1 to 3 substituents selected from a $C_{6-12}$ aryl group (e.g., phenyl group), a $C_{1-3}$ alkoxy group (e.g., methoxy) and a $C_{1-3}$ alkyl-carbonyl group (e.g., acetylamino),
  (c) a 5- to 7-membered aromatic or nonaromatic heterocyclic group containing, besides carbon atoms, 1 to 4 hetero atoms selected from an oxygen atom, a sulfur atom and a nitrogen atom (e.g., piperidyl, tetrahydropyranyl, tetrahydrothiopyranyl), and optionally having 1 to 3 substituents selected from a $C_{1-6}$ alkyl-carbonyl group (e.g., acetyl), a $C_{1-6}$ alkoxy-carbonyl group (e.g., methoxycarbonyl, tert-butoxycarbonyl), a $C_{1-6}$ alkyl group (e.g., methyl) and an oxo group,
  (d) a $C_{3-8}$ cycloalkyl group (e.g., cyclopropyl, cyclopentyl, cyclohexyl) optionally substituted by 1 to 3 substituents selected from (i) a halogen atom (e.g., fluorine atom), (ii) a $C_{1-6}$ alkoxy-carbonylamino group (e.g., methoxycarbonylamino, ethoxycarbonylamino, tert-butoxycarbonylamino), (iii) a $C_{1-3}$ alkyl group, (iv) an amino group and (v) a 5- to 10-membered aromatic or nonaromatic heterocyclic group containing, besides carbon atoms, 1 to 4 hetero atoms of one or two kinds selected from a nitrogen atom, a sulfur atom and an oxygen atom, and optionally substituted by 1 to 3 substituents selected from a $C_{1-6}$ alkyl group optionally having 1 to 3 halogen atoms (e.g., methyl, trifluoromethyl) and an oxo group (e.g., tetrazolyl, 5-trifluoromethyltetrazolyl, oxazolidinyl), or
  (e) a phenyl group optionally substituted by a $C_{1-3}$ alkoxy group (e.g., methoxy).
(Explanation of L, $R^2$, $R^3$, $R^{4a}$ and $R^{4b}$)
In the aforementioned formula (I), L is a group represented by the formula

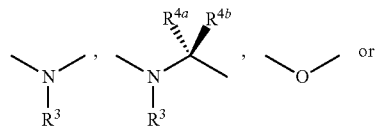

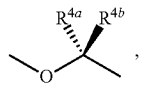

$R^2$, $R^3$, $R^{4a}$ and $R^{4b}$ are each independently a hydrogen atom, an optionally halogenated $C_{1-6}$ alkyl group or an optionally halogenated $C_{3-6}$ cycloalkyl group, or $R^2$ and $R^3$ may be bonded via an alkylene chain or an alkenylene chain or $R^{4a}$ and $R^{4b}$ may be bonded via an alkylene chain or an alkenylene chain.

Examples of the "optionally halogenated $C_{1-6}$ alkyl group" for $R^2$, $R^3$, $R^{4a}$ or $R^{4b}$ include a $C_{1-6}$ alkyl group optionally having 1 to 5 (preferably 1 to 3) halogen atoms (e.g., fluorine, chlorine, bromine, iodine etc.) (e.g., methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl etc.) and the like.

Examples of the "optionally halogenated $C_{3-6}$ cycloalkyl group" for $R^2$, $R^3$, $R^{4a}$ or $R^{4b}$ include a $C_{3-6}$ cycloalkyl group (e.g., cyclopropyl, cyclobutyl, cyclopentyl, cyclohexyl etc.) optionally having 1 to 5, preferably 1 to 3, halogen atoms (e.g., fluorine, chlorine, bromine, iodine etc.), and the like.

Examples of the alkylene chain mediating the bond of $R^2$ and $R^3$, and $R^{4a}$ and $R^{4b}$ include a $C_{2-6}$ alkylene group such as ethylene, trimethylene, propylene and the like.

Examples of the alkenylene chain mediating the bond of $R^2$ and $R^3$, and $R^{4a}$ and $R^{4b}$ include a $C_{2-6}$ alkenylene group such as $-CH=CH-$, $-CH_2-CH=CH-$, $-CH=CH-CH_2-$ and the like.

$R^2$ is preferably a hydrogen atom or a $C_{1-6}$ alkyl group, more preferably a $C_{1-4}$ alkyl group (e.g., methyl, ethyl), and particularly preferably a methyl group.

$R^3$ is preferably a hydrogen atom, a $C_{1-6}$ alkyl group or a $C_{3-6}$ cycloalkyl group (e.g., cyclopropyl), more preferably a $C_{1-4}$ alkyl group (e.g., methyl), and particularly preferably a hydrogen atom or a methyl group.

In addition, an embodiment wherein $R^2$ and $R^3$ are bonded via an ethylene, a trimethylene or $-CH=CH-$ is also preferable.

$R^{4a}$ and $R^{4b}$ are preferably both hydrogen atoms, or an embodiment wherein they are bonded via an alkylene chain (e.g., ethylene) is preferable.

L is preferably a group represented by the formula

wherein $R^{3'}$ is a hydrogen atom, a $C_{1-6}$ alkyl group or a $C_{3-6}$ cycloalkyl group (e.g., cyclopropyl). In this case, $R^{3'}$ is preferably a hydrogen atom or a $C_{1-6}$ alkyl group, more preferably a hydrogen atom or a $C_{1-4}$ alkyl group (e.g., methyl), and particularly preferably a hydrogen atom or a methyl group.

In the formula (I), when L is a group represented by the formula

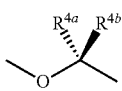

wherein each symbol is as defined above, ring D is an aromatic ring having substituent(s), preferably a phenyl group having substituent(s).

Compound (I) does not include N-(4-amino-2-isopropylquinolin-6-yl)-N'-[2-phenylpiperidin-3-yl]urea, N-(4-amino-2-isopropylquinolin-6-yl)-N'-[1-(tert-butoxycarbonyl)-2-phenylpiperidin-3-yl]urea and N-[4-(biphenyl-4-yl)piperidin-3-yl]-N'-(naphthalen-2-yl)urea.

As compound (I), the following are preferably used.

[Compound (I)-1]

Compound (I) wherein
ring A is a piperidine ring or a pyrrolidine ring,
ring B is a phenyl group optionally having substituent(s) or a thienyl group optionally having substituent(s),
ring D is a phenyl group optionally having substituent(s),
L is a group represented by the formula

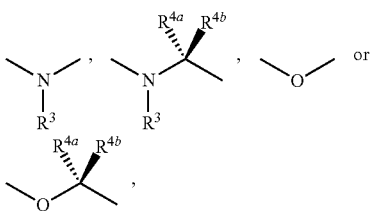

$R^2$ and $R^3$ are each independently a hydrogen atom or a $C_{1-6}$ alkyl group, or bonded via an alkylene chain or an alkenylene chain,
$R^{4a}$ and $R^{4b}$ are each independently a hydrogen atom, or bonded via an alkylene chain or an alkenylene chain,
$R^1$ is a hydrogen atom, a hydrocarbon group optionally having substituent(s), an acyl group, a heterocyclic group optionally having substituent(s), or a group represented by —$NR^5R^6$ ($R^5$ and $R^6$ are each independently a hydrogen atom, a hydrocarbon group optionally having substituent(s), or an acyl group),
m and n are each independently an integer of 1 or 2,
m+n is an integer of 2 or 3,
----- is a single bond,
provided when L is a group represented by the formula

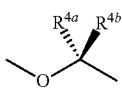

wherein each symbol is as defined above, then ring D is a phenyl group having substituent(s).

[Compound (I)-2]

Compound (I) wherein
ring A is a piperidine ring or a pyrrolidine ring,
ring B is (1) a phenyl group optionally having 1 to 3 substituents selected from a $C_{1-6}$ alkyl group optionally having 1 to 3 halogen atoms and a halogen atom or (2) a thienyl group optionally having 1 to 3 $C_{1-6}$ alkyl groups optionally having 1 to 3 halogen atoms,
ring D is a phenyl group optionally having 1 or 2 substituents selected from (1) a $C_{1-6}$ alkyl group optionally having 1 to 3 halogen atoms (e.g., fluorine atom) (e.g., methyl, trifluoromethyl), (2) a halogen atom (e.g., chlorine atom, bromine atom), (3) a $C_{1-6}$ alkoxy group optionally having 1 to 3 halogen atoms (e.g., fluorine atom) (e.g., methoxy, trifluoromethoxy) and (4) a 5- to 10-membered aromatic heterocyclic group containing, besides carbon atoms, 1 to 4 hetero atoms of one or two kinds selected from a nitrogen atom, a sulfur atom and an oxygen atom, and optionally substituted by a $C_{1-6}$ alkyl group optionally having 1 to 3 halogen atoms (e.g., fluorine atom) (e.g., methyl, trifluoromethyl) (e.g., tetrazolyl, trifluoromethyltetrazolyl, 5-trifluoromethyltetrazolyl),
L is a group represented by the formula

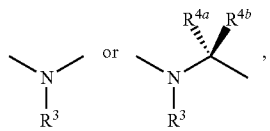

$R^2$ and $R^3$ are each independently a hydrogen atom or a $C_{1-6}$ alkyl group (e.g., methyl), or bonded via an alkylene chain,
$R^{4a}$ and $R^{4b}$ are each independently a hydrogen atom, or bonded via an alkylene chain,
$R^1$ is
(1) a hydrogen atom,
(2) a $C_{1-6}$ alkyl group optionally having 1 to 3 substituents selected from (a) a carbamoyl group, (b) a hydroxy group, (c) a $C_{1-6}$ alkoxy-carbonyl group (e.g., methoxycarbonyl, ethoxycarbonyl, propoxycarbonyl, tert-butoxycarbonyl etc.) and (d) a 5- to 7-membered aromatic or nonaromatic heterocyclic group containing, besides carbon atoms, 1 to 4 hetero atoms selected from an oxygen atom, a sulfur atom and a nitrogen atom (e.g., piperidyl), and optionally substituted by 1 to 3 $C_{1-6}$ alkyl-carbonyl groups (e.g., acetyl etc.) (e.g., methyl, ethyl, carbamoylmethyl),
(3) a $C_{3-6}$ cycloalkenyl group (e.g., cyclopentenyl, cyclohexenyl etc.) optionally substituted by an oxo group,
(4) a 5- to 7-membered aromatic or nonaromatic heterocyclic group containing, besides carbon atoms, 1 to 4 hetero atoms selected from an oxygen atom, a sulfur atom and a nitrogen atom (e.g., piperidyl, tetrahydrothiopyranyl), and optionally having 1 to 3 substituents selected from a $C_{1-6}$ alkyl-carbonyl group (e.g., acetyl), a $C_{1-6}$ alkoxy-carbonyl group (e.g., tert-butoxycarbonyl) and an oxo group,
(5) a group represented by the formula: —(C=O)—$R^{7'}$ wherein $R^{7'}$ is
  (a) a $C_{1-6}$ alkyl group optionally having 1 to 3 substituents selected from (i) a hydroxy group, (ii) a $C_{1-6}$ alkyl-carbonylamino group (e.g., acetylamino), (iii) a 5- to 7-membered aromatic or nonaromatic heterocyclic group containing, besides carbon atoms, 1 to 4 hetero atoms selected from an oxygen atom, a sulfur atom and a nitrogen atom (e.g., oxazolidinyl), and optionally having 1 to 4 substituents selected from a $C_{1-6}$ alkyl group (e.g., methyl) and an oxo group and (iv) a $C_{1-6}$ alkylsulfonyl group (e.g., methylsulfonyl) (e.g., methyl, hydroxymethyl, acetylaminomethyl),
  (b) a 4- to 7-membered aromatic or nonaromatic heterocyclic group containing, besides carbon atoms, 1 to 4 hetero atoms selected from an oxygen atom, a sulfur atom and a nitrogen atom, and optionally having 1 to 3 substituents selected from (i) an oxo group, (ii) a $C_{1-6}$ alkyl-carbonyl group optionally having a hydroxy group (e.g., acetyl, hydroxyacetyl), (iii) a $C_{6-14}$ aryl-carbonyl group (e.g., benzoyl) and (iv) a $C_{1-6}$ alkoxy-carbonyl group (e.g., tert-butoxycarbonyl) (e.g., piperidyl, azetinyl, 1-acetylpiperidyl, 2,6-dioxo-4-piperidyl),
  (c) a $C_{3-8}$ cycloalkyl group (e.g., cyclohexyl) optionally having 1 to 3 $C_{1-6}$ alkyl-carbonylamino groups (e.g., acetylamino), or
  (d) a carbamoyl group,
(6) a group represented by the formula: —(C=O)—OR$^{7''}$
  wherein R$^{7''}$ is a $C_{1-6}$ alkyl group (e.g., methyl, tert-butyl),
(7) a group represented by the formula: —SO$_2$—R$^{9'}$
  wherein R$^{9'}$ is
  (a) a $C_{1-6}$ alkyl group (e.g., methyl), or
  (b) a 5- to 7-membered aromatic or nonaromatic heterocyclic group containing, besides carbon atoms, 1 to 4 hetero atoms selected from an oxygen atom, a sulfur atom and a nitrogen atom (e.g., piperidyl), and optionally having 1 to 3 substituents selected from a $C_{1-6}$ alkyl-carbonyl group (e.g., acetyl) and a $C_{7-14}$ aralkyloxy-carbonyl group (e.g., benzyloxycarbonyl), or
(8) a group represented by the formula: —NR$^{5'}$R$^{6'}$
  wherein R$^{5'}$ and R$^{6'}$ are independently
  (a) a hydrogen atom,
  (b) a $C_{1-6}$ alkyl group (e.g., methyl)
  (c) a $C_{1-6}$ alkyl-carbonyl group (e.g., acetyl), or
  (d) a 5- to 7-membered aromatic or nonaromatic heterocyclylcarbonyl group containing, besides carbon atoms, 1 to 4 hetero atoms selected from an oxygen atom, a sulfur atom and a nitrogen atom (e.g., piperidylcarbonyl), and optionally having 1 to 3 $C_{1-6}$ alkyl-carbonyl groups (e.g., acetyl).

[Compound (I)-3]
Compound (I) wherein
ring A is a ring represented by

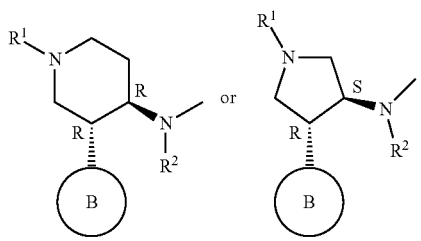

ring B is (1) a phenyl group optionally having 1 or 2 substituents selected from a $C_{1-6}$ alkyl group (e.g., methyl) and a halogen atom (e.g., fluorine atom, chlorine atom) or (2) a thienyl group optionally having one $C_{1-6}$ alkyl group (e.g., methyl),
ring D is a phenyl group optionally having 1 or 2 substituents selected from a $C_{1-6}$ alkyl group (e.g., methyl) optionally having 1 to 3 halogen atoms (e.g., fluorine atom) (particularly preferably a 3,5-bis(trifluoromethyl)phenyl group),
L is a group represented by the formula

R$^2$ and R$^3$ are each independently a $C_{1-6}$ alkyl group (e.g., methyl),

R$^1$ is
(1) a $C_{1-6}$ alkyl group optionally having 1 to 3 substituents selected from (a) a carbamoyl group, (b) a hydroxy group and (c) a 5- to 7-membered aromatic or nonaromatic heterocyclic group containing, besides carbon atoms, 1 to 4 hetero atoms selected from an oxygen atom, a sulfur atom and a nitrogen atom (e.g., piperidyl), and optionally having 1 to 3 $C_{1-6}$ alkoxy-carbonyl groups (e.g., methoxycarbonyl, ethoxycarbonyl, propoxycarbonyl, tert-butoxycarbonyl etc.) (e.g., methyl, ethyl, carbamoylmethyl), or
(2) a group represented by the formula: —(C=O)—R$^{7'''}$
  wherein R$^{7'''}$ is a 4- to 7-membered aromatic or nonaromatic heterocyclic group containing, besides carbon atoms, 1 to 4 hetero atoms selected from an oxygen atom, a sulfur atom and a nitrogen atom (e.g., piperidyl, azetinyl), and optionally having 1 to 3 substituents selected from (i) an oxo group, (ii) a $C_{1-6}$ alkyl-carbonyl group (e.g., acetyl) optionally having 1 to 3 hydroxy groups and (iii) a $C_{6-14}$ aryl-carbonyl group (e.g., benzoyl).

[Compound (I)-4]
Compound (I) wherein
ring A is a ring represented by

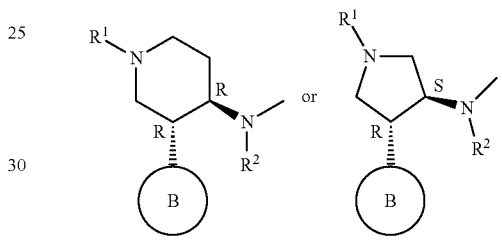

ring B is (1) a phenyl group optionally having 1 to 3 substituents selected from a $C_{1-6}$ alkyl group optionally having 1 to 3 halogen atoms and a halogen atom or (2) a pyridyl group optionally having one halogen atom (e.g., fluorine atom) (particularly preferably 5-fluoropyridin-2-yl group),
ring D is a phenyl group optionally having 1 to 3 substituents selected from (1) a $C_{1-6}$ alkyl group optionally having 1 to 3 halogen atoms (e.g., fluorine atom) (e.g., methyl, trifluoromethyl), (2) a halogen atom (e.g., chlorine atom, bromine atom), (3) a $C_{1-6}$ alkoxy group optionally having 1 to 3 halogen atoms (e.g., fluorine atom) (e.g., methoxy, trifluoromethoxy) and (4) a phenyl group optionally substituted by a $C_{1-6}$ alkyl group optionally having 1 to 3 halogen atoms (e.g., fluorine atom) (e.g., methyl, trifluoromethyl), a halogen atom, and a cyano group,
L is a group represented by the formula

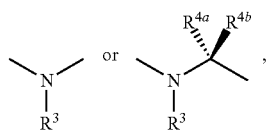

R$^2$ and R$^3$ are each independently a hydrogen atom or a $C_{1-6}$ alkyl group (e.g., methyl), or bonded via an alkylene chain,
R$^{4a}$ and R$^{4b}$ are each independently a hydrogen atom, or bonded via an alkylene chain,
R$^1$ is
(1) a hydrogen atom,
(2) a $C_{1-6}$ alkyl group (e.g., methyl, ethyl) optionally having 1 to 3 substituents selected from (a) a carbamoyl group, (b) a hydroxy group, (c) a $C_{1-6}$ alkoxy-carbonyl group (e.g., methoxycarbonyl, ethoxycarbonyl, propoxycarbonyl, tert-butoxycarbonyl etc.) and (d) a 5- to 7-membered aromatic or nonaromatic heterocyclic group containing, besides carbon atoms, 1 to 4 hetero atoms selected from an oxygen atom, a sulfur atom and a nitrogen atom (e.g., piperidyl), and optionally substituted by a $C_{1-6}$ alkyl-carbonyl group (e.g., acetyl etc.), (3) a $C_{3-6}$ cycloalkenyl group (e.g., cyclopentenyl, cyclohexenyl etc.) optionally substituted by an oxo group, (4) a 4- to 7-membered aromatic or nonaromatic heterocyclic group containing, besides carbon atoms, 1 to 4 hetero atoms selected from an oxygen atom, a sulfur atom, and a nitrogen atom (e.g., piperidyl, tetrahydrothiopyranyl, oxadiazolyl, pyridyl, oxazolinyl, dihydrofuranyl), and optionally having 1 to 3 substituents selected from (a) a $C_{1-6}$ alkyl-carbonyl group (e.g., acetyl), (b) a $C_{1-6}$ alkoxy-carbonyl group (e.g., tert-butoxycarbonyl), (c) an oxo group, (d) a 5- to 7-membered aromatic or nonaromatic heterocyclic group containing, besides carbon atoms, 1 to 4 hetero atoms selected from an oxygen atom, a sulfur atom and a nitrogen atom (e.g., piperidyl), and optionally having 1 to 3 substituents selected from a $C_{1-6}$ alkyl-carbonyl group (e.g., acetyl), a $C_{1-6}$ alkoxycarbonyl group (e.g., tert-butoxycarbonyl) and an oxo group and (e) a halogen atom, (5) a group represented by the formula: —(C=O)—$R^{7'}$ wherein $R^{7'}$ is
  (a) a $C_{1-6}$ alkyl group (e.g., methyl) optionally having 1 to 3 substituents selected from
    (i) a hydroxy group,
    (ii) a $C_{1-6}$ alkyl-carbonylamino group (e.g., acetylamino),
    (iii) a 5- to 7-membered aromatic or nonaromatic heterocyclic group containing, besides carbon atoms, 1 to 4 hetero atoms selected from an oxygen atom, a sulfur atom and a nitrogen atom (e.g., oxazolidinyl, tetrazolyl, piperidyl), and optionally having 1 to 4 substituents selected from a $C_{1-6}$ alkyl group (e.g., methyl), a $C_{1-3}$ alkyl-carbonyl group (e.g., acetyl), a $C_{1-6}$ alkoxy-carbonyl group (e.g., tert-butoxycarbonyl) and an oxo group,
    (iv) a $C_{1-6}$ alkylsulfonyl group (e.g., methylsulfonyl),
    (v) a $C_{6-12}$ aryl-carbonylamino group (e.g., benzoylamino), and
    (vi) a 5- to 7-membered aromatic or nonaromatic heterocyclyl-carbonylamino group containing, besides carbon atoms, 1 to 4 hetero atoms selected from an oxygen atom, a sulfur atom and a nitrogen atom (e.g., pyridylcarbonylamino group),
  (b) a 4- to 7-membered aromatic or nonaromatic heterocyclic group containing, besides carbon atoms, 1 to 4 hetero atoms selected from an oxygen atom, a sulfur atom and a nitrogen atom (e.g., piperidyl, azetinyl, piperazinyl, tetrahydropyranyl, tetrahydrothiopyranyl, pyridyl, pyrimidinyl, thiazolyl, tetrahydrofuranyl, pyrrolidinyl, morpholinyl, thiomorpholinyl), and optionally having 1 to 3 substituents selected from
    (i) an oxo group,
    (ii) a $C_{1-6}$ alkyl-carbonyl group (e.g., acetyl, propionyl, isobutyryl) optionally having 1 to 4 substituents selected from (a) a halogen atom (e.g., fluorine atom), (b) a $C_{1-3}$ alkoxy group (e.g., methoxy, ethoxy), (c) a $C_{3-8}$ cycloalkyl group (e.g., cyclopropyl), (d) a cyano group, (e) a hydroxy group, (f) a $C_{1-6}$ alkylsulfonyl group (e.g., methylsulfonyl), (g) a 4- to 7-membered aromatic or nonaromatic heterocyclic group containing, besides carbon atoms, 1 to 4 hetero atoms selected from an oxygen atom, a sulfur atom and a nitrogen atom (e.g., tetrazolyl), and optionally having 1 to 3 substituents selected from a $C_{1-6}$ alkyl-carbonyl group and a $C_{1-6}$ alkoxy-carbonyl group, (h) a $C_{1-3}$ alkyl-carbonylamino group (e.g., acetylamino),
    (iii) a $C_{1-6}$ alkoxy-carbonyl group (e.g., methoxycarbonyl, ethoxycarbonyl, tert-butoxycarbonyl etc.),
    (iv) a $C_{6-14}$ aryl-carbonyl group (e.g., benzoyl),
    (v) a $C_{1-6}$ alkylsulfonyl group or $C_{3-6}$ cycloalkylsulfonyl group (e.g., methylsulfonyl, ethylsulfonyl, isopropylsulfonyl, cyclopropylsulfonyl) each of which is optionally substituted by 1 to 3 halogen atoms,
    (vi) an aminosulfonyl group optionally mono- or di-substituted by a $C_{1-6}$ alkyl group (e.g., dimethylaminosulfonyl),
    (vii) a halogen atom (e.g., fluorine atom),
    (viii) a $C_{3-6}$ cycloalkenyl group (e.g., cyclopentenyl) optionally substituted by an oxo group,
    (ix) a $C_{3-8}$ cycloalkyl-carbonyl group (e.g., cyclopropylcarbonyl, cyclohexylcarbonyl) optionally substituted by 1 to 3 substituents selected from a halogen atom and a hydroxy group,
    (x) a 4- to 7-membered aromatic or nonaromatic heterocyclic group containing, besides carbon atoms, 1 to 4 hetero atoms selected from an oxygen atom, a sulfur atom and a nitrogen atom (e.g., dihydrofuranyl, oxazolinyl), and optionally substituted by an oxo group,
    (xi) a 5- to 7-membered aromatic or nonaromatic heterocyclylcarbonyl group containing, besides carbon atoms, 1 to 4 hetero atoms selected from an oxygen atom, a sulfur atom and a nitrogen atom (e.g., tetrahydropyranylcarbonyl),
    (xii) a $C_{1-6}$ alkyl or $C_{6-14}$ aryl-carbamoyl group (e.g., ethylcarbamoyl, phenylcarbamoyl),
    (xiii) a $C_{1-3}$ alkyl group (e.g., methyl) optionally having 1 to 3 substituents selected from a $C_{1-6}$ alkoxy-carbonylamino group (e.g., methoxycarbonylamino), a $C_{1-3}$ alkyl-carbonylamino group (e.g., acetylamino), a carbamoyl group and a $C_{1-3}$ alkoxy group,
    (xiv) a formyl group, and
    (xv) a cyano group,
  (c) a $C_{3-8}$ cycloalkyl group (e.g., cyclohexyl, cyclobutyl) optionally having 1 to 3 substituents selected from
    (i) a $C_{1-6}$ alkyl-carbonylamino group (e.g., acetylamino, propionylamino, isobutyrylamino, pivaloylamino) optionally having 1 to 3 substituents selected from a hydroxy group and a $C_{1-3}$ alkoxy group (e.g., methoxy), the nitrogen atom of which is optionally substituted by a $C_{1-3}$ alkyl group (e.g., methyl),
    (ii) a $C_{1-6}$ alkoxy-carbonylamino group (e.g., methoxycarbonylamino, ethoxycarbonylamino, isopropoxycarbonylamino, isobutoxycarbonylamino, tert-butoxycarbonylamino), the nitrogen atom of which is optionally substituted by a $C_{1-3}$ alkyl group (e.g., methyl),
    (iii) a $C_{6-14}$ aryl-carbonylamino group (e.g., benzoylamino),
    (iv) a halogen atom (e.g., fluorine atom),
    (v) a 5- to 10-membered aromatic or nonaromatic heterocyclic group containing, besides carbon atoms, 1 to 4 hetero atoms of one or two kinds selected from a nitrogen atom, a sulfur atom and an oxygen atom, and optionally having 1 to 3 substituents selected from a $C_{1-6}$ alkyl group optionally having 1 to 3 halogen atoms (e.g., methyl, trifluoromethyl) and an oxo group (e.g., tetrazolyl, 5-trifluoromethyltetrazolyl, oxazolidinyl, pyrrolidinyl, isothiazolidinyl, morpholinyl, imidazolidinyl), (vi) a $C_{1-6}$ alkyl group optionally having 1 to 3 substituents selected from a $C_{1-6}$ alkoxy-carbonylamino group (e.g., methoxycarbonylamino, tert-butoxycarbonylamino), a $C_{1-6}$ alkyl-carbonylamino group (e.g., acetylamino) and an amino group, (vii) a ureido group optionally substituted by 1 to 3 substituents selected from a $C_{1-3}$ alkyl group (e.g., methyl, ethyl) and a $C_{3-6}$ cycloalkyl group (e.g., cyclopropyl group), (viii) a $C_{1-3}$ alkylsulfonylamino group (e.g., methylsulfonylamino), the nitrogen atom of which is optionally substituted by a $C_{1-3}$ alkyl group, (ix) a $C_{1-6}$ alkoxy-carbonyl group, (x) a carbamoyl group, (xi) an amino group optionally mono- or di-substituted by a $C_{1-3}$ alkyl group, (xii) a 5- to 10-membered aromatic or nonaromatic heterocyclecarbonylamino group containing, besides carbon atoms, 1 to 4 hetero atoms of one or two kinds selected from a nitrogen atom, a sulfur atom and an oxygen atom (e.g., pyridylcarbonylamino), and optionally substituted by 1 to 3 substituents selected from a $C_{1-3}$ alkyl group (e.g., methyl) and or a halogen atom (e.g., fluorine atom), (xiii) a $C_{3-8}$ cycloalkyl-carbonylamino group (e.g., cyclopropylcarbonylamino, cyclobutylcarbonylamino, cyclohexylcarbonylamino), and (xiv) a 5- to 7-membered aromatic or nonaromatic heterocyclyl(e.g., tetrahydropyranyl)oxy-carbonylamino group containing, besides carbon atoms, 1 to 4 hetero atoms selected from an oxygen atom, a sulfur atom and a nitrogen atom, (d) a $C_{6-12}$ aryl group (e.g., phenyl) optionally having 1 to 3 substituents selected from (i) a $C_{1-6}$ alkyl-carbonylamino group (e.g., acetylamino) optionally having a hydroxy group, and (ii) a 5- to 10-membered aromatic or nonaromatic heterocyclic group containing, besides carbon atoms, 1 to 4 hetero atoms of one or two kinds selected from a nitrogen atom, a sulfur atom and an oxygen atom (e.g., tetrazolyl, pyrazolyl, imidazolyl, morpholinyl), and optionally substituted by 1 to 3 substituents selected from a $C_{1-6}$ alkyl group optionally having 1 to 3 halogen atoms (e.g., methyl, trifluoromethyl) and an oxo group, or (e) a carbamoyl group, (6) a group represented by the formula: —(C=O)—OR$^{7''}$ wherein is a $C_{1-6}$ alkyl group (e.g., methyl, tert-butyl) or a 5- to 7-membered aromatic or nonaromatic heterocyclic group containing, besides carbon atoms, 1 to 4 hetero atoms selected from an oxygen atom, a sulfur atom and a nitrogen atom (e.g., tetrahydropyranyl), (7) a group represented by the formula: —SO$_2$—R$^{9'}$
wherein R$^{9'}$ is (a) a $C_{1-6}$ alkyl group (e.g., methyl), or (b) a 5- to 7-membered aromatic or nonaromatic heterocyclic group containing, besides carbon atoms, 1 to 4 hetero atoms selected from an oxygen atom, a sulfur atom and a nitrogen atom (e.g., piperidyl, pyridyl), and optionally having 1 to 3 substituents selected from a $C_{1-6}$ alkyl-carbonyl group (e.g., acetyl) and a $C_{7-14}$ aralkyloxy-carbonyl group (e.g., benzyloxycarbonyl), (8) a group represented by the formula: —NR$^{5'}$R$^{6'}$
wherein R$^{5'}$ and R$^{6'}$ are independently (a) a hydrogen atom, (b) a $C_{1-6}$ alkyl group (e.g., methyl), (c) a $C_{1-6}$ alkyl-carbonyl group (e.g., acetyl), or (d) a 5- to 7-membered aromatic or nonaromatic heterocyclylcarbonyl group containing, besides carbon atoms, 1 to 4 hetero atoms selected from an oxygen atom, a sulfur atom and a nitrogen atom (e.g., piperidylcarbonyl), and optionally having a $C_{1-6}$ alkyl-carbonyl group (e.g., acetyl), or (9) a group represented by the formula: —(C=O)—NR$^{7'''}$R$^{8''}$
wherein R$^{7'''}$ and R$^{8''}$ are independently (a) a hydrogen atom, (b) a $C_{1-6}$ alkyl group (e.g., methyl, ethyl, propyl, isopropyl, tert-butyl) optionally substituted by 1 to 3 substituents selected from a $C_{6-12}$ aryl group (e.g., phenyl group), a $C_{1-3}$ alkoxy group (e.g., methoxy) and a $C_{1-3}$ alkyl-carbonyl group (e.g., acetylamino), (c) a 5- to 7-membered aromatic or nonaromatic heterocyclic group containing, besides carbon atoms, 1 to 4 hetero atoms selected from an oxygen atom, a sulfur atom and a nitrogen atom (e.g., piperidyl, tetrahydropyranyl, tetrahydrothiopyranyl), and optionally having 1 to 3 substituents selected from a $C_{1-6}$ alkyl-carbonyl group (e.g., acetyl), a $C_{1-6}$ alkoxy-carbonyl group (e.g., methoxycarbonyl, tert-butoxycarbonyl), a $C_{1-6}$ alkyl group (e.g., methyl) and an oxo group, (d) a $C_{3-8}$ cycloalkyl group (e.g., cyclopropyl, cyclopentyl, cyclohexyl) optionally substituted by 1 to 3 substituents selected from (i) a halogen atom (e.g., fluorine atom), (ii) a $C_{1-6}$ alkoxy-carbonylamino group (e.g., methoxycarbonylamino, ethoxycarbonylamino, tert-butoxycarbonylamino), (iii) a $C_{1-3}$ alkyl group, (iv) an amino group and (v) a 5- to 10-membered aromatic or nonaromatic heterocyclic group containing, besides carbon atoms, 1 to 4 hetero atoms of one or two kinds selected from a nitrogen atom, a sulfur atom and an oxygen atom, and optionally substituted by 1 to 3 substituents selected from a alkyl group optionally having 1 to 3 halogen atoms (e.g., methyl, trifluoromethyl) and an oxo group (e.g., tetrazolyl, 5-trifluoromethyltetrazolyl, oxazolidinyl), or (e) a phenyl group optionally substituted by a $C_{1-3}$ alkoxy group (e.g., methoxy).

Compound (I)-4 shows a good NK1 receptor antagaonistic activity.

[Compound (I)-5]

Compound (I) wherein ring A is a ring represented by

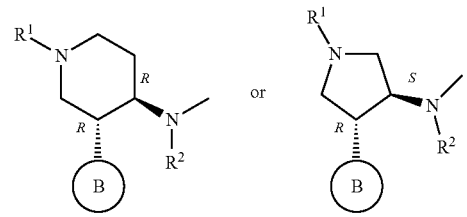

ring B is (1) a phenyl group optionally having 1 to 3 substituents selected from a $C_{1-6}$ alkyl group optionally having 1 to 3 halogen atoms and a halogen atom or (2) a pyridyl group optionally having 1 to 3 substituents selected from a $C_{1-6}$ alkyl group optionally having 1 to 3 halogen atoms and a halogen atom, ring D is a phenyl group optionally having 1 to 3 substituents selected from (1) a $C_{1-6}$ alkyl group optionally having 1 to 3 halogen atoms (e.g., fluorine atom) (e.g., methyl, trifluoromethyl), and (2) a halogen atom (e.g., chlorine atom, bromine atom), L is a group represented by the formula

$R^2$ and $R^3$ are each independently a $C_{1-6}$ alkyl group (e.g., methyl), $R^1$ is (1) a group represented by the formula: —(C=O)—$R^{7'}$
  wherein $R^{7'}$ is
  (a) a $C_{1-6}$ alkyl group (e.g., methyl) optionally having 1 to 3 substituents selected from
    (i) a hydroxy group,
    (ii) a $C_{1-6}$ alkyl-carbonylamino group (e.g., acetylamino),
    (iii) a 5- to 7-membered aromatic or nonaromatic heterocyclic group containing, besides carbon atoms, 1 to 4 hetero atoms selected from an oxygen atom, a sulfur atom and a nitrogen atom (e.g., oxazolidinyl, tetrazolyl, piperidyl), and optionally having 1 to 4 substituents selected from a $C_{1-6}$ alkyl group (e.g., methyl), a $C_{1-3}$ alkyl-carbonyl group (e.g., acetyl), a $C_{1-6}$ alkoxy-carbonyl group (e.g., tert-butoxycarbonyl) and an oxo group, and
    (iv) a $C_{1-6}$ alkylsulfonyl group (e.g., methylsulfonyl),
  (b) a 4- to 7-membered aromatic or nonaromatic heterocyclic group containing, besides carbon atoms, 1 to 4 hetero atoms selected from an oxygen atom, a sulfur atom and a nitrogen atom (e.g., piperidyl, azetinyl, piperazinyl, tetrahydropyranyl, tetrahydrothiopyranyl, pyridyl, pyrimidinyl, thiazolyl, tetrahydrofuranyl, pyrrolidinyl, morpholinyl, thiomorpholinyl), and optionally having 1 to 3 substituents selected from
    (i) an oxo group,
    (ii) a $C_{1-6}$ alkyl-carbonyl group (e.g., acetyl, propionyl, isobutyryl) optionally having 1 to 4 substituents selected from (a) a halogen atom (e.g., fluorine atom), (b) a $C_{1-3}$ alkoxy group (e.g., methoxy, ethoxy), (c) a $C_{3-8}$ cycloalkyl group (e.g., cyclopropyl), (d) a cyano group, (e) a hydroxy group, (f) a $C_{1-6}$ alkylsulfonyl group (e.g., methylsulfonyl), (g) a 4- to 7-membered aromatic or nonaromatic heterocyclic group containing, besides carbon atoms, 1 to 4 hetero atoms selected from an oxygen atom, a sulfur atom and a nitrogen atom (e.g., tetrazolyl), and optionally having 1 to 3 substituents selected from a $C_{1-6}$ alkyl-carbonyl group and a $C_{1-6}$ alkoxy-carbonyl group, and (h) a $C_{1-3}$ alkyl-carbonylamino group (e.g., acetylamino),
    (iii) a $C_{1-6}$ alkoxy-carbonyl group (e.g., methoxycarbonyl, ethoxycarbonyl, tert-butoxycarbonyl etc.),
    (iv) a $C_{6-14}$ aryl-carbonyl group (e.g., benzoyl),
    (v) a $C_{1-6}$ alkylsulfonyl group or a $C_{3-6}$ cycloalkylsulfonyl group (e.g., methylsulfonyl, ethylsulfonyl, isopropylsulfonyl, cyclopropylsulfonyl) each of which is optionally substituted by 1 to 3 halogen atoms,
    (vi) an aminosulfonyl group optionally mono- or di-substituted by a $C_{1-6}$ alkyl group (e.g., dimethylaminosulfonyl),
    (vii) a halogen atom (e.g., fluorine atom),
    (viii) a $C_{3-6}$ cycloalkenyl group (e.g., cyclopentenyl) optionally substituted by an oxo group,
    (ix) a $C_{3-8}$ cycloalkyl-carbonyl group (e.g., cyclopropylcarbonyl, cyclohexylcarbonyl) optionally substituted by 1 to 3 substituents selected from a halogen atom and a hydroxy group,
    (x) a 4- to 7-membered aromatic or nonaromatic heterocyclic group containing, besides carbon atoms, 1 to 4 hetero atoms selected from an oxygen atom, a sulfur atom and a nitrogen atom (e.g., dihydrofuranyl, oxazolinyl), and optionally substituted by an oxo group,
    (xi) a 5- to 7-membered aromatic or nonaromatic heterocyclylcarbonyl group containing, besides carbon atoms, 1 to 4 hetero atoms selected from an oxygen atom, a sulfur atom and a nitrogen atom (e.g., tetrahydropyranylcarbonyl), and
    (xii) a $C_{1-6}$ alkyl or $C_{6-14}$ aryl-carbamoyl group (e.g., ethylcarbamoyl, phenylcarbamoyl), or
  (c) a $C_{3-8}$ cycloalkyl group (e.g., cyclohexyl, cyclobutyl) optionally having 1 to 3 substituents selected from
    (i) a $C_{1-6}$ alkyl-carbonylamino group (e.g., acetylamino, propionylamino, isobutyrylamino, pivaloylamino) optionally having 1 to 3 substituents selected from a hydroxy group and a $C_{1-3}$ alkoxy group (e.g., methoxy), the nitrogen atom of which is optionally substituted by a $C_{1-3}$ alkyl group,
    (ii) a $C_{1-6}$ alkoxy-carbonylamino group (e.g., methoxycarbonylamino, ethoxycarbonylamino, isopropoxycarbonylamino, isobutoxycarbonylamino, tert-butoxycarbonylamino), the nitrogen atom of which is optionally substituted by a $C_{1-3}$ alkyl group (e.g., methyl),
    (iii) a $C_{6-14}$ aryl-carbonylamino group (e.g., benzoylamino),
    (iv) a halogen atom (e.g., fluorine atom),
    (v) a 5- to 10-membered aromatic or nonaromatic heterocyclic group containing, besides carbon atoms, 1 to 4 hetero atoms of one or two kinds selected from a nitrogen atom, a sulfur atom and an oxygen atom, and optionally having 1 to 3 substituents selected from a $C_{1-6}$ alkyl group optionally having 1 to 3 halogen atoms (e.g., methyl, trifluoromethyl) and an oxo group (e.g., tetrazolyl, 5-trifluoromethyltetrazolyl, oxazolidinyl, pyrrolidinyl, isothiazolidinyl, morpholinyl, imidazolidinyl),
    (vi) a $C_{1-6}$ alkyl group optionally having a $C_{1-6}$ alkoxy-carbonylamino group (e.g., methoxycarbonylamino, tert-butoxycarbonylamino),
    (vii) a ureido group optionally substituted by 1 to 3 $C_{1-3}$ alkyl groups (e.g., methyl, ethyl),
    (viii) a $C_{1-3}$ alkylsulfonylamino group (e.g., methylsulfonylamino), the nitrogen atom of which is optionally substituted by a $C_{1-3}$ alkyl group, and
    (ix) a $C_{1-6}$ alkoxy-carbonyl group,
  or
(2) a group represented by the formula: —(C=O)—$NR^{7''}R^{8''}$
  wherein $R^{7''}$ and $R^{8''}$ are independently
  (a) a hydrogen atom,
  (b) a $C_{1-6}$ alkyl group (e.g., methyl, ethyl, propyl, isopropyl, tert-butyl),
  (c) a 5- to 7-membered aromatic or nonaromatic heterocyclic group containing, besides carbon atoms, 1 to 4 hetero atoms selected from an oxygen atom, a sulfur atom and a nitrogen atom (e.g., piperidyl, tetrahydropyranyl, tetrahydrothiopyranyl), and optionally having 1 to 3 substituents selected from a $C_{1-6}$ alkyl-carbonyl group (e.g., acetyl), a $C_{1-6}$ alkoxy-carbonyl group (e.g., methoxycarbonyl, tert-butoxycarbonyl), a $C_{1-6}$ alkyl group (e.g., methyl) and an oxo group, or (d) a $C_{3-8}$ cycloalkyl group (e.g., cyclopropyl, cyclopentyl, cyclohexyl) optionally substituted by 1 to 3 substituents selected from (i) a halogen atom (e.g., fluorine atom), (ii) a $C_{1-6}$ alkoxy-carbonylamino group (e.g., methoxycarbonylamino, ethoxycarbonylamino, tert-butoxycarbonylamino), and (iii) a 5- to 10-membered aromatic or nonaromatic heterocyclic group containing, besides carbon atoms, 1 to 4 hetero atoms of one or two kinds selected from a nitrogen atom, a sulfur atom and an oxygen atom, and optionally substituted by 1 to 3 substituents selected from a alkyl group optionally having 1 to 3 halogen atoms (e.g., methyl, trifluoromethyl) and an oxo group (e.g., tetrazolyl, 5-trifluoromethyltetrazolyl, oxazolidinyl).

Compound (I)-5 shows a good NK2 receptor antagaonistic activity.

[Compound (I)-6]

Compound (I) wherein
ring A is a ring represented by

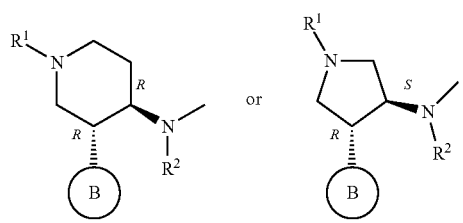

ring B is a phenyl group optionally having 1 to 3 substituents selected from a $C_{1-6}$ alkyl group optionally having 1 to 3 halogen atoms and a halogen atom, ring D is a phenyl group optionally having 1 to 3 substituents selected from (1) a $C_{1-6}$ alkyl group optionally having 1 to 3 halogen atoms (e.g., fluorine atom) (e.g., methyl, trifluoromethyl), and (2) a halogen atom (e.g., chlorine atom, bromine atom) (particularly preferably 3,5-bis(trifluoromethyl)phenyl group, 3,5-dichlorophenyl group or 4-chlorophenyl group), L is a group represented by the formula

$R^2$ and $R^3$ are each independently a hydrogen atom or a $C_{1-6}$ alkyl group (e.g., methyl), or bonded via an alkylene chain, $R^1$ is (1) a group represented by the formula: —(C=O)—$R^{7'}$
wherein $R^{7'}$ is
(a) a $C_{1-6}$ alkyl group (e.g., methyl) optionally having 1 to 3 substituents selected from
(i) a hydroxy group,
(ii) a $C_{1-6}$ alkyl-carbonylamino group (e.g., acetylamino),
(iii) a 5- to 7-membered aromatic or nonaromatic heterocyclic group containing, besides carbon atoms, 1 to 4 hetero atoms selected from an oxygen atom, a sulfur atom and a nitrogen atom (e.g., oxazolidinyl, tetrazolyl, piperidyl), and optionally having 1 to 4 substituents selected from a $C_{1-6}$ alkyl group (e.g., methyl) and an oxo group and
(iv) a $C_{1-6}$ alkylsulfonyl group (e.g., methylsulfonyl), (b) a 4- to 7-membered aromatic or nonaromatic heterocyclic group containing, besides carbon atoms, 1 to 4 hetero atoms selected from an oxygen atom, a sulfur atom and a nitrogen atom (e.g., piperidyl, azetinyl, piperazinyl, tetrahydropyranyl, tetrahydrothiopyranyl, pyridyl, pyrimidinyl, thiazolyl, tetrahydrofuranyl, pyrrolidinyl, morpholinyl, thiomorpholinyl), and optionally having 1 to 3 substituents selected from
(i) an oxo group,
(ii) a $C_{1-6}$ alkyl-carbonyl group (e.g., acetyl, propionyl, isobutyryl) optionally having 1 to 4 substituents selected from a halogen atom (e.g., fluorine atom), a $C_{1-3}$ alkoxy group (e.g., methoxy, ethoxy), a $C_{3-8}$ cycloalkyl group (e.g., cyclopropyl), a cyano group, and a hydroxy group,
(iii) a $C_{1-6}$ alkoxy-carbonyl group (e.g., methoxycarbonyl, ethoxycarbonyl, tert-butoxycarbonyl etc.),
(iv) a $C_{6-14}$ aryl-carbonyl group (e.g., benzoyl),
(v) a $C_{1-6}$ alkylsulfonyl group or a $C_{3-6}$ cycloalkylsulfonyl group (e.g., methylsulfonyl, ethylsulfonyl, isopropylsulfonyl, cyclopropylsulfonyl),
(vi) an aminosulfonyl group mono- or di-substituted by a $C_{1-6}$ alkyl group (e.g., dimethylaminosulfonyl),
(vii) a halogen atom (e.g., fluorine atom),
(viii) a $C_{3-6}$ cycloalkenyl group (e.g., cyclopentenyl) optionally substituted by an oxo group, and
(ix) a $C_{6-14}$ aryl-carbamoyl group (e.g., phenylcarbamoyl), or (c) a $C_{3-6}$ cycloalkyl group (e.g., cyclohexyl, cyclobutyl) optionally having 1 to 3 substituents selected from
(i) a $C_{1-6}$ alkyl-carbonylamino group (e.g., acetylamino) optionally having a hydroxy group,
(ii) a $C_{1-6}$ alkoxy-carbonylamino group (e.g., methoxycarbonylamino, ethoxycarbonylamino, isopropoxycarbonylamino, isobutoxycarbonylamino, tert-butoxycarbonylamino),
(iii) a $C_{6-14}$ aryl-carbonylamino group (e.g., benzoylamino),
(iv) a halogen atom (e.g., fluorine atom),
(v) a 5- to 10-membered aromatic or nonaromatic heterocyclic group containing, besides carbon atoms, 1 to 4 hetero atoms of one or two kinds selected from a nitrogen atom, a sulfur atom and an oxygen atom, and optionally having 1 to 3 substituents selected from a $C_{1-6}$ alkyl group optionally having 1 to 3 halogen atoms (e.g., methyl, trifluoromethyl) and an oxo group (e.g., tetrazolyl, 5-trifluoromethyltetrazolyl, oxazolidinyl, pyrrolidinyl, isothiazolidinyl, morpholinyl, imidazolidinyl),
(vi) a $C_{1-6}$ alkyl group optionally having a $C_{1-6}$ alkoxycarbonylamino group (e.g., methoxycarbonylamino, tert-butoxycarbonylamino),
or (2) a group represented by the formula: —(C=O)—$NR^{7'''}R^{8''}$
wherein $R^{7'''}$ and $R^{8''}$ are independently
(a) a hydrogen atom,
(b) a $C_{1-6}$ alkyl group (e.g., methyl, ethyl, propyl, isopropyl, tert-butyl), or
(c) a 5- to 7-membered aromatic or nonaromatic heterocyclic group containing, besides carbon atoms, 1 to 4 hetero atoms selected from an oxygen atom, a sulfur atom and a nitrogen atom (e.g., piperidyl, tetrahydropyranyl, tetrahydrothiopyranyl), and optionally having 1 to 3 substituents selected from a $C_{1-6}$ alkyl-carbonyl group (e.g., acetyl), a $C_{1-6}$ alkoxy-carbonyl group (e.g., methoxycarbonyl, tert-butoxycarbonyl), a $C_{1-6}$ alkyl group (e.g., methyl) and an oxo group.

Compound (I)-6 shows a good NK3 receptor antagaonistic activity.

As compound (I), the compounds shown below are particularly preferable:

1-[(3R,4R)-1-[(1-acetylpiperidin-4-yl)carbonyl]-3-(3,4-dichlorophenyl)piperidin-4-yl]-3-[3,5-bis(trifluoromethyl)phenyl]-1,3-dimethylurea (Example 25)

1-[(3R,4R)-1-[(1-acetylpiperidin-4-yl)carbonyl]-3-(3,4-dichlorophenyl)piperidin-4-yl]-3-[3,5-bis(trifluoromethyl)benzyl]imidazolidin-2-one (Example 37)

1-[(3R,4R)-1-[(1-acetylpiperidin-4-yl)carbonyl]-3-(4-fluorophenyl)piperidin-4-yl]-3-[3,5-bis(trifluoromethyl)phenyl]-1,3-dimethylurea (Example 52)

1-[(3R,4R)-1-[(1-acetylpiperidin-4-yl)carbonyl]-3-(4-chloro-3-methylphenyl)piperidin-4-yl]-3-[3,5-bis(trifluoromethyl)phenyl]-1,3-dimethylurea (Example 60)

(1-[(3S,4R)-1-[(1-acetylpiperidin-4-yl)carbonyl]-4-(4-fluorophenyl)pyrrolidin-3-yl]-3-[3,5-bis(trifluoromethyl)phenyl]-1,3-dimethylurea (Example 71b)

1-[(3R,4R)-1-[(1-acetylpiperidin-4-yl)methyl]-3-(4-fluorophenyl)piperidin-4-yl]-3-[3,5-bis(trifluoromethyl)phenyl]-1,3-dimethylurea (Example 85)

N-(trans-4-{[(3R,4R)-4-[{[3,5-bis(trifluoromethyl)phenyl](methyl)carbamoyl}(methyl)amino]-3-(4-fluorophenyl)piperidin-1-yl]carbonyl}cyclohexyl)acetamide (Example 95)

1-[3,5-bis(trifluoromethyl)phenyl]-3-[(3R,4R)-3-(4-fluorophenyl)-1-{[1-(phenylcarbonyl)piperidin-4-yl]carbonyl}piperidin-4-yl]-1,3-dimethylurea (Example 97)

1-[(3S,4R)-4-(4-chlorophenyl)-1-{[4-(methylsulfonyl)piperazin-1-yl]carbonyl}pyrrolidin-3-yl]-3-(3,5-dichlorophenyl)-1,3-dimethylurea (Example 184)

methyl 4-{[(3S,4R)-3-[{[3,5-bis(trifluoromethyl)phenyl](methyl)carbamoyl}(methyl)amino]-4-(4-fluorophenyl)pyrrolidin-1-yl]carbonyl}piperidine-1-carboxylate (Example 305)

1-[3,5-bis(trifluoromethyl)phenyl]-3-[(3S,4R)-4-(5-fluoropyridin-2-yl)-1-({trans-4-[5-(trifluoromethyl)-1H-tetrazol-1-yl]cyclohexyl}carbonyl)pyrrolidin-3-yl]-1,3-dimethylurea (Example 425)

A salt of compound (I) includes, for example, a metal salt, an ammonium salt, a salt with an organic base, a salt with an inorganic acid, a salt with an organic acid, a salt with basic or acidic amino acid, etc. Suitable examples of the metal salt include an alkali metal salt such as a sodium salt, a potassium salt, etc.; an alkaline earth metal salt such as a calcium salt, a magnesium salt, a barium salt, etc.; an aluminum salt, etc. Suitable examples of the salts with an organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine, etc. Suitable examples of the salts with an inorganic acid include salts with hydrochloric acid, hydrobromic acid, nitric acid, sulfuric acid, phosphoric acid, etc. Suitable examples of the salts with an organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid, etc. Suitable examples of the salts with basic amino acid include salts with arginine, lysine, ornithine, etc. Suitable examples of the salts with acidic amino acid include salts with aspartic acid and glutamic acid, etc.

Among these, pharmaceutically acceptable salts are preferred. For example, if the compound has acidic functional group, preferred salts are inorganic salts such as an alkali metal salt (e.g., sodium salt, potassium salt, etc.), an alkaline earth metal salt (e.g., calcium salt, magnesium salt, barium salt, etc.), an ammonium salt, etc. If the compound has a basic functional group, preferred salts are salts with an inorganic acid such as hydrochloric acid, hydrobromic acid, nitric acid, sulfuric acid, phosphoric acid, etc., or salts with an organic acid such as acetic acid, phthalic acid, fumaric acid, oxalic acid, tartaric acid, maleic acid, citric acid, succinic acid, methanesulfonic acid, p-toluenesulfonic acid, etc.

The prodrug of compound (I) or a salt thereof of the present invention means a compound which is converted to compound (I) of the present invention under the physiological condition in the living body by a reaction with an enzyme, a gastric acid, or the like, that is, by enzymatic oxidation, reduction, hydrolysis, etc.; by hydrolysis with gastric acid, etc.

The prodrug of compound (I) of the present invention includes a compound wherein an amino group of compound (I) is modified with acyl, alkyl or phosphoryl (e.g., a compound wherein an amino group of compound (I) of the present invention is modified with eicosanoyl, alanyl, pentylaminocarbonyl, (5-methyl-2-oxo-1,3-dioxolen-4-yl)methoxycarbonyl, tetrahydrofuranyl, pyrrolidylmethyl, pivaloyloxymethyl or t-butyl, etc.); a compound wherein a hydroxyl group of compound (I) of the present invention is modified with acyl, alkyl, phosphoric acid or boric acid (e.g., a compound wherein a hydroxyl group of compound (I) is modified with acetyl, palmitoyl, propanoyl, pivaloyl, succinyl, fumaryl, alanyl or dimethylaminomethylcarbonyl, etc.); a compound wherein a carboxy group of compound (I) of the present invention is modified to ester or amide (e.g., a compound wherein a carboxy group of compound (I) of the present invention is modified to ethyl ester, phenyl ester, carboxymethyl ester, dimethylaminomethyl ester, pivaloyloxymethyl ester, ethoxycarbonyloxyethyl ester, phthalidyl ester, (5-methyl-2oxo-1,3-dioxolen-4-yl)methyl ester, cyclohexyloxycarbonylethyl ester or methylamide, etc.); and the like. These prodrugs can be produced from compound (I) of the present invention by a method known per se.

In addition, the prodrug of compound (I) of the present invention may be a compound, which is converted into compound (I) of the present invention under the physiological conditions, as described in "Pharmaceutical Research and Development", Vol. 7 (Drug Design), pp. 163-198 (1990), published by Hirokawa Publishing Co.

The present invention encompasses a solvate (e.g., hydrate) of compound (I) or a salt thereof. Compound (I) may be labeled with an isotope (e.g., $^{3}H$, $^{14}C$, $^{35}S$, $^{125}I$, etc.) and the like. Compound (I) may also be a deuterated compound.

When compound (I) has chiral center, isomers such as an enantiomer or a diastereomer may exist. Such isomers and a mixture thereof are all included in the scope of the present invention. In addition, there can be instances where the isomers by conformation are generated in cases, but such isomers or a mixture thereof are also included in compound (I) or a salt thereof.

For the activity, compound (I) wherein m=1 and n=1 is preferably an optically active compound represented by the formula

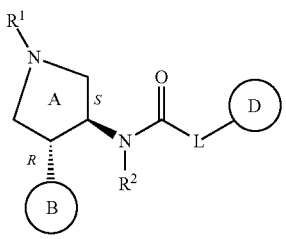

wherein each symbol is as defined above; or compound (I) wherein m=1 and n=2 is preferably an optically active compound of the above-mentioned [1] represented by the formula

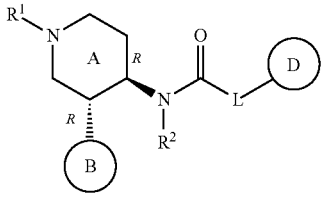

wherein each symbol is as defined above.

The production method of compound (I) or a salt thereof of the present invention is explained in the following.

The intermediates produced in the following production methods may be isolated and purified by column chromatography, recrystallization, distillation and the like, or may be used as they are for the next step without isolation.

The compound (I) of the present invention or a salt thereof can be produced by the following method A to method F.

For example, when compound (I) is a compound represented by the formula (VII) or a salt thereof (hereinafter to be referred to as compound (VII)), and $R^{2a}=R^{3a}$, it can be produced by the following method A.

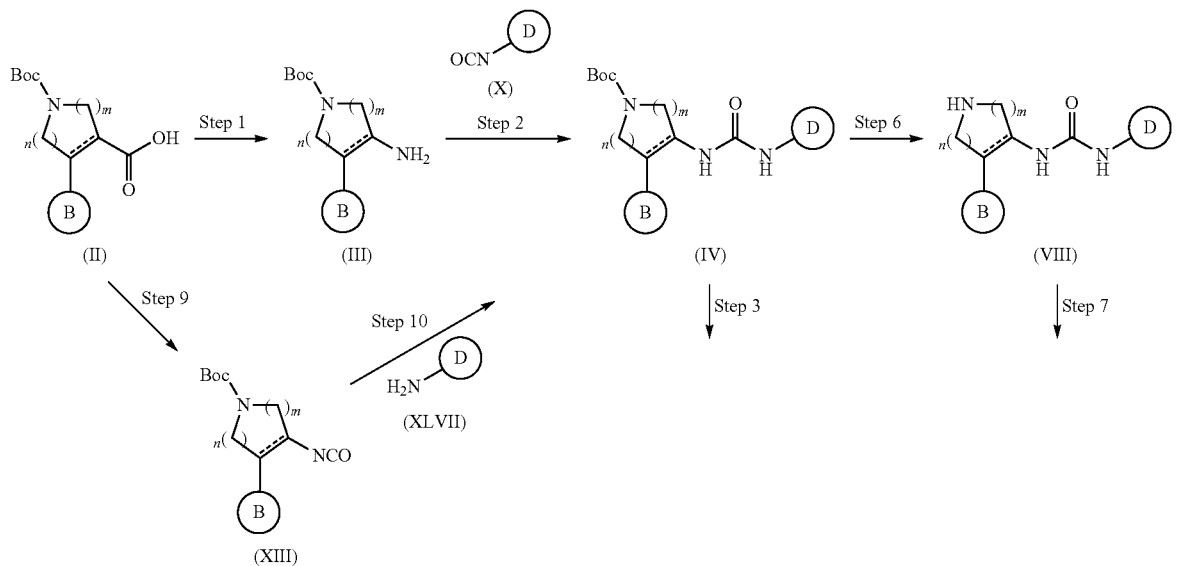

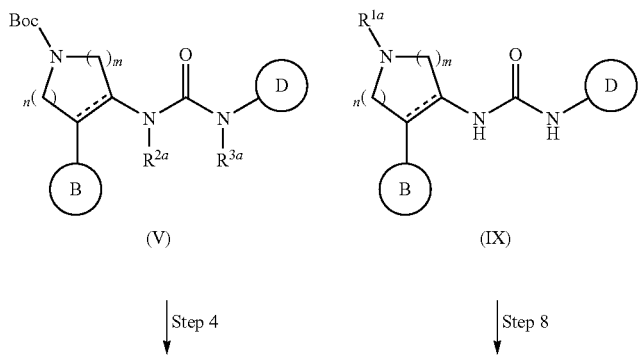

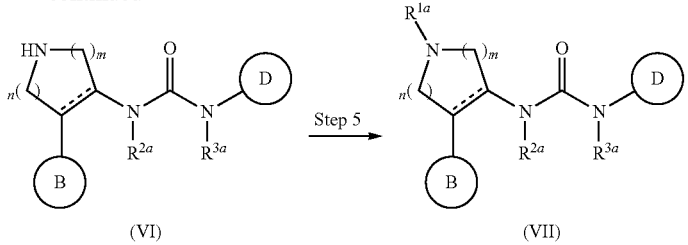

(VI) → (VII)

wherein $R^{1a}$ is a hydrocarbon group optionally having substituent(s), an acyl group, an amino group or a heterocyclic group, $R^{2a}$ and $R^{3a}$ are each an optionally halogenated $C_{1-6}$ alkyl group or an optionally halogenated $C_{3-6}$ cycloalkyl group, Boc is a tert-butoxycarbonyl group, and other symbols are as defined above.

The "hydrocarbon group optionally having substituent(s)", "acyl group" and "heterocyclic group" for $R^{1a}$ are as defined for the "hydrocarbon group optionally having substituent(s)", "acyl group" and "heterocyclic group" for $R^1$.

(Step 1)

In this step, a compound represented by the formula (II) or a salt thereof (hereinafter to be referred to as compound (II)) is subjected to a rearrangement reaction step (step 1-1), then subsequently to a hydrolysis step (step 1-2) to convert to a compound represented by the formula (III) or a salt thereof (hereinafter to be referred to as compound (III)).

(Step 1-1)

This step can be performed according to a method known per se (e.g., the methods described in "4th Ed. Jikken Kagaku Koza (Courses in Experimental Chemistry) 20, Organic Synthesis II", The Chemical Society of Japan Ed., 1991 and the like), or a method analogous thereto.

Examples of the rearrangement reaction include Hofmann rearrangement reaction, Schmidt rearrangement reaction, Curtius rearrangement reaction and the like. While the rearrangement reaction varies depending on compound (II), generally, it is preferably the Curtius rearrangement reaction.

The Curtius rearrangement reaction is generally carried out by reacting compound (II) with an azidating agent in a solvent that does not adversely influence the reaction in the presence of a base, and heating.

Examples of the base include inorganic bases (alkali metal hydroxides such as lithium hydroxide, sodium hydroxide, potassium hydroxide and the like; alkali metal hydrogen carbonates such as sodium hydrogen carbonate, potassium hydrogen carbonate and the like; alkali metal carbonates such as sodium carbonate, potassium carbonate and the like; alkoxides such as sodium methoxide, sodium ethoxide and the like, and the like), organic bases (amines such as trimethylamine, triethylamine, diisopropylethylamine and the like; aromatic amines such as pyridine, 4-dimethylaminopyridine and the like; and the like) and the like. Of these, organic bases (triethylamine, diisopropylethylamine and the like) and the like are preferable. While the amount of the base to be used varies depending on the kind of the solvent and the other reaction conditions, it is generally about 1 to 10 molar equivalents, preferably about 1 to 5 molar equivalents, per 1 mol of compound (II).

Preferable examples of the azidating agent include diphenylphosphoryl azide (DPPA).

Examples of the solvent that does not adversely influence the reaction include hydrocarbons (benzene, toluene, xylene, hexane, heptane and the like), halogenated hydrocarbons (dichloromethane, chloroform and the like), ethers (diethyl ether, diisopropyl ether, t-butyl methyl ether, tetrahydrofuran, dioxane, dimethoxyethane and the like), nitriles (acetonitrile and the like), amides (N,N-dimethylformamide, N,N-dimethylacetamide and the like), sulfoxides (dimethyl sulfoxide and the like) and the like. Such solvent may be used in a mixture of two or more at a suitable ratio.

The reaction temperature is, for example, within the range of about −50° C. to 200° C., preferably about 0° C. to 100° C. While the reaction time varies depending on the kind of compound (II), the reaction temperature and the like, it is, for example, about 0.5 to 24 hr, preferably about 0.5 to 2 hr.

(Step 1-2)

The hydrolysis can be carried out according to a method known per se, for example, in the presence of a base, as necessary in a solvent that does not adversely influence the reaction.

Examples of the base include inorganic bases (alkali metal hydroxides such as lithium hydroxide, sodium hydroxide, potassium hydroxide and the like; alkali metal hydrogen carbonates such as sodium hydrogen carbonate, potassium hydrogen carbonate and the like; alkali metal carbonates such as sodium carbonate, potassium carbonate and the like; alkoxides such as sodium methoxide, sodium ethoxide and the like, and the like), organic bases (amines such as trimethylamine, triethylamine, diisopropylethylamine and the like; aromatic amines such as pyridine, 4-dimethylaminopyridine and the like; and the like) and the like. Of these, lithium hydroxide, sodium hydroxide, potassium hydroxide and the like are preferable. While the amount of the base to be used varies depending on the kind of the solvent and the other reaction conditions, it is generally about 1 to 100 molar equivalents, preferably about 1 to 20 molar equivalents, per 1 mol of compound (II).

Examples of the solvent that does not adversely influence the reaction include hydrocarbons (benzene, toluene, xylene, hexane, heptane and the like), halogenated hydrocarbons (dichloromethane, chloroform and the like), ethers (diethyl ether, diisopropyl ether, t-butyl methyl ether, tetrahydrofuran, dioxane, dimethoxyethane and the like), nitriles (acetonitrile and the like), amides (N,N-dimethylformamide, N,N-dimethylacetamide and the like), sulfoxides (dimethyl sulfoxide and the like), water and the like. Such solvent may be used in a mixture of two or more at a suitable ratio.

The reaction temperature is, for example, within the range of about −50° C. to 200° C., preferably about 0° C. to 100° C. While the reaction time varies depending on the kind of compound (II), the reaction temperature and the like, it is, for example, about 0.5 to 24 hr, preferably about 0.5 to 2 hr.

(Step 2)

In this step, compound (III) is reacted with a compound represented by the formula

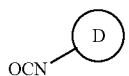 (X)

wherein each symbol is as defined above, or a salt thereof (hereinafter to be referred to as compound (X)) to give a compound represented by the formula (IV) or a salt thereof (hereinafter to be referred to as compound (IV)). Compound (X) is commercially available or can be produced by a known method. The amount thereof to be used is about 1 to 10 molar equivalents, preferably about 1 to 2 molar equivalents, of compound (X) per 1 mol of compound (III).

The above-mentioned reaction is generally performed in a solvent that does not adversely influence the reaction, and a convenient base may be added for the progress of the reaction. Examples of the solvent include hydrocarbons (benzene, toluene and the like), ethers (diethyl ether, dioxane, tetrahydrofuran and the like), esters (ethyl acetate and the like), halogenated hydrocarbons (chloroform, dichloromethane and the like), amides (N,N-dimethylformamide and the like), aromatic amines (pyridine and the like), water and the like, which may be appropriately mixed. Examples of the base include metal hydrides (lithium hydride, sodium hydride, potassium hydride, calcium hydride and the like), alkali metal hydroxides (sodium hydroxide, potassium hydroxide and the like), hydrogen carbonates (sodium hydrogen carbonate, potassium hydrogen carbonate and the like), carbonates (sodium carbonate, potassium carbonate and the like), acetates (sodium acetate and the like), tertiary amines (trimethylamine, triethylamine, N-methylmorpholine and the like), aromatic amines (pyridine, picoline, N,N-dimethylaniline and the like) and the like. The amount of the base to be used is generally about 1 to 100 molar equivalents, preferably about 1 to 5 molar equivalents, per 1 mol of compound (III). The reaction temperature is generally about −80 to 150° C., preferably about 0 to 50° C., and the reaction time is generally about 0.5 to 48 hr, preferably about 0.5 to 16 hr.

(Step 3)

In this step, compound (1V) is reacted with a compound represented by the formula $R^{2a}-X$ (XI)

or $R^{3a}-X$ (XI')

wherein X is a leaving group, or a salt thereof (hereinafter to be referred to as compound (XI)) to give a compound represented by the formula (V) or a salt thereof (hereinafter to be referred to as compound (V)).

Examples of the leaving group for X include a halogen atom (chlorine atom, bromine atom, iodine atom and the like), a substituted sulfonyloxy group (a $C_{1-6}$ alkylsulfonyloxy group such as methylsulfonyloxy, ethylsulfonyloxy and the like; a $C_{6-14}$ arylsulfonyloxy group such as benzenesulfonyloxy, p-toluenesulfonyloxy and the like; a $C_{7-16}$ aralkylsulfonyloxy group such as benzylsulfonyloxy and the like, and the like), an acyloxy group (acetoxy group, benzoyloxy group and the like), an oxy group substituted by a hetero ring or an aryl group (succinimideoxy, benzotriazolyloxy, quinolyloxy, 4-nitrophenoxy and the like), a hetero ring (imidazole and the like) and the like, and a halogen atom is particularly preferable. The amount of compound (XI) to be used is, for example, about 1 to 100 molar equivalents, preferably about 1 to 10 molar equivalents, per 1 mol of compound (IV).

This reaction can be generally performed by reacting compound (XI) in a solvent in the presence of a base. Examples of the solvent include alcohols (methanol, ethanol, propanol and the like), ethers (dimethoxyethane, dioxane, tetrahydrofuran and the like), ketones (acetone and the like), nitriles (acetonitrile and the like), amides (N,N-dimethylformamide and the like), sulfoxides (dimethyl sulfoxide and the like), water and the like, which may be appropriately mixed and used. The base includes, for example, organic bases (trimethylamine, triethylamine, N-methylmorpholine, pyridine, picoline, N,N-dimethylaniline and the like), inorganic bases (potassium carbonate, sodium carbonate, potassium hydroxide, sodium hydroxide and the like), metal amides (lithium hexamethyl disilazide, sodium hexamethyl disilazide, potassium hexamethyl disilazide, lithium diisopropylamide and the like), metal hydrides (lithium hydride, sodium hydride, calcium hydride) and the like. The amount of the base to be used is, for example, about 1 to 100 molar equivalents, preferably about 1 to 10 molar equivalents, per 1 mol of compound (IV).

Where necessary, an additive can also be used to promote the reaction. Examples of the additive include an iodide (sodium iodide, potassium iodide and the like) and the like. The amount thereof to be used is about 0.1 to 10 molar equivalents, preferably about 0.1 to 5 molar equivalents, per 1 mol of compound (XI).

The reaction temperature is generally −10 to 200° C., preferably about 0 to 110° C., and the reaction time is generally 0.5 to 48 hr, preferably about 0.5 to 16 hr.

(Step 4)

In this step, compound (V) is subjected to deprotection to produce compound represented by the formula (VI) or a salt thereof (hereinafter to be referred to as compound (VI)).

The deprotection can be carried out according to a known method (e.g., "Protective Groups in Organic Synthesis, $3^{rd}$ Ed." by Theodora W. Greene, Peter G. M. Wuts, published by Wiley-Interscience, 1999). While the deprotection varies depending on, for example, the kind of compound (IV), it is generally in the presence of an acid, as necessary in a solvent that does not adversely influence the reaction.

Examples of the acid include mineral acids (hydrochloric acid, hydrobromic acid, sulfuric acid etc.), carboxylic acids (acetic acid, trifluoroacetic acid, trichloroacetic acid, etc.), sulfonic acids (methanesulfonic acid, toluenesulfonic acid, etc.), Lewis acids (aluminum chloride, tin chloride, zinc bromide, etc.) and the like. If necessary, it may be used in a mixture of two or more. While the amount of the acid to be used varies depending on the kinds of the solvent and other reaction conditions, it is usually about 0.1 molar equivalents or more, per 1 mol of compound (V), and it can be used as a solvent.

The solvent that does not adversely influence the reaction includes alcohols (methanol, ethanol, propanol, 2-propanol, butanol, isobutanol, t-butanol, etc.), aromatic hydrocarbons (benzene, toluene, xylene, etc.), aliphatic hydrocarbons (hexane, heptane, etc.), halogenated hydrocarbons (dichloromethane, chloroform, etc.), ethers (diethyl ether, diisopropyl ether, t-butyl methyl ether, tetrahydrofuran, dioxane, dimethoxyethane, etc.), nitriles (acetonitrile, etc.), esters (ethyl acetate, etc.), carboxylic acids (acetic acid, etc.), amides (N,N-dimethylformamide, etc.), sulfoxides (dimethyl sulfoxide, etc.), water and the like. Such solvent may be used in a mixture of two or more at a suitable ratio.

The reaction temperature is, for example, about −50° C. to 200° C., preferably about 0° C. to 100° C. While the reaction time varies depending on the kinds of compound (V), the reaction temperature and the like, it is, for example, about 0.5 to 100 hr, preferably about 0.5 to 24 hr.

(Step 5)

In this step, compound (VI) is subjected to an alkylation reaction, acylation reaction, enamine formation reaction, reductive condensation reaction or amination reaction to give compound (VII).

In alkylation reaction and acylation reaction, compound (VI) is reacted with a compound represented by the formula

$$R^{1b}\text{—OH} \quad (XII)$$

or

$$R^{1b}\text{—X} \quad (XIIa)$$

wherein $R^{1b}$ is a hydrocarbon group optionally having substituent(s), an acyl group or a heterocyclic group, and other symbols are as defined above, or a salt thereof (hereinafter to be referred to as compound (XII) and compound (XIIa), respectively) to give compound (VII). The "hydrocarbon group optionally having substituent(s)", "acyl group" and "heterocyclic group" for $R^{1b}$, are as defined for "hydrocarbon group optionally having substituent(s)", "acyl group" and "heterocyclic group" for $R^1$. Compound (XII) and compound (XIIa) are commercially available or can be produced by a known method. The amount thereof to be used is about 1 to 10 molar equivalents, preferably about 1 to 2 molar equivalents, of compound (XII) or compound (XIIa) per 1 mol of compound (VI).

While the alkylation reaction can be performed by a method known per se, it can be generally performed by reacting compound (XIIa) in a solvent in the presence of a base, and can be performed by a method similar to the method described in Method A, step 3.

The acylation reaction can be performed by a method known per se, for example, the method described in "4th Ed. Jikken Kagaku Koza (Courses in Experimental Chemistry) 22, Organic Synthesis IV", The Chemical Society of Japan Ed., 1991 and the like, or a method analogous thereto. Examples of such method include a method using a condensing agent, a method via a reactive derivative and the like.

Examples of the condensing agent to be used for the "method using a condensing agent" include dicyclohexylcarbodiimide, diisopropylcarbodiimide, N-ethyl-N'-3-dimethylaminopropylcarbodiimide and hydrochloride thereof, benzotriazol-1-yl-tris(dimethylamino)phosphonium hexafluorophosphate, diphenylphosphoryl azide and the like. These can be used alone, or in combination with an additive (e.g., N-hydroxysuccinimide, 1-hydroxybenzotriazole or 3-hydroxy-4-oxo-3,4-dihydro-1,2,3-benzotriazine and the like). The amount of the condensing agent to be used is about 1 to 10 molar equivalents, preferably about 1 to 2 molar equivalents, per 1 mol of compound (VI). The amount of the additive to be used is about 1 to 10 molar equivalents, preferably about 1 to 2 molar equivalents, per 1 mol of compound (VI).

The above-mentioned reaction is generally performed in a solvent that does not adversely influence the reaction, and a convenient base may be added for the progress of the reaction. Examples of the solvent include hydrocarbons (benzene, toluene and the like), ethers (diethyl ether, dioxane, tetrahydrofuran and the like), esters (ethyl acetate and the like), halogenated hydrocarbons (chloroform, dichloromethane and the like), amides (N,N-dimethylformamide and the like), aromatic amines (pyridine and the like), water and the like, which may be appropriately mixed. Examples of the base include alkali metal hydroxides (sodium hydroxide, potassium hydroxide and the like), hydrogen carbonates (sodium hydrogen carbonate, potassium hydrogen carbonate and the like), carbonates (sodium carbonate, potassium carbonate and the like), acetates (sodium acetate and the like), tertiary amines (trimethylamine, triethylamine, N-methylmorpholine and the like), aromatic amines (pyridine, picoline, N,N-dimethylaniline and the like) and the like. The amount of the base to be used is generally about 1 to 100 molar equivalents, preferably about 1 to 5 molar equivalents, per 1 mol of compound (VI). The reaction temperature is generally about −80 to 150° C., preferably about 0 to 50° C., and the reaction time is generally about 0.5 to 48 hr, preferably about 0.5 to 16 hr.

As the reactive derivative shown in the "method via reactive derivative", a compound represented by the formula (XIIa) (e.g., an acid halide, an acid anhydride, a mixed acid anhydride, an activity ester and the like), an isocyanic acid ester, an isothiocyanic acid ester and the like can be mentioned. The conversion of compound (XII) to a reactive derivative (compound (XIIa)) can be performed according to a method known per se. For example, for conversion to an acid halide, a method using an acid halide (e.g., thionyl chloride, oxalyl chloride and the like), a method using a halide of phosphorus or phosphoric acid (e.g., phosphorus trichloride, phosphorus pentachloride and the like) and the like can be mentioned. While the above-mentioned reaction using a reactive derivative varies depending on the kind of reactive derivative or compound (VI), the reaction is generally performed in a solvent that does not adversely influence the reaction, and a convenient base may be added for the progress of the reaction. The kind of the solvent and base to be used for the reaction, amount of use, reaction temperature and reaction time are similar to those described for the above-mentioned "method using a condensing agent".

In the enamine formation reaction, compound (VI) is condensed with aldehyde or ketone to give an enamine.

The enamine formation reaction is carried out generally in a solvent that does not adversely influence the reaction. Examples of the solvent include aromatic hydrocarbons (toluene, xylene and the like), aliphatic hydrocarbons (heptane, hexane and the like), halogenated hydrocarbons (chloroform, dichloromethane and the like), ethers (diethyl ether, tetrahydrofuran, dioxane and the like), alcohols (methanol, ethanol, 2-propanol, butanol, benzyl alcohol and the like), nitriles (acetonitrile and the like), amides (N,N-dimethylformamide and the like), sulfoxides (dimethyl sulfoxide and the like) and the like. Such solvent may be used in a mixture at a suitable ratio. Examples of the aldehyde include formalin, aliphatic aldehydes (acetaldehyde and the like) optionally having substituent(s), aromatic aldehydes (benzaldehyde and the like) optionally having substituent(s) and the like. Examples of the ketone include aliphatic ketones (acetone, cyclohexanone, piperidone and the like) optionally having substituent(s), aromatic ketones (acetophenone, benzophenone and the like) optionally having substituent(s) and the like. The amount thereof to be used is, for example, about 1 to 100 molar equivalents, preferably about 1 to 5 molar equivalents, per 1 mol of compound (VI).

Where necessary, the reaction may be advantageously promoted using a catalyst. Examples of the catalyst include mineral acids (hydrochloric acid, hydrobromic acid, sulfuric acid and the like), carboxylic acids (formic acid, acetic acid, propionic acid, trifluoroacetic acid and the like), sulfonic acids (methanesulfonic acid, p-toluenesulfonic acid and the like), Lewis acids (aluminum chloride, zinc chloride, zinc bromide, boron trifluoride, titanium chloride and the like), acetates (sodium acetate, potassium acetate and the like), molecular sieves (molecular sieves 3A, 4A, 5A and the like) and the like. The amount of the catalyst to be used is, for example, about 0.01 to 50 molar equivalents, preferably about 0.1 to 10 molar equivalents, per 1 mol of compound (VI).

The reaction temperature is generally about 0° C. to 200° C., preferably about 20° C. to 150° C. The reaction time is generally 0.5 to 48 hr, preferably 0.5 to 24 hr.

In the reductive condensation reaction, the above-mentioned enamine or iminium ion is subjected to a reduction reaction to give compound (VII). The iminium on can be obtained by a method similar to the above-mentioned enamine formation reaction. The reduction reaction of enamine or iminium ion, can be carried out according to a method known per se, for example, a method using a metal hydride and a method by catalytic hydrogenation reaction.

Examples of the metal hydride as a reducing agent include metal hydrides (sodium borohydride, lithium borohydride, zinc borohydride, sodium cyanoborohydride, sodium triacetoxyborohydride, lithium cyanoborohydride, diisobutylaluminum hydride, aluminum hydride, lithium aluminum hydride and the like), borane complexes (borane-tetrahydrofuran complex, catecholborane and the like) and the like. Sodium borohydride, sodium cyanoborohydride, sodium triacetoxyborohydride and the like are preferable metal hydride. The amount of the reducing agent to be used is, for example, about 1 to 50 molar equivalents, preferably about 1 to 10 molar equivalents, per 1 mol of compound (VI). Examples of the solvent include aromatic hydrocarbons (toluene, xylene and the like), aliphatic hydrocarbons (heptane, hexane and the like), halogenated hydrocarbons (chloroform, dichloromethane and the like), ethers (diethyl ether, tetrahydrofuran, dioxane and the like), alcohols (methanol, ethanol, 2-propanol, butanol, benzyl alcohol and the like), nitriles (acetonitrile and the like), amides (N,N-dimethylformamide and the like), sulfoxides (dimethyl sulfoxide and the like) and the like. Such solvent may be used in a mixture at a suitable ratio. The reaction temperature is generally about −80° C. to 80° C., preferably about −40° C. to 40° C. The reaction time is generally 5 min to 48 hr, preferably 1 to 24 hr.

The catalytic hydrogenation reaction can be carried out in the presence of a catalyst under a hydrogen atmosphere. Examples of the catalyst include palladium compounds (palladium carbon, palladium hydroxide, palladium oxide, etc.), nickel compounds (Raney-nickel, etc.), platinum compounds (platinum oxide, platinum carbon, etc.), rhodium compounds (rhodium acetate, etc.) and the like. The amount thereof to be used is about 0.001 to 1 equivalent, preferably about 0.01 to 0.5 equivalent, per 1 mol of compound (VI).

The catalytic hydrogenation reaction can be generally carried out in a solvent inert to the reaction. Examples of the solvent include alcohols (methanol, ethanol, propanol, butanol, etc.), hydrocarbons (benzene, toluene, xylene, etc.), halogenated hydrocarbons (dichloromethane, chloroform, etc.), ethers (diethyl ether, dioxane, tetrahydrofuran, etc.), esters (ethyl acetate, etc.), amides (N,N-dimethylformamide, etc.), carboxylic acids (acetic acid, etc.), water and a mixture thereof. The hydrogen pressure at which the reaction is carried out is generally about 1 to 50 atm, preferably about 1 to 10 atm. The reaction temperature is generally about 0° C. to 150° C., preferably about 20° C. to 100° C., and the reaction time is generally about 5 min to 72 hr, preferably about 0.5 to 40 hr.

In this reaction, the above-mentioned formation reaction and reduction reaction of the enamine or iminium ion are simultaneously carried our without isolation of the intermediate enamine or iminium ion. In this case, the pH of the reaction mixture is preferably about 4 to 5.

In the amination reaction, N-nitroso compound obtained by subjecting compound (VI) to N-nitrosation is reduced and, for example, the above-mentioned alkylation reaction or acylation reaction and the like are performed by a method known per se to give compound (VII).

The N-nitrosation reaction can be carried out according to a method known per se, for example, the methods described in "4th Ed. Jikken Kagaku Koza (Courses in Experimental Chemistry) 20, Organic Synthesis II", The Chemical Society of Japan Ed. 1991 and the like, or a method analogous thereto. Examples of the method include a method using tert-butyl nitrite or sodium nitrite. The amount thereof to be used is about 1 equivalent to 20 equivalents, preferably about 1 equivalent to 5 equivalents. The reaction is generally carried out in a solvent that does not adversely influence the reaction. The reaction may be promoted using an acid. Examples of the solvent include hydrocarbons (benzene, toluene, xylene and the like), halogenated hydrocarbons (dichloromethane, chloroform and the like), ethers (diethyl ether, dioxane, tetrahydrofuran and the like), carboxylic acids (acetic acid and the like), water and a mixture thereof. Examples of the acid include hydrochloric acid, nitric acid and the like. The reaction temperature is generally about 0° C. to 150° C., preferably about 0° C. to 100° C. The reaction time is generally 5 min to 72 hr, preferably 0.5 to 40 hr.

The reduction reaction of N-nitroso compound can be generally carried out by using a metal or a metal salt or a metal hydride. Examples of the metal or metal salt to be used include alkali metals (lithium, sodium, potassium and the like), alkaline earth metals (magnesium, calcium and the like), other metals (zinc, chrome, titanium, iron, samarium, selenium and the like), metal salts (zinc-amalgam, zinc-copper alloy, aluminum-amalgam, sodium hydrosulfite and the like) and the like. Examples of the metal hydride include lithium aluminum hydride. The amount of the reducing agent to be used is 1 to 50 molar equivalents, preferably about 1 to 5 molar equivalents, per 1 mol of the substrate.

Examples of the solvent to be used for the reaction include alcohols (methanol, ethanol, 2-propanol, t-butanol, benzyl alcohol and the like), amines (liquid ammonia, methylamine, ethylamine, ethylenediamine and the like), ethers (diethyl ether, tetrahydrofuran, dioxane, dimethoxyethane and the like), mineral acids (hydrochloric acid, hydrobromic acid, sulfuric acid and the like), carboxylic acids (acetic acid and the like), amides (hexamethylphosphoramide), water and the like. Such solvent may be used alone or in a mixture.

The reaction temperature is generally about −80° C. to 150° C., preferably about −80° C. to 100° C. The reaction time is generally 5 min to 48 hr, preferably 1 to 24 hr.

(Step 6)

In this step, compound (IV) is deprotected to give a compound represented by the formula (VIII) or a salt thereof (hereinafter to be referred to as compound (VIII)). This step can be performed by a method similar to the method described in Method A, step 4.

(Step 7)

In this step, compound (VIII) is subjected to an alkylation reaction, acylation reaction, enamine formation reaction, reductive condensation reaction, or amination reaction to give a compound represented by the formula (IX) or a salt thereof (hereinafter to be referred to as compound (IX)). This step can be performed by a method similar to the method described in Method A, step 5.

(Step 8)

In this step, compound (IX) is reacted with a compound represented by the formula

　(XI)

or

　(XI')

wherein each symbol is as defined above, or a salt thereof to give compound (VII).

This step can be performed by a method similar to the method described in Method A, step 3.

(Step 9)

In this step, compound (II) is subjected to a rearrangement reaction to convert to a compound represented by the formula (XIII) or a salt thereof (hereinafter to be referred to as compound (XIII)). This step can be performed by a method similar to the rearrangement reaction described in Method A, step 1-1.

(Step 10)

In this step, compound (XIII) is reacted with a compound represented by the formula (XLVII)

wherein each symbol is as defined above, or a salt thereof (hereinafter to be referred to as compound (XLVII)) to give compound (IV). Compound (XLVII) is commercially available or can be produced by a known method. The amount thereof to be used is about 1 to 10 molar equivalents, preferably about 1 to 2 molar equivalents, of compound (XIX) per 1 mol of compound (XIII). This step can be performed by a method similar to the method described in Method A, step 2.

For example, when compound (I) is a compound represented by the formula (VIIa) or a salt thereof (hereinafter to be referred to as compound (VIIa)), it can be produced by the following Method B.

[Method B]

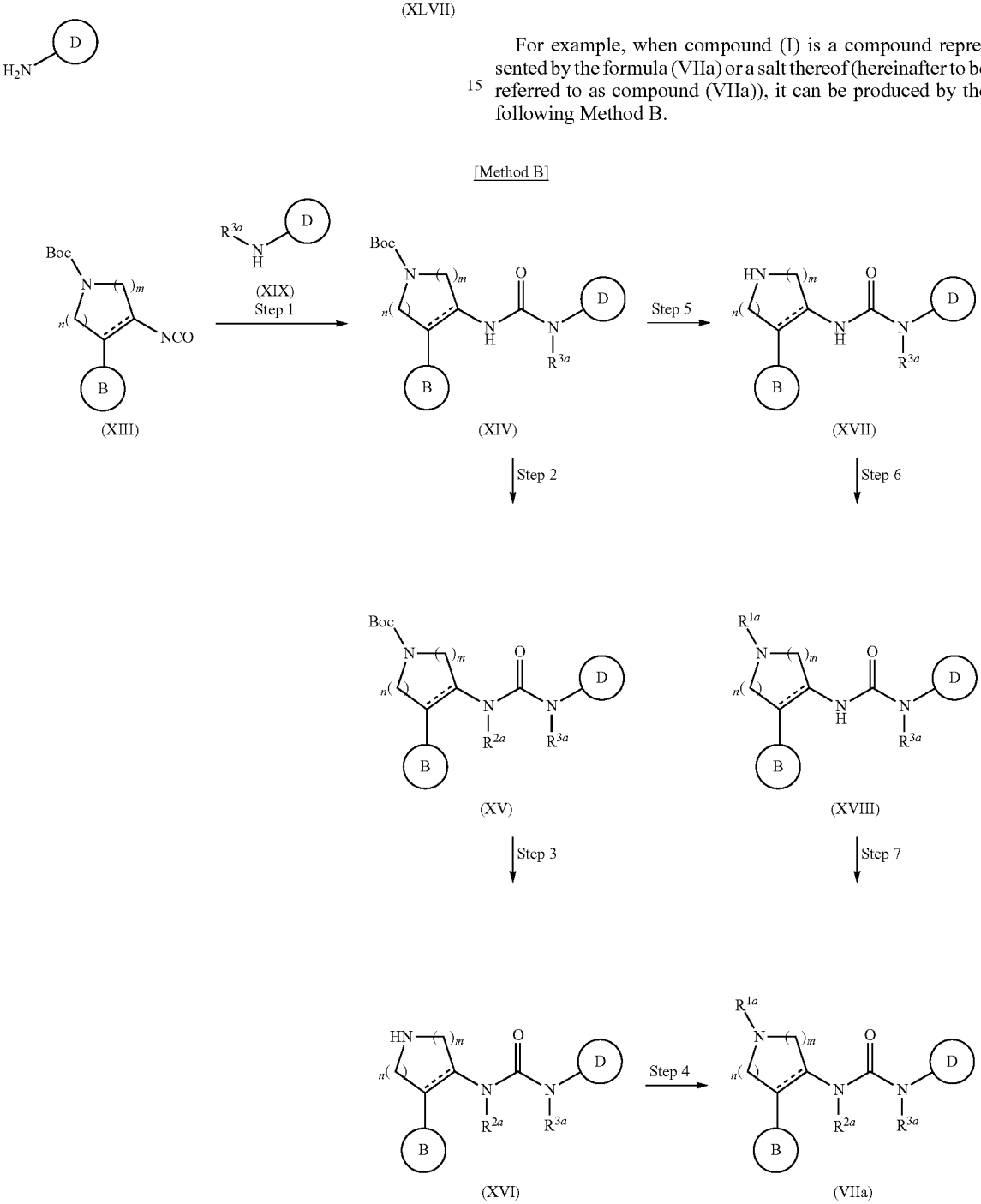

wherein each symbol is as defined above.

(Step 1)

In this step, compound (XIII) is reacted with a compound represented by the formula

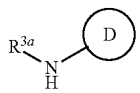 (XIX)

wherein each symbol is as defined above, or a salt thereof (hereinafter to be referred to as compound (XIX)) to give a compound represented by the formula (XIV) or a salt thereof (hereinafter to be referred to as compound (XIV)). Compound (XIX) is commercially available or can be produced by a known method. The amount thereof to be used is about 1 to 10 molar equivalents, preferably about 1 to 2 molar equivalents, of compound (XIX) per 1 mol of compound (XIII). This step can be performed by a method similar to the method described in Method A, step 2.

(Step 2)

In this step, compound (XIV) is reacted with a compound represented by the formula $R^{2a}$—X  (XI)

wherein each symbol is as defined above, or a salt thereof to give a compound represented by the formula (XV) or a salt thereof (hereinafter to be referred to as compound (XV)).

This step can be performed by a method similar to the method described in Method A, step 3.

(Step 3)

In this step, compound (XV) is deprotected to give a compound represented by the formula (XVI) or a salt thereof (hereinafter to be referred to as compound (XVI)). This step can be performed by a method similar to the method described in Method A, step 4.

(Step 4)

In this step, compound (XVI) is subjected to an alkylation reaction, acylation reaction, enamine formation reaction, reductive condensation reaction, or amination reaction to give compound (VIIa). This step can be performed by a method similar to the method described in Method A, step 5.

(Step 5)

In this step, compound (XIV) is deprotected to give a compound represented by the formula (XVII) or a salt thereof (hereinafter to be referred to as compound (XVII)). This step can be performed by a method similar to the method described in Method A, step 4.

(Step 6)

In this step, compound (XVII) is subjected to an alkylation reaction, acylation reaction, enamine formation reaction, reductive condensation reaction, or amination reaction to give a compound represented by the formula (XVIII) or a salt thereof (hereinafter to be referred to as compound (XVIII)). This step can be performed by a method similar to the method described in Method A, step 5.

(Step 7)

In this step, compound (XVIII) is reacted with a compound represented by the formula $R^{2a}$—X  (XI)

wherein each symbol is as defined above, or a salt thereof to give compound (VIIa). This step can be performed by a method similar to the method described in Method A, step 3.

Compound (VIIa) can be produced by the following Method C.

[Method C]

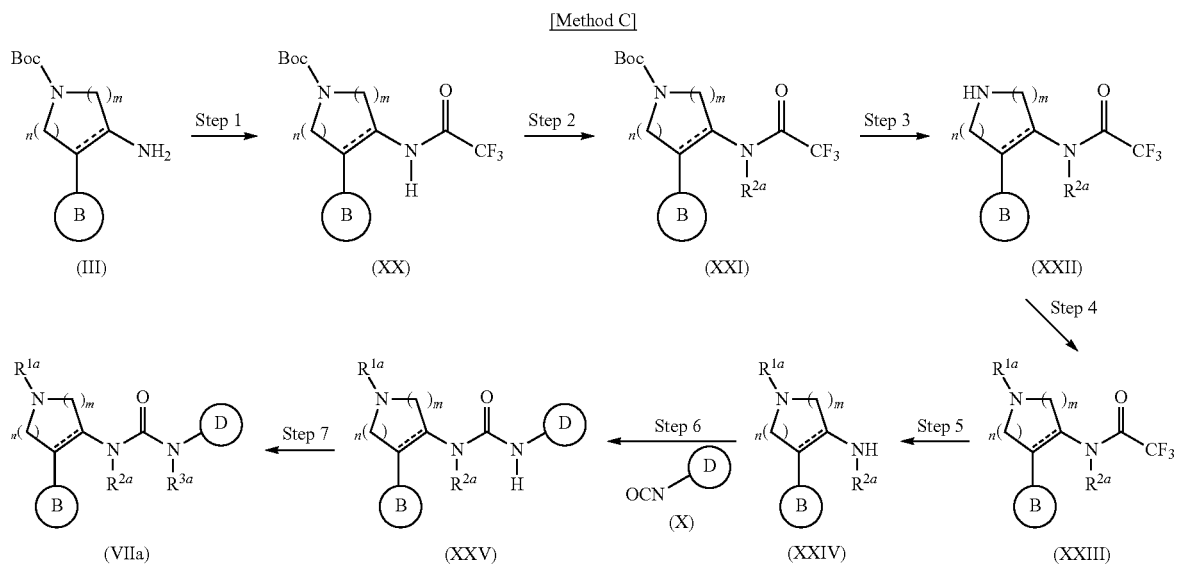

wherein each symbol is as defined above.

(Step 1)

In this step, compound (III) is subjected to trifluoroacetylation reaction to give the compound represented by the formula (XX) or a salt thereof (hereinafter to be referred to as compound (XX)).

This reaction can be carried out according to a known method (e.g., "Protective Groups in Organic Synthesis, 3$^{rd}$ Ed." by Theodara W. Greene, Peter G. M. Wuts, published by Wiley-Interscience, 1999). This reaction can be generally carried out by reacting compound (III) with a trifluoroacetylating agent in a solvent that does not adversely influence the reaction in the presence of a base.

Examples of the trifluoroacetylating agent include trifluoroacetates (ethyl trifluoroacetate and the like), trifluoroacetic anhydride, succinimide trifluoroacetate and the like. The amount of the trifluoroacetylating agent to be used is generally about 1 to 100 molar equivalents, preferably about 1 to 10 molar equivalents, per 1 mol of compound (III).

Examples of the base include alkali metal hydroxides (sodium hydroxide, potassium hydroxide and the like), hydrogen carbonates (sodium hydrogen carbonate, potassium hydrogen carbonate and the like), carbonates (sodium carbonate, potassium carbonate and the like), acetates (sodium acetate and the like), tertiary amines (trimethylamine, triethylamine, N-methylmorpholine) aromatic amines (pyridine, picoline, N,N-dimethylaniline and the like) and the like. The amount of the base to be used is generally about 1 to 100 molar equivalents, preferably about 1 to 10 molar equivalents, per 1 mol of compound (III).

Examples of the solvent that does not adversely influence the reaction include alcohols (methanol, ethanol, propanol, 2-propanol, butanol, isobutanol, t-butanol and the like), aromatic hydrocarbons (benzene, toluene, xylene and the like), aliphatic hydrocarbons (hexane, heptane and the like), halogenated hydrocarbons (dichloromethane, chloroform and the like), ethers (diethyl ether, diisopropyl ether, t-butyl methyl ether, tetrahydrofuran, dioxane, dimethoxyethane and the like), nitriles (acetonitrile and the like), esters (ethyl acetate and the like), carboxylic acids (acetic acid and the like), amides (N,N-dimethylformamide and the like), sulfoxides (dimethyl sulfoxide and the like) and the like. Such solvent may be used in a mixture of two or more at a suitable ratio.

The reaction temperature is, for example, within the range of about −50° C. to 200° C., preferably about 0° C. to 100° C. While the reaction time varies depending on the kind of compound (III) or a salt thereof, the reaction temperature and the like, it is, for example, about 0.5 to 100 hr, preferably about 0.5 to 24 hr.

(Step 2)

In this step, compound (XX) is reacted with a compound represented by the formula

$$R^{2a}-X \qquad (XI)$$

wherein each symbol is as defined above, or a salt thereof to give a compound represented by the formula (XXI) or a salt thereof (hereinafter to be referred to as compound (XXI)). This step can be performed by a method similar to the method described in Method A, step 3.

(Step 3)

In this step, compound (XXI) is deprotected to give a compound represented by the formula (XXII) or a salt thereof (hereinafter to be referred to as compound (XXII)). This step can be performed by a method similar to the method described in Method A, step 4.

(Step 4)

In this step, compound (XXII) is subjected to an alkylation reaction, acylation reaction, enamine formation reaction, reductive condensation reaction, or amination reaction to give a compound represented by the formula (XXIII) or a salt thereof (hereinafter to be referred to as compound (XXIII)). This step can be performed by a method similar to the method described in Method A, step 5.

(Step 5)

In this step, compound (XXIII) is deprotected to give the compound represented by the formula (XXIV) or a salt thereof.

This reaction can be carried out according to a known method (e.g., "Protective Groups in Organic Synthesis, 3rd Ed.," by Theodara W. Greene, Peter G. M. Wuts, published by Wiley-Interscience, 1999). For example, while the reaction varies depending on the kind of compound (XXIII), it is generally in the presence of a base, as necessary in a solvent that does not adversely influence the reaction.

Examples of the base include alkali metal hydroxides (sodium hydroxide, potassium hydroxide and the like), hydrogen carbonates (sodium hydrogen carbonate, potassium hydrogen carbonate and the like), carbonates (sodium carbonate, potassium carbonate and the like), acetates (sodium acetate), ammonium salts (benzyltriethylammonium hydroxide and the like) and the like. The amount of the base to be used is generally about 1 to 100 molar equivalents, preferably about 1 to 10 molar equivalents, per 1 mol of compound (XXIII).

Examples of the solvent that does not adversely influence the reaction include alcohols (methanol, ethanol, propanol, 2-propanol, butanol, isobutanol, t-butanol and the like), aromatic hydrocarbons (benzene, toluene, xylene and the like), aliphatic hydrocarbons (hexane, heptane and the like), halogenated hydrocarbons (dichloromethane, chloroform and the like), ethers (diethyl ether, diisopropyl ether, t-butyl methyl ether, tetrahydrofuran, dioxane, dimethoxyethane and the like), nitriles (acetonitrile and the like), esters (ethyl acetate and the like), carboxylic acids (acetic acid and the like), amides (N,N-dimethylformamide and the like), sulfoxides (dimethyl sulfoxide and the like), water and the like. Such solvent may be used in a mixture of two or more at a suitable ratio.

The reaction temperature is, for example, within the range of about −50° C. to 200° C., preferably about 0° C. to 100° C. While the reaction time varies depending on the kind of compound (XXIII), the reaction temperature and the like, it is, for example, about 0.5 to 400 hr, preferably about 0.5 to 120 hr.

(Step 6)

In this step, compound (XXIV) is reacted with a compound represented by the formula

wherein each symbol is as defined above, or a salt thereof to give a compound represented by the formula (XXV) or a salt thereof (hereinafter to be referred to as compound (XXV)). This step can be performed by a method similar to the method described in Method A, step 2.

(Step 7)

In this step, compound (XXV) is reacted with a compound represented by the formula

$$R^{3a}-X \qquad (XI')$$

[wherein each symbol is as defined above, or a salt thereof (hereinafter to be referred to as compound (XI')) to give compound (VIIa). Compound (XI') is commercially available or can be produced by a known method. The amount thereof to be used is about 1 to 10 molar equivalents, preferably about 1 to 4 molar equivalents, of compound (XI') per 1 mol of compound (XXV). This step can be performed by a method similar to the method described in Method A, step 3.

For example, when compound (I) is a compound represented by the formula (XXX) or a salt thereof (hereinafter to be referred to as compound (XXX)), and $R^{2a}=R^{3a}$, can be produced by the following Method D.

[Method D]

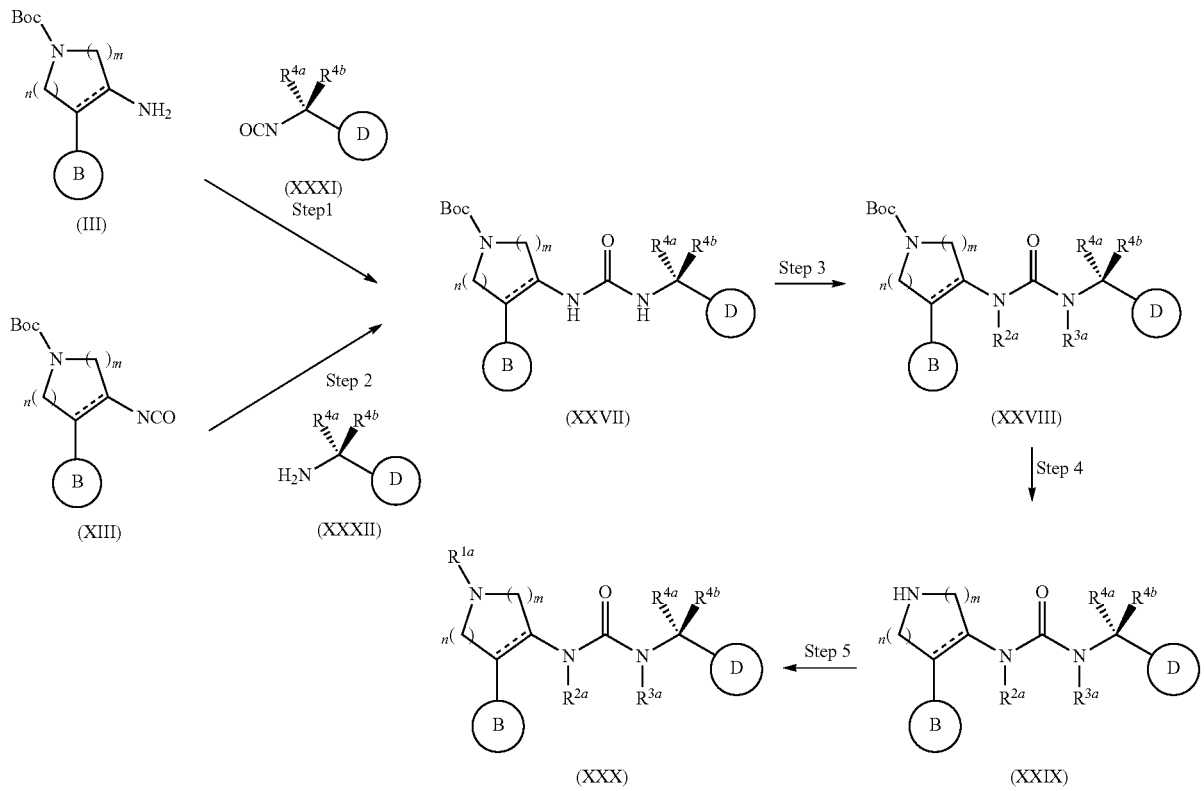

wherein each symbol is as defined above.
(Step 1)
In this step, compound (III) is reacted with a compound represented by the formula (XXXI)

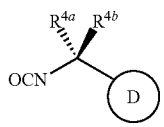

wherein each symbol is as defined above, or a salt thereof (hereinafter to be referred to as compound (XXXI)) to give a compound represented by the formula (XXVII) or a salt thereof (hereinafter to be referred to as compound (XXVII)). Compound (XXXI) is commercially available or can be produced by a known method. The amount thereof to be used is about 1 to 10 molar equivalents, preferably about 1 to 2 molar equivalents, of compound (XXXI) per 1 mol of compound (III). This step can be performed by a method similar to the method described in Method A, step 2.
(Step 2)
In this step, compound (XIII) is reacted with a compound represented by the formula (XXXII)

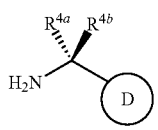

wherein each symbol is as defined above, or a salt thereof (hereinafter to be referred to as compound (XXXII)) to give compound (XXVII). Compound (XXXII) is commercially available or can be produced by a known method. The amount thereof to be used is about 1 to 10 molar equivalents, preferably about 1 to 2 molar equivalents, of compound (XXXII) per 1 mol of compound (XIII). This step can be performed by a method similar to the method described in Method A, step 2.
(Step 3)
In this step, compound (XXVII) is reacted with a compound represented by the formula $R^{2a}$—X                                    (XI)

or $R^{3a}$—X                                    (XI')

wherein each symbol is as defined above, or a salt thereof to give a compound represented by the formula (XXVIII) or a salt thereof (hereinafter to be referred to as compound (XXVIII)). This step can be performed by a method similar to the method described in Method A, step 3.
(Step 4)
In this step, compound (XXVIII) is deprotected to give a compound represented by the formula (XXIX) or a salt thereof (hereinafter to be referred to as compound (XXIX)). This step can be performed by a method similar to the method described in Method A, step 4.
(Step 5)
In this step, compound (XXIX) is subjected to an alkylation reaction, acylation reaction, enamine formation reaction, reductive condensation reaction, or amination reaction to give compound (XXX). This step can be performed by a method similar to the method described in Method A, step 5.

For example, when compound (I) is a compound represented by the formula (XXXVII) or a salt thereof (hereinafter to be referred to as compound (XXXVII)), it can be produced by the following Method E.

[Method E]

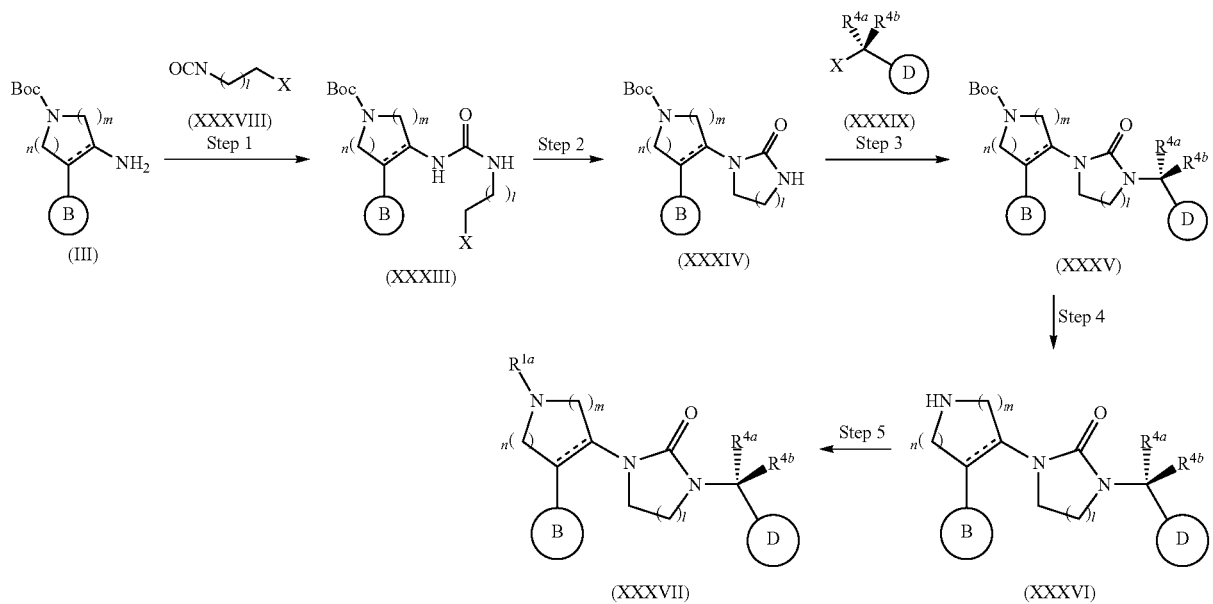

wherein l is an integer of 1 to 3, and each of other symbols is as defined above.

(Step 1)

In this step, compound (III) is reacted with a compound represented by the formula

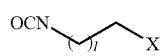 (XXXVIII)

wherein each symbol is as defined above, or a salt thereof (hereinafter to be referred to as compound (XXXVIII)) to give a compound represented by the formula (XXXIII) or a salt thereof (hereinafter to be referred to as compound (XXXIII)). Compound (XXXVIII) is commercially available or can be produced by a known method. The amount thereof to be used is about 1 to 10 molar equivalents, preferably about 1 to 2 molar equivalents, of compound (XXXVIII) per 1 mol of compound (III). This step can be performed by a method similar to the method described in Method A, step 2.

(Step 2)

In this step, compound (XXXIII) is treated with a base to give a compound represented by the formula (XXXIV) or a salt thereof (hereinafter to be referred to as compound (XXXIV)). Where necessary, the reaction is performed in a solvent that does not adversely influence the reaction.

Examples of the base include organic bases (trimethylamine, triethylamine, N-methylmorpholine, pyridine, picoline, N,N-dimethylaniline and the like), inorganic bases (potassium carbonate, sodium carbonate, potassium hydroxide, sodium hydroxide and the like), alkali metal alkoxide (sodium methoxide, sodium ethoxide, sodium-t-butoxide, potassium-t-butoxide and the like), metal amides (lithium disilazide, sodium disilazide, potassium disilazide, lithium diisopropylamide and the like), metal hydrides (lithium hydride, sodium hydride, potassium hydride, calcium hydride) and the like. The amount of the base to be used is, for example, about 1 to 100 molar equivalents, preferably about 1 to 10 molar equivalents, per 1 mol of compound (XXXIII).

Examples of the solvent that does not adversely influence the reaction include alcohols (methanol, ethanol, propanol and the like), ethers (dimethoxyethane, dioxane, tetrahydrofuran and the like), ketones (acetone and the like), nitriles (acetonitrile and the like), amides (N,N-dimethylformamide and the like), sulfoxides (dimethyl sulfoxide and the like), water and the like, which may be appropriately mixed and used.

Where necessary, an additive can also be used to promote the reaction. Examples of the additive include iodides (sodium iodide, potassium iodide, tetrabutylammonium iodide and the like) and the like. The amount thereof to be used is about 0.1 to 10 molar equivalents, preferably about 0.1 to 5 molar equivalents, per 1 mol of compound (XXXIII).

The reaction temperature is generally −10 to 200° C., preferably about 0 to 120° C., and the reaction time is generally 0.5 to 48 hr, preferably about 0.5 to 16 hr.

(Step 3)

In this step, compound (XXXIV) is reacted with a compound represented by the formula

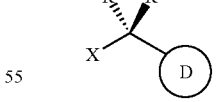 (XXXIX)

wherein each symbol is as defined above, or a salt thereof (hereinafter to be referred to as compound (XXXIX)) to give a compound represented by the formula (XXXV) or a salt thereof (hereinafter to be referred to as compound (XXXV)). Compound (XXXIX) is commercially available or can be produced by a known method. The amount thereof to be used is about 1 to 10 molar equivalents, preferably about 1 to 2 molar equivalents, of compound (XXXIX) per 1 mol of compound (XXXIV). This step can be performed by a method similar to the method described in Method A, step 3.

(Step 4)

In this step, compound (XXXV) is deprotected to give a compound represented by the formula (XXXVI) or a salt thereof (hereinafter to be referred to as compound (XXXVI)). This step can be performed by a method similar to the method described in Method A, step 4.

(Step 5)

In this step, compound (XXXVI) is subjected to an alkylation reaction, acylation reaction, enamine formation reaction, reductive condensation reaction, or amination reaction to give compound (XXXVII). This step can be performed by a method similar to the method described in Method A, step 5.

For example, compound (I) is a compound represented by the formula (XLV) or a salt thereof (hereinafter to be referred to as compound (XLV)), it can be produced by the following method F.

wherein each symbol is as defined above, or a salt thereof (hereinafter to be referred to as compound (XLVI)) to give imine, which is then subjected to a reduction reaction to give a compound represented by the formula (XL) or a salt thereof (hereinafter to be referred to as compound (XL)). Compound (XLVI) is commercially available or can be produced by a known method. The amount thereof to be used is about 1 to 10 molar equivalents, preferably about 1 to 2 molar equivalents, of compound (XLVI) per 1 mol of compound (III). This step can be performed by a method similar to the reductive condensation reaction described in Method A, step 5.

(Step 2)

In this step, compound (XL) is deprotected to give a compound represented by the formula (XLI) or a salt thereof (hereinafter to be referred to as compound (XLI)). This step

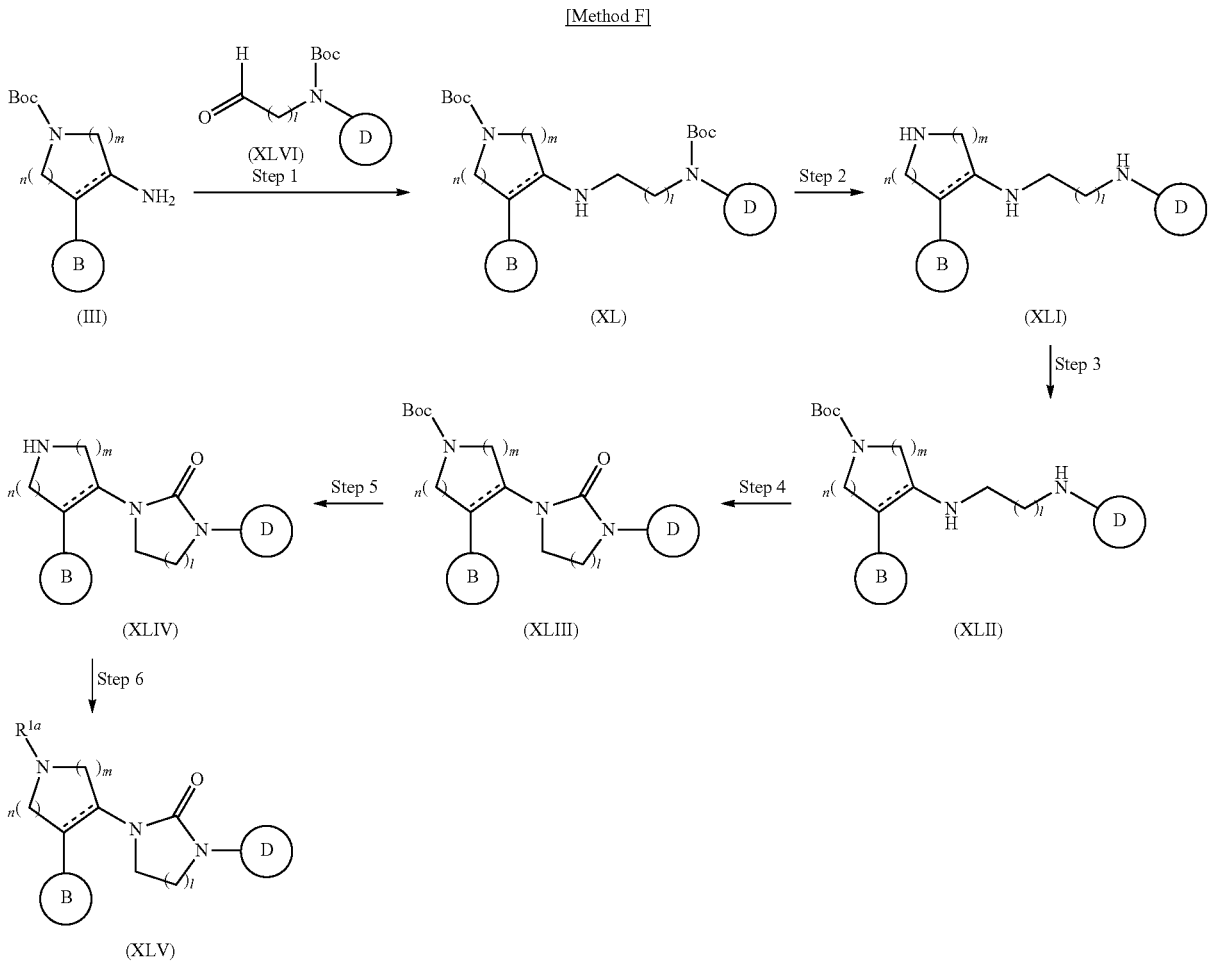

wherein each symbol is as defined above.

(Step 1)

In this step, compound (III) is reacted with a compound represented by the formula

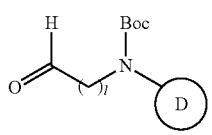

(XLVI)

can be performed by a method similar to the method described in Method A, step 4.

(Step 3)

In this step, compound (XLI) is subjected to tert-butoxycarbonylation reaction to give the compound represented by the formula (XLII) or a salt thereof (hereinafter to be referred to as compound (XLII)).

This reaction can be carried out according to a known method (e.g., "Protective Groups in Organic Synthesis, 3$^{rd}$ Ed." by Theodara W. Greene, Peter G. M. Wuts, published by Wiley-Interscience, 1999). For example, while the reaction varies depending on the kind of compound (XLI), it is generally carried out by reacting compound (XLI) or a salt thereof with a tert-butoxycarbonylating agent in the presence of a base, as necessary in a solvent that does not adversely influence the reaction.

Examples of the base include alkali metal hydroxides (sodium hydroxide, potassium hydroxide and the like), hydrogen carbonates (sodium hydrogen carbonate, potassium hydrogen carbonate and the like), carbonates (sodium carbonate, potassium carbonate and the like), acetates (sodium acetate and the like), tertiary amines (trimethylamine, triethylamine, N-methylmorpholine and the like), aromatic amines (pyridine, picoline, N,N-dimethylaniline and the like) and the like. The amount of the base to be used is generally about 1 to 10 molar equivalents, preferably about 1 to 2 molar equivalents, per 1 mol of compound (XLI).

Examples of the tert-butoxycarbonylating agent include di-tert-butyl bicarbonate and the like. The amount thereof to be used is about 1 to 10 molar equivalents, preferably about 1 to 2 molar equivalents, per 1 mol of compound (XLI).

Examples of the solvent that does not adversely influence the reaction include alcohols (methanol, ethanol, propanol, 2-propanol, butanol, isobutanol, t-butanol and the like), aromatic hydrocarbons (benzene, toluene, xylene and the like), aliphatic hydrocarbons (hexane, heptane and the like), halogenated hydrocarbons (dichloromethane, chloroform and the like), ethers (diethyl ether, diisopropyl ether, t-butyl methyl ether, tetrahydrofuran, dioxane, dimethoxyethane and the like), nitriles (acetonitrile and the like), esters (ethyl acetate and the like), carboxylic acids (acetic acid and the like), amides (N,N-dimethylformamide and the like), sulfoxides (dimethyl sulfoxide and the like), water and the like. Such solvent may be used in a mixture of two or more at a suitable ratio.

The reaction temperature is, for example, within the range of about −50° C. to 200° C., preferably about 0° C. to 100° C. While the reaction time varies depending on the kind of compound (XLI), the reaction temperature and the like, it is, for example, about 0.5 to 100 hr, preferably about 0.5 to 24 hr.

(Step 4)

In this step, compound (XLII) is subjected to a carbonylation reaction to give a compound represented by the formula (XLIII) or a salt thereof (hereinafter to be referred to as compound (XLIII)).

As a carbonylating agent for the carbonylation reaction, carbonates such as N,N'-carbonyldiimidazole, phosgene, bis(trichloromethyl) carbonate or diethyl carbonate and the like are used. The reaction is generally performed in a solvent that does not adversely influence the reaction, and a convenient base may be added for the progress of the reaction.

Examples of the solvent include alcohols (methanol, ethanol, propanol, 2-propanol, butanol, isobutanol, t-butanol and the like), hydrocarbons (benzene, toluene and the like), ethers (ethylether, dioxane, tetrahydrofuran and the like), amides (N,N-dimethylformamide and the like), aromatic amines (pyridine and the like), water and the like, which may be appropriately mixed. Examples of the base include metal hydrides (lithium hydride, sodium hydride, potassium hydride, calcium hydride and the like), alkali metal hydroxides (sodium hydroxide, potassium hydroxide and the like), hydrogen carbonates (sodium hydrogen carbonate, potassium hydrogen carbonate and the like), carbonates (sodium carbonate, potassium carbonate and the like), acetates (sodium acetate and the like), tertiary amines (trimethylamine, triethylamine, N-methylmorpholine and the like), aromatic amines (pyridine, picoline, N,N-dimethylaniline and the like) and the like. The amount of the base to be used is generally about 1 to 100 molar equivalents, preferably about 1 to 5 molar equivalents, per 1 mol of compound (XLII).

The reaction temperature is, for example, about −50 to 200° C., preferably about 0 to 100° C., and the reaction time varies depending on the kind of compound (XLII), reaction temperature and the like. It is, for example, about 0.5 to 100 hr, preferably about 0.5 to 24 hr.

(Step 5)

In this step, compound (XLIII) is deprotected to give a compound represented by the formula (XLIV) or a salt thereof (hereinafter to be referred to as compound (XLIV)). This step can be performed by a method similar to the method described in Method A, step 4.

(Step 6)

In this step, compound (XLIV) is subjected to an alkylation reaction, acylation reaction, enamine formation reaction, reductive condensation reaction, or amination reaction to give compound (XLV). This step can be performed by a method similar to the method described in Method A, step 5.

Compound (II) produced in the above-mentioned Method A and Method B can also be produced according to a known method (e.g., WO2005/068427, WO2006/004195, Bioorganic & Medicinal Chemistry Letters 13 (2003) 4431-4435, Bioorganic & Medicinal Chemistry Letters 15 (2005) 4023-4028, Bioorganic & Medicinal Chemistry Letters 17 (2007) 5310-5315 and the like).

In each of the reactions for the synthesis of the objective compounds and the starting materials, when the starting compounds have an amino group, a carboxyl group or a hydroxyl group as a substituent, such groups may be protected with the protecting groups which are generally used in peptide chemistry, etc. In such case, if necessary, such protecting groups can be removed to obtain the objective compounds after the reactions.

Such protecting group includes, for example, protecting groups described in "Protective Groups in Organic Synthesis, 3$^{rd}$ Ed." by Theodora W. Greene, Peter G. M. Wuts, published by Wiley-Interscience, 1999.

The protecting group for the amino group includes, for example, a formyl group, a $C_{1-6}$ alkyl-carbonyl group (an acetyl group, a propionyl group, etc.), a phenylcarbonyl group, a $C_{1-6}$ alkyl oxycarbonyl group (a methoxycarbonyl group, an ethoxycarbonyl group, etc.), a aryloxycarbonyl group (a phenyloxycarbonyl group, etc.), a $C_{7-10}$ aralkyl-carbonyl group (a benzyloxycarbonyl group, etc.), a benzyl group, a benzhydryl group, a trityl group, a phthaloyl, etc., each of which may be substituted. Such substituent includes, for example, a halogen atom (a fluorine atom, a chlorine atom, a bromine atom, an iodine atom, etc.), a $C_{1-6}$ alkyl-carbonyl group (an acetyl group, a propionyl group, a butylcarbonyl group, etc.), a nitro group and the like. The number of substituent is in the order of 1 to 3.

A protecting group for the carboxyl group includes, for example, a $C_{1-6}$ alkyl group (a methyl group, an ethyl group, an n-propyl group, an isopropyl group, an n-butyl group, a tert-butyl group, etc.), a phenyl group, a trityl group, a silyl group and the like, each of which may be substituted. Such substituent includes, for example, a halogen atom (a fluorine atom, a chlorine atom, a bromine atom, an iodine atom, etc.), a formyl group, a $C_{1-6}$ alkyl-carbonyl group (an acetyl group, a propionyl group, a butylcarbonyl group, etc.), a nitro group and the like. The number of substituent is in the order of 1 to 3.

The protecting group for the hydroxyl group includes, for example, a $C_{1-6}$ alkyl group (a methyl group, an ethyl group, an n-propyl group, an isopropyl group, an n-butyl group, a tert-butyl group, etc.), a phenyl group, a $C_{7-10}$ aralkyl group (a benzyl group, etc.), a formyl group, a $C_{1-6}$ alkyl-carbonyl group (an acetyl group, a propionyl group, etc.), a aryloxy-carbonyl group (a phenyloxycarbonyl group, etc.), a $C_{7-10}$ aralkyl-carbonyl group (a benzyloxycarbonyl group, etc.), a pyranyl group, a furanyl group, a silyl group and the like, each of which may be substituted. Such substituent includes, for example, a halogen atom (a fluorine atom, a chlorine atom, a bromine atom, an iodine atom, etc.), a $C_{1-6}$ alkyl group, a phenyl group, a $C_{7-10}$ aralkyl group, a nitro group and the like. The number of substituent is in the order of 1 to 4.

Such protecting groups can be removed by a known deprotection method or the method described in "Protective Groups in Organic Synthesis, 3$^{rd}$ Ed." by Theodora W. Greene, Peter G. M. Wuts, published by Wiley-Interscience, 1999, or an analogous method thereto. For example, treatment with an acid, a base, reduction, ultraviolet radiation, hydrazine, phenylhydrazine, sodium N-methyldithiocarbamate, tetrabutylammonium fluoride, palladium acetate or the like, can be used.

When compound (I) is obtained as a free compound in the above-mentioned method, a salt with for example, inorganic acids (hydrochloric acid, sulfuric acid, hydrobromic acid, etc.), organic acids (methanesulfonic acid, benzenesulfonic acid, p-toluenesulfonic acid, oxalic acid, fumaric acid, maleic acid, tartaric acid, etc.), inorganic bases (alkali metals such as sodium, potassium, etc., alkaline earth metals such as calcium, magnesium, etc., aluminum, ammonium, etc.), or organic bases (trimethylamine, triethylamine, pyridine, picoline, ethanolamine, diethanolamine, triethanolamine, dicyclohexylamine, N,N'-dibenzylethylenediamine, etc.) and the like can be produced in a routine manner. When compound (I) is obtained in the form of a salt, the compound can be converted to a free compound or another salt in a routine manner.

In addition, when the starting compound forms a salt in each of the above-mentioned reactions, the compound may be used as a salt. Such salt includes, for example, those exemplified as a salt of compound (I).

Compound (I) of the present invention thus produced by such method, can be isolated and purified by a typical separation means such as recrystallization, distillation, chromatography, etc.

When compound (I) contains an optical isomer, a stereoisomer, a regioisomer or a rotamer, these are also encompassed in compound (I), and can be obtained as a single product according to synthesis and separation methods known per se (concentration, solvent extraction, column chromatography, recrystallization, etc.). For example, when compound (I) has an optical isomer, an optical isomer resolved from this compound is also encompassed in compound (I).

The optical isomer can be produced by a method known per se. To be specific, an optically active synthetic intermediate is used, or the final racemate product is subjected to optical resolution according to a conventional method to give an optical isomer.

The method of optical resolution may be a method known per se, such as a fractional recrystallization method, a chiral column method, a diastereomer method, etc.

1) Fractional Recrystallization Method

A method wherein a salt of a racemate with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine, etc.) is formed, which is separated by a fractional recrystallization method, and if desired, a free optical isomer is obtained by a neutralization step.

2) Chiral Column Method

A method wherein a racemate or a salt thereof is applied to a column for separation of an optical isomer (a chiral column) to allow separation. In the case of a liquid chromatography, for example, a mixture of the optical isomers is applied to a chiral column such as ENANTIO-OVM (manufactured by Tosoh Corporation), CHIRAL series and the like, and developed with water, various buffers (phosphate buffer, etc.) and organic solvents (ethanol, methanol, isopropanol, acetonitrile, trifluoroacetic acid, diethylamine, etc.) solely or in admixture to separate the optical isomer. In the case of a gas chromatography, for example, a chiral column such as CP-Chirasil-DeX CB (manufactured by GL Sciences Inc.) and the like is used to allow separation.

3) Diastereomer Method

A method wherein a racemic mixture is prepared into a diastereomeric mixture by chemical reaction with an optically active reagent, which is made into a single substance by a typical separation means (a fractional recrystallization method, a chromatography method, etc.) and the like, and is subjected to a chemical treatment such as hydrolysis and the like to separate an optically active reagent moiety, whereby an optical isomer is obtained. For example, when compound (I) contains hydroxy, or primary or secondary amino in a molecule, the compound and an optically active organic acid (MTPA [α-methoxy-α-(trifluoromethyl)phenylacetic acid], (−)-menthoxyacetic acid, etc.) and the like are subjected to condensation reaction to give diastereomers in the ester form or in the amide form, respectively. When compound (I) has a carboxylic acid group, this compound and an optically active amine or an alcohol reagent are subjected to condensation reaction to give diastereomers in the amide form or in the ester form, respectively. The separated diastereomer is converted to an optical isomer of the original compound by acid hydrolysis or base hydrolysis.

Compound (I) or a salt thereof may be in the form of a crystal.

The crystal of compound (I) or a salt thereof (hereinafter, it may be referred to as crystal of the present invention) can be produced by crystallization of compound (I) or a salt thereof by a crystallization method known per se.

Examples of the crystallization method include a method of crystallization from a solution, a method of crystallization from vapor, a method of crystallization from the melts and the like.

The "crystallization from a solution" is typically a method of shifting a non-saturated state to supersaturated state by varying factors involved in solubility of compounds (solvent composition, pH, temperature, ionic strength, redox state, etc.) or the amount of solvent. To be specific, for example, a concentration method, a cooling method, a reaction method (a diffusion method, an electrolysis method), a hydrothermal growth method, a flux method and the like can be mentioned. Examples of the solvent to be used include aromatic hydrocarbons (benzene, toluene, xylene, etc.), halogenated hydrocarbons (dichloromethane, chloroform, etc.), saturated hydrocarbons (hexane, heptane, cyclohexane, etc.), ethers (diethyl ether, diisopropyl ether, tetrahydrofuran, dioxane, etc.), nitriles (acetonitrile, etc.), ketones (acetone, etc.), sulfoxides (dimethyl sulfoxide, etc.), amides (N,N-dimethylformamide, etc.), esters (ethyl acetate, etc.), alcohols (methanol, ethanol, isopropyl alcohol, etc.), water and the like. These solvents are used alone or in a combination of two or more at a suitable ratio (e.g., 1:1 to 1:100 (a volume ratio)).

The "crystallization from vapor" is, for example, a vaporization method (a sealed tube method, a gas stream method), a gas phase reaction method, a chemical transportation method and the like.

The "crystallization from the melts" is, for example, a normal freezing method (a Czockralski method, a temperature gradient method and a Bridgman method, etc.), a zone melting method (a zone leveling method and a floating zone method, etc.), a special growth method (a VLS method and a liquid phase epitaxy method, etc.) and the like.

Preferable examples of the crystallization method include a method of dissolving compound (I) or a salt thereof in a suitable solvent (e.g., alcohols such as methanol, ethanol, etc., etc.) at a temperature of 20 to 120° C., and cooling the resulting solution to a temperature not higher than the temperature of dissolution (e.g., 0 to 50° C., preferably 0 to 20° C.) and the like.

The thus obtained crystals of the present invention can be isolated, for example, by filtration and the like.

In the present specification, the melting point means that measured using, for example, a micro melting point apparatus (Yanako, MP-500D) or a DSC (differential scanning calorimetry) device (SEIKO, EXSTAR6000) and the like.

In the present specification, the peak by a powder X-ray diffraction means that measured using, for example, RINT2100 (Rigaku Corporation), etc. with a Cu—Kα1 ray (tube voltage: 40 KV; tube current: 50 mA) as a ray source.

In the present specification, moreover, the specific rotation ($[\alpha]_D$) means, for example, a specific rotation measured using a polarimeter (JASCO, P-1030 polarimeter (No. AP-2)) and the like.

In general, the melting points and the peak by a powder X-ray diffraction vary depending on the measurement apparatuses, the measurement conditions and the like. The crystal in the present specification may show different values from the melting point described in the present specification or the peak by a powder X-ray diffraction vary depending on the measurement apparatuses, as long as they are within each of a general error range.

The crystal of the present invention is superior in physico-chemical properties (melting point, solubility, stability, etc.) and biological properties (pharmacokinetics (absorption, distribution, metabolism, excretion), efficacy expression, etc.), and thus it is extremely useful as a medicament.

Compound (I) or a salt thereof or a prodrug thereof of the present invention (hereinafter sometimes to be abbreviated as the compound of the present invention) has a suppressive action on the promotion of tracheal vascular permeability induced by capsaicin, as well as a superior tachykinin receptor antagonistic action, for example, an SP receptor antagonistic action (an NK-1 receptor antagonistic action), NK-2 and NK-3 receptor antagonistic action and the like. It may concurrently have an NK-1 receptor antagonistic action and an NK-3 receptor antagonistic action, or an NK-2 receptor antagonistic action and an NK-3 receptor antagonistic action. The compound of the present invention is superior in an NK-1 and NK-2 receptors antagonistic action, particularly an NK-1 receptor antagonistic action. Moreover, the compound of the present invention is superior in an NK-1 and NK-2 dual receptor antagonistic action, and an NK-1, NK-2 and NK-3 triple receptor antagonistic action. Such compound of the present invention has low toxicity and is safe.

Accordingly, the compound of the present invention having the above-mentioned superior action can be used for mammals (e.g., mouse, rat, hamster, rabbit, cat, dog, bovine, sheep, monkey, human etc.) as a safe prophylactic or therapeutic drug for the SP-associated diseases indicated below.

(1) Lower urinary tract diseases (including lower urinary tract dysfunction, lower urinary tract symptom and the like) [for example, overactive bladder, prostatic hyperplasia, interstitial cystitis, chronic prostatitis, urine collection symptom (diurnal urinary frequency, nocturnal urinary frequency, urinary urgency, urinary incontinence, stress urinary incontinence, urge urinary incontinence, mixed urinary incontinence, enuresis, nocturnal enuresis, continuous urinary incontinence, other urinary incontinence, enhanced, decreased or missing bladder sensation etc.), voiding symptom (weak urinary stream (or slow stream), split urinary stream (or splitting stream), spraying stream, intermittent urinary stream (or intermittent stream), voiding postponement (or hesitancy), straining at urination (or straining), terminal dribbling (or terminal dribble) etc.), post-micturition symptom (sense of residual urine, post-micturition dribble etc.), symptom due to sexual intercourse (coital pain, vaginal dryness, urinary incontinence etc.), pelvic organ pain, symptom due to pelvic organ prolapse (foreign body sensation, lumbago etc.), genital organ pain or lower urinary tract pain (bladder pain, urethral pain, pudendalgia, vaginodynia, scrotal pain, perineal pain, pelvic pain etc.), genital organ or urinary tract pain syndrome (bladder pain syndrome, urethral pain syndrome, pudendalgia syndrome, vaginal syndrome, scrotal pain syndrome, perineal pain syndrome, pelvic pain syndrome etc.), symptom syndrome suggesting lower urinary tract dysfunction (overactive bladder syndrome, lower urinary tract symptom suggesting bladder outlet obstruction etc.), polyuria, urolithiasis (urinary duct, urethra) and the like]

(2) Digestive tract diseases (e.g., functional digestive tract disease, irritable bowel syndrome, functional dyspepsia, gastroesophageal reflux disease, dyschezia, constipation, diarrhea, malabsorption, dyspepsia, gastritis, duodenitis, erosive esophagitis, inflammatory bowel disease, ulcerative colitis, Crohn's disease, gastric ulcer, peptic ulcer, digestive tract diseases caused by *H. pylori* infection), vomiting, nausea, pain (e.g., organ pain, abdominal pain, gastric pain, heartburn, somatic pain, neuropathic pain, migraine, neuralgia, pruritus)

(3) Inflammatory or allergic diseases [for example, inflammatory bowel disease, allergic rhinitis, conjunctivitis, gastrointestinal allergy, pollinosis, anaphylaxis, dermatitis, herpes, psoriasis, bronchitis, expectoration, retinopathy, postoperative and posttraumatic inflammation, regression of puffiness, pharyngitis, cystitis, meningitidis, inflammatory ocular disease, etc.]

(4) Osteoarthropathy diseases [for example, rheumatoid arthritis (rheumatoid arthritis), arthritis deformans, rheumatoid myelitis, osteoporosis, abnormal growth of cells, bone fracture, bone refracture, osteomalacia, osteopenia, Peget's disease of bone, rigid myelitis, articular tissue destruction by gonarthrosis deformans and similar diseases thereto, etc.]

(5) Respiratory diseases [for example, cold syndrome, pneumonia, asthma, pulmonary hypertension, pulmonary thrombi/pulmonary embolism, pulmonary sarcoidosis, pulmonary tuberculosis, interstitial pneumonia, silicosis, adult respiratory distress syndrome, chronic obstructive pulmonary diseases, cough, etc.]

(6) Infectious diseases [for example, HIV infectious diseases, virus infectious diseases due to cytomegalo virus, influenza virus, herpes virus and the like, *rickettsia* infectious diseases, bacterial infectious diseases, sexually-transmitted diseases, carinii pneumonia, *H. pylori* infectious disease, systemic fungal infectious diseases, tuberculosis, invasive staphylococcal infectious diseases, acute viral encephalitis, acute bacterial meningitidis, AIDS encephalitis, septicemia, sepsis, sepsis gravis, septic shock, endotoxin shock, toxic shock syndromes, etc.]

(7) Cancers [for example, primary, metastatic or recurrent breast cancer, prostatic cancer, pancreatic cancer, gastric cancer, lung cancer, colorectal cancer (colorectal cancer, rectal cancer, anal cancer), esophagus cancer, duodenal cancer, head and neck cancer (cancer of the tongue, pharynx cancer, laryngeal cancer), brain tumor, schwannoma, non-small cell lung cancer, small cell lung cancer, liver cancer, kidney cancer, biliary tract cancer, uterine cancer (uterine body cancer, cervical cancer), ovarian cancer, urinary bladder cancer, skin cancer, Hemangioma, malignant lymphoma, malignant melanoma, thyroid cancer, bone tumor, Hemangioma, vascular fibroma, retinosarcoma, penile cancer, solid cancer in childhood, Kaposi's sarcoma, Kaposi's sarcoma caused by acquired immunodeficiency syndrome (AIDS), maxillary tumor, fibrous histiocytoma, leiomyosarcoma, rhabdomyosarcoma, liposarcoma, fibroid tumors of the uterus, osteoblastoma, osteosarcoma, chondrosarcoma, cancerous mesothelioma, tumors such as leukemia, Hodgkin's disease, etc.]

(8) Central nervous system diseases [for example, neurodegenerative diseases (e.g., Alzheimer's disease, Down's disease, Parkinson's disease, Creutzfeldt-Jakob's disease, amyotrophic lateral sclerosis (ALS), Huntington chorea, diabetic neuropathy, multiple sclerosis, etc.), mental diseases (e.g., schizophrenia, depression, mania, anxiety neurosis, obsessive-compulsive neurosis, panic disorder, epilepsy, alcohol dependence, an anxiety symptom, anxious mental state, etc.), central and peripheral nerve disorders (e.g., head trauma, spinal cord injury, brain edema, disorders of sensory function, abnormality of sensory function, disorders of autonomic nervous function and abnormality of autonomic nervous function, whiplash injury, etc.), memory disorders (e.g., senile dementia, amnesia, cerebrovascular dementia, etc.), cerebrovascular disorders (e.g., disorders and aftereffect and/or complication from intracerebral hemorrhage, brain infarction, etc., asymptomatic cerebro-vascular accident, transient cerebral ischemic attack, hypertensive encephalopathia, blood-brain barrier disorder, etc.), recurrence and aftereffect of cerebro-vascular accident (neural symptoms, mental symptoms, subjective symptoms, disorders of daily living activities, etc.), post-cerebrovascular occlusion central hypofunction, disorder or abnormality of autoregulation of cerebral circulation and/or renal circulation]

(9) Circulatory diseases [for example, acute coronary artery syndromes (e.g., acute myocardial infarction, unstable angina, etc.), peripheral arterial obstruction, Raynaud's disease, Buerger disease, restenosis after coronary-artery intervention (percutaneous transluminal coronary angioplasty (PTCA), atherectomy (DCA), stenting, etc.), restenosis after coronary-artery bypass operation, restenosis after intervention (angioplasty, atherectomy, stenting, etc.) or bypass operation in other peripheral artery, ischemic cardiac diseases (e.g., myocardial infarction, angina, etc.), myocarditis, intermittent claudication, lacunar infarction, arteriosclerosis (e.g., atherosclerosis, etc.), cardiac failure (acute cardiac failure, chronic cardiac failure including congestive cardiac failure), arrhythmia, progress of atherosclerotic plaque, thrombosis, hypertension, hypertensive tinnitus, hypotension, etc.]

(10) Pains [e.g., migraine, neuralgia etc.]

(11) Autoimmune diseases [for example, collagen disease, systemic lupus erythematosus, scleroderma, polyarteritis, myasthenia gravis, multiple sclerosis, Sjogren's syndrome, Behcet's disease, etc.]

(12) Hepatic diseases [e.g., hepatitis (including chronic hepatitis), cirrhosis, interstitial hepatic diseases, etc.]

(13) Pancreatic diseases [e.g., pancreatitis (including chronic pancreatitis), etc.]

(14) Renal diseases [e.g., nephritis, glomerulonephritis, glomerulosclerosis, renal failure, thrombotic microangiopathy, dialysis complications, organ disorders including nephropathia by radiation, diabetic nephropathy, etc.]

(15) Metabolic diseases [e.g., diabetic diseases (insulin-dependent diabetes, diabetic complications, diabetic retinopathy, diabetic microangiopathy, diabetic neuropathy, etc.), impaired glucose tolerance, obesity, benign prostatic hyperplasia, sexual dysfunction, etc.]

(16) Endocrine diseases [e.g., Addison's disease, Cushing's syndrome, melanocytoma, primary aldosteronism, etc.]

(17) Other diseases (i) Transplant rejection [e.g., posttransplantational rejection, posttransplantational polycythemia, hypertension, organ disorder and/or vascular hypertrophy, graft-versus-host disease, etc.]

(ii) Abnormality in characteristic of blood and/or blood components [e.g., enhancement in platelet aggregation, abnormality of erythrocyte deformability, enhancement in leukocyte adhesiveness, increase in blood viscosity, polycythemia, vascular peliosis, autoimmune hemolytic anemia, disseminated intravascular coagulation syndrome (DIC), multiple myelopathy, etc.]

(iii) Gynecologic diseases [e.g., climacteric disorder, gestational toxicosis, endometriosis, hysteromyoma, ovarian disease, mammary disease, etc.]

(iv) Dermatic diseases [e.g., keloid, Hemangioma, psoriasis, pruritus, etc.]

(v) Ophthalmic diseases [e.g., glaucoma, ocular hypertension disease, etc.]

(vi) Otolaryngological diseases [e.g., Menuel syndrome, tinnitus, gustation disorder, dizziness, disequilibrium, dysphagia, etc.]

(vii) Diseases due to environmental and/or occupational factors (e.g., radiation disorder, disorders by ultraviolet ray•infrared ray•laser ray, altitude sickness, etc.)

(viii) Ataxia (ix) Chronic Fatigue Syndrome

The compound of the present invention is useful as a tachykinin receptor antagonist, particularly, as an agent for the prophylaxis or treatment of the above-mentioned lower urinary tract diseases, digestive tract diseases, central nervous system diseases and the like.

The compound of the present invention is useful as a tachykinin receptor antagonist, particularly, as an agent for the prophylaxis or treatment of the above-mentioned lower urinary tract diseases, digestive tract diseases, central nervous system diseases and the like.

A pharmaceutical preparation containing the compound of the present invention may be in the form of a solid preparation such as powder, granule, tablet, capsule, suppository, orally disintegrable film and the like or a liquid such as syrup, emulsion, injection, suspension and the like.

The pharmaceutical preparations of the present invention can be produced by any conventional methods, for example, blending, kneading, granulation, tabletting, coating, sterilization, emulsification, etc., in accordance with the forms of the preparations to be produced. For the production of such pharmaceutical preparations, for example, each of the items in General Rules for Preparations in the Japanese Pharmacopoeia, can be made reference to. In addition, the pharmaceutical preparations of the present invention may be formulated into a sustained release preparation containing active ingredients and biodegradable polymer compounds. The sustained release preparation can be produced according to the method described in JP-A-9-263545.

In the pharmaceutical preparations of the present invention, the content of the compound of the present invention or a salt thereof varies depending on the forms of the preparations, but is generally in the order of about 0.01 to 100% by weight, preferably about 0.1 to 50% by weight, more preferably 0.5 to 20% by weight, relative to the total weight of each preparation.

When the compound of the present invention is used in the above-mentioned pharmaceutical preparations, it may be used alone, or in admixture with a suitable, pharmaceutically acceptable carrier, for example, excipients (e.g., starch, lactose, sucrose, calcium carbonate, calcium phosphate, etc.), binders (e.g., starch, arabic gum, carboxymethyl cellulose, hydroxypropyl cellulose, crystalline cellulose, alginic acid, gelatin, polyvinylpyrrolidone, etc.), lubricants (e.g., stearic acid, magnesium stearate, calcium stearate, talc, etc.), disintegrants (e.g., calcium carboxymethylcellulose, talc, etc.), diluents (e.g., water for injection, physiological saline, etc.) and if desired, with the additives (e.g., a stabilizer, a preservative, a colorant, a fragrance, a solubilizing agent, an emulsifier, a buffer, an isotonic agent, etc.) and the like, by ordinary methods. It can be formulated into the solid preparations such as powders, fine granules, granules, tablets, capsules, orally disintegrable films, etc., or into the liquid preparations such as injections, etc., and can be administered non-parenterally or parenterally.

The dose of the pharmaceutical preparation of the present invention varies depending on the kinds of the compound of the present invention or a pharmaceutically acceptable salt thereof, the administration route, the condition and the age of patients, etc. For example, the dose for oral administration of the pharmaceutical preparation to an adult patient suffering from abnormal micturition is generally from about 0.005 to 50 mg/kg body/day, preferably from about 0.05 to 10 mg/kg body/day, more preferably from about 0.2 to 4 mg/kg body/day, in terms of the compound of the present invention, which may be administered once a day or in two or three divided portions a day.

The dose of the pharmaceutical composition of the present invention in the form of a sustained release preparation varies depending on the kinds and the content of compound (I) or a salt thereof, the formulation, the duration time of drug release, the animals to be administered (e.g., mammals such as humans, rats, mice, cats, dogs, rabbits, bovines, pigs, etc.), and the purpose of administration. For example, when it is applied by parenteral administration, preferably about 0.1 to about 100 mg of compound (I) or a salt thereof is released from the preparation for 1 week.

The compound of the present invention can be used in a mixture or combination with other pharmaceutically active ingredients at a suitable ratio.

Combination of the compound of the present invention with other pharmaceutically active ingredients can give the following excellent effects:
(1) a dose can be reduced as compared with separate administration of the compound of the present invention or other pharmaceutically active ingredients. More specifically, when the compound of the present invention is combined with anticholinergic agents or NK-2 receptor antagonists, the dose can be reduced as compared with separate administration of anticholinergic agents or NK-2 receptor antagonists, and therefore, side effects such as dry mouth can be reduced;

(2) according to symptoms of patient (mild symptoms, severe symptoms, etc.), a drug to be combined with the compound of the present invention can be selected;
(3) by choosing other pharmaceutically active ingredients which have different mechanism of action from that of the compound of the present invention, the therapeutic period can be designed longer;
(4) by choosing other pharmaceutically active ingredients which have different mechanism of action from that of the compound of the present invention, continuation of therapeutic effects can be obtained; and
(5) by combining the compound of the present invention and other pharmaceutically active ingredients, excellent effects such as synergic effects can be obtained.

A drug which is mixed or combined with the compound of the present invention (hereinafter, briefly referred to as combination drugs) includes the following:
(1) Agent for Treating Diabetes Insulin preparations (e.g., animal insulin preparations extracted from the bovine or swine pancreas; human insulin preparations synthesized by a genetic engineering technique using *Escherichia coli* or a yeast; insulin zinc; protamine zinc insulin; a fragment or a derivative of insulin (e.g., INS-1, etc.), insulin sensitizers (e.g., pioglitazone hydrochloride, troglitazone, rosiglitazone or its maleate, JTT-501, MCC-555, YM-440, GI-262570, KRP-297, FK-614, CS-011, etc.), α-glucosidase inhibitors (e.g., voglibose, acarbose, miglitol, emiglitate, etc.), biguanides (e.g., phenformin, metformin, buformin, etc.), sulfonylureas (e.g., tolbutamide, glibenclamide, gliclazide, chlorpropamide, tolazamide, acetohexamide, glyclopyramide, glimepiride, etc.) and other insulin secretagogues (e.g., repaglinide, senaglinide, mitiglinide or its calcium salt hydrate, GLP-1, nateglinide, etc.), dipeptidylpeptidase IV inhibitors (e.g., sitagliptin, vildagliptin, saxagliptin, alogliptin etc.), $\beta_3$ agonists (e.g., CL-316243, SR-58611-A, UL-TG-307, AJ-9677, AZ40140, YM178 etc.), amylin agonists (e.g., pramlintide, etc.), phosphotyrosine phosphatase inhibitors (e.g., vanadic acid, etc.), gluconeogenesis inhibitors (e.g., glycogen phosphorylase inhibitors, glucose-6-phosphatase inhibitors, glucagon antagonists, etc.), SGLT (sodium-glucose cotransporter) inhibitors (e.g., T-1095, etc.) and the like.

(2) Agent for Treating Diabetic Complications

Aldose reductase inhibitors (e.g., tolrestat, epalrestat, zenarestat, zopolrestat, fidarestat (SNK-860), minalrestat (ARI-509), CT-112, etc.), neurotrophic factors (e.g., NGF, NT-3, etc.), AGE inhibitors (e.g., ALT-945, pimagedine, pyratoxathine, N-phenacylthiazolium bromide (ALT-766), EXO-226, etc.), active oxygen scavengers (e.g., thioctic acid, etc.), cerebral vasodilators (e.g., tiapride, etc.) and the like.

(3) Antihyperlipidemic Agent

Statin compounds inhibiting cholesterol synthesis (e.g., pravastatin, simvastatin, lovastatin, atorvastatin, fluvastatin, cerivastatin or their salt (e.g., sodium salt, etc.), etc.), squalene synthase inhibitors or fibrate compounds having triglyceride lowering action (e.g., bezafibrate, clofibrate, simfibrate, clinofibrate, etc.) and the like.

(4) Hypotensive Agent

Angiotensin converting enzyme inhibitors (e.g., captopril, enalapril, delapril, etc.), angiotensin II antagonists (e.g., losartan, candesartan cilexetil, etc.), calcium antagonists (e.g., manidipine, nifedipine, amlodipine, efonidipine, nicardipine, etc.), clonidine, and the like.

(5) Antiobesity Agent

Antiobesity drugs acting on the central nervous system (e.g., dexfenfluramine, fenfluramine, phentermine, sibutramine, anfepramone, dexamphetamine, mazindol, phenylpropanolamine, clobenzorex, etc.), pancreatic lipase inhibitors (e.g., orlistat, etc.), β3 agonists (e.g., CL-316243, SR-58611-A, UL-TG-307, AJ-9677, AZ40140, etc.), anorectic peptides (e.g., leptin, CNTF (Ciliary Neurotrophic Factor), etc.), cholecystokinin agonists (e.g., lintitript, FPL-15849, etc.).

(6) Diuretic Agent

Xanthine derivatives (e.g., theobromine sodium salicylate, theobromine calcium salicylate, etc.), thiazide preparations (e.g., ethiazide, cyclopenthiazide, trichlormethiazide, hydrochlorothiazide, hydroflumethiazide, benzylhydrochlorothiazide, penflutizide, polythiazide, methyclothiazide, etc.), antialdosterone preparations (e.g., spironolactone, triamterene, etc.), carbonic anhydrase inhibitors (e.g., acetazolamide, etc.), chlorobenzenesulfonamide preparations (e.g., chlorthalidone, mefruside, indapamide, etc.), azosemide, isosorbide, ethacrynic acid, piretanide, bumetanide, furosemide, etc.

(7) Chemotherapeutic Agent

Alkylating agents (e.g., cyclophosphamide, ifosamide, etc.), metabolic antagonists (e.g., methotrexate, 5-fluorouracil, etc.), antitumor antibiotics (e.g., mitomycin, adriamycin, etc.), plant-derived antitumor agents (e.g., vincristine, vindesine, taxol, etc.), cisplatin, carboplatin, etoposide, etc. Among these, 5-fluorouracil derivatives such as Furtulon and Neo-Furtulon are preferred.

(8) Immunotherapeutic Agent

Microorganism- or bacterium-derived components (e.g., muramyl dipeptide derivatives, Picibanil, etc.), immunopotentiator polysaccharides (e.g., lentinan, schizophyllan, krestin, etc.), genetically engineered cytokines (e.g., interferons, interleukins (IL), etc.), colony stimulating factors (e.g., granulocyte colony stimulating factor, erythropoietin, etc.) and the like. Among these, IL-1, IL-2, IL-12, etc. are preferred.

(9) Therapeutic Agent Recognized to Ameliorate Cachexia in Animal Models or Clinical Practice Progesterone derivatives (e.g., megestrol acetate) [Journal of Clinical Oncology, vol. 12, pp. 213-225, 1994], metoclopramide pharmaceuticals, tetrahydrocannabinol pharmaceuticals (the above references are applied to both), fat metabolism ameliorating agents (e.g., eicosapentanoic acid) [British Journal of Cancer, vol. 68, pp. 314-318, 1993], growth hormones, IGF-1, and antibodies to the cachexia-inducing factors such as TNF-α, LIF, IL-6 and oncostatin M.

(10) Antiinflammatory Agent

Steroids (e.g., dexamethasone, etc.), sodium hyaluronate, cyclooxygenase inhibitors (e.g., indomethacin, ketoprofen, loxoprofen, meloxicam, ampiroxicam, celecoxib, rofecoxib, etc.) and the like.

(11) Miscellaneous

Glycosylation inhibitors (e.g., ALT-711, etc.), nerve regeneration promoting drugs (e.g., Y-128, VX853, prosaptide, etc.), drugs acting on the central nervous system (e.g., antidepressants such as desipramine, amitriptyline, imipramine, fluoxetine, paroxetine, doxepin, etc.), anticonvulsants (e.g., lamotrigine, carbamazepine), antiarrhythmic drugs (e.g., mexiletine), acetylcholine receptor ligands (e.g., ABT-594), endothelin receptor antagonists (e.g., ABT-627), monoamine uptake inhibitors (e.g., tramadol), indoleamine uptake inhibitors (e.g., fluoxetine, paroxetine), narcotic analgesics (e.g., morphine), opioid receptor complete agonist (e.g., pentazocine), opioid receptor partial agonist (e.g., buprenorphine, axomadol, TRK-130), γ-aminobutyric acid (GABA) receptor agonists, GABA uptake inhibitors (e.g., tiagabine), $\alpha_2$ receptor agonists (e.g., clonidine), local analgesics (e.g., capsaicin), protein kinase C inhibitors (e.g., LY-333531), antianxiety drugs (e.g., benzodiazepines), phosphodiesterase inhibitors (e.g., sildenafil), dopamine receptor agonists (e.g., apomorphine), dopamine receptor antagonists (e.g., haloperidol), serotonin receptor agonists (e.g., tandospirone citrate, sumatryptan), serotonin receptor antagonists (e.g., cyproheptadine hydrochloride, ondansetron), serotonin uptake inhibitors (e.g., fluvoxamine maleate, fluoxetine, paroxetine), serotonin noradrenaline uptake inhibitors (e.g., duloxetine, venlafaxine), hypnotics (e.g., triazolam, zolpidem), anticholinergic agents, $\alpha_1$ receptor blocking agents (e.g., tamsulosin, naftopidil, silodosin), muscle relaxants (e.g., baclofen, etc.), potassium channel openers (e.g., nicorandil), calcium channel blocking agents (e.g., nifedipine, gabapentin), agents for preventing and/or treating Alzheimer's disease (e.g., donepezil, rivastigmine, galanthamine), agents for treating Parkinson's disease (e.g., L-dopa), agents for preventing and/or treating multiple sclerosis (e.g., interferon β-1a), histamine $H_1$ receptor inhibitors (e.g., promethazine hydrochloride), proton pump inhibitors (e.g., lansoprazole, omeprazole), antithrombotic agents (e.g., aspirin, cilostazol), NK-2 receptor antagonists, agents of treating HIV infection (saquinavir, zidovudine, lamivudine, nevirapine), agents of treating chronic obstructive pulmonary diseases (salmeterol, thiotropium bromide, cilomilast), etc.

Anticholinergic agents include, for example, atropine, scopolamine, homatropine, tropicamide, cyclopentolate, butylscopolamine bromide, propantheline bromide, methylbenactyzium bromide, mepenzolate bromide, flavoxate, pirenzepine, ipratropium bromide, trihexyphenidyl, oxybutynin, propiverine, darifenacin, tolterodine, temiverine, trospium chloride or a salt thereof (e.g., atropine sulfate, scopolamine hydrogen bromide, homatropine hydrogen bromide, cyclopentolate hydrochloride, flavoxate hydrochloride, pirenzepine hydrochloride, trihexyphenidyl hydrochloride, oxybutynin chloride, tolterodine tartrate, etc.), preferably, oxybutynin, propiverine, darifenacin, tolterodine, temiverine, trospium chloride or a salt thereof (e.g., oxybutynin chloride, tolterodine tartrate, etc.). In addition, acetylcholinesterase inhibitors (e.g., distigmine, etc.) and the like can be used.

NK-2 receptor antagonists include, for example, a piperidine derivative such as GR159897, GR149861, SR48968 (saredutant), SR144190, YM35375, YM38336, ZD7944, L-743986, MDL105212A, ZD6021, MDL105172A, SCH205528, SCH62373, R-113281, etc., a perhydroisoindole derivative such as RPR-106145, etc., a quinoline derivative such as SB-414240, etc., a pyrrolopyrimidine derivative such as ZM-253270, etc., a pseudopeptide derivative such as MEN11420 (nepadutant), SCH217048, L-659877, PD-147714 (CAM-2291), MEN10376, S16474, etc., and others such as GR100679, DNK333, GR94800, UK-224671, MEN10376, MEN10627, or a salt thereof, and the like.

The pharmaceutical composition comprising a mixture or combination of the compound of the present invention and the combination drugs may be formulated into (1) a single formulation as a pharmaceutical composition containing the compound of the present invention and the combination drugs, or (2) a formulation comprising the compound of the present invention and the combination drugs which are separately formulated.

Hereinafter, it is generally briefly referred to as the combination preparation of the present invention.

The combination preparation of the present invention can be formulated by mixing the compound of the present invention and active ingredients of the combination drugs separately or at the same time as itself or with pharmaceutically acceptable carriers in the same manner as in the method of producing the pharmaceutical preparation comprising the compound of the present invention.

A daily dose of the combination preparation of the present invention varies depending on severity of the symptoms, age, sex, weight and sensitivity of the subject to be administered, time and interval of administration, property, formulation and kinds of pharmaceutical preparation, kinds of active ingredients, etc., and is not particularly limited. The dose in terms of the compound of the present invention is not particularly limited if it causes no problems of side effects. In the case of oral administration, a daily dosage is usually in a range of about 0.005 to 100 mg, preferably about 0.05 to 50 mg, and more preferably about 0.2 to 30 mg, per 1 kg body weight of mammals, which may be administered once a day or in two or three divided portions a day.

The dose of the compound or the combination preparation of the present invention may be set within the range such that it causes no problems of side effects. The daily dose as the compound or the combination preparation of the present invention varies depending on severity of symptoms, age, sex, weight and sensitivity of the subject to be administered, time and interval of administration, property, formulation and kinds of pharmaceutical preparation, kinds of active ingredients, etc., and is not particularly limited. In the case of oral administration, a daily dosage in terms of active ingredients is usually in the order of about 0.001 to 2000 mg, preferably about 0.01 to 500 mg, and more preferably about 0.1 to 100 mg, per 1 kg body weight of mammals, which may be administered once a day or in two to four divided portions a day.

In administering the combination preparation of the present invention, the compound of the present invention and the combination drugs may be administered at the same time or, the combination drugs may be administered before administering the compound of the present invention, and vice versa. In case of staggered administration, the time interval varies depending on the active ingredients to be administered, a formulation and an administration route. For example, if the combination drugs are administered first, the compound of the present invention may be administered 1 minute to 3 days, preferably 10 minutes to 1 day, more preferably 15 minutes to 1 hour after administering the combination drugs. If the compound of the present invention is administered first, the combination drugs may be administered 1 minute to 1 day, preferably 10 minutes to 6 hours, more preferably 15 minutes to 1 hour after administering the compound of the present invention.

In a preferred administration method, about 0.001 to 200 mg/kg of the combination drugs formulated as an oral preparation is administered orally and then after about 15 minutes, about 0.005 to 100 mg/kg of the compound of the present invention formulated as an oral preparation is administered orally as a daily dose.

In the combination preparation of the present invention, the content of the compound of the present invention varies depending on the forms of the preparation, but usually in the order of 0.01 to 100 wt %, preferably 0.1 to 50 wt %, and further preferably 0.5 to 20 wt %, relative to the total preparation.

EXAMPLE

The present invention is further described in detail with reference to Reference Examples, Examples, Preparative Examples and Experimental Example, which are not intended to restrict the invention and may be modified without departing from the scope of the invention.

Elution in the column chromatography in the following Reference Examples and Examples was conducted under observation by TLC (thin layer chromatography), unless otherwise indicated. In the TLC observation, 60F254, TLC plates, produced by Merck & Co., Inc. was used, and the solvent employed as an elution solvent in the column chromatography was used as an eluent. For the detection, a UV detector was used. As silica gel for the column chromatography, Silica Gel 60 (70 to 230 mesh) produced by Merck & Co., Inc. was used. The "room temperature" here means a temperature of generally from about 10° C. to 35° C. For drying extracts, sodium sulfate or magnesium sulfate was used.

The abbreviations used in the following Examples and Reference Examples Mean the Following LC: liquid chromatography
MS: mass spectrum
ESI: electrospray ionization
NMR: nuclear magnetic resonance
Hz: hertz
J: coupling constant
m: multiplet
q: quartet
t: triplet
d: doublet
s: singlet
br: broad
$^t$Bu: tert-butyl group, t-butyl group
Boc: tert-butyloxycarbonyl
Rf: retardation factor
Rt: retention time
N: normal concentration
M: molar concentration
MPa: mega pascal
wt %: percent by weight
DMF: N,N-dimethylformamide
DMAc: N,N-dimethylacetamide
THF: tetrahydrofuran
DMSO: dimethyl sulfoxide
p-TsOH: p-toluenesulfonic acid
IPE: diisopropyl ether
HOBt: 1-hydroxybenzotriazole hydrate
WSC.HCl: 1-ethyl-3-(dimethylaminopropyl)carbodiimide hydrochloride
$Boc_2O$: di-tert-butyl dicarbonate
DPPA: diphenylphosphoryl azide
DEPC: diethyl phosphorocyanidate LC-MS in Examples and Reference Examples was measured under the following conditions.

Analysis by LC-MS

Measurement instrument: LC-MS system, Waters Corporation
   HPLC part: HP1100, Agilent Technologies, Inc.
   MS part: Micromass ZMD
HPLC conditions
Column: CAPCELL PAK C18UG120, S-3 µm, 1.5×35 mm (Shiseido Co. Ltd.)
Solvent: Solution A; 0.05% trifluoroacetic acid-containing water,
Solution B; 0.05% trifluoroacetic acid-containing acetonitrile
   Gradient cycle: 0.00 minute (Solution A/Solution B=90/10), 2.00 minutes (Solution A/Solution B=5/95), 2.75 minutes (Solution A/Solution B=5/95), 2.76 minutes (Solution A/Solution B=90/10), 3.60 minutes (Solution A/Solution B=90/10)
Injection volume: 2 µL, Flow rate: 0.5 mL/min,
Detection method: UV 220 nm MS conditions
Ionization method: ESI
In the description of the mass spectrometry of the compounds exemplified in the following, the molecular weight of the corresponding compound is indicated as M.
Analysis by LC
Measurement instrument: CLASS-VP system, Shimadzu Corporation
HPLC conditions
Column: Inertsil ODS-2, CAPCELL PAK C18UG120, 5 μm, 4.6×150 mm (GL Sciences Inc.)
Solvent: Solution A; 0.1% trifluoroacetic acid-containing water,
Solution B; 0.1% trifluoroacetic acid-containing acetonitrile
Gradient cycle: 0.00 minute (Solution A/Solution B=70/30), 15.00 minutes (Solution A/Solution B=15/85), 15.01 minutes (Solution A/Solution B=5/95), 20.00 minutes (Solution A/Solution B=5/95), 20.01 minutes (Solution A/Solution B=70/30), 25.00 minutes (Solution A/Solution B=70/30)
Injection volume: 10 μL, Flow rate: 1.0 mL/min, Detection method: UV 220 nm
Purification by preparative HPLC in Examples and Reference Examples was carried out under the following conditions.
Instrument: High Throughput Purification System, Gilson Company, Inc.
Column: YMC CombiPrep ODS-A S-5 μm, 50×20 mm
Solvent: Solution A; 0.1% trifluoroacetic acid-containing water,
Solution B; 0.1% trifluoroacetic acid-containing acetonitrile
Gradient cycle: 0.00 minute (Solution A/Solution B=95/5), 1.00 minutes (Solution A/Solution B=95/5), 5.20 minutes (Solution A/Solution B=5/95), 6.40 minutes (Solution A/Solution B=5/95), 6.50 minutes (Solution A/Solution B=95/5), 6.60 minutes (Solution A/Solution B=95/5)
Flow rate: 25 mL/min, Detection method: UV 220 nm
$^1$H-NMR was measured at 300 MHz or 400 MHz.
In the following, "*" in the steric configuration of the compound names shows the relative configuration, and unless specifically indicated, it means a racemic mixture.

Reference Example 1 tert-butyl (3R*,4R*)-4-amino-3-(3,4-dichlorophenyl) piperidine-1-carboxylate p-toluenesulfonate (Step 1)
To a solution of ethyl isonicotinate (151 g) in ethyl acetate (1000 mL) was added methyl iodide (126 mL), and the mixture was stirred at 80° C. for 3 hr. The reaction mixture was cooled, and an orange precipitate was collected by filtration. The precipitate was suspended in ethanol (1000 mL), sodium borohydride (37.8 g) was added with cooling at −40° C., and the mixture was stirred at room temperature for 2 hr. The reaction mixture was poured into water, and ethanol was evaporated under reduced pressure. The residue was extracted with ethyl acetate-THF, the organic layer was dried, and the solvent was evaporated under reduced pressure. The residue was distilled under reduced pressure to give ethyl 1-methyl-1,2,3,6-tetrahydropyridine-4-carboxylate (85.8 g, 51%) as a pale-yellow oil.
boiling point: 64-77° C. (1 mmHg)
$^1$H-NMR(CDCl$_3$) δ 1.29 (3H, t, J=7.2 Hz), 2.37 (3H, s), 2.40-2.50 (2H, m), 2.54 (2H, t, J=3.3 Hz), 3.09 (2H, q, J=3.0 Hz), 4.20 (2H, q, J=7.2 Hz), 6.86-6.91 (1H, m)

(Step 2)
To a suspension of magnesium (10.76 g) in diethyl ether (110 mL) was added a trace amount of iodine. About 1/10 amount of a solution of 3,4-dichlorobromobenzene (100 g) in diethyl ether (110 ml) was added slowly at 35-40° C., and the mixture was vigorously stirred until the reaction started. Once the initiation was occurred, the rest of 3,4-dichlorobromobenzene/diethyl ether solution was added slowly with cooling to maintain the reaction temperature at 35-40° C. When everything was added, and the mixture was stirred at 40° C. for 1 hr, then cooled to 0° C. To the reaction mixture was added copper iodide(I) (12.6 g), and the compound (56.2 g) obtained in step 1 was slowly added dropwise at 0° C. The reaction mixture was stirred at 0° C. for 1 hr, and further at room temperature for 1 hr. The reaction mixture was poured into water (40 mL), diethyl ether (500 mL) was added, and the precipitate was removed by decantation. The reaction solution was washed with aqueous ammonium chloride solution and saturated brine and dried, and the solvent was evaporated under reduced pressure. The obtained residue was purified by silica gel column chromatography (solvent gradient; 20% ethyl acetate/hexane→>2.5% aqueous ammonia/17.5% methanol/ethyl acetate) to give crude ethyl 3-(3,4-dichlorophenyl)-1-methylpiperidine-4-carboxylate (cis/trans mixture) (75.5 g) as a brown oil.

(Step 3)
To a solution of the compound (75.1 g) obtained in step 2 in acetonitrile (200 mL) was added α-chloroethyl chloroformate (ACE-Cl) (38.4 g), and the mixture was stirred at 90° C. for 1 hr. The reaction solution was cooled, and the solvent was evaporated under reduced pressure. To the residue was added methanol (300 mL), and the mixture was stirred at 80° C. for 1 hr. The reaction solution was cooled, and the solvent was evaporated under reduced pressure. The residue was suspended in acetonitrile (400 mL) solution, and triethylamine (36.4 mL) was added. A solution of Boc$_2$O (57.0 g) in acetonitrile (28 mL) was slowly added, and the mixture was stirred at room temperature for 14 hr. The reaction mixture was poured into water and extracted with ethyl acetate. The organic layer was washed with aqueous ammonium chloride solution and saturated brine and dried, and the solvent was evaporated under reduced pressure. The obtained residue was purified by silica gel column chromatography (solvent gradient; 5→20% ethyl acetate/hexane) to give a pale-yellow oil (73.7 g). The obtained oil (70.0 g) was dissolved in ethanol (348 mL). 1N sodium ethoxide/ethanol solution (348 mL) was added, and the mixture was stirred at 90° C. for 2 hr. The reaction solution was cooled, 8N aqueous sodium hydroxide solution (70 mL) and water (478 mL) were added, and the mixture was stirred at 90° C. for 2 hr. The reaction solution was cooled, and citric acid (173 g) was added. Ethanol was evaporated under reduced pressure, and extracted with ethyl acetate (500 mL) with heating. The mixture was further extracted with ethyl acetate (200 mL×2) with heating. The organic layer was washed with water and dried, and the solvent was under reduced pressure to give a pale-yellow powder. The obtained pale-yellow powder was recrystallized from THF-IPE to give (3R*,4R*)-1-(tert-butoxycarbonyl)-3-(3,4-dichlorophenyl)piperidine-4-carboxylic acid (58.6 g, 47%) as a white powder.
$^1$H-NMR(CDCl$_3$) δ 1.46 (9H, s), 1.65-1.80 (1H, m), 2.00-2.10 (1H, m), 2.60-2.95 (4H, m), 4.00-4.35 (2H, m), 7.05 (1H, dd, J=8.1&2.1 Hz), 7.30 (1H, d, J=2.1 Hz), 7.36 (1H, d, J=8.1 Hz)

(Step 4)
To a solution of the compound (2.0 g) obtained in step 3 in toluene (13.6 mL) were added DPPA (1.62 g) and triethylamine (0.82 mL) at room temperature, and the mixture was stirred at 100° C. for 30 min. The reaction solution was cooled, 8N aqueous sodium hydroxide solution (6.8 mL) and water (478 mL) were added, and the mixture was stirred at room temperature for 2 hr. The reaction mixture was poured into water and extracted with ethyl acetate. The organic layer was washed with water and saturated brine and dried, and the solvent was evaporated under reduced pressure. The obtained residue was dissolved in ethyl acetate (20 mL) and methanol (0.5 mL), and p-toluenesulfonic acid monohydrate (0.62 g) was added. The precipitate was collected by filtration to give tert-butyl (3R*,4R*)-4-amino-3-(3,4-dichlorophenyl)piperidine-1-carboxylate p-toluenesulfonate (1.58 g, 57%) as a white powder.

$^1$H-NMR(CDCl$_3$+DMSO-d$_6$) δ 1.45 (9H, s), 1.60-1.80 (1H, m), 2.20-2.30 (1H, m), 2.37 (3H, s), 2.60-2.95 (4H, m), 3.28-3.38 (1H, m), 3.95-4.30 (2H, br), 7.10-7.20 (3H, m), 7.36 (1H, d, J=8.4 Hz), 7.38 (1H, d, J=1.8 Hz), 7.69 (2H, d, J=6.6 Hz), 7.90-8.20 (2H, br)

Reference Example 2 tert-butyl (3R,4R)-4-amino-3-(3,4-dichlorophenyl)piperidine-1-carboxylate p-toluenesulfonate (Step 1)
A solution of the compound (93.6 g) obtained in Reference Example 1, step 3 in DMF (750 mL) was stirred with heating to 60° C., and a solution of (R)-(−)-1-phenylethylamine (15.1 g) in DMF (250 mL) and water (100 mL) were added dropwise. The reaction mixture was stood at room temperature for 1 day, and the precipitate was collected by filtration, and washed with DMF and ethyl acetate to give (R)-(−)-1-phenylethylamine salt of (3R,4R)-1-(tert-butoxycarbonyl)-3-(3,4-dichlorophenyl)piperidine-4-carboxylic acid (39.1 g, 32%, 98.8% de) as a white powder. The obtained white powder (39.1 g (98.8% de)) was dissolved in a solution of citric acid (16.7 g) in water (250 mL) and ethyl acetate (250 mL) and the mixture was stirred at room temperature for 1 hr. The organic layer was separated, washed with water and saturated brine, and dried. The solvent was evaporated under reduced pressure to give (3R,4R)-1-(tert-butoxycarbonyl)-3-(3,4-dichlorophenyl)piperidine-4-carboxylic acid (28.7 g, 97%) as a white powder.
MS(ESI+): 300 (M−$^t$BuO)
(Step 2)
By reaction and purification in the same manner as in the method described in Reference Example 1, step 4 and using the compound obtained in step 1, the title compound was obtained.
MS(ESI+): 289 (M−p-TsOH−$^t$Bu+H)

Reference Example 3 tert-butyl (3R,4R)-4-amino-3-phenylpiperidine-1-carboxylate p-toluenesulfonate (Step 1)
To a solution of sodium hydride (60% in oil, 6.36 g) in DMF (100 mL) was added ethyl 1-benzyl-3-oxopiperidine-4-carboxylate monohydrochloride (19.0 g) at 0° C., and the mixture was stirred for 5 min. N-phenyl bis(trifluoromethanesulfonimide) (25.0 g) was added, and the mixture was stirred at 0° C. for 1 hr. The reaction mixture was poured into ice water and extracted with ethyl acetate. The organic layer was washed with water and saturated brine and dried, and the solvent was evaporated under reduced pressure. To a mixture of the obtained residue in toluene (125 mL) and water (7.5 mL) were added dihydroxyphenylborane (5.82 g), potassium carbonate (4.40 g) and tetrakis(triphenylphosphine)palladium(0) (3.67 g), and the mixture was stirred under an argon atmosphere at 100° C. for 14 hr. The reaction mixture was poured into water and extracted with ethyl acetate. The organic layer was washed with aqueous saturated sodium hydrogen carbonate and saturated brine and dried, and the solvent was evaporated under reduced pressure. The obtained residue was separated and purified by silica gel column chromatography (solvent gradient; 10→20% ethyl acetate/hexane) to give ethyl 1-benzyl-5-phenyl-1,2,3,6-tetrahydropyridine-4-carboxylate (10.2 g) as a pale-yellow oil.

$^1$H-NMR(CDCl$_3$): δ 0.83 (3H, t, J=7, 2 Hz), 2.54-2.62 (2H, m), 2.70 (2H, t, J=5.7 Hz), 3.26 (2H, t, J=2.9 Hz), 3.67 (2H, s), 3.87 (2H, q, J=7.2 Hz), 7.08-7.14 (2H, m), 7.20-7.40 (8H, m)
(Step 2)
A solution of the compound (10.5 g) obtained in step 1 and 20% palladium hydroxide-carbon (50% wet, 2.63 g) in ethanol (250 mL) was stirred under a hydrogen atmosphere (1 atm) at room temperature for 14 hr. The catalyst was filtered off, and the filtrate was concentrated under reduced pressure. To a solution of the obtained residue in acetonitrile (50 mL) were added triethylamine (4.6 mL) and Boc$_2$O (7.14 g), and the mixture was stirred at room temperature for 14 hr. The reaction mixture was poured into water and extracted with ethyl acetate. The organic layer was washed with aqueous saturated sodium hydrogen carbonate and saturated brine and dried, and the solvent was evaporated under reduced pressure. The obtained residue was separated and purified by silica gel column chromatography (solvent gradient; 10→20% ethyl acetate/hexane) to give 4-ethyl 1-tert-butyl (3R*,4S*)-3-phenylpiperidine-1,4-dicarboxylate (8.31 g, 76%) as a colorless oil.

$^1$H-NMR(CDCl$_3$): δ 1.01 (3H, t, J=7.7 Hz), 1.43 (9H, s), 1.80-2.05 (2H, m), 2.93-3.00 (1H, q like), 3.10-3.20 (1H, q like), 3.50-4.10 (6H, m), 7.05-7.30 (5H, m)
(Step 3)
To a solution of the compound (6.3 g) obtained in step 2 in ethanol (60 mL) was added $^t$BuONa (3.63 g), and the mixture was stirred at 90° C. for 1 hr. The reaction solution was cooled, 8N aqueous sodium hydroxide solution (60 mL) and water (60 mL) were added, and the mixture was stirred at 85° C. for 2 hr. The reaction solution was cooled, and citric acid (51 g) was added. Ethanol was evaporated under reduced pressure, and the mixture was extracted with ethyl acetate (200 mL). The organic layer was washed with water and dried, and the solvent was evaporated under reduced pressure and crystallized from ethyl acetate-IPE-hexane to give (3R*,4R*)-1-(tert-butoxycarbonyl)-3-phenylpiperidine-4-carboxylic acid (5.26 g, 91%) as a white powder.

$^1$H-NMR(CDCl$_3$): δ 1.45 (9H, s), 1.65-1.75 (1H, m), 1.98-2.05 (1H, m), 2.65-3.00 (4H, m), 4.00-4.40 (2H, m), 7.17-7.32 (5H, m)
(Step 4)
A solution of the compound (30.5 g) obtained in step 3 in THF (200 mL) was heated to 55° C., and a solution of (R)-(−)-1-phenylethylamine (6.06 g) in THF (99 mL) and water (30.0 mL) were added dropwise. The reaction mixture was stirred at room temperature for 24 hr, and the precipitate was collected by filtration, and washed with THF and hexane to give (R)-(−)-1-phenylethylamine salt of (3R,4R)-1-(tert-butoxycarbonyl)-3-phenylpiperidine-4-carboxylic acid (14.9 g, 35%, 98.9% de) as a white powder. The obtained white powder (14.9 g (98.9% de)) and citric acid (8.07 g) were dissolved in water and THF/ethyl acetate, and the organic layer was separated. The organic layer was washed with water and saturated brine, and dried. The solvent was evaporated under reduced pressure to give (3R,4R)-1-(tert-butoxycarbonyl)-3-phenylpiperidine-4-carboxylic acid (10.1 g, 95%) as a white powder.
MS(ESI+): 232 (M−$^t$BuO)
(Step 5)
By reaction and purification in the same manner as in the method described in Reference Example 1, step 4 and using the compound obtained in step 4, the title compound was obtained.
MS(ESI+): 221 (M−p-TsOH−$^t$Bu+2H)

Reference Example 4 tert-butyl (3R*,4R*)-4-amino-3-(4-fluorophenyl)piperidine-1-carboxylate p-toluenesulfonate (Step 1)
By reaction and purification in the same manner as in the method described in Reference Example 3, steps 1-3 and using 4-fluorophenylboronic acid, (3R*,4R*)-1-(tert-butoxycarbonyl)-3-(4-fluorophenyl)piperidine-4-carboxylic acid was obtained.
MS(ESI+): 250 (M−$^t$BuO)
(Step 2)
By reaction and purification in the same manner as in the method described in Example 1, step 4 and using the compound obtained in step 1, the title compound was obtained.
MS(ESI+): 239 (M−p-TsOH−$^t$Bu+2H)

Reference Example 5 tert-butyl (3R,4R)-4-amino-3-(4-fluorophenyl)piperidine-1-carboxylate p-toluenesulfonate (Step 1)
A solution of the compound (30.9 g) obtained in Reference Example 4, step 1 in acetone (143 mL) was heated to 50° C., and a solution of (R)-(−)-1-phenylethylamine (5.79 g) in acetone (95.6 mL) and water (23.9 mL) were added dropwise. The reaction mixture was stirred at 50° C. for 1 hr, and stood at room temperature for 24 hr. To the reaction mixture was added acetone (100 mL), and the precipitate was collected by filtration, and washed with acetone to give (R)-(−)-1-phenylethylamine salt of (3R,4R)-1-(tert-butoxycarbonyl)-3-(4-fluorophenyl)piperidine-4-carboxylic acid (16.2 g, 38%, >99.9% de) as a pale-brown powder. The obtained powder (18.7 g (>99.9% de)) and citric acid (8.88 g) were dissolved in water and THF/ethyl acetate, and the organic layer was separated. The organic layer was washed with water and saturated brine, and dried. The solvent was evaporated under reduced pressure to give (3R,4R)-1-(tert-butoxycarbonyl)-3-(4-fluorophenyl)piperidine-4-carboxylic acid (13.0 g, 96%) as a white powder.
MS(ESI) 250 (M−$^t$BuO)
(Step 2)
By reaction and purification in the same manner as in the method described in Reference Example 1, step 4 and using the compound obtained in step 1, the title compound was obtained.
MS(ESI+): 240 (M−p-TsOH−$^t$Bu+2H)

Reference Example 6 tert-butyl (3R,4R)-4-amino-3-(4-chloro-3-methylphenyl)piperidine-1-carboxylate p-toluenesulfonate (Step 1)
By reaction and purification in the same manner as in the method described in Reference Example 1, steps 1 to 3 and using 5-bromo-2-chlorotoluene, (3R*,4R*)-1-(tert-butoxycarbonyl)-3-(4-chloro-3-methylphenyl)piperidine-4-carboxylic acid was obtained.
MS(ESI+): 280 (M−$^t$BuO)
(Step 2)
A solution of the compound (19.1 g) obtained in step 1 in THF (216 mL) was heated to 60° C., and a solution of (R)-(−)-1-phenylethylamine (3.27 g) in THF (54 mL) and water (27 mL) were added dropwise. A seed crystal was added, and the mixture was stirred at room temperature for 24 hr. The reaction mixture was stirred at room temperature 6 hr, and the precipitate was collected by filtration, and washed with THF and hexane to give (R)-(−)-1-phenylethylamine salt (3.58 g, 14%, 98% de) of (3R,4R)-1-(tert-butoxycarbonyl)-3-(4-chloro-3-methylphenyl)piperidine-4-carboxylic acid (2.65 g, 86%) as a white powder. The obtained powder (3.58 g (98% de) and 0.57 g (96% de)) and citric acid (2.52 g) were dissolved in water and THF/ethyl acetate, and the organic layer was separated. The organic layer was washed with water and saturated brine, and dried. The solvent was evaporated under reduced pressure to give (3R,4R)-1-(tert-butoxycarbonyl)-3-(4-chloro-3-methylphenyl)piperidine-4-carboxylic acid (2.65 g, 86%) as a white powder.
MS(ESI) 280 (M−$^t$BuO)
(Step 3)
By reaction and purification in the same manner as in the method described in Reference Example 1, step 4 and using the compound obtained in step 2, the title compound was obtained.
MS(ESI+): 269 (M−p-TsOH−$^t$Bu+2H)

Reference Example 7 tert-butyl (3R*,4R*)-4-amino-3-(3,5-dichlorophenyl)piperidine-1-carboxylate (Step 1)
By reaction and purification in the same manner as in the method described in Reference Example 1, steps 1 to 3 and using 3,5-dichloro-bromobenzene, (3R*,4R*)-1-(tert-butoxycarbonyl)-3-(3,5-dichloromethylphenyl)piperidine-4-carboxylic acid was obtained.
(Step 2)
By reaction in the same manner as in the method described in Reference Example 1, step 4 and using the compound (9.1 g) obtained in step 1, DPPA (10.0 g), and triethylamine (5.0 mL), and purification by silica gel column chromatography (NH Chromatorex) (30% ethyl acetate/hexane) to give the title compound (4.78 g, 57%) as a white powder.
MS(ESI+): 289 (M−$^t$Bu+2H)

Reference Example 8 tert-butyl (3R*,4S*)-4-amino-3-(4-fluorophenyl)piperidine-1-carboxylate p-toluenesulfonate (Step 1)
By reaction and purification in the same manner as in the method described in Reference Example 3, step 1 and using 4-fluorophenylboronic acid, ethyl 1-benzyl-5-(4-fluorophenyl)-1,2,3,6-tetrahydropyridine-4-carboxylate was obtained.
MS(ESI+): 340 (M+2H)
(Step 2)
To the compound (11.1 g) obtained in step 1 were added acetic acid (25 mL) and hydrochloric acid (25 mL), and the mixture was heated at 100° C. for 2 hr. The reaction mixture was cooled and concentrated to give 1-benzyl-5-(4-fluorophenyl)-1,2,3,6-tetrahydropyridine-4-carboxylic acid monohydrochloride (8.82 g, 78%). $^1$H-NMR (DMSO-$d_6$): δ 2.70-2.80 (2H, m), 3.10-3.60 (2H, m), 3.85-4.00 (2H, m), 4.30-4.50 (2H, m), 7.18-7.25 (4H, m), 7.42-7.48 (3H, m), 7.62-7.68 (2H, m), 11.3-11.5 (1H, brs), 12.4-13.0 (1H, br)

(Step 3)

A mixture of the compound (8.78 g) obtained in step 2 and 10% palladium-carbon (50% wet, 1.5 g) in ethanol (200 mL) was stirred under a hydrogen atmosphere (5 atm) at 50° C. for 3 hr. The catalyst was filtered off, and the filtrate was concentrated under reduced pressure. The residue was dissolved in methanol (100 mL), 20% palladium hydroxide (50% wet, 1.4 g) was added, and the mixture was stirred under a hydrogen atmosphere (5 atm) at 60° C. for 6 hr. The catalyst was filtered off, and the mixture was concentrated under reduced pressure. To a solution of the obtained residue and triethylamine (6.48 mL) in acetonitrile (50 mL) was added dropwise a solution of Boc$_2$O (6.42 g) in acetonitrile (25 mL), and the mixture was stirred at room temperature for 1 day. The solvent was evaporated under reduced pressure, and the residue was diluted with ethyl acetate (100 mL) and extracted twice with 1N aqueous sodium hydroxide solution (20 mL). The extract was washed with ethyl acetate, acidified with aqueous citric acid solution, and extracted with ethyl acetate. The extract was washed with water and saturated brine, dried, and concentrated under reduced pressure to give (3R*,4S*)-1-(tert-butoxycarbonyl)-3-(4-fluorophenyl)piperidine-4-carboxylic acid (1.66 g, 26%) as a white powder.

$^1$H-NMR(CDCl$_3$) δ 1.42 (9H, s), 1.80-2.05 (2H, m), 2.92-3.00 (1H, m), 3.10-3.20 (1H, m), 3.30-4.10 (4H, m), 6.90-6.97 (2H, m), 7.15-7.26 (2H, m)

(Step 4)

By reaction and purification in the same manner as in the method described in Reference Example 1, step 4 and using the compound obtained in step 3, the title compound was obtained.

MS(ESI+): 239 (M–p-TsOH–$^t$Bu+2H)

Reference Example 9 tert-butyl (3R*,4R*)-4-amino-3-(4-methylphenyl)piperidine-1-carboxylate p-toluenesulfonate By reaction and purification in the same manner as in the method described in Reference Example 3, steps 1 to 3 and Reference Example 1, step 4 and using 4-methylphenylboronic acid, the title compound was obtained.

MS(ESI+): 291 (M–p-TsOH+H)

Reference Example 10 tert-butyl (3R*,4R*)-4-amino-3-(4-chlorophenyl)piperidine-1-carboxylate p-toluenesulfonate By reaction and purification in the same manner as in the method described in Reference Example 1, steps 1 to 4 and using p-bromochlorobenzene, the title compound was obtained.

MS(ESI+): 255 (M–p-TsOH–$^t$Bu+2H)

Reference Example 11

(3R*,4R*)-1-[(1-acetylpiperidin-4-yl) carbonyl]-3-(3,4-dichlorophenyl)-N-methylpiperidine-4-amine (Step 1)

To a solution of the compound (1.03 g) obtained in Reference Example 1 and pyridine (0.40 mL) in THF (10 mL) was added trifluoroacetic anhydride (0.35 mL) at 0° C., and the mixture was stirred at 0° C. for 3 hr. To the reaction solution was added aqueous sodium hydrogen carbonate solution, and the resultant mixture was extracted with ethyl acetate. The organic layer was washed with water, 1N hydrochloric acid and saturated brine and dried, and the solvent was evaporated under reduced pressure. The obtained residue was purified by silica gel column chromatography (solvent gradient; 10→40% ethyl acetate/hexane) to give tert-butyl (3R*,4R*)-3-(3,4-dichlorophenyl)-4-[(trifluoroacetyl)amino]piperidine-1-carboxylate (0.84 g, 95%) as a white amorphous solid.

MS(ESI+): 385 (M–$^t$Bu+2H)

(Step 2)

To a solution of the compound (0.80 g) obtained in step 1 in DMF (8 mL) was added sodium hydride (60% in oil, 0.094 g) at 0° C., and the mixture was stirred at 0° C. for 15 min. Further, methyl iodide (0.17 mL) was added at 0° C., and the mixture was stirred at room temperature for 4 hr. The reaction mixture was poured into water and extracted with ethyl acetate. The organic layer was washed with 1N aqueous potassium hydrogen sulfate solution and saturated brine and dried, and the solvent was evaporated under reduced pressure. The obtained residue was purified by silica gel column chromatography (solvent gradient; 5→40% ethyl acetate/hexane) to give tert-butyl (3R*,4R*)-3-(3,4-dichlorophenyl)-4-[methyl(trifluoroacetyl)amino]piperidine-1-carboxylate (0.72 g, 89%) as a pale-yellow amorphous solid.

MS(ESI+): 381 (M–$^t$BuO)

(Step 3)

To a solution of the compound (0.69 g) obtained in step 2 in ethyl acetate (6 mL) was added 4N hydrogen chloride/ethyl acetate (3 mL) at room temperature, and the mixture was stirred at room temperature for 4 hr. The reaction solution was evaporated under reduced pressure to give N-[(3R*,4R*)-3-(3,4-dichlorophenyl)piperidin-4-yl]-2,2,2-trifluoro-N-methylacetamide monohydrochloride (0.51 g, 85%) as a white powder.

MS(ESI+): 355 (M–HCl+H)

(Step 4)

To a solution of the compound (0.49 g) obtained in step 3,1-acetylpiperidine-4-carboxylic acid (0.33 g) and triethylamine (0.53 mL) in DMF (5 mL) was added DEPC (0.29 mL), and the mixture was stirred at room temperature for 14 hr. The reaction mixture was poured into water and extracted with ethyl acetate. The organic layer was washed with saturated aqueous sodium hydrogen carbonate solution and saturated brine and dried, and the solvent was evaporated under reduced pressure. The obtained residue was purified by silica gel column chromatography (solvent gradient; 0→9% methanol/ethyl acetate) to give N-[(3R*,4R*)-1-[(1-acetylpiperidin-4-yl)carbonyl]-3-(3,4-dichlorophenyl)piperidin-4-yl]-2,2,2-trifluoro-N-methylacetamide (0.66 g, 100%) as a white amorphous solid.

MS(ESI+): 508 (M+H)

(Step 5)

To a mixed solution of the compound (0.66 g) obtained in step 4 in methanol (6.5 mL) and water (1.3 mL) was added potassium carbonate (0.35 g) at room temperature, and the mixture was stirred at 50° C. for 24 hr. Furthermore, potassium carbonate (1.70 g) was added, and the mixture was stirred at 50° C. for 6 days. The organic solvent was evaporated under reduced pressure, and the residue was poured into saturated aqueous sodium hydrogen carbonate solution and ethyl acetate. The organic layer was washed with saturated brine and dried, and the solvent was evaporated under reduced pressure. The obtained residue was purified by silica gel column chromatography (NH Chromatorex) (solvent gradient; 0→9% methanol/ethyl acetate) to give the title compound (0.30 g, 58%) as a white amorphous solid.

MS(ESI+): 412 (M+H)

Reference Example 12

(3R,4R)-1-[(1-acetylpiperidin-4-yl)carbonyl]-3-(3,4-dichlorophenyl)-N-methylpiperidine-4-amine By reaction and purification in the same manner as in the method described in Reference Example 11, steps 1 to 5 and using the compound obtained in Reference Example 2, the title compound was obtained.

MS(ESI+): 412 (M+H)

Reference Example 13 tert-butyl (3S*,4R*)-3-amino-4-(3,4-dichlorophenyl)pyrrolidine-1-carboxylate (Step 1)

To a solution of 3,4-dichlorocinnamic acid (21.7 g) and cesium carbonate (22.8 g) in DMF (200 mL) was added methyl iodide (7.47 mL) at 0° C., and the mixture was stirred at room temperature for 12 hr. The reaction mixture was poured into water and extracted with ethyl acetate. The organic layer was washed with saturated aqueous sodium hydrogen carbonate solution, water, 1N aqueous potassium hydrogen sulfate solution and saturated brine and dried, and the solvent was evaporated under reduced pressure to give methyl 3,4-dichlorocinnamate (22.4 g, 97%) as a white powder.

$^1$H-NMR(CDCl$_3$) δ 3.81 (3H, s), 6.42 (1H, d, J=16.2 Hz), 7.35 (1H, d, J=8.3 Hz), 7.47 (1H, d, J=8.3 Hz), 7.56-7.61 (2H, m)

(Step 2)

To a solution of the compound (20.4 g) obtained in step 1 and N-(methoxymethyl)-N-(trimethylsilylmethyl)benzylamine (22.0 g) in toluene (180 mL) was added a solution of trifluoroacetic acid (1.31 mL) in toluene (18 mL) at 0° C., and the mixture was stirred at room temperature for 14 hr. To the reaction solution was added ethyl acetate (300 mL), and the mixture was washed with saturated aqueous sodium hydrogen carbonate solution, water and saturated brine and dried, and the solvent was evaporated under reduced pressure. The obtained residue was purified by silica gel column chromatography (solvent gradient; 10→25% ethyl acetate/hexane) to give methyl (3R*,4S*)-1-benzyl-4-(3,4-dichlorophenyl)pyrrolidine-3-carboxylate (33.4 g, 100%) as a pale-yellow oil.

MS(ESI+): 364 (M+H)

(Step 3)

To a solution of the compound (33.4 g) obtained in step 2 in acetonitrile (250 mL) was added ACE-Cl (13.9 g) at room temperature, and the mixture was stirred at 90° C. for 2 hr. The reaction solution was cooled, and the solvent was evaporated under reduced pressure. To the residue was added methanol (250 mL), and the mixture was stirred at 80° C. for 2 hr. The reaction solution was cooled, the solvent was evaporated under reduced pressure, and the residue was washed with ethyl acetate/IPE to give methyl (3R*,4S*)-4-(3,4-dichlorophenyl)pyrrolidine-3-carboxylate monohydrochloride (26.9 g, 98%) as a pale-yellow powder.

MS(ESI+): 274 (M−HCl+H)

(Step 4)

To a solution of the compound (26.4 g) obtained in step 3 and triethylamine (13.0 mL) in acetonitrile (260 mL) was added Boc$_2$O (20.4 g) at 0° C., and the mixture was stirred at room temperature for 5 hr. The reaction mixture was poured into water and extracted with ethyl acetate. The organic layer was washed with 1N hydrochloric acid and saturated brine and dried, and the solvent was evaporated under reduced pressure. The obtained residue was purified by silica gel column chromatography (solvent gradient; 10→25% ethyl acetate/hexane) to give 3-methyl 1-tert-butyl (3R*,4S*)-4-(3,4-dichlorophenyl)pyrrolidine-1,3-dicarboxylate (31.2 g, 98%) as a pale-yellow oil.

MS(ESI+): 318 (M−$^t$Bu+2H)

(Step 5)

To a mixed solution of the compound (31.2 g) obtained in step 4 in ethanol (160 mL), THF (30 mL) and water (31.3 mL) was added 8N aqueous sodium hydroxide solution (31.3 mL), and the mixture was heated under reflux for 2 hr. The reaction solution was cooled to 0° C., and the reaction solution was weak acidified with 1N hydrochloric acid (270 mL) solution. The organic solvent was evaporated under reduced pressure, and the residue was extracted with ethyl acetate. The organic layer was washed with water and saturated brine and dried, and the solvent was evaporated under reduced pressure. The obtained residue was crystallized from ethyl acetate-hexane to give (3R*, 4S*)-1-(tert-butoxycarbonyl)-4-(3,4-dichlorophenyl)pyrrolidine-3-carboxylic acid (19.2 g, 64%) as a white powder.

$^1$H-NMR(CDCl$_3$) δ 1.47 (9H, s), 3.17 (1H, dd, J=9.1&17.0 Hz), 3.36 (1H, q, J=10.3 Hz), 3.61 (2H, t, J=9.4 Hz), 3.80-3.90 (2H, br), 7.10 (1H, dd, J=2.3&8.3 Hz), 7.35 (1H, d, J=2.2 Hz), 7.41 (1H, d, J=8.3 Hz)

(Step 6)

To a solution of the compound (14.4 g) obtained in step 5 in toluene (120 mL) was added DPPA (16.5 g) and triethylamine (8.36 mL) at room temperature, and the mixture was stirred at 100° C. for 2 hr. The reaction solution was cooled, 8N aqueous sodium hydroxide solution (50 mL) was added, and the mixture was stirred at room temperature for 14 hr. The reaction mixture was poured into water and extracted with ethyl acetate. The organic layer was washed with saturated aqueous ammonium chloride solution and saturated brine, dried, and concentrated under reduced pressure to give tert-butyl (3R*, 4S*)-3-amino-4-(3,4-dichlorophenyl)pyrrolidine-1-carboxylate (13.3 g, 100%) as an orange oil.

MS(ESI+): 258 (M−$^t$BuO+H)

Reference Example 14 tert-butyl (3S*,4R*)-3-amino-4-(4-fluorophenyl)pyrrolidine-1-carboxylate

By reaction and purification in the same manner as in the method described in Reference Example 13, steps 1 to step 6 and using 4-fluorocinnamic acid, the title compound was obtained.

MS(ESI+): 225 (M−$^t$Bu+2H)

Reference Example 15

N-methyl-3,5-bis(trifluoromethyl)aniline monohydrochloride (Step 1)

To a solution of 3,5-bis(trifluoromethyl)aniline (10.0 g), triethylamine (7.37 mL) and dimethylaminopyridine (0.54 g) in acetonitrile (100 mL) was added $Boc_2O$ (11.5 g) at room temperature, and the mixture was stirred for 14 hr. To the reaction mixture was added $Boc_2O$ (6.0 g), and the mixture was further stirred at room temperature for 1 day. The reaction mixture was poured into water and extracted with ethyl acetate. The organic layer was washed with saturated aqueous sodium chloride solution and saturated brine, dried and concentrated under reduced pressure. The residue was dissolved in methanol, sodium tert-butoxide (4.74 g) was added, and the mixture was stirred at room temperature for 3 hr. Methanol was evaporated under reduced pressure, and the residue was partitioned between water and ethyl acetate. The organic layer was separated, washed with saturated brine, dried and concentrated under reduced pressure to give tert-butyl [3,5-bis(trifluoromethyl)phenyl]carbamate (12.5 g, 86%) as a white powder.

$^1$H-NMR(CDCl$_3$) δ 1.53 (9H, s), 6.75 (1H, s), 7.51 (1H, s), 7.85 (1H, s)

(Step 2)

To a solution of the compound (12.1 g) obtained in step 1 in DMF (55 mL) was added sodium hydride (1.82 g) at 0° C. The reaction mixture was stirred at 0° C. for 5 min, methyl iodide (11.4 mL) was added dropwise, and the mixture was stirred at room temperature for 3 hr. The reaction mixture was poured into water, and extracted twice with ethyl acetate. The extract was washed with saturated brine, dried and concentrated under reduced pressure. The residue was separated and purified by silica gel column chromatography (10% ethyl acetate/hexane) to give tert-butyl [3,5-bis(trifluoromethyl)phenyl](methyl)carbamate (12.5 g, 99%) as a colorless oil.

$^1$H-NMR(CDCl$_3$) δ 1.49 (9H, s), 3.33 (3H, s), 7.62 (1H, s), 7.72 (2H, s)

(Step 3)

To the compound (12.4 g) obtained in step 2 was added 2N hydrogen chloride/2-propanol (100 mL), and the mixture was stirred at 50° C. for 2 hr. The reaction mixture was concentrated under reduced pressure to give the title compound (9.36 g, 93%) as a white powder.

$^1$H-NMR (DMSO-d$_6$) δ 2.76 (3H, s), 7.04 (3H, s), 6.00-9.00 (2H, br)

Reference Example 16

1-[3,5-bis(trifluoromethyl)phenyl]cyclopropanecarboxylic acid (Step 1)

To a solution of [3,5-bis(trifluoromethyl)phenyl]acetic acid (10 g) in methanol (50 mL) was added concentrated sulfuric acid (0.5 mL), and the mixture was stirred at 80° C. for 14 hr. The reaction mixture was cooled, basified with saturated aqueous sodium hydrogen carbonate solution, and concentrated under reduced pressure. The residue was diluted with ethyl acetate, and washed with saturated brine. The aqueous layer was extracted again with ethyl acetate, and the combined extract was dried, and concentrated to give methyl [3,5-bis(trifluoromethyl)phenyl]acetate (10.8 g, 100%) as a colorless oil.

$^1$H-NMR(CDCl$_3$) δ 3.73 (3H, s), 3.76 (2H, s), 7.74 (2H, s), 7.79 (1H, s)

(Step 2)

The compound (1.76 g) obtained in step 1 was dissolved in DMSO (30 mL), sodium hydride (0.59 g) was added at 0° C., and the mixture was stirred for 5 min. To the reaction mixture was added 2-bromo-1-chloroethane (0.77 mL), and the mixture was stirred at room temperature for 45 min. The reaction mixture was poured into water, and extracted twice with ethyl acetate. The extract was washed with saturated aqueous ammonium chloride solution, dried and concentrated under reduced pressure. The residue was separated and purified by silica gel column chromatography (10% ethyl acetate/hexane) to give methyl 1-[3,5-bis(trifluoromethyl)phenyl]cyclopropanecarboxylate (1.80 g, 94%).

$^1$H-NMR(CDCl$_3$) δ 1.25 (2H, dd, J=7.2, 4.2 Hz), 1.73 (2H, dd, J=7.2, 4.2 Hz), 2.04 (3H, s), 7.78 (3H, s)

(Step 3)

To a solution of the compound (1.80 g) obtained in step 2 in methanol (10 mL) was added 8N aqueous sodium hydroxide solution (10 mL), and the mixture was stirred at 60° C. for 1.5 hr. The reaction mixture was cooled, and the mixture was acidified with 6N hydrochloric acid, and methanol was evaporated under reduced pressure. The residue was extracted twice with ethyl acetate, dried and concentrated under reduced pressure to give the title compound (1.39 g, 81%) as a white powder.

$^1$H-NMR(CDCl$_3$) δ 1.34 (2H, dd, J=7.2, 4.2 Hz), 1.80 (2H, dd, J=7.2, 4.2 Hz), 7.78 (3H, s)

Reference Example 17 tert-butyl (2-oxoethyl)phenylcarbamate (Step 1)

A solution of 2-(phenylamino)ethanol (10.0 g) and $Boc_2O$ (23.9 g) in THF (100 mL) was stirred at 55° C. for 7 hr, and concentrated under reduced pressure. The residue was washed with hexane to give tert-butyl (2-hydroxyethyl)(phenyl)carbamate (15.0 g, 88%) as a white powder.

$^1$H-NMR(CDCl$_3$) δ 1.41 (9H, s), 1.60-1.80 (1H, br), 3.74-3.85 (4H, m), 7.17-7.24 (3H, m), 7.29-7.37 (2H, m)

(Step 2)

A solution of oxalyl chloride (0.37 mL) in THF (5.0 mL) was cooled to −78° C., and DMSO (0.39 mL) and THF (2.0 mL) were slowly added dropwise. The reaction mixture was stirred for 5 min, and a solution of the compound (0.50 g) obtained in step 1 in THF (3.0 mL) was added dropwise. The reaction mixture was stirred at −78° C. to −20° C. for 1 hr, and triethylamine (2.0 mL) was added. The reaction mixture was stirred at room temperature for 30 min, poured into water, and the mixture was extracted with ethyl acetate. The extract was washed with saturated aqueous ammonium chloride solution and saturated brine, dried and concentrated under reduced pressure. The residue was separated and purified by silica gel column chromatography (solvent gradient; 5→15% ethyl acetate/hexane) to give the title compound (0.38 g, 77%) as a colorless oil.

$^1$H-NMR(CDCl$_3$) δ 1.44 (9H, s), 4.33 (2H, s), 7.17-7.25 (3H, m), 7.30-7.37 (2H, m), 9.70 (1H, s)

Reference Example 18 tert-butyl (3R,4R)-4-amino-3-(4-fluoro-2-methylphenyl)piperidine-1-carboxylate To a solution of (3R,4R)-1-(tert-butoxycarbonyl)-3-(4-fluoro-2-methylphenyl)piperidine-4-carboxylic acid (4.33 g)

synthesized by a known method (WO2006/004195) in toluene (24 mL) were added DPPA (5.30 g) and triethylamine (2.7 mL) at room temperature, and the mixture was stirred at 100° C. for 1 hr. The reaction solution was cooled, 8N aqueous sodium hydroxide solution (16 mL) was added, and the mixture was stirred at room temperature for 3 hr. The reaction mixture was poured into water and extracted with ethyl acetate. The organic layer was washed with water and saturated brine and dried, and the solvent was evaporated under reduced pressure. The obtained residue was purified by silica gel column chromatography (NH Chromatorex) (solvent gradient; 30→70% ethyl acetate/hexane) to give the title compound (3.79 g, 96%) as a pale-yellow oil.

MS(ESI+): 253 (M−$^t$Bu+2H)

The compounds of Reference Examples 1 to 18 are as described below (Table A-1).

TABLE A-1

| Ref. Ex. No. | Chemical formula |
|---|---|
| 1 | Boc-piperidine-(±)-(3,4-dichlorophenyl)-NH₂ · p-TsOH |
| 2 | Boc-piperidine-(R,R)-(3,4-dichlorophenyl)-NH₂ · p-TsOH |
| 3 | Boc-piperidine-(R,R)-phenyl-NH₂ · p-TsOH |
| 4 | Boc-piperidine-(±)-(4-fluorophenyl)-NH₂ · p-TsOH |
| 5 | Boc-piperidine-(R,R)-(4-fluorophenyl)-NH₂ · p-TsOH |
| 6 | Boc-piperidine-(R,R)-(3-methyl-4-chlorophenyl)-NH₂ · p-TsOH |
| 7 | Boc-piperidine-(±)-(3,5-dichlorophenyl)-NH₂ · p-TsOH |
| 8 | Boc-piperidine-(±)-(4-fluorophenyl)-NH₂ · p-TsOH |
| 9 | Boc-piperidine-(±)-(4-methylphenyl)-NH₂ · p-TsOH |
| 10 | Boc-piperidine-(±)-(4-chlorophenyl)-NH₂ · p-TsOH |

TABLE A-1-continued

| Ref. Ex. No. | Chemical formula |
|---|---|
| 11 | (±)- H₃C-N(C(=O))-piperidine-C(=O)-N-piperidine with NHCH₃ and 3,4-dichlorophenyl substituents |
| 12 | H₃C-N(C(=O))-piperidine-C(=O)-N-piperidine (R,R) with NHCH₃ and 3,4-dichlorophenyl substituents |
| 13 | Boc-N-pyrrolidine with NH₂ and 3,4-dichlorophenyl (±) |
| 14 | Boc-N-pyrrolidine with NH₂ and 4-fluorophenyl (±) |
| 15 | Me-NH-(3,5-bis(trifluoromethyl)phenyl) · HCl |
| 16 | HO-C(=O)-cyclopropyl-(3,5-bis(trifluoromethyl)phenyl) |
| 17 | PhN(Boc)-CH₂-CHO |
| 18 | Boc-N-piperidine (R,R) with NH₂ and 2-methyl-4-fluorophenyl |

Reference Example 19 tert-butyl (3S,4R)-3-amino-4-(4-fluorophenyl)pyrrolidine-1-carboxylate (Step 1)

To a solution of 4-fluorocinnamic acid (85 g) and DMF (2.5 mL) in THF (850 mL) was added dropwise oxalyl chloride (97.4 g) at 5° C. over 10 min, and the mixture was stirred at 5° C. for 1 hr. The mixture was concentrated under reduced pressure, and the residue was suspended in THF (300 mL). This suspension was added dropwise at 5° C. to a mixture of (4R)-4-benzyl-1,3-oxazolidin-2-one (100 g), triethylamine (259 g), lithium chloride (108 g) and THF (850 mL) over 30 min, and the mixture was stirred at room temperature for 1 hr. The mixture was poured into water (850 mL), and the mixture was extracted with ethyl acetate (500 mL), washed with saturated aqueous ammonium chloride solution (500 mL) and saturated brine (500 mL), dried and concentrated under reduced pressure. The residue was recrystallized from ethyl acetate/IPE to give (4R)-4-benzyl-3-[(2E)-3-(4-fluorophenyl)prop-2-enoyl]-1,3-oxazolidin-2-one (134 g, 80%) as a white powder.

MS(ESI+): 326 (M+H)

$^1$H-NMR(CDCl$_3$) δ 2.85 (1H, dd, J=13.2, 9.3 Hz), 3.37 (1H, dd, J=13.2, 3.0 Hz), 4.18-4.29 (2H, m), 4.76-4.84 (1H, m), 7.04-7.14 (2H, m), 7.20-7.40 (5H, m), 7.58-7.68 (2H, m), 7.86 (2H, s)

(Step 2)

To a solution of the compound (23.4 g) obtained in step 1 and N-(methoxymethyl)-N-(trimethylsilylmethyl)benzylamine (17.9 g) in toluene (238 mL) was added dropwise a solution of trifluoroacetic acid (1.07 mL) in toluene (11.7 mL) at 5° C., and the mixture was stirred at room temperature for 14 hr. The reaction mixture was diluted with saturated aqueous sodium hydrogen carbonate solution/water, extracted with ethyl acetate, washed with saturated brine, dried and concentrated under reduced pressure. The residue was separated and purified by silica gel column chromatography (solvent gradient; 20→75% ethyl acetate/hexane) to give (4R)-4-benzyl-3-{[(3S,4R)-1-benzyl-4-(4-fluorophenyl)pyrrolidin-3-yl]carbonyl}-1,3-oxazolidin-2-one (less polar product, 17.1 g, 52%) and (4R)-4-benzyl-3-{[(3R,4S)-

1-benzyl-4-(4-fluorophenyl)pyrrolidin-3-yl]carbonyl}-1,3-oxazolidin-2-one (more polar product, 14.5 g, 44%) each as a white powder.

(4R)-4-benzyl-3-{[(3S,4R)-1-benzyl-4-(4-fluorophenyl)pyrrolidin-3-yl]carbonyl}-1,3-oxazolidin-2-one (less polar product)

$^1$H-NMR(CDCl$_3$) δ 2.61-2.70 (1H, m), 2.74-2.88 (2H, m), 3.14-3.29 (3H, m), 3.63 (1H, d, J=13.2 Hz), 3.76 (1H, d, J=13.2 Hz), 4.02-4.20 (4H, m), 4.60-4.70 (1H, m), 6.92-7.00 (2H, m), 7.15-7.20 (2H, m), 7.25-7.40 (10H, m) (4R)-4-benzyl-3-{[(3R,4S)-1-benzyl-4-(4-fluorophenyl)pyrrolidin-3-yl]carbonyl}-1,3-oxazolidin-2-one (more polar product)

$^1$H-NMR(CDCl$_3$) δ 2.64-2.82 (3H, m), 3.13-3.23 (3H, m), 3.63 (1H, d, J=12.9 Hz), 3.73 (1H, d, J=12.9 Hz), 4.00-4.28 (4H, m), 4.62-4.70 (1H, m), 6.95-7.06 (3H, m), 7.18-7.36 (11H, m)

(Step 3)

To a solution of (4R)-4-benzyl-3-{[(3S,4R)-1-benzyl-4-(4-fluorophenyl)pyrrolidin-3-yl]carbonyl}-1,3-oxazolidin-2-one (92.4 g) obtained in step 2 in DMAc (500 mL) was added under a nitrogen atmosphere 20% palladium hydroxide (9.2 g). Hydrogen was bubbled in at 40° C. for 4 hr, and the catalyst was filtered off through celite. To the filtrate were added triethylamine (20.4 g) and Boc$_2$O (46.2 g), and the mixture was stirred at room temperature for 1.5 hr, and concentrated under reduced pressure. The residue was diluted with ethyl acetate, washed with saturated aqueous ammonium chloride solution/water (1:1) and saturated brine, dried and concentrated under reduced pressure. The residue was separated and purified by silica gel column chromatography (30% ethyl acetate/hexane) to give tert-butyl (3S,4R)-3-{[(4R)-4-benzyl-2-oxo-1,3-oxazolidin-3-yl]carbonyl}-4-(4-fluorophenyl)pyrrolidine-1-carboxylate (96 g, 100%) as a white powder.

MS(ESI+): 369 (M–Boc+2H)

(Step 4)

To a solution of the compound (96 g) obtained in step 3 in water/THF (75/222 mL) was added 4N aqueous sodium hydroxide solution (185 mL), and the mixture was stirred at room temperature for 1 hr. The reaction mixture was concentrated under reduced pressure, diluted with methyl tert-butyl ether, and extracted with water. The aqueous layer was acidified with citric acid (62 g), and the mixture was stirred at 0° C. for 30 min. The precipitated crystals were collected by filtration, and recrystallized from ethyl acetate/IPE to give (3S,4R)-1-(tert-butoxycarbonyl)-4-(4-fluorophenyl)pyrrolidine-3-carboxylic acid (48.7 g, 78%) as a white powder.

MS(ESI+): 254 (M–$^t$Bu+2H)

(Step 5)

To a solution of the compound (24.7 g) obtained in step 4 in toluene (240 mL) were added DPPA (26.4 g) and triethylamine (13.4 mL), and the mixture was stirred at 65° C. for 30 min. The mixture was cooled to –10° C., 8N aqueous sodium hydroxide solution (100 mL) was added dropwise, and the mixture was stirred at –10° C. to 0° C. for 2 hr. The mixture was diluted with toluene (400 mL), and extracted with water (400 mL) and 1N aqueous sodium hydroxide solution (80 mL, 2 times). The combined aqueous layer was extracted with ethyl acetate (400 mL, 3 times), washed with saturated brine, dried, and filtered through silica gel column chromatography (NH Chromatorex) (eluted with ethyl acetate). The filtrate was concentrated under reduced pressure, and the residue was diluted with IPE. The insoluble material was filtered off, and the filtrate was concentrated under reduced pressure to give the title compound (21.7 g, 97%) as a pink solid.

MS(ESI+): 208 (M–$^t$BuO+H)

$^1$H-NMR(CDCl$_3$) δ 1.46-1.49 (11H, m), 2.91 (1H, quin, J=9.8 Hz), 3.01-3.20 (1H, m), 3.27-3.58 (2H, m), 3.70-4.00 (2H, m), 6.98-7.11 (2H, m), 7.17-7.30 (2H, m)

Reference Example 20 tert-butyl (3R,4S)-3-amino-4-(4-fluorophenyl)pyrrolidine-1-carboxylate (Step 1)

By reaction and purification in the same manner as in the method described in Reference Example 13, steps 1 to 5 and using 4-fluorocinnamic acid, (3R*, 4S*)-1-(tert-butoxycarbonyl)-4-(4-fluorophenyl)pyrrolidine-3-carboxylic acid was obtained as a white powder.

$^1$H-NMR(CDCl$_3$) δ 1.47 (9H, s), 3.10-3.22 (1H, m), 3.30-3.44 (1H, m), 3.54-3.70 (2H, m), 3.80-3.96 (2H, m), 6.97-7.04 (2H, m), 7.18-7.25 (2H, m)

(Step 2)

To a solution of the compound (1.04 g) obtained in step 1 and DMF (22 µL) in THF (22 mL) was added oxalyl chloride (578 µL) at 0° C. and the mixture was stirred for 45 min and concentrated under reduced pressure. The obtained residue was dissolved in THF (5 mL), (R)-4-benzyl-2-oxazolidinone (0.653 g), triethylamine (2.34 mL) and lithium chloride (0.71 g) were added at 0° C., and the mixture was stirred at room temperature for 14 hr. The reaction mixture was diluted with water, and the mixture was extracted with ethyl acetate. The extract was washed with saturated aqueous ammonium chloride solution, 1N sodium hydroxide water and saturated brine, dried and concentrated under reduced pressure. The residue was separated and purified by silica gel column chromatography (solvent gradient; 20→33% ethyl acetate/hexane) to give tert-butyl (3S,4R)-3-{[(4R)-4-benzyl-2-oxo-1,3-oxazolidin-3-yl]carbonyl}-4-(4-fluorophenyl)pyrrolidine-1-carboxylate (less polar product, 0.76 g, 48%) as a colorless oil and tert-butyl (3R,4S)-3-{[(4R)-4-benzyl-2-oxo-1,3-oxazolidin-3-yl]carbonyl}-4-(4-fluorophenyl)pyrrolidine-1-carboxylate (more polar product, 0.56 g, 36%) as a white powder. The absolute configuration was determined by single crystal X-ray crystal structure analysis of tert-butyl (3R,4S)-3-{[(4R)-4-benzyl-2-oxo-1,3-oxazolidin-3-yl]carbonyl}-4-(4-fluorophenyl)pyrrolidine-1-carboxylate.

tert-butyl (3S,4R)-3-{[(4R)-4-benzyl-2-oxo-1,3-oxazolidin-3-yl]carbonyl}-4-(4-fluorophenyl)pyrrolidine-1-carboxylate (less polar product)

$^1$H-NMR(CDCl$_3$) δ 1.50 (9H, s), 2.72-2.83 (1H, m), 3.18-3.28 (1H, m), 3.38-3.58 (2H, m), 3.78-4.20 (5H, m), 4.36 (1H, q, J=8.7 Hz), 4.56-4.64 (1H, m), 6.96-7.03 (2H, m), 7.14-7.18 (2H, m), 7.24-7.36 (5H, m) tert-butyl (3R,4S)-3-{[(4R)-4-benzyl-2-oxo-1,3-oxazolidin-3-yl]carbonyl}-4-(4-fluorophenyl)pyrrolidine-1-carboxylate (more polar product)

$^1$H-NMR(CDCl$_3$) δ 1.48 (9H, s), 2.58-2.70 (1H, m), 2.98-3.06 (1H, m), 3.38-3.56 (2H, m), 3.80-4.00 (3H, m), 4.08-4.16 (2H, m), 4.50 (1H, q, J=8.7 Hz), 4.62-4.72 (1H, m), 6.80-6.97 (2H, m), 7.00-7.08 (2H, m), 7.18-7.27 (3H, m), 7.28-7.35 (2H, m)

(Step 3)

To a mixed solution of tert-butyl (3R,4S)-3-{[(4R)-4-benzyl-2-oxo-1,3-oxazolidin-3-yl]carbonyl}-4-(4-fluorophenyl)pyrrolidine-1-carboxylate (0.32 g) obtained in step 2 in THF (14.4 mL) and water (4.8 mL) were added 30% aqueous hydrogen peroxide (939 µL) and 4N aqueous lithium hydroxide solution (518 µL) at 0° C., and the mixture was stirred at room temperature for 8 hr. The reaction mixture was diluted with aqueous sodium thiosulfate solution, and extracted with ethyl acetate. The extract was washed with water and extracted with 0.5N aqueous sodium hydroxide solution. The extract was washed with ethyl acetate, acidified with 10% aqueous citric acid solution, and extracted with ethyl acetate. The extract was washed with water and saturated brine, dried and concentrated under reduced pressure to give (3R,4S)-1-(tert-butoxycarbonyl)-4-(4-fluorophenyl)pyrrolidine-3-carboxylic acid (0.185 g, 88%) as a white powder.

$[\alpha]_D^{25}$+34.6° (c0.25, MeOH)

(Step 4)

To a solution of the compound (0.25 g) obtained in step 3 in toluene (5 mL) were added triethylamine (150 μL) and DPPA (0.29 g) at room temperature, and the mixture was stirred at 95° C. for 1.5 hr. The reaction solution was cooled, 8N aqueous sodium hydroxide solution (1.2 mL) was added, and the mixture was stirred at room temperature for 2 hr. The reaction mixture was poured into water and extracted with ethyl acetate. The organic layer was washed with saturated aqueous ammonium chloride solution and saturated brine, dried and concentrated under reduced pressure to give the title compound (0.25 g, quantitatively) as a colorless oil.

MS(ESI+): 225 (M-$^t$Bu+2H)

Reference Example 21 tert-butyl (3R*,4R*)-3-amino-4-(4-fluorophenyl)pyrrolidine-1-carboxylate p-toluenesulfonate (Step 1)

To a solution of methyl [bis(2,2,2-trifluoroethoxy)phosphoryl]acetate (5.0 g) and 18-crown-6 (10.3 g) in THF (200 mL) was added dropwise at −78° C. potassium bis(trimethylsilyl)amide (15% toluene solution, 21 mL), and 4-fluorobenzaldehyde (1.95 g) was added. The reaction mixture was stirred at −78° C. for 20 min, and the mixture was stirred at room temperature for 1 hr. The mixture was diluted with saturated aqueous ammonium chloride solution, and extracted with ethyl acetate. The extract was washed with saturated brine, dried and concentrated under reduced pressure. The residue was separated and purified by silica gel column chromatography (solvent gradient; 5→15% ethyl acetate/hexane) to give methyl (2Z)-3-(4-fluorophenyl)prop-2-enoate (2.24 g, 79%) as a colorless oil.

$^1$H-NMR(CDCl$_3$) δ 3.27 (3H, s), 5.93 (1H, d, J=12.6 Hz), 6.89 (1H, d, J=12.6 Hz), 7.00-7.06 (2H, m), 7.61-7.66 (2H, m)

(Step 2)

By reaction and purification in the same manner as in the method described in Reference Example 13, step 2 and using the compound obtained in step 1, methyl (3R*,4R*)-1-benzyl-4-(4-fluorophenyl)pyrrolidine-3-carboxylate was obtained.

MS(ESI+): 314 (M+H)

(Step 3)

A mixture of the compound (2.97 g) obtained in step 2, 10% palladium carbon (0.30 g) and dimethylacetamide (30 mL) was stirred under a hydrogen atmosphere (3 atm) at 50° C. for 2 hr. This mixture was cooled to 0° C., Boc$_2$O (2.1 g) and triethylamine (1.3 mL) were added, and the mixture was stirred at 30 min. The mixture was diluted with water, and the catalyst was filtered off through celite. The filtrate was extracted with ethyl acetate, washed with water, dried and concentrated under reduced pressure. The residue was separated and purified by silica gel column chromatography (15% ethyl acetate/hexane) to give 3-methyl 1-tert-butyl (3R*,4R*)-4-(4-fluorophenyl)pyrrolidine-1,3-dicarboxylate (2.7 g, 89%) as a colorless oil.

$^1$H-NMR(CDCl$_3$) δ 1.50 (9H, s), 3.30-3.50 (1H, m), 3.43 (3H, s), 3.60-3.85 (5H, m), 6.94-7.00 (2H, m), 7.07-7.16 (2H, m)

(Step 4)

A mixture of the compound (2.7 g) obtained in step 3 and concentrated hydrochloric acid/acetic acid (4.2/4.2 mL) was stirred at 90 to 100° C. for 3 hr, and concentrated under reduced pressure. The residue was dissolved in DMAc (8.0 mL), Boc$_2$O (2.8 g) and triethylamine (3.0 mL) were added at 0° C. and the mixture was stirred for 30 min. The mixture was poured into saturated aqueous ammonium chloride solution, and extracted twice with ethyl acetate. The extract was washed twice with water and with saturated brine, dried and concentrated under reduced pressure to give (3R*,4R*)-1-(tert-butoxycarbonyl)-4-(4-fluorophenyl)pyrrolidine-3-carboxylic acid (1.5 g, 56%) as a white powder.

$^1$H-NMR(CDCl$_3$) δ 1.44 (9H, s), 3.10-3.44 (1H, m), 3.60-3.80 (5H, m), 6.95 (2H, t, J=8.6 Hz), 7.08-7.18 (2H, m)

(Step 5)

By reaction and purification in the same manner as in the method described in Reference Example 1, step 4 and using the compound obtained in step 4, the title compound was obtained.

MS(ESI+): 225 (M–p-TsOH–$^t$Bu+2H)

Reference Example 22 tert-butyl (3S,4R)-3-amino-4-(3,4-dichlorophenyl)pyrrolidine-1-carboxylate (Step 1)

By reaction and purification in the same manner as in the method described in Reference Example 20, step 2 and using the compound obtained in Reference Example 13, step 5, tert-butyl (3S,4R)-3-{[(4R)-4-benzyl-2-oxo-1,3-oxazolidin-3-yl]carbonyl}-4-(3,4-dichlorophenyl)pyrrolidine-1-carboxylate (less polar product) and tert-butyl (3R,4S)-3-{[(4R)-4-benzyl-2-oxo-1,3-oxazolidin-3-yl]carbonyl}-4-(3,4-dichlorophenyl)pyrrolidine-1-carboxylate (more polar product) were obtained each as a white powder.

tert-butyl (3S,4R)-3-{[(4R)-4-benzyl-2-oxo-1,3-oxazolidin-3-yl]carbonyl}-4-(3,4-dichlorophenyl)pyrrolidine-1-carboxylate (less polar product)

$^1$H-NMR(CDCl$_3$) δ 1.48-1.50 (9H, m), 2.66-2.88 (1H, m), 3.18-3.23 (1H, m), 3.32-3.59 (2H, m), 3.72-4.22 (5H, m), 4.23-4.38 (1H, m), 4.53-4.70 (1H, m), 7.10-7.22 (3H, m), 7.27-7.44 (5H, m) tert-butyl (3R,4S)-3-{[(4R)-4-benzyl-2-oxo-1,3-oxazolidin-3-yl]carbonyl}-4-(3,4-dichlorophenyl)pyrrolidine-1-carboxylate (more polar product)

$^1$H-NMR(CDCl$_3$) δ 1.48 (9H, s), 2.70-2.74 (1H, m), 3.04-3.09 (1H, m), 3.31-3.56 (2H, m), 3.72-4.04 (3H, m), 4.10-4.31 (2H, m), 4.36-4.52 (1H, m), 4.57-4.77 (1H, m), 6.96 (2H, brs), 7.15-7.29 (4H, m), 7.39-7.47 (2H, m)

(Step 2)

By reaction and purification in the same manner as in the method described in Reference Example 20, step 3 and using tert-butyl (3S,4R)-3-{[(4R)-4-benzyl-2-oxo-1,3-oxazolidin-3-yl]carbonyl}-4-(3,4-dichlorophenyl)pyrrolidine-1-carboxylate obtained in step 1, (3S,4R)-1-(tert-butoxycarbonyl)-4-(3,4-dichlorophenyl)pyrrolidine-3-carboxylic acid was obtained.

$^1$H-NMR(CDCl$_3$) δ 1.47 (9H, s), 3.05-3.26 (1H, m), 3.27-3.48 (1H, m), 3.52-3.71 (2H, m), 3.77-4.03 (2H, m), 7.10 (1H, dd, J=8.3, 2.3 Hz), 7.35 (1H, d, J=2.3 Hz), 7.40 (1H, d, J=8.3 Hz)

(Step 3)

By reaction and purification in the same manner as in the method described in Reference Example 13, step 6 and using the compound obtained in step 2, the title compound was obtained.

MS(ESI+): 258 (M−$^t$BuO+H)

Reference Example 23 tert-butyl (3S,4R)-3-amino-4-(3,4-difluorophenyl)pyrrolidine-1-carboxylate

By reaction and purification in the same manner as in the method described in Reference Example 25, steps 1 and 2, Reference Example 21, step 3 and Reference Example 25, steps 5 and 6 and using (E)-3-(3,4-difluorophenyl)-2-propenoic acid synthesized by reference to a known method (US2003/148888), the title compound was obtained.

MS(ESI+): 299 (M+H)

Reference Example 24 tert-butyl (3S,4R)-3-amino-4-(2,4-difluorophenyl)pyrrolidine-1-carboxylate

By reaction and purification in the same manner as in the method described in Reference Example 19, step 1 to step 5 and using 2,4-difluorocinnamic acid, the title compound was obtained.

MS(ESI+): 243 (M−$^t$Bu+2H)

Reference Example 25 tert-butyl (3S,4R)-3-amino-4-(4-chlorophenyl)pyrrolidine-1-carboxylate (Step 1)

To a mixed solution of (2E)-3-(4-chlorophenyl)prop-2-enoic acid (30.0 g) in THF (350 mL) and DMF (0.90 mL) was slowly added oxalyl chloride (21.6 mL) at 5° C., and the mixture was stirred for 1 hr. The reaction mixture was concentrated under reduced pressure, and the residue was dissolved in THF (150 mL). This THF solution was added to a suspension of (R)-4-benzyloxazolidin-2-one (31.0 g), triethylamine (114 mL) and lithium chloride (34.8 g) in THF (350 mL) at 5° C., and the mixture was stirred at room temperature for 14 hr. The reaction mixture was concentrated under reduced pressure, and water and ethyl acetate were added to the residue. The organic layer was washed with 10% aqueous citric acid solution and saturated brine, dried and concentrated under reduced pressure to give (4R)-4-benzyl-3-[(2E)-3-(4-chlorophenyl)prop-2-enoyl]-1,3-oxazolidin-2-one (40.0 g, 71%) as a white powder.

$^1$H-NMR(CDCl$_3$) δ 2.85 (1H, dd, J=13.6, 9.6 Hz), 3.37 (1H, dd, J=13.6, 3.2 Hz), 4.18-4.32 (2H, m), 4.75-4.87 (1H, m), 7.21-7.32 (3H, m), 7.32-7.42 (4H, m), 7.54-7.60 (2H, m), 7.85 (1H, d, J=15.6 Hz), 7.91 (1H, d, J=16.0 Hz)

(Step 2)

To a solution of the compound (40.0 g) obtained in step 1 and N-benzyl-1-methoxy-N-((trimethylsilyl)methyl)methanamine (30.5 g) in toluene (230 mL) was added at 0° C. a solution of trifluoroacetic acid (1.80 mL) in toluene (20 mL), and the mixture was stirred at room temperature for 12 hr. To the reaction mixture was poured saturated aqueous sodium hydrogen carbonate solution, and the resultant mixture was extracted with ethyl acetate. The organic layer was washed with water and saturated brine and dried, and the solvent was evaporated under reduced pressure. The obtained residue was purified by silica gel column chromatography (solvent gradient; 10→50% ethyl acetate/hexane) to give (4R)-4-benzyl-3-{[(3S,4R)-1-benzyl-4-(4-chlorophenyl)pyrrolidin-3-yl]carbonyl}-1,3-oxazolidin-2-one (20.0 g, 36%) as a less polar compound, and (4R)-4-benzyl-3-{[(3R,4S)-1-benzyl-4-(4-chlorophenyl)pyrrolidin-3-yl]carbonyl}-1,3-oxazolidin-2-one (15.6 g, 28%) as a more polar compound, each as a white powder. property data of less polar compound:

$^1$H-NMR(CDCl$_3$) δ 2.60-2.68 (1H, m), 2.74-2.86 (2H, m), 3.13-3.30 (3H, m), 3.63 (1H, d, J=13.2 Hz), 3.76 (1H, d, J=13.2 Hz), 4.02-4.10 (2H, m), 4.12-4.18 (2H, m), 4.60-4.69 (1H, m), 7.14-7.20 (2H, m), 7.23-7.29 (8H, m), 7.30-7.39 (4H, m)

property data of more polar compound:

$^1$H-NMR(CDCl$_3$) δ 2.63-2.82 (3H, m), 3.10-3.28 (3H, m), 3.63 (1H, d, J=13.2 Hz), 3.73 (1H, d, J=13.2 Hz), 4.04 (1H, q, J=7.6 Hz), 4.09-4.28 (3H, m), 4.61-4.72 (1H, m), 7.10-7.08 (2H, m), 7.18-7.28 (5H, m), 7.28-7.38 (7H, m)

(Step 3)

To a solution of the less polar compound (21.6 g) obtained in step 2 in dichloromethane (90 mL) was added ACE-Cl (7.81 g) at room temperature, and the mixture was heated under reflux for 2 hr. The reaction mixture was concentrated under reduced pressure, methanol (90 mL) was added to the residue, and the mixture was heated under reflux for 1.5 hr. The reaction mixture was concentrated under reduced pressure, ethyl acetate was added to the residue, and the precipitated crystals were collected by filtration with diethyl ether and dichloromethane to give (4R)-4-benzyl-3-{[(3S,4R)-4-(4-chlorophenyl)pyrrolidin-3-yl]carbonyl}-1,3-oxazolidin-2-one monohydrochloride (15.5 g, 81%).

$^1$H-NMR (MeOH-d$_4$) δ 2.96 (1H, dd, J=13.6, 8.4 Hz), 3.17 (1H, dd, J=13.8, 3.4 Hz), 3.42-3.58 (2H, m), 3.78 (1H, dd, J=11.4, 7.8 Hz), 3.92 (1H, dd, J=12.0, 8.8 Hz), 4.02-4.12 (1H, m), 4.26 (2H, d, J=5.6 Hz), 4.38-4.47 (1H, m), 4.64-4.72 (1H, m), 7.20-7.29 (3H, m), 7.30-7.42 (6H, m) (proton of NH and HCl was not observed)

(Step 4)

To a solution of the compound (15.5 g) obtained in step 3 in acetonitrile (73 mL) was added triethylamine (6.15 mL), Boc$_2$O (9.62 g) was added at 0° C., and the mixture was stirred at room temperature for 6 hr. The reaction mixture was poured into water and extracted with dichloromethane. The organic layer was dried, and the solvent was evaporated under reduced pressure to give tert-butyl (3S,4R)-3-{[(4R)-4-benzyl-2-oxo-1,3-oxazolidin-3-yl]carbonyl}-4-(4-chlorophenyl)pyrrolidine-1-carboxylate (17.8 g, quantitatively) as a colorless oil.

$^1$H-NMR(CDCl$_2$) δ 1.48&1.50 (9H, each s), 2.70-2.85 (1H, m), 3.15-3.26 (1H, m), 3.35-3.58 (2H, m), 3.75-4.20 (5H, m), 4.29-4.40 (1H, m), 4.52-4.65 (1H, m), 7.14-7.20 (2H, m), 7.24-7.37 (7H, m)

(Step 5)

To a mixed solution of the compound (17.0 g) obtained in step 4 in THF (60 mL) and water (15 mL) was added at 0° C. 4N lithium hydroxide (35.1 mL), and the mixture was stirred at room temperature for 16 hr. To the reaction mixture was added ethyl acetate, and the mixture was acidified with 2N hydrochloric acid. The organic layer was dried, and the solvent was evaporated under reduced pressure to give (3S,4R)-1-(tert-butoxycarbonyl)-4-(4-chlorophenyl)pyrrolidine-3-carboxylic acid (7.35 g) as a white powder.

$^1$H-NMR(CDCl$_3$) δ 1.47 (9H, s), 3.07-3.22 (1H, m), 3.27-3.45 (1H, m), 3.50-3.68 (2H, m), 3.75-3.98 (2H, m), 7.18 (2H, d, J=8.4 Hz), 7.29 (2H, d, J=8.8 Hz)(The proton of COOH was not observed) optical purity: 99.9% ee (Step 6)

To a solution of the compound (3.26 g) obtained in step 5 in toluene (15 mL) were added DPPA (3.58 g) and triethylamine (1.81 mL) at room temperature, and the mixture was stirred at 70° C. for 1 hr.

The reaction solution was cooled, 8N aqueous sodium hydroxide solution (15 mL) was added, and the mixture was stirred at room temperature for 2 hr. The reaction mixture was poured into water and extracted with ethyl acetate. The organic layer was washed with water and saturated brine and dried, and the solvent was evaporated under reduced pressure to give the title compound (0.76 g, 26%) as a colorless oil.

MS(ESI+): 224 (M−$^t$BuO+H)

Reference Example 26 tert-butyl (3R,4S)-3-amino-4-(4-chlorophenyl)pyrrolidine-1-carboxylate

By reaction and purification in the same manner as in the method described in Reference Example 25, step 3 to 6 and using the more polar compound obtained in Reference Example 25, step 2, the title compound was obtained.

MS(ESI+): 224 (M−$^t$BuO+H)

Reference Example 27 tert-butyl (3S,4R)-3-amino-4-(4-fluoro-2-methylphenyl)pyrrolidine-1-carboxylate (Step 1)

To a mixture of pyridine (0.035 mL) and piperidine (1.43 mL) was added malonic acid (30 g), and the mixture was heated to 75° C. To this mixture was added dropwise 4-fluoro-2-methylbenzaldehyde (20 g), and the mixture was stirred at 90° C. for 6 hr. The reaction mixture was cooled to room temperature, and diluted with water (100 ml), and concentrated under reduced pressure. The residue was suspended in 0.1N hydrochloric acid (250 mL), and the mixture was stirred at room temperature for 30 min. The precipitate was collected by filtration, washed with 0.1N hydrochloric acid (250 mL) and water (50 mL, 0.3 times) and dried to give 4-fluoro-2-methylcinnamic acid (24 g, 93%) as a white powder.

$^1$H-NMR (DMSO-d$_6$) δ 2.40 (3H, s), 6.40 (1H, d, J=15.4 Hz), 6.95-7.26 (2H, m), 7.65-7.88 (2H, m), 12.46 (1H, brs)

(Step 2)

By reaction and purification in the same manner as in the method described in Reference Example 19, step 1 to step 5 and using the compound obtained in step 1, the title compound was obtained.

MS(ESI+): 222 (M−$^t$BuO+H)

Reference Example 28 tert-butyl (3S,4R)-3-amino-4-(5-fluoropyridin-2-yl)pyrrolidine-1-carboxylate (Step 1)

To a solution of 2-bromo-5-fluoropyridine (25 g) in toluene (142 mL) was added at −78° C. n-butyllithium (2.5M toluene solution, 68 mL), and the mixture was stirred at −78° C. for 1 hr. To this mixture was added at −78° C. DMF (16.5 mL), and the mixture was stirred at −78° C. for 2 hr, and saturated aqueous ammonium chloride solution (300 mL) was added. The mixture was extracted with ethyl acetate (300 mL), dried and concentrated under reduced pressure. The residue was separated and purified by silica gel column chromatography (20% ethyl acetate/hexane) to give 5-fluoropyridine-2-carbaldehyde (4.7 g, 26%) as a yellow oil.

$^1$H-NMR(CDCl$_3$, 400 MHz) δ 7.57-7.62 (1H, m), 8.03-8.07 (1H, m), 8.64 (1H, d, J=2.8 Hz), 10.05 (1H, s)

(Step 2)

To a suspension of sodium hydride (55 wt %, 1.97 g) in THF (200 ml) was added at 0° C. ethyl (diethoxyphosphoryl)acetate (9.3 g), and the mixture was stirred at 30 min. To this mixture was added a solution of the compound (4.7 g) obtained in step 1 in THF (200 mL) at 0° C., and the mixture was stirred at room temperature for 12 hr. The mixture was diluted with water (500 mL), extracted with ethyl acetate (500 mL), dried and concentrated under reduced pressure. The residue was separated and purified by silica gel column chromatography (25% ethyl acetate/hexane) to give ethyl (2E)-3-(5-fluoropyridin-2-yl)prop-2-enoate (6.2 g, 85%) as a white powder.

$^1$H-NMR(CDCl$_3$, 400 MHz) δ 1.34 (3H, t, J=7.2 Hz), 4.28 (2H, q, J=7.2 Hz), 6.84 (1H, dd, J=15.6, 0.8 Hz), 7.39-7.47 (2H, m), 7.66 (1H, d, J=15.6 Hz), 8.50 (1H, d, J=2.4 Hz)

(Step 3)

To a solution of the compound (4.7 g) obtained in step 2 in ethanol (48 mL) was added 2N aqueous sodium hydroxide solution (24 mL) at room temperature, and the mixture was stirred at 50° C. for 2 hr, and concentrated under reduced pressure. The residue was diluted with water (200 mL), and washed with ethyl acetate (200 mL). The aqueous layer was acidified (pH 2) with trifluoroacetic acid, and the mixture was extracted with ethyl acetate (2×200 mL). The extract was concentrated under reduced pressure to give (2E)-3-(5-fluoropyridin-2-yl)prop-2-enoic acid trifluoroacetate (4.7 g, 70%).

$^1$H-NMR (CD$_3$OD, 400 MHz) δ 6.80 (1H, dd, J=16.0, 0.8 Hz), 7.62-7.73 (2H, m), 7.66 (1H, d, J=15.6 Hz), 8.52 (1H, d, J=2.8 Hz)

(Step 4)

To a solution of the compound (2.5 g) obtained in step 3 in THF (180 mL) were added at −78° C. pivaloyl chloride (12.9 g) and triethylamine (2.25 g) and the mixture was stirred for 2 hr. To this mixture was added at −78° C. a solution of oxazolidinone lithium anion (prepared by adding n-butyllithium (2.5M hexane solution, 5.34 mL) to (R)-4-benzyloxazolidin-2-one (1.73 g) in THF (180 mL) at −78° C. and stirring for 1 hr), and the mixture was stirred at room temperature for 18 hr. The reaction was discontinued by adding saturated aqueous ammonium chloride solution (200 mL), and the mixture was extracted with ethyl acetate (300 mL). The extract was dried, concentrated under reduced pressure, and the residue was separated and purified by silica gel column chromatography (25% ethyl acetate/hexane) to give (4R)-4-benzyl-3-[(2E)-3-(5-fluoropyridin-2-yl)prop-2-enoyl]-1,3-oxazolidin-2-one (2.3 g, 80%) as a pale-yellow oil.

$^1$H-NMR(CDCl$_3$, 400 MHz) δ 2.86 (1H, dd, J=13.4, 9.4 Hz), 3.38 (1H, dd, J=13.4, 3.4 Hz), 4.21-4.29 (2H, m), 4.78-4.84 (1H, m), 7.23-7.37 (5H, m), 7.41-7.46 (1H, m), 7.59 (1H, dd, J=8.6, 4.6 Hz), 7.88 (1H, d, J=15.6 Hz), 8.22 (1H, dd, J=15.4, 0.6 Hz), 8.54 (1H, d, J=2.8 Hz)

(Step 5)

To a solution of the compound (8.26 g) obtained in step 4 in dichloromethane (100 mL) were added at room temperature N-(methoxymethyl)-N-(trimethylsilylmethyl)benzylamine (9.6 g) and trifluoroacetic acid (0.58 g), and the mixture was stirred at 18 hr. The mixture was diluted with water (200 mL), extracted with dichloromethane (2×200 mL), dried and concentrated under reduced pressure. The residue was separated and purified by silica gel column chromatography (25% ethyl acetate/hexane) to give (4R)-4-benzyl-3-{[(3S,4S)-1-benzyl-4-(5-fluoropyridin-2-yl)pyrrolidin-3-yl]carbonyl}-1,3-oxazolidin-2-one (less polar product, 11.8 g, 47%) as a yellow oil, and (4R)-4-benzyl-3-{[(3R,4R)-1-benzyl-4-(5-fluoropyridin-2-yl)pyrrolidin-3-yl]carbonyl}-1,3-oxazolidin-2-one (more polar product, 10.5 g, 41%) as a yellow oil.

(4R)-4-benzyl-3-{[(3S,4S)-1-benzyl-4-(5-fluoropyridin-2-yl)pyrrolidin-3-yl]carbonyl}-1,3-oxazolidin-2-one (less polar product)

$^1$H-NMR(CDCl$_3$, 400 MHz) δ 2.72 (1H, t, J=8.6 Hz), 2.80 (1H, dd, J=13.6, 9.2 Hz), 2.95 (1H, dd, J=9.8, 5.0 Hz), 3.20-3.30 (3H, m), 3.66 and 3.75 (2H, ABq, J=16.4 Hz), 4.11-4.24 (2H, m), 4.26-4.36 (1H, m), 4.37-4.40 (1H, m), 4.65-4.71 (1H, m), 7.16-7.19 (2H, m), 7.24-7.36 (10H, m), 8.37 (1H, d, J=2.4 Hz) (4R)-4-benzyl-3-{[(3R,4R)-1-benzyl-4-(5-fluoropyridin-2-yl)pyrrolidin-3-yl]carbonyl}-1,3-oxazolidin-2-one (more polar product)

$^1$H-NMR(CDCl$_3$, 400 MHz) δ 2.73 (1H, t, J=8.8 Hz), 2.78 (1H, dd, J=13.6, 9.2 Hz), 2.92 (1H, dd, J=10.0, 5.2 Hz), 3.15-3.29 (3H, m), 3.34 and 3.73 (2H, ABq, J=16.4 Hz), 4.11-4.19 (2H, m), 4.28 (1H, dd, J=16.0, 7.6 Hz), 4.48-4.53 (1H, m), 4.64-4.70 (1H, m), 7.14-7.17 (2H, m), 7.24-7.36 (10H, m), 8.40 (1H, d, J=2.8 Hz)

(Step 6)

A mixture of (4R)-4-benzyl-3-{[(3S,4S)-1-benzyl-4-(5-fluoropyridin-2-yl)pyrrolidin-3-yl]carbonyl}-1,3-oxazolidin-2-one (5.4 g) obtained in step 5, palladium-carbon (1.26 g) and methanol (118 mL) was stirred under a hydrogen atmosphere (1 atm) at room temperature for 18 hr. The mixture was filtrated through celite, and the filtrate was concentrated under reduced pressure to give methyl (3S,4S)-4-(5-fluoropyridin-2-yl)pyrrolidine-3-carboxylate (4.61 g, 98%) as a yellow oil.

MS(ESI+): 225 (M+H)

(Step 7)

To a solution of the compound (2.65 g) obtained in step 6 in dichloromethane (118 mL) were added Boc$_2$O (6.0 mL) and triethylamine (3.6 mL), and the mixture was stirred at room temperature for 1 hr. The mixture was diluted with water (100 mL), extracted with dichloromethane (100 mL), dried and concentrated under reduced pressure. The residue was separated and purified by silica gel column chromatography (25% ethyl acetate/hexane) to give 3-methyl 1-tert-butyl (3S,4S)-4-(5-fluoropyridin-2-yl)pyrrolidine-1,3-dicarboxylate (2.8 g, 74%) as a colorless oil.

$^1$H-NMR(CDCl$_3$, 400 MHz) δ 1.47 (9H, d, J=6.4 Hz), 3.46-3.64 (3H, m), 3.65 (3H, s), 3.66-3.97 (3H, m), 7.19-7.23 (1H, m), 7.32-7.37 (1H, m), 8.42 (1H, s)

(Step 8)

To a methanol solution of the compound (2.8 g) obtained in step 7 was added a solution of sodium hydroxide (0.7 g) in water (30 mL), and the mixture was stirred at room temperature for 3 hr. The mixture was concentrated under reduced pressure, diluted with water, and washed with ethyl acetate. The aqueous layer was acidified (pH 5) with acetic acid, extracted with dichloromethane, dried and concentrated under reduced pressure to give (3S,4S)-1-(tert-butoxycarbonyl)-4-(5-fluoropyridin-2-yl)pyrrolidine-3-carboxylic acid (2.3 g, 85%) as a white oil.

MS(ESI+): 311 (M+H)

(Step 9)

To a solution of the compound (2.29 g) obtained in step 8 in toluene (24.0 mL) were added DPPA (2.44 g) and triethylamine (1.23 mL), and the mixture was stirred at 65° C. for 1 hr. The mixture was cooled to −10° C., 8N aqueous sodium hydroxide solution (9.23 mL) was added dropwise, and the mixture was stirred at −10° C. to 0° C. for 1.5 hr. The mixture was diluted with toluene, and extracted with water and 1N aqueous sodium hydroxide solution. The combined aqueous layer was extracted with ethyl acetate (4 times), dried and concentrated under reduced pressure. The residue was diluted with ethyl acetate, and the insoluble material was filtered off, and the filtrate was concentrated under reduced pressure to give the title compound (1.83 g, 88%) as a yellow oil.

$^1$H-NMR(CDCl$_3$) δ 1.38-1.55 (9H, m), 2.98-3.27 (2H, m), 3.55 (1H, t, J=10.4 Hz), 3.65-4.02 (3H, m), 7.14-7.26 (1H, m), 7.37 (1H, td, J=8.3, 3.0 Hz), 8.44 (1H, brs)

Reference Example 29 tert-butyl [3,5-bis(trifluoromethyl)phenyl](2-oxoethyl)carbamate (Step 1)

A solution of 3,5-bis(trifluoromethyl)aniline (4.6 g) in 2-bromoethanol (25.0 g) was stirred at 70° C. for 14 hr, and concentrated under reduced pressure. The residue was poured into water, and the mixture was extracted with ethyl acetate. The extract was washed with saturated aqueous sodium hydrogen carbonate solution, water and saturated brine, dried and concentrated under reduced pressure. The residue was purified by silica gel column chromatography (33% ethyl acetate/hexane) to give 2-{[3,5-bis(trifluoromethyl)phenyl]amino}ethanol (3.1 g, 58%) as a brown powder.

$^1$H-NMR(CDCl$_3$) δ 3.36 (2H, t, J=5.3 Hz), 3.90 (2H, t, J=5.3 Hz), 6.99 (2H, s), 7.17 (1H, s)(The protons of NH and OH were not observed)

(Step 2)

A solution of the compound (0.38 g) obtained in step 1, imidazole (0.12 g) and tert-butyldimethylchlorosilane (0.26 g) in DMAc (5 mL) was stirred at room temperature for 14 hr, poured into water, and the mixture was extracted with ethyl acetate. The extract was washed with saturated ammonium chloride solution and saturated brine, dried and concentrated under reduced pressure. The residue was separated and purified by silica gel column chromatography (solvent gradient; 3→10% ethyl acetate/hexane) to give N-(2-{[tert-butyl(dimethyl)silyl]oxy}ethyl)-3,5-bis(trifluoromethyl)aniline (0.48 g, 89%) as a colorless oil.

$^1$H-NMR(CDCl$_3$) δ 0.01 (6H, s), 0.91 (9H, s), 3.23-3.30 (2H, m), 3.81-3.89 (2H, m), 4.40-4.50 (1H, m), 6.94 (2H, s), 7.13 (1H, s)

(Step 3)

A solution of the compound (0.48 g) obtained in step 2, Boc$_2$O (0.41 g), triethylamine (0.17 mL) and dimethylaminopyridine (0.15 g) in DMAc (5 mL) was stirred at room temperature for 1.5 hr, poured into water, and the mixture was extracted with ethyl acetate. The extract was washed with saturated aqueous ammonium chloride solution and saturated brine, dried and concentrated under reduced pressure. The residue was separated and purified by silica gel column chromatography (solvent gradient; 3→10% ethyl acetate/hexane) to give tert-butyl [3,5-bis(trifluoromethyl)phenyl](2-{[tert-butyl(dimethyl)silyl]oxy}ethyl)carbamate (0.53 g, 88%) as a colorless oil.

$^1$H-NMR(CDCl$_3$) δ 0.03 (6H, s), 0.84 (9H, s), 1.47 (9H, s), 3.78 (2H, t, J=5.4 Hz), 3.86 (2H, t, J=5.4 Hz), 7.63 (1H, brs), 7.86 (2H, s)

(Step 4)

A mixed solution of the compound (0.50 g) obtained in step 3 in acetic acid (6 mL), water (2 mL) and THF (2 mL) was stirred at 50° C. for 14 hr, poured into water, and extracted with diethyl ether. The extract was washed with saturated aqueous sodium hydrogen carbonate solution and saturated brine, dried and concentrated under reduced pressure. The residue was separated and purified by silica gel column chromatography (solvent gradient; 10→33% ethyl acetate/hexane) to give tert-butyl [3,5-bis(trifluoromethyl)phenyl](2-hydroxyethyl)carbamate (0.34 g, 87%) as a colorless oil.

$^1$H-NMR(CDCl$_3$) δ 1.45 (9H, s), 2.10-2.30 (1H, br), 3.85 (4H, s like), 7.69 (1H, brs), 7.77 (2H, s)

(Step 5)

A solution of oxalyl chloride (0.15 mL) in THF (5.0 mL) was cooled to −78° C., DMSO (0.17 mL) in THF (2.0 mL) was slowly added dropwise. The reaction mixture was stirred for 5 min, a solution of the compound (0.34 g) obtained in step 4 in THF (3.0 mL) was added dropwise. The reaction mixture was stirred at −78° C. to −20° C. for 1 hr, and triethylamine (0.88 mL) was added. The reaction mixture was stirred at room temperature for 30 min, poured into water, and the mixture was extracted with ethyl acetate. The extract was washed with saturated aqueous ammonium chloride solution and saturated brine, dried and concentrated under reduced pressure. The residue was separated and purified by silica gel column chromatography (solvent gradient; 3→20% ethyl acetate/hexane) to give the title compound (0.23 g, 69%) as a colorless oil.

$^1$H-NMR(CDCl$_3$) δ 1.46 (9H, s), 4.46 (2H, s), 7.69 (3H, s like), 9.71 (1H, s)

Reference Example 30

4-nitrophenyl [3-methyl-5-(trifluoromethyl)phenyl]carbamate

3-Methyl-5-(trifluoromethyl)aniline monohydrochloride (2.93 g) synthesized in reference to a known method (U.S. Pat. No. 4,532,353) was dissolved in THF (25 mL), and 4-nitrophenyl chlorocarbonate (3.07 g) and N,N-diisopropylethylamine (1.97 mL) were added dropwise at 5° C. The reaction mixture was stirred at 5° C. for 1 hr, poured into saturated aqueous ammonium chloride solution, and the mixture was extracted with ethyl acetate. The extract was washed with water and saturated brine, dried and concentrated under reduced pressure to give the title compound (4.66 g) as a white powder.

melting point: 136-138° C.

Reference Example 31

4-nitrophenyl [3-chloro-5-(trifluoromethyl)phenyl]carbamate

By reaction and purification in the same manner as in the method described in Reference Example 30 and using 3-chloro-5-(trifluoromethyl)aniline monohydrochloride synthesized in reference to a known method (US2003/158409), the title compound was obtained.

melting point: 144-146° C.

Reference Example 32

4-nitrophenyl [3-bromo-5-(trifluoromethyl)phenyl]carbamate

By reaction and purification in the same manner as in the method described in Reference Example 30 and using 3-bromo-5-(trifluoromethyl)aniline, the title compound was obtained.

melting point: 140-142° C.

Reference Example 33

4-nitrophenyl (3,5-dibromophenyl)carbamate

By reaction and purification in the same manner as in the method described in Reference Example 30 and using 3,5-dibromoaniline, the title compound was obtained.

melting point: 171-173° C.

Reference Example 34

4-{[(tert-butoxycarbonyl)amino]methyl}tetrahydro-2H-pyran-4-carboxylic acid (Step 1)

A solution of ethyl cyanoacetate (7.0 g) and 1,8-diazabicyclo[5,4,0]undec-7-ene (19 mL) in DMF (310 mL) was stirred at room temperature for 10 min, and cooled to 0° C. To this mixture was added 1,1'-oxybis(2-bromoethane) (15.8 g) at 0° C., and the mixture was stirred at 80° C. for 4 hr and cooled to room temperature. Water was poured into the reaction mixture, and the mixture was extracted with ethyl acetate. The extract was washed with water and saturated brine, dried and concentrated under reduced pressure to give ethyl 4-cyanotetrahydro-2H-pyran-4-carboxylate (10.1 g, 89%) as a deep brown oil.

$^1$H-NMR(CDCl$_3$) δ 1.34 (3H, t, J=7.2 Hz), 1.99-2.07 (2H, m), 2.10-2.20 (2H, m), 3.70-3.80 (2H, m), 3.95-4.03 (2H, m), 4.30 (2H, q, J=7.2 Hz)

(Step 2)

A mixture of the compound (8.09 g) obtained in step 1, Raney-nickel (containing water (50%), 5.18 g) washed with ethanol and ammonia (0.5% ethanol solution, 200 mL) was stirred under a hydrogen atmosphere (1 atm) at room temperature for 3 hr. The mixture was filtered, and concentrated under reduced pressure to give ethyl 4-(aminomethyl)tetrahydro-2H-pyran-4-carboxylate (6.79 g, 82%) as a yellow oil.

$^1$H-NMR(CDCl$_3$) δ 1.15 (2H, brs), 1.29 (3H, t, J=7.2 Hz), 1.45-1.55 (2H, m), 2.05-2.12 (2H, m), 2.79 (2H, s), 3.42-3.52 (2H, m), 3.80-3.90 (2H, m), 4.22 (2H, q, J=7.2 Hz)

(Step 3)

To a solution of the compound (8.29 g) obtained in step 2 in dichloromethane (200 mL) was added Boc$_2$O (19.3 g) at room temperature, and the mixture was stirred for 2 hr. The mixture was poured into water, and extracted with dichloromethane. The extract was washed with saturated brine, dried, and concentrated under reduced pressure to give ethyl 4-{[(tert-butoxycarbonyl)amino]methyl}tetrahydro-2H-pyran-4-carboxylate (11.7 g, 89%) as a colorless oil.

$^1$H-NMR(CDCl$_3$) δ 1.29 (3H, t, J=7.2 Hz), 1.43 (9H, s), 1.50-1.57 (2H, m), 2.04-2.11 (2H, m), 3.32 (2H, d, J=6.8 Hz), 3.46-3.56 (2H, m), 3.79-3.88 (2H, m), 4.20 (2H, q, J=7.2 Hz), 4.66-4.88 (1H, m)

(Step 4)

To a solution of the compound (11.3 g) obtained in step 3 in methanol (190 mL) was added 2N aqueous sodium hydroxide solution (79 mL), and the mixture was stirred at 40° C. for 2 hr. The mixture was concentrated, diluted with ethyl acetate, and neutralized with 1N hydrochloric acid. The separated aqueous layer was extracted with ethyl acetate. The combined organic layer was dried, and concentrated under reduced pressure to give the title compound (9.3 g, 91%) as a white powder.

¹H-NMR (DMSO-d₆) δ 1.37 (9H, s), 1.36-1.44 (2H, m), 1.76-1.84 (2H, m), 3.09 (2H, d, J=6.4 Hz), 3.24-3.34 (2H, m), 3.61-3.76 (2H, m), 6.88 (1H, t, J=6.2 Hz)

Reference Example 35

4-fluorotetrahydro-2H-pyran-4-carboxylic acid (Step 1)
To a mixture of tetrahydro-2H-pyran-4-carboxylic acid (4.8 g) and potassium carbonate (7.6 g) and DMF (73 mL) was added dropwise benzyl bromide (4.6 mL) at 0° C. The reaction mixture was stirred at room temperature for one day, diluted with ice water, and extracted with ethyl acetate. The extract was washed with water, 0.5N hydrochloric acid, water and saturated brine, dried and concentrated under reduced pressure. The obtained residue was separated and purified by silica gel column chromatography (solvent gradient; 0→20% ethyl acetate/hexane) to give benzyl tetrahydro-2H-pyran-4-carboxylate (7.6 g, 94%) as a colorless oil.

¹H-NMR(CDCl₃) δ 1.67-1.97 (4H, m), 2.46-2.70 (1H, m), 3.43 (2H, td, J=11.0, 3.4 Hz), 3.96 (2H, dt, J=11.6, 3.5 Hz), 5.14 (2H, s), 7.28-7.44 (5H, m)

(Step 2)
To a solution of the compound (0.22 g) obtained in step 1 in THF (3.5 mL) was added dropwise at −78° C. lithium bis(trimethylsilyl)amide (1.1M THF solution, 1.82 mL), and the mixture was stirred for 30 min. The mixture was warmed to 0° C. and stirred for 15 min. The reaction mixture was cooled to −78° C., a solution of N-fluoro-N-(phenylsulfonyl)benzene-sulfonamide (0.63 g) in THF (2.0 mL) was added dropwise, and the mixture was stirred at −78° C. for 1 hr. To the reaction mixture was added saturated aqueous ammonium chloride solution, and the mixture was diluted with water and extracted with ethyl acetate. The extract was washed with water and saturated brine, dried and concentrated under reduced pressure. The residue was separated and purified by silica gel column chromatography (solvent gradient; 0→20% ethyl acetate/hexane) to give benzyl 4-fluorotetrahydro-2H-pyran-4-carboxylate (0.10 g, 44%) as a colorless oil.

¹H-NMR(CDCl₃) δ 1.79-1.98 (2H, m), 2.04-2.33 (2H, m), 3.68-3.81 (2H, m), 3.81-3.95 (2H, m), 5.23 (2H, s), 7.28-7.45 (5H, m)

(Step 3)
A mixture of the compound (0.18 g) obtained in step 2 and 20% palladium hydroxide (0.02 g) in ethanol/ethyl acetate (2/1 mL) was stirred under a hydrogen atmosphere (1 atm) at room temperature for 4 hr. The reaction mixture was filtered, and concentrated under reduced pressure. The residue was crystallized from ethyl acetate/hexane to give the title compound (0.084 g, 78%) as a gray powder.

¹H-NMR (DMSO-d₆) δ 1.67-1.88 (2H, m), 1.88-2.19 (2H, m), 3.56 (2H, td, J=11.6, 2.1 Hz), 3.77 (2H, ddd, J=11.6, 5.0, 2.6 Hz), 13.40 (1H, brs)

Reference Example 36 trans-4-(5,5-dimethyl-2,4-dioxo-1,3-oxazolidin-3-yl)cyclohexanecarboxylic acid (Step 1)
To a solution of ethyl 2-hydroxy-2-methylpropanoate (1.2 g) and 4-nitrophenyl chlorocarbonate (1.2 g) in acetonitrile (20 mL) was added DMAP (0.77 g) at 0° C., and the mixture was stirred at room temperature for 3 days. The mixture was diluted with water, and extracted with ethyl acetate. The extract was washed with water and saturated brine, dried and concentrated under reduced pressure. The residue was separated and purified by silica gel column chromatography (solvent gradient; 0→25% ethyl acetate/hexane) to give ethyl 2-methyl-2-{[(4-nitrophenoxy)carbonyl]oxy}propanoate (1.3 g, 74%) as a pale-yellow oil.

¹H-NMR(CDCl₃) δ 1.24-1.35 (3H, m), 1.70 (6H, s), 4.26 (2H, q, J=6.9 Hz), 7.34-7.44 (2H, m), 8.23-8.33 (2H, m)

(Step 2)
A mixture of the compound (1.3 g) obtained in step 1, benzyl trans-4-aminocyclohexanecarboxylate monohydrochloride (1.1 g), potassium carbonate (0.88 g) and DMF (30 mL) was stirred at 60° C. for 6 hr. The mixture was diluted with water, and extracted with ethyl acetate. The extract was washed with water and saturated brine, dried and concentrated under reduced pressure. The residue was separated and purified by silica gel column chromatography (solvent gradient; 0→25% ethyl acetate/hexane) to give benzyl trans-4-(5,5-dimethyl-2,4-dioxo-1,3-oxazolidin-3-yl)cyclohexanecarboxylate (1.2 g, 81%) as a white powder.

¹H-NMR(CDCl₃) δ 1.45-1.66 (8H, m), 1.71-1.89 (2H, m), 2.07-2.29 (4H, m), 2.41 (1H, tt, J=12.3, 3.5 Hz), 3.89 (1H, tt, J=12.2, 3.9 Hz), 5.12 (2H, s), 7.28-7.44 (5H, m)

(Step 3)
By reaction and purification in the same manner as in the method described in Reference Example 35, step 3 and using the compound obtained in step 2, the title compound was obtained.

¹H-NMR(CDCl₃) δ 1.42-1.66 (8H, m), 1.72-1.89 (2H, m), 2.07-2.31 (4H, m), 2.39 (1H, tt, J=12.4, 3.4 Hz), 3.90 (1H, tt, J=12.1, 4.0 Hz)

Reference Example 37 trans-4-(2,4-dioxo-1,3-oxazolidin-3-yl)cyclohexanecarboxylic acid

By reaction and purification in the same manner as in the method described in Reference Example 36, step 1 to step 3 and using ethyl glycolate, the title compound was obtained.

¹H-NMR(CDCl₃) δ 1.43-1.68 (2H, m), 1.74-1.92 (2H, m), 2.10-2.31 (4H, m), 2.39 (1H, tt, J=12.3, 3.4 Hz), 3.96 (1H, tt, J=12.1, 4.0 Hz), 4.64 (2H, s)

Reference Example 38 trans-4-(2,5-dioxoimidazolidin-1-yl)cyclohexanecarboxylic acid

By reaction and purification in the same manner as in the method described in Reference Example 36, step 2 and step 3 and using ethyl isocyanatoacetate, the title compound was obtained.

¹H-NMR (DMSO-d₆) δ 1.23-1.48 (2H, m), 1.62 (2H, dd, J=13.2, 3.4 Hz), 1.90-2.26 (5H, m), 3.72 (1H, tt, J=12.1, 3.8 Hz), 3.83 (2H, s), 7.98 (1H, s), 12.08 (1H, brs)

Reference Example 39 trans-4-(1H-tetrazol-1-yl)cyclohexanecarboxylic acid (Step 1)
To a mixture of triethyl orthoformate (25 mL) and benzyl trans-4-aminocyclohexanecarboxylate monohydrochloride (1.4 g) were added triethylamine (0.77 mL) and acetic acid (2.0 mL), and the mixture was stirred at 90° C. for 30 min. To this mixture was added sodium azide (1.6 g), and the mixture was stirred at 90° C. for 12 hr. The mixture was cooled, diluted with saturated aqueous sodium hydrogen carbonate solution, and extracted with ethyl acetate. The extract was washed with saturated aqueous sodium hydrogen carbonate solution, water and saturated brine, dried and concentrated under reduced pressure. The residue was washed with hexane, filtered through silica gel (eluted with ethyl acetate), and the filtrate was concentrated to give benzyl trans-4-(1H-tetrazol-1-yl)cyclohexanecarboxylate (0.78 g, 54%) as a white powder.

$^1$H-NMR (DMSO-$d_6$) δ 1.63-1.81 (2H, m), 1.82-2.01 (2H, m), 2.20-2.43 (4H, m), 2.49 (1H, tt, J=12.0, 3.6 Hz), 4.50 (1H, tt, J=11.7, 3.9 Hz), 5.15 (2H, s), 7.29-7.43 (5H, m), 8.60 (1H, s)

(Step 2)

By reaction and purification in the same manner as in the method described in Reference Example 35, step 3 and using the compound obtained in step 1, the title compound was obtained.

$^1$H-NMR (DMSO-$d_6$) δ 1.43-1.66 (2H, m), 1.73-1.93 (2H, m), 1.97-2.12 (2H, m), 2.13-2.25 (2H, m), 2.32 (1H, tt, J=12.0, 3.6 Hz), 4.61 (1H, tt, J=11.7, 3.9 Hz), 12.22 (1H, brs)

Reference Example 40 trans-4-[5-(trifluoromethyl)-1H-tetrazol-1-yl]cyclohexanecarboxylic acid (Step 1)

To a mixture of benzyl trans-4-aminocyclohexanecarboxylate monohydrochloride (2.7 g), pyridine (2.0 mL) and THF (20 mL) was added dropwise trifluoroacetic anhydride (1.5 mL) at 0° C., and the mixture was stirred at 0° C. for 2.5 hr. The mixture was diluted with ice water, and extracted with toluene/ethyl acetate. The extract was washed with water, 1N hydrochloric acid, water and saturated brine, dried and concentrated under reduced pressure. The residue was separated and purified by silica gel column chromatography (solvent gradient; 0→33% ethyl acetate/hexane) to give benzyl trans-4-[(trifluoroacetyl)amino]cyclohexanecarboxylate (1.7 g, 51%) as a white powder.

$^1$H-NMR(CDCl$_3$) δ 1.10-1.43 (2H, m), 1.48-1.80 (2H, m), 2.09-2.13 (4H, m), 2.23-2.47 (1H, m), 3.65-4.00 (1H, m), 5.12 (2H, s), 6.10 (1H, brs), 7.28-7.49 (5H, m)

(Step 2)

A mixture of the compound (1.7 g) obtained in step 1, triphenylphosphine (1.6 g) and carbon tetrachloride (25 mL) was heated under reflux for 12 hr. To this mixture was added triphenylphosphine (1.6 g), and the mixture was heated under reflux for 24 hr. The mixture was concentrated under reduced pressure, and the residue was diluted with DMF (30 mL), sodium azide (0.49 g) was added and the mixture was stirred at room temperature for 12 hr. The mixture was diluted with water, and extracted with toluene/ethyl acetate. The extract was washed with water, 0.5N hydrochloric acid, water and saturated brine, dried and concentrated under reduced pressure. The residue was separated and purified by silica gel column chromatography (solvent gradient; 0→20% ethyl acetate/hexane) to give benzyl trans-4-[5-(trifluoromethyl)-1H-tetrazol-1-yl]cyclohexanecarboxylate (1.7 g, 93%) as a pale-yellow oil.

$^1$H-NMR(CDCl$_3$) δ 1.60-1.80 (2H, m), 2.06-2.39 (6H, m), 2.45-2.66 (1H, m), 4.49 (1H, dt, J=10.5, 5.2 Hz), 5.15 (2H, s), 7.29-7.50 (5H, m)

(Step 3)

By reaction and purification in the same manner as in the method described in Reference Example 35, step 3 and using the compound obtained in step 2, the title compound was obtained.

$^1$H-NMR (DMSO-$d_6$) δ 1.45-1.75 (2H, m), 1.86-2.25 (6H, m), 2.30-2.46 (1H, m), 4.51-4.89 (1H, m), 12.25 (1H, brs)

Reference Example 41

4-[5-(trifluoromethyl)-1H-tetrazol-1-yl]benzoic acid (Step 1)

By reaction and purification in the same manner as in the method described in Reference Example 40, step 1 and step 2 and using methyl p-aminobenzoate, methyl 4-[5-(trifluoromethyl)-1H-tetrazol-1-yl]benzoate was obtained.

$^1$H-NMR(CDCl$_3$) δ 4.00 (3H, s), 7.57-7.70 (2H, m), 8.25-8.35 (2H, m)

(Step 2)

To a solution of the compound (5.2 g) obtained in step 1 in THF/methanol/water (6.0/18/9.5 mL) was added 4N aqueous lithium hydroxide solution (9.5 mL), and the mixture was stirred at room temperature for 4 hr. The mixture was acidified with 1N hydrochloric acid, concentrated under reduced pressure, diluted with water, and extracted with ethyl acetate. The extract was washed with water and saturated brine, dried, filtered through silica gel (eluted with ethyl acetate). The filtrate was concentrated under reduced pressure, and crystallized from ethyl acetate/hexane to give the title compound (4.3 g, 86%) as a pale-yellow powder.

$^1$H-NMR (DMSO-$d_6$) δ 7.90 (2H, d, J=8.7 Hz), 8.13-8.36 (2H, m), 13.55 (1H, brs)

Reference Example 42 tert-butyl 4-[5-(methylsulfonyl)-1,3,4-oxadiazol-2-yl]piperidine-1-carboxylate (Step 1)

To a solution of tert-butyl 4-(hydrazinocarbonyl)piperidine-1-carboxylate (0.97 g) in DMF (8.0 mL) was added 1,1'-thiocarbonyldiimidazole (0.86 g), and the mixture was stirred at room temperature for 1 hr. The mixture was heated at 100° C. for 2 hr, cooled to 0° C., and methyl iodide (0.5 mL) was added. The mixture was stirred at 0° C. for 1 hr, diluted with ice water, and extracted with ethyl acetate. The extract was washed with 1N hydrochloric acid, water and saturated brine, dried and concentrated under reduced pressure. The residue was separated and purified by silica gel column chromatography (solvent gradient; 0→60% ethyl acetate/hexane) to give tert-butyl 4-[5-(methylsulfanyl)-1,3,4-oxadiazol-2-yl]piperidine-1-carboxylate (1.1 g, 91%) as a yellow oil.

MS(ESI+): 244 (M−$^t$Bu+2H)

(Step 2)

To a solution of the compound (0.11 g) obtained in step 1 in ethyl acetate (4.0 mL) was added m-chlorobenzoic acid (0.35 g) at 0° C., and the mixture was stirred at room temperature for 12 hr. The mixture was diluted with saturated aqueous sodium hydrogen carbonate solution, and extracted with ethyl acetate. The extract was washed with water and saturated brine, dried and concentrated under reduced pressure. The residue was separated and purified by silica gel column chromatography (solvent gradient; 0→60% ethyl acetate/hexane) to give the title compound (0.082 g, 68%) as a colorless oil.

MS(ESI+): 276 (M−$^t$Bu+2H)

The compounds of Reference Examples 19 to 42 are as described below (Table A-2).

TABLE A-2

| Ref. Ex. No. | Chemical formula |
|---|---|
| 19 | (3S,4R)-tert-butyl 3-amino-4-(4-fluorophenyl)pyrrolidine-1-carboxylate |
| 20 | (3R,4S)-tert-butyl 3-amino-4-(4-fluorophenyl)pyrrolidine-1-carboxylate |
| 21 | (±)-tert-butyl 3-amino-4-(4-fluorophenyl)pyrrolidine-1-carboxylate, p-TsOH |
| 22 | (3S,4R)-tert-butyl 3-amino-4-(3,4-dichlorophenyl)pyrrolidine-1-carboxylate |
| 23 | (3S,4R)-tert-butyl 3-amino-4-(3,4-difluorophenyl)pyrrolidine-1-carboxylate |
| 24 | (3S,4R)-tert-butyl 3-amino-4-(2,4-difluorophenyl)pyrrolidine-1-carboxylate |

TABLE A-2-continued

| Ref. Ex. No. | Chemical formula |
|---|---|
| 25 | (3S,4R)-tert-butyl 3-amino-4-(3-chlorophenyl)pyrrolidine-1-carboxylate |
| 26 | (3R,4S)-tert-butyl 3-amino-4-(4-chlorophenyl)pyrrolidine-1-carboxylate |
| 27 | (3S,4R)-tert-butyl 3-amino-4-(4-fluoro-2-methylphenyl)pyrrolidine-1-carboxylate |
| 28 | (3S,4R)-tert-butyl 3-amino-4-(5-fluoropyridin-2-yl)pyrrolidine-1-carboxylate |
| 29 | tert-butyl (3,5-bis(trifluoromethyl)phenyl)(2-oxoethyl)carbamate |
| 30 | 4-nitrophenyl 3,5-bis(trifluoromethyl)phenylcarbamate |
| 31 | 4-nitrophenyl 3-chloro-5-(trifluoromethyl)phenylcarbamate |

TABLE A-2-continued

| Ref. Ex. No. | Chemical formula |
|---|---|
| 32 | 4-nitrophenyl N-(3-bromo-5-(trifluoromethyl)phenyl)carbamate |
| 33 | 4-nitrophenyl N-(3,5-dibromophenyl)carbamate |
| 34 | 4-((Boc-aminomethyl))-tetrahydropyran-4-carboxylic acid |
| 35 | 4-fluoro-tetrahydropyran-4-carboxylic acid |
| 36 | trans-4-(5,5-dimethyl-2,4-dioxooxazolidin-3-yl)cyclohexanecarboxylic acid |
| 37 | trans-4-(2,4-dioxooxazolidin-3-yl)cyclohexanecarboxylic acid |
| 38 | trans-4-(2,5-dioxoimidazolidin-1-yl)cyclohexanecarboxylic acid |
| 39 | trans-4-(1H-tetrazol-1-yl)cyclohexanecarboxylic acid |
| 40 | trans-4-(5-(trifluoromethyl)-1H-tetrazol-1-yl)cyclohexanecarboxylic acid |
| 41 | 4-(5-(trifluoromethyl)-1H-tetrazol-1-yl)benzoic acid |
| 42 | tert-butyl 4-(5-(methylsulfonyl)-1,3,4-oxadiazol-2-yl)piperidine-1-carboxylate |

Example 1 tert-butyl (3R*, 4R*)-4-({[3,5-bis(trifluoromethyl)phenyl]carbamoyl}amino)-3-(4-fluorophenyl)piperidine-1-carboxylate The compound (0.93 g) obtained in Reference Example 4 was dissolved in THF, 3,5-bis(trifluoromethyl)phenyl isocyanate (0.38 ml) and triethylamine (0.36 mL) were added dropwise at room temperature. The reaction mixture was stirred at room temperature for 4 days, poured into saturated aqueous sodium hydrogen carbonate solution, and the mixture was extracted with ethyl acetate. The extract was washed with water and saturated brine, dried and concentrated under reduced pressure. The residue was purified by silica gel column chromatography (solvent gradient; 0→40% ethyl acetate/hexane) to give the title compound (0.99 g, 90%) as a white powder.
MS(ESI+): 494 (M−$^t$Bu+2H)

Example 2 tert-butyl (3R*,4R*)-4-[{[3,5-bis(trifluoromethyl)phenyl](methyl)carbamoyl}(methyl)amino]-3-(4-fluorophenyl)piperidine-1-carboxylate The compound (0.97 g) obtained in Example 1 was dissolved in DMF (10 mL), sodium hydride (0.21 g) was added at 0° C., and the mixture was stirred for 15 min. To the reaction mixture was added dropwise methyl iodide (0.55 mL), and the mixture was stirred at room temperature overnight. The reaction mixture was poured into water, and the mixture was extracted with ethyl acetate. The extract was washed with 0.5N hydrochloric acid, water and saturated brine, dried and concentrated under reduced pressure. The residue was purified by silica gel column chromatography (solvent gradient; 0→33% ethyl acetate/hexane) to give the title compound (0.85 g, 84%) as a white powder.
MS(ESI+): 522 (M−$^t$Bu+2H)

Example 3

1-[3,5-bis(trifluoromethyl)phenyl]-3-[(3R*,4R*)-3-(4-fluorophenyl)piperidin-4-yl]-1,3-dimethylurea monohydrochloride To the compound (0.83 g) obtained in Example 2 was added 2N hydrogen chloride/2-propanol (15 mL), and the mixture was stirred at room temperature overnight. The reaction mixture was concentrated under reduced pressure to give the title compound (0.71 g, 97%) as a white powder.
MS(ESI+): 478 (M−HCl+H)

Example 4

1-[(3R*,4R*)-1-[(1-acetylpiperidin-4-yl) carbonyl]-3-(4-fluorophenyl)piperidin-4-yl]-3-[3,5-bis(trifluoromethyl)phenyl]-1,3-dimethylurea To a solution of the compound (0.15 g) obtained in Example 3, 1-acetylpiperidine-4-carboxylic acid (0.06 g) and triethylamine (0.05 mL) in acetonitrile (15 mL) were added WSC.HCl (0.069 g) and HOBt (0.046 g), and the mixture was stirred at room temperature overnight. The reaction mixture was diluted with ethyl acetate, and washed with saturated aqueous sodium hydrogen carbonate solution, water and saturated brine and dried, and the solvent was evaporated under reduced pressure. The obtained residue was purified by silica gel column chromatography (NH Chromatorex)(solvent gradient; 0→100% ethyl acetate/hexane) to give the title compound (0.18 g, 97%) as a white powder.
MS(ESI+): 631 (M+H)

Example 5 tert-butyl (3R*, 4S*)-4-({[3,5-bis(trifluoromethyl)phenyl](methyl)carbamoyl}amino)-3-(4-fluorophenyl)piperidine-1-carboxylate To a solution of the compound (0.32 g) obtained in Reference Example 8, step 3 and triethylamine (0.18 mL) in toluene (5 mL) was added DPPA (0.36 g), and the mixture was stirred at 100° C. for 1 hr. The reaction mixture was cooled to 0° C., triethylamine (0.21 g) and the compound (0.42 g) obtained in Reference Example 15 was added, and the mixture was stirred at room temperature for 14 hr. The reaction mixture was poured into water, and extracted twice with ethyl acetate. The extract was washed with saturated aqueous ammonium chloride solution and saturated brine, dried and concentrated. The residue was purified by silica gel column chromatography (solvent gradient; 5→40% ethyl acetate/hexane) to give the title compound (0.022 g, 4%) as a white powder.
MS(ESI+): 508 (M−$^t$Bu+2H)

Example 6 tert-butyl (3R*,4S*)-4-({[3,5-bis(trifluoromethyl)phenyl]carbamoyl}amino)-3-(4-fluorophenyl)piperidine-1-carboxylate By reaction and purification in the same manner as in the method described in Example 1 and using the compound obtained in Reference Example 8, the title compound was obtained.
MS(ESI+): 494 (M−$^t$Bu+2H)

Example 7 tert-butyl (3R*,4S*)-4-[{[3,5-bis(trifluoromethyl)phenyl](methyl)carbamoyl}(methyl)amino]-3-(4-fluorophenyl)piperidine-1-carboxylate By reaction and purification in the same manner as in the method described in Example 2 and using the compound obtained in Example 6, the title compound was obtained.
MS(ESI+): 522 (M−$^t$Bu+2H)

Example 8

1-[3,5-bis(trifluoromethyl)phenyl]-3-[(3R*,4S*)-3-(4-fluorophenyl)piperidin-4-yl]-1,3-dimethylurea monohydrochloride By reaction and purification in the same manner as in the method described in Example 3 and using the compound obtained in Example 7, the title compound was obtained.
MS(ESI+): 478 (M−HCl+H)

Example 9

1-[(3R*,4S*)-1-[(1-acetylpiperidin-4-yl)carbonyl]-3-(4-fluorophenyl)piperidin-4-yl]-3-[3,5-bis(trifluoromethyl)phenyl]-1,3-dimethylurea By reaction and purification in the same manner as in the method described in Example 4 and using the compound obtained in Example 8, the title compound was obtained.
MS(ESI+): 631 (M+H)

Example 10

1-[(3R*,4R*)-1-[(1-acetylpiperidin-4-yl) carbonyl]-3-dichlorophenyl)piperidin-4-yl]-3-[3,5-bis(trifluoromethyl)phenyl]-1-methylurea To a solution of the compound (0.21 g) obtained in Reference Example 11 in THF (4.0 mL) was added 3,5-bis(trifluoromethyl)phenyl isocyanate (0.13 mL), and the mixture was stirred at room temperature for 2 days. The reaction mixture was concentrated under reduced pressure, and the residue was purified by silica gel column chromatography (NH Chromatorex) (solvent gradient; 0→10% methanol/ethyl acetate) to give the title compound (0.32 g, 94%) as a white powder.
MS(ESI+): 667 (M+H)

Example 11

1-[3,5-bis(trifluoromethyl)phenyl]-3-{(3R*,4R*)-3-(3,4-dichlorophenyl)-1-[(1-acetylpiperidin-4-yl)carbonyl]piperidin-4-yl}-1-ethyl-3-methylurea The compound (0.19 g) obtained in Example 10 was dissolved in DMF, and sodium hydride (0.016 g) was added at 0° C., and the mixture was stirred for 15 min. To the reaction mixture was added ethyl iodide, and the mixture was stirred at room temperature for 4 hr. The reaction mixture was poured into water, and the mixture was extracted with ethyl acetate. The extract was washed with 1N aqueous potassium hydrogen sulfate solution, water and saturated brine, dried and concentrated under reduced pressure. The residue was purified by silica gel column chromatography (NH Chromatorex)

Example 12 tert-butyl (3R*, 4R*)-4-({[3,5-bis(trifluoromethyl)phenyl]carbamoyl}amino)-3-(4-methylphenyl)piperidine-1-carboxylate By reaction and purification in the same manner as in the method described in Example 1 and using the compound obtained in Reference Example 9, the title compound was obtained.
MS(ESI+): 490 (M−<sup>t</sup>Bu+2H)

Example 13 tert-butyl (3R*, 4R*)-4-[{[3,5-bis(trifluoromethyl)phenyl](methyl)carbamoyl}(methyl)amino]-3-(4-methylphenyl)piperidine-1-carboxylate By reaction and purification in the same manner as in the method described in Example 2 and using the compound obtained in Example 12, the title compound was obtained.
MS(ESI+): 518 (M−$^t$Bu+2H)

Example 14

1-[3,5-bis(trifluoromethyl)phenyl]-1,3-dimethyl-3-[(3R*,4R*)-3-(4-methylphenyl)piperidin-4-yl]urea monohydrochloride By reaction and purification in the same manner as in the method described in Example 3 and using the compound obtained in Example 13, the title compound was obtained.
MS(ESI+): 474 (M−HCl+H)

Example 15

1-[(3R*, 4R*)-1-[(1-acetylpiperidin-4-yl)carbonyl]-3-(4-methylphenyl)piperidin-4-yl]-3-[3,5-bis(trifluoromethyl)phenyl]-1,3-dimethylurea By reaction and purification in the same manner as in the method described in Example 4 and using the compound obtained in Example 14, the title compound was obtained.
MS(ESI+): 627 (M+H)

Example 16 tert-butyl (3R*, 4R*)-4-({[3,5-bis(trifluoromethyl)phenyl]carbamoyl}amino)-3-(4-chlorophenyl)piperidine-1-carboxylate By reaction and purification in the same manner as in the method described in Example 1 and using the compound obtained in Reference Example 10, the title compound was obtained.
MS(ESI+): 510 (M−$^t$Bu+2H)

Example 17 tert-butyl (3R*, 4R*)-4-[{[3,5-bis(trifluoromethyl)phenyl](methyl)carbamoyl}(methyl)amino]-3-(4-chlorophenyl)piperidine-1-carboxylate By reaction and purification in the same manner as in the method described in Example 2 and using the compound obtained in Example 16, the title compound was obtained.
MS(ESI+): 538 (M−$^t$Bu+2H)

Example 18

1-[3,5-bis(trifluoromethyl)phenyl]-3-[(3R*,4R*)-3-(4-chlorophenyl)piperidin-4-yl]-1,3-dimethylurea monohydrochloride By reaction and purification in the same manner as in the method described in Example 3 and using the compound obtained in Example 17, the title compound was obtained.
MS(ESI+): 494 (M−HCl+H)

Example 19

1-[(3R*, 4R*)-1-[(1-acetylpiperidin-4-yl)carbonyl]-3-(4-chlorophenyl)piperidin-4-yl]-3-[3,5-bis(trifluoromethyl)phenyl]-1,3-dimethylurea By reaction and purification in the same manner as in the method described in Example 4 and using the compound obtained in Example 18, the title compound was obtained.
MS(ESI+): 647 (M+H)

Example 20 tert-butyl (3R*, 4R*)-4-[({1-[3,5-bis(trifluoromethyl)phenyl]cyclopropyl}carbamoyl)amino]-3-(3,5-dichlorophenyl)piperidine-1-carboxylate To a solution of the compound (0.6 g) obtained in Reference Example 16 and triethylamine (0.42 mL) in toluene (5 mL) was added DPPA (0.83 g), and the mixture was stirred at 100° C. for 1 hr. The reaction mixture was cooled, the compound (0.69 g) obtained in Reference Example 7 was added, and the mixture was stirred at room temperature for 14 hr. The reaction mixture was poured into water, and extracted twice with ethyl acetate. The extract was washed with saturated aqueous ammonium chloride solution and saturated brine, dried and concentrated. The residue was purified by silica gel column chromatography (solvent gradient; 33→50% ethyl acetate/hexane) to give the title compound (0.83 g, 65%) as a white powder.
MS(ESI+): 584 (M−$^t$Bu+2H)

Example 21 tert-butyl (3R*,4R*)-4-{[{1-[3,5-bis(trifluoromethyl)phenyl]cyclopropyl}(methyl)carbamoyl](methyl)amino}-3-(3,5-dichlorophenyl)piperidine-1-carboxylate By reaction and purification in the same manner as in the method described in Example 2 and using the compound obtained in Example 20, the title compound was obtained.
MS(ESI+): 612 (M−$^t$Bu+2H)

Example 22

1-{1-[3,5-bis(trifluoromethyl)phenyl]cyclopropyl}-3-[(3R*,4R*)-3-(3,5-dichlorophenyl)piperidin-4-yl]-1,3-dimethylurea monohydrochloride By reaction and purification in the same manner as in the method described in Example 3 and using the compound obtained in Example 21, the title compound was obtained.
MS(ESI+): 568 (M−HCl+H)

Example 23

1-[(3R*,4R*)-1-[(1-acetylpiperidin-4-yl) carbonyl]-3-(3,5-dichlorophenyl)piperidin-4-yl]-3-{1-[3,5-bis(trifluoromethyl)phenyl]cyclopropyl}-1,3-dimethylurea By reaction and purification in the same manner as in the method described in Example 4 and using the compound obtained in Example 22, the title compound was obtained.
MS(ESI+): 721 (M+H)

Example 24

1-[(3R,4R)-1-[(1-acetylpiperidin-4-yl)carbonyl]-3-(3,4-dichlorophenyl)piperidin-4-yl]-3-[3,5-bis(trifluoromethyl)phenyl]-1-methylurea By reaction and purification in the same manner as in the method described in Example 10 and using the compound obtained in Reference Example 12, the title compound was obtained.
MS(ESI+): 667 (M+H)

Example 25

1-[(3R,4R)-1-[(1-acetylpiperidin-4-yl)carbonyl]-3-(3,4-dichlorophenyl)piperidin-4-yl]-3-[3,5-bis(trifluoromethyl)phenyl]-1,3-dimethylurea By reaction and purification in the same manner as in the method described in Example 2 and using the compound obtained in Example 24, the title compound was obtained.
MS(ESI+): 681 (M+H)

Example 26

1-[(3R,4R)-1-[(1-acetylpiperidin-4-yl)carbonyl]-3-(3,4-dichlorophenyl)piperidin-4-yl]-3-[3,5-bis(trifluoromethyl)phenyl]-3-ethyl-1-methylurea By reaction and purification in the same manner as in the method described in Example 11 and using the compound obtained in Example 24, the title compound was obtained.
MS(ESI+): 695 (M+H)

Example 27 tert-butyl (3R,4R)-4-({[3,5-bis(trifluoromethyl)benzyl](methyl)carbamoyl}amino)-3-(3,4-dichlorophenyl)piperidine-1-carboxylate To a solution of the compound (1.12 g) obtained in Reference Example 2, step 1 and DPPA (1.24 g) in toluene (12 mL) was added dropwise triethylamine (0.627 mL) at room temperature, and the mixture was stirred at 100° C. for 1.5 hr. The reaction mixture was cooled to room temperature, N-[3,5-bis(trifluoromethyl)benzyl]methylamine monohydrochloride (1.32 g) and triethylamine (0.627 mL) were added, and the mixture was stirred at room temperature for 3 days. The reaction mixture was poured into saturated aqueous sodium hydrogen carbonate solution, and the mixture was extracted with ethyl acetate. The extract was washed with water, 1N hydrochloric acid, water and saturated brine, dried and concentrated under reduced pressure. The residue was purified by silica gel column chromatography (solvent gradient; 0→60% ethyl acetate/hexane) to give the title compound (1.83 g, 97%) as a white powder.
MS(ESI+): 572 (M−$^t$Bu+2H)

Example 28 tert-butyl (3R,4R)-4-[{[3,5-bis(trifluoromethyl)benzyl](methyl)carbamoyl}(methyl)amino]-3-(3,4-dichlorophenyl)piperidine-1-carboxylate To a solution of the compound (0.63 g) obtained in Example 27 in DMF (4.0 mL) were added sodium tert-butoxide (0.14 g) and methyl iodide (0.13 mL) at 0° C., and the mixture was stirred at room temperature overnight. To the reaction mixture were added sodium tert-butoxide (0.072 g) and methyl iodide (0.062 mL), and the mixture was stirred at room temperature for 6 hr. The reaction mixture was poured into water, and the mixture was extracted with ethyl acetate. The organic layer was washed with water and saturated brine, dried and concentrated under reduced pressure. The residue was purified by silica gel column chromatography (solvent gradient; 10→50% ethyl acetate/hexane) to give the title compound (0.5 g, 78%) as a white powder.
MS(ESI+): 586 (M−$^t$Bu+2H)

Example 29

1-[3,5-bis(trifluoromethyl)benzyl]-3-[(3R,4R)-3-(3,4-dichlorophenyl)piperidin-4-yl]-1,3-dimethylurea monohydrochloride By reaction and purification in the same manner as in the method described in Example 3 and using the compound obtained in Example 28, the title compound was obtained.
MS(ESI+): 542 (M−HCl+H)

Example 30

1-[(3R,4R)-1-[(1-acetylpiperidin-4-yl)carbonyl]-3-(3,4-dichlorophenyl)piperidin-4-yl]-3-[3,5-bis(trifluoromethyl)benzyl]-1,3-dimethylurea By reaction and purification in the same manner as in the method described in Example 4 and using the compound obtained in Example 29, the title compound was obtained.
MS(ESI+): 695 (M+H)

Example 31 tert-butyl (3R,4R)-4-[({1-[3,5-bis(trifluoromethyl)phenyl]cyclopropyl}carbamoyl)amino]-3-(3,4-dichlorophenyl)piperidine-1-carboxylate By reaction and purification in the same manner as in the method described in Example 20 and using the compounds obtained in Reference Example 2 and Reference Example 16, the title compound was obtained.
MS(ESI+): 584 (M−$^t$Bu+2H)

Example 32 tert-butyl (3R,4R)-4-{[{1-[3,5-bis(trifluoromethyl)phenyl]cyclopropyl}(methyl)carbamoyl](methyl)amino}-3-(3,4-dichlorophenyl)piperidine-1-carboxylate By reaction and purification in the same manner as in the method described in Example 2 and using the compound obtained in Example 31, the title compound was obtained.
MS(ESI+): 612 (M−$^t$Bu+2H)

Example 33

1-{1-[3,5-bis(trifluoromethyl)phenyl]cyclopropyl}-
3-[(3R,4R)-3-(3,4-dichlorophenyl)piperidin-4-yl]-1,
3-dimethylurea monohydrochloride By reaction and purification in the same manner as in the method described in Example 3 and using the compound obtained in Example 32, the title compound was obtained.
MS(ESI+): 568 (M−HCl+H)

Example 34

1-[(3R,4R)-1-[(1-acetylpiperidin-4-yl)carbonyl]-3-
(3,4-dichlorophenyl)piperidin-4-yl]-3-{1-[3,5-bis
(trifluoromethyl)phenyl]cyclopropyl}-1,3-dimethylurea By reaction and purification in the same manner as in the method described in Reference Example 4 and using the compound obtained in Example 33, the title compound was obtained.
MS(ESI+): 721 (M+H)

Example 35 tert-butyl (3R,4R)-4-{3-[3,5-bis(trifluoromethyl)
benzyl]-2-oxoimidazolidin-1-yl}-3-(3,4-dichlorophenyl)piperidine-1-carboxylate (Step 1)
To a solution of the compound (1.03 g) obtained in Reference Example 2 and 2-chloroethyl isocyanate (0.21 mL) in THF (10 mL) was added triethylamine (0.34 mL), and the mixture was stirred at room temperature for 4 hr. The reaction mixture was poured into water, and the mixture was extracted with ethyl acetate. The extract was washed with saturated brine, dried and concentrated under reduced pressure. The residue was purified by silica gel column chromatography (solvent gradient; 50→100% ethyl acetate/hexane) to give tert-butyl (3R,4R)-4-{[(2-chloroethyl)carbamoyl]amino}-3-(3,4-dichlorophenyl)piperidine-1-carboxylate (0.91 g, 100%) as a colorless oil.
MS(ESI+): 396 (M−$^t$Bu+2H)

(Step 2)
To a solution of the compound (0.91 g) obtained in step 1 in THF (40 mL) was added sodium hydride (0.096 g) at 0° C., and the mixture was stirred at room temperature overnight. The reaction mixture was poured into water, and the mixture was extracted with ethyl acetate. The extract was washed with saturated aqueous ammonium chloride solution and saturated brine, dried and concentrated under reduced pressure. The residue was purified by silica gel column chromatography (solvent gradient; 50→100% ethyl acetate/hexane) to give tert-butyl (3R,4R)-3-(3,4-dichlorophenyl)-4-(2-oxoimidazolidin-1-yl)piperidine-1-carboxylate (0.65 g, 78%) as a white powder.
MS(ESI+): 358 (M−$^t$Bu+2H)

(Step 3)
The compound (0.63 g) obtained in step 2 was dissolved in DMF, and sodium hydride (0.073 g) was added at 0° C. The reaction mixture was stirred at 0° C. for 20 min, and 3,5-bis(trifluoromethyl)benzyl bromide (0.33 mL) was added dropwise. The reaction mixture was stirred at room temperature overnight, poured into water, and the mixture was extracted with ethyl acetate. The extract was washed with 1N hydrochloric acid, water and saturated brine, dried and concentrated under reduced pressure. The residue was purified by silica gel column chromatography (solvent gradient; 0→60% ethyl acetate/hexane) to give the title compound (0.77 g, 80%) as a white powder.
MS(ESI+): 584 (M−$^t$Bu+2H)

Example 36

1-[3,5-bis(trifluoromethyl)benzyl]-3-[(3R,4R)-3-(3,
4-dichlorophenyl)piperidin-4-yl]imidazolidin-2-one
monohydrochloride By reaction and purification in the same manner as in the method described in Example 3 and using the compound obtained in Example 35, the title compound was obtained.
MS(ESI+): 540 (M−HCl+H)

Example 37

1-[(3R,4R)-1-[(1-acetylpiperidin-4-yl)carbonyl]-3-
(3,4-dichlorophenyl)piperidin-4-yl]-3-[3,5-bis(trifluoromethyl)benzyl]imidazolidin-2-one By reaction and purification in the same manner as in the method described in Example 4 and using the compound obtained in Example 36, the title compound was obtained.
MS(ESI+): 693 (M+H)

Example 38 tert-butyl (3R,4R)-4-({[3,5-bis(trifluoromethyl)phenyl](methyl)carbamoyl}amino)-3-(3,4-dichlorophenyl)piperidine-1-carboxylate To a solution of the compound (0.75 g) obtained in Reference Example 2, step 1 and DPPA (0.72 g) in toluene (10 mL) was added triethylamine (0.36 mL), and the mixture was stirred at 90° C. for 1 hr. The reaction mixture was cooled, triethylamine (0.42 mL) and the compound (0.73 g) obtained in Reference Example 15 were added, and the mixture was stirred at 75° C. for 14 hr. The reaction mixture was cooled, diluted with ethyl acetate, and washed with saturated aqueous sodium hydrogen carbonate solution, water and saturated brine, dried and concentrated under reduced pressure. The residue was dissolved in DMF (15 mL), and sodium hydride (0.16 g) was added at 0° C. The reaction mixture was stirred at room temperature 2 hr, poured into water, and the mixture was extracted with ethyl acetate. The extract was washed with 1N hydrochloric acid, water and saturated brine, dried and concentrated under reduced pressure. The residue was purified by silica gel column chromatography (solvent gradient; 0→50% ethyl acetate/hexane) to give the title compound (0.80 g, 65%) as a white powder.
MS(ESI+): 558 (M−$^t$Bu+2H)

Example 39

1-[3,5-bis(trifluoromethyl)phenyl]-3-[(3R,4R)-3-(3,
4-dichlorophenyl)piperidin-4-yl]-1-methylurea
monohydrochloride By reaction and purification in the same manner as in the method described in Example 3 and using the compound obtained in Example 38, the title compound was obtained.
MS(ESI+): 514 (M−HCl+H)

Example 40

3-[(3R,4R)-1-[(1-acetylpiperidin-4-yl)carbonyl]-3-(3,4-dichlorophenyl)piperidin-4-yl]-1-[3,5-bis(trifluoromethyl)phenyl]-1-methylurea By reaction and purification in the same manner as in the method described in Example 4 and using the compound obtained in Example 39, the title compound was obtained.
MS(ESI+): 667 (M+H)

Example 41

1-[(3R,4R)-1-[(1-acetylpiperidin-4-yl)carbonyl]-3-(3,4-dichlorophenyl)piperidin-4-yl]-3-[3,5-bis(trifluoromethyl)phenyl]-1-ethyl-3-methylurea By reaction and purification in the same manner as in the method described in Example 2 and using the compound obtained in Example 40 and ethyl iodide, the title compound was obtained.
MS(ESI+): 695 (M+H)

Example 42 tert-butyl (3R,4R)-3-(3,4-dichlorophenyl)-4-(2-oxo-3-phenylimidazolidin-1-yl)piperidine-1-carboxylate (Step 1)
To a solution of the compound (0.77 g) obtained in Reference Example 2, the compound (0.35 g) obtained in Reference Example 17 and triethylamine (0.21 mL) in ethyl acetate (10 mL) was added sodium triacetoxyborohydride (0.94 g), and the mixture was stirred at room temperature for 14 hr. The reaction mixture was poured into aqueous sodium hydrogen carbonate solution, and the mixture was extracted twice with ethyl acetate. The extract was washed with saturated brine, dried and concentrated under reduced pressure. The residue was purified by silica gel column chromatography (solvent gradient; 40→66% ethyl acetate/hexane) to give tert-butyl (3R,4R)-4-({2-[(tert-butoxycarbonyl)(phenyl)amino]ethyl}amino)-3-(3,4-dichlorophenyl)piperidine-1-carboxylate (0.67 g, 80%) as a colorless oil.
MS(ESI+): 564 (M+H)
(Step 2)
To the compound (0.49 g) obtained in step 1 was added 2N hydrogen chloride/2-propanol, and the mixture was stirred at 50° C. for 2 hr. The reaction mixture was concentrated under reduced pressure to give N-[(3R,4R)-3-(3,4-dichlorophenyl)piperidin-4-yl]-N'-phenylethane-1,2-diamine trihydrochloride (0.41 g, 100%).
MS(ESI+): 364 (M−3HCl+H)
(Step 3)
To a solution of the compound (0.31 g) obtained in step 2 and triethylamine (0.27 mL) in acetonitrile (10 mL) was added Boc$_2$O (0.14 g) at 5° C. The reaction mixture was stirred at 5° C. for 30 min, poured into water, and the mixture was extracted with ethyl acetate. The extract was washed with saturated aqueous ammonium chloride solution, dried and concentrated under reduced pressure. The residue was purified by silica gel column chromatography (solvent gradient; 50→80% ethyl acetate/hexane) to give tert-butyl (3R,4R)-3-(3,4-dichlorophenyl)-4-{[2-(phenylamino)ethyl]amino}piperidine-1-carboxylate (0.27 g, 90%) as a colorless oil.
MS(ESI+): 464 (M+H)
(Step 4)
To a solution of the compound (0.21 g) obtained in step 3 and triethylamine (0.19 mL) in THF (10 mL) was added bis(trichloromethyl) carbonate (0.13 g) at 5° C. The reaction mixture was stirred at 0° C. for 30 min and at room temperature for 1 hr, poured into water, and the mixture was extracted with ethyl acetate. The extract was washed with saturated aqueous ammonium chloride solution and saturated brine, dried and concentrated under reduced pressure. The residue was purified by silica gel column chromatography (solvent gradient; 10→33% ethyl acetate/hexane) to give the title compound (0.04 g, 18%) as a colorless oil.
MS(ESI+): 434 (M−$^t$Bu+2H)

Example 43

1-[(3R,4R)-3-(3,4-dichlorophenyl)piperidin-4-yl]-3-phenylimidazolidin-2-one monohydrochloride By reaction and purification in the same manner as in the method described in Example 3 and using the compound obtained in Example 42, the title compound was obtained.
MS(ESI+): 390 (M−HCl+H)

Example 44

1-[(3R,4R)-1-[(1-acetylpiperidin-4-yl)carbonyl]-3-(3,4-dichlorophenyl)piperidin-4-yl]-3-phenylimidazolidin-2-one By reaction and purification in the same manner as in the method described in Example 4 and using the compound obtained in Example 43, the title compound was obtained.
MS(ESI+): 543 (M+H)

Example 45 tert-butyl (3R,4R)-4-({[3,5-bis(trifluoromethyl)phenyl]carbamoyl}amino)-3-phenylpiperidine-1-carboxylate By reaction and purification in the same manner as in the method described in Example 1 and using the compound obtained in Reference Example 3, the title compound was obtained.
MS(ESI+): 476 (M−$^t$Bu+2H)

Example 46 tert-butyl (3R,4R)-4-[{[3,5-bis(trifluoromethyl)phenyl](methyl)carbamoyl}(methyl)amino]-3-phenylpiperidine-1-carboxylate By reaction and purification in the same manner as in the method described in Example 2 and using the compound obtained in Example 45, the title compound was obtained.
MS(ESI+): 504 (M−$^t$Bu+2H)

Example 47

1-[3,5-bis(trifluoromethyl)phenyl]-1,3-dimethyl-3-[(3R,4R)-3-phenylpiperidin-4-yl]urea monohydrochloride By reaction and purification in the same manner as in the method described in Example 3 and using the compound obtained in Example 46, the title compound was obtained.
MS(ESI+): 460 (M−HCl+H)

Example 48

1-{(3R,4R)-1-[(1-acetylpiperidin-4-yl)carbonyl]-3-phenylpiperidin-4-yl}-3-[3,5-bis(trifluoromethyl)phenyl]-1,3-dimethylurea By reaction and purification in the same manner as in the method described in Example 4 and using the compound obtained in Example 47, the title compound was obtained.
MS(ESI+): 613 (M+H)

Example 49 tert-butyl (3R,4R)-4-({[3,5-bis(trifluoromethyl)phenyl]carbamoyl}amino)-3-(4-fluorophenyl)piperidine-1-carboxylate By reaction and purification in the same manner as in the method described in Example 1 and using the compound obtained in Reference Example 5, the title compound was obtained.
MS(ESI+): 494 (M−$^t$Bu+2H)

Example 50 tert-butyl (3R,4R)-4-[{[3,5-bis(trifluoromethyl)phenyl](methyl)carbamoyl}(methyl)amino]-3-(4-fluorophenyl)piperidine-1-carboxylate By reaction and purification in the same manner as in the method described in Example 2 and using the compound obtained in Example 49, the title compound was obtained.
MS(ESI+): 522 (M−$^t$Bu+2H)

Example 51

1-[3,5-bis(trifluoromethyl)phenyl]-3-[(3R,4R)-3-(4-fluorophenyl)piperidin-4-yl]-1,3-dimethylurea monohydrochloride By reaction and purification in the same manner as in the method described in Example 3 and using the compound obtained in Example 50, the title compound was obtained.
MS(ESI+): 478 (M−HCl+H)

Example 52

1-[(3R,4R)-1-[(1-acetylpiperidin-4-yl)carbonyl]-3-(4-fluorophenyl)piperidin-4-yl]-3-[3,5-bis(trifluoromethyl)phenyl]-1,3-dimethylurea By reaction and purification in the same manner as in the method described in Example 4 and using the compound obtained in Example 51, the title compound was obtained.
MS(ESI+): 631 (M+H)

Example 53 tert-butyl (3R,4R)-4-({[3,5-bis(trifluoromethyl)phenyl]carbamoyl}amino)-3-(4-fluoro-2-methylphenyl)piperidine-1-carboxylate By reaction and purification in the same manner as in the method described in Example 1 and using the compound obtained in Reference Example 18, the title compound was obtained.
MS(ESI+): 508 (M−$^t$Bu+2H)

Example 54 tert-butyl (3R,4R)-4-[{[3,5-bis(trifluoromethyl)phenyl](methyl)carbamoyl}(methyl)amino]-3-(4-fluoro-2-methylphenyl)piperidine-1-carboxylate By reaction and purification in the same manner as in the method described in Example 2 and using the compound obtained in Example 53, the title compound was obtained.
MS(ESI+): 536 (M−$^t$Bu+2H)

Example 55

1-[3,5-bis(trifluoromethyl)phenyl]-3-[(3R,4R)-3-(4-fluoro-2-methylphenyl)piperidin-4-yl]-1,3-dimethylurea monohydrochloride By reaction and purification in the same manner as in the method described in Example 3 and using the compound obtained in Example 54, the title compound was obtained.
MS(ESI+): 492 (M−HCl+H)

Example 56

1-[(3R,4R)-1-[(1-acetylpiperidin-4-yl)carbonyl]-3-(4-fluoro-2-methylphenyl)piperidin-4-yl]-3-[3,5-bis(trifluoromethyl)phenyl]-1,3-dimethylurea By reaction and purification in the same manner as in the method described in Example 4 and using the compound obtained in Example 55, the title compound was obtained.
MS(ESI+): 645 (M+H)

Example 57 tert-butyl (3R,4R)-4-({[3,5-bis(trifluoromethyl)phenyl]carbamoyl}amino)-3-(4-chloro-3-methylphenyl)piperidine-1-carboxylate By reaction and purification in the same manner as in the method described in Example 1 and using the compound obtained in Reference Example 6, the title compound was obtained.
MS(ESI+): 524 (M−$^t$Bu+2H)

Example 58 tert-butyl (3R,4R)-4-[{[3,5-bis(trifluoromethyl)phenyl](methyl)carbamoyl}(methyl)amino]-3-(4-chloro-3-methylphenyl)piperidine-1-carboxylate By reaction and purification in the same manner as in the method described in Example 2 and using the compound obtained in Example 57, the title compound was obtained.
MS(ESI+): 552 (M−$^t$Bu+2H)

Example 59

1-[3,5-bis(trifluoromethyl)phenyl]-3-[(3R,4R)-3-(4-chloro-3-methylphenyl)piperidin-4-yl]-1,3-dimethylurea monohydrochloride By reaction and purification in the same manner as in the method described in Example 3 and using the compound obtained in Example 58, the title compound was obtained.
MS(ESI+): 508 (M−HCl+H)

Example 60

1-[(3R,4R)-1-[(1-acetylpiperidin-4-yl)carbonyl]-3-(4-chloro-3-methylphenyl)piperidin-4-yl]-3-[3,5-bis(trifluoromethyl)phenyl]-1,3-dimethylurea By reaction and purification in the same manner as in the method described in Example 4 and using the compound obtained in Example 59, the title compound was obtained.
MS(ESI+): 661 (M+H)

Example 61

1-[(3R,4R)-1-[(1-acetylpiperidin-4-yl)carbonyl]-3-(3,4-dichlorophenyl)piperidin-4-yl]-3-(4-chlorophenyl)-1-methylurea By reaction and purification in the same manner as in the method described in Example 10 and using the compound obtained in Reference Example 12 and 4-chlorophenyl isocyanate, the title compound was obtained.
MS(ESI+): 567 (M+H)

Example 62

1-[(3R,4R)-1-[(1-acetylpiperidin-4-yl)carbonyl]-3-(3,4-dichlorophenyl)piperidin-4-yl]-3-(4-chlorophenyl)-1,3-dimethylurea By reaction and purification in the same manner as in the method described in Example 28 and using the compound obtained in Example 61, the title compound was obtained.
MS(ESI+): 581 (M+H)

Example 63 tert-butyl (3S*, 4R*)-3-({[3,5-bis(trifluoromethyl)phenyl]carbamoyl}amino)-4-(3,4-dichlorophenyl)pyrrolidine-1-carboxylate By reaction and purification in the same manner as in the method described in Example 1 and using the compound obtained in Reference Example 13, the title compound was obtained.
MS(ESI+): 530 (M−$^t$Bu+2H)

Example 64 tert-butyl (3S*,4R*)-3-[{[3,5-bis(trifluoromethyl)phenyl](methyl)carbamoyl}(methyl)amino]-4-(3,4-dichlorophenyl)pyrrolidine-1-carboxylate By reaction and purification in the same manner as in the method described in Example 2 and using the compound obtained in Example 63, the title compound was obtained.
MS(ESI+): 558 (M−$^t$Bu+2H)

Example 65

1-[3,5-bis(trifluoromethyl)phenyl]-3-[(3S*, 4R*)-4-(3,4-dichlorophenyl)pyrrolidin-3-yl]-1,3-dimethylurea monohydrochloride By reaction and purification in the same manner as in the method described in Example 3 and using the compound obtained in Example 64, the title compound was obtained.
MS(ESI+): 514 (M−HCl+H)

Example 66

1-[(3S*, 4R*)-1-[(1-acetylpiperidin-4-yl)carbonyl]-4-(3,4-dichlorophenyl)pyrrolidin-3-yl]-3-[3,5-bis(trifluoromethyl)phenyl]-1,3-dimethylurea By reaction and purification in the same manner as in the method described in Example 4 and using the compound obtained in Example 65, the title compound was obtained.
MS(ESI+): 667 (M+H)

Example 67 tert-butyl (3S*, 4R*)-3-({[3,5-bis(trifluoromethyl)phenyl]carbamoyl}amino)-4-(4-fluorophenyl)pyrrolidine-1-carboxylate By reaction and purification in the same manner as in the method described in Example 1 and using the compound obtained in Reference Example 14, the title compound was obtained.
MS(ESI+): 480 (M−$^t$Bu+2H)

Example 68 tert-butyl (3S*, 4R*)-3-[{[3,5-bis(trifluoromethyl)phenyl](methyl)carbamoyl}(methyl)amino]-4-(4-fluorophenyl)pyrrolidine-1-carboxylate By reaction and purification in the same manner as in the method described in Example 2 and using the compound obtained in Example 67, the title compound was obtained.
MS(ESI+): 508 (M−$^t$Bu+2H)

Example 69

1-[3,5-bis(trifluoromethyl)phenyl]-3-[(3S*,4R*)-4-(4-fluorophenyl)pyrrolidin-3-yl]-1,3-dimethylurea monohydrochloride By reaction and purification in the same manner as in the method described in Example 3 and using the compound obtained in Example 68, the title compound was obtained.
MS(ESI+): 464 (M−HCl+H)

Example 70

1-[(3S*,4R*)-1-[(1-acetylpiperidin-4-yl)carbonyl]-4-(4-fluorophenyl)pyrrolidin-3-yl]-3-[3,5-bis(trifluoromethyl)phenyl]-1,3-dimethylurea By reaction and purification in the same manner as in the method described in Example 4 and using the compound obtained in Example 69, the title compound was obtained.
MS(ESI+): 617 (M+H)

Example 71

1-[(3R,4S)-1-[(1-acetylpiperidin-4-yl)carbonyl]-4-(4-fluorophenyl)pyrrolidin-3-yl]-3-[3,5-bis(trifluoromethyl)phenyl]-1,3-dimethylurea (Example 71a) and (1-[(3S,4R)-1-[(1-acetylpiperidin-4-yl)carbonyl]-4-(4-fluorophenyl)pyrrolidin-3-yl]-3-[3,5-bis(trifluoromethyl)phenyl]-1,3-dimethylurea (Example 71b)

The compound (0.95 g) obtained in obtained in Example 70 was optically resolved by chiral column chromatography.

The collected fraction with a short retention time was concentrated to give 1-[(3R,4S)-1-[(1-acetylpiperidin-4-yl)carbonyl]-4-(4-fluorophenyl)pyrrolidin-3-yl]-3-[3,5-bis(trifluoromethyl)phenyl]-1,3-dimethylurea (0.44 g), and the collected fraction with a long retention time was concentrated to give 1-[(3S,4R)-1-[(1-acetylpiperidin-4-yl)carbonyl]-4-(4-fluorophenyl)pyrrolidin-3-yl]-3-[3,5-bis(trifluoromethyl)phenyl]-1,3-dimethylurea (0.42 g), each as a colorless oil.
purification conditions by chiral column chromatography
   column: CHIRALPAK AD 50 mmID×500 mini
   solvent: hexane/2-propanol=300/700
   flow rate: 60 mL/min
   temperature: 30° C.
   detection method: UV 220 nm
1-[(3R,4S)-1-[(1-acetylpiperidin-4-yl)carbonyl]-4-(4-fluorophenyl)pyrrolidin-3-yl]-3-[3,5-bis(trifluoromethyl)phenyl]-1,3-dimethylurea (Example 71a, compound with a short retention time)
   MS(ESI+): 617 (M+H)
1-[(3S,4R)-1-[(1-acetylpiperidin-4-yl)carbonyl]-4-(4-fluorophenyl)pyrrolidin-3-yl]-3-[3,5-bis(trifluoromethyl)phenyl]-1,3-dimethylurea (Example 71b, compound with a long retention time MS(ESI+): 617 (M+H)

Example 72

1-(4-chlorophenyl)-3-[(3S*,4R*)-4-(3,4-dichlorophenyl)pyrrolidin-3-yl]urea

By reaction and purification in the same manner as in the method described in Example 1 and Example 3 and using the compound obtained in Reference Example 13 and p-chlorophenyl isocyanate, the title compound was obtained.
   MS(ESI+): 384 (M−HCl+H)

Example 73

1-[(3S*,4R*)-1-[(1-acetylpiperidin-4-yl)carbonyl]-4-(3,4-dichlorophenyl)pyrrolidin-3-yl]-3-(4-chlorophenyl)urea By reaction and purification in the same manner as in the method described in Example 4 and using the compound obtained in Example 72, the title compound was obtained.
   MS(ESI+): 537 (M+H)

Example 74

1-[(3S*,4R*)-1-[(1-acetylpiperidin-4-yl)carbonyl]-4-(3,4-dichlorophenyl)pyrrolidin-3-yl]-3-(4-chlorophenyl)-1,3-dimethylurea By reaction and purification in the same manner as in the method described in Example 2 and using the compound obtained in Example 73, the title compound was obtained.
   MS(ESI+): 565 (M+H)

Example 75

1-[(3R,4R)-1-acetyl-3-(4-fluorophenyl)piperidin-4-yl]-3-[3,5-bis(trifluoromethyl)phenyl]-1,3-dimethylurea To a solution of the compound (0.18 g) obtained in Example 51 and triethylamine (0.073 mL) in acetonitrile (7.0 mL) was added acetyl chloride (0.038 mL), and the mixture was stirred at room temperature overnight. The reaction mixture was diluted with ethyl acetate, and washed with saturated aqueous sodium hydrogen carbonate solution, water and saturated brine, dried and concentrated under reduced pressure. The residue was purified by silica gel column chromatography (NH Chromatorex) (solvent gradient; 0→100% ethyl acetate/hexane) to give the title compound (0.15 g, 82%) as a white powder.
   MS(ESI+): 520 (M+H)

Example 76

1-[3,5-bis(trifluoromethyl)phenyl]-3-[(3R,4R)-3-(4-fluorophenyl)-1-(methylsulfonyl)piperidin-4-yl]-1,3-dimethylurea By reaction and purification in the same manner as in the method described in Example 75 and using the compound obtained in Example 51 and methanesulfonyl chloride, the title compound was obtained.
   MS(ESI+): 556 (M+H)

Example 77 methyl (3R,4R)-4-[{[3,5-bis(trifluoromethyl)phenyl](methyl)carbamoyl}(methyl)amino]-3-(4-fluorophenyl)piperidine-1-carboxylate By reaction and purification in the same manner as in the method described in Example 75 and using the compound obtained in Example 51 and methyl chlorocarbonate, the title compound was obtained.
   MS(ESI+): 536 (M+H)

Example 78

1-[3,5-bis(trifluoromethyl)phenyl]-3-[(3R,4R)-3-(4-fluorophenyl)-1-(3-oxocyclopent-1-en-1-yl)piperidin-4-yl]-1,3-dimethylurea The compound (0.15 g) obtained in Example 51 was dissolved in saturated aqueous sodium hydrogen carbonate solution and ethyl acetate, and the separated organic layer was dried, and concentrated under reduced pressure. To a solution of the obtained residue and 1,3-cyclopentanedione (0.043 g) in toluene (4.5 mL) was added p-toluenesulfonic acid monohydrate (0.006 g), and the mixture was stirred at 100° C. overnight. The reaction mixture was cooled, diluted with ethyl acetate, and washed with saturated aqueous sodium hydrogen carbonate solution and saturated brine, dried and concentrated under reduced pressure. The residue was purified by silica gel column chromatography (solvent gradient; 0→10% methanol/ethyl acetate) to give the title compound (0.14 g, 87%) as a white powder.
   MS(ESI+): 558 (M+H)

Example 79

2-[(3R,4R)-4-[{[3,5-bis(trifluoromethyl)phenyl](methyl)carbamoyl}(methyl)amino]-3-(4-fluorophenyl)piperidin-1-yl]acetamide monohydrochloride To a solution of the compound (0.15 g) obtained in Example 51 and 2-iodoacetamide (0.083 g) in DMF (6.0 mL) was added potassium carbonate (0.12 g), and the mixture was stirred at room temperature overnight. The reaction mixture was poured into water, and the mixture was extracted with ethyl acetate. The extract was washed with water and saturated brine, dried and concentrated under reduced pressure. The residue was purified by silica gel column chromatography (NH Chromatorex) (solvent gradient; 0→100% ethyl acetate/hexane) and treated with 4N hydrogen chloride/ethyl acetate to give the title compound (0.15 g, 89%) as a white powder.
MS(ESI+): 535 (M−HCl+H)

Example 80 tert-butyl (3R,4R)-4-[{[3,5-bis(trifluoromethyl)phenyl](methyl)carbamoyl}(methyl)amino]-3-(4-fluorophenyl)-1,4'-bipiperidine-1'-carboxylate To a solution of the compound (1.0 g) obtained in Example 51 and 1-Boc-4-piperidone (1.94 g) in ethyl acetate (10 mL) were added triethylamine (0.32 mL) and acetic acid (2.0 mL) at 0° C. The reaction mixture was stirred at 0° C. for 30 min, sodium triacetoxyborohydride (1.24 g) was added, and the mixture was stirred at room temperature overnight. The reaction mixture was diluted with saturated sodium hydrogen carbonate, and the mixture was extracted with ethyl acetate. The extract was washed with saturated aqueous sodium hydrogen carbonate solution, dried and concentrated under reduced pressure. The residue was purified by silica gel column chromatography (solvent gradient; 50→100% ethyl acetate/hexane→10% methanol/ethyl acetate) to give the title compound (1.19 g, 92%) as a white powder.
MS(ESI+): 661 (M+H)

Example 81

1-[3,5-bis(trifluoromethyl)phenyl]-3-[(3R,4R)-3-(4-fluorophenyl)-1,4'-bipiperidin-4-yl]-1,3-dimethylurea dihydrochloride By reaction and purification in the same manner as in the method described in Example 3 and using the compound obtained in Example 80, the title compound was obtained.
MS(ESI+): 561 (M−2HCl+H)

Example 82

1-[(3R,4R)-1'-acetyl-3-(4-fluorophenyl)-1,4'-bipiperidin-4-yl]-3-[3,5-bis(trifluoromethyl)phenyl]-1,3-dimethylurea monohydrochloride To a solution of the compound (0.18 g) obtained in Example 81 and triethylamine (0.13 mL) in acetonitrile (6.0 mL) was added acetyl chloride (0.032 mL), and the mixture was stirred at room temperature overnight. The reaction mixture was diluted with ethyl acetate, washed with saturated aqueous sodium hydrogen carbonate solution, dried and concentrated under reduced pressure. The residue was purified by silica gel column chromatography (NH Chromatorex) (solvent gradient; 60→100% ethyl acetate/hexane) and treated with 2N hydrogen chloride/2-propanol to give the title compound (0.15 g, 80%) as a white powder.
MS(ESI+): 603 (M−HCl+H)

Example 83 tert-butyl 4-{[(3R,4R)-4-[{[3,5-bis(trifluoromethyl)phenyl](methyl)carbamoyl}(methyl)amino]-3-(4-fluorophenyl)piperidin-1-yl]methyl}piperidine-1-carboxylate By reaction and purification in the same manner as in the method described in Example 80 and using the compound obtained in Example 51 and tert-butyl 4-formylpiperidine-1-carboxylate, the title compound was obtained.
MS(ESI+): 675 (M+H)

Example 84

1-[3,5-bis(trifluoromethyl)phenyl]-3-[(3R,4R)-3-(4-fluorophenyl)-1-(piperidin-4-ylmethyl)piperidin-4-yl]-1,3-dimethylurea dihydrochloride By reaction and purification in the same manner as in the method described in Example 3 and using the compound obtained in Example 83, the title compound was obtained.
MS(ESI+): 575 (M−2HCl+H)

Example 85

1-[(3R,4R)-1-[(1-acetylpiperidin-4-yl)methyl]-3-(4-fluorophenyl)piperidin-4-yl]-3-[3,5-bis(trifluoromethyl)phenyl]-1,3-dimethylurea By reaction and purification in the same manner as in the method described in Example 75 and using the compound obtained in Example 84, the title compound was obtained.
MS(ESI+): 617 (M+H)

Example 86 tert-butyl 3-{[(3R,4R)-4-[{[3,5-bis(trifluoromethyl)phenyl](methyl)carbamoyl}(methyl)amino]-3-(4-fluorophenyl)piperidin-1-yl]carbonyl}azetidine-1-carboxylate By reaction and purification in the same manner as in the method described in Example 4 and using the compound obtained in Example 51 and 1-(tert-butoxycarbonyl)azetidine-3-carboxylic acid, the title compound was obtained.
MS(ESI+): 561 (M−Boc+2H)

Example 87

1-[(3R,4R)-1-[(1-acetylazetidin-3-yl)carbonyl]-3-(4-fluorophenyl)piperidin-4-yl]-3-[3,5-bis(trifluoromethyl)phenyl]-1,3-dimethylurea By reaction and purification in the same manner as in the method described in Example 3 and Example 75 and using the compound obtained in Example 86, the title compound was obtained.
MS(ESI+): 603 (M+H)

Example 88 benzyl 4-{[(3R,4R)-4-[{[3,5-bis(trifluoromethyl)phenyl](methyl)carbamoyl}(methyl)amino]-3-(4-fluorophenyl)piperidin-1-yl]sulfonyl}piperidine-1-carboxylate By reaction and purification in the same manner as in the method described in Example 75 and using the compound obtained in Example 51 and benzyl 4-(chlorosulfonyl)piperidine-1-carboxylate, the title compound was obtained.
MS(ESI+): 759 (M+H)

Example 89

1-[3,5-bis(trifluoromethyl)phenyl]-3-[(3R,4R)-3-(4-fluorophenyl)-1-(piperidin-4-ylsulfonyl)piperidin-4-yl]-1,3-dimethylurea monohydrochloride To a solution of the compound (0.57 g) obtained in Example 88 in methanol (4.0 mL)/ethyl acetate (16.0 mL) was added 10% palladium-carbon (50% wet, 0.057 g), and the mixture was stirred under a hydrogen atmosphere (1 atm) at room temperature overnight. The catalyst was filtered off, and the filtrate was concentrated under reduced pressure. A mixture of the obtained residue and 10% palladium-carbon (50% wet, 0.057 g) in methanol (8.0 mL) was stirred under a hydrogen atmosphere (1 atm) at room temperature for 3 hr. The catalyst was filtered off, and the filtrate was concentrated under reduced pressure. The residue was treated with 2N hydrogen chloride/2-propanol to give the title compound (0.43 g) as a white powder.
MS(ESI+): 625 (M−HCl+H)

Example 90

1-[(3R,4R)-1-[(1-acetylpiperidin-4-yl)sulfonyl]-3-(4-fluorophenyl)piperidin-4-yl]-3-[3,5-bis(trifluoromethyl)phenyl]-1,3-dimethylurea By reaction and purification in the same manner as in the method described in Example 75 and using the compound obtained in Example 89, the title compound was obtained.
MS(ESI+): 667 (M+H)

Example 91

N-{2-[(3R,4R)-4-[{[3,5-bis(trifluoromethyl)phenyl](methyl)carbamoyl}(methyl)amino]-3-(4-fluorophenyl)piperidin-1-yl]-2-oxoethyl}acetamide By reaction and purification in the same manner as in the method described in Example 4 and using the compound obtained in Example 51 and N-acetylglycine, the title compound was obtained.
MS(ESI+): 577 (M+H)

Example 92

1-[3,5-bis(trifluoromethyl)phenyl]-3-[(3R,4R)-1-[(5,5-dimethyl-2,4-dioxo-1,3-oxazolidin-3-yl)acetyl]-3-(4-fluorophenyl)piperidin-4-yl]-1,3-dimethylurea By reaction and purification in the same manner as in the method described in Example 4 and using the compound obtained in Example 51 and (5,5-dimethyl-2,4-dioxo-1,3-oxazolidin-3-yl)acetic acid, the title compound was obtained.
MS(ESI+): 647 (M+H)

Example 93

1-[3,5-bis(trifluoromethyl)phenyl]-3-[(3R,4R)-1-[(2,6-dioxopiperidin-4-yl)carbonyl]-3-(4-fluorophenyl)piperidin-4-yl]-1,3-dimethylurea By reaction and purification in the same manner as in the method described in Example 4 and using the compound obtained in Example 51 and 2,6-dioxopiperidine-4-carboxylic acid, the title compound was obtained.
MS(ESI+): 617 (M+H)

Example 94

2-[(3R,4R)-4-[{[3,5-bis(trifluoromethyl)phenyl](methyl)carbamoyl}(methyl)amino]-3-(4-fluorophenyl)piperidin-1-yl]-2-oxoacetamide By reaction and purification in the same manner as in the method described in Example 4 and using the compound obtained in Example 51 and oxamic acid, the title compound was obtained.
MS(ESI+): 549 (M+H)

Example 95

N-(trans-4-{[(3R,4R)-4-[{[3,5-bis(trifluoromethyl)phenyl](methyl)carbamoyl}(methyl)amino]-3-(4-fluorophenyl)piperidin-1-yl]carbonyl}cyclohexyl)acetamide By reaction and purification in the same manner as in the method described in Example 4 and using the compound obtained in Example 51 and trans-4-(acetylamino)cyclohexylcarboxylic acid, the title compound was obtained.
MS(ESI+): 645 (M+H)

Example 96

1-[3,5-bis(trifluoromethyl)phenyl]-3-[(3R,4R)-3-(4-fluorophenyl)-1-(hydroxyacetyl)piperidin-4-yl]-1,3-dimethylurea By reaction and purification in the same manner as in the method described in Example 4 and using the compound obtained in Example 51 and glycolic acid, the title compound was obtained.
MS(ESI+): 536 (M+H)

Example 97

1-[3,5-bis(trifluoromethyl)phenyl]-3-[(3R,4R)-3-(4-fluorophenyl)-1-{[1-(phenylcarbonyl)piperidin-4-yl]carbonyl}piperidin-4-yl]-1,3-dimethylurea By reaction and purification in the same manner as in the method described in Example 4 and using the compound obtained in Example 51 and 1-benzoylpiperidine-4-carboxylic acid, the title compound was obtained.
MS(ESI+): 693 (M+H)

Example 98

1-[3,5-bis(trifluoromethyl)phenyl]-3-[(3R,4R)-3-(4-fluorophenyl)-1-{[1-(hydroxyacetyl)piperidin-4-yl]carbonyl}piperidin-4-yl]-1,3-dimethylurea By reaction and purification in the same manner as in the method described in Example 4 and using the compound obtained in Example 51 and 1-glycoloylpiperidine-4-carboxylic acid, the title compound was obtained.
MS(ESI+): 647 (M+H)

Example 99

1-[3,5-bis(trifluoromethyl)phenyl]-3-{(3R,4R)-3-(4-fluorophenyl)-1-[(methylsulfonyl)acetyl]piperidin-4-yl}-1,3-dimethylurea By reaction and purification in the same manner as in the method described in Example 4 and using the compound obtained in Example 51 and (methylsulfonyl)acetic acid, the title compound was obtained.

MS(ESI+): 598 (M+H)

Example 100

1-acetyl-N-[(3R,4R)-4-[{[3,5-bis(trifluoromethyl)phenyl](methyl)carbamoyl}(methyl)amino]-3-(4-fluorophenyl)piperidin-1-yl]piperidine-4-carboxamide To a solution of the compound (0.6 g) obtained in Example 51 in acetic acid (3:3 mL) was added dropwise a solution of sodium nitrite (0.089 g) in water (0.7 mL) at room temperature. The reaction mixture was stirred at room temperature for 2 hr, sodium nitrite (0.048 g) was added, and the mixture was stirred at room temperature overnight. The reaction mixture was diluted with ethyl acetate, washed with saturated brine, dried and concentrated under reduced pressure. The residue was dissolved in acetic acid (5.0 mL), zinc powder (0.45 g) was added, and the mixture was stirred at room temperature for 3 hr. To the reaction mixture was added a zinc powder (0.45 g), and the mixture was stirred at room temperature for 2 hr. The reaction mixture was diluted with aqueous sodium hydrogen carbonate solution, and the insoluble material was filtered off. The filtrate was extracted with ethyl acetate, dried and concentrated under reduced pressure. The residue was treated with 2N hydrogen chloride/2-propanol to give a white powder (0.57 g). To a solution of the obtained white powder (0.57 g), 1-acetylpiperidine-4-carboxylic acid (0.24 g) and triethylamine (0.19 mL) in acetonitrile (20 mL) were added WSC.HCl (0.27 g) and HOBt (0.21 g), and the mixture was stirred at room temperature for 1 hr. The reaction mixture was diluted with ethyl acetate, and washed with saturated aqueous sodium hydrogen carbonate solution and dried, and the solvent was evaporated under reduced pressure. The obtained residue was purified by silica gel column chromatography (NH Chromatorex) (solvent gradient; 50→100% ethyl acetate/hexane) to give the title compound (0.25 g, 33%) as a white powder.

MS(ESI+): 646 (M+H)

Example 101

1-acetyl-N-[(3R,4R)-4-[{[3,5-bis(trifluoromethyl)phenyl](methyl)carbamoyl}(methyl)amino]-3-(4-fluorophenyl)piperidin-1-yl]-N-methylpiperidine-4-carboxamide By reaction and purification in the same manner as in the method described in Example 2 and using the compound obtained in Example 100, the title compound was obtained.

MS(ESI+): 660 (M+H)

Example 102

1-[3,5-bis(trifluoromethyl)phenyl]-3-[(3R,4R)-3-(4-fluorophenyl)-1-(tetrahydro-2H-thiopyran-4-yl)piperidin-4-yl]-1,3-dimethylurea monohydrochloride To a solution of the compound (0.51 g) obtained in Example 51 and tetrahydro-4H-thiopyran-4-one (0.58 g) in DMF (6.0 mL) were added triethylamine (0.17 mL) and acetic acid (1.0 mL) at 0° C., and the mixture was stirred at 0° C. for 1 hr. To the reaction mixture was added sodium triacetoxyborohydride (0.64 g), and the mixture was stirred at room temperature for 3 days. The reaction mixture was diluted with saturated sodium hydrogen carbonate, and extracted with ethyl acetate. The extract was washed with water and saturated brine, dried and concentrated under reduced pressure. The residue was purified by silica gel column chromatography (solvent gradient; 50→100% ethyl acetate/hexane) and treated with 2N hydrogen chloride/2-propanol to give the title compound (0.57 g, 92%) as a white powder.

MS(ESI+): 578 (M−HCl+H)

Example 103

1-[3,5-bis(trifluoromethyl)phenyl]-3-[(3R,4R)-3-(4-fluorophenyl)-1-(1-oxidetetrahydro-2H-thiopyran-4-yl)piperidin-4-yl]-1,3-dimethylurea monohydrochloride To a solution of the compound (0.15 g) obtained in Example 102 in DMF (5.0 mL) was added m-chloroperbenzoic acid (0.048 g) at 0° C., and the mixture was stirred at room temperature overnight. The reaction mixture was diluted with saturated sodium hydrogen carbonate, and extracted with ethyl acetate. The extract was washed with water and saturated brine, dried and concentrated under reduced pressure. The residue was purified by silica gel column chromatography (NH Chromatorex) (solvent gradient; 10→100% ethyl acetate/hexane) and treated with 2N hydrogen chloride/2-propanol to give the title compound (0.094 g, 60%) as a white powder.

MS(ESI+): 594 (M−HCl+H)

Example 104

1-[3,5-bis(trifluoromethyl)phenyl]-3-[(3R,4R)-1-(1,1-dioxidetetrahydro-2H-thiopyran-4-yl)-3-(4-fluorophenyl)piperidin-4-yl]-1,3-dimethylurea monohydrochloride To a solution of the compound (0.15 g) obtained in Example 102 in water (2.0 mL)/acetone (4.0 mL) was added Oxone-persulfate compound (0.18 g) at 0° C., and the mixture was stirred at room temperature for 4 hr. The reaction mixture was diluted with saturated sodium hydrogen carbonate, and extracted with ethyl acetate. The extract was washed with water and saturated brine, dried and concentrated under reduced pressure. The residue was purified by silica gel column chromatography (NH Chromatorex) (solvent gradient; 0→60% ethyl acetate/hexane) and treated with 2N hydrogen chloride/2-propanol to give the title compound (0.11 g, 69%) as a white powder.

MS(ESI+): 610 (M−HCl+H)

The compounds of Reference Examples 1 to 104 are as described below (Tables B-1 to B-9).

TABLE B-1

| Ex. No. | R¹ | A | B | R² / D group | additive |
|---|---|---|---|---|---|
| 1 | tBuO-C(O)-CH₂- | (±)- 1-methyl-3,4-dimethylpiperidine | 4-F-C₆H₄- | -NH-C(O)-NH-(3,5-(CF₃)₂-C₆H₃), N-CH₃ | |
| 2 | tBuO-C(O)-CH₂- | (±)- 1-methyl-3,4-dimethylpiperidine | 4-F-C₆H₄- | (CH₃)N-C(O)-N(CH₃)-(3,5-(CF₃)₂-C₆H₃) | |
| 3 | H | (±)- 1-methyl-3,4-dimethylpiperidine | 4-F-C₆H₄- | (CH₃)N-C(O)-N(CH₃)-(3,5-(CF₃)₂-C₆H₃) | HCl |
| 4 | 1-acetyl-piperidin-4-yl-C(O)- | (±)- 1-methyl-3,4-dimethylpiperidine | 4-F-C₆H₄- | (CH₃)N-C(O)-N(CH₃)-(3,5-(CF₃)₂-C₆H₃) | |
| 5 | tBuO-C(O)-CH₂- | (±)- 1-methyl-3,4-dimethylpiperidine | 4-F-C₆H₄- | -NH-C(O)-N(CH₃)-(3,5-(CF₃)₂-C₆H₃) | |

TABLE B-1-continued

| Ex. No. | R¹ | A | B | R² | additive |
|---|---|---|---|---|---|
| 6 | tert-butyl ester (H₃C)₃C-O-C(O)-CH₂- | (±)- 1-methyl-3,4-piperidinyl (trans) | 4-F-phenyl | HN(H)C(O)N(H)CH₃, 3,5-bis(CF₃)phenyl | |
| 7 | tert-butyl ester (H₃C)₃C-O-C(O)-CH₂- | (±)- 1-methyl-3,4-piperidinyl (trans) | 4-F-phenyl | N(CH₃)C(O)N(CH₃), 3,5-bis(CF₃)phenyl | |
| 8 | H | (±)- 1-methyl-3,4-piperidinyl (trans) | 4-F-phenyl | N(CH₃)C(O)N(CH₃), 3,5-bis(CF₃)phenyl | HCl |
| 9 | 1-acetyl-piperidin-4-yl-carbonyl | (±)- 1-methyl-3,4-piperidinyl (trans) | 4-F-phenyl | N(CH₃)C(O)N(CH₃), 3,5-bis(CF₃)phenyl | |
| 10 | 1-acetyl-piperidin-4-yl-carbonyl | (±)- 1-methyl-3,4-piperidinyl (trans) | 3,4-diCl-phenyl | N(CH₃)C(O)N(H), 3,5-bis(CF₃)phenyl | |

TABLE B-1-continued
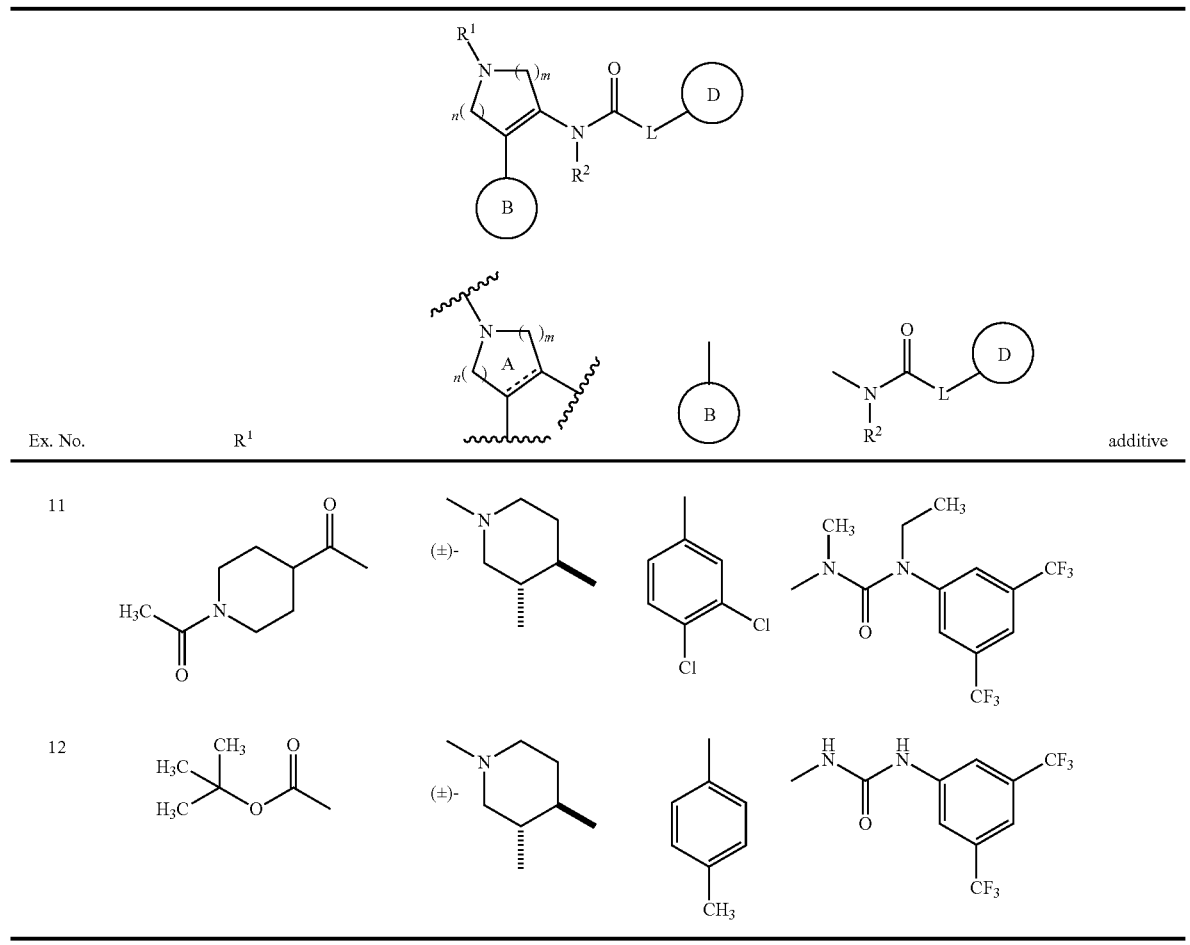
TABLE B-2
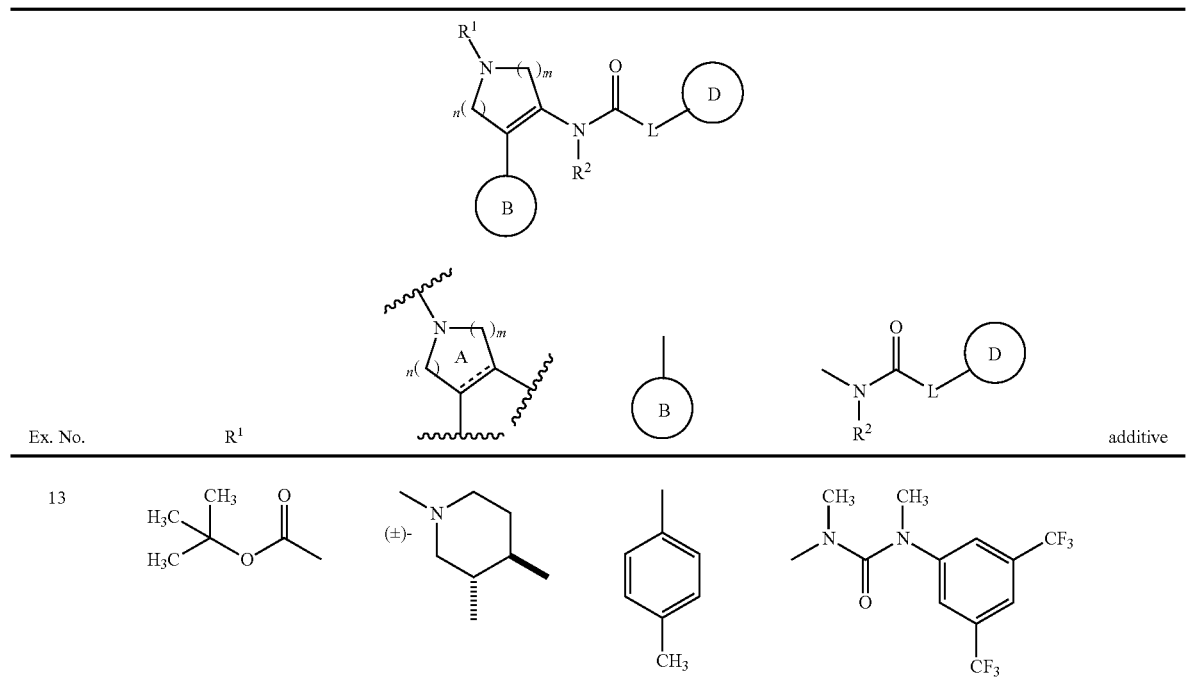

TABLE B-2-continued

| Ex. No. | R¹ | A | B | R² | additive |
|---|---|---|---|---|---|
| 14 | H | (±)- 1-methyl-3,4-dimethylpiperidine | 4-methylphenyl | N,N'-dimethyl-N'-(3,5-bis(trifluoromethyl)phenyl)urea | HCl |
| 15 | 1-acetyl-piperidin-4-yl methyl ketone | (±)- 1-methyl-3,4-dimethylpiperidine | 4-methylphenyl | N,N'-dimethyl-N'-(3,5-bis(trifluoromethyl)phenyl)urea | |
| 16 | tert-butyl acetate | (±)- 1-methyl-3,4-dimethylpiperidine | 4-chlorophenyl | N-methyl-N'-(3,5-bis(trifluoromethyl)phenyl)urea | |
| 17 | tert-butyl acetate | (±)- 1-methyl-3,4-dimethylpiperidine | 4-chlorophenyl | N,N'-dimethyl-N'-(3,5-bis(trifluoromethyl)phenyl)urea | |
| 18 | H | (±)- 1-methyl-3,4-dimethylpiperidine | 4-chlorophenyl | N,N'-dimethyl-N'-(3,5-bis(trifluoromethyl)phenyl)urea | HCl |

TABLE B-2-continued

| Ex. No. | R¹ | A | B | (N-R²)-C(O)-L-D | additive |
|---|---|---|---|---|---|
| 19 | 1-acetylpiperidin-4-yl carbonyl | (±)- 1,3-dimethylpiperidin-4-yl | 4-chlorophenyl | N,N',N'-trimethyl-N-(3,5-bis(trifluoromethyl)phenyl)urea | |
| 20 | tert-butoxycarbonyl | (±)- 1,3-dimethylpiperidin-4-yl | 3,5-dichlorophenyl | N-methyl-N'-(1-(3,5-bis(trifluoromethyl)phenyl)cyclopropyl)urea | |
| 21 | tert-butoxycarbonyl | (±)- 1,3-dimethylpiperidin-4-yl | 3,5-dichlorophenyl | N,N'-dimethyl-N'-(1-(3,5-bis(trifluoromethyl)phenyl)cyclopropyl)urea | |
| 22 | H | (±)- 1,3-dimethylpiperidin-4-yl | 3,5-dichlorophenyl | N,N'-dimethyl-N'-(1-(3,5-bis(trifluoromethyl)phenyl)cyclopropyl)urea | HCl |
| 23 | 1-acetylpiperidin-4-yl carbonyl | (±)- 1,3-dimethylpiperidin-4-yl | 3,5-dichlorophenyl | N,N'-dimethyl-N'-(1-(3,5-bis(trifluoromethyl)phenyl)cyclopropyl)urea | |

TABLE B-2-continued

| Ex. No. | R¹ | A | B | N(R²)-C(O)-L-D | additive |
|---|---|---|---|---|---|
| 24 | 1-acetylpiperidin-4-yl carbonyl | trans-1,3,4-trimethylpiperidin-4-yl | 3,4-dichlorophenyl | N-methyl-N'-methyl-N'-(3,5-bis(trifluoromethyl)phenyl)urea | |

TABLE B-3

| Ex. No. | R¹ | A | B | N(R²)-C(O)-L-D | additive |
|---|---|---|---|---|---|
| 25 | 1-acetylpiperidin-4-yl carbonyl | trans-1,3,4-trimethylpiperidin-4-yl | 3,4-dichlorophenyl | N,N'-dimethyl-N'-(3,5-bis(trifluoromethyl)phenyl)urea | |
| 26 | 1-acetylpiperidin-4-yl carbonyl | trans-1,3,4-trimethylpiperidin-4-yl | 3,4-dichlorophenyl | N-methyl-N'-ethyl-N'-(3,5-bis(trifluoromethyl)phenyl)urea | |

TABLE B-3-continued

| Ex. No. | R¹ | A | B | R² / D group | additive |
|---|---|---|---|---|---|
| 27 | tert-butyl acetate (H₃C)₃C-O-C(O)-CH₂- | N-methyl piperidine (3R,4R) | 3,4-dichlorophenyl | N,N'-dimethyl-N-(3,5-bis(trifluoromethyl)benzyl)urea | |
| 28 | tert-butyl acetate | N-methyl piperidine (3R,4R) | 3,4-dichlorophenyl | N,N'-dimethyl-N-(3,5-bis(trifluoromethyl)benzyl)urea | |
| 29 | H | N-methyl piperidine (3R,4R) | 3,4-dichlorophenyl | N,N'-dimethyl-N-(3,5-bis(trifluoromethyl)benzyl)urea | HCl |
| 30 | 1-acetyl-4-acetylpiperidine | N-methyl piperidine (3R,4R) | 3,4-dichlorophenyl | N,N'-dimethyl-N-(3,5-bis(trifluoromethyl)benzyl)urea | |
| 31 | tert-butyl acetate | N-methyl piperidine (3R,4R) | 3,4-dichlorophenyl | N-methyl-N'-(1-(3,5-bis(trifluoromethyl)phenyl)cyclopropyl)urea | |

TABLE B-3-continued
| Ex. No. | R¹ | 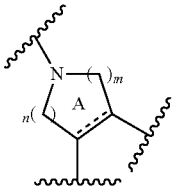 | B | N(R²)-C(O)-L-D | additive |
|---|---|---|---|---|---|
| 32 | 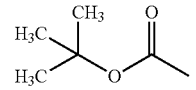 | 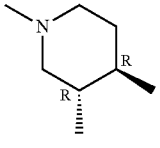 | 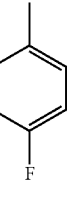 | 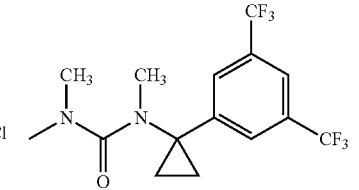 | |
| 33 | H | 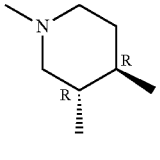 | 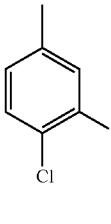 | 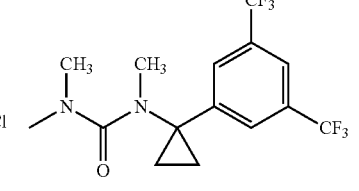 | HCl |
| 34 | 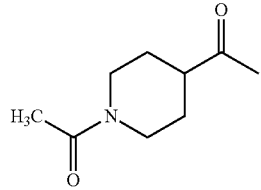 | 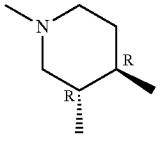 | 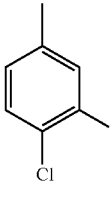 | 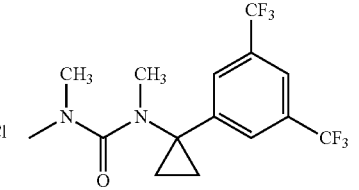 | |
| 35 | 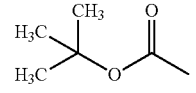 | 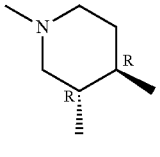 | 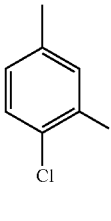 | 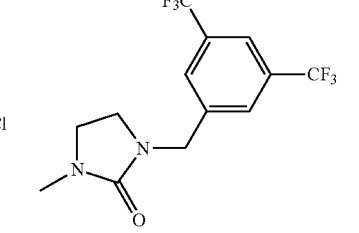 | |
| 36 | H | 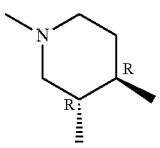 | 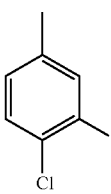 | 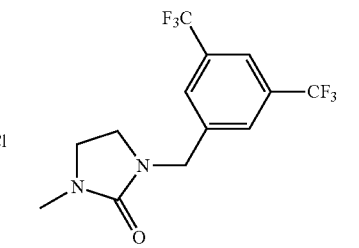 | HCl |

TABLE B-4

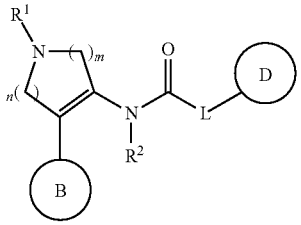

| Ex. No. | R¹ | A | B | R² / D group | additive |
|---|---|---|---|---|---|
| 37 | 1-acetylpiperidin-4-yl-carbonyl | 1-methyl-3,4-trans-dimethylpiperidin-4-yl (R,R) | 3,4-dichlorophenyl | 1-[3,5-bis(trifluoromethyl)benzyl]-3-methylimidazolidin-2-one | |
| 38 | tert-butoxycarbonyl (Boc) | 1-methyl-3,4-trans-dimethylpiperidin-4-yl (R,R) | 3,4-dichlorophenyl | N-methyl-N'-methyl-N-[3,5-bis(trifluoromethyl)phenyl]urea | |
| 39 | H | 1-methyl-3,4-trans-dimethylpiperidin-4-yl (R,R) | 3,4-dichlorophenyl | N-methyl-N'-methyl-N-[3,5-bis(trifluoromethyl)phenyl]urea | HCl |
| 40 | 1-acetylpiperidin-4-yl-carbonyl | 1-methyl-3,4-trans-dimethylpiperidin-4-yl (R,R) | 3,4-dichlorophenyl | N-methyl-N'-methyl-N-[3,5-bis(trifluoromethyl)phenyl]urea | |
| 41 | 1-acetylpiperidin-4-yl-carbonyl | 1-methyl-3,4-trans-dimethylpiperidin-4-yl (R,R) | 3,4-dichlorophenyl | N-ethyl-N-methyl-N'-methyl-N'-[3,5-bis(trifluoromethyl)phenyl]urea | |

TABLE B-4-continued

| Ex. No. | R¹ | A | B | N(R²)-C(O)-L-D | additive |
|---|---|---|---|---|---|
| 42 | tert-butyl ester (H₃C)₃C-O-C(O)-CH₂- | N-methylpiperidine (3R,4R) | 3,4-dichlorophenyl | 1-methyl-3-phenyl-imidazolidin-2-one | |
| 43 | H | N-methylpiperidine (3R,4R) | 3,4-dichlorophenyl | 1-methyl-3-phenyl-imidazolidin-2-one | HCl |
| 44 | 1-acetyl-piperidin-4-yl carbonyl | N-methylpiperidine (3R,4R) | 3,4-dichlorophenyl | 1-methyl-3-phenyl-imidazolidin-2-one | |
| 45 | tert-butyl ester (H₃C)₃C-O-C(O)-CH₂- | N-methylpiperidine (3R,4R) | phenyl | N-methyl-N'-[3,5-bis(trifluoromethyl)phenyl]urea | |
| 46 | tert-butyl ester (H₃C)₃C-O-C(O)-CH₂- | N-methylpiperidine (3R,4R) | phenyl | N,N-dimethyl-N'-methyl-N'-[3,5-bis(trifluoromethyl)phenyl]urea | |
| 47 | H | N-methylpiperidine (3R,4R) | phenyl | N,N-dimethyl-N'-methyl-N'-[3,5-bis(trifluoromethyl)phenyl]urea | HCl |

TABLE B-4-continued

| Ex. No. | R¹ | A | B | N(R²)-C(O)-L-D | additive |
|---|---|---|---|---|---|
| 48 | 1-acetylpiperidin-4-yl carbonyl | 1,3-dimethylpiperidin-4-yl | phenyl | N,N'-dimethyl-N-(3,5-bis(trifluoromethyl)phenyl)urea | |

TABLE B-5

| Ex. No. | R¹ | A | B | N(R²)-C(O)-L-D | additive |
|---|---|---|---|---|---|
| 49 | tert-butyl acetate group | 1,3-dimethylpiperidin-4-yl | 4-fluorophenyl | N-methyl-N'-(3,5-bis(trifluoromethyl)phenyl)urea | |
| 50 | tert-butyl acetate group | 1,3-dimethylpiperidin-4-yl | 4-fluorophenyl | N,N'-dimethyl-N-(3,5-bis(trifluoromethyl)phenyl)urea | |

TABLE B-5-continued

| Ex. No. | R¹ | A | B | R²/D group | additive |
|---|---|---|---|---|---|
| 51 | H | 1-methylpiperidine (3R,4R) | 4-fluorophenyl | N,N'-dimethyl-N-(3,5-bis(trifluoromethyl)phenyl)urea | HCl |
| 52 | 1-acetyl-4-acetylpiperidine | 1-methylpiperidine (3R,4R) | 4-fluorophenyl | N,N'-dimethyl-N-(3,5-bis(trifluoromethyl)phenyl)urea | |
| 53 | tert-butyl acetate | 1-methylpiperidine (3R,4R) | 4-fluoro-2-methylphenyl | N'-methyl-N-(3,5-bis(trifluoromethyl)phenyl)urea | |
| 54 | tert-butyl acetate | 1-methylpiperidine (3R,4R) | 4-fluoro-2-methylphenyl | N,N'-dimethyl-N-(3,5-bis(trifluoromethyl)phenyl)urea | |
| 55 | H | 1-methylpiperidine (3R,4R) | 4-fluoro-2-methylphenyl | N,N'-dimethyl-N-(3,5-bis(trifluoromethyl)phenyl)urea | HCl |

TABLE B-5-continued
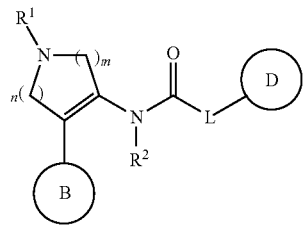
| Ex. No. | R¹ | A | B | R² | additive |
|---|---|---|---|---|---|
| 56 | 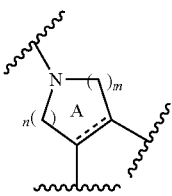 |  | 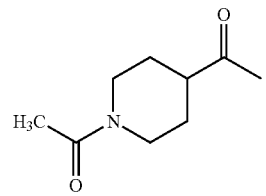 | 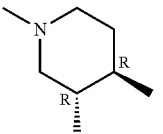 | |
| 57 | 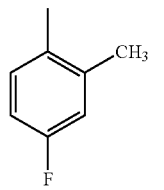 | 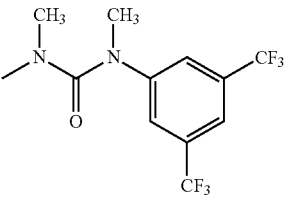 | 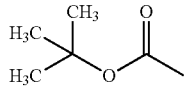 | 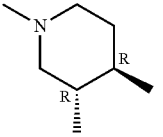 | |
| 58 | 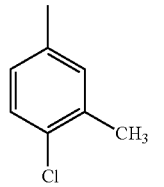 | 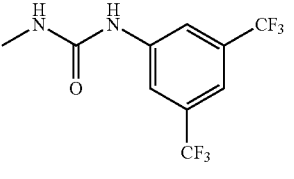 | 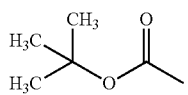 | 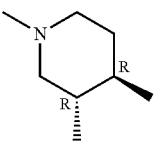 | |
| 59 | H | 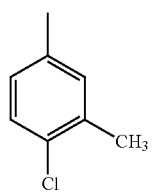 |  | 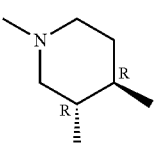 | HCl |
| 60 | 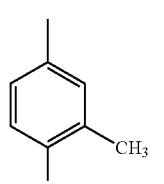 | 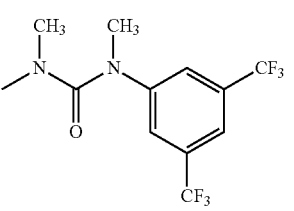 | 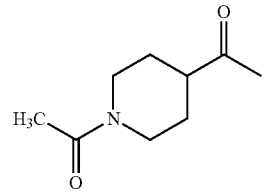 | 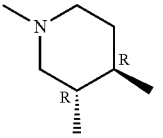 | |

TABLE B-6

| Ex. No. | R¹ | A | B | D (with R²) | additive |
|---------|----|----|----|------------|----------|
| 61 | 1-acetylpiperidine-4-carbonyl | (R,R)-1,3,4-trimethylpyrrolidine | 3,4-dichlorophenyl | N-methyl-N'-(4-chlorophenyl)urea | |
| 62 | 1-acetylpiperidine-4-carbonyl | (R,R)-1,3,4-trimethylpyrrolidine | 3,4-dichlorophenyl | N,N'-dimethyl-N'-(4-chlorophenyl)urea | |
| 63 | tert-butoxycarbonyl | (±)-1,3-dimethylpyrrolidine | 3,4-dichlorophenyl | N-methyl-N'-(3,5-bistrifluoromethylphenyl)urea | |
| 64 | tert-butoxycarbonyl | (±)-1,3-dimethylpyrrolidine | 3,4-dichlorophenyl | N,N'-dimethyl-N'-(3,5-bistrifluoromethylphenyl)urea | |
| 65 | H | (±)-1,3-dimethylpyrrolidine | 3,4-dichlorophenyl | N,N'-dimethyl-N'-(3,5-bistrifluoromethylphenyl)urea | HCl |

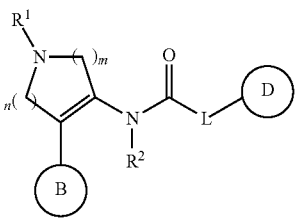

TABLE B-6-continued

| Ex. No. | R¹ | (A ring) | B | R² (D group) | additive |
|---|---|---|---|---|---|
| 66 | 1-acetylpiperidin-4-yl carbonyl | (±)- 1-methyl-pyrrolidine (trans) | 3,4-dichlorophenyl | N,N'-dimethyl-N'-(3,5-bis(trifluoromethyl)phenyl)urea | |
| 67 | tert-butoxycarbonyl | (±)- 1-methyl-pyrrolidine (trans) | 4-fluorophenyl | N-methyl-N'-(3,5-bis(trifluoromethyl)phenyl)urea | |
| 68 | tert-butoxycarbonyl | (±)- 1-methyl-pyrrolidine (trans) | 4-fluorophenyl | N,N'-dimethyl-N'-(3,5-bis(trifluoromethyl)phenyl)urea | |
| 69 | H | (±)- 1-methyl-pyrrolidine (trans) | 4-fluorophenyl | N,N'-dimethyl-N'-(3,5-bis(trifluoromethyl)phenyl)urea | HCl |
| 70 | 1-acetylpiperidin-4-yl carbonyl | (±)- 1-methyl-pyrrolidine (trans) | 4-fluorophenyl | N,N'-dimethyl-N'-(3,5-bis(trifluoromethyl)phenyl)urea | |

TABLE B-6-continued

| Ex. No. | R¹ | A | B | NR²-C(O)-L-D | additive |
|---|---|---|---|---|---|
| 71a | 1-acetylpiperidin-4-yl-C(O)- | (3R,4S)-1-methyl-3,4-dimethylpyrrolidine | 4-fluorophenyl | N,N'-dimethyl-N'-(3,5-bis(trifluoromethyl)phenyl)urea | |
| 71b | 1-acetylpiperidin-4-yl-C(O)- | (3S,4R)-1-methyl-3,4-dimethylpyrrolidine | 4-fluorophenyl | N,N'-dimethyl-N'-(3,5-bis(trifluoromethyl)phenyl)urea | |

TABLE B-7

| Ex. No. | R¹ | A | B | NR²-C(O)-L-D | additive |
|---|---|---|---|---|---|
| 72 | H | (±)-1-methyl-3,4-dimethylpyrrolidine | 3,4-dichlorophenyl | N-methyl-N'-(4-chlorophenyl)urea | HCl |

TABLE B-7-continued
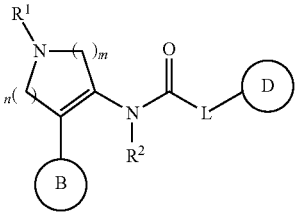
| Ex. No. | R[1] | A | B | R[2] | additive |
|---|---|---|---|---|---|
| 73 | 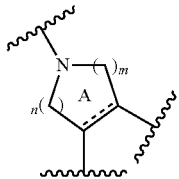 | (±)- 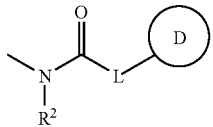 | 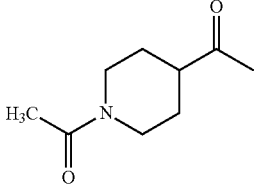 | 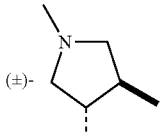 | |
| 74 | 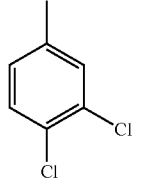 | (±)- 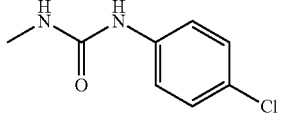 | 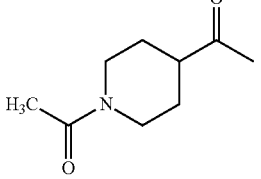 | 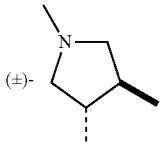 | |
| 75 | CH$_3$CO | 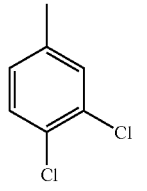 | 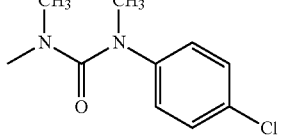 | 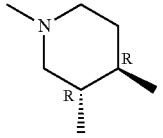 | |
| 76 | CH$_3$SO$_2$ | 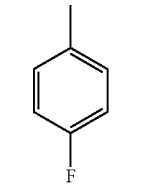 | 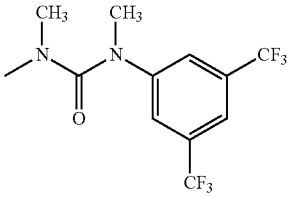 | 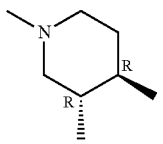 | |
| 77 | CH$_3$OCO | 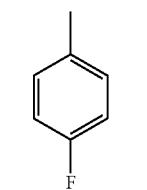 | 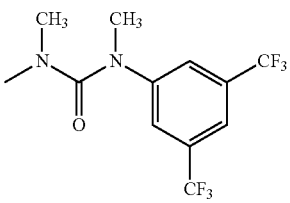 | 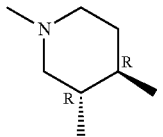 | |

TABLE B-7-continued

| Ex. No. | R¹ | A | B | R² | additive |
|---|---|---|---|---|---|
| 78 | 3-methylcyclopent-2-enone | 1-methyl-piperidine (3R,4R) | 4-fluorophenyl | N,N'-dimethyl-N'-(3,5-bis(trifluoromethyl)phenyl)urea | |
| 79 | propanamide | 1-methyl-piperidine (3R,4R) | 4-fluorophenyl | N,N'-dimethyl-N'-(3,5-bis(trifluoromethyl)phenyl)urea | HCl |
| 80 | tert-butyl 4-methylpiperidine-1-carboxylate | 1-methyl-piperidine (3R,4R) | 4-fluorophenyl | N,N'-dimethyl-N'-(3,5-bis(trifluoromethyl)phenyl)urea | |
| 81 | 4-methylpiperidine | 1-methyl-piperidine (3R,4R) | 4-fluorophenyl | N,N'-dimethyl-N'-(3,5-bis(trifluoromethyl)phenyl)urea | 2HCl |
| 82 | 1-acetyl-4-methylpiperidine | 1-methyl-piperidine (3R,4R) | 4-fluorophenyl | N,N'-dimethyl-N'-(3,5-bis(trifluoromethyl)phenyl)urea | HCl |

TABLE B-7-continued

| Ex. No. | R¹ | A | B | NR²-C(O)-L-D | additive |
|---|---|---|---|---|---|
| 83 | Boc-N-(4-ethylpiperidine) | 1-methyl-3,4-dimethylpiperidine (R,R) | 4-fluorophenyl | N,N'-dimethyl-N'-(3,5-bis(trifluoromethyl)phenyl)urea | |

TABLE B-8

| Ex. No. | R¹ | A | B | NR²-C(O)-L-D | additive |
|---|---|---|---|---|---|
| 84 | 4-ethylpiperidine (HN) | 1-methyl-3,4-dimethylpiperidine (R,R) | 4-fluorophenyl | N,N'-dimethyl-N'-(3,5-bis(trifluoromethyl)phenyl)urea | 2HCl |
| 85 | 1-acetyl-4-ethylpiperidine | 1-methyl-3,4-dimethylpiperidine (R,R) | 4-fluorophenyl | N,N'-dimethyl-N'-(3,5-bis(trifluoromethyl)phenyl)urea | |

TABLE B-8-continued
| Ex. No. | R¹ | A | B | R² | additive |
|---|---|---|---|---|---|
| 86 | 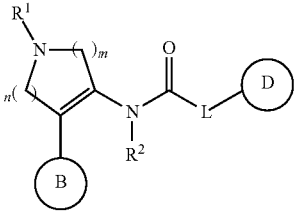 | 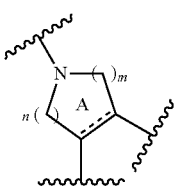 | 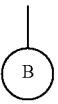 | 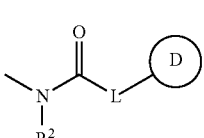 | |
| 87 | 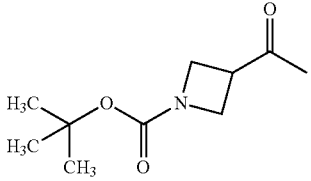 | 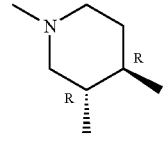 | 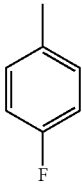 | 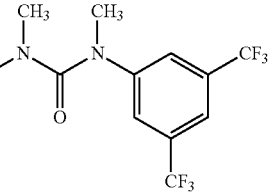 | |
| 88 | 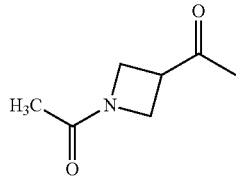 | 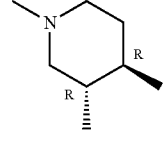 | 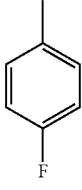 | 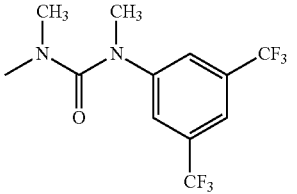 | |
| 89 | 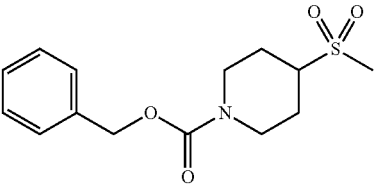 | 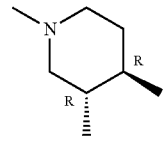 | 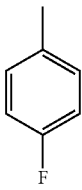 | 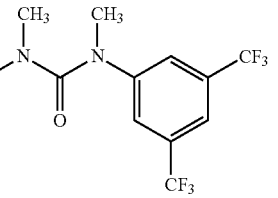 | HCl |
| 90 | 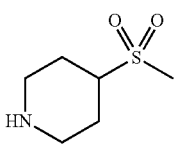 | 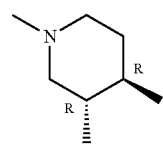 | 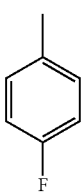 | 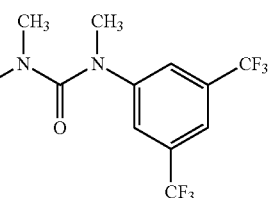 | |

TABLE B-8-continued

| Ex. No. | R¹ | A | B | R² | additive |
|---|---|---|---|---|---|
| 91 | H₃C-C(=O)-NH-CH₂-C(=O)-CH₃ | 1-methyl-3,4-dimethylpiperidine | 4-fluorophenyl | N,N'-dimethyl-N-(3,5-bis(trifluoromethyl)phenyl)urea | |
| 92 | 5,5-dimethyl-3-(2-oxopropyl)oxazolidine-2,4-dione | 1-methyl-3,4-dimethylpiperidine | 4-fluorophenyl | N,N'-dimethyl-N-(3,5-bis(trifluoromethyl)phenyl)urea | |
| 93 | 4-acetyl-2,6-dioxopiperidine | 1-methyl-3,4-dimethylpiperidine | 4-fluorophenyl | N,N'-dimethyl-N-(3,5-bis(trifluoromethyl)phenyl)urea | |
| 94 | H₂N-C(=O)-C(=O)-CH₃ | 1-methyl-3,4-dimethylpiperidine | 4-fluorophenyl | N,N'-dimethyl-N-(3,5-bis(trifluoromethyl)phenyl)urea | |
| 95 | 4-acetamidocyclohexyl methyl ketone | 1-methyl-3,4-dimethylpiperidine | 4-fluorophenyl | N,N'-dimethyl-N-(3,5-bis(trifluoromethyl)phenyl)urea | |

TABLE B-9
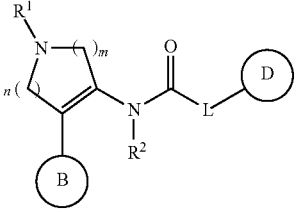
| Ex. No. | R¹ | A | B | R² | additive |
|---|---|---|---|---|---|
| 96 | 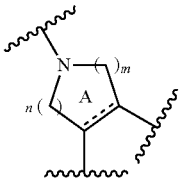 | 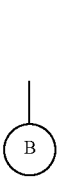 | 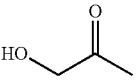 | 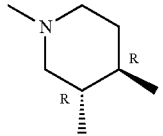 | |
| 97 | 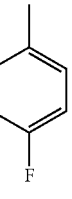 | 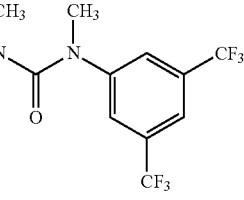 | 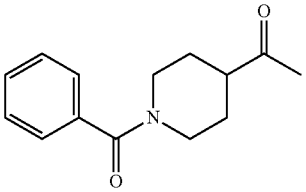 | 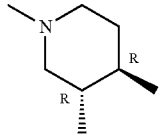 | |
| 98 | 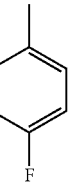 | 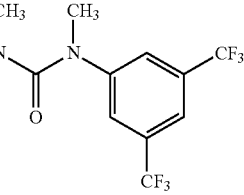 | 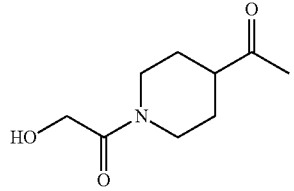 | 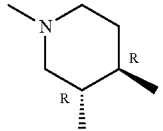 | |
| 99 | 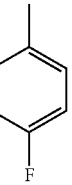 | 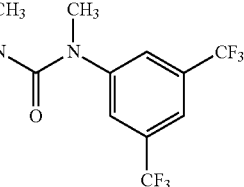 | 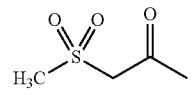 | 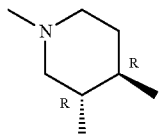 | |
| 100 | 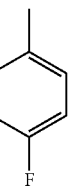 | 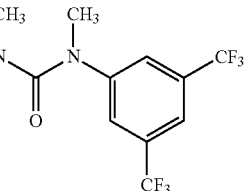 | 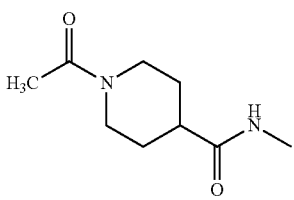 | 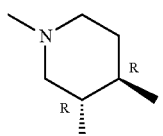 | |

TABLE B-9-continued

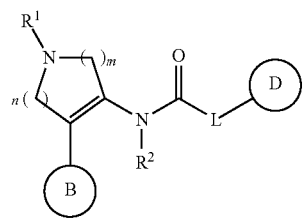

| Ex. No. | R¹ | 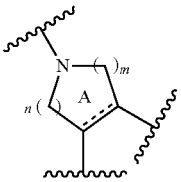 A | B | 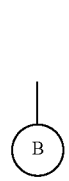 R² | additive |
|---|---|---|---|---|---|
| 101 | 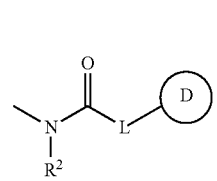 | 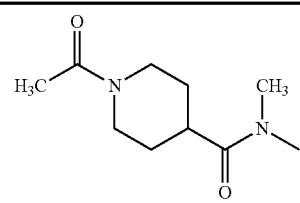 | 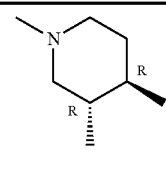 | 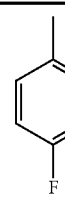 | |
| 102 | 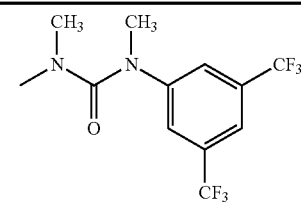 | 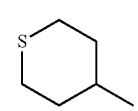 | 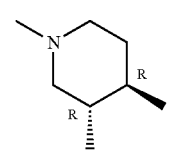 | 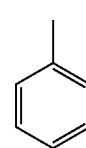 | HCl |
| 103 | 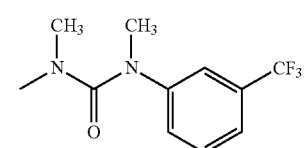 | 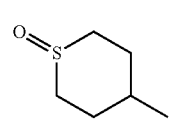 | 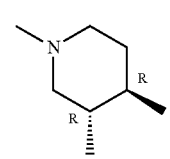 | 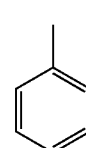 | HCl |
| 104 | 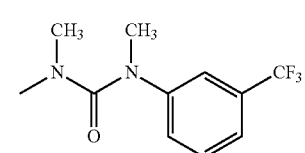 | 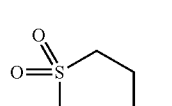 | 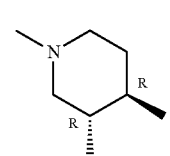 | 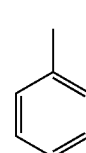 | HCl |

Example 105 tert-butyl (3R,4R)-4-({[3,5-bis(trifluoromethyl)phenyl](cyclopropyl)carbamoyl}amino)-3-(3,4-dichlorophenyl)piperidine-1-carboxylate (Step 1)

To a solution of 3,5-bis(trifluoromethyl)bromobenzene (10 g), cyclopropylamine (2.4 g) and (±)-2,2'-bis(diphenylphosphino)-1,1'-binaphthyl (1.3 g) in toluene (100 mL) was added palladium acetate (0.16 g) under a nitrogen atmosphere, and the mixture was stirred at room temperature for 20 min. To this mixture was added sodium tert-butoxide (4.7 g), and the mixture was stirred at 100° C. for 2 hr. The mixture was cooled, diluted with water, and extracted with ethyl acetate. The extract was washed with water and saturated brine, dried, filtered through silica gel (eluted with 20% ethyl acetate/hexane), and concentrated under reduced pressure. The residue was diluted with hexane, the insoluble material was filtered off, and the filtrate was concentrated under reduced pressure. The residue was separated and purified by silica gel column chromatography (solvent gradient; 0→10% ethyl acetate/hexane) to give N-cyclopropyl-3,5-bis(trifluoromethyl)aniline (7.0 g, 74%) as an orange oil.

$^1$H-NMR(CDCl$_3$) δ 0.51-0.60 (2H, m), 0.79-0.89 (2H, m), 2.42-2.56 (1H, m), 4.55 (1H, brs), 7.11 (2H, s), 7.18 (1H, s)

(Step 2)

A solution of the compound (0.75 g) obtained in Reference Example 2, step 1, DPPA (0.72 g) and triethylamine (0.36 mL) in toluene (10 mL) was stirred at 90° C. for 1 hr, cooled to room temperature, diluted with saturated aqueous sodium hydrogen carbonate solution, and extracted with ethyl acetate. The extract was washed with water and saturated brine, dried and concentrated under reduced pressure. The obtained residue and N-cyclopropyl-3,5-bis(trifluoromethyl) aniline (0.7 g) obtained in step 1 were dissolved in DMF (10 mL), and sodium hydride (0.16 g) was added at 0° C. The mixture was stirred at room temperature for 12 hr, diluted with ice water, and the mixture was extracted with ethyl acetate. The extract was washed with water, 1N hydrochloric acid, water and saturated brine, dried and concentrated under reduced pressure. The residue was separated and purified by silica gel column chromatography (solvent gradient; 0→10% ethyl acetate/hexane) to give the title compound (0.26 g, 20%) as a white powder.

MS(ESI+): 584 (M−$^t$Bu+2H)

Example 106 tert-butyl (3R*, 4R*)-4-({[3,5-bis(trifluoromethyl) phenyl]carbamoyl}amino)-3-[4-(trifluoromethyl) phenyl]piperidine-1-carboxylate By reaction and purification in the same manner as in the method described in Example 1 and using tert-butyl (3R*, 4R*)-4-amino-3-[4-(trifluoromethyl)phenyl]piperidine-1-carboxylate p-toluenesulfonate, the title compound was obtained.

MS(ESI+): 544 (M−$^t$Bu+2H)

Example 107 tert-butyl (3R*,4R*)-4-[{[3,5-bis(trifluoromethyl) phenyl](methyl)carbamoyl}(methyl)amino]-3-[4-(trifluoromethyl)phenyl]piperidine-1-carboxylate By reaction and purification in the same manner as in the method described in Example 2 and using the compound obtained in Example 106, the title compound was obtained.

MS(ESI+): 572 (M−$^t$Bu+2H)

Example 108

1-[3,5-bis(trifluoromethyl)phenyl]-1,3-dimethyl-3-{(3R*,4R*)-3-[4-(trifluoromethyl)phenyl]piperidin-4-yl}urea monohydrochloride By reaction and purification in the same manner as in the method described in Example 3 and using the compound obtained in Example 107, the title compound was obtained.

MS(ESI+): 528 (M−HCl+H)

Example 109

1-{(3R*,4R*)-1-[(1-acetylpiperidin-4-yl)carbonyl]-3-[4-(trifluoromethyl)phenyl]piperidin-4-yl}-3-[3,5-bis(trifluoromethyl)phenyl]-1,3-dimethylurea By reaction and purification in the same manner as in the method described in Example 4 and using the compound obtained in Example 108, the title compound was obtained.

MS(ESI+): 681 (M+H)

Example 110 tert-butyl (3R,4R)-4-[{[4'-chloro-4-(trifluoromethoxy)biphenyl-3-yl](methyl)carbamoyl}(methyl)amino]-3-(4-fluorophenyl)piperidine-1-carboxylate (Step 1)

A solution of 4'-chloro-4-(trifluoromethoxy)biphenyl-3-carboxylic acid (0.63 g), DPPA (0.52 mL) and triethylamine (0.34 mL) in toluene (8.0 mL) was stirred at 80° C. for 1 hr and cooled to room temperature. To this mixture were added the compound (0.93 g) obtained in Reference Example 5 and triethylamine (0.67 mL), and the mixture was stirred at room temperature for 6 hr. To this mixture were added triethylamine (0.67 mL) and THF (4.0 mL), and the mixture was stirred at room temperature overnight, diluted with aqueous sodium hydrogen carbonate solution, and extracted with ethyl acetate. The extract was washed with water and saturated brine, dried and concentrated under reduced pressure. The residue was separated and purified by silica gel column chromatography (solvent gradient; 0→33% ethyl acetate/hexane) to give tert-butyl (3R,4R)-4-({[4'-chloro-4-(trifluoromethoxy)biphenyl-3-yl]carbamoyl}amino)-3-(4-fluorophenyl)piperidine-1-carboxylate (0.70 g, 57%) as a pale-yellow oil.

MS(ESI+): 552 (M−$^t$Bu+2H)

(Step 2)

By reaction and purification in the same manner as in the method described in Example 2 and using the compound obtained in step 1, the title compound was obtained.

MS(ESI+): 580 (M−$^t$Bu+2H)

Example 111

1-[4'-chloro-4-(trifluoromethoxy)biphenyl-3-yl]-3-[(3R,4R)-3-(4-fluorophenyl)piperidin-4-yl]-1,3-dimethylurea monohydrochloride By reaction and purification in the same manner as in the method described in Example 3 and using the compound obtained in Example 110, the title compound was obtained.

MS(ESI+): 536 (M−HCl+H)

Example 112

1-[(3R,4R)-1-[(1-acetylpiperidin-4-yl)carbonyl]-3-(4-fluorophenyl)piperidin-4-yl]-3-[4'-chloro-4-(trifluoromethoxy)biphenyl-3-yl]-1,3-dimethylurea By reaction and purification in the same manner as in the method described in Example 4 and using the compound obtained in Example 111, the title compound was obtained.

MS(ESI+): 689 (M+H)

Example 113 tert-butyl (3R,4R)-4-{3-[3,5-bis(trifluoromethyl) phenyl]-2-oxoimidazolidin-1-yl}-3-(4-fluorophenyl) piperidine-1-carboxylate By reaction and purification in the same manner as in the method described in Example 42 and using the compound obtained in Reference Example 5 and the compound obtained in Reference Example 29, the title compound was obtained.

MS(ESI+): 520 (M−$^t$Bu+2H)

Example 114

1-[3,5-bis(trifluoromethyl)phenyl]-3-[(3R,4R)-3-(4-fluorophenyl)piperidin-4-yl]imidazolidin-2-one monohydrochloride By reaction and purification in the same manner as in the method described in Example 3 and using the compound obtained in Example 113, the title compound was obtained.

MS(ESI+): 475 (M–HCl+H)

Example 115

1-[(3R,4R)-1-[(1-acetylpiperidin-4-yl)carbonyl]-3-(4-fluorophenyl)piperidin-4-yl]-3-[3,5-bis(trifluoromethyl)phenyl]imidazolidin-2-one By reaction and purification in the same manner as in the method described in Example 4 and using the compound obtained in Example 114, the title compound was obtained.

MS(ESI+): 629 (M+H)

Example 116

1-[3,5-bis(trifluoromethyl)phenyl]-3-[(3R,4R)-1-[(4,4-difluorocyclohexyl)carbonyl]-3-(4-fluorophenyl)piperidin-4-yl]-1,3-dimethylurea By reaction and purification in the same manner as in the method described in Example 4 and using the compound obtained in Example 51 and 4,4-difluorocyclohexanecarboxylic acid, the title compound was obtained.

MS(ESI+): 624 (M+H)

Example 117

1-[3,5-bis(trifluoromethyl)phenyl]-3-[(3R,4R)-3-(4-fluorophenyl)-1-({trans-4-[5-(trifluoromethyl)-1H-tetrazol-1-yl]cyclohexyl}carbonyl)piperidin-4-yl]-1,3-dimethylurea By reaction and purification in the same manner as in the method described in Example 4 and using the compound obtained in Example 51 and the compound obtained in Reference Example 40, the title compound was obtained.

MS(ESI+): 724 (M+H)

Example 118

1-[3,5-bis(trifluoromethyl)phenyl]-3-[(3R,4R)-3-(4-fluorophenyl)-1-({4-[5-(trifluoromethyl)-1H-tetrazol-1-yl]phenyl}carbonyl)piperidin-4-yl]-1,3-dimethylurea By reaction and purification in the same manner as in the method described in Example 4 and using the compound obtained in Example 51 and the compound obtained in Reference Example 41, the title compound was obtained.

MS(ESI+): 718 (M+H)

Example 119 tert-butyl (2R)-2-{[(3R,4R)-4-[{[3,5-bis(trifluoromethyl)phenyl](methyl)carbamoyl}(methyl)amino]-3-(4-fluorophenyl)piperidin-1-yl]carbonyl}piperidine-1-carboxylate By reaction and purification in the same manner as in the method described in Example 4 and using the compound obtained in Example 51 and (2R)-1-(tert-butoxycarbonyl)piperidine-2-carboxylic acid, the title compound was obtained.

MS(ESI+): 689 (M+H)

Example 120

1-[3,5-bis(trifluoromethyl)phenyl]-3-{(3R,4R)-3-(4-fluorophenyl)-1-[(2R)-piperidin-2-ylcarbonyl]piperidin-4-yl}-1,3-dimethylurea monohydrochloride By reaction and purification in the same manner as in the method described in Example 3 and using the compound obtained in Example 119, the title compound was obtained.

MS(ESI+): 589 (M–HCl+H)

Example 121

1-[(3R,4R)-1-{[(2R)-1-acetylpiperidin-2-yl]carbonyl}-3-(4-fluorophenyl)piperidin-4-yl]-3-[3,5-bis(trifluoromethyl)phenyl]-1,3-dimethylurea By reaction and purification in the same manner as in the method described in Example 75 and using the compound obtained in Example 120, the title compound was obtained.

MS(ESI+): 631 (M+H)

Example 122

1-[3,5-bis(trifluoromethyl)phenyl]-3-[(3R,4R)-1-({(2R)-1-[(4-cyanophenyl)carbonyl]piperidin-2-yl}carbonyl)-3-(4-fluorophenyl)piperidin-4-yl]-1,3-dimethylurea By reaction and purification in the same manner as in the method described in Example 75 and using the compound obtained in Example 120 and 4-cyanobenzoyl chloride, the title compound was obtained.

MS(ESI+): 718 (M+H)

Example 123

(3R,4R)-4-[{[3,5-bis(trifluoromethyl)phenyl](methyl)carbamoyl}(methyl)amino]-N-ethyl-3-(4-fluorophenyl)piperidine-1-carboxamide By reaction and purification in the same manner as in the method described in Example 1 and using the compound obtained in Example 51 and ethyl isocyanate, the title compound was obtained.

MS(ESI+): 549 (M+H)

Example 124

1-[3,5-bis(trifluoromethyl)phenyl]-3-[(3R,4R)-3-(4-fluorophenyl)-1-(2-hydroxyethyl)piperidin-4-yl]-1,3-dimethylurea monohydrochloride To a solution of the compound (0.18 g) obtained in Example 51 and 2-iodoethanol (0.055 mL) in DMF (6.0 mL) was added N,N-diisopropylethylamine (0.184 mL) at room temperature, and the mixture was heated to 40° C. and stirred overnight. The reaction mixture was diluted with ethyl acetate, washed with water and saturated brine, dried and concentrated under reduced pressure. The residue was purified by silica gel column chromatography (NH Chromatorex) (solvent gradient; 0→100% ethyl acetate/hexane) and treated with 2N hydrogen chloride/2-propanol to give the title compound (0.16 g, 83%) as a white powder.
MS(ESI+): 522 (M−HCl+H)

Example 125

1-[3,5-bis(trifluoromethyl)phenyl]-3-[(3R,4R)-1-(5-cyanopyridin-2-yl)-3-(4-fluorophenyl)piperidin-4-yl]-1,3-dimethylurea To a solution of the compound (0.15 g) obtained in Example 51 and 6-chloropyridine-3-carbonitrile (0.061 g) in DMSO (3.0 mL) was added N,N-diisopropylethylamine (0.049 mL) at room temperature, heated to 80° C. and stirred for 4 hr. The reaction mixture was diluted with ethyl acetate, washed with water and saturated brine, dried and concentrated under reduced pressure. The residue was purified by silica gel column chromatography (NH Chromatorex) (solvent gradient; 25→50% ethyl acetate/hexane) to give the title compound (0.11 g, 67%) as a white powder.
MS(ESI+): 581 (M+H)

Example 126

1-[3,5-bis(trifluoromethyl)phenyl]-3-[(3R,4R)-3-(4-fluorophenyl)-1-(tetrahydro-2H-thiopyran-4-ylcarbonyl)piperidin-4-yl]-1,3-dimethylurea By reaction and purification in the same manner as in the method described in Example 4 and using the compound obtained in Example 51 and tetrahydro-2H-thiopyran-4-carboxylic acid, the title compound was obtained.
MS(ESI+): 606 (M+H)

Example 127

1-[3,5-bis(trifluoromethyl)phenyl]-3-{(3R,4R)-3-(4-fluorophenyl)-1-[(1-oxidetetrahydro-2H-thiopyran-4-yl)carbonyl]piperidin-4-yl}-1,3-dimethylurea To a solution of the compound (0.23 g) obtained in Example 126 in DMF (4.0 mL) was added m-chloroperbenzoic acid (0.071 g) at 0° C., and the mixture was stirred at room temperature for 10 hr. The mixture was diluted with ethyl acetate, and washed with saturated aqueous sodium hydrogen carbonate solution, water and saturated brine, dried and concentrated under reduced pressure. The residue was purified by silica gel column chromatography (NH Chromatorex) (solvent gradient; 0→100% ethyl acetate/hexane) to give the title compound (0.18 g, 76%) as a white powder.
MS(ESI+): 622 (M+H)

Example 128

1-[3,5-bis(trifluoromethyl)phenyl]-3-[(3R,4R)-1-[(1,1-dioxidetetrahydro-2H-thiopyran-4-yl)carbonyl]-3-(4-fluorophenyl)piperidin-4-yl]-1,3-dimethylurea To a solution of the compound (0.25 g) obtained in Example 126 in water/acetone (2/8 mL) was added Oxone-persulfate compound (0.31 g) at 0° C., and the mixture was stirred at room temperature for 12 hr. The mixture was diluted with ethyl acetate, and washed with water and saturated brine, dried and concentrated under reduced pressure. The residue was separated and purified by silica gel column chromatography (NH Chromatorex) (solvent gradient; 0→100% ethyl acetate/hexane) to give the title compound (0.23 g, 86%) as a white powder.
MS(ESI+): 638 (M+H)

Example 129

1-[3,5-bis(trifluoromethyl)phenyl]-3-{(3R,4R)-3-(4-fluorophenyl)-1-[(1-methyl-2,6-dioxopiperidin-4-yl)carbonyl]piperidin-4-yl}-1,3-dimethylurea By reaction and purification in the same manner as in the method described in Example 2 and using the compound obtained in Example 93, the title compound was obtained.
MS(ESI+): 631 (M+H)

Example 130a tert-butyl (3R,4S)-3-({[3,5-bis(trifluoromethyl)phenyl]carbamoyl}amino)-4-(3,4-dichlorophenyl)pyrrolidine-1-carboxylate

Example 130b tert-butyl (3S,4R)-3-({[3,5-bis(trifluoromethyl)phenyl]carbamoyl}amino)-4-(3,4-dichlorophenyl)pyrrolidine-1-carboxylate The compound (2.7 g) obtained in Example 63 was optically resolved by chiral column chromatography. The collected fraction with a short retention time was concentrated to give tert-butyl (3R,4S)-3-({[3,5-bis(trifluoromethyl)phenyl]carbamoyl}amino)-4-(3,4-dichlorophenyl)pyrrolidine-1-carboxylate (1.36 g), and the collected fraction with a long retention time was concentrated to give tert-butyl (3S,4R)-3-({[3,5-bis(trifluoromethyl)phenyl]carbamoyl}amino)-4-(3,4-dichlorophenyl)pyrrolidine-1-carboxylate (1.41 g), each as a white powder.

purification conditions by chiral column chromatography
 column: CHIRALPAK AD 50 mmID×500 mL
 solvent: hexane/2-propanol=950/50
 flow rate: 80 mL/min
 temperature: 30° C.
 detection method: UV 220 nm
tert-butyl (3R,4S)-3-({[3,5-bis(trifluoromethyl)phenyl]carbamoyl}amino)-4-(3,4-dichlorophenyl)pyrrolidine-1-carboxylate (compound with a short retention time, Example 130a)
 MS(ESI+): 530 (M−$^t$Bu+2H)
 $[\alpha]_D^{25}$ +20.9° (c0.25, MeOH)
tert-butyl (3S,4R)-3-({[3,5-bis(trifluoromethyl)phenyl]carbamoyl}amino)-4-(3,4-dichlorophenyl)pyrrolidine-1-carboxylate (compound with a long retention time, Example 130b)

MS(ESI+): 530 (M−$^t$Bu+2H)
[α]$_D^{25}$ −21.4° (c0.25, MeOH)

Example 131 tert-butyl (3S,4R)-3-({[3,5-bis(trifluoromethyl)phenyl]carbamoyl}amino)-4-(3,4-dichlorophenyl)pyrrolidine-1-carboxylate By reaction and purification in the same manner as in the method described in Example 1 and using the compound obtained in Reference Example 22, the title compound was obtained.
MS(ESI+): 530 (M−$^t$Bu+2H)
[α]$_D^{25}$ −22.6° (c0.25, MeOH)

Example 132 tert-butyl (3R,4S)-3-[{[3,5-bis(trifluoromethyl)phenyl](methyl)carbamoyl}(methyl)amino-4-(3,4-dichlorophenyl)pyrrolidine-1-carboxylate By reaction and purification in the same manner as in the method described in Example 2 and using the compound obtained in Example 130a, the title compound was obtained.
MS(ESI+):558 (M−$^t$Bu+2H)

Example 133

1-[3,5-bis(trifluoromethyl)phenyl]-3-[(3R,4S)-4-(3,4-dichlorophenyl)pyrrolidin-3-yl]-1,3-dimethylurea monohydrochloride By reaction and purification in the same manner as in the method described in Example 3 and using the compound obtained in Example 132, the title compound was obtained.
MS(ESI+): 514 (M−HCl+H)

Example 134

1-[(3R,4S)-1-[(1-acetylpiperidin-4-yl)carbonyl]-4-(3,4-dichlorophenyl)pyrrolidin-3-yl]-3-[3,5-bis(trifluoromethyl)phenyl]-1,3-dimethylurea By reaction and purification in the same manner as in the method described in Example 4 and using the compound obtained in Example 133, the title compound was obtained.
MS(ESI+): 667 (M+H)

Example 135 tert-butyl (3S,4R)-3-[{[3,5-bis(trifluoromethyl)phenyl](methyl)carbamoyl}(methyl)amino]-4-(3,4-dichlorophenyl)pyrrolidine-1-carboxylate By reaction and purification in the same manner as in the method described in Example 2 and using the compound obtained in Example 130b, the title compound was obtained.
MS(ESI+): 558 (M−$^t$Bu+2H)

Example 136

1-[3,5-bis(trifluoromethyl)phenyl]-3-[(3S,4R)-4-(3,4-dichlorophenyl)pyrrolidin-3-yl]-1,3-dimethylurea monohydrochloride By reaction and purification in the same manner as in the method described in Example 3 and using the compound obtained in Example 135, the title compound was obtained.
MS(ESI+): 514 (M−HCl+H)

Example 137

1-[(3S,4R)-1-[(1-acetylpiperidin-4-yl)carbonyl]-4-(3,4-dichlorophenyl)pyrrolidin-3-yl]-3-[3,5-bis(trifluoromethyl)phenyl]-1,3-dimethylurea By reaction and purification in the same manner as in the method described in Example 4 and using the compound obtained in Example 136, the title compound was obtained.
MS(ESI+): 667 (M+H)

Example 138 tert-butyl (3R,4S)-3-({[3,5-bis(trifluoromethyl)phenyl]carbamoyl}amino)-4-(4-fluorophenyl)pyrrolidine-1-carboxylate The compound (0.25 g) obtained in Reference Example 20 was dissolved in acetonitrile (5 mL), 3,5-bis(trifluoromethyl)phenyl isocyanate (0.17 mL) and triethylamine (0.14 mL) were added dropwise at room temperature. The reaction mixture was stirred at room temperature for 3 hr, poured into saturated aqueous ammonium chloride solution, and the mixture was extracted with ethyl acetate. The extract was washed with water and saturated brine, dried and concentrated under reduced pressure. The residue was purified by silica gel column chromatography (solvent gradient; 10→33% ethyl acetate/hexane) to give the title compound (0.36 g, 83%) as a white powder.
MS(ESI+): 480 (M−$^t$Bu+2H)

Example 139 tert-butyl (3R,4S)-3-[{[3,5-bis(trifluoromethyl)phenyl](methyl)carbamoyl}(methyl)amino]-4-(4-fluorophenyl)pyrrolidine-1-carboxylate The compound (0.36 g) obtained in Example 138 was dissolved in DMF (3.6 mL), sodium hydride (0.16 g) was added at 0° C., and the mixture was stirred for 5 min. To the reaction mixture was added dropwise methyl iodide (0.44 mL), and the mixture was stirred at room temperature overnight. The reaction mixture was poured into water, and the mixture was extracted with ethyl acetate. The extract was washed with saturated aqueous ammonium chloride solution, water and saturated brine, dried and concentrated under reduced pressure. The residue was purified by silica gel column chromatography (solvent gradient; 10→33% ethyl acetate/hexane) to give the title compound (0.30 g, 79%) as a white powder.
MS(ESI+): 564 (M+H)

Example 140

1-[3,5-bis(trifluoromethyl)phenyl]-3-[(3R,4S)-4-(4-fluorophenyl)pyrrolidin-3-yl]-1,3-dimethylurea monohydrochloride To the compound (0.30 g) obtained in Example 139 was added 2N hydrogen chloride/2-propanol (5 mL), and the mixture was stirred at 50° C. for 2 hr. The reaction mixture was concentrated under reduced pressure to give the title compound (0.23 g, 87%) as a white powder.
MS(ESI+): 464 (M−HCl+H)
$[\alpha]_D^{25}$ +90.8° (c0.26, MeOH)

Example 141

1-[(3R,4S)-1-[(1-acetylpiperidin-4-yl)carbonyl]-4-(4-fluorophenyl)pyrrolidin-3-yl]-3-[3,5-bis(trifluoromethyl)phenyl]-1,3-dimethylurea To a solution of the compound (0.18 g) obtained in Example 140, 1-acetylpiperidine-4-carboxylic acid (0.092 g) and triethylamine (0.050 mL) in acetonitrile (4.5 mL) were added WSC.HCl (0.14 g) and HOBt (0.11 g), and the mixture was stirred at room temperature for 14 hr. The reaction mixture was diluted with ethyl acetate, and washed with saturated aqueous sodium hydrogen carbonate solution, water and saturated brine and dried, and the solvent was evaporated under reduced pressure. The obtained residue was purified by silica gel column chromatography (NH Chromatorex) (solvent gradient; 0→20% methanol/ethyl acetate) to give the title compound (0.11 g, 50%) as a white powder.
MS(ESI+): 617 (M+H)
$[\alpha]_D^{25}$ +98.9° (c0.25, MeOH)

Example 142 tert-butyl (3S,4R)-3-({[3,5-bis(trifluoromethyl)phenyl]carbamoyl}amino)-4-(4-fluorophenyl)pyrrolidine-1-carboxylate To a solution of the compound (20 g) obtained in Reference Example 19 in THF (300 mL) was added dropwise a solution of 3,5-bis(trifluoromethyl)phenyl isocyanate (19.1 g) in THF (50 mL), and the mixture was stirred at room temperature for 4 hr. The mixture was concentrated under reduced pressure, and the residue was separated and purified by silica gel column chromatography (solvent gradient; 0→33% ethyl acetate/hexane) to give the title compound (40 g, 100%) as a white powder.
MS(ESI+): 480 (M−$^t$Bu+2H)

Example 143 tert-butyl (3S,4R)-3-[{[3,5-bis(trifluoromethyl)phenyl](methyl)carbamoyl}(methyl)amino]-4-(4-fluorophenyl)pyrrolidine-1-carboxylate To a solution of the compound (20 g) obtained in Example 142 in DMF (120 mL) was added sodium hydride (4.4 g) at 0° C., and the mixture was stirred for 15 min. To this mixture was added methyl iodide (9.1 mL) at 0° C., and the mixture was stirred at 0° C. for 2 hr. The mixture was diluted with ice water, and extracted with ethyl acetate. The extract was washed with 1N hydrochloric acid, water and saturated brine, dried and concentrated under reduced pressure. The residue was separated and purified by silica gel column chromatography (solvent gradient; 0→40% ethyl acetate/hexane) to give the title compound (20 g, 95%) as a white powder.
MS(ESI+): 508 (M−$^t$Bu+2H)

Example 144

1-[3,5-bis(trifluoromethyl)phenyl]-3-[(3S,4R)-4-(4-fluorophenyl)pyrrolidin-3-yl]-1,3-dimethylurea monohydrochloride A mixture of the compound (20 g) obtained in Example 143 and 2N hydrogen chloride/2-propanol (130 mL) was stirred at room temperature for 1 hr, then at 45° C. for 1.5 hr. The mixture was concentrated, and the residue was recrystallized from methanol/ethanol/IPE to give the title compound (15 g, 85%) as a white powder.
MS(ESI+): 464 (M−HCl+H)

Example 145

1-[(3S,4R)-1-[(1-acetylpiperidin-4-yl)carbonyl]-4-(4-fluorophenyl)pyrrolidin-3-yl]-3-[3,5-bis(trifluoromethyl)phenyl]-1,3-dimethylurea To a mixture of the compound (1.5 g) obtained in Example 144, 1-acetylpiperidine-4-carboxylic acid (0.62 g), WSC.HCl (0.69 g) and HOBt (0.41 g) in acetonitrile (15 mL) was added triethylamine (0.50 mL), and the mixture was stirred at room temperature for 3 hr. The reaction mixture was diluted with ethyl acetate, and washed with saturated aqueous sodium hydrogen carbonate solution, water and saturated brine and dried, and the solvent was evaporated under reduced pressure. The obtained residue was purified by silica gel column chromatography (NH Chromatorex) (solvent gradient; 0→100% ethyl acetate/hexane) and recrystallized from tert-butyl methyl ether/IPE to give the title compound (1.7 g, 91%) as a white powder.
MS(ESI+): 617 (M+H)
$[\alpha]_D^{25}$ −104.7° (c0.26, MeOH)

Example 146 tert-butyl (3R*, 4R*)-3-({[3,5-bis(trifluoromethyl)phenyl]carbamoyl}amino)-4-(4-fluorophenyl)pyrrolidine-1-carboxylate By reaction and purification in the same manner as in the method described in Example 1 and using the compound obtained in Reference Example 21, the title compound was obtained.
MS(ESI+): 536 (M+H)

Example 147 tert-butyl (3R*, 4R*)-3-[{[3,5-bis(trifluoromethyl)phenyl](methyl)carbamoyl}(methyl)amino]-4-(4-fluorophenyl)pyrrolidine-1-carboxylate The compound (0.99 g) obtained in Example 146 was dissolved in DMAc (10 mL), sodium hydride (0.44 g) was added at 0° C., and the mixture was stirred for 5 min. To the reaction mixture was added dropwise methyl iodide (1.2 mL), and the mixture was stirred at room temperature for 4 hr. The reaction mixture was poured into water, and the mixture was extracted with ethyl acetate. The extract was washed with saturated aqueous ammonium chloride solution, water and saturated brine, dried and concentrated under reduced pres-

Example 148

1-[3,5-bis(trifluoromethyl)phenyl]-3-[(3R*, 4R*)-4-(4-fluorophenyl)pyrrolidin-3-yl]-1,3-dimethylurea monohydrochloride By reaction and purification in the same manner as in the method described in Example 3 and using the compound obtained in Example 147, the title compound was obtained.
MS(ESI+): 464 (M−HCl+H)

Example 149

1-[(3R*,4R*)-1-[(1-acetylpiperidin-4-yl)carbonyl]-4-(4-fluorophenyl)pyrrolidin-3-yl]-3-[3,5-bis(trifluoromethyl)phenyl]-1,3-dimethylurea By reaction and purification in the same manner as in the method described in Example 4 and using the compound obtained in Example 148, the title compound was obtained.
MS(ESI+): 617 (M+H)

Example 150 tert-butyl (3S,4R)-3-({[3,5-bis(trifluoromethyl)phenyl]carbamoyl}amino)-4-(3,4-difluorophenyl)pyrrolidine-1-carboxylate By reaction and purification in the same manner as in the method described in Example 1 and using the compound obtained in Reference Example 23, the title compound was obtained.
MS(ESI+): 554 (M+H)

Example 151

1-[3,5-bis(trifluoromethyl)phenyl]-3-[(3S,4R)-4-(3,4-difluorophenyl)pyrrolidin-3-yl]-1,3-dimethylurea monohydrochloride By reaction and purification in the same manner as in the method described in Example 2 to 3 and using the compound obtained in Example 150, the title compound was obtained.
MS(ESI+): 482 (M−HCl+H)

Example 152

1-[(3S,4R)-1-[(1-acetylpiperidin-4-yl)carbonyl]-4-(3,4-difluorophenyl)pyrrolidin-3-yl]-3-[3,5-bis(trifluoromethyl)phenyl]-1,3-dimethylurea By reaction and purification in the same manner as in the method described in Example 4 and using the compound obtained in Example 151, the title compound was obtained.
MS(ESI+): 635 (M+H)

Example 153 tert-butyl (3S,4R)-3-({[3,5-bis(trifluoromethyl)phenyl]carbamoyl}amino)-4-(2,4-difluorophenyl)pyrrolidine-1-carboxylate By reaction and purification in the same manner as in the method described in Example 142 and using the compound obtained in Reference Example 24, the title compound was obtained.
MS(ESI+): 498 (M−$^t$Bu+2H)

Example 154 tert-butyl (3S,4R)-3-[{[3,5-bis(trifluoromethyl)phenyl](methyl)carbamoyl}(methyl)amino]-4-(2,4-difluorophenyl)pyrrolidine-1-carboxylate By reaction and purification in the same manner as in the method described in Example 2 and using the compound obtained in Example 153, the title compound was obtained.
MS(ESI+): 526 (M−$^t$Bu+2H)

Example 155

1-[3,5-bis(trifluoromethyl)phenyl]-3-[(3S,4R)-4-(2,4-difluorophenyl)pyrrolidin-3-yl]-1,3-dimethylurea monohydrochloride By reaction and purification in the same manner as in the method described in Example 3 and using the compound obtained in Example 154, the title compound was obtained.
MS(ESI+): 482 (M−HCl+H)

Example 156

1-[(3S,4R)-1-[(1-acetylpiperidin-4-yl)carbonyl]-4-(2,4-difluorophenyl)pyrrolidin-3-yl]-3-[3,5-bis(trifluoromethyl)phenyl]-1,3-dimethylurea By reaction and purification in the same manner as in the method described in Example 4 and using the compound obtained in Example 155, the title compound was obtained.
MS(ESI+): 635 (M+H)

Example 157 tert-butyl (3S,4R)-3-({[3,5-bis(trifluoromethyl)phenyl]carbamoyl}amino)-4-(4-fluoro-2-methylphenyl)pyrrolidine-1-carboxylate By reaction and purification in the same manner as in the method described in Example 142 and using the compound obtained in Reference Example 27, the title compound was obtained.
MS(ESI+): 550 (M+H)

Example 158 tert-butyl (3S,4R)-3-[{[3,5-bis(trifluoromethyl)phenyl](methyl)carbamoyl}(methyl)amino]-4-(4-fluoro-2-methylphenyl)pyrrolidine-1-carboxylate By reaction and purification in the same manner as in the method described in Example 2 and using the compound obtained in Example 157, the title compound was obtained.
MS(ESI+): 522 (M−$^t$Bu+2H)

--- sure. The residue was purified by silica gel column chromatography (solvent gradient; 10→33% ethyl acetate/hexane) to give the title compound (1.08 g, quantitatively) as a white powder.
MS(ESI+): 508 (M−$^t$Bu+2H)

Example 159

1-[3,5-bis(trifluoromethyl)phenyl]-3-[(3S,4R)-4-(4-fluoro-2-methylphenyl)pyrrolidin-3-yl]-1,3-dimethylurea monohydrochloride By reaction and purification in the same manner as in the method described in Example 3 and using the compound obtained in Example 158, the title compound was obtained.
MS(ESI+): 478 (M−HCl+H)

Example 160

1-[(3S,4R)-1-[(1-acetylpiperidin-4-yl)carbonyl]-4-(4-fluoro-2-methylphenyl)pyrrolidin-3-yl]-3-[3,5-bis(trifluoromethyl)phenyl]-1,3-dimethylurea By reaction and purification in the same manner as in the method described in Example 4 and using the compound obtained in Example 159, the title compound was obtained.
MS(ESI+): 631 (M+H)

Example 161 tert-butyl (3S,4R)-3-({[3-bromo-5-(trifluoromethyl)phenyl]carbamoyl}amino)-4-(4-fluorophenyl)pyrrolidine-1-carboxylate A solution of the compound (0.56 g) obtained in Reference Example 19 and the compound (0.82 g) obtained in Reference Example 32 in 1-methyl-2-pyrrolidone (5.6 mL) was stirred at 110° C. for 2 hr. The reaction mixture was diluted with ethyl acetate, washed with water, saturated aqueous sodium hydrogen carbonate solution, saturated aqueous ammonium chloride solution and saturated brine, dried and concentrated under reduced pressure. The residue was purified by silica gel column chromatography (solvent gradient; 30→50% ethyl acetate/hexane) to give the title compound (0.92 g, 84%) as a white powder.
MS(ESI+): 546 (M+H)

Example 162 tert-butyl (3S,4R)-3-[{[3-bromo-5-(trifluoromethyl)phenyl](methyl)carbamoyl}(methyl)amino]-4-(4-fluorophenyl)pyrrolidine-1-carboxylate By reaction and purification in the same manner as in the method described in Example 2 and using the compound obtained in Example 161, the title compound was obtained.
MS(ESI+): 518 (M−$^t$Bu+2H)

Example 163

1-[3-bromo-5-(trifluoromethyl)phenyl]-3-[(3S,4R)-4-(4-fluorophenyl)pyrrolidin-3-yl]-1,3-dimethylurea monohydrochloride By reaction and purification in the same manner as in the method described in Example 3 and using the compound obtained in Example 162, the title compound was obtained.
MS(ESI+): 474 (M−HCl+H)

Example 164

1-[(3S,4R)-1-[(1-acetylpiperidin-4-yl)carbonyl]-4-(4-fluorophenyl)pyrrolidin-3-yl]-3-[3-bromo-5-(trifluoromethyl)phenyl]-1,3-dimethylurea By reaction and purification in the same manner as in the method described in Example 4 and using the compound obtained in Example 163, the title compound was obtained.
MS(ESI+): 627 (M+H)

Example 165 tert-butyl (3S,4R)-3-{[(3,5-dibromophenyl)carbamoyl]amino}-4-(4-fluorophenyl)pyrrolidine-1-carboxylate By reaction and purification in the same manner as in the method described in Example 161 and using the compound obtained in Reference Example 19 and the compound obtained in Reference Example 33, the title compound was obtained.
MS(ESI+): 502 (M−$^t$Bu+2H)

Example 166 tert-butyl (3S,4R)-3-{[(3,5-dibromophenyl)(methyl)carbamoyl](methyl)amino}-4-(4-fluorophenyl)pyrrolidine-1-carboxylate By reaction and purification in the same manner as in the method described in Example 2 and using the compound obtained in Example 165, the title compound was obtained.
MS(ESI+): 530 (M−$^t$Bu+2H)

Example 167

1-(3,5-dibromophenyl)-3-[(3S,4R)-4-(4-fluorophenyl)pyrrolidin-3-yl]-1,3-dimethylurea monohydrochloride By reaction and purification in the same manner as in the method described in Example 3 and using the compound obtained in Example 166, the title compound was obtained.
MS(ESI+): 486 (M−HCl+H)

Example 168

1-[(3S,4R)-1-[(1-acetylpiperidin-4-yl)carbonyl]-4-(4-fluorophenyl)pyrrolidin-3-yl]-3-(3,5-dibromophenyl)-1,3-dimethylurea By reaction and purification in the same manner as in the method described in Example 4 and using the compound obtained in Example 167, the title compound was obtained.
MS(ESI+): 639 (M+H)

Example 169 tert-butyl (3S,4R)-3-({[3-chloro-5-(trifluoromethyl)phenyl]carbamoyl}amino)-4-(4-fluorophenyl)pyrrolidine-1-carboxylate By reaction and purification in the same manner as in the method described in Example 161 and using the compound obtained in Reference Example 19 and the compound obtained in Reference Example 31, the title compound was obtained.
MS(ESI+): 446 (M−$^t$Bu+2H)

Example 170 tert-butyl (3S,4R)-3-[{[3-chloro-5-(trifluoromethyl)phenyl](methyl)carbamoyl}(methyl)amino]-4-(4-fluorophenyl)pyrrolidine-1-carboxylate By reaction and purification in the same manner as in the method described in Example 2 and using the compound obtained in Example 169, the title compound was obtained.
MS(ESI+): 474 (M−$^t$Bu+2H)

Example 171

1-[3-chloro-5-(trifluoromethyl)phenyl]-3-[(3S,4R)-4-(4-fluorophenyl)pyrrolidin-3-yl]-1,3-dimethylurea monohydrochloride By reaction and purification in the same manner as in the method described in Example 3 and using the compound obtained in Example 170, the title compound was obtained.
MS(ESI+): 430 (M−HCl+H)

Example 172

1-[(3S,4R)-1-[(1-acetylpiperidin-4-yl)carbonyl]-4-(4-fluorophenyl)pyrrolidin-3-yl]-3-[3-chloro-5-(trifluoromethyl)phenyl]-1,3-dimethylurea By reaction and purification in the same manner as in the method described in Example 4 and using the compound obtained in Example 171, the title compound was obtained.
MS(ESI+): 583 (M+H)

Example 173 tert-butyl (3S,4R)-3-{[(3,5-dichlorophenyl)carbamoyl]amino}-4-(4-fluorophenyl)pyrrolidine-1-carboxylate The compound (1.0 g) obtained in Reference Example 19 was dissolved in acetonitrile (10 mL), and 3,5-dichlorophenyl isocyanate (0.81 g) and triethylamine (0.60 mL) were added dropwise at room temperature. The reaction mixture was stirred at room temperature for 14 hr, poured into saturated aqueous ammonium chloride solution, and the mixture was extracted with ethyl acetate. The extract was washed with water and saturated brine, dried and concentrated under reduced pressure. The residue was purified by silica gel column chromatography (solvent gradient; 25→50% ethyl acetate/hexane) to give the title compound (0.99 g, 90%) as a white powder.
MS(ESI+): 412 (M−$^t$Bu+2H)

Example 174 tert-butyl (3S,4R)-3-{[(3,5-dichlorophenyl)(methyl)carbamoyl](methyl)amino}-4-(4-fluorophenyl)pyrrolidine-1-carboxylate By reaction and purification in the same manner as in the method described in Example 2 and using the compound obtained in Example 173, the title compound was obtained.
MS(ESI+): 440 (M−$^t$Bu+2H)

Example 175

1-(3,5-dichlorophenyl)-3-[(3S,4R)-4-(4-fluorophenyl)pyrrolidin-3-yl]-1,3-dimethylurea monohydrochloride By reaction and purification in the same manner as in the method described in Example 3 and using the compound obtained in Example 174, the title compound was obtained.
MS(ESI+): 396 (M−HCl+H)

Example 176

1-[(3S,4R)-1-[(1-acetylpiperidin-4-yl)carbonyl]-4-(4-fluorophenyl)pyrrolidin-3-yl]-3-(3,5-dichlorophenyl)-1,3-dimethylurea By reaction and purification in the same manner as in the method described in Example 4 and using the compound obtained in Example 175, the title compound was obtained.
MS(ESI+): 549 (M+H)

Example 177 tert-butyl (3R,4S)-3-(4-fluorophenyl)-4-({[3-methyl-5-(trifluoromethyl)phenyl]carbamoyl}amino)pyrrolidine-1-carboxylate By reaction and purification in the same manner as in the method described in Example 161 and using the compound obtained in Reference Example 19 and the compound obtained in Reference Example 30, the title compound was obtained.
MS(ESI+): 426 (M−$^t$Bu+2H)

Example 178 tert-butyl (3R,4S)-3-(4-fluorophenyl)-4-({methyl}{(methyl)[3-methyl-5-(trifluoromethyl)phenyl]carbamoyl}amino)pyrrolidine-1-carboxylate By reaction and purification in the same manner as in the method described in Example 2 and using the compound obtained in Example 177, the title compound was obtained.
MS(ESI+): 454 (M−$^t$Bu+2H)

Example 179

1-[(3S,4R)-4-(4-fluorophenyl)pyrrolidin-3-yl]-1,3-dimethyl-3-[3-methyl-5-(trifluoromethyl)phenyl]urea monohydrochloride By reaction and purification in the same manner as in the method described in Example 3 and using the compound obtained in Example 178, the title compound was obtained.
MS(ESI+): 410 (M−HCl+H)

Example 180

1-[(3S,4R)-1-[(1-acetylpiperidin-4-yl)carbonyl]-4-(4-fluorophenyl)pyrrolidin-3-yl]-1,3-dimethyl-3-[3-methyl-5-(trifluoromethyl)phenyl]urea By reaction and purification in the same manner as in the method described in Example 4 and using the compound obtained in Example 179, the title compound was obtained.
MS(ESI+): 563 (M+H)

Example 181 tert-butyl (3R,4S)-3-(4-chlorophenyl)-4-{[(3,5-dichlorophenyl)carbamoyl]amino}pyrrolidine-1-carboxylate The compound (0.76 g) obtained in Reference Example 25 was dissolved in acetonitrile (15 mL), 3,5-dichlorophenyl isocyanate (0.58 g) and triethylamine (0.43 mL) were added dropwise at room temperature. The reaction mixture was stirred at room temperature for 14 hr, poured into saturated aqueous ammonium chloride solution, and the mixture was extracted with ethyl acetate. The extract was washed with water and saturated brine, dried and concentrated under reduced pressure. The residue was purified by silica gel column chromatography (solvent gradient; 10→30% ethyl acetate/hexane) to give the title compound (0.62 g, 50%) as a pale-yellow powder.
MS(ESI+): 486 (M+H)

Example 182 tert-butyl (3R,4S)-3-(4-chlorophenyl)-4-{[(3,5-dichlorophenyl)(methyl)carbamoyl](methyl)amino}pyrrolidine-1-carboxylate The compound (0.60 g) obtained in Example 181 was dissolved in DMAc (10 mL), sodium hydride (0.30 g) was added at 0° C., and the mixture was stirred for 5 min. To the reaction mixture was added dropwise methyl iodide (0.77 and the mixture was stirred at room temperature for 2 hr. The reaction mixture was poured into water, and the mixture was extracted with ethyl acetate. The extract was washed with saturated aqueous ammonium chloride solution, water and saturated brine, dried and concentrated under reduced pressure. The residue was purified by silica gel column chromatography (solvent gradient; 10→30% ethyl acetate/hexane) to give the title compound (0.32 g, 51%) as a white powder.
MS(ESI+): 456 (M−$^t$Bu+2H)

Example 183

1-[(3S,4R)-4-(4-chlorophenyl)pyrrolidin-3-yl]-3-(3,5-dichlorophenyl)-1,3-dimethylurea monohydrochloride To the compound (0.28 g) obtained in Example 182 was added 2N hydrogen chloride/2-propanol (5 mL), and the mixture was stirred at 50° C. for 2 hr. The reaction mixture was concentrated under reduced pressure to give the title compound (0.24 g, 98%) as a white powder.
MS(ESI+): 412 (M−HCl+H)

Example 184

1-[(3S,4R)-4-(4-chlorophenyl)-1-{[4-(methylsulfonyl)piperazin-1-yl]carbonyl}pyrrolidin-3-yl]-3-(3,5-dichlorophenyl)-1,3-dimethylurea (Step 1)
The compound (0.20 g) obtained in Example 183 was dissolved in THF (5 mL), and 4-nitrophenyl chlorocarbonate (0.099 g) and N,N-diisopropylethylamine (0.086 mL) were added dropwise at 5° C. The reaction mixture was stirred at 5° C. for 1 hr, poured into saturated aqueous ammonium chloride solution, and the mixture was extracted with ethyl acetate. The extract was washed with water and saturated brine, dried and concentrated under reduced pressure. The residue was purified by silica gel column chromatography (solvent gradient; 10→30% ethyl acetate/hexane) to give a white powder (0.23 g).
(Step 2)
A solution of the compound (0.23 g) obtained in step 1 and 1-(methylsulfonyl)piperazine (0.22 g) in 1-methyl-2-pyrrolidone (5 mL) was stirred at 135° C. for 11 hr. The reaction mixture was poured into water, and extracted twice with ethyl acetate. The extract was washed with saturated aqueous ammonium chloride solution and saturated brine, dried and concentrated. The residue was purified by silica gel column chromatography (solvent gradient; 0→10% methanol/ethyl acetate) to give the title compound (0.25 g, 93%) as a pale-yellow powder.
MS(ESI+): 604 (M+H)
$^1$H-NMR(CDCl$_3$) δ 2.50 (3H, s), 2.77 (3H, s), 3.12 (3H, s), 3.10-3.55 (11H, m), 3.60-3.80 (2H, m), 4.84-4.94 (1H, m), 6.57 (2H, d, J=1.8 Hz), 7.00 (1H, t, J=1.8 Hz), 7.18-7.22 (2H, m), 7.34-7.37 (2H, m)
$[α]_D^{25}$ −87.1° (c0.27, MeOH)

Example 185 tert-butyl (3S,4R)-3-(4-chlorophenyl)-4-{[(3,5-dichlorophenyl)carbamoyl]amino}pyrrolidine-1-carboxylate By reaction and purification in the same manner as in the method described in and Example 181 and using the compound obtained in Reference Example 26, the title compound was obtained.
MS(ESI+): 486 (M+H)

Example 186 tert-butyl (3S,4R)-3-(4-chlorophenyl)-4-{[(3,5-dichlorophenyl)(methyl)carbamoyl](methyl)amino}pyrrolidine-1-carboxylate By reaction and purification in the same manner as in the method described in Example 182 and using the compound obtained in Example 185, the title compound was obtained.
MS(ESI+): 456 (M−$^t$Bu+2H)

Example 187

1-[(3R,4S)-4-(4-chlorophenyl)pyrrolidin-3-yl]-3-(3,5-dichlorophenyl)-1,3-dimethylurea monohydrochloride By reaction and purification in the same manner as in the method described in Example 183 and using the compound obtained in Example 186, the title compound was obtained.
MS(ESI+): 412 (M−HCl+H)

Example 188

1-[(3R,4S)-4-(4-chlorophenyl)-1-{[4-(methylsulfonyl)piperazin-1-yl]carbonyl}pyrrolidin-3-yl]-3-(3,5-dichlorophenyl)-1,3-dimethylurea By reaction and purification in the same manner as in the method described in Example 184 and using the compound obtained in Example 187, the title compound was obtained.
MS(ESI+): 604 (M+H)

Example 189 tert-butyl (3S,4R)-3-({[3,5-bis(trifluoromethyl)phenyl]carbamoyl}amino)-4-(5-fluoropyridin-2-yl)pyrrolidine-1-carboxylate To a solution of the compound (1.9 g) obtained in Reference Example 28 in THF (22 mL) was added dropwise a solution of 3,5-bis(trifluoromethyl)phenyl isocyanate (1.3 mL) in THF (2.0 mL), and the mixture was stirred at room temperature for 3 hr. The mixture was concentrated under reduced pressure, and the residue was purified by silica gel column chromatography (solvent gradient; 0→60% ethyl acetate/hexane) to give the title compound (3.3 g, 91%) as a white powder.

MS(ESI+): 537 (M+H)

Example 190 tert-butyl (3S,4R)-3-[{[3,5-bis(trifluoromethyl)phenyl](methyl)carbamoyl}(methyl)amino]-4-(5-fluoropyridin-2-yl)pyrrolidine-1-carboxylate The compound (3.1 g) obtained in Example 189 was dissolved in DMF (30 mL), and sodium hydride (0.58 g) was added at 0° C., and the mixture was stirred for 10 min. To the reaction mixture was added dropwise methyl iodide (1.1 mL), and the mixture was stirred at 0° C. for 1.5 hr. The reaction mixture was poured into water, and the mixture was extracted with ethyl acetate. The extract was washed with water (2 times) and saturated brine, dried and concentrated under reduced pressure. The residue was purified by silica gel column chromatography (solvent gradient; 0→60% ethyl acetate/hexane) to give the title compound (2.6 g, 79%) as a white powder.

MS(ESI+): 565 (M+H)

Example 191

1-[3,5-bis(trifluoromethyl)phenyl]-3-[(3S,4R)-4-(5-fluoropyridin-2-yl)pyrrolidin-3-yl]-1,3-dimethylurea dihydrochloride A mixture of the compound (2.5 g) obtained in Example 190 and 2N hydrogen chloride/2-propanol (25 mL) was stirred at 45 to 55° C. for 4 hr, concentrated under reduced pressure and recrystallized from ethanol/IPE to give the title compound.

MS(ESI+): 465 (M−2HCl+H)

Example 192

1-[(3S,4R)-1-[(1-acetylpiperidin-4-yl)carbonyl]-4-(5-fluoropyridin-2-yl)pyrrolidin-3-yl]-3-[3,5-bis(trifluoromethyl)phenyl]-1,3-dimethylurea By reaction and purification in the same manner as in the method described in Example 4 and using the compound obtained in Example 191, the title compound was obtained.

MS(ESI+): 618 (M+H)

Example 193 tert-butyl (3S,4R)-3-{3-[3,5-bis(trifluoromethyl)phenyl]-2-oxoimidazolidin-1-yl}-4-(4-fluorophenyl)pyrrolidine-1-carboxylate By reaction and purification in the same manner as in the method described in Example 42 and using the compound obtained in Reference Example 19 and the compound obtained in Reference Example 29, the title compound was obtained.

MS(ESI+): 506 (M−$^t$Bu+2H)

Example 194

1-[3,5-bis(trifluoromethyl)phenyl]-3-[(3S,4R)-4-(4-fluorophenyl)pyrrolidin-3-yl]imidazolidin-2-one monohydrochloride By reaction and purification in the same manner as in the method described in Example 3 and using the compound obtained in Example 193, the title compound was obtained.

MS(ESI+): 462 (M−HCl+H)

Example 195

1-[(3S,4R)-1-[(1-acetylpiperidin-4-yl)carbonyl]-4-(4-fluorophenyl)pyrrolidin-3-yl]-3-[3,5-bis(trifluoromethyl)phenyl]imidazolidin-2-one By reaction and purification in the same manner as in the method described in Example 4 and using the compound obtained in Example 194, the title compound was obtained.

MS(ESI+): 615 (M+H)

Example 196

1-[3,5-bis(trifluoromethyl)phenyl]-3-[(3S,4R)-4-(3,4-dichlorophenyl)-1-(tetrahydro-2H-pyran-4-ylcarbonyl)pyrrolidin-3-yl]-1,3-dimethylurea By reaction and purification in the same manner as in the method described in Example 4 and using the compound obtained in Example 136 and tetrahydro-2H-pyran-4-carboxylic acid, the title compound was obtained.

MS(ESI+): 626 (M+H)

Example 197

1-[3,5-bis(trifluoromethyl)phenyl]-3-[(3S,4R)-4-(3,4-dichlorophenyl)-1-{[1-(hydroxyacetyl)piperidin-4-yl]carbonyl}pyrrolidin-3-yl]-1,3-dimethylurea By reaction and purification in the same manner as in the method described in Example 4 and using the compound obtained in Example 136 and 1-glycoloylpiperidine-4-carboxylic acid, the title compound was obtained.

MS(ESI+): 683 (M+H)

Example 198

1-[3,5-bis(trifluoromethyl)phenyl]-3-[(3R,4S)-4-(4-fluorophenyl)-1-{[1-(phenylcarbonyl)piperidin-4-yl]carbonyl}pyrrolidin-3-yl]-1,3-dimethylurea By reaction and purification in the same manner as in the method described in Example 4 and using the compound

Example 199

1-[(3S,4R)-1-acetyl-4-(4-fluorophenyl)pyrrolidin-3-yl]-3-[3,5-bis(trifluoromethyl)phenyl]-1,3-dimethylurea By reaction and purification in the same manner as in the method described in Example 75 and using the compound obtained in Example 144, the title compound was obtained.
MS(ESI+): 506 (M+H)

Example 200

1-[3,5-bis(trifluoromethyl)phenyl]-3-[(3S,4R)-4-(4-fluorophenyl)-1-(methylsulfonyl)pyrrolidin-3-yl]-1,3-dimethylurea By reaction and purification in the same manner as in the method described in Example 75 and using the compound obtained in Example 144 and methanesulfonyl chloride, the title compound was obtained.
MS(ESI+): 542 (M+H)

Example 201 methyl (3S,4R)-3-[{[3,5-bis(trifluoromethyl)phenyl](methyl)carbamoyl}(methyl)amino]-4-(4-fluorophenyl)pyrrolidine-1-carboxylate By reaction and purification in the same manner as in the method described in Example 75 and using the compound obtained in Example 144 and methyl chlorocarbonate, the title compound was obtained.
MS(ESI+): 522 (M+H)

Example 202

1-[3,5-bis(trifluoromethyl)phenyl]-3-[(3S,4R)-1-(cyanoacetyl)-4-(4-fluorophenyl)pyrrolidin-3-yl]-1,3-dimethylurea By reaction and purification in the same manner as in the method described in Example 4 and using the compound obtained in Example 144 and cyanoacetic acid, the title compound was obtained.
MS(ESI+): 531 (M+H)

Example 203

1-[3,5-bis(trifluoromethyl)phenyl]-3-[(3S,4R)-4-(4-fluorophenyl)-1-(3-oxocyclopent-1-en-1-yl)pyrrolidin-3-yl]-1,3-dimethylurea By reaction and purification in the same manner as in the method described in Example 78 and using the compound obtained in Example 144, the title compound was obtained.
MS(ESI+): 544 (M+H)

Example 204

1-[3,5-bis(trifluoromethyl)phenyl]-3-[(3S,4R)-1-[(2,6-dioxopiperidin-4-yl)carbonyl]-4-(4-fluorophenyl)pyrrolidin-3-yl]1,3-dimethylurea By reaction and purification in the same manner as in the method described in Example 4 and using the compound obtained in Example 144 and 2,6-dioxopiperidine-4-carboxylic acid, the title compound was obtained.
MS(ESI+): 603 (M+H)

Example 205

1-[3,5-bis(trifluoromethyl)phenyl]-3-[(3S,4R)-4-(4-fluorophenyl)-1-{[1-(phenylcarbonyl)piperidin-4-yl]carbonyl}pyrrolidin-3-yl]-1,3-dimethylurea By reaction and purification in the same manner as in the method described in Example 4 and using the compound obtained in Example 144 and 1-(phenylcarbonyl)piperidine-4-carboxylic acid, the title compound was obtained.
MS(ESI+): 679 (M+H)

Example 206

2-[(3S,4R)-3-[{[3,5-bis(trifluoromethyl)phenyl](methyl)carbamoyl}(methyl)amino]-4-(4-fluorophenyl)pyrrolidin-1-yl]-2-oxoacetamide By reaction and purification in the same manner as in the method described in Example 4 and using the compound obtained in Example 144 and amino(oxo)acetic acid, the title compound was obtained.
MS(ESI+): 535 (M+H)

Example 207

1-[3,5-bis(trifluoromethyl)phenyl]-3-[(3S,4R)-1-[(5,5-dimethyl-2,4-dioxo-1,3-oxazolidin-3-yl)acetyl]-4-(4-fluorophenyl)pyrrolidin-3-yl]-1,3-dimethylurea By reaction and purification in the same manner as in the method described in Example 4 and using the compound obtained in Example 144 and (5,5-dimethyl-2,4-dioxo-1,3-oxazolidin-3-yl)acetic acid, the title compound was obtained.
MS(ESI+): 633 (M+H)

Example 208

1-[3,5-bis(trifluoromethyl)phenyl]-3-[(3S,4R)-4-(4-fluorophenyl)-1-{[1-(hydroxyacetyl)piperidin-4-yl]carbonyl}pyrrolidin-3-yl]-1,3-dimethylurea By reaction and purification in the same manner as in the method described in Example 4 and using the compound obtained in Example 144 and 1-(hydroxyacetyl)piperidine-4-carboxylic acid, the title compound was obtained.
MS(ESI+): 633 (M+H)

Example 209

N-{2-[(3S,4R)-3-[{[3,5-bis(trifluoromethyl)phenyl](methyl)carbamoyl}(methyl)amino]-4-(4-fluorophenyl)pyrrolidin-1-yl]-2-oxoethyl}acetamide By reaction and purification in the same manner as in the method described in Example 4 and using the compound obtained in Example 144 and N-acetylglycine, the title compound was obtained.
MS(ESI+): 563 (M+H)

Example 210

N-(trans-4-{[(3S,4R)-3-[{[3,5-bis(trifluoromethyl)phenyl](methyl)carbamoyl}(methyl)amino]-4-(4-fluorophenyl)pyrrolidin-1-yl]carbonyl}cyclohexyl)acetamide By reaction and purification in the same manner as in the method described in Example 4 and using the compound obtained in Example 144 and trans-4-(acetylamino)cyclohexanecarboxylic acid, the title compound was obtained.

MS(ESI+): 631 (M+H)

Example 211

N-{2-[(3S,4R)-3-[{[3,5-bis(trifluoromethyl)phenyl](methyl)carbamoyl}(methyl)amino]-4-(4-fluorophenyl)pyrrolidin-1-yl]-2-oxoethyl}pyridine-2-carboxamide By reaction and purification in the same manner as in the method described in Example 4 and using the compound obtained in Example 144 and N-(pyridin-2-ylcarbonyl)glycine, the title compound was obtained.

MS(ESI+): 626 (M+H)

Example 212

1-[3,5-bis(trifluoromethyl)phenyl]-3-{(3S,4R)-4-(4-fluorophenyl)-1-[(methylsulfonyl)acetyl]pyrrolidin-3-yl}-1,3-dimethylurea By reaction and purification in the same manner as in the method described in Example 4 and using the compound obtained in Example 144 and (methylsulfonyl)acetic acid, the title compound was obtained.

MS(ESI+): 584 (M+H)

Example 213

1-[3,5-bis(trifluoromethyl)phenyl]-3-[(3S,4R)-4-(4-fluorophenyl)-1-(1H-tetrazol-1-ylacetyl)pyrrolidin-3-yl]-1,3-dimethylurea By reaction and purification in the same manner as in the method described in Example 4 and using the compound obtained in Example 144 and 1H-tetrazol-1-ylacetic acid, the title compound was obtained.

MS(ESI+): 574 (M+H)

Example 214

1-[3,5-bis(trifluoromethyl)phenyl]-3-[(3S,4R)-1-(5-cyanopyridin-2-yl)-4-(4-fluorophenyl)pyrrolidin-3-yl]-1,3-dimethylurea By reaction and purification in the same manner as in the method described in Example 125 and using the compound obtained in Example 144, the title compound was obtained.

MS(ESI+): 566 (M+H)

Example 215

(3S,4R)-3-[{[3,5-bis(trifluoromethyl)phenyl](methyl)carbamoyl}(methyl)amino]-N-ethyl-4-(4-fluorophenyl)pyrrolidine-1-carboxamide By reaction and purification in the same manner as in the method described in Example 1 and using the compound obtained in Example 144 and ethyl isocyanate, the title compound was obtained.

MS(ESI+): 535 (M+H)

Example 216 tetrahydro-2H-pyran-4-yl (3S,4R)-3-[{[3,5-bis(trifluoromethyl)phenyl](methyl)carbamoyl}(methyl)amino]-4-(4-fluorophenyl)pyrrolidine-1-carboxylate A mixture of the compound (0.20 g) obtained in Example 144, tetrahydro-2H-pyran-4-yl 4-nitrophenyl carbonate (0.21 g), potassium carbonate (0.17 g) and DMF (6.0 mL) was stirred at 60° C. for 8 hr, and then at room temperature for 4 days. The mixture was diluted with water, and extracted with ethyl acetate. The extract was washed with water and saturated brine, dried and concentrated under reduced pressure. The residue was separated and purified by silica gel column chromatography (NH Chromatorex) (solvent gradient; 0→60% ethyl acetate/hexane) to give the title compound (0.23 g, 96%) as a white powder.

MS(ESI+): 592 (M+H)

Example 217 tert-butyl 4-[(3S,4R)-3-[{[3,5-bis(trifluoromethyl)phenyl](methyl)carbamoyl}(methyl)amino]-4-(4-fluorophenyl)pyrrolidin-1-yl]piperidine-1-carboxylate By reaction and purification in the same manner as in the method described in Example 80 and using the compound obtained in Example 144, the title compound was obtained.

MS(ESI+): 647 (M+H)

Example 218 tert-butyl 4-{[(3S,4R)-3-[{[3,5-bis(trifluoromethyl)phenyl](methyl)carbamoyl}(methyl)amino]-4-(4-fluorophenyl)pyrrolidin-1-yl]methyl}piperidine-1-carboxylate By reaction and purification in the same manner as in the method described in Example 80 and using the compound obtained in Example 144 and tert-butyl 4-formylpiperidine-1-carboxylate, the title compound was obtained.

MS(ESI+): 661 (M+H)

Example 219

1-[3,5-bis(trifluoromethyl)phenyl]-3-[(3S,4R)-4-(4-fluorophenyl)-1-(piperidin-4-ylmethyl)pyrrolidin-3-yl]-1,3-dimethylurea dihydrochloride By reaction and purification in the same manner as in the method described in Example 3 and using the compound obtained in Example 218, the title compound was obtained.

MS(ESI+): 561 (M−2HCl+H)

Example 220

1-[(3S,4R)-1-[(1-acetylpiperidin-4-yl)methyl]-4-(4-fluorophenyl)pyrrolidin-3-yl]-3-[3,5-bis(trifluoromethyl)phenyl]-1,3-dimethylurea By reaction and purification in the same manner as in the method described in Example 75 and using the compound obtained in Example 219, the title compound was obtained.
MS(ESI+): 603 (M+H)

Example 221

1-[3,5-bis(trifluoromethyl)phenyl]-3-{(3S,4R)-4-(4-fluorophenyl)-1-[(1-methyl-6-oxopiperidin-3-yl)carbonyl]pyrrolidin-3-yl}-1,3-dimethylurea By reaction and purification in the same manner as in the method described in Example 4 and using the compound obtained in Example 144 and 1-methyl-6-oxopiperidine-3-carboxylic acid, the title compound was obtained.
MS(ESI+): 603 (M+H)

Example 222

1-[3,5-bis(trifluoromethyl)phenyl]-3-[(3S,4R)-4-(4-fluorophenyl)-1-(tetrahydro-2H-thiopyran-4-ylcarbonyl)pyrrolidin-3-yl]-1,3-dimethylurea By reaction and purification in the same manner as in the method described in Example 4 and using the compound obtained in Example 144 and tetrahydro-2H-thiopyran-4-carboxylic acid, the title compound was obtained.
MS(ESI+): 592 (M+H)

Example 223

1-[3,5-bis(trifluoromethyl)phenyl]-3-{(3S,4R)-4-(4-fluorophenyl)-1-[(1-oxidetetrahydro-2H-thiopyran-4-yl)carbonyl]pyrrolidin-3-yl}-1,3-dimethylurea By reaction and purification in the same manner as in the method described in Example 127 and using the compound obtained in Example 222, the title compound was obtained.
MS(ESI+): 608 (M+H)

Example 224

1-[3,5-bis(trifluoromethyl)phenyl]-3-[(3S,4R)-1-[(1,1-dioxidetetrahydro-2H-thiopyran-4-yl)carbonyl]-4-(4-fluorophenyl)pyrrolidin-3-yl]-1,3-dimethylurea By reaction and purification in the same manner as in the method described in Example 128 and using the compound obtained in Example 222, the title compound was obtained.
MS(ESI+): 624 (M+H)

Example 225

1-[3,5-bis(trifluoromethyl)phenyl]-3-[(3S,4R)-4-(4-fluorophenyl)-1-(tetrahydro-2H-pyran-4-ylcarbonyl)pyrrolidin-3-yl]-1,3-dimethylurea By reaction and purification in the same manner as in the method described in Example 4 and using the compound obtained in Example 144 and tetrahydro-2H-pyran-4-carboxylic acid, the title compound was obtained.
MS(ESI+): 576 (M+H)

Example 226

1-[3,5-bis(trifluoromethyl)phenyl]-3-[(3S,4R)-1-[(4,4-difluorocyclohexyl)carbonyl]-4-(4-fluorophenyl)pyrrolidin-3-yl]-1,3-dimethylurea By reaction and purification in the same manner as in the method described in Example 4 and using the compound obtained in Example 144 and 4,4-difluorocyclohexanecarboxylic acid, the title compound was obtained.
MS(ESI+): 610 (M+H)

Example 227 tert-butyl 4-{2-[(3S,4R)-3-[{[3,5-bis(trifluoromethyl)phenyl](methyl)carbamoyl}(methyl)amino]-4-(4-fluorophenyl)pyrrolidin-1-yl]-2-oxoethyl}piperidine-1-carboxylate By reaction and purification in the same manner as in the method described in Example 4 and using the compound obtained in Example 144 and [1-(tert-butoxycarbonyl)piperidin-4-yl]acetic acid, the title compound was obtained.
MS(ESI+): 589 (M−Boc+2H)

Example 228

1-[3,5-bis(trifluoromethyl)phenyl]-3-[(3S,4R)-4-(4-fluorophenyl)-1-(piperidin-4-ylacetyl)pyrrolidin-3-yl]-1,3-dimethylurea monohydrochloride By reaction and purification in the same manner as in the method described in Example 3 and using the compound obtained in Example 227, the title compound was obtained.
MS(ESI+): 589 (M−HCl+H)

Example 229

1-[(3S,4R)-1-[(1-acetylpiperidin-4-yl)acetyl]-4-(4-fluorophenyl)pyrrolidin-3-yl]-3-[3,5-bis(trifluoromethyl)phenyl]-1,3-dimethylurea By reaction and purification in the same manner as in the method described in Example 75 and using the compound obtained in Example 228, the title compound was obtained.
MS(ESI+): 631 (M+H)

Example 230 tert-butyl (trans-4-{[(3S,4R)-3-[{[3,5-bis(trifluoromethyl)phenyl](methyl)carbamoyl}(methyl)amino]-4-(4-fluorophenyl)pyrrolidin-1-yl]carbonyl}cyclohexyl)carbamate By reaction and purification in the same manner as in the method described in Example 4 and using the compound obtained in Example 144 and trans-4-[(tert-butoxycarbonyl)amino]cyclohexanecarboxylic acid, the title compound was obtained.
MS(ESI+): 633 (M−$^t$Bu+2H)

Example 231

1-[(3S,4R)-1-[(trans-4-aminocyclohexyl)carbonyl]-4-(4-fluorophenyl)pyrrolidin-3-yl]-3-[3,5-bis(trifluoromethyl)phenyl]-1,3-dimethylurea monohydrochloride By reaction and purification in the same manner as in the method described in Example 3 and using the compound obtained in Example 230, the title compound was obtained.
MS(ESI+): 589 (M−HCl+H)

Example 232

N-(trans-4-{[(3S,4R)-3-[{[3,5-bis(trifluoromethyl)phenyl](methyl)carbamoyl}(methyl)amino]-4-(4-fluorophenyl)pyrrolidin-1-yl]carbonyl}cyclohexyl)benzamide By reaction and purification in the same manner as in the method described in Example 75 and using the compound obtained in Example 231 and benzoyl chloride, the title compound was obtained.
MS(ESI+): 693 (M+H)

Example 233 methyl (trans-4-{[(3S,4R)-3-[{[3,5-bis(trifluoromethyl)phenyl](methyl)carbamoyl}(methyl)amino]-4-(4-fluorophenyl)pyrrolidin-1-yl]carbonyl}cyclohexyl)carbamate By reaction and purification in the same manner as in the method described in Example 75 and using the compound obtained in Example 231 and methyl chlorocarbonate, the title compound was obtained.
MS(ESI+): 647 (M+H)

Example 234

1-[3,5-bis(trifluoromethyl)phenyl]-3-[(3S,4R)-4-(4-fluorophenyl)-1-{[trans-4-(2-oxopyrrolidin-1-yl)cyclohexyl]carbonyl}pyrrolidin-3-yl]-1,3-dimethylurea (Step 1)
By reaction and purification in the same manner as in the method described in Example 75 and using the compound obtained in Example 231 and 4-chlorobutanoyl chloride, N-(trans-4-{[(3S,4R)-3-[{[3,5-bis(trifluoromethyl)phenyl](methyl)carbamoyl}(methyl)amino]-4-(4-fluorophenyl)pyrrolidin-1-yl]carbonyl}cyclohexyl)-4-chlorobutanamide was obtained.
MS(ESI+): 693 (M+H)

(Step 2)
To a solution of the compound (0.2 g) obtained in step 1 in DMF (5.6 mL) was added sodium hydride (0.017 g) at 0° C., and the mixture was stirred at room temperature for 6 hr. To the mixture was added sodium hydride (0.017 g), and the mixture was stirred at room temperature for 12 hr, and sodium hydride (0.017 g) was further added. The mixture was stirred at room temperature for 6 hr, diluted with water and extracted with ethyl acetate. The extract was washed with 1N hydrochloric acid, water and saturated brine, dried and concentrated under reduced pressure. The residue was separated and purified by silica gel column chromatography (solvent gradient; 0→10% methanol/ethyl acetate) to give the title compound (0.14 g, 76%) as a white powder.
MS(ESI+): 657 (M+H)

Example 235

1-[3,5-bis(trifluoromethyl)phenyl]-3-[(3S,4R)-4-(4-fluorophenyl)-1-{[trans-4-(2-oxo-1,3-oxazolidin-3-yl)cyclohexyl]carbonyl}pyrrolidin-3-yl]-1,3-dimethylurea (Step 1)
By reaction and purification in the same manner as in the method described in Example 75 and using the compound obtained in Example 231 and 2-chloroethyl chlorocarbonate, 2-chloroethyl (trans-4-{[(3S,4R)-3-[{[3,5-bis(trifluoromethyl)phenyl](methyl)carbamoyl}(methyl)amino]-4-(4-fluorophenyl)pyrrolidin-1-yl]carbonyl}cyclohexyl)carbamate was obtained.
MS(ESI+): 695 (M+H)

(Step 2)
To a solution of the compound (0.19 g) obtained in step 1 in DMF (5.0 mL) was added sodium hydride (0.022 g) at 0° C., and the mixture was stirred at room temperature for 4 days. The mixture was diluted with water, and extracted with ethyl acetate. The extract was washed with 1N hydrochloric acid, water and saturated brine, dried and concentrated under reduced pressure. The residue was separated and purified by silica gel column chromatography (NH Chromatorex) (solvent gradient; 10→100% ethyl acetate/hexane) to give the title compound (0.12 g, 65%) as a white powder.
MS(ESI+): 659 (M+H)

Example 236

N-(trans-4-{[(3S,4R)-3-[{[3,5-bis(trifluoromethyl)phenyl](methyl)carbamoyl}(methyl)amino]-4-(4-fluorophenyl)pyrrolidin-1-yl]carbonyl}cyclohexyl)-2-methylpropanamide By reaction and purification in the same manner as in the method described in Example 75 and using the compound obtained in Example 231 and isobutyryl chloride, the title compound was obtained.
MS(ESI+): 659 (M+H)

Example 237

2-methylpropyl(trans-4-{[(3S,4R)-3-[{[3,5-bis(trifluoromethyl)phenyl](methyl)carbamoyl}(methyl)amino]-4-(4-fluorophenyl)pyrrolidin-1-yl]carbonyl}cyclohexyl)carbamate By reaction and purification in the same manner as in the method described in Example 75 and using the compound obtained in Example 231 and isobutyl chloroformate, the title compound was obtained.
MS(ESI+): 689 (M+H)

Example 238

N-(trans-4-{[(3S,4R)-3-[{[3,5-bis(trifluoromethyl)phenyl](methyl)carbamoyl}(methyl)amino]-4-(4-fluorophenyl)pyrrolidin-1-yl]carbonyl}cyclohexyl)-2-hydroxy-2-methylpropanamide By reaction and purification in the same manner as in the method described in Example 4 and using the compound obtained in Example 231 and 2-hydroxyisobutyric acid, the title compound was obtained.
MS(ESI+): 675 (M+H)

Example 239 tert-butyl (trans-4-{[(3S,4R)-3-[{[3,5-bis(trifluoromethyl)phenyl](methyl)carbamoyl}(methyl)amino]-4-(4-fluorophenyl)pyrrolidin-1-yl]carbonyl}cyclohexyl)(methyl)carbamate By reaction and purification in the same manner as in the method described in Example 2 and using the compound obtained in Example 230, the title compound was obtained.
MS(ESI+): 647 (M−ᵗBu+2H)

Example 240

1-[3,5-bis(trifluoromethyl)phenyl]-3-[(3S,4R)-4-(4-fluorophenyl)-1-{[trans-4-(methylamino)cyclohexyl]carbonyl}pyrrolidin-3-yl]-1,3-dimethylurea monohydrochloride By reaction and purification in the same manner as in the method described in Example 3 and using the compound obtained in Example 239, the title compound was obtained.
MS(ESI+): 603 (M−HCl+H)

Example 241 methyl (trans-4-{[(3S,4R)-3-[{[3,5-bis(trifluoromethyl)phenyl](methyl)carbamoyl}(methyl)amino]-4-(4-fluorophenyl)pyrrolidin-1-yl]carbonyl}cyclohexyl)(methyl) carbamate By reaction and purification in the same manner as in the method described in Example 75 and using the compound obtained in Example 240 and methyl chlorocarbonate, the title compound was obtained.
MS(ESI+): 661 (M+H)

Example 242

N-(trans-4-{[(3S,4R)-3-[{[3,5-bis(trifluoromethyl)phenyl](methyl)carbamoyl}(methyl)amino]-4-(4-fluorophenyl)pyrrolidin-1-yl]carbonyl}cyclohexyl)methanesulfonamide By reaction and purification in the same manner as in the method described in Example 75 and using the compound obtained in Example 231 and methanesulfonyl chloride, the title compound was obtained.
MS(ESI+): 667 (M+H)

Example 243

N-(trans-4-{[(3S,4R)-3-[{[3,5-bis(trifluoromethyl)phenyl](methyl)carbamoyl}(methyl)amino]-4-(4-fluorophenyl)pyrrolidin-1-yl]carbonyl}cyclohexyl)-N-methylmethanesulfonamide To a solution of the compound (0.23 g) obtained in Example 242 in DMF (7.0 mL) were added potassium tert-butoxide (0.079 g) and methyl iodide (0.055 mL) at 0° C. The mixture was stirred at room temperature for 12 hr, diluted with ice water, and extracted with ethyl acetate. The extract was washed with water, 1N aqueous potassium hydrogen sulfate solution and saturated brine, dried and concentrated under reduced pressure. The residue was separated and purified by silica gel column chromatography (solvent gradient; 50→100% ethyl acetate/hexane) to give the title compound (0.17 g, 70%) as a white powder.
MS(ESI+): 681 (M+H)

Example 244

1-[3,5-bis(trifluoromethyl)phenyl]-3-[(3S,4R)-1-{[trans-4-(1,1-dioxideisothiazolidin-2-yl)cyclohexyl]carbonyl}-4-(4-fluorophenyl)pyrrolidin-3-yl]-1,3-dimethylurea (Step 1)

By reaction and purification in the same manner as in the method described in Reference Example 75 and using the compound obtained in Example 231 and 3-chloropropane-1-sulfonyl chloride, N-(trans-4-{[(3S,4R)-3-[{[3,5-bis(trifluoromethyl)phenyl](methyl)carbamoyl}(methyl)amino]-4-(4-fluorophenyl)pyrrolidin-1-yl]carbonyl}cyclohexyl)-3-chloropropane-1-sulfonamide was obtained.
MS(ESI+): 729 (M+H)

(Step 2)

To a solution of the compound (0.29 g) obtained in step 1 in DMF (6.0 mL) was added potassium tert-butoxide (0.090 g) at 0° C., and the mixture was stirred at room temperature for 12 hr. The mixture was diluted with ice water, and extracted with ethyl acetate. The extract was washed with water, 1N hydrochloric acid, water and saturated brine, dried and concentrated under reduced pressure. The residue was separated and purified by silica gel column chromatography (solvent gradient; 10→100% ethyl acetate/hexane) to give the title compound (0.21 g, 75%) as a white powder.
MS(ESI+): 693 (M+H)

Example 245

N-(trans-4-{[(3S,4R)-3-[{[3,5-bis(trifluoromethyl)phenyl](methyl)carbamoyl}(methyl)amino]-4-(4-fluorophenyl)pyrrolidin-1-yl]carbonyl}cyclohexyl)-2-hydroxyacetamide By reaction and purification in the same manner as in the method described in Example 4 and using the compound obtained in Example 231 and glycolic acid, the title compound was obtained.
MS(ESI+): 647 (M+H)

Example 246

N-(trans-4-{[(3S,4R)-3-[{[3,5-bis(trifluoromethyl) phenyl](methyl)carbamoyl}(methyl)amino]-4-(4-fluorophenyl)pyrrolidin-1-yl]carbonyl}cyclohexyl) cyclopropanecarboxamide By reaction and purification in the same manner as in the method described in Example 4 and using the compound obtained in Example 231 and cyclopropanecarboxylic acid, the title compound was obtained.
MS(ESI+): 657 (M+H)

Example 247

N-(trans-4-{[(3S,4R)-3-[{[3,5-bis(trifluoromethyl) phenyl](methyl)carbamoyl}(methyl)amino]-4-(4-fluorophenyl)pyrrolidin-1-yl]carbonyl}cyclohexyl)-2-methoxyacetamide By reaction and purification in the same manner as in the method described in Example 4 and using the compound obtained in Example 231 and methoxyacetic acid, the title compound was obtained.
MS(ESI+): 661 (M+H)

Example 248

N-(trans-4-{[(3S,4R)-3-[{[3,5-bis(trifluoromethyl) phenyl](methyl)carbamoyl}(methyl)amino]-4-(4-fluorophenyl)pyrrolidin-1-yl]carbonyl}cyclohexyl)-2,2-dimethylpropanamide To a solution of the compound (0.20 g) obtained in Example 231 and triethylamine (0.11 mL) in THF (5 mL) was added pivaloyl chloride (0.060 mL), and the mixture was stirred at room temperature for 14 hr. The reaction mixture was poured into water, and the mixture was extracted with ethyl acetate. The extract was washed with saturated aqueous ammonium chloride solution, water and saturated brine, dried and concentrated under reduced pressure. The residue was purified by silica gel column chromatography (solvent gradient; 0→5% methanol/ethyl acetate) to give the title compound (0.21 g, 95%) as a white powder.
MS(ESI+): 673 (M+H)

Example 249

N-(trans-4-{[(3S,4R)-3-[{3,5-bis(trifluoromethyl) phenyl](methyl)carbamoyl}(methyl)amino]-4-(4-fluorophenyl)pyrrolidin-1-yl]carbonyl}cyclohexyl) propanamide By reaction and purification in the same manner as in the method described in Example 248 and using the compound obtained in Example 231 and propionyl chloride, the title compound was obtained.
MS(ESI+): 645 (M+H)

Example 250

N-(trans-4-{[(3S,4R)-3-[{[3,5-bis(trifluoromethyl) phenyl](methyl)carbamoyl}(methyl)amino]-4-(4-fluorophenyl)pyrrolidin-1-yl]carbonyl}cyclohexyl)-3-fluoropyridine-2-carboxamide By reaction and purification in the same manner as in the method described in Example 4 and using the compound obtained in Example 231 and 3-fluoropyridine-2-carboxylic acid, the title compound was obtained.
MS(ESI+): 712 (M+H)

Example 251

N-(trans-4-{[(3S,4R)-3-[{[3,5-bis(trifluoromethyl) phenyl](methyl)carbamoyl}(methyl)amino]-4-(4-fluorophenyl)pyrrolidin-1-yl]carbonyl}cyclohexyl)-2-methylpyridine-4-carboxamide By reaction and purification in the same manner as in the method described in Example 4 and using the compound obtained in Example 231 and 2-methylisonicotinic acid, the title compound was obtained.
MS(ESI+): 708 (M+H)

Example 252

N-(trans-4-{[(3S,4R)-3-[{[3,5-bis(trifluoromethyl) phenyl](methyl)carbamoyl}(methyl)amino]-4-(4-fluorophenyl)pyrrolidin-1-yl]carbonyl}cyclohexyl) pyridine-2-carboxamide By reaction and purification in the same manner as in the method described in Example 248 and using the compound obtained in Example 231 and picolinoyl chloride hydrochloride, the title compound was obtained.
MS(ESI+): 694 (M+H)

Example 253

N-(trans-4-{[(3S,4R)-3-[{[3,5-bis(trifluoromethyl) phenyl](methyl)carbamoyl}(methyl)amino]-4-(4-fluorophenyl)pyrrolidin-1-yl]carbonyl}cyclohexyl) cyclobutanecarboxamide By reaction and purification in the same manner as in the method described in Example 4 and using the compound obtained in Example 231 and cyclobutanecarboxylic acid, the title compound was obtained.
MS(ESI+): 671 (M+H)

Example 254

N-(trans-4-{[(3S,4R)-3-[{[3,5-bis(trifluoromethyl) phenyl](methyl)carbamoyl}(methyl)amino]-4-(4-fluorophenyl)pyrrolidin-1-yl]carbonyl}cyclohexyl)-N-methylacetamide By reaction and purification in the same manner as in the method described in Example 2 and using the compound obtained in Example 210, the title compound was obtained.
MS(ESI+): 645 (M+H)

Example 255

N-(trans-4-{[(3S,4R)-3-[{[3,5-bis(trifluoromethyl) phenyl](methyl)carbamoyl}(methyl)amino]-4-(4-fluorophenyl)pyrrolidin-1-yl]carbonyl}cyclohexyl)-4,4-difluorocyclohexanecarboxamide By reaction and purification in the same manner as in the method described in Example 4 and using the compound obtained in Example 231 and 4,4-difluorocyclohexanecarboxylic acid, the title compound was obtained.
MS(ESI+): 735 (M+H)

Example 256 tetrahydro-2H-pyran-4-yl(trans-4-{[(3S,4R)-3-[{[3,5-bis(trifluoromethyl)phenyl](methyl)carbamoyl}(methyl)amino]-4-(4-fluorophenyl)pyrrolidin-1-yl]carbonyl}cyclohexyl)carbamate By reaction and purification in the same manner as in the method described in Example 216 and using the compound obtained in Example 231, the title compound was obtained.
MS(ESI+): 717 (M+H)

Example 257 ethyl (trans-4-{[(3S,4R)-3-[{[3,5-bis(trifluoromethyl)phenyl](methyl)carbamoyl}(methyl)amino]-4-(4-fluorophenyl)pyrrolidin-1-yl]carbonyl}cyclohexyl)carbamate By reaction and purification in the same manner as in the method described in Example 75 and using the compound obtained in Example 231 and ethyl chlorocarbonate, the title compound was obtained.
MS(ESI+): 661 (M+H)

Example 258

1-methylethyl(trans-4-{[(3S,4R)-3-[{[3,5-bis(trifluoromethyl)phenyl](methyl)carbamoyl}(methyl)amino]-4-(4-fluorophenyl)pyrrolidin-1-yl]carbonyl}cyclohexyl)carbamate By reaction and purification in the same manner as in the method described in Example 75 and using the compound obtained in Example 231 and 1-methylethyl chlorocarbonate, the title compound was obtained.
MS(ESI+): 675 (M+H)

Example 259

1-[3,5-bis(trifluoromethyl)phenyl]-3-[(3S,4R)-1-({trans-4-[(ethylcarbamoyl)amino]cyclohexyl}carbonyl)-4-(4-fluorophenyl)pyrrolidin-3-yl]-1,3-dimethylurea By reaction and purification in the same manner as in the method described in Example 1 and using the compound obtained in Example 231 and ethyl isocyanate, the title compound was obtained.
MS(ESI+): 660 (M+H)

Example 260

1-[3,5-bis(trifluoromethyl)phenyl]-3-[(3S,4R)-1-({trans-4-[(cyclopropylcarbamoyl)amino]cyclohexyl}carbonyl)-4-(4-fluorophenyl)pyrrolidin-3-yl]-1,3-dimethylurea The compound (0.20 g) obtained in Example 231 was dissolved in THF, 4-nitrophenyl chlorocarbonate (0.077 mL) and N,N-diisopropylethylamine (0.14 mL) were added at room temperature. The reaction mixture was stirred at room temperature overnight, cyclopropylamine (0.027 mL) was added, and the mixture was stirred at room temperature for 2 hr. The reaction mixture was diluted with ethyl acetate, and washed with water and saturated brine, dried and concentrated under reduced pressure. The residue was purified by silica gel column chromatography (solvent gradient; 0→10% methanol/ethyl acetate) to give the title compound (0.20 g, 91%) as a white powder.
MS(ESI+): 672 (M+H)

Example 261

4-nitrophenyl(trans-4-{[(3S,4R)-3-[{[3,5-bis(trifluoromethyl)phenyl](methyl)carbamoyl}(methyl)amino]-4-(4-fluorophenyl)pyrrolidin-1-yl]carbonyl}cyclohexyl)carbamate By reaction and purification in the same manner as in the method described in Example 75 and using the compound obtained in Example 231 and 4-nitrophenyl chlorocarbonate, the title compound was obtained.
MS(ESI+): 754 (M+H)

Example 262

1-[3,5-bis(trifluoromethyl)phenyl]-3-[(3S,4R)-1-[(trans-4-{[ethyl(methyl)carbamoyl]amino}cyclohexyl)carbonyl]-4-(4-fluorophenyl)pyrrolidin-3-yl]-1,3-dimethylurea A solution of the compound (0.20 g) obtained in Example 261 and N-methylethanamine (0.11 mL) in acetonitrile (2.7 mL) was stirred at room temperature for 3 hr. The reaction mixture was diluted with ethyl acetate, washed with water, saturated aqueous sodium hydrogen carbonate solution, saturated aqueous ammonium chloride solution and saturated brine, dried and concentrated under reduced pressure. The residue was purified by silica gel column chromatography (solvent gradient; 80→100% ethyl acetate/hexane) to give the title compound (0.15 g, 83%) as a white powder.
MS(ESI+): 674 (M+H)

Example 263

1-[3,5-bis(trifluoromethyl)phenyl]-3-[(3S,4R)-1-[(trans-4-{[ethyl(methyl)carbamoyl](methyl)amino}cyclohexyl)carbonyl]-4-(4-fluorophenyl)pyrrolidin-3-yl]-1,3-dimethylurea By reaction and purification in the same manner as in the method described in Example 2 and using the compound obtained in Example 259, the title compound was obtained.
MS(ESI+): 688 (M+H)

Example 264

1-[3,5-bis(trifluoromethyl)phenyl]-3-{(3S,4R)-4-(4-fluorophenyl)-1-[(trans-4-(morpholin-4-yl)cyclohexyl)carbonyl]pyrrolidin-3-yl}-1,3-dimethylurea A mixture of the compound (0.22 g) obtained in Example 231, 1,1'-oxybis(2-bromoethane) (0.046 mL), potassium carbonate (0.19 g) and DMF (6.0 mL) was stirred at 60° C. for 6 hr. The mixture was diluted with water, and extracted with ethyl acetate. The extract was washed with water and saturated brine, dried and concentrated under reduced pressure. The residue was separated and purified by silica gel column chromatography (NH Chromatorex) (solvent gradient; 5→100% ethyl acetate/hexane) to give the title compound (0.098 g, 43%) as a white powder.
MS(ESI+): 659 (M+H)

Example 265 tert-butyl (cis-4-{[(3S,4R)-3-[{[3,5-bis(trifluoromethyl)phenyl](methyl)carbamoyl}(methyl)amino]-4-(4-fluorophenyl)pyrrolidin-1-yl]carbonyl}cyclohexyl)carbamate By reaction and purification in the same manner as in the method described in Example 4 and using the compound obtained in Example 144 and cis-4-[(tert-butoxycarbonyl)amino]cyclohexanecarboxylic acid, the title compound was obtained.
MS(ESI+): 689 (M+H)

Example 266

1-[(3S,4R)-1-[(cis-4-aminocyclohexyl)carbonyl]-4-(4-fluorophenyl)pyrrolidin-3-yl]-3-[3,5-bis(trifluoromethyl)phenyl]-1,3-dimethylurea monohydrochloride By reaction and purification in the same manner as in the method described in Example 3 and using the compound obtained in Example 265, the title compound was obtained.
MS(ESI+): 589 (M−HCl+H)

Example 267

N-(cis-4-{[(3S,4R)-3-[{[3,5-bis(trifluoromethyl)phenyl](methyl)carbamoyl}(methyl)amino]-4-(4-fluorophenyl)pyrrolidin-1-yl]carbonyl}cyclohexyl)acetamide By reaction and purification in the same manner as in the method described in Example 75 and using the compound obtained in Example 266, the title compound was obtained.
MS(ESI+): 631 (M+H)

Example 268 methyl (cis-4-{[(3S,4R)-3-[{[3,5-bis(trifluoromethyl)phenyl](methyl)carbamoyl}(methyl)amino]-4-(4-fluorophenyl)pyrrolidin-1-yl]carbonyl}cyclohexyl)carbamate By reaction and purification in the same manner as in the method described in Example 75 and using the compound obtained in Example 266 and methyl chlorocarbonate, the title compound was obtained.
MS(ESI+): 647 (M+H)

Example 269

1-[3,5-bis(trifluoromethyl)phenyl]-3-[(3S,4R)-1-{[trans-4-(5,5-dimethyl-2,4-dioxo-1,3-oxazolidin-3-yl)cyclohexyl]carbonyl}-4-(4-fluorophenyl)pyrrolidin-3-yl]-1,3-dimethylurea By reaction and purification in the same manner as in the method described in Example 4 and using the compound obtained in Example 144 and the compound obtained in Reference Example 36, the title compound was obtained.
MS(ESI+): 701 (M+H)

Example 270

1-[3,5-bis(trifluoromethyl)phenyl]-3-[(3S,4R)-1-{[trans-4-(2,4-dioxo-1,3-oxazolidin-3-yl)cyclohexyl]carbonyl}-4-(4-fluorophenyl)pyrrolidin-3-yl]-1,3-dimethylurea By reaction and purification in the same manner as in the method described in Example 4 and using the compound obtained in Example 144 and the compound obtained in Reference Example 37, the title compound was obtained.
MS(ESI+): 673 (M+H)

Example 271

1-[3,5-bis(trifluoromethyl)phenyl]-3-[(3S,4R)-1-{[trans-4-(2,5-dioxoimidazolidin-1-yl)cyclohexyl]carbonyl}-4-(4-fluorophenyl)pyrrolidin-3-yl]-1,3-dimethylurea By reaction and purification in the same manner as in the method described in Example 4 and using the compound obtained in Example 144 and the compound obtained in Reference Example 38, the title compound was obtained.
MS(ESI+): 672 (M+H)

Example 272

1-[3,5-bis(trifluoromethyl)phenyl]-3-[(3S,4R)-4-(4-fluorophenyl)-1-{[trans-4-(1H-tetrazol-1-yl)cyclohexyl]carbonyl}pyrrolidin-3-yl]-1,3-dimethylurea By reaction and purification in the same manner as in the method described in Example 4 and using the compound obtained in Example 144 and the compound obtained in Reference Example 39, the title compound was obtained.
MS(ESI+): 642 (M+H)

Example 273

1-[3,5-bis(trifluoromethyl)phenyl]-3-[(3S,4R)-4-(4-fluorophenyl)-1-({trans-4-[5-(trifluoromethyl)-1H-tetrazol-1-yl]cyclohexyl}carbonyl)pyrrolidin-3-yl]-1,3-dimethylurea By reaction and purification in the same manner as in the method described in Example 4 and using the compound obtained in Example 144 and the compound obtained in Reference Example 40, the title compound was obtained.
MS(ESI+): 710 (M+H)

Example 274

1-[3,5-bis(trifluoromethyl)phenyl]-3-[(3S,4R)-4-(4-fluorophenyl)-1-({cis-4-[5-(trifluoromethyl)-1H-tetrazol-1-yl]cyclohexyl}carbonyl)pyrrolidin-3-yl]-1,3-dimethylurea (Step 1)

To a mixture of the compound (0.27 g) obtained in Example 266, triphenylphosphine (0.37 g), trifluoroacetic acid (0.035 mL) and carbon tetrachloride (8.0 mL) was added triethylamine (0.14 mL) at room temperature. The mixture was heated under reflux for 24 hr, and concentrated under reduced pressure. The residue was diluted with saturated aqueous sodium hydrogen carbonate solution, and extracted with ethyl acetate. The extract was washed with saturated brine, dried and concentrated under reduced pressure. To the residue were added carbon tetrachloride (8.0 mL) and triphenylphosphine (0.17 g), and the mixture was heated under reflux for 6 hr. Triphenylphosphine (0.17 g) was added again, and the mixture was heated under reflux for 12 hr. The mixture was concentrated under reduced pressure, and the residue was diluted with ethyl acetate, and filtered through silica gel (eluted with ethyl acetate/hexane=1:1). The filtrate was concentrated under reduced pressure, and the residue was purified by silica gel column chromatography (NH Chromatorex) (solvent gradient; 10→50% ethyl acetate/hexane) to give N-(cis-4-{[(3S,4R)-3-[{[3,5-bis(trifluoromethyl)phenyl](methyl)carbamoyl}(methyl)amino]-4-(4-fluorophenyl)pyrrolidin-1-yl]carbonyl}cyclohexyl)-2,2,2-trifluoroethanimidyl chloride (0.22 g, 74%) as a white powder.

MS(ESI+): 703 (M+H)

(Step 2)

To a solution of the compound (0.22 g) obtained in step 1 in DMF (5.0 mL) was added sodium azide (0.027 g), and the mixture was stirred at room temperature for 2.5 hr. The mixture was diluted with ethyl acetate, and washed with water and saturated brine, dried and concentrated under reduced pressure. The residue was purified by silica gel column chromatography (NH Chromatorex) (solvent gradient; 0→60% ethyl acetate/hexane) to give the title compound (0.20 g, 89%) as a white powder.

MS(ESI+): 710 (M+H)

Example 275

1-[3,5-bis(trifluoromethyl)phenyl]-3-[(3S,4R)-4-(4-fluorophenyl)-1-{[trans-4-(trifluoromethyl)cyclohexyl]carbonyl}pyrrolidin-3-yl]-1,3-dimethylurea By reaction and purification in the same manner as in the method described in Example 4 and using the compound obtained in Example 144 and trans-4-(trifluoromethyl)cyclohexanecarboxylic acid, the title compound was obtained.

MS(ESI+): 642 (M+H)

Example 276

1-[3,5-bis(trifluoromethyl)phenyl]-3-{(3S,4R)-4-(4-fluorophenyl)-1-[(4-fluorophenyl)carbonyl]pyrrolidin-3-yl}-1,3-dimethylurea By reaction and purification in the same manner as in the method described in Example 4 and using the compound obtained in Example 144 and 4-fluorobenzoic acid, the title compound was obtained.

MS(ESI+): 586 (M+H)

Example 277

N-(4-{[(3S,4R)-3-[{[3,5-bis(trifluoromethyl)phenyl](methyl)carbamoyl}(methyl)amino]-4-(4-fluorophenyl)pyrrolidin-1-yl]carbonyl}phenyl)acetamide By reaction and purification in the same manner as in the method described in Example 4 and using the compound obtained in Example 144 and 4-(acetylamino)benzoic acid, the title compound was obtained.

MS(ESI+): 625 (M+H)

Example 278

1-[3,5-bis(trifluoromethyl)phenyl]-3-[(3S,4R)-4-(4-fluorophenyl)-1-(pyridin-2-ylcarbonyl)pyrrolidin-3-yl]-1,3-dimethylurea By reaction and purification in the same manner as in the method described in Example 4 and using the compound obtained in Example 144 and pyridine-2-carboxylic acid, the title compound was obtained.

MS(ESI+): 569 (M+H)

Example 279

1-[3,5-bis(trifluoromethyl)phenyl]-3-[(3S,4R)-4-(4-fluorophenyl)-1-(pyrimidin-5-ylcarbonyl)pyrrolidin-3-yl]-1,3-dimethylurea By reaction and purification in the same manner as in the method described in Example 4 and using the compound obtained in Example 144 and pyrimidine-5-carboxylic acid, the title compound was obtained.

MS(ESI+): 570 (M+H)

Example 280

1-[3,5-bis(trifluoromethyl)phenyl]-3-[(3S,4R)-4-(4-fluorophenyl)-1-(1,3-thiazol-2-ylcarbonyl)pyrrolidin-3-yl]-1,3-dimethylurea By reaction and purification in the same manner as in the method described in Example 4 and using the compound obtained in Example 144 and 1,3-thiazole-2-carboxylic acid, the title compound was obtained.

MS(ESI+): 575 (M+H)

Example 281

1-[3,5-bis(trifluoromethyl)phenyl]-3-[(3S,4R)-4-(4-fluorophenyl)-1-({4-[5-(trifluoromethyl)-1H-tetrazol-1-yl]phenyl}carbonyl)pyrrolidin-3-yl]-1,3-dimethylurea By reaction and purification in the same manner as in the method described in Example 4 and using the compound obtained in Example 144 and the compound obtained in Reference Example 41, the title compound was obtained.

MS(ESI+): 704 (M+H)

Example 282 tert-butyl [(trans-4-{[(3S,4R)-3-[{[3,5-bis(trifluoromethyl)phenyl](methyl)carbamoyl}(methyl)amino]-4-(4-fluorophenyl)pyrrolidin-1-yl]carbonyl}cyclohexyl)methyl] carbamate By reaction and purification in the same manner as in the method described in Example 4 and using the compound obtained in Example 144 and Boc-tranexamic acid, the title compound was obtained.

MS(ESI+): 647 (M−$^t$Bu+2H)

Example 283

1-[(3S,4R)-1-{[trans-4-(aminomethyl)cyclohexyl]carbonyl}-4-(4-fluorophenyl)pyrrolidin-3-yl]-3-[3,5-bis(trifluoromethyl)phenyl]-1,3-dimethylurea monohydrochloride By reaction and purification in the same manner as in the method described in Example 3 and using the compound obtained in Example 282, the title compound was obtained.
MS(ESI+): 603 (M−HCl+H)

Example 284

N-[(trans-4-{[(3S,4R)-3-[{[3,5-bis(trifluoromethyl)phenyl](methyl)carbamoyl}(methyl)amino]-4-(4-fluorophenyl)pyrrolidin-1-yl]carbonyl}cyclohexyl)methyl]acetamide By reaction and purification in the same manner as in the method described in Example 248 and using the compound obtained in Example 283 and acetyl chloride, the title compound was obtained.
MS(ESI+): 645 (M+H)

Example 285 methyl [(trans-4-{[(3S,4R)-3-[{[3,5-bis(trifluoromethyl)phenyl](methyl)carbamoyl}(methyl)amino]-4-(4-fluorophenyl)pyrrolidin-1-yl]carbonyl}cyclohexyl)methyl]carbamate By reaction and purification in the same manner as in the method described in Example 248 and using the compound obtained in Example 283 and methyl chlorocarbonate, the title compound was obtained.
MS(ESI+): 661 (M+H)

Example 286

1-[3,5-bis(trifluoromethyl)phenyl]-3-[(3S,4R)-4-(4-fluorophenyl)-1-{[4-(3-methyl-1H-pyrazol-1-yl)phenyl]carbonyl}pyrrolidin-3-yl]-1,3-dimethylurea By reaction and purification in the same manner as in the method described in Example 4 and using the compound obtained in Example 144 and 4-(3-methyl-1H-pyrazol-1-yl)benzoic acid, the title compound was obtained.
MS(ESI+): 648 (M+H)

Example 287

1-[3,5-bis(trifluoromethyl)phenyl]-3-[(3S,4R)-1-{[4-(difluoromethoxy)phenyl]carbonyl}-4-(4-fluorophenyl)pyrrolidin-3-yl]-1,3-dimethylurea By reaction and purification in the same manner as in the method described in Example 4 and using the compound obtained in Example 144 and 4-(difluoromethoxy)benzoic acid, the title compound was obtained.
MS(ESI+): 634 (M+H)

Example 288

1-[3,5-bis(trifluoromethyl)phenyl]-3-{(3S,4R)-4-(4-fluorophenyl)-1-[(4-{morpholin-4-yl}phenyl)carbonyl]pyrrolidin-3-yl}-1,3-dimethylurea By reaction and purification in the same manner as in the method described in Example 4 and using the compound obtained in Example 144 and 4-(morpholin-4-yl)benzoic acid, the title compound was obtained.
MS(ESI+): 653 (M+H)

Example 289

1-[3,5-bis(trifluoromethyl)phenyl]-3-[(3S,4R)-4-(4-fluorophenyl)-1-{[4-(1H-imidazol-1-yl)phenyl]carbonyl}pyrrolidin-3-yl]-1,3-dimethylurea By reaction and purification in the same manner as in the method described in Example 4 and using the compound obtained in Example 144 and 4-(1H-imidazol-1-yl)benzoic acid, the title compound was obtained.
MS(ESI+): 634 (M+H)

Example 290

1-[3,5-bis(trifluoromethyl)phenyl]-3-[(3S,4R)-4-(4-fluorophenyl)-1-{[4-(1H-pyrazol-1-yl)phenyl]carbonyl}pyrrolidin-3-yl]-1,3-dimethylurea By reaction and purification in the same manner as in the method described in Example 4 and using the compound obtained in Example 144 and 4-(1H-pyrazol-1-yl)benzoic acid, the title compound was obtained.
MS(ESI+): 634 (M+H)

Example 291

1-[3,5-bis(trifluoromethyl)phenyl]-3-[(3S,4R)-4-(4-fluorophenyl)-1-{[4-(5-methyl-1H-tetrazol-1-yl)phenyl]carbonyl}pyrrolidin-3-yl]-1,3-dimethylurea By reaction and purification in the same manner as in the method described in Example 4 and using the compound obtained in Example 144 and 4-(5-methyl-1H-tetrazol-1-yl)benzoic acid, the title compound was obtained.
MS(ESI+): 650 (M+H)

Example 292

1-[3,5-bis(trifluoromethyl)phenyl]-3-[(3S,4R)-4-(4-fluorophenyl)-1-{[4-(1H-tetrazol-1-yl)phenyl]carbonyl}pyrrolidin-3-yl]-1,3-dimethylurea By reaction and purification in the same manner as in the method described in Example 4 and using the compound obtained in Example 144 and 4-(1H-tetrazol-1-yl)benzoic acid, the title compound was obtained.
MS(ESI+): 636 (M+H)

Example 293

1-[3,5-bis(trifluoromethyl)phenyl]-3-{(3S,4R)-4-(4-fluorophenyl)-1-[(2S)-tetrahydrofuran-2-ylcarbonyl]pyrrolidin-3-yl}-1,3-dimethylurea By reaction and purification in the same manner as in the method described in Example 4 and using the compound

Example 294

1-[3,5-bis(trifluoromethyl)phenyl]-3-{(3S,4R)-4-(4-fluorophenyl)-1-[(2R)-tetrahydrofuran-2-ylcarbonyl]pyrrolidin-3-yl}-1,3-dimethylurea By reaction and purification in the same manner as in the method described in Example 4 and using the compound obtained in Example 144 and (2R)-tetrahydrofuran-2-carboxylic acid, the title compound was obtained.
MS(ESI+): 562 (M+H)

Example 295

1-[3,5-bis(trifluoromethyl)phenyl]-3-[(3S,4R)-1-(cyclohexylcarbonyl)-4-(4-fluorophenyl)pyrrolidin-3-yl]-1,3-dimethylurea By reaction and purification in the same manner as in the method described in Example 4 and using the compound obtained in Example 144 and cyclohexanecarboxylic acid, the title compound was obtained.
MS(ESI+): 574 (M+H)

Example 296 tert-butyl [(4-{[(3S,4R)-3-[{[3,5-bis(trifluoromethyl)phenyl](methyl)carbamoyl}(methyl)amino]-4-(4-fluorophenyl)pyrrolidin-1-yl]carbonyl}tetrahydro-2H-pyran-4-yl)methyl]carbamate By reaction and purification in the same manner as in the method described in Example 4 and using the compound obtained in Example 144 and the compound obtained in Reference Example 34, the title compound was obtained.
MS(ESI+): 705 (M+H)

Example 297

N-[(4-{[(3S,4R)-3-[{[3,5-bis(trifluoromethyl)phenyl](methyl)carbamoyl}(methyl)amino]-4-(4-fluorophenyl)pyrrolidin-1-yl]carbonyl}tetrahydro-2H-pyran-4-yl)methyl]acetamide (Step 1)

By reaction and purification in the same manner as in the method described in Example 3 and using the compound obtained in Example 296, 1-[(3S,4R)-1-{[4-(aminomethyl)tetrahydro-2H-pyran-4-yl]carbonyl}-4-(4-fluorophenyl)pyrrolidin-3-yl]-3-[3,5-bis(trifluoromethyl)phenyl]-1,3-dimethylurea monohydrochloride was obtained.
MS(ESI+): 605 (M−HCl+H)

(Step 2)

By reaction and purification in the same manner as in the method described in Example 75 and using the compound obtained in step 1, the title compound was obtained.
MS(ESI+): 647 (M+H)

Example 298

N-[(4-{[(3S,4R)-3-[{[3,5-bis(trifluoromethyl)phenyl](methyl)carbamoyl}(methyl)amino]-4-(4-fluorophenyl)pyrrolidin-1-yl]carbonyl}tetrahydro-2H-pyran-4-yl)methyl]benzamide By reaction and purification in the same manner as in the method described in Example 75 and using the compound obtained in Example 297, step 1 and benzoyl chloride, the title compound was obtained.
MS(ESI+): 709 (M+H)

Example 299 methyl [(4-{[(3S,4R)-3-[{[3,5-bis(trifluoromethyl)phenyl](methyl)carbamoyl}(methyl)amino]-4-(4-fluorophenyl)pyrrolidin-1-yl]carbonyl}tetrahydro-2H-pyran-4-yl)methyl]carbamate By reaction and purification in the same manner as in the method described in Example 75 and using the compound obtained in Example 297, step 1 and methyl chlorocarbonate, the title compound was obtained.
MS(ESI+): 663 (M+H)

Example 300

1-[3,5-bis(trifluoromethyl)phenyl]-3-[(3S,4R)-1-[(4-cyanotetrahydro-2H-pyran-4-yl)carbonyl]-4-(4-fluorophenyl)pyrrolidin-3-yl]-1,3-dimethylurea By reaction and purification in the same manner as in the method described in Example 4 and using the compound obtained in Example 144 and 4-cyanotetrahydro-2H-pyran-4-carboxylic acid, the title compound was obtained.
MS(ESI+): 601 (M+H)

Example 301

1-[3,5-bis(trifluoromethyl)phenyl]-3-{(3S,4R)-4-(4-fluorophenyl)-1-[(4-methyltetrahydro-2H-pyran-4-yl)carbonyl]pyrrolidin-3-yl}-1,3-dimethylurea By reaction and purification in the same manner as in the method described in Example 4 and using the compound obtained in Example 144 and 4-methyltetrahydro-2H-pyran-4-carboxylic acid, the title compound was obtained.
MS(ESI+): 590 (M+H)

Example 302

1-[3,5-bis(trifluoromethyl)phenyl]-3-{(3S,4R)-4-(4-fluorophenyl)-1-[(4-fluorotetrahydro-2H-pyran-4-yl)carbonyl]pyrrolidin-3-yl}-1,3-dimethylurea By reaction and purification in the same manner as in the method described in Example 4 and using the compound obtained in Example 144 and the compound obtained in Reference Example 35, the title compound was obtained.
MS(ESI+): 594 (M+H)

(Continued from previous page: obtained in Example 144 and (2S)-tetrahydrofuran-2-carboxylic acid, the title compound was obtained.
MS(ESI+): 562 (M+H))

Example 303 tert-butyl 4-{[(3S,4R)-3-[{[3,5-bis(trifluoromethyl)
phenyl](methyl)carbamoyl}(methyl)amino]-4-(4-
fluorophenyl)pyrrolidin-1-yl]carbonyl}piperidine-1-
carboxylate To a mixture of the compound (9.4 g) obtained in Example 144, 1-(tert-butoxycarbonyl)piperidine-4-carboxylic acid (5.4 g), WSC.HCl (4.3 g), HOBt (2.5 g) and acetonitrile (94 mL) was added triethylamine (3.1 mL), and the mixture was stirred at room temperature for 6 hr. The reaction mixture was diluted with ethyl acetate, and washed with saturated aqueous sodium hydrogen carbonate solution, water and saturated brine, dried, and filtered through silica gel (NH Chromatorex) (eluted with 60% ethyl acetate/hexane). The filtrate was concentrated under reduced pressure, and the residue was recrystallized from ethyl acetate/IPE/hexane to give the title compound (12 g, 92%) as a white powder.

MS(ESI+): 675 (M+H)
$^1$H-NMR(CDCl$_3$) δ 1.45 and 1.47 (9H, s x2), 1.70 (4H, brs), 2.35-2.54 (1H, m), 2.57 (3H, s), 2.62-2.86 (2H, m), 3.20 and 3.21 (3H, s x2), 3.24-3.66 (3H, m), 3.85-4.40 (4H, m), 4.78-5.10 (1H, m), 7.00-7.14 (2H, m), 7.14-7.34 (4H, m), 7.43-7.61 (1H, m)

Example 304

1-[3,5-bis(trifluoromethyl)phenyl]-3-[(3S,4R)-4-(4-
fluorophenyl)-1-(piperidin-4-ylcarbonyl)pyrrolidin-
3-yl]-1,3-dimethylurea monohydrochloride A mixture of the compound (12 g) obtained in Example 303 and 2N hydrogen chloride/2-propanol (35 mL) was stirred at 45° C. for 3 hr, and concentrated under reduced pressure to give the title compound (11 g, 100%) as a white powder.

MS(ESI+): 576 (M−HCl+H)
$^1$H-NMR (DMSO-d$_6$) δ 1.80 (4H, brs), 2.59-3.02 (6H, m), 3.03-4.11 (10H, m, overlapped with H$_2$O), 4.65-4.96 (1H, m), 7.08 (2H, td, J=8.9, 4.1 Hz), 7.22-7.26 (2H, m), 7.41 (2H, td, J=8.9, 5.5 Hz), 7.59 (1H, d, J=7.9 Hz), 8.53-9.29 (2H, m)

Example 305 methyl 4-{[(3S,4R)-3-[{[3,5-bis(trifluoromethyl)
phenyl](methyl)carbamoyl}(methyl)amino]-4-(4-
fluorophenyl)pyrrolidin-1-yl]carbonyl}piperidine-1-
carboxylate A solution of the compound (0.20 g) obtained in Example 304, methyl chlorocarbonate (0.038 mL), and triethylamine (0.14 mL) in acetonitrile (3.3 mL) was stirred at room temperature overnight. The reaction mixture was diluted with ethyl acetate, washed with water and saturated brine, dried and concentrated under reduced pressure. The residue was purified by silica gel column chromatography (solvent gradient; 80→100% ethyl acetate/hexane) and crystallized from tert-butyl methyl ether to give the title compound (0.21 g, 81%) as a white powder.

MS(ESI+): 633 (M+H)
$^1$H-NMR(CDCl$_3$) δ 1.66-1.84 (3H, m), 2.40-2.63 (4H, m), 2.80 (2H, br. s), 3.18-3.64 (8H, m), 3.67-3.75 (3H, m), 3.90-4.35 (3H, m), 4.85-5.03 (1H, m), 7.02-7.14 (2H, m), 7.15-7.32 (4H, m), 7.51 (1H, d, J=11.7 Hz)
$[α]_D^{25}$ −106.1° (c0.25, MeOH)

Example 306

1-[3,5-bis(trifluoromethyl)phenyl]-3-[(3S,4R)-1-{[1-
(cyclopropylcarbonyl)piperidin-4-yl]carbonyl}-4-(4-
fluorophenyl)pyrrolidin-3-yl]-1,3-dimethylurea By reaction and purification in the same manner as in the method described in Example 4 and using the compound obtained in Example 304 and cyclopropanecarboxylic acid, the title compound was obtained.

MS(ESI+): 643 (M+H)

Example 307

1-[3,5-bis(trifluoromethyl)phenyl]-3-[(3S,4R)-1-({1-
[(4,4-difluorocyclohexyl)carbonyl]piperidin-4-
yl}carbonyl)-4-(4-fluorophenyl)pyrrolidin-3-yl]-1,3-
dimethylurea By reaction and purification in the same manner as in the method described in Example 4 and using the compound obtained in Example 304 and 4,4-difluorocyclohexanecarboxylic acid, the title compound was obtained.

MS(ESI+): 721 (M+H)

Example 308

1-[3,5-bis(trifluoromethyl)phenyl]-3-[(3S,4R)-4-(4-
fluorophenyl)-1-{[1-(2-hydroxy-2-methylpropanoyl)
piperidin-4-yl]carbonyl}pyrrolidin-3-yl]-1,3-dim-
ethylurea By reaction and purification in the same manner as in the method described in Example 4 and using the compound obtained in Example 304 and 2-hydroxy-2-methylpropanoic acid, the title compound was obtained.

MS(ESI+): 661 (M+H)

Example 309

1-[3,5-bis(trifluoromethyl)phenyl]-3-[(3S,4R)-4-(4-
fluorophenyl)-1-({1-[(1-hydroxycyclopropyl)carbo-
nyl]piperidin-4-yl}carbonyl)pyrrolidin-3-yl]-1,3-
dimethylurea By reaction and purification in the same manner as in the method described in Example 4 and using the compound obtained in Example 304 and 1-hydroxycyclopropanecarboxylic acid, the title compound was obtained.

MS(ESI+): 659 (M+H)

Example 310

1-[3,5-bis(trifluoromethyl)phenyl]-3-[(3S,4R)-1-({1-
[(3,3-difluorocyclobutyl)carbonyl]piperidin-4-
yl}carbonyl)-4-(4-fluorophenyl)pyrrolidin-3-yl]-1,3-
dimethylurea By reaction and purification in the same manner as in the method described in Example 4 and using the compound obtained in Example 304 and 3,3-difluorocyclobutanecarboxylic acid, the title compound was obtained.

MS(ESI+): 693 (M+H)

Example 311

1-[3,5-bis(trifluoromethyl)phenyl]-3-{(3S,4R)-4-(4-fluorophenyl)-1-[(1-propanoylpiperidin-4-yl)carbonyl]pyrrolidin-3-yl}-1,3-dimethylurea By reaction and purification in the same manner as in the method described in Example 75 and using the compound obtained in Example 304 and propanoyl chloride, the title compound was obtained.
MS(ESI+): 631 (M+H)

Example 312 ethyl 4-{[(3S,4R)-3-[{[3,5-bis(trifluoromethyl)phenyl](methyl)carbamoyl}(methyl)amino]-4-(4-fluorophenyl)pyrrolidin-1-yl]carbonyl}piperidine-1-carboxylate By reaction and purification in the same manner as in the method described in Example 75 and using the compound obtained in Example 304 and ethyl chlorocarbonate, the title compound was obtained.
MS(ESI+): 647 (M+H)

Example 313

1-[3,5-bis(trifluoromethyl)phenyl]-3-[(3S,4R)-4-(4-fluorophenyl)-1-{[1-(methoxyacetyl)piperidin-4-yl]carbonyl}pyrrolidin-3-yl]-1,3-dimethylurea By reaction and purification in the same manner as in the method described in Example 4 and using the compound obtained in Example 304 and methoxyacetic acid, the title compound was obtained.
MS(ESI+): 647 (M+H)

Example 314

1-[3,5-bis(trifluoromethyl)phenyl]-3-[(3S,4R)-4-(4-fluorophenyl)-1-{[1-(1H-tetrazol-1-ylacetyl)piperidin-4-yl]carbonyl}pyrrolidin-3-yl]-1,3-dimethylurea By reaction and purification in the same manner as in the method described in Example 4 and using the compound obtained in Example 304 and 1H-tetrazol-1-ylacetic acid, the title compound was obtained.
MS(ESI+): 685 (M+H)

Example 315

1-[3,5-bis(trifluoromethyl)phenyl]-3-[(3S,4R)-1-{[1-(difluoroacetyl)piperidin-4-yl]carbonyl}-4-(4-fluorophenyl)pyrrolidin-3-yl]-1,3-dimethylurea By reaction and purification in the same manner as in the method described in Example 4 and using the compound obtained in Example 304 and difluoroacetic acid, the title compound was obtained.
MS(ESI+): 653 (M+H)

Example 316

1-[3,5-bis(trifluoromethyl)phenyl]-3-[(3S,4R)-4-(4-fluorophenyl)-1-{[1-(trifluoroacetyl)piperidin-4-yl]carbonyl}pyrrolidin-3-yl]-1,3-dimethylurea To a solution of the compound (0.20 g) obtained in Example 304 in THF (5 mL) were added trifluoroacetic anhydride (0.091 mL) and triethylamine (0.091 mL), and the mixture was stirred at room temperature for 4 hr. The reaction mixture was poured into water, and the mixture was extracted with ethyl acetate. The extract was washed with saturated aqueous sodium hydrogen carbonate solution, water and saturated brine, dried and concentrated under reduced pressure. The residue was purified by silica gel column chromatography (solvent gradient; 50→80% ethyl acetate/hexane) to give the title compound (0.15 g, 70%) as a white powder.
MS(ESI+): 671 (M+H)

Example 317

1-[3,5-bis(trifluoromethyl)phenyl]-3-[(3S,4R)-1-{[1-(cyanoacetyl)piperidin-4-yl]carbonyl}-4-(4-fluorophenyl)pyrrolidin-3-yl]-1,3-dimethylurea By reaction and purification in the same manner as in the method described in Example 4 and using the compound obtained in Example 304 and cyanoacetic acid, the title compound was obtained.
MS(ESI+): 642 (M+H)

Example 318

1-[3,5-bis(trifluoromethyl)phenyl]-3-[(3S,4R)-1-{[1-(cyclopropylacetyl)piperidin-4-yl]carbonyl}-4-(4-fluorophenyl)pyrrolidin-3-yl]-1,3-dimethylurea By reaction and purification in the same manner as in the method described in Example 4 and using the compound obtained in Example 304 and cyclopropylacetic acid, the title compound was obtained.
MS(ESI+): 657 (M+H)

Example 319

1-[3,5-bis(trifluoromethyl)phenyl]-3-[(3S,4R)-4-(4-fluorophenyl)-1-({1-[(methylsulfonyl)acetyl]piperidin-4-yl}carbonyl)pyrrolidin-3-yl]-1,3-dimethylurea By reaction and purification in the same manner as in the method described in Example 4 and using the compound obtained in Example 304 and (methylsulfonyl)acetic acid, the title compound was obtained.
MS(ESI+): 695 (M+H)

Example 320

1-[3,5-bis(trifluoromethyl)phenyl]-3-[(3S,4R)-4-(4-fluorophenyl)-1-{[1-(tetrahydro-2H-pyran-4-ylcarbonyl)piperidin-4-yl]carbonyl}pyrrolidin-3-yl]-1,3-dimethylurea By reaction and purification in the same manner as in the method described in Example 4 and using the compound obtained in Example 304 and tetrahydro-2H-pyran-4-carboxylic acid, the title compound was obtained.

¹H-NMR(CDCl₃) δ 1.48-2.03 (8H, m), 2.46-2.85 (6H, m), 2.93-3.17 (1H, m), 3.17-3.70 (8H, m), 3.85-4.19 (5H, m), 4.63 (1H, brs), 4.80-5.09 (1H, m), 7.01-7.14 (2H, m), 7.15-7.33 (4H, m), 7.52 (1H, d, J=11.7 Hz)

Example 321

N-[2-(4-{[(3S,4R)-3-[{[3,5-bis(trifluoromethyl)phenyl](methyl)carbamoyl}(methyl)amino]-4-(4-fluorophenyl)pyrrolidin-1-yl]carbonyl}piperidin-1-yl)-2-oxoethyl]acetamide By reaction and purification in the same manner as in the method described in Example 4 and using the compound obtained in Example 304 and acetylglycine, the title compound was obtained. MS(ESI+): 674 (M+H)

Example 322

1-[3,5-bis(trifluoromethyl)phenyl]-3-[(3S,4R)-1-{[1-(ethoxyacetyl)piperidin-4-yl]carbonyl}-4-(4-fluorophenyl)pyrrolidin-3-yl]-1,3-dimethylurea By reaction and purification in the same manner as in the method described in Example 4 and using the compound obtained in Example 304 and ethoxyacetic acid, the title compound was obtained.
MS(ESI+): 661 (M+H)

Example 323

1-[3,5-bis(trifluoromethyl)phenyl]-3-[(3S,4R)-4-(4-fluorophenyl)-1-{[1-(3-methoxypropanoyl)piperidin-4-yl]carbonyl}pyrrolidin-3-yl]-1,3-dimethylurea By reaction and purification in the same manner as in the method described in Example 4 and using the compound obtained in Example 304 and 3-methoxypropanoic acid, the title compound was obtained.
MS(ESI+): 661 (M+H)

Example 324

1-[3,5-bis(trifluoromethyl)phenyl]-3-{(3S,4R)-4-(4-fluorophenyl)-1-[(1-formylpiperidin-4-yl)carbonyl]pyrrolidin-3-yl}-1,3-dimethylurea By reaction and purification in the same manner as in the method described in Example 4 and using the compound obtained in Example 304 and formic acid, the title compound was obtained.
MS(ESI+): 603 (M+H)

Example 325

4-{[(3S,4R)-3-[{[3,5-bis(trifluoromethyl)phenyl](methyl)carbamoyl}(methyl)amino]-4-(4-fluorophenyl)pyrrolidin-1-yl]carbonyl}-N-ethylpiperidine-1-carboxamide By reaction and purification in the same manner as in the method described in Example 1 and using the compound obtained in Example 304 and ethyl isocyanate, the title compound was obtained.
MS(ESI+): 646 (M+H)

Example 326

4-{[(3S,4R)-3-[{[3,5-bis(trifluoromethyl)phenyl](methyl)carbamoyl}(methyl)amino]-4-(4-fluorophenyl)pyrrolidin-1-yl]carbonyl}-N-phenylpiperidine-1-carboxamide By reaction and purification in the same manner as in the method described in Example 1 and using the compound obtained in Example 304 and isocyanatobenzene, the title compound was obtained.
MS(ESI+): 694 (M+H)

Example 327

1-[3,5-bis(trifluoromethyl)phenyl]-3-[(3S,4R)-4-(4-fluorophenyl)-1-{[1-(methylsulfonyl)piperidin-4-yl]carbonyl}pyrrolidin-3-yl]-1,3-dimethylurea By reaction and purification in the same manner as in the method described in Example 75 and using the compound obtained in Example 304 and methanesulfonyl chloride, the title compound was obtained.
MS(ESI+): 653 (M+H)

Example 328

1-[3,5-bis(trifluoromethyl)phenyl]-3-[(3S,4R)-1-{[1-(ethylsulfonyl)piperidin-4-yl]carbonyl}-4-(4-fluorophenyl)pyrrolidin-3-yl]-1,3-dimethylurea By reaction and purification in the same manner as in the method described in Example 75 and using the compound obtained in Example 304 and ethanesulfonyl chloride, the title compound was obtained.
MS(ESI+): 667 (M+H)

Example 329

1-[3,5-bis(trifluoromethyl)phenyl]-3-[(3S,4R)-4-(4-fluorophenyl)-1-({1-[(1-methylethyl)sulfonyl]piperidin-4-yl}carbonyl)pyrrolidin-3-yl]-1,3-dimethylurea By reaction and purification in the same manner as in the method described in Example 75 and using the compound obtained in Example 304 and propane-2-sulfonyl chloride, the title compound was obtained.
MS(ESI+): 681 (M+H)

Example 330

1-[3,5-bis(trifluoromethyl)phenyl]-3-[(3S,4R)-1-{[1-(cyclopropylsulfonyl)piperidin-4-yl]carbonyl}-4-(4-fluorophenyl)pyrrolidin-3-yl]-1,3-dimethylurea By reaction and purification in the same manner as in the method described in Example 75 and using the compound obtained in Example 304 and cyclopropanesulfonyl chloride, the title compound was obtained.
MS(ESI+): 679 (M+H)

Example 331

1-[3,5-bis(trifluoromethyl)phenyl]-3-[(3S,4R)-4-(4-fluorophenyl)-1-({1-[(trifluoromethyl)sulfonyl]piperidin-4-yl}carbonyl)pyrrolidin-3-yl]-1,3-dimethylurea By reaction and purification in the same manner as in the method described in Example 75 and using the compound obtained in Example 304 and trifluoromethanesulfonyl chloride, the title compound was obtained.
MS(ESI+): 707 (M+H)

Example 332

1-[3,5-bis(trifluoromethyl)phenyl]-3-[(3S,4R)-4-(4-fluorophenyl)-1-({1-[(2,2,2-trifluoroethyl)sulfonyl]piperidin-4-yl}carbonyl)pyrrolidin-3-yl]-1,3-dimethylurea By reaction and purification in the same manner as in the method described in Example 75 and using the compound obtained in Example 304 and 2,2,2-trifluoroethanesulfonyl chloride, the title compound was obtained.
MS(ESI+): 721 (M+H)

Example 333

4-{[(3S,4R)-3-[{[3,5-bis(trifluoromethyl)phenyl](methyl)carbamoyl}(methyl)amino]-4-(4-fluorophenyl)pyrrolidin-1-yl]carbonyl}-N,N-dimethylpiperidine-1-sulfonamide By reaction and purification in the same manner as in the method described in Example 75 and using the compound obtained in Example 304 and dimethylsulfamoyl chloride, the title compound was obtained.
MS(ESI+): 682 (M+H)

Example 334

2-(4-{[(3S,4R)-3-[{[3,5-bis(trifluoromethyl)phenyl](methyl)carbamoyl}(methyl)amino]-4-(4-fluorophenyl)pyrrolidin-1-yl]carbonyl}piperidin-1-yl)acetamide A mixture of the compound (0.21 g) obtained in Example 304, 2-iodoacetamide (0.078 g), potassium carbonate (0.12 g) and DMF (5.0 ml) was stirred at 45 to 55° C. overnight. The mixture was diluted with ethyl acetate, and washed with water (2 times) and saturated brine, dried and concentrated under reduced pressure. The residue was purified by silica gel column chromatography (NH Chromatorex) (solvent gradient; 0→6% methanol/ethyl acetate) to give the title compound (0.19 g, 85%) as a pale-yellow powder.
MS(ESI+): 632 (M+H)

Example 335

1-[3,5-bis(trifluoromethyl)phenyl]-3-[(3S,4R)-4-(4-fluorophenyl)-1-{[1-(2-methoxyethyl)piperidin-4-yl]carbonyl}pyrrolidin-3-yl]-1,3-dimethylurea By reaction and purification in the same manner as in the method described in Example 334 and using the compound obtained in Example 304 and 2-bromoethyl methyl ether, the title compound was obtained.
MS(ESI+): 633 (M+H)

Example 336 methyl trans-4-{[(3S,4R)-3-[{[3,5-bis(trifluoromethyl)phenyl](methyl)carbamoyl}(methyl)amino]-4-(4-fluorophenyl)pyrrolidin-1-yl]carbonyl}cyclohexanecarboxylate By reaction and purification in the same manner as in the method described in Example 4 and using the compound obtained in Example 144 and trans-4-(methoxycarbonyl)cyclohexanecarboxylic acid, the title compound was obtained.
MS(ESI+): 632 (M+H)

Example 337 trans-4-{[(3S,4R)-3-[{[3,5-bis(trifluoromthyl)phenyl](methyl)carbamoyl}(methyl)amino]-4-(4-fluorophenyl)pyrrolidin-1-yl]carbonyl}cyclohexanecarboxylic acid To a solution of the compound (2.7 g) obtained in Example 336 in THF/methanol (4/16 mL) was added 1N aqueous sodium hydroxide solution (6.4 mL) at room temperature, and the mixture was stirred for 3 days. The mixture was acidified with 1N hydrochloric acid (8 ml), diluted with water, and extracted with ethyl acetate. The extract was washed with water and saturated brine, dried, filtered through silica gel (eluted with ethyl acetate). The filtrate was concentrated under reduced pressure to give the title compound (2.5 g, 95%) as a white powder.
MS(ESI+): 618 (M+H)

Example 338

1-[3,5-bis(trifluoromethyl)phenyl]-3-[(3S,4R)-1-({trans-4-[(4,4-difluoropiperidin-1-yl)carbonyl]cyclohexyl}carbonyl)-4-(4-fluorophenyl)pyrrolidin-3-yl]-1,3-dimethylurea By reaction and purification in the same manner as in the method described in Example 4 and using the compound obtained in Example 337 and 4,4-difluoropiperidine monohydrochloride, the title compound was obtained.
MS(ESI+): 721 (M+H)

Example 339

1-[3,5-bis(trifluoromethyl)phenyl]-3-[(3S,4R)-4-(4-fluorophenyl)-1-{[trans-4-(morpholin-4-ylcarbonyl)cyclohexyl]carbonyl}pyrrolidin-3-yl]-1,3-dimethylurea A solution of the compound (0.22 g) obtained in Example 337, morpholine (0.037 g), WSC.HCl (0.081 g) and HOBt (0.047 g) in acetonitrile (6.0 mL) was stirred overnight at room temperature. The reaction mixture was diluted with ethyl acetate, and washed with saturated aqueous sodium hydrogen carbonate solution, water and saturated brine and dried, and the solvent was evaporated under reduced pressure. The obtained residue was purified by silica gel column chromatography (NH Chromatorex) (solvent gradient; 5→100% ethyl acetate/hexane) to give the title compound (0.22 g, 93%) as a white powder.
MS(ESI+): 687 (M+H)

Example 340 trans-4-{[(3S,4R)-3-[{[3,5-bis(trifluoromethyl)phenyl](methyl)carbamoyl}(methyl)amino]-4-(4-fluorophenyl)pyrrolidin-1-yl]carbonyl}-N-cyclopropyl-cyclohexanecarboxamide By reaction and purification in the same manner as in the method described in Example 339 and using the compound obtained in Example 337 and cyclopropylamine, the title compound was obtained.
MS(ESI+): 657 (M+H)

Example 341 trans-4-{[(3S,4R)-3-[{[3,5-bis(trifluoromethyl)phenyl](methyl)carbamoyl}(methyl)amino]-4-(4-fluorophenyl)pyrrolidin-1-yl]carbonyl}-N,N-dimethylcyclohexanecarboxamide By reaction and purification in the same manner as in the method described in Example 339 and using the compound obtained in Example 337 and dimethylamine (2.0 mol/L THF solution), the title compound was obtained.
MS(ESI+): 645 (M+H)

Example 342 trans-4-{[(3S,4R)-3-[{[3,5-bis(trifluoromethyl)phenyl](methyl)carbamoyl}(methyl)amino]-4-(4-fluorophenyl)pyrrolidin-1-yl]carbonyl}cyclohexanecarboxamide A solution of the compound (0.22 g) obtained in Example 337, WSC.HCl (0.081 g) and HOBt.NH$_3$ (0.064 g) in acetonitrile (6.0 mL) was stirred at room temperature for 2 days. The reaction mixture was diluted with ethyl acetate, and washed with saturated aqueous sodium hydrogen carbonate solution, water and saturated brine and dried, and the solvent was evaporated under reduced pressure. The obtained residue was recrystallized from ethyl acetate/hexane to give the title compound (0.17 g, 78%) as a white powder.
MS(ESI+): 617 (M+H)

Example 343 tert-butyl 3-{[(3S,4R)-3-[{[3,5-bis(trifluoromethyl)phenyl](methyl)carbamoyl}(methyl)amino]-4-(4-fluorophenyl)pyrrolidin-1-yl]carbonyl}azetidine-1-carboxylate By reaction and purification in the same manner as in the method described in Example 4 and using the compound obtained in Example 144 and 1-(tert-butoxycarbonyl)azetidine-3-carboxylic acid, the title compound was obtained.
MS(ESI+): 647 (M+H)

Example 344

1-[(3S,4R)-1-[(1-acetylazetidin-3-yl)carbonyl]-4-(4-fluorophenyl)pyrrolidin-3-yl]-3-[3,5-bis(trifluoromethyl)phenyl]-1,3-dimethylurea (Step 1)
By reaction and purification in the same manner as in the method described in Example 3 and using the compound obtained in Example 343, 1-[(3S,4R)-1-(azetidin-3-ylcarbonyl)-4-(4-fluorophenyl)pyrrolidin-3-yl]-3-[3,5-bis(trifluoromethyl)phenyl]-1,3-dimethylurea monohydrochloride was obtained.
MS(ESI+): 547 (M−HCl+H)

(Step 2)
By reaction and purification in the same manner as in the method described in Example 75 and using the compound obtained in step 1, the title compound was obtained.
MS(ESI+): 589 (M+H)

Example 345 methyl 3-{[(3S,4R)-3-[{[3,5-bis(trifluoromethyl)phenyl](methyl)carbamoyl}(methyl)amino]-4-(4-fluorophenyl)pyrrolidin-1-yl]carbonyl}azetidine-1-carboxylate By reaction and purification in the same manner as in the method described in Example 75 and using the compound obtained in Example 344, step 1 and methyl chlorocarbonate, the title compound was obtained.
MS(ESI+): 605 (M+H)

Example 346

1-[3,5-bis(trifluoromethyl)phenyl]-3-[(3S,4R)-4-(4-fluorophenyl)-1-{[1-(phenylcarbonyl)azetidin-3-yl]carbonyl}pyrrolidin-3-yl]-1,3-dimethylurea By reaction and purification in the same manner as in the method described in Example 75 and using the compound obtained in Example 344, step 1 and benzoyl chloride, the title compound was obtained.
MS(ESI+): 651 (M+H)

Example 347

1-[3,5-bis(trifluoromethyl)phenyl]-3-[(3S,4R)-1-[(3,3-difluorocyclobutyl)carbonyl]-4-(4-fluorophenyl)pyrrolidin-3-yl]-1,3-dimethylurea By reaction and purification in the same manner as in the method described in Example 4 and using the compound obtained in Example 144 and 3,3-difluorocyclobutanecarboxylic acid, the title compound was obtained.
MS(ESI+): 582 (M+H)

Example 348 tert-butyl 4-{[(3S,4R)-3-[{[3,5-bis(trifluoromethyl)phenyl](methyl)carbamoyl}(methyl)amino]-4-(4-fluorophenyl)pyrrolidin-1-yl]carbonyl}-4-fluoropiperidine-1-carboxylate By reaction and purification in the same manner as in the method described in Example 4 and using the compound obtained in Example 144 and 1-(tert-butoxycarbonyl)-4-fluoropiperidine-4-carboxylic acid, the title compound was obtained.
MS(ESI+): 593 (M−Boc+2H)

Example 349

1-[3,5-bis(trifluoromethyl)phenyl]-3-{(3S,4R)-4-(4-fluorophenyl)-1-[(4-fluoropiperidin-4-yl)carbonyl]pyrrolidin-3-yl}-1,3-dimethylurea monohydrochloride By reaction and purification in the same manner as in the method described in Example 3 and using the compound obtained in Example 348, the title compound was obtained.
MS(ESI+): 593 (M−HCl+H)

Example 350

1-[(3S,4R)-1-[(1-acetyl-4-fluoropiperidin-4-yl)carbonyl]-4-(4-fluorophenyl)pyrrolidin-3-yl]-3-[3,5-bis(trifluoromethyl)phenyl]-1,3-dimethylurea By reaction and purification in the same manner as in the method described in Example 75 and using the compound obtained in Example 349, the title compound was obtained.
MS(ESI+): 635 (M+H)

Example 351 methyl 4-{[(3S,4R)-3-[{[3,5-bis(trifluoromethyl)phenyl](methyl)carbamoyl}(methyl)amino]-4-(4-fluorophenyl)pyrrolidin-1-yl]carbonyl}-4-fluoropiperidine-1-carboxylate By reaction and purification in the same manner as in the method described in Example 75 and using the compound obtained in Example 349 and methyl chlorocarbonate, the title compound was obtained.
MS(ESI+): 651 (M+H)

Example 352 tert-butyl (trans-3-{[(3S,4R)-3-[{[3,5-bis(trifluoromethyl)phenyl](methyl)carbamoyl}(methyl)amino]-4-(4-fluorophenyl)pyrrolidin-1-yl]carbonyl}cyclobutyl)carbamate By reaction and purification in the same manner as in the method described in Example 4 and using the compound obtained in Example 144 and trans-3-[(tert-butoxycarbonyl)amino]cyclobutanecarboxylic acid, the title compound was obtained.
MS(ESI+): 661 (M+H)

Example 353

1-[(3S,4R)-1-[(trans-3-aminocyclobutyl)carbonyl]-4-(4-fluorophenyl)pyrrolidin-3-yl]-3-[3,5-bis(trifluoromethyl)phenyl]-1,3-dimethylurea monohydrochloride By reaction and purification in the same manner as in the method described in Example 3 and using the compound obtained in Example 352, the title compound was obtained.
MS(ESI+): 561 (M−HCl+H)

Example 354

N-(trans-3-{[(3S,4R)-3-[{[3,5-bis(trifluoromethyl)phenyl](methyl)carbamoyl}(methyl)amino]-4-(4-fluorophenyl)pyrrolidin-1-yl]carbonyl}cyclobutyl)acetamide By reaction and purification in the same manner as in the method described in Example 75 and using the compound obtained in Example 353, the title compound was obtained.
MS(ESI+): 603 (M+H)

Example 355 methyl (trans-3-{[(3S,4R)-3-[{[3,5-bis(trifluoromethyl)phenyl](methyl)carbamoyl}(methyl)amino]-4-(4-fluorophenyl)pyrrolidin-1-yl]carbonyl}cyclobutyl)carbamate By reaction and purification in the same manner as in the method described in Example 75 and using the compound obtained in Example 353 and methyl chlorocarbonate, the title compound was obtained.
MS(ESI+): 619 (M+H)

Example 356

1-[3,5-bis(trifluoromethyl)phenyl]-3-[(3S,4R)-4-(4-fluorophenyl)-1-(4-oxo-4,5-dihydro-1,3-oxazol-2-yl)pyrrolidin-3-yl]-1,3-dimethylurea A mixture of the compound (0.20 g) obtained in Example 144, chloroacetyl isocyanate (0.041 mL), triethylamine (0.13 mL) and THF (6.0 mL) was stirred at room temperature for 3 hr. To this mixture was added chloroacetyl isocyanate (0.010 mL) again, and the mixture was stirred at room temperature for 1 hr. The mixture was filtered, and the filtrate was concentrated under reduced pressure. To the residue were added water (2.0 mL) and toluene (6.0 mL), and the mixture was stirred at 100° C. overnight. The mixture was concentrated under reduced pressure, and to the residue were added 1,8-diazabicyclo[5,4,0]undec-7-ene (0.090 mL) and THF (6.0 mL), and the mixture was stirred at 60° C. for 3 hr. The mixture was diluted with ethyl acetate, washed with saturated aqueous sodium hydrogen carbonate solution and saturated brine, dried and concentrated under reduced pressure. The residue was purified by silica gel column chromatography (NH Chromatorex) (solvent gradient; 10→100% ethyl acetate/hexane) to give the title compound (0.054 g, 25%) as a white powder.
MS(ESI+): 547 (M+H)

Example 357

1-[3,5-bis(trifluoromethyl)phenyl]-3-[(3S,4R)-4-(4-fluorophenyl)-1-(5-oxo-2,5-dihydrofuran-3-yl)pyrrolidin-3-yl]-1,3-dimethylurea By reaction and purification in the same manner as in the method described in Example 358 and using the compound obtained in Example 144 and tetronic acid, the title compound was obtained.
MS(ESI+): 546 (M+H)

Example 358

1-[3,5-bis(trifluoromethyl)phenyl]-3-[(3S,4R)-4-(4-fluorophenyl)-1-{[1-(3-oxocyclopent-1-en-1-yl)piperidin-4-yl]carbonyl}pyrrolidin-3-yl]-1,3-dimethylurea A mixture of the compound (0.21 g) obtained in Example 304, 1,3-cyclopentanedione (0.041 g), p-toluenesulfonic acid monohydrate (0.007 g), triethylamine (0.059 mL) and toluene (6.0 mL) was heated under reflux for 20 hr. After cooling, the mixture was diluted with saturated aqueous sodium hydrogen carbonate solution, and extracted with ethyl acetate. The extract was washed with saturated brine, dried and concentrated under reduced pressure. The residue was purified by silica gel column chromatography (NH Chromatorex) (solvent gradient; 0→6% methanol/ethyl acetate) to give the title compound (0.19 g, 83%) as a pale-brown powder.
MS(ESI+): 655 (M+H)

Example 359

1-[3,5-bis(trifluoromethyl)phenyl]-3-[(3S,4R)-4-(4-fluorophenyl)-1-{[1-(5-oxo-2,5-dihydrofuran-3-yl)piperidin-4-yl]carbonyl}pyrrolidin-3-yl]-1,3-dimethylurea By reaction and purification in the same manner as in the method described in Example 358 and using the compound obtained in Example 304 and tetronic acid, the title compound was obtained. MS(ESI+): 657 (M+H)

Example 360

1-[3,5-bis(trifluoromethyl)phenyl]-3-[(3S,4R)-4-(4-fluorophenyl)-1-{[1-(4-oxo-4,5-dihydro-1,3-oxazol-2-yl)piperidin-4-yl]carbonyl}pyrrolidin-3-yl]-1,3-dimethylurea By reaction and purification in the same manner as in the method described in Example 356 and using the compound obtained in Example 304, the title compound was obtained.
$^1$H-NMR(CDCl$_3$) δ 1.75-2.06 (4H, m), 2.48-2.79 (4H, m), 3.03-3.71 (8H, m), 3.89-4.15 (2H, m), 4.15-4.31 (1H, m), 4.35-4.53 (1H, m), 4.53-4.70 (2H, m), 4.81-5.10 (1H, m), 7.01-7.15 (2H, m), 7.15-7.32 (4H, m), 7.52 (1H, d, J=11.7 Hz)

Example 361

1-[3,5-bis(trifluoromethyl)phenyl]-3-[(3S,4R)-4-(4-fluorophenyl)-1-nitrosopyrrolidin-3-yl]-1,3-dimethylurea To a solution of the compound (1.0 g) obtained in Example 144 in acetic acid (6.0 mL) was added a solution of sodium nitrite (0.28 g) in water (2.0 mL), and the mixture was stirred at room temperature for 3 days. To this mixture was added sodium nitrite (0.028 g), and the mixture was stirred at room temperature 5 days. The mixture was concentrated under reduced pressure, and the residue was diluted with saturated aqueous sodium hydrogen carbonate solution, and the mixture was extracted with ethyl acetate. The extract was washed with saturated aqueous sodium hydrogen carbonate solution and saturated brine, dried and concentrated under reduced pressure. The residue was purified by silica gel column chromatography (NH Chromatorex) (solvent gradient; 0→60% ethyl acetate/hexane) to give the title compound (0.98 g, 100%) as a white powder.
MS(ESI+): 493 (M+H)

Example 362

4-nitrophenyl (3S,4R)-3-[{[3,5-bis(trifluoromethyl)phenyl](methyl)carbamoyl}(methyl)amino]-4-(4-fluorophenyl)pyrrolidine-1-carboxylate By reaction and purification in the same manner as in the method described in Example 419 and using the compound obtained in Example 144, the title compound was obtained.
MS(ESI+): 629 (M+H)

Example 363

1-[3,5-bis(trifluoromethyl)phenyl]-3-[(3S,4R)-4-(4-fluorophenyl)-1-(1H-imidazol-1-ylcarbonothioyl)pyrrolidin-3-yl]-1,3-dimethylurea To a mixture of the compound (1.5 g) obtained in Example 144 and 1,1'-thiocarbonyldiimidazole (0.59 g) and THF (12 mL) was added triethylamine (0.50 mL) at 0° C., and the mixture was stirred at room temperature for 12 hr. The mixture was diluted with water, and the mixture was extracted with ethyl acetate. The extract was washed with water and saturated brine, dried and concentrated under reduced pressure. The residue was purified by silica gel column chromatography (solvent gradient; 90→100% ethyl acetate/hexane) to give the title compound (1.8 g, 100%) as a white powder.
MS(ESI+): 574 (M+H)

Example 364 tert-butyl 4-[(2-{[(3S,4R)-3-[{[3,5-bis(trifluoromethyl)phenyl](methyl)carbamoyl}(methyl)amino]-4-(4-fluorophenyl)pyrrolidin-1-yl]carbonyl}hydrazino)carbonyl]piperidine-1-carboxylate To a solution of the compound (1.5 g) obtained in Example 144 in THF (10 mL) was added pyridine (0.97 mL), and the mixture was stirred at 0° C. for 10 min. To this mixture was added dropwise at 0° C. a solution of bis(trichloromethyl)carbonate (0.45 g) in THF (3.0 mL), and the mixture was stirred at room temperature for 4 hr. The mixture was diluted with 1N hydrochloric acid, extracted with ethyl acetate, washed with saturated brine, dried and concentrated under reduced pressure. The residue was purified by silica gel column chromatography (solvent gradient; 0→40% ethyl acetate/hexane) to give (3S,4R)-3-[{[3,5-bis(trifluoromethyl)phenyl](methyl)carbamoyl}(methyl)amino]-4-(4-fluorophenyl)pyrrolidine-1-carbonyl chloride (1.5 g, 92%) as a white powder. To a mixture of the obtained compound (1.4 g), tert-butyl 4-(hydrazinocarbonyl)piperidine-1-carboxylate (0.7 g) and THF (14.0 ml) was added triethylamine (1.1 mL), and the mixture was stirred at 55° C. for 12 hr. The mixture was diluted with ethyl acetate, washed with 1N hydrochloric acid, water and saturated brine, dried and concentrated under reduced pressure. The residue was purified by silica gel column chromatography (solvent gradient; 0→9% methanol/ethyl acetate) to give the title compound (1.8 g, 87%) as a white powder.
MS(ESI+): 633 (M−Boc+2H)

Example 365

(3S,4R)—N-benzyl-3-[{[3,5-bis(trifluoromethyl) phenyl](methyl)carbamoyl}(methyl)amino]-4-(4-fluorophenyl)pyrrolidine-1-carboxamide A solution of the compound (0.20 g) obtained in Example 144, benzyl isocyanate (0.074 mL) and triethylamine (0.14 mL) in acetonitrile (5 mL) was stirred at room temperature for 14 hr. The reaction mixture was diluted with ethyl acetate, washed with water, saturated aqueous ammonium chloride solution and saturated brine, dried and concentrated under reduced pressure. The residue was purified by silica gel column chromatography (solvent gradient; 75→100% ethyl acetate/hexane) to give the title compound (0.23 g, 97%) as a white powder.
MS(ESI+): 597 (M+H)

Example 366

(3S,4R)-3-[{[3,5-bis(trifluoromethyl)phenyl](methyl)carbamoyl}(methyl)amino]-4-(4-fluorophenyl)-N-propylpyrrolidine-1-carboxamide By reaction and purification in the same manner as in the method described in Example 365 and using the compound obtained in Example 144 and propyl isocyanate, the title compound was obtained as a white powder.
MS(ESI+): 549 (M+H)

Example 367

(3S,4R)-3-[{[3,5-bis(trifluoromethyl)phenyl](methyl)carbamoyl}(methyl)amino]-N-cyclopropyl-4-(4-fluorophenyl)pyrrolidine-1-carboxamide To a solution of cyclopropanecarboxylic acid (0.096 mL) and DPPA (0.26 mL) in toluene (5 mL) was added triethylamine (0.17 mL), and the mixture was stirred at 70° C. for 20 min. The reaction mixture was cooled, triethylamine (0.14 mL) and the compound (0.20 g) obtained in Example 144 were added, and the mixture was stirred at room temperature for 3 hr. The reaction mixture was cooled, diluted with ethyl acetate, washed with saturated aqueous sodium hydrogen carbonate solution, water and saturated brine, dried and concentrated under reduced pressure. The residue was purified by silica gel column chromatography (solvent gradient; 50→75% ethyl acetate/hexane) to give the title compound (0.18 g, 81%) as a white powder.
$^1$H-NMR(CDCl$_3$) δ 0.75-0.90 (2H, m), 0.95-1.05 (2H, m), 1.50-1.65 (1H, m), 2.59 (3H, s), 3.18-3.30 (4H, m), 3.35-3.65 (3H, m), 3.90-4.20 (2H, m), 4.90-5.00 (1H, m), 7.02-7.10 (2H, m), 7.14-7.30 (4H, m), 7.48-7.51 (1H, m)

Example 368

(3S,4R)-3-[{[3,5-bis(trifluoromethyl)phenyl](methyl)carbamoyl}(methyl)amino]-4-(4-fluorophenyl)-N-(methoxymethyl)pyrrolidine-1-carboxamide By reaction and purification in the same manner as in the method described in Example 367 and using the compound obtained in Example 144 and methoxyacetic acid, the title compound was obtained as a white powder.
$^1$H-NMR(CDCl$_3$) δ 2.57 (3H, s), 3.19 (3H, s), 3.25-3.60 (3H, m), 3.35 (3H, s), 3.81-3.95 (2H, m), 4.69 (2H, d, J=6.6 Hz), 4.88-4.98 (1H, m), 5.15 (1H, brs), 7.02-7.08 (2H, m), 7.19-7.24 (4H, m), 7.49 (1H, s)

Example 369

(3S,4R)-3-[{[3,5-bis(trifluoromethyl)phenyl](methyl)carbamoyl}(methyl)amino]-N-cyclopentyl-4-(4-fluorophenyl)pyrrolidine-1-carboxamide By reaction and purification in the same manner as in the method described in Example 365 and using the compound obtained in Example 144 and cyclopentyl isocyanate, the title compound was obtained as a white powder.
MS(ESI+): 575 (M+H)

Example 370

(3S,4R)-3-[{[3,5-bis(trifluoromethyl)phenyl] (methyl)carbamoyl}(methyl)amino]-N-tert-butyl-4-(4-fluorophenyl)pyrrolidine-1-carboxamide By reaction and purification in the same manner as in the method described in Example 365 and using the compound obtained in Example 144 and tert-butyl isocyanate, the title compound was obtained as a white powder.
MS(ESI+): 563 (M+H)

Example 371

(3S,4R)-3-[{[3,5-bis(trifluoromethyl)phenyl](methyl)carbamoyl}(methyl)amino]-4-(4-fluorophenyl)-N-(4-methoxyphenyl)pyrrolidine-1-carboxamide By reaction and purification in the same manner as in the method described in Example 365 and using the compound obtained in Example 144 and (4-methoxyphenyl) isocyanate, the title compound was obtained as a white powder.
MS(ESI+): 613 (M+H)

Example 372

(3S,4R)-3-[{[3,5-bis(trifluoromethyl)phenyl](methyl)carbamoyl}(methyl)amino]-4-(4-fluorophenyl)-N-(1-methylethyl)pyrrolidine-1-carboxamide By reaction and purification in the same manner as in the method described in Example 365 and using the compound obtained in Example 144 and isopropyl isocyanate, the title compound was obtained as a white powder.
MS(ESI+): 549 (M+H)

Example 373

(3S,4R)—N-[(acetylamino)methyl]-3-[{[3,5-bis(trifluoromethyl)phenyl](methyl)carbamoyl}(methyl) amino]-4-(4-fluorophenyl)pyrrolidine-1-carboxamide By reaction and purification in the same manner as in the method described in Example 367 and using the compound obtained in Example 144 and N-acetylglycine, the title compound was obtained as a white powder.
$^1$H-NMR(CDCl$_3$) δ 1.95-2.10 (3H, m), 2.50-2.65 (3H, m), 3.20-4.60&5.40-5.50 (total 11H, m), 4.86-4.99 (1H, m), 6.42-6.50&6.62-6.74 (total 1H, m), 7.00-7.12 (2H, m), 7.16-7.30 (4H, m), 7.49 (1H, s)

Example 374

(3S,4R)—N-(1-acetylpiperidin-4-yl)-3-[{[3,5-bis(trifluoromethyl)phenyl](methyl)carbamoyl}(methyl)amino]-4-(4-fluorophenyl)pyrrolidine-1-carboxamide By reaction and purification in the same manner as in the method described in Example 367 and using the compound obtained in Example 144 and 1-acetylpiperidine-4-carboxylic acid, the title compound was obtained as a white powder.
MS(ESI+): 632 (M+H)

Example 375

1-[3,5-bis(trifluoromethyl)phenyl]-3-[(3S,4R)-1-(cyclopropylsulfonyl)-4-(4-fluorophenyl)pyrrolidin-3-yl]-1,3-dimethylurea To a solution of the compound (0.20 g) obtained in Example 144 and cyclopropanesulfonyl chloride (0.061 mL) in DMF (5 mL) was added N,N-diisopropylethylamine (0.17 mL), and the mixture was stirred at room temperature for 5 hr. The reaction mixture was poured into water, and the mixture was extracted with ethyl acetate. The organic layer was washed with 10% aqueous citric acid solution and saturated brine, dried and concentrated under reduced pressure. The residue was purified by silica gel column chromatography (solvent gradient; 20→60% ethyl acetate/hexane) to give the title compound (0.19 g, 84%) as a white powder.
MS(ESI+): 568 (M+H)

Example 376

1-[3,5-bis(trifluoromethyl)phenyl]-3-{(3S,4R)-4-(4-fluorophenyl)-1-[(2,2,2-trifluoroethyl)sulfonyl]pyrrolidin-3-yl}-1,3-dimethylurea By reaction and purification in the same manner as in the method described in Example 375 and using the compound obtained in Example 144 and 2,2,2-trifluoroethanesulfonyl chloride, the title compound was obtained as a white powder.
MS(ESI+): 610 (M+H)

Example 377

1-[3,5-bis(trifluoromethyl)phenyl]-3-[(3S,4R)-4-(4-fluorophenyl)-1-(pyridin-3-ylsulfonyl)pyrrolidin-3-yl]-1,3-dimethylurea By reaction and purification in the same manner as in the method described in Example 375 and using the compound obtained in Example 144 and 3-pyridinesulfonyl chloride, the title compound was obtained as a white powder.
MS(ESI+): 605 (M+H)

Example 378

(3S,4R)-3-[{[3,5-bis(trifluoromethyl)phenyl](methyl)carbamoyl}(methyl)amino]-4-(4-fluorophenyl)-N-(tetrahydro-2H-pyran-4-yl)pyrrolidine-1-carboxamide By reaction and purification in the same manner as in the method described in Example 367 and using the compound obtained in Example 144 and tetrahydro-2H-pyran-4-carboxylic acid, the title compound was obtained as a white powder.
MS(ESI+): 591 (M+H)

Example 379 tert-butyl [trans-4-({[(3S,4R)-3-[{[3,5-bis(trifluoromethyl)phenyl](methyl)carbamoyl}(methyl)amino]-4-(4-fluorophenyl)pyrrolidin-1-yl]carbonyl}amino)cyclohexyl]carbamate By reaction and purification in the same manner as in the method described in Example 367 and using the compound obtained in Example 144 and trans-4-[(tert-butoxycarbonyl)amino]cyclohexanecarboxylic acid, the title compound was obtained as a white powder.
MS(ESI+): 704 (M+H)

Example 380

(3S,4R)—N-(trans-4-aminocyclohexyl)-3-[{[3,5-bis(trifluoromethyl)phenyl](methyl)carbamoyl}(methyl)amino]-4-(4-fluorophenyl)pyrrolidine-1-carboxamide monohydrochloride By reaction and purification in the same manner as in the method described in Example 3 and using the compound obtained in Example 379, the title compound was obtained.
MS(ESI+): 604 (M−HCl+H)

Example 381 methyl [trans-4-({[(3S,4R)-3-[{[3,5-bis(trifluoromethyl)phenyl](methyl)carbamoyl}(methyl)amino]-4-(4-fluorophenyl)pyrrolidin-1-yl]carbonyl}amino)cyclohexyl] carbamate By reaction and purification in the same manner as in the method described in Example 75 and using the compound obtained in Example 380 and methyl chlorocarbonate, the title compound was obtained.
MS(ESI+): 662 (M+H)

Example 382 ethyl [trans-4-({[(3S,4R)-3-[{[3,5-bis(trifluoromethyl)phenyl](methyl)carbamoyl}(methyl)amino]-4-(4-fluorophenyl)pyrrolidin-1-yl]carbonyl}amino)cyclohexyl]carbamate By reaction and purification in the same manner as in the method described in Example 75 and using the compound obtained in Example 380 and ethyl chlorocarbonate, the title compound was obtained.
MS(ESI+): 676 (M+H)

Example 383

1-[3,5-bis(trifluoromethyl)phenyl]-3-[(3S,4R)-4-(4-fluorophenyl)-1-(pyrrolidin-1-ylcarbonyl)pyrrolidin-3-yl]-1,3-dimethylurea By reaction and purification in the same manner as in the method described in Example 420 and using the compound obtained in Example 362 and pyrrolidine, the title compound was obtained.
MS(ESI+): 561 (M+H)

Example 384

1-[3,5-bis(trifluoromethyl)phenyl]-3-[(3S,4R)-4-(4-fluorophenyl)-1-(morpholin-4-ylcarbonyl)pyrrolidin-3-yl]-1,3-dimethylurea By reaction and purification in the same manner as in the method described in Example 420 and using the compound obtained in Example 362 and morpholine, the title compound was obtained.
MS(ESI+): 577 (M+H)

Example 385

1-[3,5-bis(trifluoromethyl)phenyl]-3-[(3S,4R)-4-(4-fluorophenyl)-1-(thiomorpholin-4-ylcarbonyl)pyrrolidin-3-yl]-1,3-dimethylurea By reaction and purification in the same manner as in the method described in Example 420 and using the compound obtained in Example 362 and thiomorpholine, the title compound was obtained.
MS(ESI+): 593 (M+H)

Example 386

1-[3,5-bis(trifluoromethyl)phenyl]-3-[(3S,4R)-1-[(4,4-difluoropiperidin-1-yl)carbonyl]-4-(4-fluorophenyl)pyrrolidin-3-yl]-1,3-dimethylurea By reaction and purification in the same manner as in the method described in Example 420 and using the compound obtained in Example 362 and 4,4-difluoropiperidine, the title compound was obtained.
MS(ESI+): 611 (M+H)

Example 387

(3S,4R)-3-[{[3,5-bis(trifluoromethyl)phenyl](methyl)carbamoyl}(methyl)amino]-4-(4-fluorophenyl)-N-{trans-4-[5-(trifluoromethyl)-1H-tetrazol-1-yl]cyclohexyl}pyrrolidine-1-carboxamide By reaction and purification in the same manner as in the method described in Example 367 and using the compound obtained in Example 144 and the compound obtained in Reference Example 40, the title compound was obtained.
MS(ESI+): 725 (M+H)

Example 388

(3S,4R)-3-[{[3,5-bis(trifluoromethyl)phenyl](methyl)carbamoyl}(methyl)amino]-N-(4,4-difluorocyclohexyl)-4-(4-fluorophenyl)pyrrolidine-1-carboxamide By reaction and purification in the same manner as in the method described in Example 367 and using the compound obtained in Example 144 and 4,4-difluorocyclohexanecarboxylic acid, the title compound was obtained.
MS(ESI+): 625 (M+H)

Example 389

(3S,4R)-3-[{[3,5-bis(trifluoromethyl)phenyl](methyl)carbamoyl}(methyl)amino]-4-(4-fluorophenyl)-N-(tetrahydro-2H-thiopyran-4-yl)pyrrolidine-1-carboxamide By reaction and purification in the same manner as in the method described in Example 367 and using the compound obtained in Example 144 and tetrahydro-2H-thiopyran-4-carboxylic acid, the title compound was obtained.
MS(ESI+): 607 (M+H)

Example 390

(3S,4R)-3-[{[3,5-bis(trifluoromethyl)phenyl](methyl)carbamoyl}(methyl)amino]-N-(1,1-dioxidetetrahydro-2H-thiopyran-4-yl)-4-(4-fluorophenyl)pyrrolidine-1-carboxamide By reaction and purification in the same manner as in the method described in Example 128 and using the compound obtained in Example 389, the title compound was obtained.
MS(ESI+): 639 (M+H)

Example 391 tert-butyl 4-({[(3S,4R)-3-[{[3,5-bis(trifluoromethyl)phenyl](methyl)carbamoyl}(methyl)amino]-4-(4-fluorophenyl)pyrrolidin-1-yl]carbonyl}amino)-4-methylpiperidine-1-carboxylate By reaction and purification in the same manner as in the method described in Example 367 and using the compound obtained in Example 144 and 1-(tert-butoxycarbonyl)-4-methylpiperidine-4-carboxylic acid, the title compound was obtained.
MS(ESI+): 604 (M−Boc+2H)

Example 392

(3S,4R)-3-[{[3,5-bis(trifluoromethyl)phenyl](methyl)carbamoyl}(methyl)amino]-4-(4-fluorophenyl)-N-(4-methylpiperidin-4-yl)pyrrolidine-1-carboxamide monohydrochloride By reaction and purification in the same manner as in the method described in Example 3 and using the compound obtained in Example 391, the title compound was obtained.
MS(ESI+): 604 (M−HCl+H)

Example 393

(3S,4R)—N-(1-acetyl-4-methylpiperidin-4-yl)-3-[{[3,5-bis(trifluoromethyl)phenyl](methyl)carbamoyl}(methyl)amino]-4-(4-fluorophenyl)pyrrolidine-1-carboxamide By reaction and purification in the same manner as in the method described in Example 75 and using the compound obtained in Example 392, the title compound was obtained.
MS(ESI+): 646 (M+H)

Example 394 methyl 4-({[(3S,4R)-3-[{[3,5-bis(trifluoromethyl) phenyl](methyl)carbamoyl}(methyl)amino]-4-(4-fluorophenyl)pyrrolidin-1-yl]carbonyl}amino)-4-methylpiperidine-1-carboxylate By reaction and purification in the same manner as in the method described in Example 75 and using the compound obtained in Example 392 and methyl chlorocarbonate, the title compound was obtained.

MS(ESI+): 662 (M+H)

Example 395

1-[(3S,4R)-1-[5-(1-acetylpiperidin-4-yl)-1,3,4-oxadiazol-2-yl]-4-(4-fluorophenyl)pyrrolidin-3-yl]-3-[3,5-bis(trifluoromethyl)phenyl]-1,3-dimethylurea (Step 1)

A mixture of the compound (0.12 g) obtained in Example 144, the compound (0.082 g) obtained in Reference Example 42, N,N-diisopropylethylamine (0.090 mL) and DMSO (4.0 mL) was stirred at 80° C. for 14 hr. The mixture was diluted with water, and extracted with ethyl acetate. The extract was washed with water and saturated brine, and the aqueous layer was extracted again with ethyl acetate. The combined organic layer was dried, and concentrated under reduced pressure. The residue was purified by silica gel column chromatography (solvent gradient; 5→100% ethyl acetate/hexane) to give tert-butyl 4-{5-[(3S,4R)-3-[{[3,5-bis(trifluoromethyl)phenyl](methyl)carbamoyl}(methyl)amino]-4-(4-fluorophenyl)pyrrolidin-1-yl]-1,3,4-oxadiazol-2-yl}piperidine-1-carboxylate (0.10 g, 62%) as a brown oil.

MS(ESI+): 715 (M+H)

(Step 2)

A mixture of the compound (0.10 g) obtained in step 1 and 2N hydrogen chloride/2-propanol was stirred at room temperature for 3 days. The mixture was concentrated under reduced pressure, and to the residue were added acetyl chloride (0.016 mL), triethylamine (0.071 mL) and acetonitrile (4.0 mL), and the mixture was stirred at room temperature for 3 hr. The mixture was diluted with ethyl acetate, washed with saturated aqueous sodium hydrogen carbonate solution and saturated brine, dried and concentrated under reduced pressure. The residue was purified by silica gel column chromatography (NH Chromatorex) (solvent gradient; 50→100% ethyl acetate/hexane) to give the title compound (0.041 g, 43%) as a pale-brown powder.

MS(ESI+): 657 (M+H)

Example 396

N-{2-[(3S,4R)-3-[{[3,5-bis(trifluoromethyl)phenyl](methyl)carbamoyl}(methyl)amino]-4-(3,4-difluorophenyl)pyrrolidin-1-yl]-2-oxoethyl}benzamide By reaction and purification in the same manner as in the method described in Example 4 and using the compound obtained in Example 151 and hippuric acid, the title compound was obtained as a white powder.

MS(ESI+): 643 (M+H)

Example 397

1-[3,5-bis(trifluoromethyl)phenyl]-3-[(3S,4R)-4-(3,4-difluorophenyl)-1-(tetrahydro-2H-pyran-4-ylcarbonyl)pyrrolidin-3-yl]-1,3-dimethylurea By reaction and purification in the same manner as in the method described in Example 4 and using the compound obtained in Example 151 and tetrahydro-2H-pyran-4-carboxylic acid, the title compound was obtained.

MS(ESI+): 594 (M+H)

Example 398 methyl (trans-4-{[(3S,4R)-3-[{[3,5-bis(trifluoromethyl)phenyl](methyl)carbamoyl}(methyl)amino]-4-(3,4-difluorophenyl)pyrrolidin-1-yl]carbonyl}cyclohexyl)carbamate By reaction and purification in the same manner as in the method described in Example 4 and using the compound obtained in Example 151 and trans-4-[(methoxycarbonyl)amino]cyclohexanecarboxylic acid, the title compound was obtained.

MS(ESI+): 665 (M+H)

Example 399

1-[3,5-bis(trifluoromethyl)phenyl]-3-[(3S,4R)-1-[(4,4-difluorocyclohexyl)carbonyl]-4-(3,4-difluorophenyl)pyrrolidin-3-yl]-1,3-dimethylurea By reaction and purification in the same manner as in the method described in Example 4 and using the compound obtained in Example 151 and 4,4-difluorocyclohexanecarboxylic acid, the title compound was obtained.

MS(ESI+): 628 (M+H)

Example 400

1-[3,5-bis(trifluoromethyl)phenyl]-3-[(3S,4R)-4-(3,4-difluorophenyl)-1-({trans-4-[5-(trifluoromethyl)-1H-tetrazol-1-yl]cyclohexyl}carbonyl)pyrrolidin-3-yl]-1,3-dimethylurea By reaction and purification in the same manner as in the method described in Example 4 and using the compound obtained in Example 151 and the compound obtained in Reference Example 40, the title compound was obtained.

MS(ESI+): 728 (M+H)

Example 401 methyl (trans-4-{[(3S,4R)-3-[{[3,5-bis(trifluoromethyl)phenyl](methyl)carbamoyl}(methyl)amino]-4-(2,4-difluorophenyl)pyrrolidin-1-yl]carbonyl}cyclohexyl)carbamate By reaction and purification in the same manner as in the method described in Example 4 and using the compound obtained in Example 155 and trans-4-[(methoxycarbonyl)amino]cyclohexanecarboxylic acid, the title compound was obtained.

MS(ESI+): 665 (M+H)

Example 402

1-[3,5-bis(trifluoromethyl)phenyl]-3-[(3S,4R)-4-(2,
4-difluorophenyl)-1-(tetrahydro-2H-pyran-4-ylcarbonyl)pyrrolidin-3-yl]-1,3-dimethylurea By reaction and purification in the same manner as in the method described in Example 4 and using the compound obtained in Example 155 and tetrahydro-2H-pyran-4-carboxylic acid, the title compound was obtained.
MS(ESI+): 594 (M+H)

Example 403

1-[3,5-bis(trifluoromethyl)phenyl]-3-[(3S,4R)-1-[(4,
4-difluorocyclohexyl)carbonyl]-4-(2,4-difluorophenyl)pyrrolidin-3-yl]-1,3-dimethylurea By reaction and purification in the same manner as in the method described in Example 4 and using the compound obtained in Example 155 and 4,4-difluorocyclohexanecarboxylic acid, the title compound was obtained.
MS(ESI+): 628 (M+H)

Example 404

1-[3,5-bis(trifluoromethyl)phenyl]-3-[(3S,4R)-4-(2,
4-difluorophenyl)-1-({trans-4-[5-(trifluoromethyl)-
1H-tetrazol-1-yl]cyclohexyl}carbonyl)pyrrolidin-3-
yl]-1,3-dimethylurea By reaction and purification in the same manner as in the method described in Example 4 and using the compound obtained in Example 155 and the compound obtained in Reference Example 40, the title compound was obtained.
MS(ESI+): 728 (M+H)

Example 405 methyl (trans-4-{[(3S,4R)-3-[{[3-bromo-5-(trifluoromethyl)phenyl](methyl)carbamoyl}(methyl)
amino]-4-(4-fluorophenyl)pyrrolidin-1-yl]
carbonyl}cyclohexyl)carbamate By reaction and purification in the same manner as in the method described in Example 4 and using the compound obtained in Example 163 and, trans-4-[(methoxycarbonyl)amino]cyclohexanecarboxylic acid, the title compound was obtained.
MS(ESI+): 657 (M+H)

Example 406

1-[3-bromo-5-(trifluoromethyl)phenyl]-3-[(3S,4R)-
1-[(4,4-difluorocyclohexyl)carbonyl]-4-(4-fluorophenyl)pyrrolidin-3-yl]-1,3-dimethylurea By reaction and purification in the same manner as in the method described in Example 4 and using the compound obtained in Example 163 and 4,4-difluorocyclohexanecarboxylic acid, the title compound was obtained.
MS(ESI+): 620 (M+H)

Example 407

1-[3-bromo-5-(trifluoromethyl)phenyl]-3-[(3S,4R)-
4-(4-fluorophenyl)-1-(tetrahydro-2H-pyran-4-ylcarbonyl)pyrrolidin-3-yl]-1,3-dimethylurea By reaction and purification in the same manner as in the method described in Example 4 and using the compound obtained in Example 163 and tetrahydro-2H-pyran-4-carboxylic acid, the title compound was obtained.
MS(ESI+): 586 (M+H)

Example 408

1-[3-bromo-5-(trifluoromethyl)phenyl]-3-[(3S,4R)-
4-(4-fluorophenyl)-1-({trans-4-[5-(trifluoromethyl)-
1H-tetrazol-1-yl]cyclohexyl}carbonyl)pyrrolidin-3-
yl]-1,3-dimethylurea By reaction and purification in the same manner as in the method described in Example 4 and using the compound obtained in Example 163 and the compound obtained in Reference Example 40, the title compound was obtained.
MS(ESI+): 720 (M+H)

Example 409 methyl (trans-4-{[(3S,4R)-3-{[(3,5-dibromophenyl)
(methyl)carbamoyl](methyl)amino}-4-(4-fluorophenyl)pyrrolidin-1-yl]carbonyl}cyclohexyl)carbamate By reaction and purification in the same manner as in the method described in Example 4 and using the compound obtained in Example 167 and trans-4-[(methoxycarbonyl)amino]cyclohexanecarboxylic acid, the title compound was obtained.
MS(ESI+): 669 (M+H)

Example 410

1-(3,5-dibromophenyl)-3-[(3S,4R)-1-[(4,4-difluorocyclohexyl)carbonyl]-4-(4-fluorophenyl)pyrrolidin-
3-yl]-1,3-dimethylurea By reaction and purification in the same manner as in the method described in Example 4 and using the compound obtained in Example 167 and 4,4-difluorocyclohexanecarboxylic acid, the title compound was obtained.
MS(ESI+): 632 (M+H)

Example 411

1-(3,5-dibromophenyl)-3-[(3S,4R)-4-(4-fluorophenyl)-1-(tetrahydro-2H-pyran-4-ylcarbonyl)pyrrolidin-3-yl]-1,3-dimethylurea By reaction and purification in the same manner as in the method described in Example 4 and using the compound obtained in Example 167 and tetrahydro-2H-pyran-4-carboxylic acid, the title compound was obtained.
MS(ESI+): 598 (M+H)

Example 412 methyl (trans-4-{[(3S,4R)-3-[{[3-chloro-5-(trifluoromethyl)phenyl](methyl)carbamoyl}(methyl)amino]-4-(4-fluorophenyl)pyrrolidin-1-yl]carbonyl}cyclohexyl)carbamate By reaction and purification in the same manner as in the method described in Example 4 and using the compound obtained in Example 171 and trans-4-[(methoxycarbonyl)amino]cyclohexanecarboxylic acid, the title compound was obtained.
MS(ESI+): 613 (M+H)

Example 413

1-[3-chloro-5-(trifluoromethyl)phenyl]-3-[(3S,4R)-1-[(4,4-difluorocyclohexyl)carbonyl]-4-(4-fluorophenyl)pyrrolidin-3-yl]-1,3-dimethylurea By reaction and purification in the same manner as in the method described in Example 4 and using the compound obtained in Example 171 and 4,4-difluorocyclohexanecarboxylic acid, the title compound was obtained.
MS(ESI+): 576 (M+H)

Example 414

1-[3-chloro-5-(trifluoromethyl)phenyl]-3-[(3S,4R)-4-(4-fluorophenyl)-1-(tetrahydro-2H-pyran-4-ylcarbonyl)pyrrolidin-3-yl]-1,3-dimethylurea By reaction and purification in the same manner as in the method described in Example 4 and using the compound obtained in Example 171 and tetrahydro-2H-pyran-4-carboxylic acid, the title compound was obtained.
MS(ESI+): 542 (M+H)

Example 415

1-[3-chloro-5-(trifluoromethyl)phenyl]-3-[(3S,4R)-4-(4-fluorophenyl)-1-({trans-4-[5-(trifluoromethyl)-1H-tetrazol-1-yl]cyclohexyl}carbonyl)pyrrolidin-3-yl]-1,3-dimethylurea By reaction and purification in the same manner as in the method described in Example 4 and using the compound obtained in Example 171 and the compound obtained in Reference Example 40, the title compound was obtained.
MS(ESI+): 676 (M+H)

Example 416 methyl (trans-4-{[(3S,4R)-3-{[(3,5-dichlorophenyl)(methyl)carbamoyl](methyl)amino}-4-(4-fluorophenyl)pyrrolidin-1-yl]carbonyl}cyclohexyl)carbamate By reaction and purification in the same manner as in the method described in Example 4 and using the compound obtained in Example 175 and trans-4-[(methoxycarbonyl)amino]cyclohexanecarboxylic acid, the title compound was obtained.
MS(ESI+): 579 (M+H)

Example 417

1-(3,5-dichlorophenyl)-3-[(3S,4R)-1-[(4,4-difluorocyclohexyl)carbonyl]-4-(4-fluorophenyl)pyrrolidin-3-yl]-1,3-dimethylurea By reaction and purification in the same manner as in the method described in Example 4 and using the compound obtained in Example 175 and 4,4-difluorocyclohexanecarboxylic acid, the title compound was obtained.
MS(ESI+): 542 (M+H)

Example 418

1-(3,5-dichlorophenyl)-3-[(3S,4R)-4-(4-fluorophenyl)-1-(tetrahydro-2H-pyran-4-ylcarbonyl)pyrrolidin-3-yl]-1,3-dimethylurea By reaction and purification in the same manner as in the method described in Example 4 and using the compound obtained in Example 175 and tetrahydro-2H-pyran-4-carboxylic acid, the title compound was obtained.
MS(ESI+): 508 (M+H)

Example 419

4-nitrophenyl (3S,4R)-3-{[(3,5-dichlorophenyl)(methyl)carbamoyl](methyl)amino}-4-(4-fluorophenyl)pyrrolidine-1-carboxylate The compound (0.34 g) obtained in Example 175 was dissolved in THF (5 mL), 4-nitrophenyl chlorocarbonate (0.17 g) and N,N-diisopropylethylamine (0.15 mL) were added dropwise at 5° C. The reaction mixture was stirred at 5° C. for 1 hr, poured into saturated aqueous ammonium chloride solution, and the mixture was extracted with ethyl acetate. The extract was washed with water and saturated brine, dried and concentrated under reduced pressure. The residue was purified by silica gel column chromatography (solvent gradient; 30→50% ethyl acetate/hexane) to give the title compound (0.99 g, 90%) as a white powder.
MS(ESI+): 561 (M+H)

Example 420

1-(3,5-dichlorophenyl)-3-[(3S,4R)-4-(4-fluorophenyl)-1-{[4-(methylsulfonyl)piperazin-1-yl]carbonyl}pyrrolidin-3-yl]-1,3-dimethylurea A solution of the compound (0.31 g) obtained in Example 419 and 1-(methylsulfonyl)piperazine (0.14 g) in 1-methyl-2-pyrrolidone (5 mL) was stirred at 110° C. for 24 hr and at 135° C. for 14 hr. The reaction mixture was poured into water, and extracted twice with ethyl acetate. The extract was washed with saturated aqueous ammonium chloride solution and saturated brine, dried and concentrated. The residue was purified by silica gel column chromatography (solvent gradient; 75→100% ethyl acetate/hexane) to give the title compound (0.16 g, 48%) as a pale-yellow powder.
MS(ESI+): 586 (M+H)

Example 421 methyl (trans-4-{[(3R,4S)-3-(4-fluorophenyl)-4-([methyl]{(methyl)[3-methyl-5-(trifluoromethyl)phenyl]carbamoyl}amino)pyrrolidin-1-yl]carbonyl}cyclohexyl)carbamate By reaction and purification in the same manner as in the method described in Example 4 and using the compound obtained in Example 179 and trans-4-[(methoxycarbonyl)amino]cyclohexanecarboxylic acid, the title compound was obtained.
MS(ESI+): 593 (M+H)

Example 422

1-[(3S,4R)-1-[(4,4-difluorocyclohexyl)carbonyl]-4-(4-fluorophenyl)pyrrolidin-3-yl]-1,3-dimethyl-3-[3-methyl-5-(trifluoromethyl)phenyl]urea By reaction and purification in the same manner as in the method described in Example 4 and using the compound obtained in Example 179 and 4,4-difluorocyclohexanecarboxylic acid, the title compound was obtained.
MS(ESI+): 556 (M+H)

Example 423

1-[(3S,4R)-4-(4-fluorophenyl)-1-(tetrahydro-2H-pyran-4-ylcarbonyl)pyrrolidin-3-yl]-1,3-dimethyl-3-[3-methyl-5-(trifluoromethyl)phenyl]urea By reaction and purification in the same manner as in the method described in Example 4 and using the compound obtained in Example 179 and tetrahydro-2H-pyran-4-carboxylic acid, the title compound was obtained.
MS(ESI+): 522 (M+H)

Example 424 methyl (trans-4-{[(3S,4R)-3-[{[3,5-bis(trifluoromethyl)phenyl](methyl)carbamoyl}(methyl)amino]-4-(5-fluoropyridin-2-yl)pyrrolidin-1-yl]carbonyl}cyclohexyl)carbamate By reaction and purification in the same manner as in the method described in Example 4 and using the compound obtained in Example 191 and trans-4-[(methoxycarbonyl)amino]cyclohexanecarboxylic acid, the title compound was obtained.
MS(ESI+): 648 (M+H)

Example 425

1-[3,5-bis(trifluoromethyl)phenyl]-3-[(3S,4R)-4-(5-fluoropyridin-2-yl)-1-({trans-4-[5-(trifluoromethyl)-1H-tetrazol-1-yl]cyclohexyl}carbonyl)pyrrolidin-3-yl]-1,3-dimethylurea To a solution of the compound (0.18 g) obtained in Example 191, the compound (0.10 g) obtained in Reference Example 40, WSC.HCl (0.081 g) and HOBt (0.047 g) in acetonitrile (6.0 mL) was added triethylamine (0.12 and the mixture was stirred at room temperature for 5 hr. The reaction mixture was diluted with ethyl acetate, washed with saturated aqueous sodium hydrogen carbonate solution, water and saturated brine and dried, and the solvent was evaporated under reduced pressure. The obtained residue was purified by silica gel column chromatography (NH Chromatorex) (solvent gradient; 0→60% ethyl acetate/hexane) and recrystallized from ethyl acetate/hexane to give the title compound (0.21 g, 85%) as a white powder.
MS(ESI+): 711 (M+H)
$^1$H-NMR(CDCl$_3$) δ 1.70-1.97 (2H, m), 1.97-2.34 (6H, m), 2.54 (1H, tt, J=11.8, 3.2 Hz), 2.63 (3H, d, J=7.5 Hz), 3.24 (3H, d, J=13.6 Hz), 3.34-4.21 (5H, m), 4.45-4.67 (1H, m), 4.89-5.24 (1H, m), 7.13-7.33 (3H, m), 7.33-7.48 (1H, m), 7.52 (1H, brs), 8.43 (1H, dd, J=6.6, 2.8 Hz)
$[\alpha]_D^{25}$ −89.7° (c0.27, MeOH)

Example 426 methyl [trans-4-({[(3S,4R)-3-[{[3,5-bis(trifluoromethyl)phenyl](methyl)carbamoyl}(methyl)amino]-4-(5-fluoropyridin-2-yl)pyrrolidin-1-yl]carbonyl}amino)cyclohexyl]carbamate By reaction and purification in the same manner as in the method described in Example 367 and using the compound obtained in Example 191 and trans-4-[(methoxycarbonyl)amino]cyclohexanecarboxylic acid, the title compound was obtained.
MS(ESI+): 663 (M+H)

Example 427

(3S,4R)-3-[{[3,5-bis(trifluoromethyl)phenyl](methyl)carbamoyl}(methyl)amino]-N-(4,4-difluorocyclohexyl)-4-(5-fluoropyridin-2-yl)pyrrolidine-1-carboxamide By reaction and purification in the same manner as in the method described in Example 367 and using the compound obtained in Example 191 and 4,4-difluorocyclohexanecarboxylic acid, the title compound was obtained.
$^1$H-NMR(CDCl$_3$) δ 1.33-1.62 (2H, m), 1.71-2.24 (6H, m), 2.64 (3H, s), 3.22 (3H, s), 3.31-3.51 (2H, m), 3.64-3.97 (4H, m), 4.04 (1H, d, J=7.6 Hz), 4.98-5.20 (1H, m), 7.13-7.31 (3H, m), 7.38 (1H, td, J=8.3, 3.0 Hz), 7.50 (1H, s), 8.40 (1H, d, J=2.7 Hz)

Example 428

1-[3,5-bis(trifluoromethyl)phenyl]-3-[(3S,4R)-4-(4-fluorophenyl)-1-(tetrahydro-2H-pyran-4-ylcarbonyl)pyrrolidin-3-yl]imidazolidin-2-one By reaction and purification in the same manner as in the method described in Example 4 and using the compound obtained in Example 194 and tetrahydro-2H-pyran-4-carboxylic acid, the title compound was obtained.
MS(ESI+): 574 (M+H)

Example 429 tert-butyl (trans-4-{[(3S,4R)-3-{3-[3,5-bis(trifluoromethyl)phenyl]-2-oxoimidazolidin-1-yl}-4-(4-fluorophenyl)pyrrolidin-1-yl]carbonyl}cyclohexyl)carbamate By reaction and purification in the same manner as in the method described in Example 4 and using the compound obtained in Example 194 and trans-4-[(tert-butoxycarbonyl)amino]cyclohexanecarboxylic acid, the title compound was obtained.
MS(ESI+): 687 (M+H)

Example 430

1-[(3S,4R)-1-[(trans-4-aminocyclohexyl)carbonyl]-4-(4-fluorophenyl)pyrrolidin-3-yl]-3-[3,5-bis(trifluoromethyl)phenyl]imidazolidin-2-one monohydrochloride By reaction and purification in the same manner as in the method described in Example 3 and using the compound obtained in Example 429, the title compound was obtained.
MS(ESI+): 587 (M−HCl+H)

Example 431 methyl (trans-4-{[(3S,4R)-3-{3-[3,5-bis(trifluoromethyl)phenyl]-2-oxoimidazolidin-1-yl}-4-(4-fluorophenyl)pyrrolidin-1-yl]carbonyl}cyclohexyl)carbamate By reaction and purification in the same manner as in the method described in Example 75 and using the compound obtained in Example 430 and methyl chlorocarbonate, the title compound was obtained.
MS(ESI+): 645 (M+H)

Example 432

N-(trans-4-{[(3S,4R)-3-{3-[3,5-bis(trifluoromethyl)phenyl]-2-oxoimidazolidin-1-yl}-4-(4-fluorophenyl)pyrrolidin-1-yl]carbonyl}cyclohexyl)-6-fluoropyridine-2-carboxamide By reaction and purification in the same manner as in the method described in Example 4 and using the compound obtained in Example 430 and 6-fluoropyridine-2-carboxylic acid, the title compound was obtained.
MS(ESI+): 710 (M+H)

The compounds of Reference Examples 105 to 432 are as described below (Tables B-10 to B-37).

TABLE B-10

TABLE B-10-continued

| Ex. No. | R¹ | A | B | R² / L-D | additive |
|---|---|---|---|---|---|
| 107 | tert-butyl acetate group | (±)- 1-methyl-3,4-dimethylpiperidinyl | 4-CF₃-phenyl | N,N'-dimethyl-N'-(3,5-bis(trifluoromethyl)phenyl)urea | |
| 108 | H | (±)- 1-methyl-3,4-dimethylpiperidinyl | 4-CF₃-phenyl | N,N'-dimethyl-N'-(3,5-bis(trifluoromethyl)phenyl)urea | HCl |
| 109 | 1-acetylpiperidin-4-yl carbonyl | (±)- 1-methyl-3,4-dimethylpiperidinyl | 4-CF₃-phenyl | N,N'-dimethyl-N'-(3,5-bis(trifluoromethyl)phenyl)urea | |
| 110 | tert-butyl acetate group | (R,R)- 1-methyl-3,4-dimethylpiperidinyl | 4-F-phenyl | N,N'-dimethyl-N'-(4'-chloro-4-(trifluoromethoxy)biphenyl-3-yl)urea | |
| 111 | H | (R,R)- 1-methyl-3,4-dimethylpiperidinyl | 4-F-phenyl | N,N'-dimethyl-N'-(4'-chloro-4-(trifluoromethoxy)biphenyl-3-yl)urea | HCl |

TABLE B-10-continued

| Ex. No. | R¹ | A | B | R² | additive |
|---|---|---|---|---|---|
| 112 | 1-acetylpiperidin-4-yl carbonyl | (3R,4R)-1-methylpiperidine | 4-fluorophenyl | N,N',N'-trimethyl-N-(4'-chloro-6-methoxy-[1,1'-biphenyl]-3-yl-OCF₃)urea | |
| 113 | tert-butoxycarbonylmethyl | (3R,4R)-1-methylpiperidine | 4-fluorophenyl | 3-methyl-1-(3,5-bis(trifluoromethyl)phenyl)imidazolidin-2-one | |
| 114 | H | (3R,4R)-1-methylpiperidine | 4-fluorophenyl | 3-methyl-1-(3,5-bis(trifluoromethyl)phenyl)imidazolidin-2-one | HCl |
| 115 | 1-acetylpiperidin-4-yl carbonyl | (3R,4R)-1-methylpiperidine | 4-fluorophenyl | 3-methyl-1-(3,5-bis(trifluoromethyl)phenyl)imidazolidin-2-one | |
| 116 | 4,4-difluorocyclohexylcarbonyl | (3R,4R)-1-methylpiperidine | 4-fluorophenyl | N,N,N'-trimethyl-N'-(3,5-bis(trifluoromethyl)phenyl)urea | |

TABLE B-11
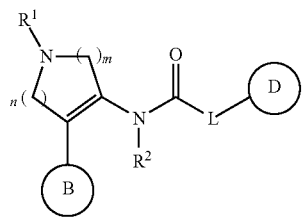
| Ex. No. | R¹ | A | B | R² | additive |
|---|---|---|---|---|---|
| 117 | 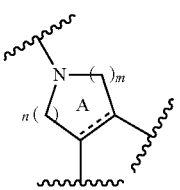 | 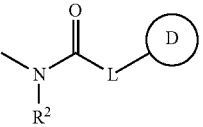 | 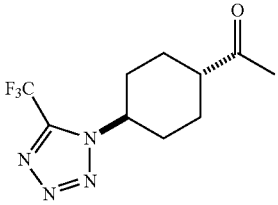 | 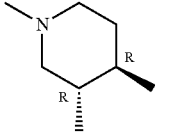 | |
| 118 | 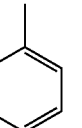 | 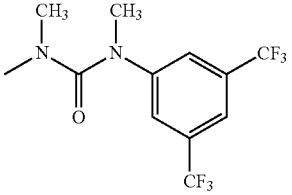 | 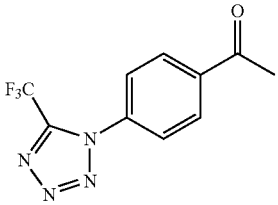 | 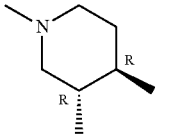 | |
| 119 | 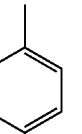 | 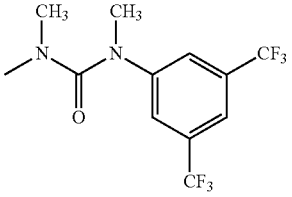 | 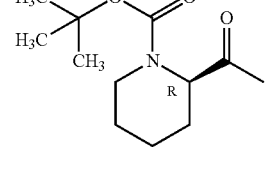 | 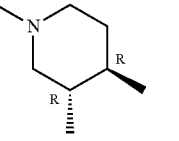 | |
| 120 | 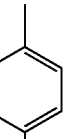 | 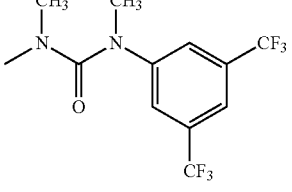 | 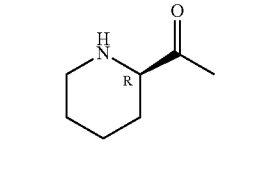 | 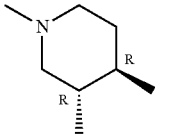 | HCl |
| 121 | 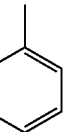 | 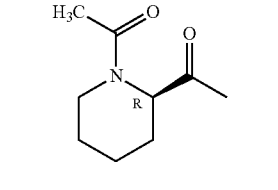 | 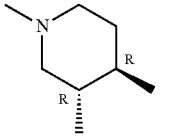 | 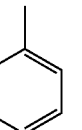 | |

TABLE B-11-continued
| Ex. No. | R¹ | A | B | L-D / R² | additive |
|---|---|---|---|---|---|
| 122 | 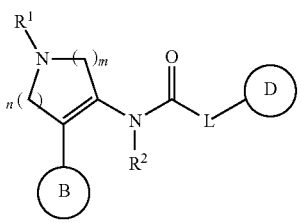 | 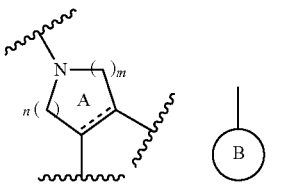 | 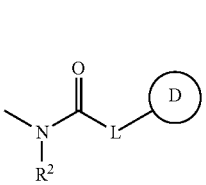 | 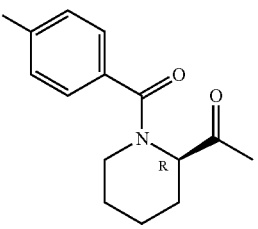 | |
| 123 | 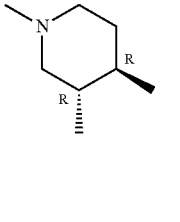 | 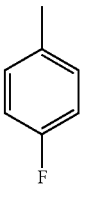 | 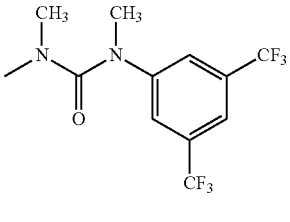 | 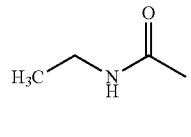 | |
| 124 | 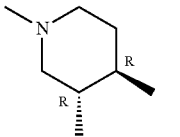 | 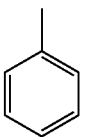 | 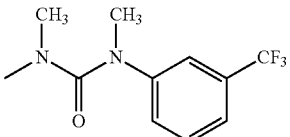 | 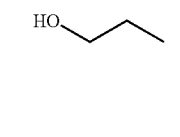 | HCl |
| 125 | 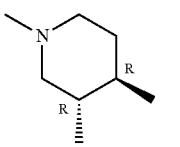 | 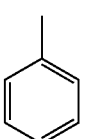 | 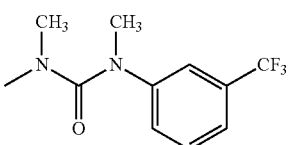 | 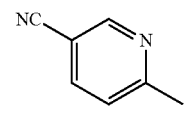 | |
| 126 | 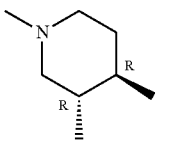 | 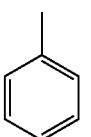 | 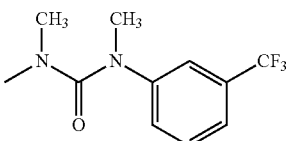 | 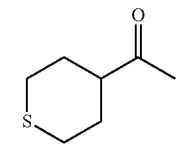 | |

TABLE B-11-continued

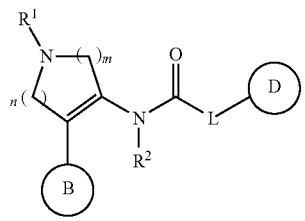

| Ex. No. | R¹ | [ring A] | B | [amide group] | additive |
|---|---|---|---|---|---|
| 127 | (1-oxo-tetrahydrothiopyran-4-yl)carbonyl | 1-methyl-3,4-dimethylpiperidin-4-yl | 4-fluorophenyl | N,N'-dimethyl-N'-(3,5-bis(trifluoromethyl)phenyl)urea-N-methyl | |
| 128 | (1,1-dioxo-tetrahydrothiopyran-4-yl)carbonyl | 1-methyl-3,4-dimethylpiperidin-4-yl | 4-fluorophenyl | N,N'-dimethyl-N'-(3,5-bis(trifluoromethyl)phenyl)urea-N-methyl | |

TABLE B-12

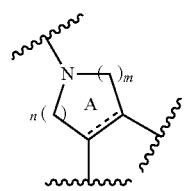

| Ex. No. | R¹ | [ring A] | B | [amide group] | additive |
|---|---|---|---|---|---|
| 129 | (1-methyl-2,6-dioxopiperidin-4-yl)carbonyl | 1-methyl-3,4-dimethylpiperidin-4-yl | 4-fluorophenyl | N,N'-dimethyl-N'-(3,5-bis(trifluoromethyl)phenyl)urea-N-methyl | |

TABLE B-12-continued

| Ex. No. | R¹ | A (pyrrolidine) | B | R² / urea-D | additive |
|---|---|---|---|---|---|
| 130a | H₃C-C(CH₃)₂-O-C(O)-CH₂- | N-methyl pyrrolidine (3R,4S) | 3,4-dichlorophenyl | CH₃-NH-C(O)-NH-(3,5-bis(CF₃)phenyl) | |
| 130b | H₃C-C(CH₃)₂-O-C(O)-CH₂- | N-methyl pyrrolidine (3S,4R) | 3,4-dichlorophenyl | CH₃-NH-C(O)-NH-(3,5-bis(CF₃)phenyl) | |
| 131 | H₃C-C(CH₃)₂-O-C(O)-CH₂- | N-methyl pyrrolidine (3R,4S) | 3,4-dichlorophenyl | CH₃-NH-C(O)-NH-(3,5-bis(CF₃)phenyl) | |
| 132 | H₃C-C(CH₃)₂-O-C(O)-CH₂- | N-methyl pyrrolidine (3R,4S) | 3,4-dichlorophenyl | CH₃-N-C(O)-N(CH₃)-(3,5-bis(CF₃)phenyl) | |
| 133 | H | N-methyl pyrrolidine (3R,4S) | 3,4-dichlorophenyl | CH₃-N-C(O)-N(CH₃)-(3,5-bis(CF₃)phenyl) | HCl |
| 134 | 1-acetyl-piperidin-4-yl-C(O)- | N-methyl pyrrolidine (3R,4S) | 3,4-dichlorophenyl | CH₃-N-C(O)-N(CH₃)-(3,5-bis(CF₃)phenyl) | |

TABLE B-12-continued
| Ex. No. | R¹ | A | B | R² | additive |
|---|---|---|---|---|---|
| 135 | 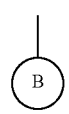 | 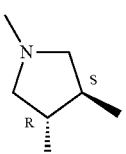 | 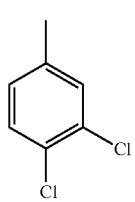 | 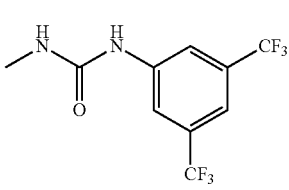 | |
| 136 | H | 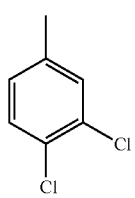 | 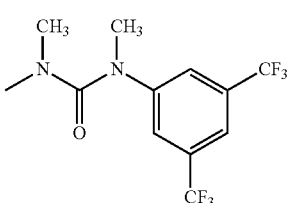 | 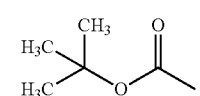 | HCl |
| 137 | 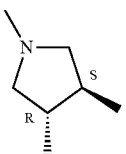 | 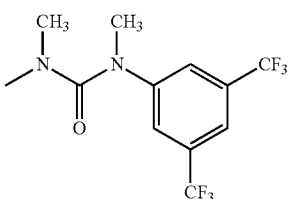 | 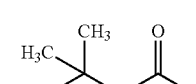 | 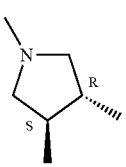 | |
| 138 | 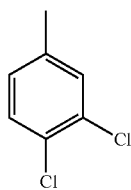 | 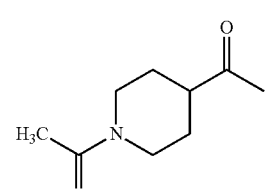 | 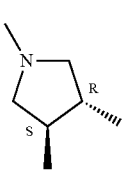 | 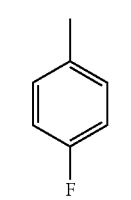 | |
| 139 | 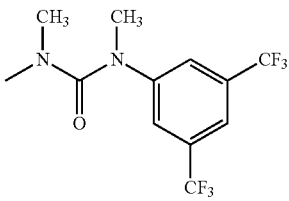 | 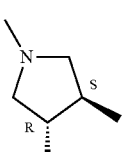 | 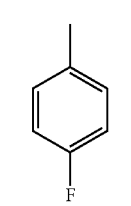 | 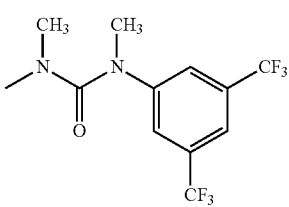 | |

TABLE B-13

| Ex. No. | R¹ | A | B | R² | additive |
|---|---|---|---|---|---|
| 140 | H | (3R,4S) N-methylpyrrolidine | 4-fluorophenyl | N,N'-dimethyl-N'-(3,5-bis(trifluoromethyl)phenyl)urea | HCl |
| 141 | 1-acetylpiperidin-4-yl-carbonyl | (3R,4S) N-methylpyrrolidine | 4-fluorophenyl | N,N'-dimethyl-N'-(3,5-bis(trifluoromethyl)phenyl)urea | |
| 142 | tert-butoxycarbonyl | (3S,4R) N-methylpyrrolidine | 4-fluorophenyl | N'-methyl-N'-(3,5-bis(trifluoromethyl)phenyl)urea | |
| 143 | tert-butoxycarbonyl | (3S,4R) N-methylpyrrolidine | 4-fluorophenyl | N,N'-dimethyl-N'-(3,5-bis(trifluoromethyl)phenyl)urea | |
| 144 | H | (3S,4R) N-methylpyrrolidine | 4-fluorophenyl | N,N'-dimethyl-N'-(3,5-bis(trifluoromethyl)phenyl)urea | HCl |
| 145 | 1-acetylpiperidin-4-yl-carbonyl | (3S,4R) N-methylpyrrolidine | 4-fluorophenyl | N,N'-dimethyl-N'-(3,5-bis(trifluoromethyl)phenyl)urea | |

TABLE B-13-continued

| Ex. No. | R¹ | [pyrrolidine A] | B | [R² amide D] | additive |
|---|---|---|---|---|---|
| 146 | H₃C-C(CH₃)(CH₃)-O-C(O)-CH₂- | (±)- N-methyl pyrrolidine | 4-F-C₆H₄- | HN-C(O)-N(CH₃)-(3,5-(CF₃)₂-C₆H₃) | |
| 147 | H₃C-C(CH₃)(CH₃)-O-C(O)-CH₂- | (±)- | 4-F-C₆H₄- | (CH₃)N-C(O)-N(CH₃)-(3,5-(CF₃)₂-C₆H₃) | |
| 148 | H | (±)- | 4-F-C₆H₄- | (CH₃)N-C(O)-N(CH₃)-(3,5-(CF₃)₂-C₆H₃) | HCl |
| 149 | 1-acetyl-piperidin-4-yl-C(O)- | (±)- | 4-F-C₆H₄- | (CH₃)N-C(O)-N(CH₃)-(3,5-(CF₃)₂-C₆H₃) | |
| 150 | H₃C-C(CH₃)(CH₃)-O-C(O)-CH₂- | (3S,4R) | 3,4-F₂-C₆H₃- | HN-C(O)-N(CH₃)-(3,5-(CF₃)₂-C₆H₃) | |

TABLE B-13-continued
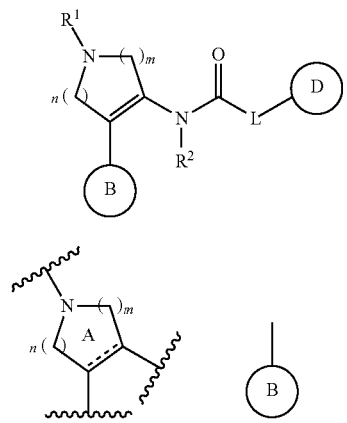
| Ex. No. | R[1] | [ring A structure] | B | [amide structure] | additive |
|---|---|---|---|---|---|
| 151 | H | 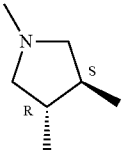 | 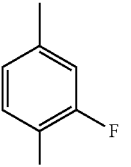 | 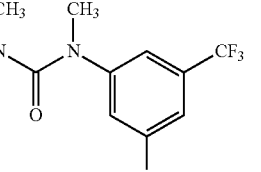 | HCl |
TABLE B-14
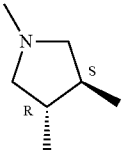
| Ex. No. | R[1] | [ring A structure] | B | [amide structure] | additive |
|---|---|---|---|---|---|
| 152 | 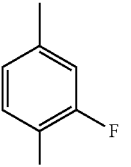 | 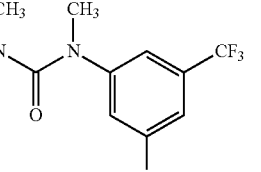 | 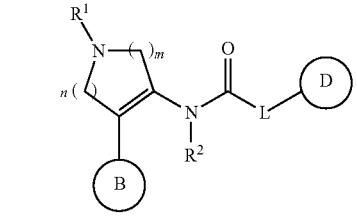 | 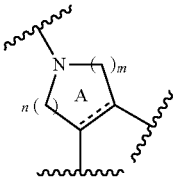 | |
| 153 | 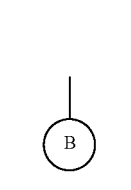 | 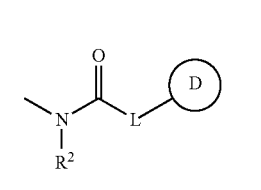 | 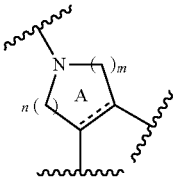 | 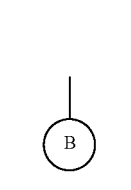 | |

TABLE B-14-continued
| Ex. No. | R¹ | 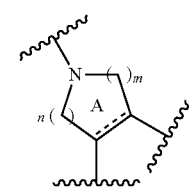 |  | 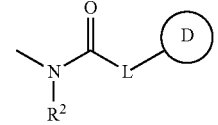 | additive |
|---|---|---|---|---|---|
| 154 | 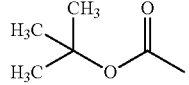 | 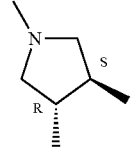 | 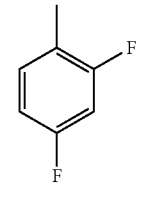 | 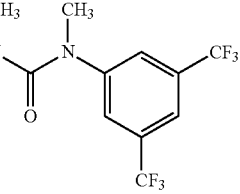 | |
| 155 | H | 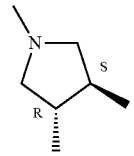 | 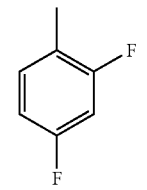 | 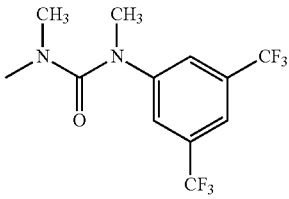 | HCl |
| 156 | 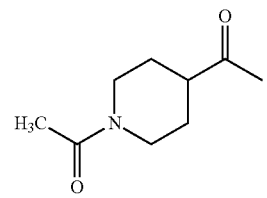 | 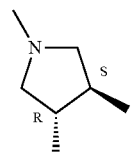 | 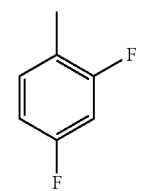 | 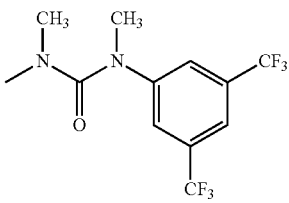 [SMILES: CN(C)C(=O)N(C)c1cc(C(F)(F)F)cc(C(F)(F)F)c1] | |
| 157 | 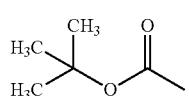 | 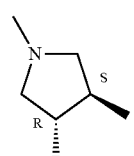 | 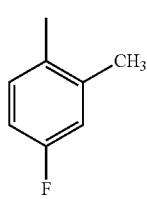 | 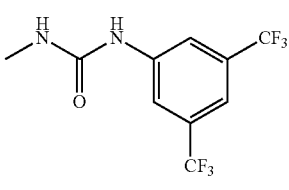 [SMILES: CNC(=O)Nc1cc(C(F)(F)F)cc(C(F)(F)F)c1] | |
| 158 | 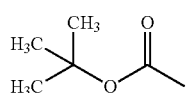 | 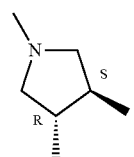 | 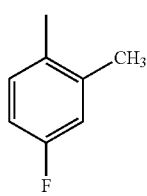 | 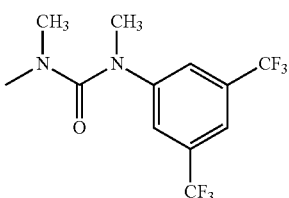 | |
| 159 | H | 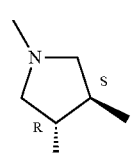 | 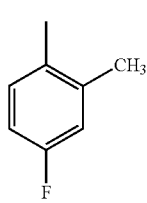 | 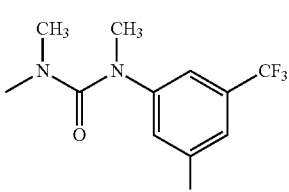 | HCl |

TABLE B-14-continued
| Ex. No. | R¹ | A | B | R² / D group | additive |
|---|---|---|---|---|---|
| 160 | 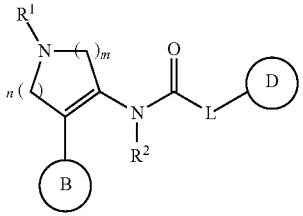 | 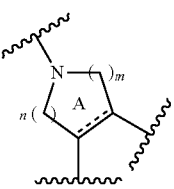 | 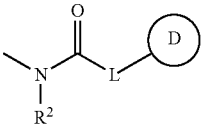 | 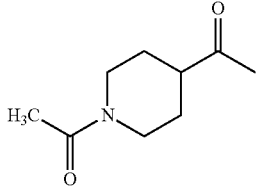 | |
| 161 | 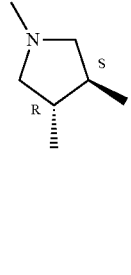 | 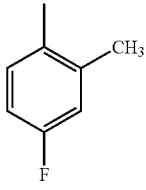 | 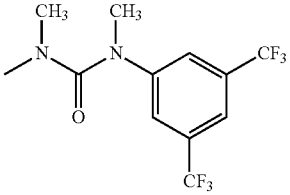 | 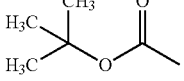 | |
| 162 | 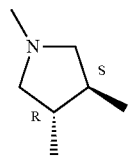 | 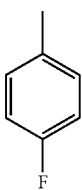 | 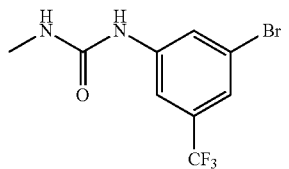 | 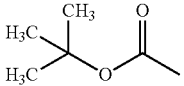 | |
| 163 | H | 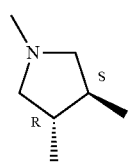 | 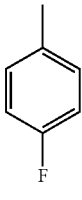 | 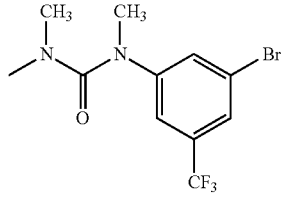 | HCl |

TABLE B-15

| Ex. No. | R¹ | A | B | D R² | additive |
|---|---|---|---|---|---|
| 164 | 1-acetylpiperidin-4-yl-C(=O)- | (3S,4R)-1-methyl-4-methylpyrrolidin-3-yl | 4-fluorophenyl | N,N'-dimethyl-N'-(3-bromo-5-trifluoromethylphenyl)urea | |
| 165 | tert-butoxycarbonyl | (3S,4R)-1-methyl-4-methylpyrrolidin-3-yl | 4-fluorophenyl | N-methyl-N'-(3,5-dibromophenyl)urea | |
| 166 | tert-butoxycarbonyl | (3S,4R)-1-methyl-4-methylpyrrolidin-3-yl | 4-fluorophenyl | N,N'-dimethyl-N'-(3,5-dibromophenyl)urea | |
| 167 | H | (3S,4R)-1-methyl-4-methylpyrrolidin-3-yl | 4-fluorophenyl | N,N'-dimethyl-N'-(3,5-dibromophenyl)urea | HCl |
| 168 | 1-acetylpiperidin-4-yl-C(=O)- | (3S,4R)-1-methyl-4-methylpyrrolidin-3-yl | 4-fluorophenyl | N,N'-dimethyl-N'-(3,5-dibromophenyl)urea | |
| 169 | tert-butoxycarbonyl | (3S,4R)-1-methyl-4-methylpyrrolidin-3-yl | 4-fluorophenyl | N-methyl-N'-(3-chloro-5-trifluoromethylphenyl)urea | |

TABLE B-15-continued

| Ex. No. | R¹ | A | B | R² / D group | additive |
|---|---|---|---|---|---|
| 170 | (H₃C)₃C-O-C(O)-CH₂- | (3R,4S)-1,3,4-trimethylpyrrolidin-yl | 4-F-C₆H₄ | N,N'-dimethyl-N'-(3-Cl-5-CF₃-phenyl)urea | |
| 171 | H | (3R,4S)-1,3,4-trimethylpyrrolidin-yl | 4-F-C₆H₄ | N,N'-dimethyl-N'-(3-Cl-5-CF₃-phenyl)urea | HCl |
| 172 | 1-acetyl-piperidin-4-yl-C(O)-CH₂- | (3R,4S)-1,3,4-trimethylpyrrolidin-yl | 4-F-C₆H₄ | N,N'-dimethyl-N'-(3-Cl-5-CF₃-phenyl)urea | |
| 173 | (H₃C)₃C-O-C(O)-CH₂- | (3R,4S)-1,3,4-trimethylpyrrolidin-yl | 4-F-C₆H₄ | N-methyl-N'-(3,5-diCl-phenyl)urea | |
| 174 | (H₃C)₃C-O-C(O)-CH₂- | (3R,4S)-1,3,4-trimethylpyrrolidin-yl | 4-F-C₆H₄ | N,N'-dimethyl-N'-(3,5-diCl-phenyl)urea | |
| 175 | H | (3R,4S)-1,3,4-trimethylpyrrolidin-yl | 4-F-C₆H₄ | N,N'-dimethyl-N'-(3,5-diCl-phenyl)urea | HCl |

TABLE B-16
| Ex. No. | R¹ | A | B | R² | additive |
|---|---|---|---|---|---|
| 176 | 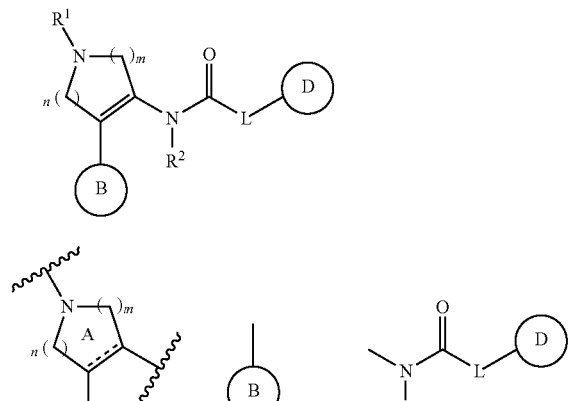 | 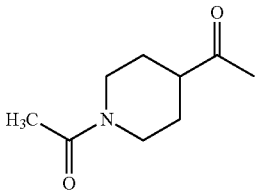 | 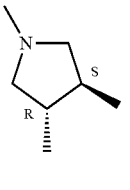 | 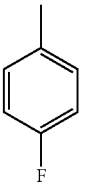 | |
| 177 | 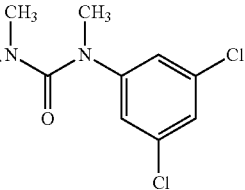 | 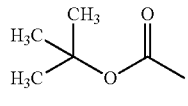 | 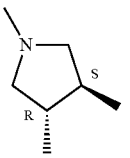 | 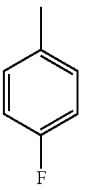 | |
| 178 | 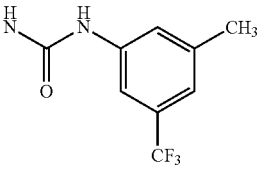 | 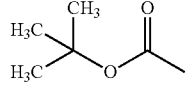 | 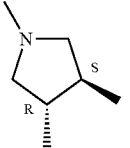 | 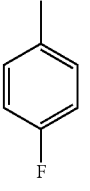 | |
| 179 | H | 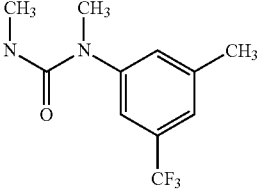 | 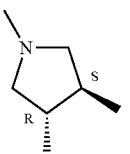 | 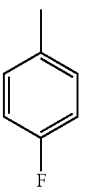 | HCl |
| 180 | 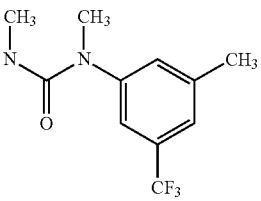 | 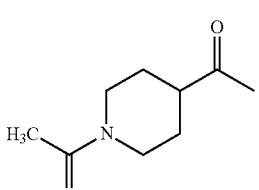 | 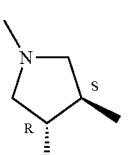 | 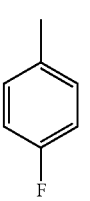 | |
| 181 | 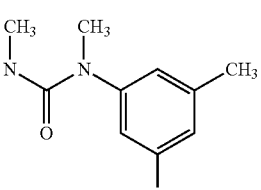 | 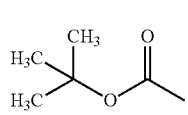 | 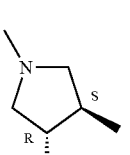 | 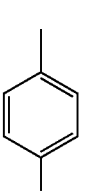 | |

US 8,592,454 B2

TABLE B-16-continued

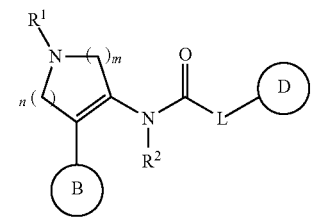

| Ex. No. | R¹ | (structure A) | B | (structure with R²) | additive |
|---|---|---|---|---|---|
| 182 | H₃C-C(CH₃)(CH₃)-O-C(O)-CH₃ (tert-butyl acetate group) | N-methyl pyrrolidine (3R,4S) | 4-Cl-phenyl | N,N'-dimethyl-N'-(3,5-dichlorophenyl)urea | |
| 183 | H | N-methyl pyrrolidine (3R,4S) | 4-Cl-phenyl | N,N'-dimethyl-N'-(3,5-dichlorophenyl)urea | HCl |
| 184 | CH₃SO₂-N(piperazine)-C(O)CH₃ | N-methyl pyrrolidine (3R,4S) | 4-Cl-phenyl | N,N'-dimethyl-N'-(3,5-dichlorophenyl)urea | |
| 185 | H₃C-C(CH₃)(CH₃)-O-C(O)-CH₃ | N-methyl pyrrolidine (3S,4R) | 4-Cl-phenyl | N-methyl-N'-(3,5-dichlorophenyl)urea | |
| 186 | H₃C-C(CH₃)(CH₃)-O-C(O)-CH₃ | N-methyl pyrrolidine (3S,4R) | 4-Cl-phenyl | N,N'-dimethyl-N'-(3,5-dichlorophenyl)urea | |

TABLE B-16-continued

| Ex. No. | R¹ | A | B | N(R²)-C(O)-L-D | additive |
|---|---|---|---|---|---|
| 187 | H | 1-methyl pyrrolidine (3R,4S) dimethyl | 4-chlorophenyl | N,N'-dimethyl-N'-(3,5-dichlorophenyl)urea | HCl |

TABLE B-17

| Ex. No. | R¹ | A | B | N(R²)-C(O)-L-D | additive |
|---|---|---|---|---|---|
| 188 | 4-acetyl-1-(methylsulfonyl)piperazine | 1-methyl pyrrolidine (3R,4S) dimethyl | 4-chlorophenyl | N,N'-dimethyl-N'-(3,5-dichlorophenyl)urea | |
| 189 | tert-butyl acetate | 1-methyl pyrrolidine (3S,4R) dimethyl | 5-fluoro-2-methylpyridin-3-yl | N-methyl-N'-(3,5-bis(trifluoromethyl)phenyl)urea | |

TABLE B-17-continued

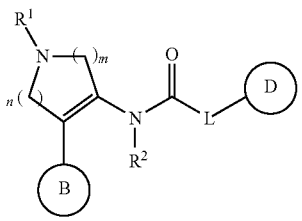

| Ex. No. | R¹ | A | B | R² / D group | additive |
|---|---|---|---|---|---|
| 190 | tert-butyl acetate group | (3R,4S)-1,3,4-trimethylpyrrolidine | 2-methyl-5-fluoropyridine | N,N'-dimethyl-N'-[3,5-bis(trifluoromethyl)phenyl]urea | |
| 191 | H | (3R,4S)-1,3,4-trimethylpyrrolidine | 2-methyl-5-fluoropyridine | N,N'-dimethyl-N'-[3,5-bis(trifluoromethyl)phenyl]urea | 2HCl |
| 192 | 1-acetyl-4-acetylpiperidine | (3R,4S)-1,3,4-trimethylpyrrolidine | 2-methyl-5-fluoropyridine | N,N'-dimethyl-N'-[3,5-bis(trifluoromethyl)phenyl]urea | |
| 193 | tert-butyl acetate group | (3R,4S)-1,3,4-trimethylpyrrolidine | 4-fluorophenyl | 1-methyl-3-[3,5-bis(trifluoromethyl)phenyl]imidazolidin-2-one | |
| 194 | H | (3R,4S)-1,3,4-trimethylpyrrolidine | 4-fluorophenyl | 1-methyl-3-[3,5-bis(trifluoromethyl)phenyl]imidazolidin-2-one | HCl |
| 195 | 1-acetyl-4-acetylpiperidine | (3R,4S)-1,3,4-trimethylpyrrolidine | 4-fluorophenyl | 1-methyl-3-[3,5-bis(trifluoromethyl)phenyl]imidazolidin-2-one | |

TABLE B-17-continued
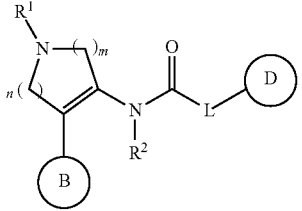
| Ex. No. | R¹ | [A ring] | [B ring] | [amide D] | additive |
|---|---|---|---|---|---|
| 196 | 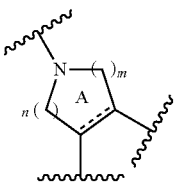 | 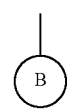 | 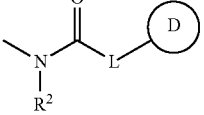 | 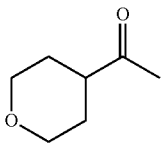 | |
| 197 | 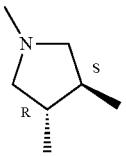 | 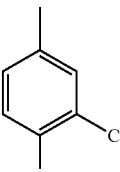 | 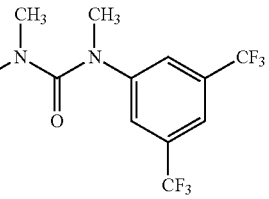 | 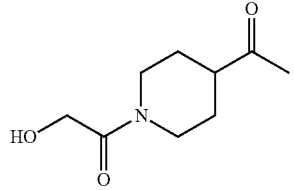 | |
| 198 | 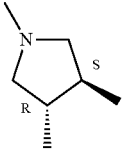 | 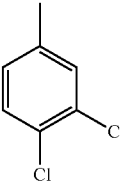 | 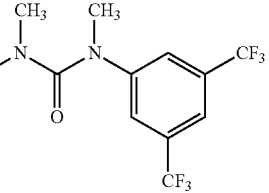 | 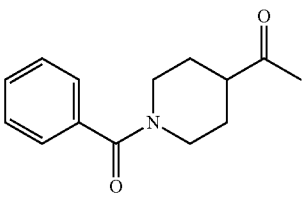 [SMILES: CC(=O)C1CCN(C(=O)c2ccccc2)CC1] | |
| 199 | $CH_3CO$ | 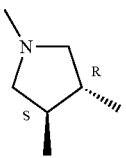 | 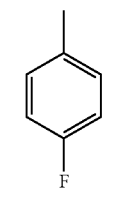 | 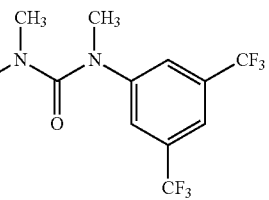 | |

TABLE B-18

| Ex. No. | R¹ | A | B | R² | additive |
|---|---|---|---|---|---|
| 200 | CH₃SO₂ | (3S,4R)-1,4-dimethylpyrrolidin-3-yl | 4-fluorophenyl | N,N'-dimethyl-N'-(3,5-bis(trifluoromethyl)phenyl)urea | |
| 201 | CH₃OCO | (3S,4R)-1,4-dimethylpyrrolidin-3-yl | 4-fluorophenyl | N,N'-dimethyl-N'-(3,5-bis(trifluoromethyl)phenyl)urea | |
| 202 | NCCH₂C(O)— | (3S,4R)-1,4-dimethylpyrrolidin-3-yl | 4-fluorophenyl | N,N'-dimethyl-N'-(3,5-bis(trifluoromethyl)phenyl)urea | |
| 203 | 3-methylcyclopent-2-en-1-one | (3S,4R)-1,4-dimethylpyrrolidin-3-yl | 4-fluorophenyl | N,N'-dimethyl-N'-(3,5-bis(trifluoromethyl)phenyl)urea | |
| 204 | 4-acetyl-2,6-dioxopiperidine | (3S,4R)-1,4-dimethylpyrrolidin-3-yl | 4-fluorophenyl | N,N'-dimethyl-N'-(3,5-bis(trifluoromethyl)phenyl)urea | |

TABLE B-18-continued
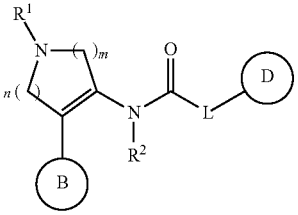
| Ex. No. | R[1] | [A structure] | B | [R[2] / D structure] | additive |
|---|---|---|---|---|---|
| 205 | 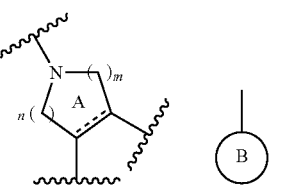 | 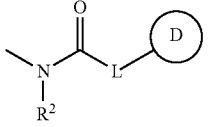 | 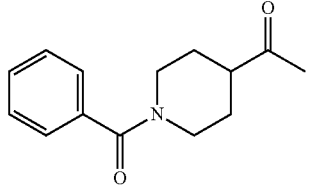 | 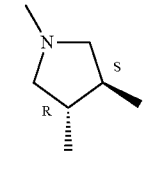 | |
| 206 | 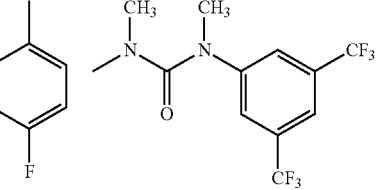 | 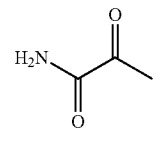 | 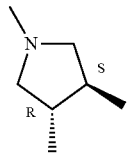 | 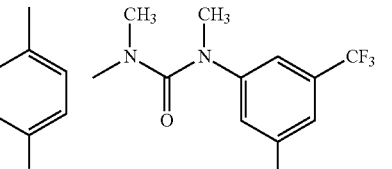 | |
| 207 | 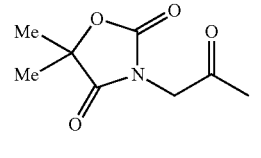 | 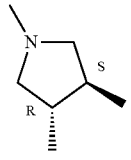 | 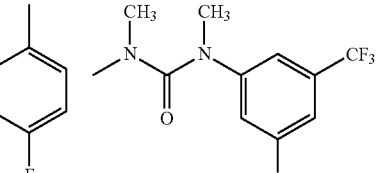 | 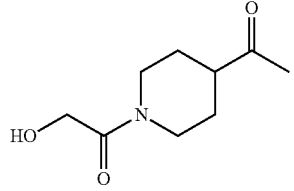 | |
| 208 | 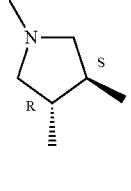 | 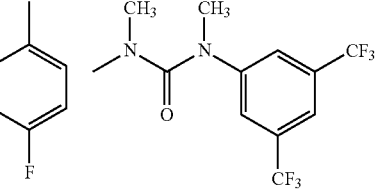 | 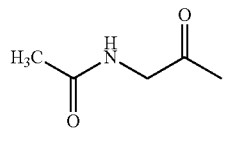 | 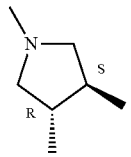 | |
| 209 | 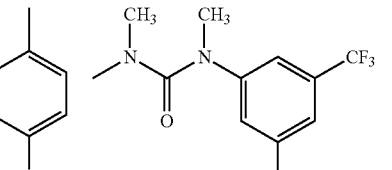 | | | | |

TABLE B-18-continued
| Ex. No. | R¹ |  | B | R² | additive |
|---|---|---|---|---|---|
| 210 | 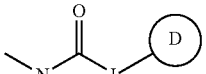 | 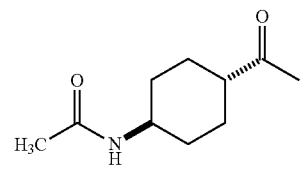 | 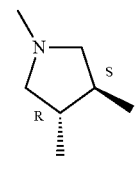 | 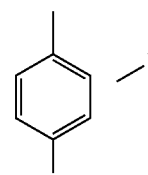 | |
| 211 | 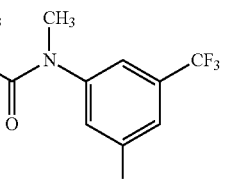 | 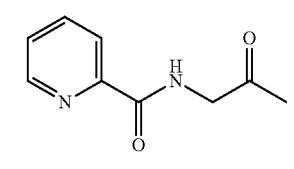 | 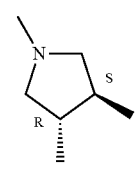 | 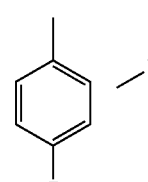 | |
TABLE B-19
| Ex. No. | R¹ |  | B | R² | additive |
|---|---|---|---|---|---|
| 212 | 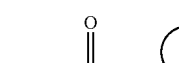 | 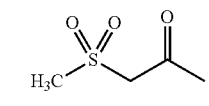 | 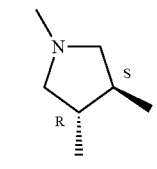 | 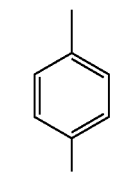 | |

TABLE B-19-continued

| Ex. No. | R¹ | [ring A] | [ring B] | [amide/D] | additive |
|---|---|---|---|---|---|
| 213 | tetrazolyl-CH₂-C(O)CH₃ | (3S,4R)-1-methylpyrrolidinyl | 4-fluorophenyl | N,N'-dimethyl-N'-(3,5-bis(trifluoromethyl)phenyl)urea | |
| 214 | 5-cyano-2-pyridyl (6-methyl) | (3S,4R)-1-methylpyrrolidinyl | 4-fluorophenyl | N,N'-dimethyl-N'-(3,5-bis(trifluoromethyl)phenyl)urea | |
| 215 | CH₃CH₂NHC(O)CH₂– | (3S,4R)-1-methylpyrrolidinyl | 4-fluorophenyl | N,N'-dimethyl-N'-(3,5-bis(trifluoromethyl)phenyl)urea | |
| 216 | tetrahydropyran-4-yl-O-C(O)CH₂– | (3S,4R)-1-methylpyrrolidinyl | 4-fluorophenyl | N,N'-dimethyl-N'-(3,5-bis(trifluoromethyl)phenyl)urea | |
| 217 | N-Boc-piperidin-4-yl-CH₂– | (3S,4R)-1-methylpyrrolidinyl | 4-fluorophenyl | N,N'-dimethyl-N'-(3,5-bis(trifluoromethyl)phenyl)urea | |

TABLE B-19-continued

| Ex. No. | R¹ | A | B | R² | additive |
|---|---|---|---|---|---|
| 218 | tert-butyl 4-ethylpiperidine-1-carboxylate | (3S,4R)-1-methylpyrrolidine | 4-fluorophenyl | N,N'-dimethyl-N-(3,5-bis(trifluoromethyl)phenyl)urea | |
| 219 | 4-ethylpiperidine | (3S,4R)-1-methylpyrrolidine | 4-fluorophenyl | N,N'-dimethyl-N-(3,5-bis(trifluoromethyl)phenyl)urea | 2HCl |
| 220 | 1-acetyl-4-ethylpiperidine | (3S,4R)-1-methylpyrrolidine | 4-fluorophenyl | N,N'-dimethyl-N-(3,5-bis(trifluoromethyl)phenyl)urea | |
| 221 | 5-acetyl-1-methylpiperidin-2-one | (3S,4R)-1-methylpyrrolidine | 4-fluorophenyl | N,N'-dimethyl-N-(3,5-bis(trifluoromethyl)phenyl)urea | |
| 222 | 1-(tetrahydro-2H-thiopyran-4-yl)ethanone | (3S,4R)-1-methylpyrrolidine | 4-fluorophenyl | N,N'-dimethyl-N-(3,5-bis(trifluoromethyl)phenyl)urea | |

TABLE B-19-continued

| Ex. No. | R¹ | (pyrrolidine A) | B | amide/D | additive |
|---|---|---|---|---|---|
| 223 | 1-(1-oxo-tetrahydro-2H-thiopyran-4-yl)ethanone | (3S,4R)-1-methyl-3,4-dimethylpyrrolidine | 4-fluorophenyl | N,N'-dimethyl-N'-(3,5-bis(trifluoromethyl)phenyl)urea | |

TABLE B-20

| Ex. No. | R¹ | (pyrrolidine A) | B | amide/D | additive |
|---|---|---|---|---|---|
| 224 | 1-(1,1-dioxo-tetrahydro-2H-thiopyran-4-yl)ethanone | (3S,4R)-1-methyl-3,4-dimethylpyrrolidine | 4-fluorophenyl | N,N'-dimethyl-N'-(3,5-bis(trifluoromethyl)phenyl)urea | |
| 225 | 1-(tetrahydro-2H-pyran-4-yl)ethanone | (3S,4R)-1-methyl-3,4-dimethylpyrrolidine | 4-fluorophenyl | N,N'-dimethyl-N'-(3,5-bis(trifluoromethyl)phenyl)urea | |

TABLE B-20-continued

| Ex. No. | R¹ | A | B | (R²)N-C(O)-L-D | additive |
|---|---|---|---|---|---|
| 226 | 4,4-difluorocyclohexyl-C(O)-CH₂- | (3R,4S)-1-methyl-3-methylpyrrolidin-4-yl | 4-fluorophenyl | N,N'-dimethyl-N'-(3,5-bis(trifluoromethyl)phenyl)urea | |
| 227 | 1-Boc-piperidin-4-yl-CH₂-C(O)-CH₂- | (3R,4S)-1-methyl-3-methylpyrrolidin-4-yl | 4-fluorophenyl | N,N'-dimethyl-N'-(3,5-bis(trifluoromethyl)phenyl)urea | |
| 228 | piperidin-4-yl-CH₂-C(O)-CH₂- | (3R,4S)-1-methyl-3-methylpyrrolidin-4-yl | 4-fluorophenyl | N,N'-dimethyl-N'-(3,5-bis(trifluoromethyl)phenyl)urea | HCl |
| 229 | 1-acetyl-piperidin-4-yl-CH₂-C(O)-CH₂- | (3R,4S)-1-methyl-3-methylpyrrolidin-4-yl | 4-fluorophenyl | N,N'-dimethyl-N'-(3,5-bis(trifluoromethyl)phenyl)urea | |
| 230 | 4-(Boc-amino)cyclohexyl-C(O)-CH₂- | (3R,4S)-1-methyl-3-methylpyrrolidin-4-yl | 4-fluorophenyl | N,N'-dimethyl-N'-(3,5-bis(trifluoromethyl)phenyl)urea | |

TABLE B-20-continued

| Ex. No. | R¹ | A | B | (R² amide) | additive |
|---|---|---|---|---|---|
| 231 | 4-aminocyclohexyl-C(O)- | (3S,4R)-1-methyl-3,4-dimethylpyrrolidinyl | 4-F-phenyl | N,N'-dimethyl-N-(3,5-bis(CF₃)phenyl)urea | HCl |
| 232 | 4-benzamidocyclohexyl-C(O)- | (3S,4R)-1-methyl-3,4-dimethylpyrrolidinyl | 4-F-phenyl | N,N'-dimethyl-N-(3,5-bis(CF₃)phenyl)urea | |
| 233 | 4-(methoxycarbonylamino)cyclohexyl-C(O)- | (3S,4R)-1-methyl-3,4-dimethylpyrrolidinyl | 4-F-phenyl | N,N'-dimethyl-N-(3,5-bis(CF₃)phenyl)urea | |
| 234 | 4-(2-oxopyrrolidin-1-yl)cyclohexyl-C(O)- | (3S,4R)-1-methyl-3,4-dimethylpyrrolidinyl | 4-F-phenyl | N,N'-dimethyl-N-(3,5-bis(CF₃)phenyl)urea | |
| 235 | 4-(2-oxooxazolidin-3-yl)cyclohexyl-C(O)- | (3S,4R)-1-methyl-3,4-dimethylpyrrolidinyl | 4-F-phenyl | N,N'-dimethyl-N-(3,5-bis(CF₃)phenyl)urea | |

TABLE B-21

| Ex. No. | R¹ | A | B | R² / L-D | additive |
|---|---|---|---|---|---|
| 236 | H₃C-CH(CH₃)-C(O)-NH-cyclohexyl-C(O)CH₃ | (3S,4R)-1-methyl-3,4-dimethylpyrrolidine | 4-F-C₆H₄ | N,N'-dimethyl-N'-(3,5-bis(trifluoromethyl)phenyl)urea | |
| 237 | isobutyl-O-C(O)-NH-cyclohexyl-C(O)CH₃ | (3S,4R)-1-methyl-3,4-dimethylpyrrolidine | 4-F-C₆H₄ | N,N'-dimethyl-N'-(3,5-bis(trifluoromethyl)phenyl)urea | |
| 238 | HO-C(CH₃)₂-C(O)-NH-cyclohexyl-C(O)CH₃ | (3S,4R)-1-methyl-3,4-dimethylpyrrolidine | 4-F-C₆H₄ | N,N'-dimethyl-N'-(3,5-bis(trifluoromethyl)phenyl)urea | |
| 239 | tBuO-C(O)-N(CH₃)-cyclohexyl-C(O)CH₃ | (3S,4R)-1-methyl-3,4-dimethylpyrrolidine | 4-F-C₆H₄ | N,N'-dimethyl-N'-(3,5-bis(trifluoromethyl)phenyl)urea | |
| 240 | CH₃-NH-cyclohexyl-C(O)CH₃ | (3S,4R)-1-methyl-3,4-dimethylpyrrolidine | 4-F-C₆H₄ | N,N'-dimethyl-N'-(3,5-bis(trifluoromethyl)phenyl)urea | HCl |

TABLE B-21-continued

| Ex. No. | R¹ | A | B | R² | additive |
|---|---|---|---|---|---|
| 241 | methyl (methyl)carbamate-cyclohexyl-acetyl | (3S,4R)-1-methylpyrrolidine | 4-fluorophenyl | N,N'-dimethyl-N'-(3,5-bis(trifluoromethyl)phenyl)urea | |
| 242 | methanesulfonamido-cyclohexyl-acetyl | (3S,4R)-1-methylpyrrolidine | 4-fluorophenyl | N,N'-dimethyl-N'-(3,5-bis(trifluoromethyl)phenyl)urea | |
| 243 | N-methyl-methanesulfonamido-cyclohexyl-acetyl | (3S,4R)-1-methylpyrrolidine | 4-fluorophenyl | N,N'-dimethyl-N'-(3,5-bis(trifluoromethyl)phenyl)urea | |
| 244 | isothiazolidine-1,1-dioxide-N-cyclohexyl-acetyl | (3S,4R)-1-methylpyrrolidine | 4-fluorophenyl | N,N'-dimethyl-N'-(3,5-bis(trifluoromethyl)phenyl)urea | |
| 245 | 2-hydroxy-N-cyclohexylacetamide-acetyl | (3S,4R)-1-methylpyrrolidine | 4-fluorophenyl | N,N'-dimethyl-N'-(3,5-bis(trifluoromethyl)phenyl)urea | |

TABLE B-21-continued
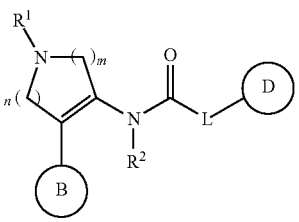
| Ex. No. | R¹ | 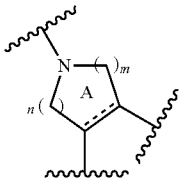 | B |  | additive |
|---|---|---|---|---|---|
| 246 | 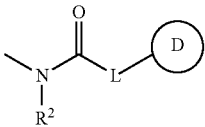 | 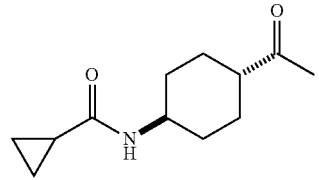 | 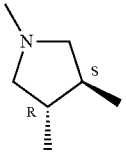 | 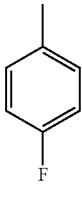 | |
| 247 | 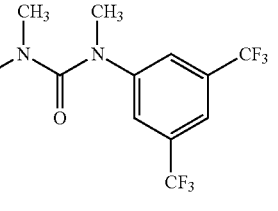 | 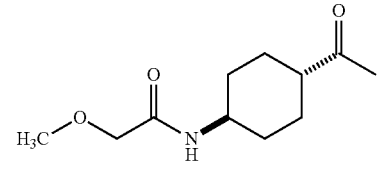 | 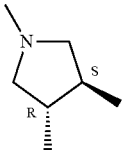 | 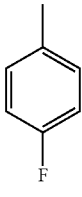 | |
TABLE B-22
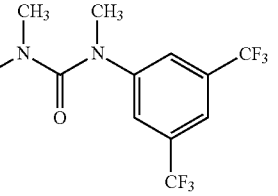
| Ex. No. | R¹ | 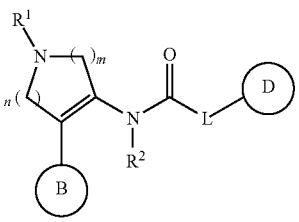 | B | 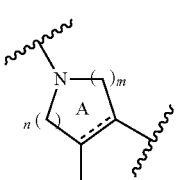 | additive |
|---|---|---|---|---|---|
| 248 |  | 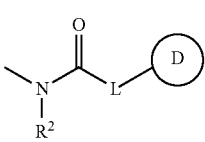 | 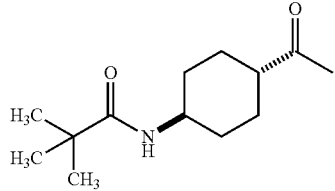 | 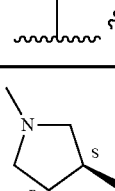 | |

TABLE B-22-continued

| Ex. No. | R¹ | A | B | (D with R²) | additive |
|---|---|---|---|---|---|
| 249 | CH₃CH₂C(O)NH-cyclohexyl-C(O)- | (3R,4S)-N-methyl-3,4-dimethylpyrrolidine | 4-fluorophenyl | N,N'-dimethyl-N'-(3,5-bis(trifluoromethyl)phenyl)urea | |
| 250 | 3-fluoropyridine-2-C(O)NH-cyclohexyl-C(O)- | (3R,4S)-N-methyl-3,4-dimethylpyrrolidine | 4-fluorophenyl | N,N'-dimethyl-N'-(3,5-bis(trifluoromethyl)phenyl)urea | |
| 251 | 2-methylpyridine-4-C(O)NH-cyclohexyl-C(O)- | (3R,4S)-N-methyl-3,4-dimethylpyrrolidine | 4-fluorophenyl | N,N'-dimethyl-N'-(3,5-bis(trifluoromethyl)phenyl)urea | |
| 252 | pyridine-2-C(O)NH-cyclohexyl-C(O)- | (3R,4S)-N-methyl-3,4-dimethylpyrrolidine | 4-fluorophenyl | N,N'-dimethyl-N'-(3,5-bis(trifluoromethyl)phenyl)urea | |
| 253 | cyclobutyl-C(O)NH-cyclohexyl-C(O)- | (3R,4S)-N-methyl-3,4-dimethylpyrrolidine | 4-fluorophenyl | N,N'-dimethyl-N'-(3,5-bis(trifluoromethyl)phenyl)urea | |

TABLE B-22-continued

| Ex. No. | R¹ | A | B | R² | additive |
|---|---|---|---|---|---|
| 254 | N-methyl-N-(4-acetylcyclohexyl)acetamide | (3S,4R)-1-methyl-3,4-dimethylpyrrolidine | 4-fluorophenyl | N,N'-dimethyl-N'-(3,5-bis(trifluoromethyl)phenyl)urea | |
| 255 | 4,4-difluoro-N-(4-acetylcyclohexyl)cyclohexanecarboxamide | (3S,4R)-1-methyl-3,4-dimethylpyrrolidine | 4-fluorophenyl | N,N'-dimethyl-N'-(3,5-bis(trifluoromethyl)phenyl)urea | |
| 256 | tetrahydropyran-4-yl (4-acetylcyclohexyl)carbamate | (3S,4R)-1-methyl-3,4-dimethylpyrrolidine | 4-fluorophenyl | N,N'-dimethyl-N'-(3,5-bis(trifluoromethyl)phenyl)urea | |
| 257 | ethyl (4-acetylcyclohexyl)carbamate | (3S,4R)-1-methyl-3,4-dimethylpyrrolidine | 4-fluorophenyl | N,N'-dimethyl-N'-(3,5-bis(trifluoromethyl)phenyl)urea | |
| 258 | isopropyl (4-acetylcyclohexyl)carbamate | (3S,4R)-1-methyl-3,4-dimethylpyrrolidine | 4-fluorophenyl | N,N'-dimethyl-N'-(3,5-bis(trifluoromethyl)phenyl)urea | |

TABLE B-22-continued

| Ex. No. | R¹ | A | B | NR²-C(O)-L-D | additive |
|---|---|---|---|---|---|
| 259 | H₃C-CH₂-NH-C(O)-NH-[cyclohexyl]-C(O)-CH₃ | (3S,4R)-1,3-dimethylpyrrolidin-4-yl | 4-fluorophenyl | (CH₃)N-C(O)-N(CH₃)-[3,5-bis(CF₃)phenyl] | |

TABLE B-23

| Ex. No. | R¹ | A | B | NR²-C(O)-L-D | additive |
|---|---|---|---|---|---|
| 260 | cyclopropyl-NH-C(O)-NH-[cyclohexyl]-C(O)-CH₃ | (3S,4R)-1,3-dimethylpyrrolidin-4-yl | 4-fluorophenyl | (CH₃)N-C(O)-N(CH₃)-[3,5-bis(CF₃)phenyl] | |
| 261 | 4-O₂N-C₆H₄-O-C(O)-NH-[cyclohexyl]-C(O)-CH₃ | (3S,4R)-1,3-dimethylpyrrolidin-4-yl | 4-fluorophenyl | (CH₃)N-C(O)-N(CH₃)-[3,5-bis(CF₃)phenyl] | |

TABLE B-23-continued

| Ex. No. | R¹ | A | B | (N(CH₃)(R²)-C(O)-L-D) | additive |
|---|---|---|---|---|---|
| 262 | H₃C-N(CH₃)-C(O)-NH-cyclohexyl-C(O)CH₃ | (3S,4R)-1-methyl-4-methylpyrrolidine | 4-F-C₆H₄ | N,N'-dimethyl-N-(3,5-bis(trifluoromethyl)phenyl)urea | |
| 263 | H₃C-N(CH₃)-C(O)-N(CH₃)-cyclohexyl-C(O)CH₃ | (3S,4R)-1-methyl-4-methylpyrrolidine | 4-F-C₆H₄ | N,N'-dimethyl-N-(3,5-bis(trifluoromethyl)phenyl)urea | |
| 264 | morpholino-cyclohexyl-C(O)CH₃ | (3S,4R)-1-methyl-4-methylpyrrolidine | 4-F-C₆H₄ | N,N'-dimethyl-N-(3,5-bis(trifluoromethyl)phenyl)urea | |
| 265 | Boc-NH-cyclohexyl-C(O)CH₃ | (3S,4R)-1-methyl-4-methylpyrrolidine | 4-F-C₆H₄ | N,N'-dimethyl-N-(3,5-bis(trifluoromethyl)phenyl)urea | |
| 266 | H₂N-cyclohexyl-C(O)CH₃ | (3S,4R)-1-methyl-4-methylpyrrolidine | 4-F-C₆H₄ | N,N'-dimethyl-N-(3,5-bis(trifluoromethyl)phenyl)urea | HCl |
| 267 | H₃C-C(O)-NH-cyclohexyl-C(O)CH₃ | (3S,4R)-1-methyl-4-methylpyrrolidine | 4-F-C₆H₄ | N,N'-dimethyl-N-(3,5-bis(trifluoromethyl)phenyl)urea | |

TABLE B-23-continued
| Ex. No. | R¹ | A | B | $\underset{R^2}{\overset{O}{\underset{N}{\parallel}}}\!\!-\!\!L\!-\!D$ | additive |
|---|---|---|---|---|---|
| 268 | 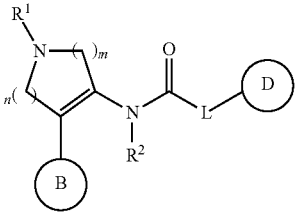 | 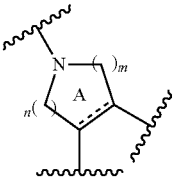 |  | 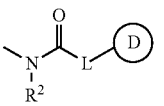 | |
| 269 | 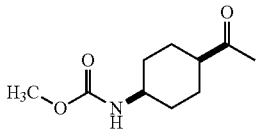 | 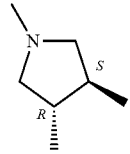 | 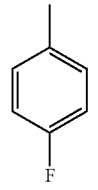 | 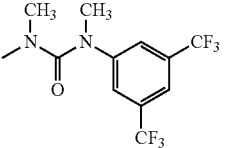 [SMILES: CN(C)C(=O)N(C)c1cc(C(F)(F)F)cc(C(F)(F)F)c1] | |
| 270 | 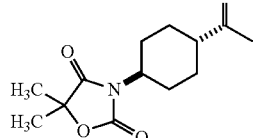 | 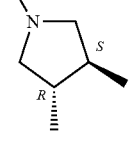 | 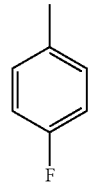 | 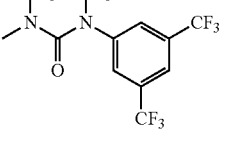 | |
| 271 | 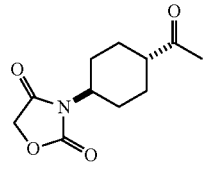 | 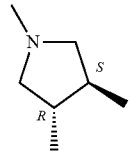 | 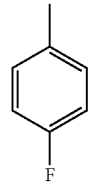 | 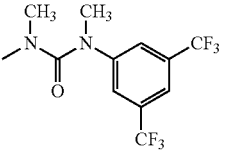 | |

TABLE B-24
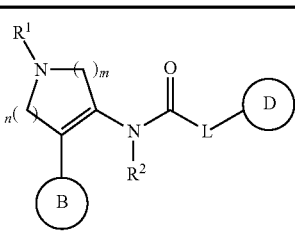
| Ex. No. | R¹ | [A ring] | B | [D group with R²] | additive |
|---|---|---|---|---|---|
| 272 | 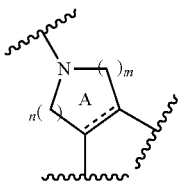 | 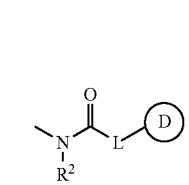 | 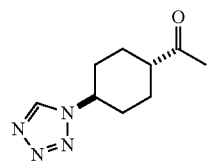 | 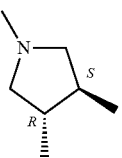 | |
| 273 | 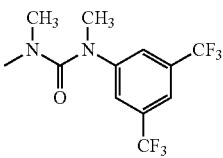 | 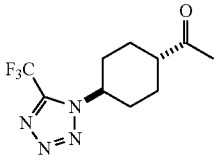 | 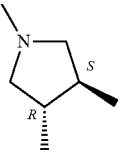 | 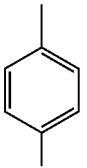 | |
| 274 | 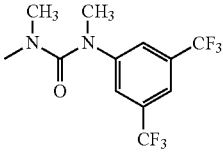 | 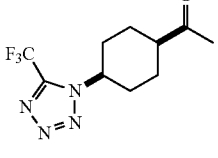 | 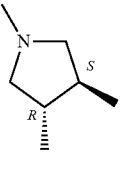 | 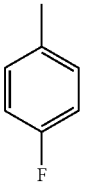 | |
| 275 | 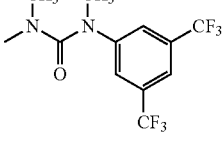 | 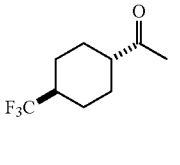 | 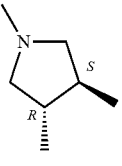 | 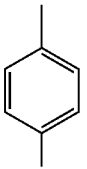 | |
| 276 | 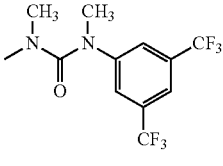 | 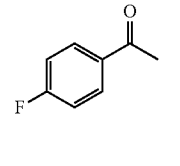 | 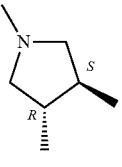 | 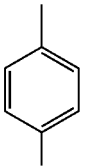 | |
| 277 | 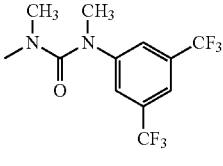 |  | 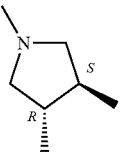 | 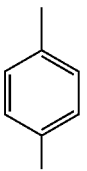 | |

TABLE B-24-continued

| Ex. No. | R¹ | A | B | $\underset{R^2}{\overset{O}{\underset{\|}{N-C-L-D}}}$ | additive |
|---|---|---|---|---|---|
| 278 | 2-acetylpyridine | (3S,4R)-1-methyl-4-methylpyrrolidin-3-yl | 4-fluorophenyl | N,N'-dimethyl-N'-(3,5-bis(trifluoromethyl)phenyl)urea | |
| 279 | 5-acetylpyrimidine | (3S,4R)-1-methyl-4-methylpyrrolidin-3-yl | 4-fluorophenyl | N,N'-dimethyl-N'-(3,5-bis(trifluoromethyl)phenyl)urea | |
| 280 | 2-acetylthiazole | (3S,4R)-1-methyl-4-methylpyrrolidin-3-yl | 4-fluorophenyl | N,N'-dimethyl-N'-(3,5-bis(trifluoromethyl)phenyl)urea | |
| 281 | 1-(4-(5-(trifluoromethyl)-1H-tetrazol-1-yl)phenyl)ethanone | (3S,4R)-1-methyl-4-methylpyrrolidin-3-yl | 4-fluorophenyl | N,N'-dimethyl-N'-(3,5-bis(trifluoromethyl)phenyl)urea | |
| 282 | tert-butyl ((4-acetylcyclohexyl)methyl)carbamate | (3S,4R)-1-methyl-4-methylpyrrolidin-3-yl | 4-fluorophenyl | N,N'-dimethyl-N'-(3,5-bis(trifluoromethyl)phenyl)urea | |
| 283 | 1-(4-(aminomethyl)cyclohexyl)ethanone | (3S,4R)-1-methyl-4-methylpyrrolidin-3-yl | 4-fluorophenyl | N,N'-dimethyl-N'-(3,5-bis(trifluoromethyl)phenyl)urea | HCl |

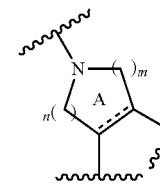
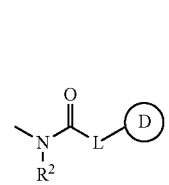
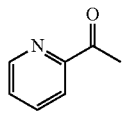
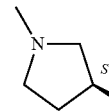
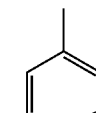
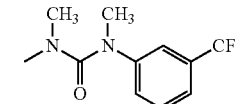
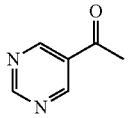
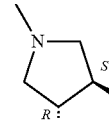
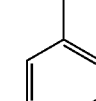
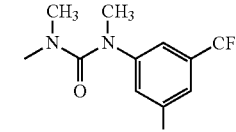
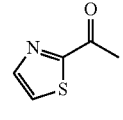
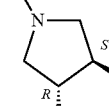
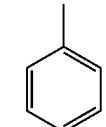
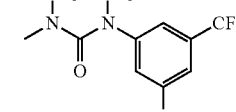
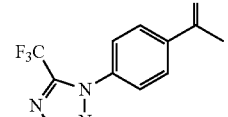
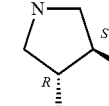
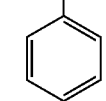
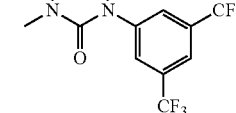
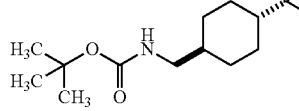
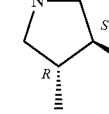
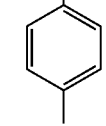
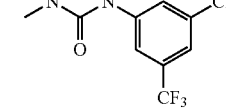
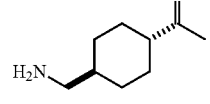
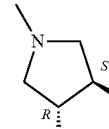
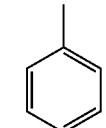
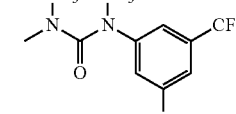

TABLE B-25
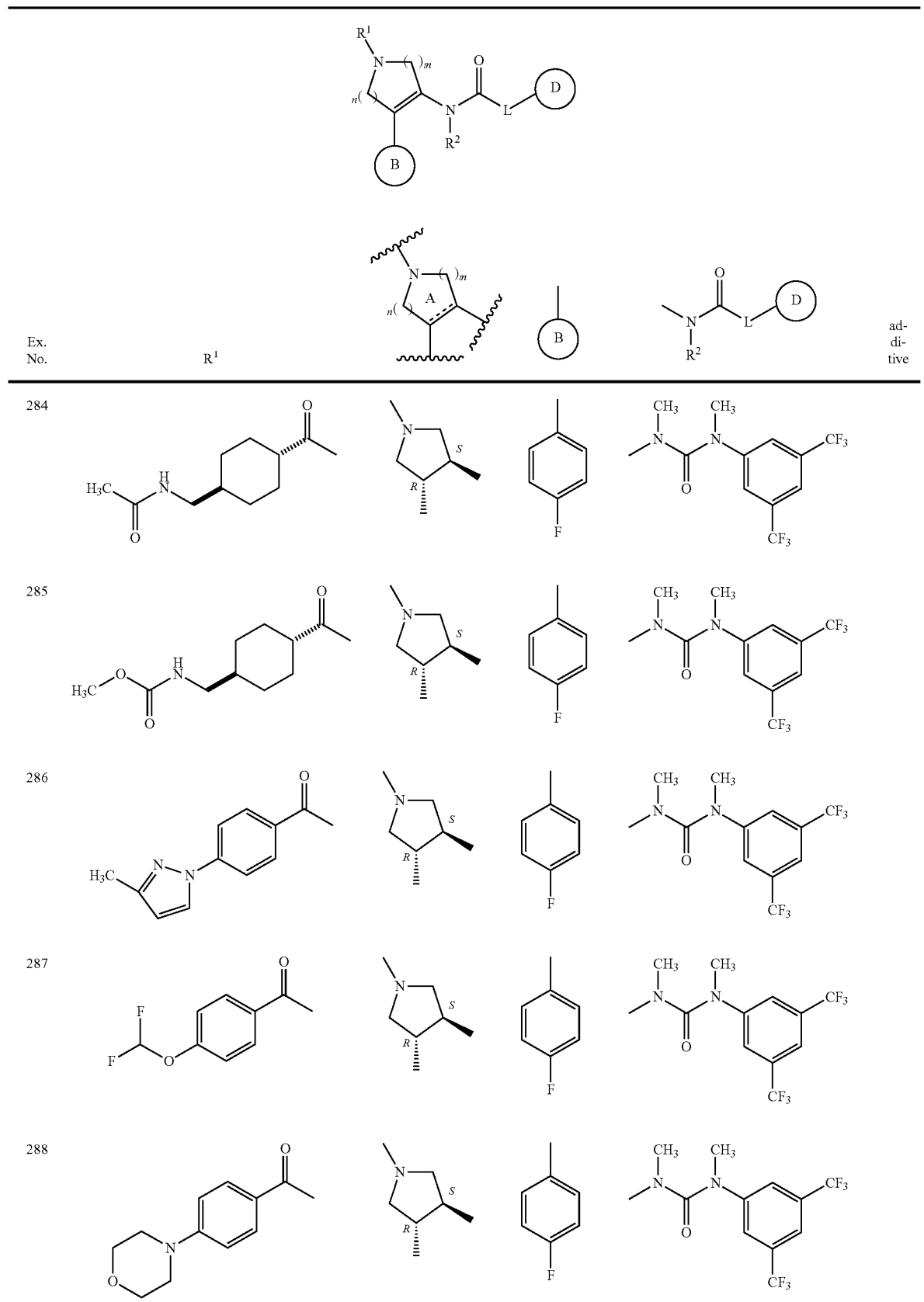

TABLE B-25-continued

| Ex. No. | R¹ | A | B | R² | additive |
|---|---|---|---|---|---|
| 289 | 4-(imidazol-1-yl)phenyl C(O) | (3S,4R)-1-methyl-3,4-dimethylpyrrolidine | 4-F-phenyl | N,N'-dimethyl-N'-(3,5-bis(trifluoromethyl)phenyl)urea | |
| 290 | 4-(pyrazol-1-yl)phenyl C(O) | (3S,4R)-1-methyl-3,4-dimethylpyrrolidine | 4-F-phenyl | N,N'-dimethyl-N'-(3,5-bis(trifluoromethyl)phenyl)urea | |
| 291 | 4-(5-methyltetrazol-1-yl)phenyl C(O) | (3S,4R)-1-methyl-3,4-dimethylpyrrolidine | 4-F-phenyl | N,N'-dimethyl-N'-(3,5-bis(trifluoromethyl)phenyl)urea | |
| 292 | 4-(tetrazol-1-yl)phenyl C(O) | (3S,4R)-1-methyl-3,4-dimethylpyrrolidine | 4-F-phenyl | N,N'-dimethyl-N'-(3,5-bis(trifluoromethyl)phenyl)urea | |
| 293 | (S)-tetrahydrofuran-2-yl C(O) | (3S,4R)-1-methyl-3,4-dimethylpyrrolidine | 4-F-phenyl | N,N'-dimethyl-N'-(3,5-bis(trifluoromethyl)phenyl)urea | |

TABLE B-25-continued
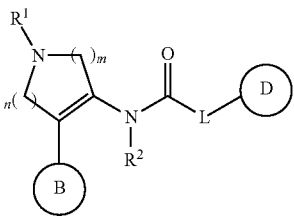
| Ex. No. | R¹ | 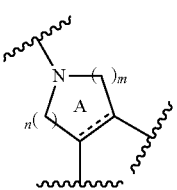 | B | 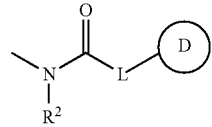 | additive |
|---|---|---|---|---|---|
| 294 | 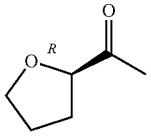 | 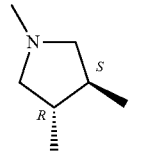 | 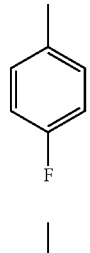 | 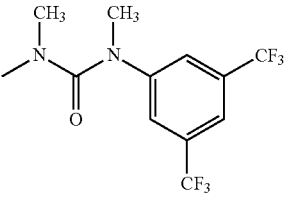 | |
| 295 | 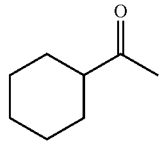 | 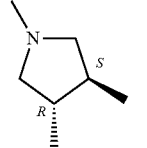 | 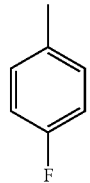 | 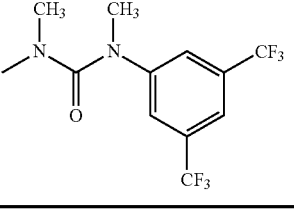 | |
TABLE B-26
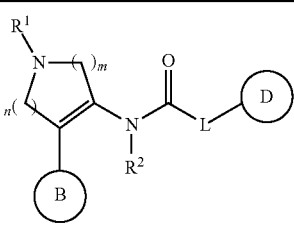
| Ex. No. | R¹ | 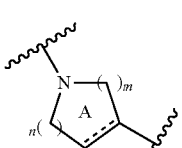 | B | 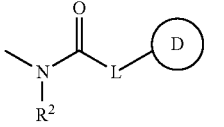 | additive |
|---|---|---|---|---|---|
| 296 | 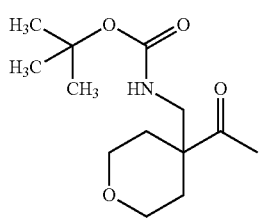 | 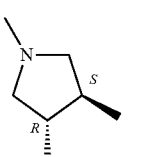 | 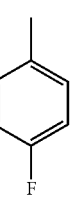 | 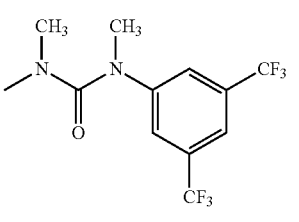 | |

TABLE B-26-continued
| Ex. No. | R[1] | A | B | R[2]/D | additive |
|---|---|---|---|---|---|
| 297 | 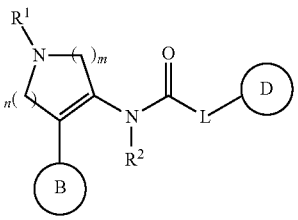 | 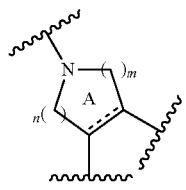 | 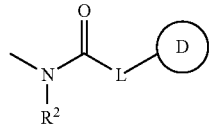 | 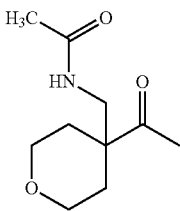 | |
| 298 | 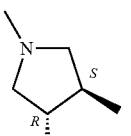 | 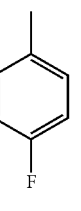 | 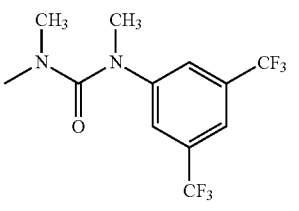 | 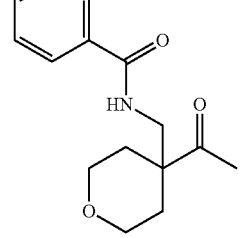 | |
| 299 | 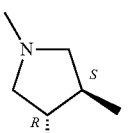 | 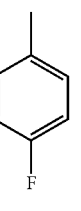 | 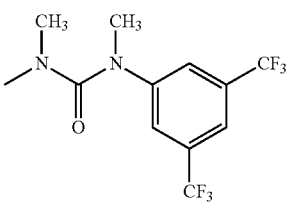 | 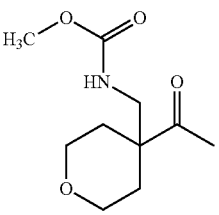 | |
| 300 | 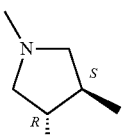 | 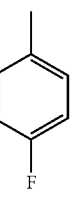 | 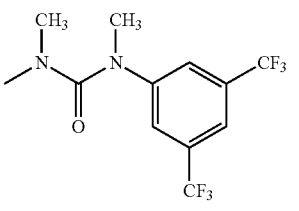 | 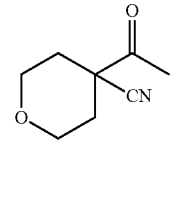 | |
| 301 | 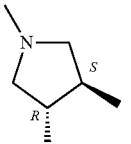 | 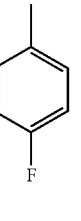 | 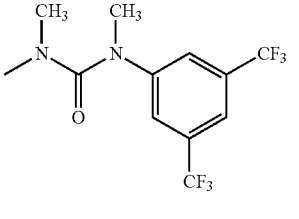 | 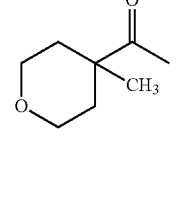 | |

TABLE B-26-continued
| Ex. No. | R[1] | A | B | R[2] | additive |
|---|---|---|---|---|---|
| 302 | 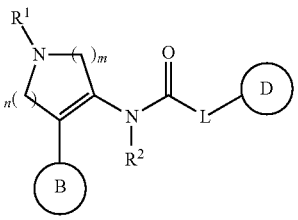 | 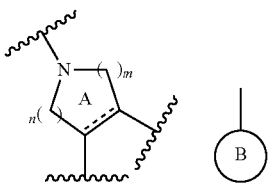 | 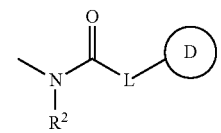 | 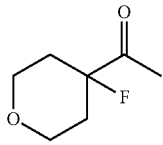 | |
| 303 | 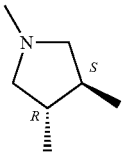 | 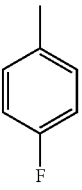 | 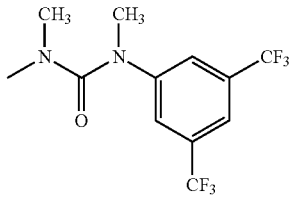 | 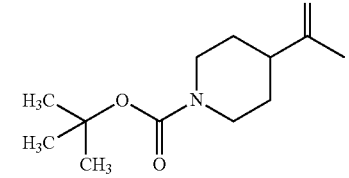 | |
| 304 | 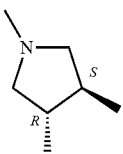 | 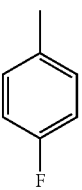 | 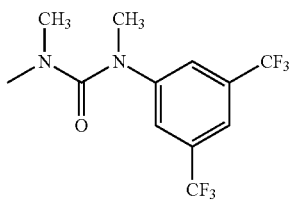 | 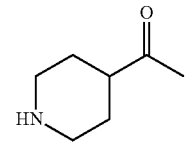 | HCl |
| 305 | 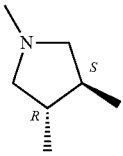 | 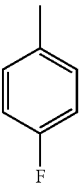 | 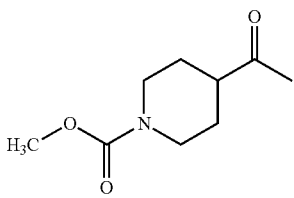 | 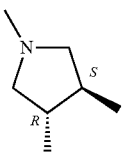 | |
| 306 | 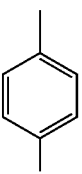 | 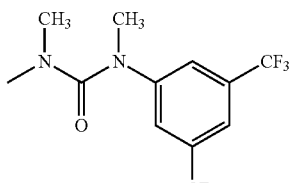 | 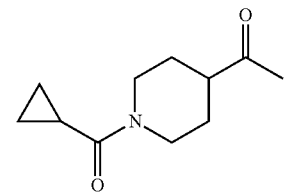 | 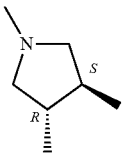 | |

TABLE B-26-continued
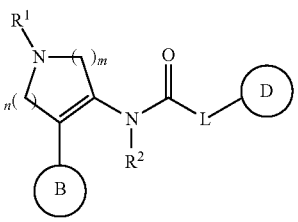
| Ex. No. | R¹ | 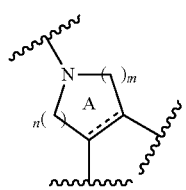 | B |  | additive |
|---|---|---|---|---|---|
| 307 | 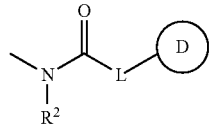 | 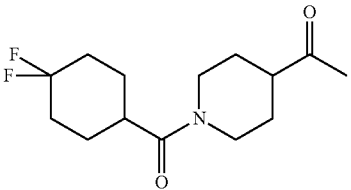 [SMILES: CC(=O)C1CCN(C(=O)C2CCC(F)(F)CC2)CC1] | 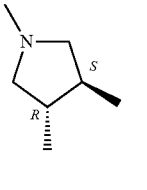 | 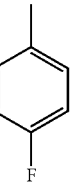 | |
TABLE B-27
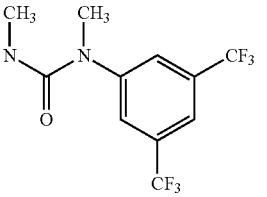
| Ex. No. | R¹ | 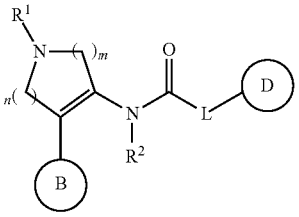 | B | 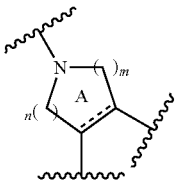 | additive |
|---|---|---|---|---|---|
| 308 | 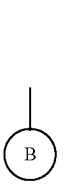 | 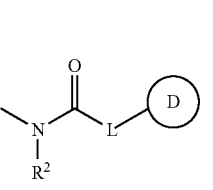 | 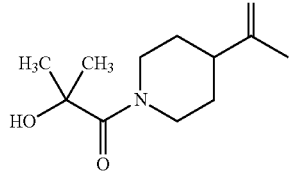 | 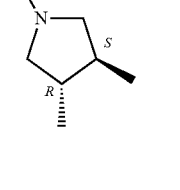 | |
| 309 | 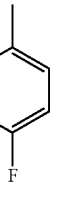 | 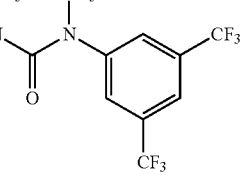 | 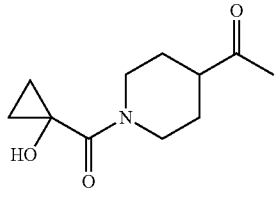 | 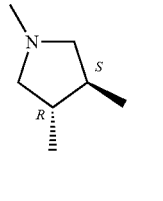 | |

TABLE B-27-continued

| Ex. No. | R¹ | 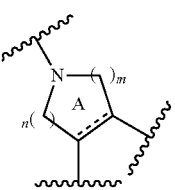 | B | R² | additive |
|---|---|---|---|---|---|
| 310 | 3,3-difluorocyclobutyl-C(O)-piperidin-4-yl-C(O)- | (3R,4S)-1,3-dimethylpyrrolidin-4-yl | 4-fluorophenyl | N,N'-dimethyl-N'-(3,5-bis(trifluoromethyl)phenyl)urea | |
| 311 | propionyl-piperidin-4-yl-C(O)- | (3R,4S)-1,3-dimethylpyrrolidin-4-yl | 4-fluorophenyl | N,N'-dimethyl-N'-(3,5-bis(trifluoromethyl)phenyl)urea | |
| 312 | ethoxycarbonyl-piperidin-4-yl-C(O)- | (3R,4S)-1,3-dimethylpyrrolidin-4-yl | 4-fluorophenyl | N,N'-dimethyl-N'-(3,5-bis(trifluoromethyl)phenyl)urea | |
| 313 | methoxyacetyl-piperidin-4-yl-C(O)- | (3R,4S)-1,3-dimethylpyrrolidin-4-yl | 4-fluorophenyl | N,N'-dimethyl-N'-(3,5-bis(trifluoromethyl)phenyl)urea | |
| 314 | (1H-tetrazol-1-yl)acetyl-piperidin-4-yl-C(O)- | (3R,4S)-1,3-dimethylpyrrolidin-4-yl | 4-fluorophenyl | N,N'-dimethyl-N'-(3,5-bis(trifluoromethyl)phenyl)urea | |

TABLE B-27-continued

| Ex. No. | R¹ | A | B | R² | additive |
|---|---|---|---|---|---|
| 315 | difluoroacetyl-piperidin-4-yl ketone | (3S,4R)-1-methyl-4-methylpyrrolidin-3-yl | 4-fluorophenyl | N,N'-dimethyl-N'-(3,5-bis(trifluoromethyl)phenyl)urea | |
| 316 | trifluoroacetyl-piperidin-4-yl ketone | (3S,4R)-1-methyl-4-methylpyrrolidin-3-yl | 4-fluorophenyl | N,N'-dimethyl-N'-(3,5-bis(trifluoromethyl)phenyl)urea | |
| 317 | cyanoacetyl-piperidin-4-yl ketone | (3S,4R)-1-methyl-4-methylpyrrolidin-3-yl | 4-fluorophenyl | N,N'-dimethyl-N'-(3,5-bis(trifluoromethyl)phenyl)urea | |
| 318 | cyclopropylacetyl-piperidin-4-yl ketone | (3S,4R)-1-methyl-4-methylpyrrolidin-3-yl | 4-fluorophenyl | N,N'-dimethyl-N'-(3,5-bis(trifluoromethyl)phenyl)urea | |
| 319 | (methylsulfonyl)acetyl-piperidin-4-yl ketone | (3S,4R)-1-methyl-4-methylpyrrolidin-3-yl | 4-fluorophenyl | N,N'-dimethyl-N'-(3,5-bis(trifluoromethyl)phenyl)urea | |

TABLE B-28
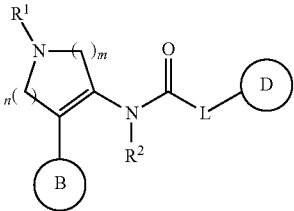
| Ex. No. | R¹ | | B | | additive |
|---|---|---|---|---|---|
| 320 | 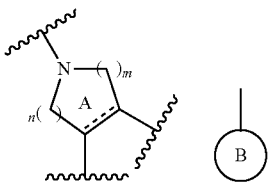 |  | 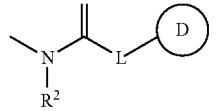 | 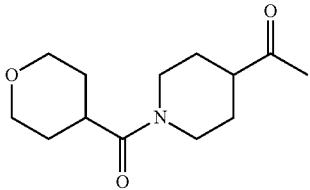 [SMILES: CC(=O)C1CCN(C(=O)C2CCOCC2)CC1] | |
| 321 | 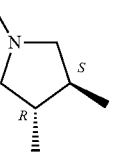 | 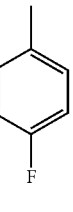 | 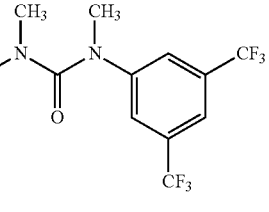 | 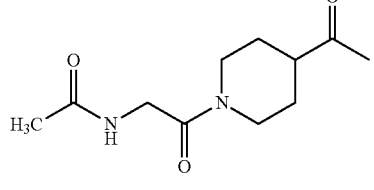 | |
| 322 | 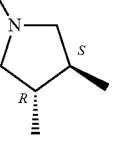 | 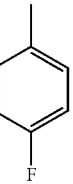 | 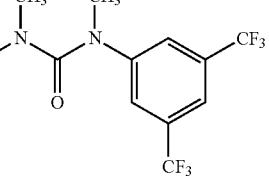 | 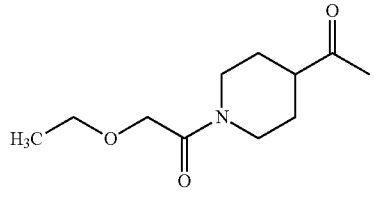 | |
| 323 | 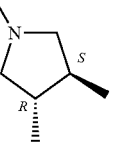 | 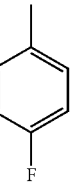 | 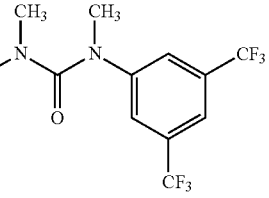 | 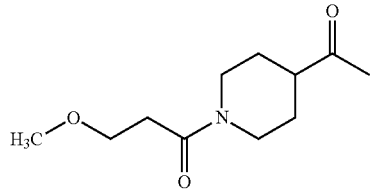 | |
| 324 | 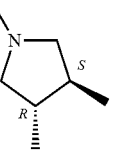 | 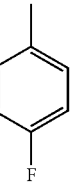 | 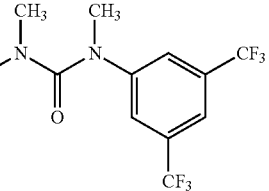 | 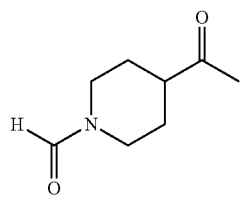 | |

TABLE B-28-continued
| Ex. No. | R¹ | A | B | R² | additive |
|---|---|---|---|---|---|
| 325 | 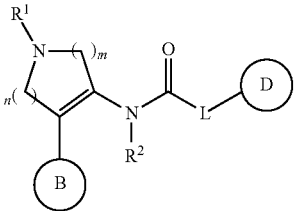 | 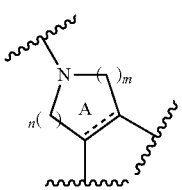 | 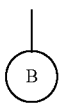 | 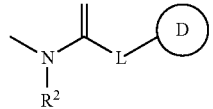 | |
| 326 | 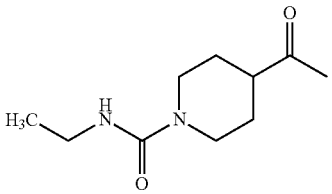 | 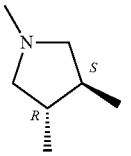 | 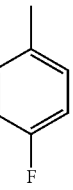 | 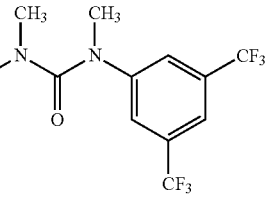 | |
| 327 | 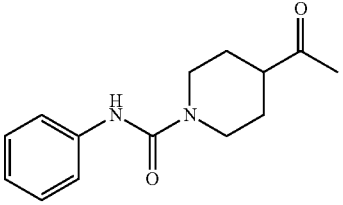 | 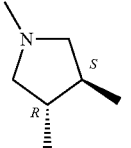 | 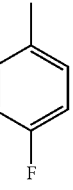 | 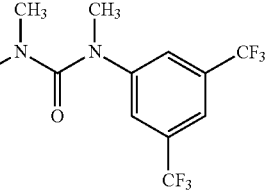 | |
| 328 | 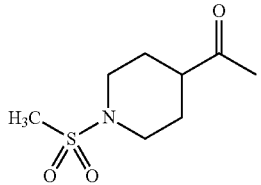 | 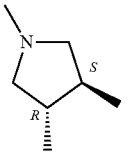 | 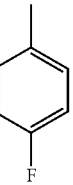 | 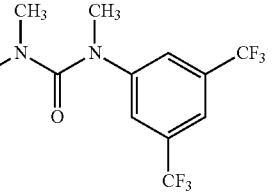 | |
| 329 | 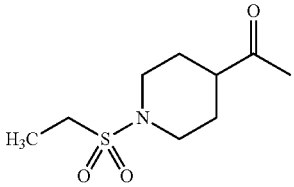 | 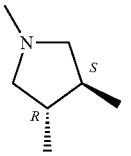 | 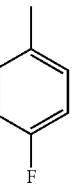 | 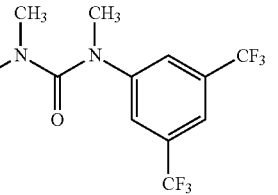 | |

TABLE B-28-continued

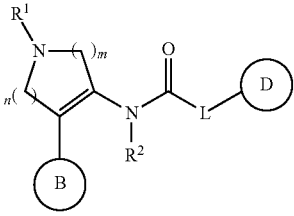

| Ex. No. | R¹ | [pyrrolidine A] | B | [urea with R²] | additive |
|---|---|---|---|---|---|
| 330 | cyclopropyl-SO₂-piperidine-C(O)- | (3S,4R)-1,4-dimethylpyrrolidin-3-yl | 4-F-C₆H₄ | N,N'-dimethyl-N'-(3,5-bis(CF₃)phenyl)urea | |
| 331 | F₃C-SO₂-piperidine-C(O)- | (3S,4R)-1,4-dimethylpyrrolidin-3-yl | 4-F-C₆H₄ | N,N'-dimethyl-N'-(3,5-bis(CF₃)phenyl)urea | |

TABLE B-29

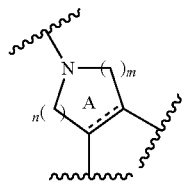

| Ex. No. | R¹ | [pyrrolidine A] | B | [urea with R²] | additive |
|---|---|---|---|---|---|
| 332 | F₃C-CH₂-SO₂-piperidine-C(O)- | (3S,4R)-1,4-dimethylpyrrolidin-3-yl | 4-F-C₆H₄ | N,N'-dimethyl-N'-(3,5-bis(CF₃)phenyl)urea | |

TABLE B-29-continued

| Ex. No. | R¹ | A | B | R² | additive |
|---|---|---|---|---|---|
| 333 | 4-acetyl-1-(N,N-dimethylsulfamoyl)piperidine | (3S,4R)-1-methyl-4-methylpyrrolidin-3-yl | 4-fluorophenyl | N,N'-dimethyl-N'-(3,5-bis(trifluoromethyl)phenyl)urea | |
| 334 | 1-(carbamoylmethyl)-4-acetylpiperidine | (3S,4R)-1-methyl-4-methylpyrrolidin-3-yl | 4-fluorophenyl | N,N'-dimethyl-N'-(3,5-bis(trifluoromethyl)phenyl)urea | |
| 335 | 1-(2-methoxyethyl)-4-acetylpiperidine | (3S,4R)-1-methyl-4-methylpyrrolidin-3-yl | 4-fluorophenyl | N,N'-dimethyl-N'-(3,5-bis(trifluoromethyl)phenyl)urea | |
| 336 | methyl 4-acetylcyclohexanecarboxylate | (3S,4R)-1-methyl-4-methylpyrrolidin-3-yl | 4-fluorophenyl | N,N'-dimethyl-N'-(3,5-bis(trifluoromethyl)phenyl)urea | |
| 337 | 4-acetylcyclohexanecarboxylic acid | (3S,4R)-1-methyl-4-methylpyrrolidin-3-yl | 4-fluorophenyl | N,N'-dimethyl-N'-(3,5-bis(trifluoromethyl)phenyl)urea | |

TABLE B-29-continued

| Ex. No. | R¹ | A | B | | additive |
|---|---|---|---|---|---|
| 338 | 4,4-difluoropiperidine-1-carbonyl-cyclohexyl-C(O)- | (3S,4R)-1-methyl-3,4-dimethylpyrrolidine | 4-fluorophenyl | N,N'-dimethyl-N'-(3,5-bis(trifluoromethyl)phenyl)urea | |
| 339 | morpholine-4-carbonyl-cyclohexyl-C(O)- | (3S,4R)-1-methyl-3,4-dimethylpyrrolidine | 4-fluorophenyl | N,N'-dimethyl-N'-(3,5-bis(trifluoromethyl)phenyl)urea | |
| 340 | cyclopropyl-NH-C(O)-cyclohexyl-C(O)- | (3S,4R)-1-methyl-3,4-dimethylpyrrolidine | 4-fluorophenyl | N,N'-dimethyl-N'-(3,5-bis(trifluoromethyl)phenyl)urea | |
| 341 | (CH₃)₂N-C(O)-cyclohexyl-C(O)- | (3S,4R)-1-methyl-3,4-dimethylpyrrolidine | 4-fluorophenyl | N,N'-dimethyl-N'-(3,5-bis(trifluoromethyl)phenyl)urea | |
| 342 | H₂N-C(O)-cyclohexyl-C(O)- | (3S,4R)-1-methyl-3,4-dimethylpyrrolidine | 4-fluorophenyl | N,N'-dimethyl-N'-(3,5-bis(trifluoromethyl)phenyl)urea | |

TABLE B-29-continued

| Ex. No. | R¹ | A | B | R² (urea portion) | additive |
|---|---|---|---|---|---|
| 343 | tert-butyl 3-acetylazetidine-1-carboxylate | (3S,4R)-1,3,4-trimethylpyrrolidine | 4-fluorophenyl | 1,3-dimethyl-1-(3,5-bis(trifluoromethyl)phenyl)urea | |

TABLE B-30

| Ex. No. | R¹ | A | B | R² (urea portion) | additive |
|---|---|---|---|---|---|
| 344 | 1-(1-acetylazetidin-3-yl)ethanone | (3S,4R)-1,3,4-trimethylpyrrolidine | 4-fluorophenyl | 1,3-dimethyl-1-(3,5-bis(trifluoromethyl)phenyl)urea | |
| 345 | methyl 3-acetylazetidine-1-carboxylate | (3S,4R)-1,3,4-trimethylpyrrolidine | 4-fluorophenyl | 1,3-dimethyl-1-(3,5-bis(trifluoromethyl)phenyl)urea | |

TABLE B-30-continued
| Ex. No. | R¹ | A | B | (D/R²) | additive |
|---|---|---|---|---|---|
| 346 | 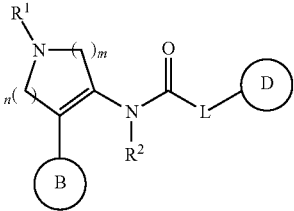 | 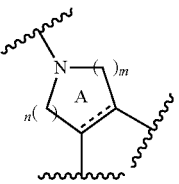 | 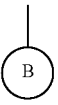 | 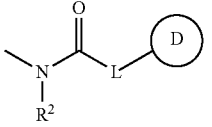 | |
| 347 | 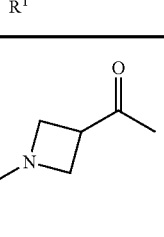 | 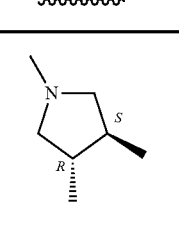 | 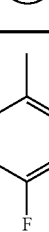 | 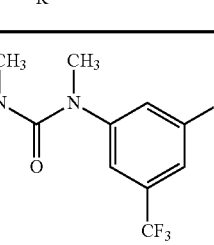 | |
| 348 | 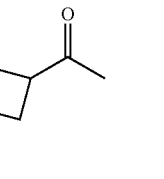 | 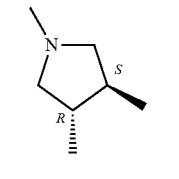 |  | 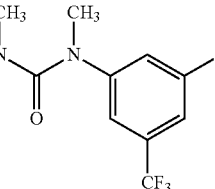 | |
| 349 | 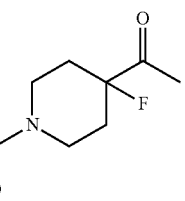 | 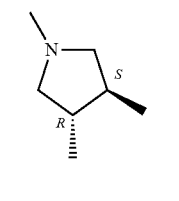 |  | 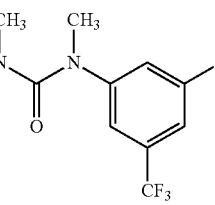 | HCl |
| 350 | 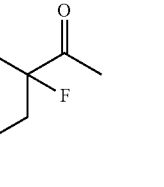 | 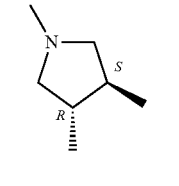 | 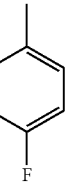 | 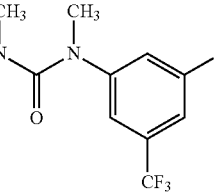 | |

TABLE B-30-continued

| Ex. No. | R¹ | A | B | R² | additive |
|---|---|---|---|---|---|
| 351 | | | | | |
| 352 | | | | | |
| 353 | | | | | HCl |
| 354 | | | | | |
| 355 | | | | | |

TABLE B-31

| Ex. No. | R¹ | A | B | (N-R²)-C(O)-L-D | additive |
|---|---|---|---|---|---|
| 356 | 2-methyl-4-oxo-oxazoline | (3S,4R)-1,4-dimethylpyrrolidin-3-yl | 4-fluorophenyl | N,N'-dimethyl-N'-(3,5-bis(trifluoromethyl)phenyl)urea | |
| 357 | 4-methyl-2-oxo-2,5-dihydrofuran-3-yl | (3S,4R)-1,4-dimethylpyrrolidin-3-yl | 4-fluorophenyl | N,N'-dimethyl-N'-(3,5-bis(trifluoromethyl)phenyl)urea | |
| 358 | 3-(4-acetylpiperidin-1-yl)-2-cyclopentenone | (3S,4R)-1,4-dimethylpyrrolidin-3-yl | 4-fluorophenyl | N,N'-dimethyl-N'-(3,5-bis(trifluoromethyl)phenyl)urea | |
| 359 | 4-(4-acetylpiperidin-1-yl)-2(5H)-furanone | (3S,4R)-1,4-dimethylpyrrolidin-3-yl | 4-fluorophenyl | N,N'-dimethyl-N'-(3,5-bis(trifluoromethyl)phenyl)urea | |
| 360 | 2-(4-acetylpiperidin-1-yl)-4-oxo-oxazoline | (3S,4R)-1,4-dimethylpyrrolidin-3-yl | 4-fluorophenyl | N,N'-dimethyl-N'-(3,5-bis(trifluoromethyl)phenyl)urea | |

TABLE B-31-continued

| Ex. No. | R¹ | A | B | D / R² | additive |
|---|---|---|---|---|---|
| 361 | NO | (S,R)-3,4-dimethylpyrrolidin-1-yl | 4-F-C6H4 | N,N'-dimethyl-N'-(3,5-bis(trifluoromethyl)phenyl)urea | |
| 362 | 4-nitrophenyl acetate | (S,R)-3,4-dimethylpyrrolidin-1-yl | 4-F-C6H4 | N,N'-dimethyl-N'-(3,5-bis(trifluoromethyl)phenyl)urea | |
| 363 | 1-(imidazol-1-yl)ethanethione | (S,R)-3,4-dimethylpyrrolidin-1-yl | 4-F-C6H4 | N,N'-dimethyl-N'-(3,5-bis(trifluoromethyl)phenyl)urea | |
| 364 | tert-butyl 4-(2-acetylhydrazinecarbonyl)piperidine-1-carboxylate | (S,R)-3,4-dimethylpyrrolidin-1-yl | 4-F-C6H4 | N,N'-dimethyl-N'-(3,5-bis(trifluoromethyl)phenyl)urea | |
| 365 | N-benzylacetamide | (S,R)-3,4-dimethylpyrrolidin-1-yl | 4-F-C6H4 | N,N'-dimethyl-N'-(3,5-bis(trifluoromethyl)phenyl)urea | |

TABLE B-31-continued

| Ex. No. | R¹ | A (pyrrolidine) | B | N(R²)C(O)L-D | additive |
|---|---|---|---|---|---|
| 366 | H₃C-CH₂-CH₂-NH-C(O)-CH₂- | (3S,4R)-1-methyl-4-methylpyrrolidin-3-yl | 4-fluorophenyl | N,N'-dimethyl-N'-(3,5-bis(trifluoromethyl)phenyl)urea-methyl | |
| 367 | cyclopropyl-NH-C(O)-CH₂- | (3S,4R)-1-methyl-4-methylpyrrolidin-3-yl | 4-fluorophenyl | N,N'-dimethyl-N'-(3,5-bis(trifluoromethyl)phenyl)urea-methyl | |

TABLE B-32

| Ex. No. | R¹ | A (pyrrolidine) | B | N(R²)C(O)L-D | additive |
|---|---|---|---|---|---|
| 368 | MeO-CH₂-NH-C(O)-CH₂- | (3S,4R)-1-methyl-4-methylpyrrolidin-3-yl | 4-fluorophenyl | N,N'-dimethyl-N'-(3,5-bis(trifluoromethyl)phenyl)urea-methyl | |

TABLE B-32-continued

| Ex. No. | R¹ | A | B | ad-di-tive |
|---|---|---|---|---|
| 369 | cyclopentyl-NH-C(O)-CH₂- | (3S,4R)-1-methyl-pyrrolidinyl | 4-F-phenyl | N,N'-dimethyl-N-(3,5-bis(CF₃)phenyl)urea |
| 370 | t-Bu-NH-C(O)-CH₂- | (3S,4R)-1-methyl-pyrrolidinyl | 4-F-phenyl | N,N'-dimethyl-N-(3,5-bis(CF₃)phenyl)urea |
| 371 | 4-MeO-phenyl-NH-C(O)-CH₂- | (3S,4R)-1-methyl-pyrrolidinyl | 4-F-phenyl | N,N'-dimethyl-N-(3,5-bis(CF₃)phenyl)urea |
| 372 | i-Pr-NH-C(O)-CH₂- | (3S,4R)-1-methyl-pyrrolidinyl | 4-F-phenyl | N,N'-dimethyl-N-(3,5-bis(CF₃)phenyl)urea |
| 373 | CH₃C(O)NH-CH₂-NH-C(O)-CH₂- | (3S,4R)-1-methyl-pyrrolidinyl | 4-F-phenyl | N,N'-dimethyl-N-(3,5-bis(CF₃)phenyl)urea |

TABLE B-32-continued

| Ex. No. | R¹ | A | B | R² | additive |
|---|---|---|---|---|---|
| 374 | 1-acetylpiperidin-4-yl-NH-acetyl | (3S,4R)-1-methyl-pyrrolidine | 4-fluorophenyl | N,N'-dimethyl-N'-(3,5-bis(trifluoromethyl)phenyl)urea | |
| 375 | cyclopropylmethylsulfonyl | (3S,4R)-1-methyl-pyrrolidine | 4-fluorophenyl | N,N'-dimethyl-N'-(3,5-bis(trifluoromethyl)phenyl)urea | |
| 376 | 2,2,2-trifluoroethylmethylsulfonyl | (3S,4R)-1-methyl-pyrrolidine | 4-fluorophenyl | N,N'-dimethyl-N'-(3,5-bis(trifluoromethyl)phenyl)urea | |
| 377 | pyridin-3-ylmethylsulfonyl | (3S,4R)-1-methyl-pyrrolidine | 4-fluorophenyl | N,N'-dimethyl-N'-(3,5-bis(trifluoromethyl)phenyl)urea | |
| 378 | tetrahydropyran-4-yl-NH-acetyl | (3S,4R)-1-methyl-pyrrolidine | 4-fluorophenyl | N,N'-dimethyl-N'-(3,5-bis(trifluoromethyl)phenyl)urea | |

TABLE B-32-continued
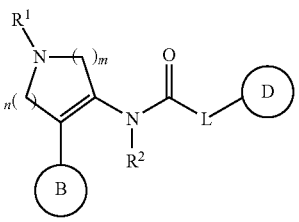
| Ex. No. | R¹ | 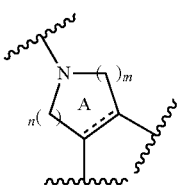 | B |  | additive |
|---|---|---|---|---|---|
| 379 | 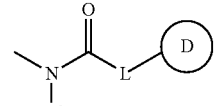 | 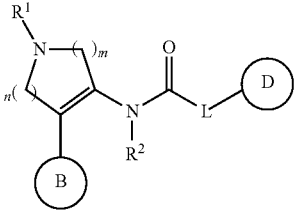 | 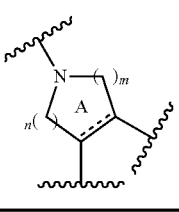 |  | |
TABLE B-33
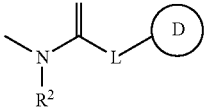
| Ex. No. | R¹ | A | B | | additive |
|---|---|---|---|---|---|
| 380 | H₂N-cyclohexyl-NHC(O)CH₃ | N-methyl pyrrolidine (3S,4R) | 4-F-C₆H₄ | CH₃N(CH₃)C(O)N(CH₃)-3,5-(CF₃)₂-C₆H₃ | HCl |
| 381 | H₃C-O-C(O)NH-cyclohexyl-NHC(O)CH₃ | N-methyl pyrrolidine (3S,4R) | 4-F-C₆H₄ | CH₃N(CH₃)C(O)N(CH₃)-3,5-(CF₃)₂-C₆H₃ | |

TABLE B-33-continued

| Ex. No. | R¹ | (pyrrolidine) | B | R² | additive |
|---|---|---|---|---|---|
| 382 | ethyl (4-acetamidocyclohexyl)carbamate | (3S,4R)-1-methyl-4-methylpyrrolidin-3-yl | 4-fluorophenyl | 3-(3,5-bis(trifluoromethyl)phenyl)-1,3-dimethylurea | |
| 383 | 1-(pyrrolidin-1-yl)ethanone | (3S,4R)-1-methyl-4-methylpyrrolidin-3-yl | 4-fluorophenyl | 3-(3,5-bis(trifluoromethyl)phenyl)-1,3-dimethylurea | |
| 384 | 1-morpholinoethanone | (3S,4R)-1-methyl-4-methylpyrrolidin-3-yl | 4-fluorophenyl | 3-(3,5-bis(trifluoromethyl)phenyl)-1,3-dimethylurea | |
| 385 | 1-thiomorpholinoethanone | (3S,4R)-1-methyl-4-methylpyrrolidin-3-yl | 4-fluorophenyl | 3-(3,5-bis(trifluoromethyl)phenyl)-1,3-dimethylurea | |
| 386 | 1-(4,4-difluoropiperidin-1-yl)ethanone | (3S,4R)-1-methyl-4-methylpyrrolidin-3-yl | 4-fluorophenyl | 3-(3,5-bis(trifluoromethyl)phenyl)-1,3-dimethylurea | |

TABLE B-33-continued
| Ex. No. | R¹ | 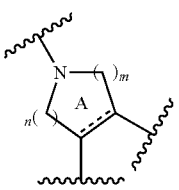 | B | 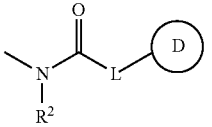 | additive |
|---|---|---|---|---|---|
| 387 | 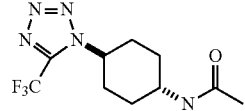 | 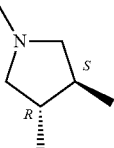 | 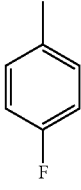 | 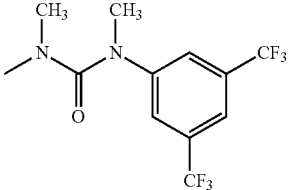 | |
| 388 | 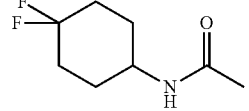 | 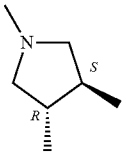 | 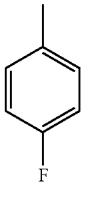 | 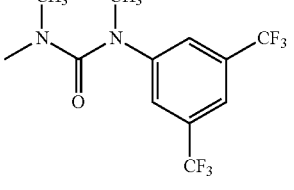 | |
| 389 | 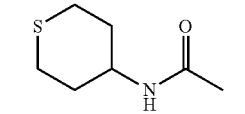 | 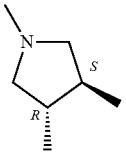 | 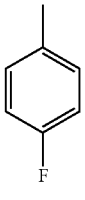 | 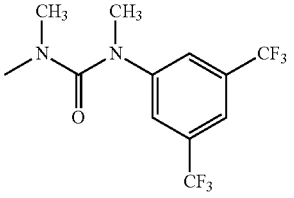 | |
| 390 | 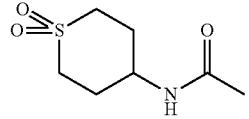 | 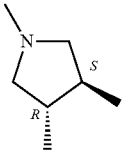 | 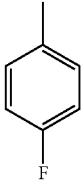 | 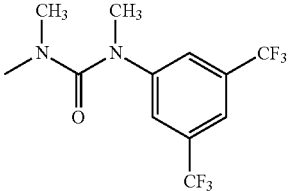 [SMILES: CN(C)C(=O)N(C)c1cc(C(F)(F)F)cc(C(F)(F)F)c1] | |
| 391 | 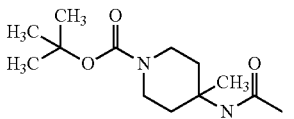 | 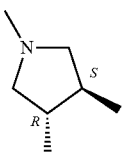 | 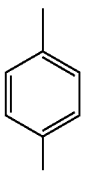 | 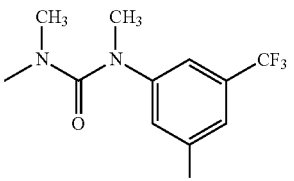 | |
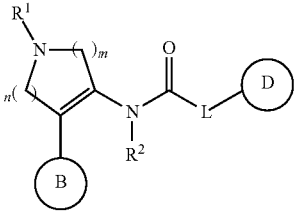

TABLE B-34

| Ex. No. | R¹ | A | B | R² | additive |
|---|---|---|---|---|---|
| 392 | 4-methyl-4-acetamidopiperidine (NH) | (3S,4R)-1,4-dimethylpyrrolidin-3-yl | 4-fluorophenyl | N,N'-dimethyl-N'-(3,5-bis(trifluoromethyl)phenyl)urea | HCl |
| 393 | 1-acetyl-4-methyl-4-acetamidopiperidine | (3S,4R)-1,4-dimethylpyrrolidin-3-yl | 4-fluorophenyl | N,N'-dimethyl-N'-(3,5-bis(trifluoromethyl)phenyl)urea | |
| 394 | 1-(methoxycarbonyl)-4-methyl-4-acetamidopiperidine | (3S,4R)-1,4-dimethylpyrrolidin-3-yl | 4-fluorophenyl | N,N'-dimethyl-N'-(3,5-bis(trifluoromethyl)phenyl)urea | |
| 395 | 1-acetyl-4-(5-methyl-1,3,4-oxadiazol-2-yl)piperidine | (3S,4R)-1,4-dimethylpyrrolidin-3-yl | 4-fluorophenyl | N,N'-dimethyl-N'-(3,5-bis(trifluoromethyl)phenyl)urea | |
| 396 | N-(2-oxopropyl)benzamide | (3S,4R)-1,4-dimethylpyrrolidin-3-yl | 3,4-difluorophenyl | N,N'-dimethyl-N'-(3,5-bis(trifluoromethyl)phenyl)urea | |

TABLE B-34-continued

| Ex. No. | R¹ | (A structure) | (B structure) | (R² structure) | additive |
|---|---|---|---|---|---|
| 397 | tetrahydropyran-4-yl acetyl | N-methyl pyrrolidine (3S,4R) | 3,4-difluorophenyl | N,N'-dimethyl-N'-(3,5-bis(trifluoromethyl)phenyl)urea | |
| 398 | methyl (4-acetylcyclohexyl)carbamate | N-methyl pyrrolidine (3S,4R) | 3,4-difluorophenyl | N,N'-dimethyl-N'-(3,5-bis(trifluoromethyl)phenyl)urea | |
| 399 | 4,4-difluorocyclohexyl acetyl | N-methyl pyrrolidine (3S,4R) | 3,4-difluorophenyl | N,N'-dimethyl-N'-(3,5-bis(trifluoromethyl)phenyl)urea | |
| 400 | 4-(5-trifluoromethyltetrazol-1-yl)cyclohexyl acetyl | N-methyl pyrrolidine (3S,4R) | 3,4-difluorophenyl | N,N'-dimethyl-N'-(3,5-bis(trifluoromethyl)phenyl)urea | |
| 401 | methyl (4-acetylcyclohexyl)carbamate | N-methyl pyrrolidine (3S,4R) | 2,4-difluorophenyl | N,N'-dimethyl-N'-(3,5-bis(trifluoromethyl)phenyl)urea | |

TABLE B-34-continued
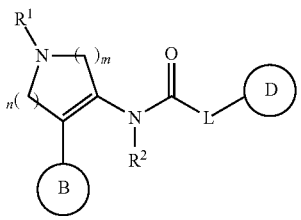
| Ex. No. | R¹ | 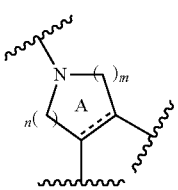 | B | 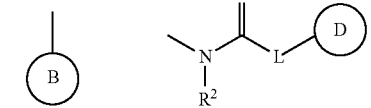 | additive |
|---|---|---|---|---|---|
| 402 | 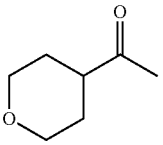 | 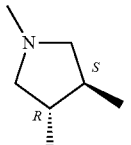 | 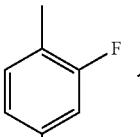 | 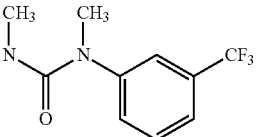 | |
| 403 | 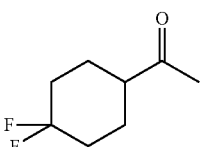 | 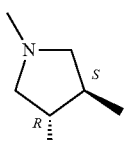 | 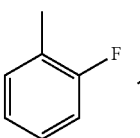 | 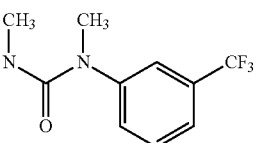 | |
TABLE B-35
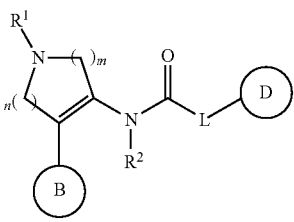
| Ex. No. | R¹ | 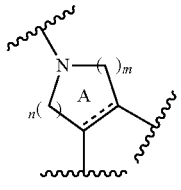 | B |  | additive |
|---|---|---|---|---|---|
| 404 | 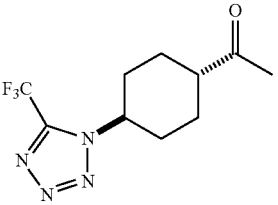 | 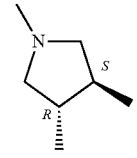 | 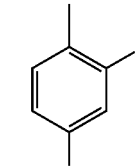 | 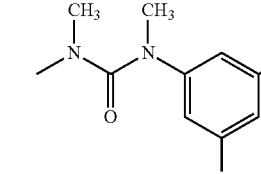 | |

TABLE B-35-continued

| Ex. No. | R¹ | [A ring] | B | [urea/D group] | additive |
|---|---|---|---|---|---|
| 405 | methyl (4-acetylcyclohexyl)carbamate | (3S,4R)-1-methyl-3,4-dimethylpyrrolidine | 4-fluorophenyl | N-(3-bromo-5-(trifluoromethyl)phenyl)-N,N'-dimethylurea | |
| 406 | 1-(4,4-difluorocyclohexyl)ethanone | (3S,4R)-1-methyl-3,4-dimethylpyrrolidine | 4-fluorophenyl | N-(3-bromo-5-(trifluoromethyl)phenyl)-N,N'-dimethylurea | |
| 407 | 1-(tetrahydro-2H-pyran-4-yl)ethanone | (3S,4R)-1-methyl-3,4-dimethylpyrrolidine | 4-fluorophenyl | N-(3-bromo-5-(trifluoromethyl)phenyl)-N,N'-dimethylurea | |
| 408 | 1-(4-(5-(trifluoromethyl)-1H-tetrazol-1-yl)cyclohexyl)ethanone | (3S,4R)-1-methyl-3,4-dimethylpyrrolidine | 4-fluorophenyl | N-(3-bromo-5-(trifluoromethyl)phenyl)-N,N'-dimethylurea | |
| 409 | methyl (4-acetylcyclohexyl)carbamate | (3S,4R)-1-methyl-3,4-dimethylpyrrolidine | 4-fluorophenyl | N-(3,5-dibromophenyl)-N,N'-dimethylurea | |

TABLE B-35-continued

| Ex. No. | R¹ | A | B | (R²/L/D group) | additive |
|---|---|---|---|---|---|
| 410 | 4,4-difluorocyclohexyl-C(O)- | (3S,4R)-1-methyl-3,4-dimethylpyrrolidine | 4-fluorophenyl | N,N'-dimethyl-N'-(3,5-dibromophenyl)urea | |
| 411 | tetrahydropyran-4-yl-C(O)- | (3S,4R)-1-methyl-3,4-dimethylpyrrolidine | 4-fluorophenyl | N,N'-dimethyl-N'-(3,5-dibromophenyl)urea | |
| 412 | 4-(methoxycarbonylamino)cyclohexyl-C(O)- | (3S,4R)-1-methyl-3,4-dimethylpyrrolidine | 4-fluorophenyl | N,N'-dimethyl-N'-(3-chloro-5-trifluoromethylphenyl)urea | |
| 413 | 4,4-difluorocyclohexyl-C(O)- | (3S,4R)-1-methyl-3,4-dimethylpyrrolidine | 4-fluorophenyl | N,N'-dimethyl-N'-(3-chloro-5-trifluoromethylphenyl)urea | |
| 414 | tetrahydropyran-4-yl-C(O)- | (3S,4R)-1-methyl-3,4-dimethylpyrrolidine | 4-fluorophenyl | N,N'-dimethyl-N'-(3-chloro-5-trifluoromethylphenyl)urea | |

TABLE B-35-continued
| Ex. No. | R¹ | 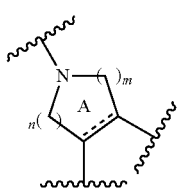 | B | 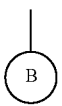 | additive |
|---|---|---|---|---|---|
| 415 | 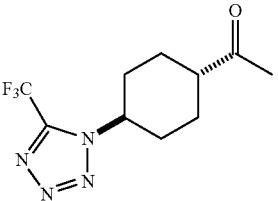 | 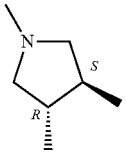 | 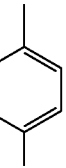 | 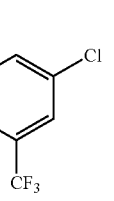 | |
TABLE B-36
| Ex. No. | R¹ | 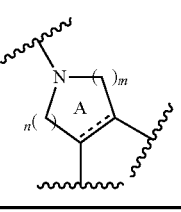 | B |  | additive |
|---|---|---|---|---|---|
| 416 | 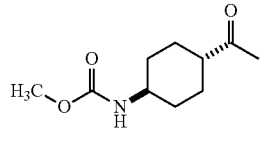 | 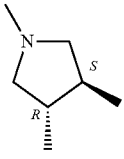 | 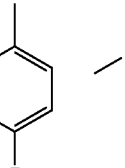 | 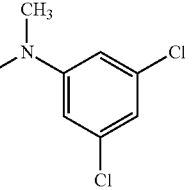 | |
| 417 | 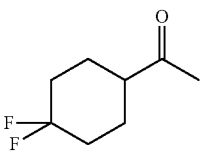 | 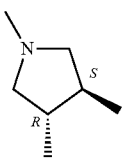 | 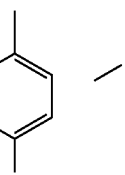 | 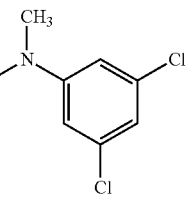 | |

US 8,592,454 B2
TABLE B-36-continued
| Ex. No. | R¹ | A | B | R² | additive |
|---|---|---|---|---|---|
| 418 | 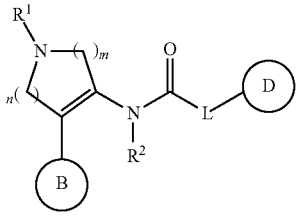 | 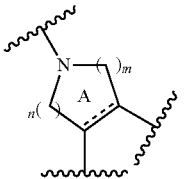 | 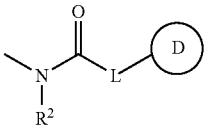 | 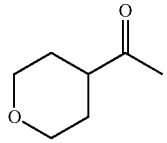 | |
| 419 | 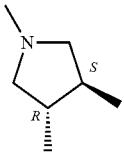 | 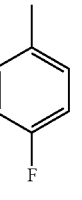 | 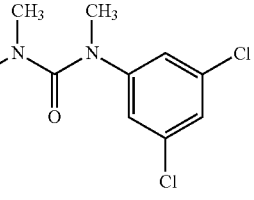 | 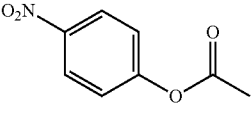 | |
| 420 | 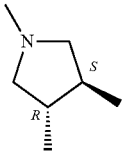 | 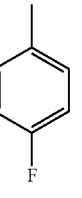 | 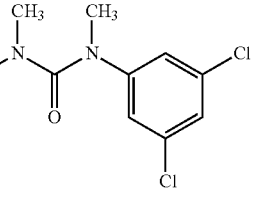 | 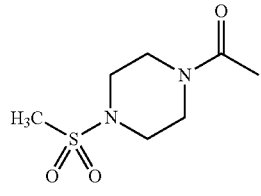 | |
| 421 | 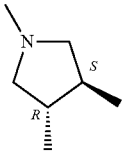 | 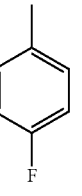 | 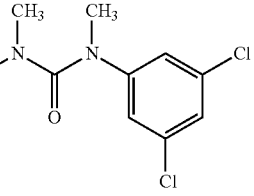 | 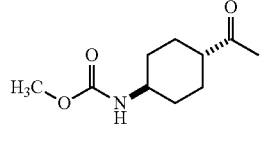 | |
| 422 | 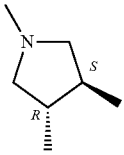 | 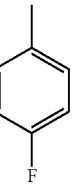 | 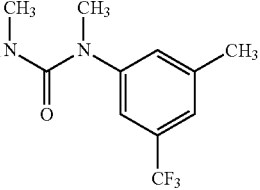 | 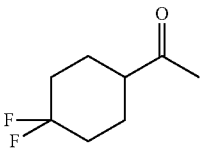 | |

TABLE B-36-continued
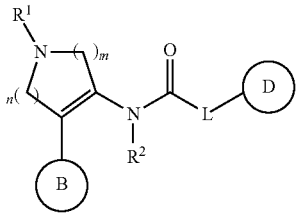
| Ex. No. | R¹ | [pyrrolidine A] | B | [urea R²] | additive |
|---|---|---|---|---|---|
| 423 | 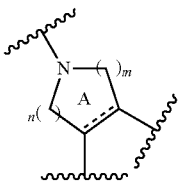 | 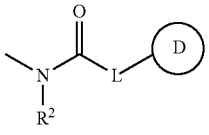 | 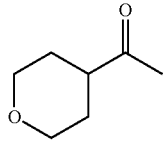 | 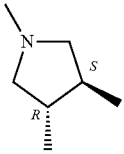 | |
| 424 | 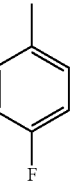 | 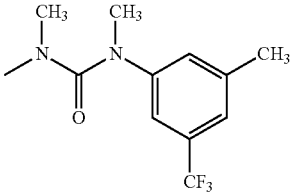 | 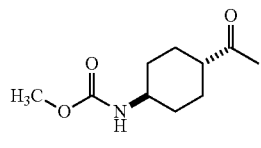 | 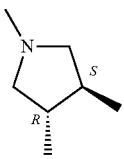 | |
| 425 | 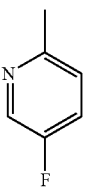 | 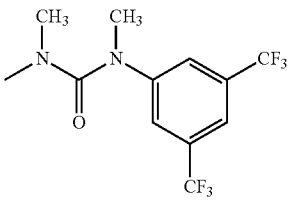 [SMILES: CN(C)C(=O)N(C)c1cc(C(F)(F)F)cc(C(F)(F)F)c1] | 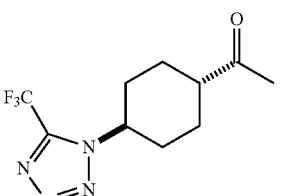 | 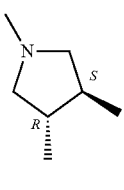 | |
| 426 | 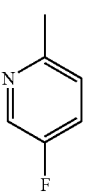 | 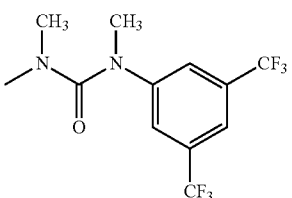 | 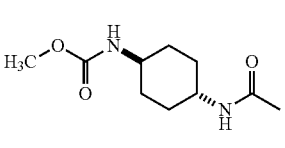 | 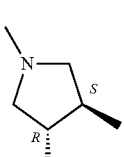 | |
| 427 | 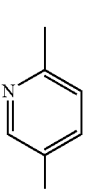 | 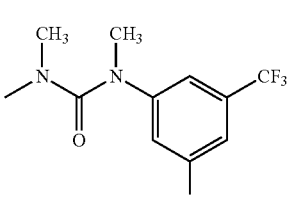 | 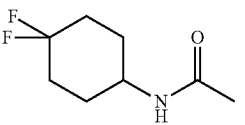 | 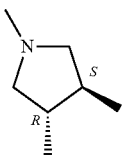 | |

TABLE B-37

| Ex. No. | R¹ | A | B | R², L, D | additive |
|---|---|---|---|---|---|
| 428 | 4-acetyl-tetrahydropyran | (3S,4R)-1-methyl-pyrrolidinyl | 4-fluorophenyl | N-methyl-N'-(3,5-bis(trifluoromethyl)phenyl)imidazolidin-2-one | |
| 429 | tert-butyl (4-acetylcyclohexyl)carbamate | (3S,4R)-1-methyl-pyrrolidinyl | 4-fluorophenyl | N-methyl-N'-(3,5-bis(trifluoromethyl)phenyl)imidazolidin-2-one | |
| 430 | 4-amino-cyclohexyl acetyl | (3S,4R)-1-methyl-pyrrolidinyl | 4-fluorophenyl | N-methyl-N'-(3,5-bis(trifluoromethyl)phenyl)imidazolidin-2-one | HCl |
| 431 | methyl (4-acetylcyclohexyl)carbamate | (3S,4R)-1-methyl-pyrrolidinyl | 4-fluorophenyl | N-methyl-N'-(3,5-bis(trifluoromethyl)phenyl)imidazolidin-2-one | |
| 432 | 6-fluoro-N-(4-acetylcyclohexyl)picolinamide | (3S,4R)-1-methyl-pyrrolidinyl | 4-fluorophenyl | N-methyl-N'-(3,5-bis(trifluoromethyl)phenyl)imidazolidin-2-one | |

Preparative Example 1

| | |
|---|---|
| (1) compound of Example 1 | 10 mg |
| (2) Lactose | 60 mg |
| (3) Corn starch | 35 mg |
| (4) Hydroxypropylmethylcellulose | 3 mg |
| (5) Magnesium stearate | 2 mg |

A mixture of the compound obtained in Example 1 (10 mg), lactose (60 mg) and corn starch (35 mg) is granulated using an aqueous solution (0.03 mL) of 10 wt % hydroxypropylmethylcellulose (3 mg as hydroxypropylmethylcellulose), and then dried at 40° C. and sieved. The obtained granules are mixed with magnesium stearate (2 mg) and compressed. The obtained uncoated tablets are sugar-coated with an aqueous suspension of sucrose, titanium dioxide, talc and gum arabic. The thus-coated tablets are glazed with beeswax to obtain finally-coated tablets.

Preparative Example 2

| (1) compound of Example 1 | 10 mg |
|---|---|
| (2) Lactose | 70 mg |
| (3) Corn starch | 50 mg |
| (4) Soluble starch | 7 mg |
| (5) Magnesium stearate | 3 mg |

The compound obtained in Example 1 (10 mg) and magnesium stearate (3 mg) are granulated with an aqueous soluble starch solution (0.07 ml, 7 mg as soluble starch), dried, and mixed with lactose (70 mg) and corn starch (50 mg). The mixture is compressed to obtain tablets.

Reference Preparative Example 1

| (1) Rofecoxib | 5.0 mg |
|---|---|
| (2) Sodium chloride | 20.0 mg |
| (3) Distilled water | to 2.0 mL of total volume |

Rofecoxib (5.0 mg) and sodium chloride (20.0 mg) are dissolved in distilled water, and water is added to make the total volume 2.0 mL. The solution is filtered, and filled into ampoule (2 mL) under sterile condition. The ampoule is sterilized, and then sealed to obtain a solution for injection.

Reference Preparative Example 2

| (1) Rofecoxib | 50 mg |
|---|---|
| (2) Lactose | 34 mg |
| (3) Corn starch | 10.6 mg |
| (4) Corn starch (paste) | 5 mg |
| (5) Magnesium stearate | 0.4 mg |
| (6) Calcium carboxymethylcellulose | 20 mg |
| Total | 120 mg |

The above-mentioned (1) to (6) are mixed according to a conventional method and tableted by a tablet machine to obtain tablets.

Preparative Example 3

The formulation prepared in Preparative Example 1 or 2, and the formulation prepared in Reference Preparative Example 1 or 2 are combined.

Experimental Example 1

Human $NK_1$ Receptor Binding Assay

Radioligand receptor binding inhibitory activity (Binding inhibitory activity using receptor from human lymphoblast cells (IM-9))

The method of M. A. Cascieri et al. [Molecular Pharmacology, vol. 42, p. 458 (1992)] was modified and used. The receptor was prepared from human lymphoblast cells (IM-9).

IM-9 cells ($2\times10^5$ cells/mL) were cultured for 3 days after inoculation, and centrifuged at 500×g for 10 min to give cell pellets. The obtained pellets were washed with PBS (Phosphate-Buffered saline) (GIBCO), disrupted in buffer A (50 mM Tris-hydrochloric acid buffer (Tris-HCl) (pH 7.4) containing 120 mM sodium chloride, 5 mM potassium chloride, 2 μg/mL chymostatin, 40 μg/ml bacitracin, 40 μg/mL APMSF (p-amidinophenylmethanesulfonyl fluoride hydrochloride) and 1 mM ethylenediaminetetraacetic acid (EDTA)) using a Polytron homogenizer (Kinematika, Germany), and centrifuged at 100,000×g for 40 min. The precipitation fraction was suspended in buffer B (50 mM Tris-HCl (pH 7.4), 0.02% bovine serum albumin, 2 μg/mL chymostatin, 40 μg/ml bacitracin, 40 μg/mL APMSF, 3 mM manganese dichloride ($MnCl_2$)) and cryopreserved (−80° C.) as a receptor reference standard.

Buffer B (50 μL) was added to a 96-well microassay plate (Corning Incorporated). The membrane reference standard suspended in buffer B at 250 μg/mL was added by 50 μL. A measurement buffer containing 2% dimethyl sulfoxide was added by 50 μL to examine the total binding, 4 μM non-labeled SP diluted with a measurement buffer containing 2% dimethyl sulfoxide was added by 50 μL to examine the non-specific binding, and a test compound diluted with a measurement buffer (containing 2% dimethyl sulfoxide) was added by 50 μL to examine the binding inhibitory activity of the test compound. Furthermore, 400 μM $^{125}$I-Bolton-Hunter-SP (BH-SP) solution was added to each well by 50 μL.

After reaction at room temperature for 30 min, the reaction was quenched using a cell harvester (PerkinElmer) by rapid filtration on a GF/C filter plate (PerkinElmer), and the cells were washed 10 times with 250 μL of a 50 mM Tris-hydrochloric acid buffer (pH 7.4) containing 0.02% bovine serum albumin. The GF/C filter plate was dried, MicroScinti-0 was added by 20 μL, and the radioactivity was measured on a TopCount (PerkinElmer). The GF/C filter plate used had been immersed in 0.3% polyethyleneimine for one day before use.

The specific binding level is shown by a value obtained by subtracting non-specific binding level from the total binding level. The binding inhibitory activity of the test compound is shown by a ratio of the value obtained by subtracting the measurement value with addition of a test compound from the total binding level, to the value of the specific binding level.

The antagonistic activity of each compound obtained in Examples was determined in terms of the drug concentration necessary to cause 50% inhibition ($IC_{50}$ value) under the above-described conditions, and the results are shown in Table (Table C).

Experimental Example 2

Human $NK_2$ Receptor Binding Assay

Radioligand Receptor Binding Inhibitory Activity Using Membrane Fraction of CHO Cell Expressing Human $NK_2$ ($hNK_2$) Receptor CHO cells expressing $hNK_2$ receptor were cultured in a HAM-F12 medium containing 400 μg/mL geneticin, 100 U/ml penicillin, 100 μg/ml streptomycin and 10% inactivated serum. The medium was removed, the adhered cells were washed with PBS, and PBS containing 5 mM EDTA was added to detach the cells from the flask. The cells were collected by centrifugation, suspended in suspension buffer A (15 mM Tris-HCl (pH 7.5), 2 mM $MgCl_2$, 0.3 mM ethylenediaminetetraacetic acid (EDTA), 1 mM O,O'-bis(2-aminoethyl)ethylene glycol-N,N,N',N'-tetraacetic acid (EGTA)), disrupted by a Polytron homogenizer (Kinematika), and centrifuged at 800×g for 10 min. The supernatant was recovered and ultracentrifuged at 100,000×g for 25 min. The precipitation fraction was suspended in suspension buffer B (7.5 mM Tris-HCl (pH 7.5), 12.5 mM $MgCl_2$, 0.3 mM EDTA, 1 mM EGTA, 250 mM sucrose), and cryopreserved (−80° C.) as a receptor reference standard.

Measurement buffer (50 mM Tris-HCl (pH 7.4), 0.02% bovine serum albumin, 2 μg/mL chymostatin, 40 μg/ml bacitracin, 40 μg/ml APMSF, 3 mM $MnCl_2$) (50 μL) was added to a 96-well microassay plate. The membrane reference standard (20 μg/mL) suspended in a measurement buffer was added by 50 μL. A measurement buffer containing 2% dimethyl sulfoxide was added by 50 μL to examine the total binding level, 4 μM non-labeled NK-A (PEPTIDE INSTITUTE, INC.) solution diluted with a measurement buffer containing 2% dimethyl sulfoxide was added by 50 μL to examine the non-specific binding level, and a test compound diluted with a measurement buffer (containing 2% dimethyl sulfoxide) was added by 50 μL to examine the binding inhibitory activity of the test compound. Furthermore, 400 μM [$^{125}$I]-NK-A (GE Healthcare Bio-Sciences KK) solution was added to each well by 50 μL.

After reaction at 25° C. for 30 min, the reaction was quenched using a cell harvester (PerkinElmer) by rapid filtration on a GF/C filter plate, and the cells were washed 5 times with 250 μL of a 50 mM Tris-HCl buffer (pH 7.4) containing 0.02% bovine serum albumin. The GF/C filter plate was dried, MicroScinti-0 (PerkinElmer) was added by 20 μL, and the radioactivity was measured on a TopCount (PerkinElmer). The GF/C filter plate used had been immersed in 0.3% polyethyleneimine for one day.

The specific binding level is shown by a value obtained by subtracting non-specific binding level from the total binding level. The binding inhibitory activity of the test compound is shown by a ratio of the value obtained by subtracting the measurement value with addition of a test compound from the total binding level, to the value of the specific binding level.

The antagonistic activity of the compounds obtained in Examples was determined in terms of the drug concentration necessary to cause 50% inhibition ($IC_{50}$ value) under the above-described conditions, and the results are shown in Table (Table C).

Experimental Example 3

Human $NK_3$ Receptor Binding Assay

Radioligand Receptor Binding Inhibitory Activity Using Membrane Fraction of CHO Cell Expressing Human $NK_3$ ($hNK_3$) Receptor CHO cells expressing $hNK_3$ receptor were cultured in a MEMα medium (Nikken Seibutsu Igaku Kenkyusho, K.K.) containing 100 U/mL penicillin, 100 μg/mL streptomycin and 10% inactivated dialyzed serum. The medium was removed, the adhered cells were washed with PBS, and PBS containing 5 mM EDTA was added to detach the cells from the flask. The cells were collected by centrifugation, suspended in suspension buffer A (50 mM Tris-HCl (pH 7.4) containing 120 mM NaCl, 5 mM KCl, 2 μg/mL chymostatin, 40 μg/mL bacitracin, 40 μg/ml APMSF, 1 mM EDTA), disrupted by a Polytron homogenizer (Kinematika), and centrifuged at 800×g for 10 min. The supernatant was recovered and ultracentrifuged at 100,000×g for 25 min. The precipitation fraction was suspended in suspension buffer B (50 mM Tris-HCl (pH 7.4), 0.02% bovine serum albumin, 2 μg/ml chymostatin, 40 μg/ml bacitracin, 40 μg/mL APMSF, 3 mM $MnCl_2$), and cryopreserved (−80° C.) as a receptor reference standard.

Measurement buffer (50 mM Tris-HCl (pH 7.4), 0.02% bovine serum albumin, 2 μg/ml chymostatin, 40 μg/mL bacitracin, 40 μg/mL APMSF, 3 mM $MnCl_2$) (50 μL) was added to a 96-well microassay plate. The membrane reference standard (300 μg/mL) suspended in a measurement buffer was added by 50 μL. A measurement buffer containing 2% dimethyl sulfoxide was added by 50 μL to examine the total binding level, 16 μM non-labeled NK-B (PEPTIDE INSTITUTE, INC.) solution diluted with a measurement buffer containing 2% dimethyl sulfoxide was added by 50 μL to examine the non-specific binding level, and a test compound diluted with a measurement buffer (containing 2% dimethyl sulfoxide) was added by 50 μL to examine the binding inhibitory activity of the test compound. Furthermore, 400 μM [$^{125}$I]-NK-B (Neurokinin-B (N-Me-Phe$^7$), [$^{125}$I]His$^3$-) (PerkinElmer) solution was added to each well by 50 μL.

After reaction at 25° C. for 30 min, the reaction was quenched using a cell harvester (PerkinElmer) by rapid filtration on a GF/C filter plate, and the cells were washed 5 times with 250 μL of a 50 mM Tris-HCl buffer (pH 7.4) containing 0.02% bovine serum albumin. The GF/C filter plate was dried, MicroScinti-0 (Perkin Elmer) was added by 20 μL, and the radioactivity was measured on a TopCount (PerkinElmer). The GF/C filter plate used had been immersed in 0.3% polyethyleneimine for one day.

The specific binding level is shown by a value obtained by subtracting non-specific binding level from the total binding level. The binding inhibitory activity of the test compound is shown by a ratio of the value obtained by subtracting the measurement value with addition of a test compound from the total binding level, to the value of the specific binding level.

The antagonistic activity of the compounds obtained in Examples was determined in terms of the drug concentration necessary to cause 50% inhibition ($IC_{50}$ value) under the above-described conditions, and the results are shown in Table (Table C).

| Ex. No. | $IC_{50}$ value (nM) | | |
|---|---|---|---|
| | $hNK_1$ | $hNK_2$ | $hNK_3$ |
| 4 | 0.11 | 4200 | N.T. |
| 25 | 0.031 | 7.1 | 1400 |
| 61 | 290 | >100 | 99 |
| 66 | 0.075 | 2.0 | 140 |
| 71b | 0.027 | 7.1 | N.T. |
| 104 | 0.073 | 100 | N.T. |
| 176 | 0.029 | 12 | 600 |
| 192 | 0.032 | 120 | 4400 |
| 233 | 0.049 | 42 | 1100 |
| 308 | 0.070 | 2.4 | N.T. |
| 378 | 0.039 | 59 | 650 |
| 420 | 0.030 | 77 | 120 |

From the results of Table C, it is appreciated that the compound of the present invention has a superior Substance P receptor, NK-A receptor and NK-B receptor antagonistic actions.

INDUSTRIAL APPLICABILITY

Compound (I) or a salt thereof or a prodrug thereof of the present invention shows a high tachykinin receptor antagonistic action, excellent in sustainability, low in toxicity, safe as a medicament and less influential to other agents. Therefore, compound (I) or a salt thereof or a prodrug thereof of the present invention is useful as a medicament, for example, a tachykinin receptor antagonist agent or an agent for the prophylaxis or treatment of lower urinary tract diseases, digestive tract diseases, central nervous system diseases and the like.

This application is based on a provisional application No. 61/136,625 filed in the US, the contents of which are incorporated in full herein.

The invention claimed is:

1. A compound represented by the formula

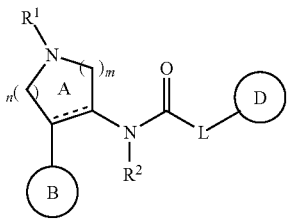

wherein:
ring A is a piperidine ring or a pyrrolidine ring and each straight line is a single bond and ----- is a single bond;
ring B is an aromatic ring optionally having substituent(s);
ring D is an aromatic ring optionally having substituent(s), wherein 6-quinolyl is excluded;
L is a group represented by the formula

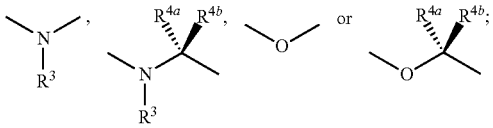

$R^2$, $R^3$, $R^{4a}$ and $R^{4b}$ are each independently a hydrogen atom, an optionally halogenated $C_{1-6}$ alkyl group or an optionally halogenated $C_{3-6}$ cycloalkyl group, or $R^2$ and $R^3$ are optionally bonded via an alkylene chain or an alkenylene chain, or $R^{4a}$ and $R^{4b}$ are optionally bonded via an alkylene chain or an alkenylene chain;
$R^1$ is a hydrogen atom or a substituent;
m and n are each independently an integer of 0 to 3; and
m+n is an integer of 2 to 3;
provided that when L is a group represented by the formula

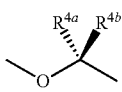

wherein each of $R^{4a}$ and $R^{4b}$ is as defined above, then ring D is an aromatic ring having substituent(s);
excluding: N-[4-(biphenyl-4-yl)piperidin-3-yl]-N'-(naphthalen-2-yl)urea;
or a salt thereof.

2. The compound or salt according to claim 1, wherein ring B is a phenyl group optionally having substituent(s) or a pyridyl group optionally having substituent(s).

3. The compound or salt according to claim 1, wherein ring B is a phenyl group optionally having substituent(s) or a thienyl group optionally having substituent(s).

4. The compound or salt according to claim 1, wherein ring D is a phenyl group optionally having substituent(s).

5. The compound or salt according to claim 1, wherein $R^1$ is a hydrogen atom, a hydrocarbon group optionally having substituent(s), an acyl group, a heterocyclic group optionally having substituent(s), or a group represented by —$NR^5R^6$ wherein $R^5$ and $R^6$ are each independently a hydrogen atom, a hydrocarbon group optionally having substituent(s) or an acyl group, or $R^5$ and $R^6$ optionally form, together with the adjacent nitrogen atom, a nitroso group (—N=O).

6. The compound or salt according to claim 1, wherein $R^2$ is a hydrogen atom or a $C_{1-6}$ alkyl group.

7. The compound or salt according to claim 1, wherein L is a group represented by the formula

wherein $R^{3'}$ is a hydrogen atom or a $C_{1-6}$ alkyl group.

8. The compound or salt according to claim 1, wherein ring D is a 3,5-bis(trifluoromethyl)phenyl group or a 3,5-dichlorophenyl group.

9. Methyl 4-{[(3S,4R)-3-[{[3,5-bis(trifluoromethyl)phenyl](methyl)carbamoyl}(methyl)amino]-4-(4-fluorophenyl)pyrrolidin-1-yl]carbonyl}piperidine-1-carboxylate, or a salt thereof.

10. 1-[(3S,4R)-4-(4-Chlorophenyl)-1-{[4-(methylsulfonyl)piperazin-1-yl]carbonyl}pyrrolidin-3-yl]-3-(3,5-dichlorophenyl)-1,3-dimethylurea, or a salt thereof.

11. 1-[3,5-Bis(trifluoromethyl)phenyl]-3-[(3S,4R)-4-(5-fluoropyridin-2-yl)-1-({trans-4-[5-(trifluoromethyl)-1H-tetrazol-1-yl]cyclohexyl}carbonyl)pyrrolidin-3-yl]-1,3-dimethylurea, or a salt thereof.

12. A pharmaceutical composition comprising the compound or salt according to claim 1 and a pharmaceutically acceptable carrier.

13. A method of antagonizing an NK1 receptor in a mammal, comprising administering the pharmaceutical composition according to claim 12 to the mammal.

14. The method according to claim 13, wherein the method further antagonizes an NK2 receptor and/or an NK3 receptor.

15. A method of antagonizing an NK2 receptor in a mammal, comprising administering the pharmaceutical composition according to claim 12 to the mammal.

16. The method according to claim 15, wherein the method further antagonizes an NK1 receptor and/or an NK3 receptor.

17. A method for the treatment of vomiting, nausea, depression, anxiety neurosis, or anxiety, comprising administering an effective amount of the compound or salt according to claim 1 to a mammal.

* * * * *